(12) United States Patent
Satomaa et al.

(10) Patent No.: US 8,691,774 B2
(45) Date of Patent: Apr. 8, 2014

(54) CARBOHYDRATE PROFILE COMPOSITIONS FROM HUMAN CELLS AND METHODS FOR ANALYSIS AND MODIFICATION THEREOF

(75) Inventors: Tero Satomaa, Helsinki (FI); Jari Natunen, Vantaa (FI); Jarmo Laine, Helsinki (FI); Annamari Heiskanen, Helsinki (FI); Maria Blomqvist, Itäsalmi (FI); Anne Olonen, Lahti (FI); Juhani Saarinen, Helsinki (FI); Taina Jaatinen, Helsinki (FI); Ulla Impola, Helsinki (FI); Milla Mikkola, Helsinki (FI); Heidi Anderson, Helsinki (FI)

(73) Assignee: Glykos Finland Oy, Helsinki (FI)

( * ) Notice: Subject to any disclaimer, the term of this patent is extended or adjusted under 35 U.S.C. 154(b) by 964 days.

(21) Appl. No.: 11/988,564

(22) PCT Filed: Jul. 11, 2006

(86) PCT No.: PCT/FI2006/050336
§ 371 (c)(1),
(2), (4) Date: Nov. 17, 2009

(87) PCT Pub. No.: WO2007/006870
PCT Pub. Date: Jan. 18, 2007

(65) Prior Publication Data
US 2010/0055710 A1    Mar. 4, 2010

(30) Foreign Application Priority Data

| Jul. 11, 2005 | (FI) | 20055403 |
| Nov. 8, 2005 | (FI) | 20051130 |
| May 9, 2006 | (FI) | 20060452 |
| Jun. 29, 2006 | (FI) | 20060630 |

(51) Int. Cl.
*G01N 33/577* (2006.01)
*G01N 33/574* (2006.01)

(52) U.S. Cl.
CPC .......... *G01N 33/577* (2013.01); *G01N 2400/38* (2013.01); *G01N 33/574* (2013.01); *G01N 33/57469* (2013.01); *G01N 2560/00* (2013.01)
USPC ........................................................ 514/23

(58) Field of Classification Search
None
See application file for complete search history.

(56) References Cited

U.S. PATENT DOCUMENTS

| 5,965,457 | A | 10/1999 | Magnani | |
| 8,236,487 | B2 * | 8/2012 | Natunen et al. | 435/4 |
| 8,313,912 | B2 * | 11/2012 | Saarinen et al. | 435/7.1 |
| 2009/0117106 | A1 * | 5/2009 | Satomaa et al. | 424/133.1 |
| 2009/0162938 | A1 * | 6/2009 | Laine et al. | 436/63 |
| 2009/0317788 | A1 * | 12/2009 | Laine et al. | 435/2 |
| 2009/0317834 | A1 * | 12/2009 | Laine et al. | 435/7.21 |
| 2010/0028913 | A1 * | 2/2010 | Laine et al. | 435/7.21 |
| 2010/0047827 | A1 * | 2/2010 | Laine et al. | 435/7.21 |
| 2010/0145032 | A1 * | 6/2010 | Laine et al. | 530/395 |
| 2011/0045497 | A1 * | 2/2011 | Natunen et al. | 435/7.21 |
| 2011/0143373 | A1 * | 6/2011 | Hirvonen et al. | 435/7.21 |

FOREIGN PATENT DOCUMENTS

| WO | WO-9915628 A1 | 4/1999 |
| WO | WO-2004019040 A1 | 3/2004 |

OTHER PUBLICATIONS

Jordan et al., "Cancer Stem Cells" The New England Journal of Medicine (2006) vol. 355 No. 12 pp. 1253-1261.*
Ciolczyk et al., "The structure of the oligosaccharides of N-cadherin from human melanoma cell lines" Glycoconjugate Journal (2004) vol. 20 pp. 483-492.*
Capela et al., "LeX/ssea-1 Is Expressed by Adult Mouse CNS Stem Cells, Identifying Them as Nonependymal" Neuron (2002) vol. 35 pp. 865-875.*
Lanctot et al., "The glycans of stem cells" Current Opinion in Chemical Biology (2007) vol. 11 pp. 373-380.*
Kannagi, R. & al., Stage specific antigens (SSA-3 and SSEA_4) are epitopes of a unique globo-series ganglioside isolated from human teratocarcinoma cells. The EMBO Journal vol. 2 (1983), 2355-2361.
Muramatsu, T. & al. Carbohydrate antigens expressed on stem cells and early embryonic cells. Glycoconjugate Journal 21 (2004), 41-45.
Takemoto, T. & al. Expression of complex-type N-glycans in developmental periods of zebrafish embryo. Glycoconjugate Journal 22 (Feb. 2005), 21-26.
Ogier-Denis, e. & al. The Processing of Asparagine-linked Oligosaccharides in HT-29 Cells is a Function of their State of Enterocytic Differentiation. The Journal of Biological Chemistry, 263 (1988), 6031-7.
Choi, O. & al. N-glycan structures of human transferrin produced by *Lymantria dispar*(Gypsy moth) cells using the LdMNPV expression system, Glycobiology vol. 13 (2003), 539-548.
Lloyd, K. O. & al. Comparison of O-linked Carbohydrate Chains in MUC-1 Mucin from Normal Breast Epithelial Cell Lines and Breast Carcinoma Cell Lines. The Journal of Biological Chemistry vol. 271 (1996), 33325-33334.
Sasaki, H. & al. Carbohydrate Structure of Erythropoietin Expressed in Chinese Hamster Ovary Cells by a Human Erythropoietin cDNA. The Journal of Biological Chemistry vol. 262 (1987), 12059-12076.

* cited by examiner

*Primary Examiner* — Eric S Olson
(74) *Attorney, Agent, or Firm* — Birch, Stewart, Kolasch & Birch, LLP

(57) ABSTRACT

The invention describes methods for production of novel composition of glycans, glycomes, from human multipotent stem cells. The invention is further directed to methods for modifying the glycomes and analysis of the glycomes and the modified glycomes. Furthermore the invention is directed to stem cells carrying the modified glycomes on their surfaces.

36 Claims, 46 Drawing Sheets

Figure 26.
A.
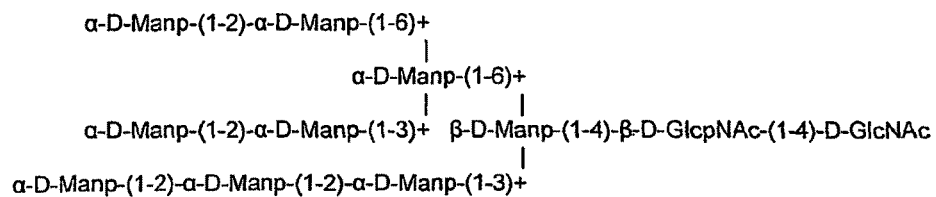
B.
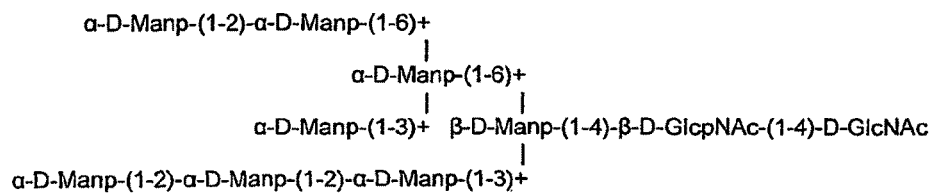
C.
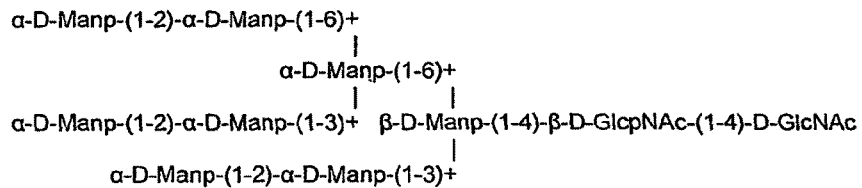
D.
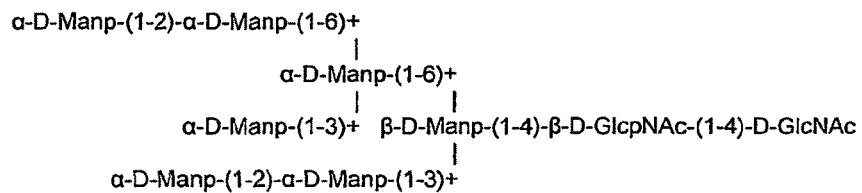

Figure 27.
A.
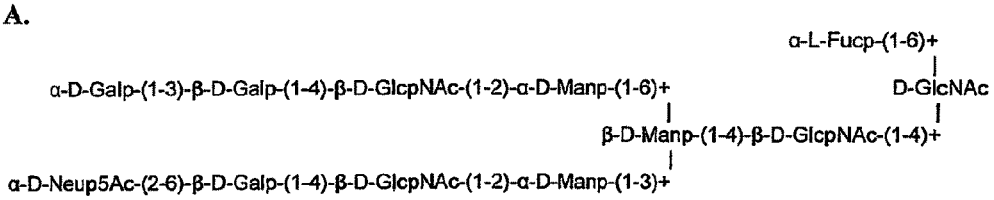
B.
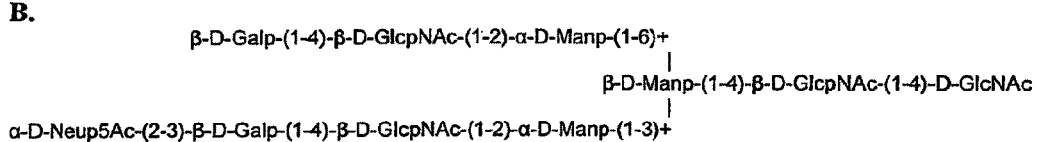
C.
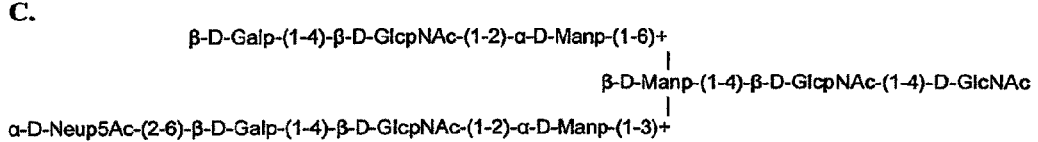
D.
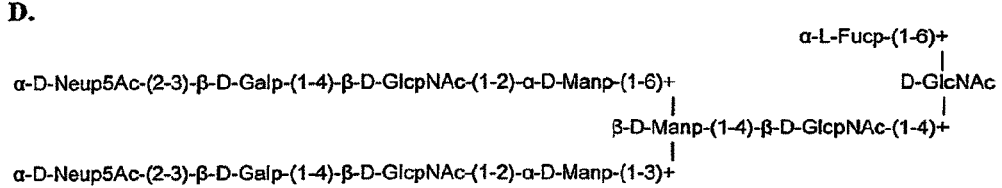
E.
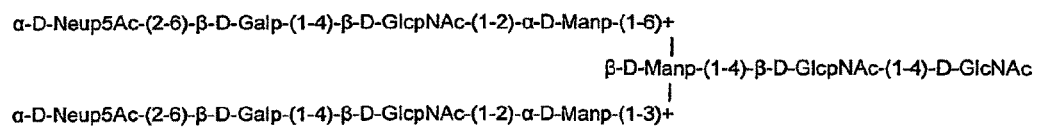

Figure 38.

| enzyme | | glycan product |
|---|---|---|

A

FUT1    H type 2    Fuc α1-2 Gal β1-4 GlcNAc→
           CD173

FUT4    Le$^x$         ←—Gal β1-4 GlcNAc—→
           CD15              Fuc α1-3
           (SSEA-1)

B

Fuc α1-6
FUT8    α1,6-Fuc    ←—GlcNAc β1-4 GlcNAc β-N—→ Asn

Stem cell nomenclature

CARBOHYDRATE PROFILE COMPOSITIONS FROM HUMAN CELLS AND METHODS FOR ANALYSIS AND MODIFICATION THEREOF

FIELD OF THE INVENTION

The invention describes methods for production of novel composition of glycans, glycomes, from human multipotent stem cells. The invention is further directed to methods for modifying the glycomes and analysis of the glycomes and the modified glycomes. Furthermore the invention is directed to stem cells carrying the modified glycomes on their surfaces.

The glycomes are preferably analysed by profiling methods able to detect reproducibly and quantitatively numerous individual glycan structures at the same time. The most preferred type of the profile is a mass spectrometric profile. The invention further describes uses of the methods for analytics and diagnostics. The methods are especially directed to analysis of glycan profiles from multipotent stem cells and effects of various reagents having effect on cell glycosylation. The present invention is specifically directed to analysis of specified N-glycan and O-glycan structure types as markers of the stem cells and further to uses of the analysed structures.

BACKGROUND OF THE INVENTION

Numerous methods have been developed for analysis of glycan structures mainly from purified proteins. These methods describe general technologies of N-glycan and O-glycan release, purification and analysis of the products by various methods including mass spectrometry. Usually exact analysis of material has required purification of specific glycans and numerous chemical and analytic methods.

The background further includes comparison of individual specific N- and O-glycans from healthy tissue and tissue affected by a disease. These methods do not show the possibility to produce mass spectrometric profiles, or quantitative data that allows comparison between samples comprising numerous components. The special purification methods of the present invention have not been described previously.

Molecular profiling methods have been described for proteins, peptides, and nucleic acids. Some of these methods use small tissue samples. The analytic conditions and sensitivity for protein and nucleic acid analytics is however very different from glycan sample analysis.

The present invention describes methods for production of free glycan mixtures from human stem cells. The novel method reveals a broad range of glycan structures observable by the novel analysis methods revealing numerous novel characteristic of special quantitative cell derived glycan compositions. The range of glycans from materials, which glycosylation is largely unknown, reveals large amount of useful information about the status. The invention shows effective very low scale purification methods allowing separation of glycans from various other cellular components.

BRIEF DESCRIPTION OF THE DRAWINGS

FIG. 26. Reference neutral N-glycan structures for NMR analysis (A-D).

FIG. 27. Reference acidic N-glycan structures for NMR analysis (A-E).

FIG. 38. Implications of hESC fucosyltransferase gene expression profile. A. hESC express three fucosyltransferase genes: FUT1, FUT4, and FUT8. B. The expression levels of FUT1 and FUT4 are increased in hESC compared to EB, which potentially leads to more complex fucosylation in hESC. Known fucosyltransferase glycan products are shown. Arrows indicate sites of glycan chain elongation. Asn indicates linkage to glycoprotein.

SUMMARY OF THE INVENTION

Figure 1:
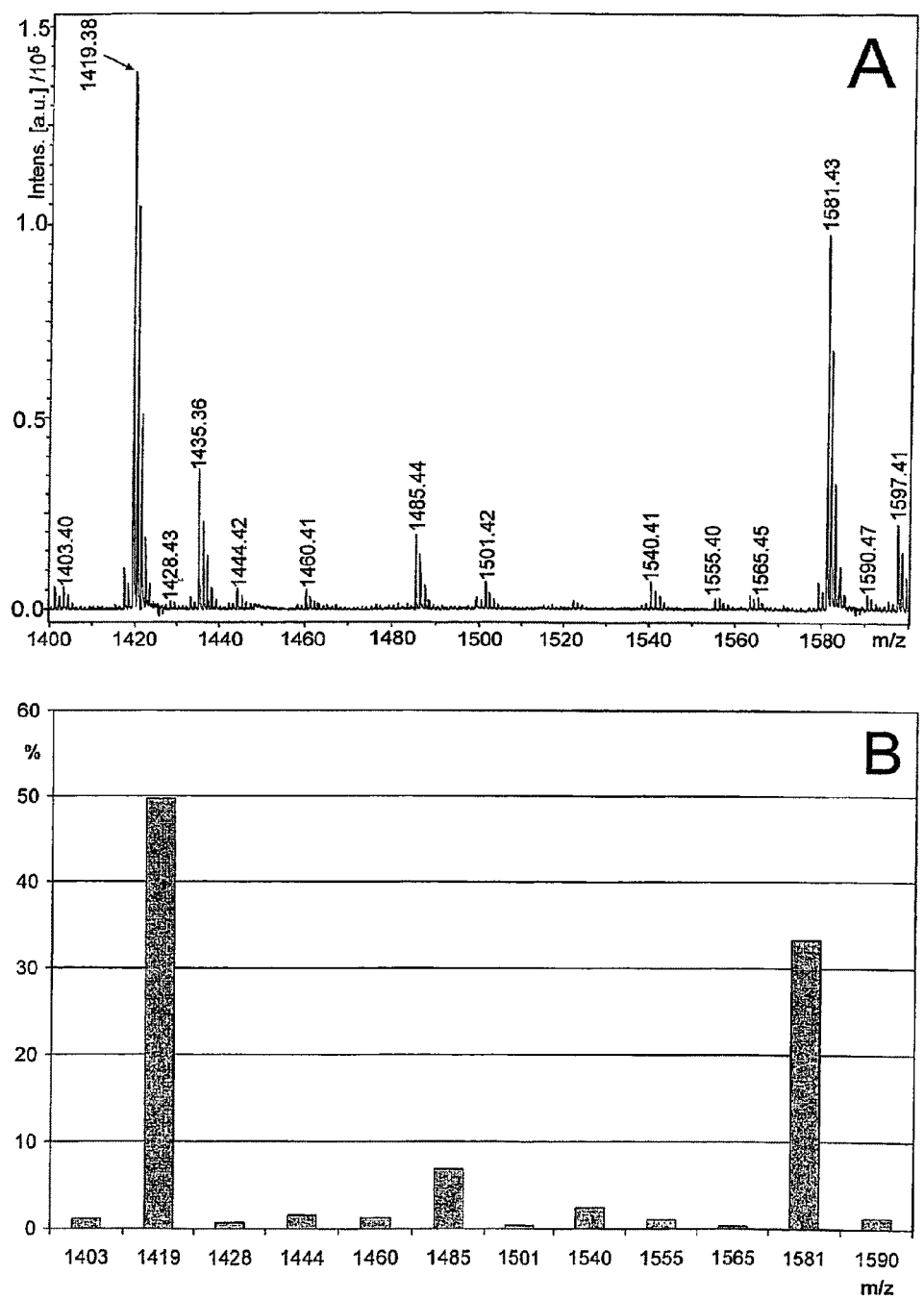
FIG. 1. Example of glycan signal analysis of MALDI-TOF mass spectrometric data. A. Mass spectrometric raw data showing a window of neutral N-glycan mass spectrum in positive ion mode, B. Glycan profile generated from the data in A.

The present invention is directed to production and analysis of broad glycan mixtures from stem cell samples.

The present invention is specifically directed to glycomes of stem cells according to the invention comprising glycan material with monosaccharide composition for each of glycan mass components according to the Formula I:

$$R_1 \text{Hex}\beta z\{R_3\}_{n1} \text{HexNAc} X y R_2 \tag{1}$$

wherein X is nothing or a glycosidically linked disaccharide epitope β4(Fucα6)$_n$GN, wherein
n is 0 or 1;
Hex is Gal or Man or GlcA;
HexNAc is GlcNAc or GalNAc;
y is anomeric linkage structure α and/or β or a linkage from a derivatized anomeric carbon,
z is linkage position 3 or 4, with the provision that when z is 4, then HexNAc is GlcNAc and Hex is Man or Hex is Gal or Hex is GlcA, and
when z is 3, then Hex is GlcA or Gal and HexNAc is GlcNAc or GalNAc;
$R_1$ indicates 1-4 natural type carbohydrate substituents linked to the core structures,
$R_2$ is reducing end hydroxyl, a chemical reducing end derivative or a natural asparagine linked N-glycoside derivative including asparagines, N-glycoside aminoacids and/or peptides derived from proteins, or a natural serine or threonine linked O-glycoside derivative including asparagines, N-glycoside aminoacids and/or peptides derived from proteins;
$R_3$ is nothing or a branching structure representing GlcNAcβ6 or an oligosaccharide with GlcNAcβ6 at its reducing end linked to GalNAc, when HexNAc is GalNAc, or $R_3$ is nothing or Fucα4, when Hex is Gal, HexNAc is GlcNAc, and z is 3, or $R_3$ is nothing or Fucα3, when z is 4.

Typical glycomes comprise of subgroups of glycans, including N-glycans, O-glycans, glycolipid glycans, and neutral and acidic subglycomes.

The preferred analysis method includes:
1) Preparing a stem cell sample containing glycans for the analysis
2) Releasing total glycans or total glycan groups from a stem cell sample, or extracting free glycans from a stem cell sample
3) Optionally modifying glycans
4) Purification of the glycan fraction/fractions from biological material of the sample
5) Optionally modifying glycans
6) Analysis of the composition of the released glycans preferably by mass spectrometry
7a) Optionally presenting the data about released glycans quantitatively and
7b) Comparing the quantitative data set with another data set from another stem cell sample
or
8) Comparing data about the released glycans quantitatively or qualitatively with data produced from another stem cell sample The invention is directed to diagnosis of clinical state of stem cell samples, based on analysis of glycans present in the samples. The invention is especially directed to diagnosing cancer and the clinical state of cancer, preferentially to differentiation between stem cells and cancerous cells and detection of cancerous changes in stem cell lines and preparations.

The invention is further directed to structural analysis of glycan mixtures present in stem cell samples.

DESCRIPTION OF THE INVENTION

Glycomes

Novel Glycan Mixtures from Stem Cells

The present invention revealed novel broad mixtures of glycans of different sizes from stem cells. The stem cells contain glycans ranging from small oligosaccharides to large complex structures. The analysis reveals compositions with substantial amounts of numerous components and structural types. Previously the total glycomes from these rare materials has not been available and nature of the releasable glycan mixtures, the glycomes, of stem cells has been unknown.

The invention revealed that the glycan structures on cell surfaces vary between the various populations of the early human cells, the preferred target cell populations according to the invention. It was revealed that the cell populations contained specifically increased "reporter structures".

The glycan structures on cell surfaces in general have been known to have numerous biological roles. Thus the knowledge about exact glycan mixtures from cell surfaces is important for knowledge about the status of cells. The invention revealed that multiple conditions (via changes in conditions or developmental state) affect the cells and cause changes in their glycomes.

Molecular Weight Distribution and Structure Groups of the Glycomes
Preferred Monosaccharide Compositions of the Glycomes
General Compositions The inventors were able to release or isolate various glycan fractions from stem cells, which are useful for the characterization of the cellular material. The glycans or major part thereof are released preferably from glycoproteins or glycolipids of human stem cells. The invention is specifically directed to such glycan fractions.

The glycan fractions of stem cells comprise typically multiple, at least about 10 "glycan mass components" typically corresponding at least ten glycans and in most cases clearly more than 10 glycan structures.

Glycan Mass Components and Corresponding Monosaccharide Compositions

The glycan mass components correspond to certain molecular weights observable by mass spectrometry and further correspond to specific monosaccharide composition or monosaccharide compositions. Each monosaccharide component is normally present in a glycan as glycosidically linked monosaccharide residue in the nonreducing end part of glycan and the reducing end monosaccharide may be in free alditol form or modified for example by reduction or conjugated to an reducing end modifying reagent well known in the art or to one, two or several amino acids in case of glycopeptides. Monosaccharide composition can be obtained from molecular mass in a mass spectrum (glycan mass component) after correcting potential effect of the ion forms observable by the specific mass spectrometry technologue such as protonation/deprotonation, $Na^+$, $K^+$, $Li^+$, or other adduct combinations, or isotope pattern derived effects. The monosaccharide compositions are calculated by fitting mixtures of individual monosaccharide (residue) masses and modification groups to corrected molecular mass of glycan mass component. Typically the molecular mass of fitting composition and the experimental mass correspond to each other very closely with similar first and even second decimals with optimal calibration.

The fitting may be further checked by measuring the experimental mass difference from the smaller and/or larger glycan mass component next in the putative biosynthetic series of a glycan type and comparing the difference with the exact molecular mass of corresponding monosaccharide unit (residue), typically the mass differences of fitting components in a good quality mass spectrum and with correct marking of peaks in decimals, preferably in second or third decimal of the mass number depending on the resolution of the specific mass spectrometric method. For optimal mass accuracy, an internal calibration may be used, where two or more known component's mass peaks are used to re-calculate masses for each components in the spectrum. Such calibration components are preferably selected among the most abundant glycan signals present in the glycan profiles, in the case of human or other animal cell derived glycan profiles most preferably selected among the most abundant glycan signals present in Figures described in the present invention.

The monosaccharide composition includes monosaccharide component names and number, typically as subscript, indicating how many of the individual mass components is present in the monosaccharide composition; and names of assigned modifying groups and numbers indicating their abundance.

It is further realized that the masses of glycan mass component may be obtained as exact monoisotopic mass of usually smallest isotope of the glycan mass component or as an average mass of the isotope distribution of the glycan mass component Exact mass is calculated form exact masses of individual mass components and average from masses average masses of individual mass components. Person skilled in art can recognize from the peak shapes (i.e. by the resolution obtained) in the mass spectrum whether to use monoisotopic or average masses to interpret the spectra. It is further realized that average and exact masses can be converted to each other when isotope abundances of molecules are known, typically natural abundance without enrichment of isotopes can be assumed, unless the material is deliberately labelled with radioactive or stable isotopes.

It is further realized that specific rounded mass numbers can be used as names for glycan mass components. The present invention uses preferably mass numbers rounded down from the exact mass of the monosaccharide composition (and usually observable or observed mass) to closest integer as names of glycan mass components.

The masses of glycan mass components are obtained by calculating molecular mass of individual monosaccharide components (Hex, HexNAc, dhex, sialic acids) from the known atom compositions (for example hexose (Hex) corresponds to $C_6H_{12}O_6$) and subtracting for water in case of monosaccharide residue, followed by calculating the sum of the monosaccharide components (and possible modifications such as $SO_3$ or $PO_3H$). It is further realized that molecular masses of glycans may be calculated from atomic compositions or any other suitable mass units corresponding molecular masses of these. The molecular masses and calculation thereof are known in the art and masses of monosaccharide components/residues are available in tables with multiple decimals from various sources.

It is further realized that many of the individual monosaccharide compositions described in the present invention further correspond to several isomeric individual glycans. In addition, there exist also monosaccharide compositions that have nearly equal masses, for example dHex2 and NeuAc monosaccharide residues that have nearly equal masses, and other examples can be presented by a person skilled in the art. It is realized that the ability to differentiate compositions with nearly equal masses depends on instrumentation, and the present method is especially directed to a possibility to select also such compositions in place of proposed compositions.

The preferred glycans in glycomes comprise at least two of following monosaccharide component residues selected from group: Hexoses (Hex) which are Gal, Glc and Man; N-acetylhexosamines (HexNAc) which are GlcNAc and GalNAc; pentose, which is Xyl; Hexuronic acids which are GlcA and IdoA; deoxyhexoses (dHex), which is fucose and sialic acids which are NeuAc and/NeuGc; and further modification groups such as acetate (Ac), sulphate and phosphate forming esters with the glycans. The monosaccharide residues are further grouped as major backbone monosaccharides including GlcNAc, HaxA, Man and Gal; and specific terminal modifying monosaccharide units Glc, GalNAc, Xyl and sialic acids.

Detection of Glycan Modifications

The present invention is directed to analyzing glycan components from biological samples, preferably as mass spectrometric signals. Specific glycan modifications can be detected among the detected signals by determined indicative signals as exemplified below. Modifications can also be detected by more specific methods such as chemical or physical methods, for example mass spectrometric fragmentation or glycosidase detection as disclosed in the present invention. In a preferred form of the present method, glycan signals are assigned to monosaccharide compositions based on the detected m/z ratios of the glycan signals, and the specific glycan modifications can be detected among the detected monosaccharide compositions.

In a further aspect of the present invention, relative molar abundances of glycan components are assigned based on their relative signal intensities detected in mass spectrometry as described in the Examples, which allows for quantification of glycan components with specific modifications in relation to other glycan components. The present method is also directed to detecting changes in relative amounts of specific modifications in cells at different time points to detect changes in cell glycan compositions.

Glycome Glycan Fraction Further Comprising Monosaccharides

The invention is specifically directed to glycan compositions, which further comprise at least one monosaccharide component in free form, preferably a preferred monosaccharide component described above. The monosaccharide comprising compositions are in a preferred embodiment derived from a cell material or released glycomes, which has been in contact with monosaccharide releasing chemicals or enzymes, preferably with exoglycosidase enzymes or chemicals such as oxidating reagents and/or acid, more preferably with a glycosidase enzyme. The invention is further directed to compositions comprising a specific preferred monosaccharide according to the invention, an exoglycosidase enzyme capable releasing all or part of the specific monosaccharide and an glycan composition according to the invention from which at least part of the terminal specific monosaccharide has been released.

Limit of Detection for Glycome Components

It is further realized that by increasing the sensitivity of detection the number of glycan mass components can be increased. The analysis according to the invention can be in most cases performed from major or significant components in the glycome mixture. The present invention is preferably directed to detection of glycan mass components from a high quality glycan preparation with optimised experimental condition, when the glycan mass components have abundance at least higher than 0.01% of total amount of glycan mass components, more preferably of glycan mass components of abundance at least higher than 0.05%, and most preferably at least higher than 0.10% are detected. The invention is further directed practical quality glycome compositions and analytic process directed to it, when glycan mass components of at least about 0.5%, of total amount of glycan mass components, more preferably of glycan mass components of abundance at least higher than 1.0%, even more preferably at least higher than 2.0%, most preferably at least higher than 4.0% (presenting lower range practical quality glycome), are detected. The invention is further directed to glycomes comprising preferred number of glycan mass components of at least the abundance of observable in high quality glycomes, and in another embodiment glycomes comprising preferred number of glycan mass components of at least the abundance of observable in practical quality glycomes.

Subglycomes Obtainable by Purification or Specific Release Method

It further realized that fractionation or differential specific release methods of glycans from glycoconjugates can be applied to produce subglycomes containing part of glycome.

The subglycomes produced by fractionation of glycomes are called "fractionated subglycomes".

The glycomes produced by specific release methods are "linkage-subglycomes". The invention is further directed to combinations of linkage-subglycomes and fractionated subglycomes to produce "fractionated linkage-subglycomes", for example preferred fractionated linkage-subglycomes includes neutral O-glycans, neutral N-glycans, acidic O-glycans, and acidic N-glycans, which were found very practical in characterising target material according to the invention.

The fractionation can be used to enrich components of low abundance. It is realized that enrichment would enhance the detection of rare components. The fractionation methods may be used for larger amounts of cell material. In a preferred embodiment the glycome is fractionated based on the molecular weight, charge or binding to carbohydrate binding agents.

These methods have been found useful for specific analysis of specific subglycomes and enrichment more rare components. The present invention is in a preferred embodiment directed to charge based separation of neutral and acidic glycans. This method gives for analysis method, preferably mass spectroscopy material of reduced complexity and it is useful for analysis as neutral molecules in positive mode mass spectrometry and negative mode mass spectrometry for acidic glycans.

Differential release methods may be applied to get separately linkage specific subglycomes such as O-glycan, N-glycan, glycolipid or proteoglycan comprising fractions or combinations thereof. Chemical and enzymatic methods are known for release of specific fractions, furthermore there are methods for simultaneous release of O-glycans and N-glycans.

Novel Complete Compositions

It is realized that at least part of the glycomes have novelty as novel compositions of very large amount of components. The glycomes comprising very broad range substances are referred as complete glycomes.

Preferably the composition is a complete composition comprising essentially all degrees of polymerisation in general from at least about disaccharides, more preferably from trisaccharides to at least about 25-mers in a high resolution case and at least to about 20-mers or at least about 15-mer in case of medium and practical quality preparations.

It is realized that especially the lower limit, but also upper limit of a subglycome depend on the type of subglycome and/or method used for its production. Different complete ranges may be produced in scope of general glycomes by fractionation, especially based on size of the molecules.

Novel Compositions with New Combinations of Subglycomes and Preferred Glycan Groups It is realized that several glycan types are present as novel glycome compositions produced from the stem cells. The invention is specifically directed to novel mixture composition comprising different subglycomes and preferred glycan groups Novel Quantitative Glycome Compositions It is realised that the glycome compositional as descried in examples represent quantitatively new data about glycomes from the preferred stem cell types. The proportions of various components cannot be derived from background data and are very useful for the analysis methods according to the invention. The invention is specifically directed to glycome compositions according to the examples when the glycan mass components are present in essentially similar relative amounts.

Preferred Composition Formulas

The present invention is specifically directed to glycomes of stem cells according to the invention comprising glycan material with monosaccharide composition for each of glycan mass components according to the Formula I:

$$NeuAc_m NeuGc_n Hex_o HexNAc_p dHex_q HexA_r Pen_s Ac_t ModX_x \qquad (I)$$

where m, n, o, p, q, r, s, t, and x are independent integers with values ≥0 and less than about 100,
with the proviso that
for each glycan mass components at least two of the backbone monosaccharide variables o, p, or r is greater than 0, and
ModX represents a modification (or N different modifications Mod1, Mod2, . . . , ModN), present in the composition in an amount of x (or in independent amounts of x1, x2, . . . , xN), Preferably examples of such modifications (Mod) including for example $SO_3$ or $PO_3H$ indicating esters of sulfate and phosphate, respectively
and the glycan composition is preferably derived from isolated human stem cells or preferred subpopulations thereof according to the invention.

It is realized that usually glycomes contain glycan material for which the variables are less much less than 100, but large figures may be obtained for polymeric material comprising glycomes with repeating polymer structures, for example ones comprising glycosaminoglycan type materials. It is further realized that abundance of the glycan mass components with variables more than 10 or 15 is in general very low and observation of the glycome components may require purification and enrichment of larger glycome components from large amounts of samples.

Broad Mass Range Glycomes

In a preferred embodiment the invention is directed to broad mass range glycomes comprising polymeric materials and rare individual components as indicated above. Observation of large molecular weight components may require enrichment of large molecular weight molecules comprising fraction. The broad general compositions according to the Formula I are as described above,
with the proviso that
m, n, o, p, q, r, s, t, and x are independent integers with preferable values between 0 and 50, with the proviso that for each glycan mass components at least two of o, p, or r is at least 1, and the sum of the monosaccharide variables; m, n, o, p, q, r, and s, indicating the degree of polymerization or oligomerization, for each glycan mass component is less than about 100 and the glycome comprises at least about 20 different glycans of at least disaccharides.

Practical Mass Range Glycomes

In a preferred embodiment the invention is directed to practical mass range and high quality glycomes comprising lower molecular weight ranges of polymeric material. The lower molecular weight materials at least in part and for preferred uses are observable by mass spectrometry without enrichment.

In a more preferred general composition according to the Formula I as described above, m, n, o, p, q, r, s, t, and x are independent integers with preferable values between 0 and about 20, more preferably between 0 and about 15, even more preferably between 0 and about 10, with the proviso that at least two of o, p, or r is at least 1,
and the sum of the monosaccharide variables; m, n, o, p, q, r, and s, indicating the degree of polymerization or oligomerization, for each glycan mass component is less than about 50 and more preferably less than about 30,
and the glycome comprises at least about 50 different glycans of at least trisaccharides.

In a preferred embodiment the invention is directed to practical mass range high quality glycomes which may comprise some lower molecular weight ranges of polymeric material. The lower molecular weight materials at least in part and for preferred uses are observable by mass spectrometry without enrichment.

In a more preferred general composition according to the Formula I as described above, m, n, o, p, q, r, s, t, and x are independent integers with preferable values between 0 and about 10, more preferably between 0 and about 9, even more preferably, between 0 and about 8, with the proviso that at least two of o, p, or r is at least 1,
and the sum of the monosaccharide variables; m, n, o, p, q, r, and s, indicating the degree of polymerization or oligomerization, for each glycan mass component is less than about 30 and more preferably less than about 25,
and the glycome comprises at least about 50 different glycans of at least trisaccharides.

The practical mass range glycomes may typically comprise tens of components, for example in positive ion mode MALDI-TOF mass spectrometry for neutral subglycomes it is usually possible to observe even more than 50 molecular mass components, even more than 100 mass component corresponding to much larger number of potentially isomeric glycans. The number of components detected depends on sample size and detection method.

Preferred Subglycomes

The present invention is specifically directed to subglycomes of stem cell glycomes according to the invention comprising glycan material with monosaccharide compositions for each of glycan mass components according to the Formula I and as defined for broad and practical mass range glycomes. Each subglycome has additional characteristics based on glycan core structures of linkage-glycomes or fractionation method used for the fractionated glycomes. The preferred linkage glycomes includes:
N-glycans, O-glycans, glycolipid glycans, neutral and acidic subglycomes, N-glycan Subglycome Protein N-glycosidase releases N-glycans comprising typically two N-acetylglycosamine units in the core, optionally a core linked fucose unit and typically then 2-3 hexoses (core mannoses), after which the structures may further comprise hexoses being mannose or in complex-type N-glycans further N-acetylglycosamines and optionally hexoses and sialic acids.

N-glycan subglycomes released by protein N-glycosidase comprise N-glycans containing N-glycan core structure and are releasable by protein N-glycosidase from cells.

The N-glycan core structure is Manβ4GlcNAcβ(Fucα6)$_n$4GlcNAc, wherein n is 0 or 1 and the N-glycan structures can be elongated from the Manβ4 with additional mannosyl residues. The protein N-glycosidase cleaves the reducing end GlcNAc from Asn in proteins. N-glycan subglycomes released by endo-type N-glycosidases cleaving between GlcNAc units contain Manβ4GlcNAcβ-core, and the N-glycan structures can be elongated from the Manβ4 with additional mannosyl residues.

In case the Subglycome and analysis representing it as Glycan profile is formed from N-glycans liberated by N-glycosidase enzyme, the preferred additional constraints for Formula I are:
p>0, more preferably 1≤p≤100, typically p is between 2 and about 20, but polymeric structures containing glycomes may comprise larger amounts of HexNAc and it is realised that in typical core of N-glycans indicating presence of at least partially complex type structure
when p≥3 it follows that o≥1.

Glycolipid Subglycome

In case the Subglycome and analysis representing it as Glycan profile is formed from lipid-linked glycans liberated by endoglycoceramidase enzyme, the preferred additional constraints for Formula I are:

o>0, more preferably 1≤o≤100, and
when p≥1 it follows that o≥2.

Typically glycolipids comprise two hexoses (a lactosyl residue) at the core. The degree of oligomerization in a usual practical glycome from glycolipids is under about 20 and more preferably under 10. Very large structures comprising glycolipids, polyglycosylceramides, may need enrichment for effective detection.

Neutral and Acidic Subglycomes

Most preferred fractionated Subglycomes includes 1) subglycome of neutral glycans and 2) subglycome of acidic glycans. The major acidic monosaccharide unit is in most cases a sialic acid, the acidic fraction may further comprise natural negatively charged structure/structures such as sulphate(s) and/phosphate(s).

In case the Subglycome and analysis representing it as Glycan profile is formed from sialylated glycans, the preferred additional constraints for Formula I are: (m+n)>0, more preferably 1≤(m+n)≤100.

Large amounts of sialic acid in a glycan mass component would indicate presence of polysailic acid type structures. Practical and high resolutions acidic glycomes usually have m+n values for individual major glycan mass components with preferred abundance between 1 and 10, more preferably and of the between 1-5 and most preferably between 14 for a usual glycomes according to the invention. For neutral glycans, (m+n)=0, and they do not contain negatively charged groups as above.

Preferred Structure Groups Observable in Glycome Profiles

The present invention is specifically directed to the glycomes of stem cell according to the invention comprising as major components at least one of structure groups selected from the groups described below.

Glycan Groups

According to the present invention, the Glycan signals are optionally organized into Glycan groups and Glycan group profiles based on analysis and classification of the assigned monosaccharide and modification compositions and the relative amounts of monosaccharide and modification units in the compositions, according to the following classification rules:

1° The glycan structures are described by the formulae:

$$Hex_m HexNAc_n dHex_o NeuAc_p NeuGc_q Pen_r Mod1_{sMod1} Mod2_{sMod2} \ldots ModX_{sModX},$$

wherein m, n, o, p, q, individual sMod, and X are each independent variables, and Mod is a functional group covalently linked to the glycan structure.

2° Glycan structures in general are classified as follows:
a. Structures (p,q=0) are classified as "non-sialylated",
b. Structures (p,q>0) are classified as "sialylated",
c. Structures (q>0) are classified as "NeuGc-containing",
d. Relation [2 (p+q): (m+n)] describes the general sialylation degree of a glycan structure,
e. In the case of mammalian glycans, structures (o=0) are classified as "non-fucosylated",
f. In the case of mammalian glycans, structures (o>0) are classified as "fucosylated",
g. Structures (Mod=Ac and sAc>0) are classified as 'acetylated',
h. Structures (Mod=SO$_3$ and sSO$_3$>0) are classified as 'sulfated', and
i. Structures (Mod=PO$_3$H and sPO$_3$H>0) are classified as 'phosphorylated'.

3° N-glycan glycan structures, generated e.g. by the action of peptide-N-glycosidases, are classified as follows:
a. Structures (n=2 and m>0 and p,q=0) are classified as "mannose-terminated N-glycans",
b. Structures (n=2 and m>5 and o,p,q=0) are classified as "high-mannose N-glycans",
c. Structures (n=2 and m>5 and o>0 and p,q=0) are classified as "fucosylated high-mannose N-glycans",
d. Structures (n=2 and 4≥m≥1 and p,q=0) are classified as "low-mannose N-glycans",
e. Structures (n=2 and 4≥m≥1 and o>0 and p,q=0) are classified as "fucosylated low-mannose N-glycans",
f. Structures (n=3 and m≥2) are classified as "hybrid-type or monoantennary N-glycans",
g. Structures (n≥4 and m≥3) are classified as "complex-type N-glycans",
h. Structures (n>m≥2) are classified as "N-glycans containing non-reducing terminal N-acetylhexosamine",
i. Structures (n=m≥5) are classified as "N-glycans potentially containing bisecting N-acetylglucosamine",
j. In the case of mammalian N-glycans, structures (o≥2) are classified as "N-glycans containing α2-, α3-, or α4-linked fucose",
k. Relation [2 (p+q): (m+n−5)] describes the "overall sialylation degree" of a sialylated N-glycan structure, and
l. Specifically, sum (p+q) describes the "sialylation degree" of a sialylated hybrid-type or monoantennary N-glycan structure.

4° Mucin-type O-glycan structures, generated e.g. by alkaline β-elimination, are classified as follows:
a. Structures (n=m), with (N=n=m), are classified as "Type N O-glycans",
b. More specifically, structures (n=m=1) are classified as "Type 1 O-glycans",
c. More specifically, structures (n=m=2) are classified as "Type 2 O-glycans",
d. More specifically, structures (n=m=3) are classified as "Type 3 O-glycans",
e. Relation [2 (p+q): (m+n)] describes the overall sialylation degree of a sialylated N-glycan structure, and
f. Specifically, relation [(p+q): N] describes the sialylation degree of a sialylated Type N O-glycan structure.

Lipid-linked can also be classified into structural groups based on their monosaccharide compositions, as adopted from the classifications above according to the invention.

For example, glycan signal corresponding to a human stem cell N-glycan structure:
$Hex_5 HexNAc_4 dHex_2 NeuAc_1 Ac_1$,
is classified as belonging to the following Glycan Groups:
sialylated (general sialylation degree: ⅔),
fucosylated,
acetylated,
complex-type N-glycans (overall sialylation degree: 0.5),
N-glycans containing α2-, α3-, or α4-linked fucose.

Glycomes Comprising Novel Glycan Types

The present invention revealed novel unexpected components among in the glycomes studied. The present invention is especially directed to glycomes comprising such unusual materials Preferred Glycome Types Derivatized Glycomes It is further realized that the glycans may be derivatized chemically during the process of release and isolation. Preferred modifications include modifications of the reducing end and or modifications directed especially to the hydroxyls- and/or N-atoms of the molecules. The reducing end modifications include modifications of reducing end of glycans involving known derivatization reactions, preferably reduction, glycosylamine, glycosylamide, oxime (aminooxy-) and reductive amination modifications. Most preferred modifications include modification of the reducing end. The derivatization of hydroxyl- and/or amine groups, such as produced by methylation or acetylation methods including permethylation and peracetylation has been found especially detrimental to the quantitative relation between natural glycome and the released glycome.

Non-Derivatized Released Glycomes

In a preferred embodiment the invention is directed to non-derivatized released glycomes. The benefit of the non-derivatized glycomes is that less processing needed for the production. The non-derivatized released glycomes correspond more exactly to the natural glycomes from which these are released. The present invention is further directed to quantitative purification according to the invention for the non-derivatized releases glycomes and analysis thereof.

The present invention is especially directed to released glycomes when the released glycome is not a permodified glycome such as permethylated glycome or peracetylated glycome. The released glycome is more preferably reducing end derivatized glycome or a non derivatized glycome, most preferably non-derivatized glycome.

Novel Cell Surface Glycomes and Released Glycomes of the Target Material

The present invention is further directed to novel total compositions of glycans or oligosaccharides referred as glycomes and in a more specific embodiment as released glycomes observed from or produced from the target material according to the invention. The released glycome indicates the total released glycans or total specific glycan subfractions released from the target material according to the invention. The present invention is specifically directed to released glycomes meaning glycans released from the target material according to the invention and to the methods according to the invention directed to the glycomes.

The present invention preferably directed to the glycomes released as truncated and/or non-truncated glycans and/or derivatized according to the invention.

The invention is especially directed to N-linked and/or O-linked and/or Lipid linked released glycomes from the target material according to the invention. The invention is more preferably directed to released glycomes comprising glycan structures according to the invention, preferably glycan structures as defined in formula I. The invention is more preferably directed to N-linked released glycomes comprising glycan structures according to the invention, preferably glycan structures as defined in formula I.

Non-Derivatized Released Cell Surface Glycomes and Production

In a preferred embodiment the invention is directed to non-derivatized released cell surface glycomes. The non-derivatized released cell surface glycomes correspond more exactly to the fractions of glycomes that are localized on the cell surfaces, and thus available for biological interactions. These cell surface localized glycans are of especial importance due to their availability for biological interactions as well as targets for reagents (e.g. antibodies, lectins etc. . . . ) targeting the cells or tissues of interest. The invention is further directed to release of the cell surface glycomes, preferably from intact cells by hydrolytic enzymes such as proteolytic enzymes, including proteinases and proteases, and/or glycan releasing enzymes, including endo-glycosidases or protein N-glycosidases. Preferably the surface glycoproteins are cleaved by proteinase such as trypsin and then glycans are analysed as glycopeptides or preferably released further by glycan releasing enzyme.

Analysis of the Glycomes

Analysis of the glycan mixtures by physical means, preferably by mass spectrometry The present invention is directed to analysis of glycan mixtures present in stem cell samples.

Quantitative and Qualitative Analysis of Glycan Profile Data

The invention is directed to novel methods for qualitative analysis of glycome data. The inventors noticed that there are specific components in glycomes according to the invention, the presence or absence of which are connected or associated with specific cell type or cell status. It is realized that qualitative comparison about the presence of absence of such signals are useful for glycome analysis. It is further realized that signals either present or absent that are derived from a general glycome analysis may be selected to more directed assay measuring only the qualitatively changing component or components optionally with a more common component or components useful for verification of data about the presence or absence of the qualitative signal.

The present invention is further specifically directed to quantitative analysis of glycan data from stem cell samples. The inventors noted that quantitative comparisons of the relative abundances of the glycome components reveal substantial differences about the glycomes useful for the analysis according to the invention.

Essential Steps of the Glycome Analysis

The process contains essential key steps which should be included in every process according to the present invention. The essential key steps of the analysis are:

1. Release of total glycans or total glycan groups from a stem cell sample
2. Purification of the glycan fraction/fractions from biological material of the sample, preferably by a small scale column array or an array of solid-phase extraction steps
3. Analysis of the composition of the released glycans, preferably by mass spectrometry In most cases it is useful to compare the data with control sample data. The control sample may be for example from a healthy tissue or cell type and the sample from same tissue altered by cancer or another disease. It is preferable to compare samples from same individual organism, preferably from the same human individual.

Specific Types of the Glycome Analysis

Comparative Analysis

The steps of a comparative analysis are:

1. Release of total glycans or total glycan groups from a cell sample
2. Purification of the glycan fraction/fractions from biological material of the sample, preferably by a small scale column array or an array of solid-phase extraction steps
3. Analysis of the composition of the released glycans, preferably by mass spectrometry
4. Comparing data about the released glycans quantitatively or qualitatively with data produced from another cell sample It may be useful to analyse the glycan structural motifs present in the sample, as well as their relative abundances. The ability to elucidate structural motifs results from the quantitative nature of the present analysis procedure, comparison of the data to data from previously analyzed samples, and knowledge of glycan biosynthesis.

Analysis Including Characterization of Structural Motives

The glycome analysis may include characterization of structural motives of released glycans. The structural motif analysis may be performed in combination with structural analysis. Preferred methods to reveal specific structural motifs include a) direct analysis of specific structural modifications of the treatment of glycans preferably by exo- or endoglycosidases and/or chemical modification or b) indirect analysis by analysis of correlating factors for the structural motives for such as mRNA-expression levels of glycosyltransferases or enzymes producing sugar donor molecules for glycosyltransferases.

The direct analyses are preferred as they are in general more effective and usually more quantitative methods, which can be combined to glycome analysis.

In a preferred embodiment the invention is directed to combination of analysis of structural motifs and glycome analysis.

The steps of a structural motif analysis are:
1. Release of total glycans or total glycan groups from a stem cell sample
2. Purification of the glycan fraction/fractions from biological material of the sample, preferably by a small scale column array or an array of solid-phase extraction steps
3. Analysis of the composition of the released glycans, preferably by mass spectrometry
4. Analysis of structural motifs present in of the glycan mixture, and optionally their relative abundancies
5. Optionally, comparing data about the glycan structural motifs with data produced from another stem cell sample The steps 3 and 4 may be combined or performed in order first 4 and then 3.

Preferred Detailed Glycome Analysis Including Quantitative Data Analysis

Detailed preferred glycome analysis according to the invention

More detailed preferred analysis method include following analysis steps:
1. Preparing a stem cell sample containing glycans for the analysis
2. Release total glycans or total glycan groups from a stem cell sample
3. Optionally modifying glycans or part of the glycans.
4. Purification of the glycan fraction/fractions from biological material and reagents of the sample by a small scale column array
5. Optionally modifying glycans and optionally purifying modified glycans
6. Analysis of the composition of the released glycans preferably by mass spectrometry using at least one mass spectrometric analysis method
7. a) Optionally presenting the data about released glycans quantitatively and
7. b) Comparing the quantitative data set with another data set from another stem cell sample
and/or alternatively to 7a) and 7b)
8. Comparing data about the released glycans quantitatively or qualitatively with data produced from another stem cell sample The present methods further allow the possibility to use part of the non-modified material or material modified in step 3 or 5 for additional modification step or step and optionally purified after modification step or steps, optionally combining modified samples, and analysis of additionally modified samples, and comparing results from differentially modified samples.

As mentioned above, It is realized that many of the individual monosaccharide compositions in a given glycome further corresponds to several isomeric individual glycans. The present methods allow for generation of modified glycomes. This is of particular use when modifications are used to reveal such information about glycomes of interest that is not directly available from a glycan profile alone (or glycome profiles to compare). Modifications can include selective removal of particular monosaccharides bound to the glycome by a defined glycosidic bond, by degradation by specific exoglycosidases or selective chemical degradation steps such as e.g. periodic acid oxidation. Modifications can also be introduced by using selective glycosyltransferase reactions to label the free acceptor structures in glycomes and thereby introduction of a specific mass label to such structures that can act as acceptors for the given enzyme. In preferred embodiment several of such modifications steps are combined and used to glycomes to be compared to gain further insights of glycomes and to facilitate their comparison.

Quantitative Presentation of Glycome Analysis

The present invention is specifically directed to quantitative presentation of glycome data.

Two-Dimensional Presentation by Quantitation and Component Indicators

The quantitative presentation means presenting quantitative signals of components of the glycome, preferably all major components of the glycome, as a two-dimensional presentation including preferably a single quantitative indicator presented together with component identifier.

The preferred two dimensional presentations includes tables and graphs presenting the two dimensional data The preferred tables list quantitative indicators in connection with, preferably beside or under or above the component identifiers, most preferably beside the identifier because in this format the data comprising usually large number of component identifier-quantitation indicator pairs.

Quantitation Indicator

The quantitation indicator is a value indicating the relative abundance of the single glycome component with regard to other components of total glycome or subglycome. The quantitation indicator can be directly derived from qualitative experimental data, or experimental data corrected to be quantitative.

Normalized Quantitation Indicator

The quantitation indicator is preferably a normalized quantitation indicator. The normalized quantitation indicator is defined as the experimental value of a single experimental quantitation indicator divided by total sum of quantitation indicators multiplied by a constant quantitation factor.

Preferred quantitation factors include integer numbers from 1-1000 0000 000, more preferably integer numbers 1, 10 or 100, and more preferably 1 or 100, most preferably 100. The quantitation number one is preferred as commonly understandable portion from 1 concept and the most preferred quantitation factor 100 corresponds to common concept of percent values.

The quantitation indicators in tables are preferably rounded to correspond to practical accuracy of the measurements from which the values are derived from. Preferred rounding includes 2-5 meaningful accuracy numbers, more preferably 24 numbers and most preferably 2-3 numbers.

Component Indicators

The preferred component indicators may be experimentally derived component indicators. Preferred components indicators in the context of mass spectrometric analysis includes mass numbers of the glycome components, monosaccharide or other chemical compositions of the components and abbreviation corresponding to thereof names of the molecules preferably selected from the group: descriptive names and abbreviations; chemical names, abbreviations and codes; and molecular formulas including graphic representations of the formulas. It is further realized that molecular mass based component indicators may include multiple isomeric structures. The invention is in a preferred embodiment directed to practical analysis using molecular mass based component indicators. In more specific embodiment the invention is further directed to chemical or enzymatic modification methods or indirect methods according to the invention in order to resolve all or part of the isomeric components corresponding to a molecular mass based component indicators.

Glycan Signals

The present invention is directed to a method of accurately defining the molecular masses of glycans present in a sample, and assigning monosaccharide compositions to the detected glycan signals.

The Glycan signals according to the present invention are glycan components characterized by:
1° mass-to-charge ratio (m/z) of the detected glycan ion,
2° molecular mass of the detected glycan component, and/or
3° monosaccharide composition proposed for the glycan component Glycan Profiles The present invention is further directed to a method of describing mass spectrometric raw data of Glycan signals as two-dimensional tables of:
1° monosaccharide composition, and
2° relative abundance,
which form the Glycan profiles according to the invention. Monosaccharide compositions are as described above. For obtaining relative abundance values for each Glycan signal, the raw data is recorded in such manner that the relative signal intensities of the glycan signals represent their relative molar proportions in the sample. Methods for relative quantitation in MALDI-TOF mass spectrometry of glycans are known in the art (Naven & Harvey, 19xx; Papac et al., 1996) and are described in the present invention. However, the relative signal intensities of each Glycan signal are preferably corrected by taking into account the potential artefacts caused by e.g. isotopic overlapping, alkali metal adduct overlapping, and other disturbances in the raw data, as described below.

By forming these Glycan profiles and using them instead of the raw data, analysis of the biological data carried by the Glycan profiles is improved, including for example the following operations:
1° identification of glycan signals present in the glycan profile,
2° comparison of glycan profiles obtained from different samples,
3° comparison of relative intensities of glycan signals within the glycan profile, and
4° organizing the glycan signals present in the glycan profile into subgroups or subprofiles.

Analysis of Associated Signals to Produce Single Quantitative Signal (Quantitation Indicator)

Analysis of Associated Signals: Isotope Correction

Glycan signals and their associated signals may have overlapping isotope patterns.

Overlapping of isotope patterns is corrected by calculating the experimental isotope patterns and subtracting overlapping isotope signals from the processed data.

Analysis of Associated Signals: Adduct Ion Correction in Positive Ion Mode

Glycan signals may be associated with signals arising from multiple adduct ions in positive ion mode, e.g. different alkali metal adduct ions. Different Glycan signals may give rise to adduct ions with similar m/z ratios: as an example, the adduct ions [Hex+Na]$^+$ and [dHex+K]$^+$ have m/z ratios of 203.05 and 203.03, respectively. Overlapping of adduct ions is corrected by calculating the experimental alkali metal adduct ion ratios in the sample and using them to correct the relative intensities of those Glycan signals that have overlapping adduct ions in the experimental data Preferably, the major adduct ion type is used for comparison of relative signal intensities of the Glycan signals, and the minor adduct ion types are removed from the processed data. The calculated proportions of minor adduct ion types are subtracted from the processed data Analysis of Associated Signals: Adduct Ion Correction in Negative Ion Mode Also in negative ion mode mass spectrometry, Glycan signals may be associated with signals arising from multiple adduct ions. Typically, this occurs with Glycan signals that correspond to multiple acidic group containing glycan structures. As an example, the adduct ions [NeuAc$_2$—H+Na]$^-$ at m/z 621.2 and [NeuAc$_2$-H+ K]$^-$ at m/z 637.1, are associated with the Glycan signal [NeuAc$_2$-H]$^-$ at m/z 599.2. These adduct ion signals are added to the Glycan signal and thereafter removed from the processed data In cases where different Glycan signals and adduct ion signals overlap, this is corrected by calculating the experimental alkali metal adduct ion ratios in the sample and using them to correct the relative intensities of those Glycan signals that have overlapping adduct ions in the experimental data.

Analysis of Associated Signals: Removal of Elimination Products

Glycan signals may be associated with signals, e.g. elimination of water (loss of $H_2O$), or lack of methyl ether or ester groups (effective loss of $CH_2$), resulting in experimental m/z values 18 or 14 mass units smaller than the Glycan signal, respectively. These signals are not treated as individual Glycan signals, but are instead treated as associated signals and removed from the processed data.

Classification of Glycan Signals into Glycan Groups

According to the present invention, the Glycan signals are optionally organized into Glycan groups and Glycan group profiles based on analysis and classification of the assigned monosaccharide and modification compositions and the relative amounts of monosaccharide and modification units in the compositions, according to the classification rules described above:

Generation of Glycan Group Profiles.

To generate Glycan group profiles, the proportions of individual Glycan signals belonging to each Glycan group are summed. The proportion of each Glycan group of the total Glycan signals equals its prevalence in the Glycan profile. The Glycan group profiles of two or more samples can be compared. The Glycan group profiles can be further analyzed by arranging Glycan groups into subprofiles, and analyzing the relative proportions of different Glycan groups in the subprofiles. Similarly formed subprofiles of two or more samples can be compared.

Specific Technical Aspects of Stem Cell Glycome Analysis

Preferred Sample Sizes

The present invention is especially useful when low sample amounts are available. Practical cellular or tissue material may be available for example for diagnostic only in very small amounts.

Sample Sizes for Preferred Pico-scale Preparation Methods

The inventors found surprisingly that glycan fraction could be produced and analysed effectively from samples containing low amount of material, for example 100 000-1 000 000 cells or a cubic millimeter (microliter) of the cells.

The combination of very challenging biological samples and very low amounts of samples forms another challenge for the present analytic method. The yield of the purification process must be very high. The estimated yields of the glycan fraction of the analytical processes according to the present invention varies between about 50% and 99%. Combined with effective removal of the contaminating various biological materials even more effectively over the wide preferred mass ranges according to the present invention show the ultimate performance of the method according to the present invention.

Isolation of Glycans and Glycan Fractions

The present invention is directed to a method of preparing an essentially unmodified glycan sample for analysis from the glycans present in a given sample.

A preferred glycan preparation process consists of the following steps:
1° isolating a glycan-containing fraction from the sample,
2° . . . Optionally purification the fraction to useful purity for glycome analysis The preferred isolation method is chosen according to the desired glycan fraction to be analyzed. The isolation method may be either one or a combination of the following methods, or other fractionation methods that yield fractions of the original sample:
1° extraction with water or other hydrophilic solvent, yielding water-soluble glycans or glycoconjugates such as free oligosaccharides or glycopeptides,
2° extraction with hydrophobic solvent, yielding hydrophilic glycoconjugates such as glycolipids,
3° N-glycosidase treatment, especially *Flavobacterium meningosepticum* N-glycosidase F treatment, yielding N-glycans,
4° alkaline treatment, such as mild (e.g. 0.1 M) sodium hydroxide or concentrated ammonia treatment, either with or without a reductive agent such as borohydride, in the former case in the presence of a protecting agent such as carbonate, yielding β-elimination products such as O-glycans and/or other elimination products such as N-glycans,
5° endoglycosidase treatment, such as endo-α-galactosidase treatment, especially *Escherichia freundii* endo-β-galactosidase treatment, yielding fragments from poly-N-acetyllactosamine glycan chains, or similar products according to the enzyme specificity, and/or
6° protease treatment, such as broad-range or specific protease treatment, especially trypsin treatment, yielding proteolytic fragments such as glycopeptides.

The released glycans are optionally divided into sialylated and non-sialylated subfractions and analyzed separately. According to the present invention, this is preferred for improved detection of neutral glycan components, especially when they are rare in the sample to be analyzed, and/or the amount or quality of the sample is low. Preferably, this glycan fractionation is accomplished by graphite chromatography.

According to the present invention, sialylated glycans are optionally modified in such manner that they are isolated together with the non-sialylated glycan fraction in the non-sialylated glycan specific isolation procedure described above, resulting in improved detection simultaneously to both non-sialylated and sialylated glycan components. Preferably, the modification is done before the non-sialylated glycan specific isolation procedure. Preferred modification processes include neuraminidase treatment and derivatization of the sialic acid carboxyl group, while preferred derivatization processes include amidation and esterification of the carboxyl group.

Glycan Release Methods

The preferred glycan release methods include, but are not limited to, the following methods:

Free glycans—extraction of free glycans with for example water or suitable water-solvent mixtures.

Protein-linked glycans including O- and N-linked glycans—alkaline elimination of protein-linked glycans, optionally with subsequent reduction of the liberated glycans.

Mucin-type and other Ser/Thr O-linked glycans—alkaline β-elimination of glycans, optionally with subsequent reduction of the liberated glycans.

N-glycans—enzymatic liberation, optionally with N-glycosidase enzymes including for example N-glycosidase F from *C. meningosepticum*, Endoglycosidase H from *Streptomyces*, or N-glycosidase A from almonds.

Lipid-linked glycans including glycosphingolipids—enzymatic liberation with endoglycoceramidase enzyme; chemical liberation; ozonolytic liberation.

Glycosaminoglycans—treatment with endo-glycosidase cleaving glycosaminoglycans such as chondroinases, chondroitin lyases, hyalurondases, heparanases, heparatinases, or keratanases/endo-beta-galactosidases; or use of O-glycan release methods for O-glycosidic Glycosaminoglycans; or N-glycan release methods for N-glycosidic glycosaminoglycans or use of enzymes cleaving specific glycosaminoglycan core structures; or specific chemical nitrous acid cleavage methods especially for amine/N-sulphate comprising glycosaminoglycans Glycan fragments—specific exo- or endoglycosidase enzymes including for example keratanase, endo-β-galactosidase, hyaluronidase, sialidase, or other exo- and endoglycosidase enzyme; chemical cleavage methods; physical methods Effective Purification Process The invention describes special purification methods for glycan mixtures from tissue samples. Previous glycan sample purification methods have required large amounts of material and involved often numerous chromatographic steps and even purification of specific proteins. It is known that protein glycosylation varies protein specifically and single protein specific data can thus not indicate the total tissue level glycosylation. Purification of single protein is a totally different task than purifying the glycan fraction according to the present invention.

When the purification starts from a tissue or cells, the old processes of prior art involve often laborious homogenisation steps affecting the quality of the material produced. The present purification directly from a biological sample such as cell or tissue material, involves only a few steps and allows quick purification directly from the biological material to analysis preferably by mass spectrometry.

Purification from Cellular Materials of Cells and/or Tissues

The cellular material contains various membranes, small metabolites, various ionic materials, lipids, peptides, proteins etc. All of the materials can prevent glycan analysis by mass spectrometry if these cannot be separated from the glycan fraction. Moreover, for example peptide or lipid materials may give rise to mass spectrometric signals within the preferred mass range within which glycans are analysed. Many mass spectrometric methods, including preferred MALDI-mass spectrometry for free glycan fractions, are more sensitive for peptides than glycans. With the MALDI method peptides in the sample may be analysed with approximately 1000-fold higher sensitivity in comparison to methods for glycans. Therefore the method according to the present invention should be able to remove for example potential peptide contaminations from free glycan fractions most effectively. The method should remove essential peptide contaminations from the whole preferred mass range to be analysed.

Purification Suitable for Mass Spectrometry, Especially MALDI-TOF Mass Spectometry The inventors discovered that the simple purification methods would separate released glycans from all possible cell materials so that 1) The sample is technically suitable for mass spectrometric analysis.

This includes two major properties,
a) the samples is soluble for preparation of mass spectrometry sample and
b) does not have negative interactions with chemicals involved in the mass spectrometric method, preferably the sample dries or crystallizes properly with matrix chemical used in MALDI-TOF mass spectrometry When using MALDI-technologies, the sample does not dry or crystallize properly if the sample contains harmful impurity material in a significant amount 2) The purity allows production of mass spectrum of suitable quality.
a) The sample has so low level of impurities that it gives mass spectrometric signals. Especially when using MALDI-TOF mass spectrometry, signals can be suppressed by background so that multiple components/peaks cannot be obtained.
b) the sample is purified so that there is no major impurity signals in the preferred mass ranges to be measured.

Preferably the present invention is directed to analysis of unusually small sample amounts. This provides a clear benefit over prior art, when there is small amount of sample available from a small region of diseased tissue or diagnostic sample such as tissue slice produced for microscopy or biopsy sample. Methods to achieve such purity (purity being a requirement for the sensitivity needed for such small sample amounts) from tissue or cell samples (or any other complex biological matices e.g. serum, saliva) has not been described in the prior art.

In a preferred embodiment the method includes use of non-derived glycans and avoiding general derived glycans. There are methods of producing glycan profiles including modification of all hydroxyl groups in the sample such as permethylation. Such processes require large sample amounts and produces chemical artefacts such as undermethylated molecules lowering the effectively of the method. These artefact peaks cover all minor signals in the spectra, and they can be misinterpreted as glycan structures. It is of importance to note that in glycome analyses the important profile to profile differences often reside in the minor signals. In a specific embodiment the present invention is directed to site specific modification of the glycans with effective chemical or enzyme reaction, preferably a quantitative reaction.

Preferred Analytical Technologies for Glycome Analysis
Mass Spectrometric Analysis of Glycomes The present invention is specifically directed to quantitative mass spectrometric methods for the analysis of glycomes. Most preferred mass spectrometric methods are MALDI-TOF mass spectrometry methods.

MALDI-TOF Analysis

The inventors were able to optimise MALDI-TOF mass spectrometry for glycome analysis.

The preferred mass spectrometric analysis process is MALDI-TOF mass spectrometry, where the relative signal intensities of the unmodified glycan signals represent their relative molar proportions in the sample, allowing relative quantification of both neutral (Naven & Harvey, 19xx) and sialylated (Papac et al., 1996) glycan signals. Preferred experimental conditions according to the present invention are described under Experimental procedures of Examples listed below.

Preferred Mass Ranges for MALDI-TOF Analysis and Released Non-modified Glycomes

For MALDI-TOF mass spectrometry of unmodified glycans in positive ion mode, optimal mass spectrometric data recording range according to the present invention is over m/z 200, more preferentially between m/z 200-10000, or even more preferably between m/z 200-4000 for improved data quality. In the most preferred form according to the present invention, the data is recorded between m/z 700-4000 for accurate relative quantification of glycan signals.

For MALDI-TOF mass spectrometry of unmodified glycans in negative ion mode, optimal mass spectrometric data recording range according to the present invention is over m/z 300, more preferentially between m/z 300-10000, or even more preferably between m/z 300-4000 for improved data quality. In the most preferred forms according to the present invention, the data is recorded between m/z 700-4000 or most preferably between m/z 800-4000 for accurate relative quantification of glycan signals.

Practical m/z-Ranges

The practical ranges comprising most of the important signals, as observed by the present invention may be more limited than these. Preferred practical ranges includes lower limit of about m/z 400, more preferably about m/z 500, and even more preferably about m/z 600, and most preferably m/z about 700 and upper limits of about m/z 4000, more preferably m/z about 3500 (especially for negative ion mode), even more preferably m/z about 3000 (especially for negative ion mode), and in particular at least about 2500 (negative or positive ion mode) and for positive ion mode to about m/z 2000 (for positive ion mode analysis). The preferred range depends on the sizes of the sample glycans, samples with high branching or polysaccharide content or high sialylation levels are preferably analysed in ranges containing higher upper limits as described for negative ion mode. The limits are preferably combined to form ranges of maximum and minimum sizes or lowest lower limit with lowest higher limit, and the other limits analogously in order of increasing size Preferred Analysis Modes for MALDI-TOF for Effective Glycome Analysis The inventors were able to show effective quantitative analysis in both negative and positive mode mass spectrometry.

Sample Handling

The inventors developed optimised sample handling process for preparation of the samples for MALDI-TOF mass spectrometry.

Glycan Purification

The glycan purification method according to the present invention consists of at least one of purification options, preferably in specific combinations described below, including the following purification options:

1) Precipitation-extraction;
2) Ion-exchange;
3) Hydrophobic interaction;
4) Hydrophilic interaction; and
5) Affinity to graphitized carbon.

1) Precipitation-extraction may include precipitation of glycans or precipitation of contaminants away from the glycans. Preferred precipitation methods include:

1. Glycan material precipitation, for example acetone precipitation of glycoproteins, oligosaccharides, glycopeptides, and glycans in aqueous acetone, preferentially ice-cold over 80% (v/v) aqueous acetone; optionally combined with extraction of glycans from the precipitate, and/or extraction of contaminating materials from the precipitate;
2. Protein precipitation, for example by organic solvents or trichloroacetic acid, optionally combined with extraction of glycans from the precipitate, and/or extraction of contaminating materials from the precipitate;
3. Precipitation of contaminating materials, for example precipitation with trichloroacetic acid or organic solvents such as aqueous methanol preferentially about ⅔ aqueous methanol for selective precipitation of proteins and other non-soluble materials while leaving glycans in solution;

2) Ion-exchange may include ion-exchange purification or enrichment of glycans or removal of contaminants away from the glycans. Preferred ion-exchange methods include:
1. Cation exchange, preferably for removal of contaminants such as salts, polypeptides, or other cationizable molecules from the glycans; and
2. Anion exchange, preferably either for enrichment of acidic glycans such as sialylated glycans or removal of charged contaminants from neutral glycans, and also preferably for separation of acidic and neutral glycans into different fractions.

3) Hydrophilic interaction may include purification or enrichment of glycans due to their hydrophilicity or specific adsorption to hydrophilic materials, or removal of contaminants such as salts away from the glycans. Preferred hydrophilic interaction methods include:
1. Hydrophilic interaction chromatography, preferably for purification or enrichment of glycans and/or glycopeptides;
2. Adsorption of glycans to cellulose in hydrophobic solvents for their purification or enrichment, preferably to microcrystalline cellulose, and even more preferably using an n-butanol:methanol:water or similar solvent system for adsorption and washing the adsorbed glycans, in most preferred system n-butanol:methanol:water in relative volumes of 10:1:2, and water or water:ethanol or similar solvent system for elution of purified glycans from cellulose.

4) Affinity to graphitized carbon may include purification or enrichment of glycans due to their affinity or specific adsorption to graphitized carbon, or removal of contaminants away from the glycans. Preferred graphitized carbon affinity methods includes porous graphitized carbon chromatography.

Preferred purification methods according to the invention include combinations of one or more purification options. Examples of the most preferred combinations include the following combinations:

1) For neutral underivatized glycan purification: 1. cation exchange of contaminants, 2. hydrophobic adsorption of contaminants, and 3. graphitized carbon affinity purification of glycans.

1) For sialylated underivatized glycan purification: 1. cation exchange of contaminants, 2. hydrophobic adsorption of contaminants, 3. adsorption of glycans to cellulose, and 4. graphitized carbon affinity purification of glycans.

NMR-Analysis of Glycomes

The present invention is directed to analysis of released glycomes by spectrometric method useful for characterization of the glycomes. The invention is directed to NMR spectroscopic analysis of the mixtures of released glycans. The inventors showed that it is possible to produce a released glycome from human stem cells in large scale enough and useful purity for NMR-analysis of the glycome.

In a preferred embodiment the NMR-analysis of the stem cell glycome is one dimensional proton NMR-analysis showing structural reporter groups of the major components in the glycome. The present invention is further directed to combination of the mass spectrometric and NMR analysis of stem cells.

Preferred Target Cell Populations and Types for Glycome Analysis According to the Invention Early Human Cell Populations Human Stem Cells And Multipotent Cells Under broadest embodiment the present invention is directed to all types of human stem cells, meaning fresh and cultured human stem cells. The stem cells according to the invention do not include traditional cancer cell lines, which may differentiate to resemble natural cells, but represent non-natural development, which is typically due to chromosomal alteration or viral transfection. Stem cells include all types of non-malignant multipotent cells capable of differentiating to other cell types. The stem cells have special capacity stay as stem cells after cell division, the self-renewal capacity.

Under the broadest embodiment for the human stem cells, the present invention describes novel special glycan profiles and novel analytics, reagents and other methods directed to the glycan profiles. The invention shows special differences in cell populations with regard to the novel glycan profiles of human stem cells.

The present invention is further directed to the novel structures and related inventions with regard to the preferred cell populations according to the invention. The present invention is further directed to specific glycan structures, especially terminal epitopes, with regard to specific preferred cell population for which the structures are new.

Preferred Types of Early Human Cells

The invention is directed to specific types of early human cells based on the tissue origin of the cells and/or their differentiation status.

The present invention is specifically directed to early human cell populations meaning multipotent cells and cell populations derived thereof based on origins of the cells including the age of donor individual and tissue type from which the cells are derived, including preferred cord blood as well as bone marrow from older individuals or adults. Preferred differentiation status based classification includes preferably "solid tissue progenitor" cells, more preferably "mesenchymal-stem cells", or cells differentiating to solid tissues or capable of differentiating to cells of either ectodermal, mesodermal, or endodermal, more preferentially to mesenchymal stem cells.

The invention is further directed to classification of the early human cells based on the status with regard to cell culture and to two major types of cell material. The present invention is preferably directed to two major cell material types of early human cells including fresh, frozen and cultured cells.

Cord Blood Cells, Embryonal-type Cells and Bone Marrow Cells

The present invention is specifically directed to early human cell populations meaning multipotent cells and cell populations derived thereof based on the origin of the cells including the age of donor individual and tissue type from which the cells are derived.
 a) from early age-cells such 1) as neonatal human, directed preferably to cord blood and related material, and 2) embryonal cell-type material
 b) from stem and progenitor cells from older individuals (non-neonatal, preferably adult), preferably derived from human "blood related tissues" comprising, preferably bone marrow cells.

Cells Differentiating to Solid Tissues, Preferably to Mesenchymal Stem Cells

The invention is specifically under a preferred embodiment directed to cells, which are capable of differentiating to non-hematopoietic tissues, referred as "solid tissue progenitors", meaning to cells differentiating to cells other than blood cells. More preferably the cell population produced for differentiation to solid tissue are "mesenchymal-type cells", which are multipotent cells capable of effectively differentiating to cells of mesodermal origin, more preferably mesenchymal stem cells.

Most of the prior art is directed to hematopoietic cells with characteristics quite different from the mesenchymal-type cells and mesenchymal stem cells according to the invention.

Preferred solid tissue progenitors according to the invention includes selected multipotent cell populations of cord blood, mesenchymal stem cells cultured from cord blood, mesenchymal stem cells cultured/obtained from bone marrow and embryonal-type cells. In a more specific embodiment the preferred solid tissue progenitor cells are mesenchymal stem cells, more preferably "blood related mesenchymal cells", even more preferably mesenchymal stem cells derived from bone marrow or cord blood.

Under a specific embodiment CD34+ cells as a more hematopoietic stem cell type of cord blood or CD34+ cells in general are excluded from the solid tissue progenitor cells.

Fresh and Cultured Cells
Fresh Cells

The invention is especially directed to fresh cells from healthy individuals, preferably non-modulated cells, and non-manipulated cells.

The invention is in a preferred embodiment directed to "fresh cells" meaning cells isolated from donor and not cultivated in a cell culture. It is realized by the invention that the current cell culture procedures change the status of the cells. The invention is specifically directed to analysis of fresh cell population because the fresh cells corresponding closely to the actual status of the individual donor with regard to the cell material and potential fresh cell population are useful for direct transplantation therapy or are potential raw material for production of further cell materials.

The inventors were able to show differences in the preferred fresh cell populations derived from early human cells, most preferably from cord blood cells. The inventors were able to produce especially "homogenous cell populations" from human cord blood, which are especially preferred with various aspects of present invention. The invention is further directed to specific aspects of present invention with regard to cell purification processes for fresh cells, especially analysis of potential contaminations and analysis thereof during the purification of cells.

In a more preferred embodiment the fresh cells are materials related to/derived from healthy individuals. The healthy individual means that the person is not under treatment of cancer, because such treatment would effectively change the status of the cells, in another preferred embodiment the healthy person is receiving treatment of any other major disease including other conditions which would change the status of the cells.

It is realized that in some cases fresh cells may be needed to be produced for example for cell transplantation to a cancer patient using cells previously harvested from such a patient, under a separate embodiment the present invention is further directed to analysis of and other aspects of invention with regard to such cell material.

Non-Modulated Cells

Even more preferably the fresh cells are "non-modulated cells" meaning that the cells have not been modulated in vivo by treatments affecting growth factor or cytokine release. For example stem cells may be released to peripheral blood by growth factors such as CSF (colony stimulating growth factor). Such treatment is considered to alter the status of cells from preferred fresh cells. The modulation may cause permanent changes in all or part of the cells, especially by causing differentiation.

Non-Manipulated Cells

Even more preferably the fresh cells are "non-manipulated cells" meaning that the cells have not been manipulated by treatments permanently altering the status of the cells, the permanent manipulation including alterations of the genetic structure of the cells. The manipulations include gene transfection, viral transduction and induction of mutations for example by radiation or by chemicals affecting the genetic structures of the cells.

Limited Fresh Cells Excluding Certain Specifically Selected Hematopoietic Stem Cell Populations A more preferred limited group of fresh cells is directed to especially to effectively solid tissue forming cells and their precursors. Under specific embodiment this group does not include specifically selected more hematopoietic stem cell like cell populations such as a) cell population selected as CD34+ cells from peripheral blood or bone marrow and b) in another limited embodiment also total bone marrow and peripheral blood mononuclear cells are excluded.

It is realized that the fresh cell populations may comprise in part same cells as CD34+ when the cells are not selected with regard to that marker. It is realized that exact cell population selected with regard to the marker are not preferred according to the invention as solid tissue forming cells.

Another limited embodiment excludes specifically selected CD34+ cell populations from cord blood and/or total mononuclear cells from cord blood. The invention is further directed to limited fresh cell populations when all CD34+ cell populations and/or all total cell populations of peripheral blood, bone marrow and cord blood are excluded. The invention is further directed to the limited fresh cell populations when CD34+ cell population were excluded, and when both CD34+ cell populations and all the three total cell populations mentioned above are excluded.

Cultured Cells

The inventors found specific glycan structures in early human cells, and preferred subpopulations thereof according to the invention when the cells are cultured. Certain specific structures according to the invention were revealed especially for cultured cells, and special alterations of the specific glycans according to the invention were revealed in cultured cell populations.

The invention revealed special cell culture related reagents, methods and analytics that can be used when there is risk for by potentially harmful carbohydrate contaminations during the cell culture process.

Cultured Modulated Cells

It is further realized that the cultured cells may be modulated in order to enhance cell proliferation. Under specific embodiment the present invention is directed to the analysis and other aspects of the invention for cultured "modulated cells", meaning cells that are modulated by the action of cytokines and/or growth factors. The inventors note that part of the early changes in cultured cells are related to certain extent to the modulation.

The present invention is preferably directed to cultured cells, when these are non-manipulated. The invention is further directed to observation of changes induced by manipulation in cell populations especially when these are non-intentionally induced by environmental factors, such as environmental radiation and potential harmful metabolites accumulating to cell preparations.

Preferred Types of Cultured Cells

The present invention is specifically directed to cultured solid tissue progenitors as preferred cultured cells. More preferably the present invention is directed to mesenchymal-type cells and embryonal-type cells as preferred cell types for cultivation. Even more preferred mesenchymal-type cells are mesenchymal stem cells, more preferably mesenchymal stem cells derived from cord blood or bone marrow.

Under separate embodiment the invention is further directed to cultured hematopoietic stem cells as a preferred group of cultured cells.

Subgroup of Multipotent Cultured Cells

The present invention is especially directed to cultured multipotent cells and cell populations. The preferred multipotent cultured cell means various multipotent cell populations enriched in cell cultures. The inventors were able to reveal special characteristics of the stem cell type cell populations grown artificially. The multipotent cells according to the invention are preferably human stem cells.

Cultured Mesenchymal Stem Cells

The present invention is especially directed to mesenchymal stem cells. The most preferred types of mesenchymal stem cells are derived from blood related tissues, referred as "blood-related mesenchymal cells", most preferably human blood or blood forming tissue, most preferably from human cord blood or human bone marrow or in a separate embodiment are derived from embryonal type cells. Mesenchymal stem cells derived from cord blood and from bone marrow are preferred separately.

Cultured Embryonal-Type Cells and Cell Populations

The inventors were able to reveal specific glycosylation nature of cultured embryonal-type cells according to the invention. The present invention is specifically directed to various embryonal type cells as preferred cultivated cells with regard to the present invention.

Early Blood Cell Populations and Corresponding Mesenchymal Stem Cells

Cord Blood

The early blood cell populations include blood cell materials enriched with multipotent cells.

The preferred early blood cell populations include peripheral blood cells enriched with regard to multipotent cells, bone marrow blood cells, and cord blood cells. In a preferred embodiment the present invention is directed to mesenchymal stem cells derived from early blood or early blood derived cell populations, preferably to the analysis of the cell populations.

Bone Marrow

Another separately preferred group of early blood cells is bone marrow blood cells. These cell do also comprise multipotent cells. In a preferred embodiment the present invention is directed to directed to mesenchymal stem cells derived from bone marrow cell populations, preferably to the analysis of the cell populations.

Preferred Subpopulations of Early Human Blood Cells

The present invention is specifically directed to subpopulations of early human cells. In a preferred embodiment the subpopulations are produced by selection by an antibody and in another embodiment by cell culture favouring a specific cell type. In a preferred embodiment the cells are produced by an antibody selection method preferably from early blood cells. Preferably the early human blood cells are cord blood cells.

The CD34 positive cell population is relatively large and heterogenous. It is not optimal for several applications aiming to produce specific cell products. The present invention is preferably directed to specifically selected non-CD34 populations meaning cells not selected for binding to the CD34-marker, called homogenous cell populations. The homogenous cell populations may be of smaller size mononuclear cell populations for example with size corresponding to CD133+ cell populations and being smaller than specifically selected CD34+ cell populations. It is further realized that preferred homogenous subpopulations of early human cells may be larger than CD34+ cell populations.

The homogenous cell population may a subpopulation of CD34+ cell population, in preferred embodiment it is specifically a CD133+ cell population or CD133-type cell population. The "CD133-type cell populations" according to the invention are similar to the CD133+ cell populations, but preferably selected with regard to another marker than CD133. The marker is preferably a CD133-coexpressed marker. In a preferred embodiment the invention is directed to CD133+ cell population or CD133+ subpopulation as CD133-type cell populations. It is realized that the preferred homogeneous cell populations further includes other cell populations than which can be defined as special CD133-type cells.

Preferably the homogenous cell populations are selected by binding a specific binder to a cell surface marker of the cell population. In a preferred embodiment the homogenous cells are selected by a cell surface marker having lower correlation with CD34-marker and higher correlation with CD133 on cell surfaces. Preferred cell surface markers include α3-sialylated structures according to the present invention enriched in CD133-type cells. Pure, preferably complete, CD133+ cell population are preferred for the analysis according to the present invention.

The present invention is directed to essential mRNA-expression markers, which would allow analysis or recognition of the cell populations from pure cord blood derived material. The present invention is specifically directed to markers specifically expressed on early human cord blood cells.

The present invention is in a preferred embodiment directed to native cells, meaning non-genetically modified cells. Genetic modifications are known to alter cells and background from modified cells. The present invention further directed in a preferred embodiment to fresh non-cultivated cells.

The invention is directed to use of the markers for analysis of cells of special differentiation capacity, the cells being preferably human blood cells or more preferably human cord blood cells.

Preferred Purities of the Cell Populations

The preferred purity depends of the affinity of the antibody used. For purification using commercial CD34-antibody preferred purity of complete cell population is at least 90%, more preferably at least 93%, and most preferably at least 95%. In a purification process according to invention by anti-CD133 antibody preferred purity of complete cell population is at least 90%, more preferably at least 93%, and most preferably at least 95%.

The present invention is directed to complete cell populations from human early blood with purity of at least at least 85%, more preferably at least 90%, even more preferably with increasing preference 91%, 92%, 93%, 94%, 95% respectively and most preferably with increasing preference at least 95%, 96%, 97% or 98%. In a specific embodiment the present invention is directed to ultrapure complete cell population in which the level of impurities is less than 10%, more preferably less than 5% and most preferably less than 3%. The innovation is specifically directed to complete cell populations purified by anti CD34 and anti-CD133 antibodies.

In a specific embodiment the present invention is directed to highly purified human complete CD133+ and CD 34+ cell populations derived from cord blood Preferred Cord Blood Cell Populations and Characteristics
Cord Blood Cell Populations Preferred cord blood cell populations according to the invention include total mononuclear cells and subpopulations thereof from cord blood. The present invention is further directed to enriched multipotent cells from cord blood. In a preferred embodiment the enriched cells are CD133+ cells, Lin− (lineage negative) cells, or CD34+ cells from cord blood, even more preferably the enriched cells are CD133+ cells, or Lin− (lineage negative) cells.

In a preferred embodiment the present invention is directed to mesenchymal stem cells derived from cord blood or cord blood derived cell populations and analysis thereof according to the invention. A preferred group of mesenchymal stem cells derived from cord blood is mesenchymal stem cells differentiating into cells forming soft tissues such as adipose tissue.

Preferred Purity of Reproducibly Highly Purified Mononuclear Complete Cell Populations from Human Cord Blood The present invention is specifically directed to production of purified cell populations from human cord blood. As described above, production of highly purified complete cell preparations from human cord blood has been a problem in the field. In the broadest embodiment the invention is directed to biological equivalents of human cord blood according to the invention, when these would comprise similar markers and which would yield similar cell populations when separated similarly as the CD133+ cell population and equivalents according to the invention or when cells equivalent to the cord blood is contained in a sample further comprising other cell types. It is realized that characteristics similar to the cord blood can be at least partially present before the birth of a human. The inventors found out that it is possible to produce highly purified cell populations from early human cells with purity useful for exact analysis of sialylated glycans and related markers.

Preferred Bone Marrow Cells

The present invention is directed to multipotent cell populations or early human blood cells from human bone marrow. Most preferred are bone marrow derived mesenchymal stem cells. In a preferred embodiment the invention is directed to mesenchymal stem cells differentiating to cells of structural support function such as bone and/or cartilage.

Embryonal-Type Cell Populations

The present invention is specifically directed to methods directed to embryonal-type cell populations, preferably when the use does not involve commercial or industrial use of human embryos nor involve destruction of human embryos. The invention is under a specific embodiment directed to use of embryonal cells and embryo derived materials such as embryonal stem cells, whenever or wherever it is legally acceptable. It is realized that the legislation varies between countries and regions.

The present invention is further directed to use of embryonal-related, discarded or spontaneously damaged material, which would not be viable as human embryo and cannot be considered as a human embryo. In yet another embodiment the present invention is directed to use of accidentally damaged embryonal material, which would not be viable as human embryo and cannot be considered as human embryo.

It is further realized that early human blood derived from human cord or placenta after birth and removal of the cord during normal delivery process is ethically uncontroversial discarded material, forming no part of human being.

The invention is further directed to cell materials equivalent to the cell materials according to the invention. It is further realized that functionally and even biologically similar cells may be obtained by artificial methods including cloning technologies.

Mesenchymal Multipotent Cells

The present invention is further directed to mesenchymal stem cells or multipotent cells as preferred cell population according to the invention. The preferred mesenchymal stem cells include cells derived from early human cells, preferably human cord blood or from human bone marrow. In a preferred embodiment the invention is directed to mesenchymal stem cells differentiating to cells of structural support function such as bone and/or cartilage, or to cells forming soft tissues such as adipose tissue.

Product by Process

The present invention is specifically directed to the glycan fraction produced according to the present invention from the pico scale stem cell sample according to the present invention. The preferred glycan fraction is essentially devoid of signals of contaminating molecules within the preferred mass range when analysed by MALDI mass spectrometry according to the present invention.

The glycome products from stem cells according to present invention are produced preferably directly from complete human stem cells or membrane fractions thereof, more preferably directly from intact cells as effectively shown in examples. In another preferred embodiment the glycome fractions are cell surface glycomes and produced directly from surfaces of complete human stem cells, preferably intact or essentially intact human stem cells according to the invention. In another embodiment the glycome products according to the invention are produced directly from membrane fraction Preferred Uses of Glycomes and Analysis Thereof with Regard to Status of Cells
Search of Novel of Novel Carbohydrate Marker Structures It is further realized that the analysis of glycome is useful for search of most effectively altering glycan structures in the early human cells for analysis by other methods. The glycome component identified by glycome analysis according to the invention can be further analysed/verified by known methods such as chemical and/or glycosidase enzymatic degradation(s) and further mass spectrometric analysis and by fragmentation mass apectrometry, the glycan component can be produced in larger scale by know chromatographic methods and structure can be verified by NMR-spectroscopy.

The other methods would preferably include binding assay using specific labelled carbohydrate binding agents including especially carbohydrate binding proteins (lectins, antibodies, enzymes and engineered proteins with carbohydrate binding activity) and other chemicals such as peptides or aptamers aimed for carbohydrate binding. It is realized that the novel marker structure can be used for analysis of cells, cell status and possible effects of contaminates to cell with similar indicative value as specific signals of the glycan mass components in glycome analysis by mass spectrometry according to the invention.

The invention is especially directed to search of novel carbohydrate marker structures from cell surfaces, preferably by using cell surface profiling methods. The cell surface carbohydrate marker structures would be further preferred for the analysis and/or sorting of cells.

Control of Cell Status and Potential Contaminations by Glycosylation Analysis

Control of Cell Status

Contamination/Harmful Effect Due to Nature of Raw Material for Producing a Cell Population Species specific, tissue specific, and individual specific differences in glycan structures are known. The difference between the origin of the cell material and the potential recipient of transplanted material may cause for example immunologic or allergic problems due to glycosylation differences. It is further noticed that culture of cells may cause changes in glycosylation. When considering human derived cell materials according to the present invention, individual specific differences in glycosylation are a potent source of harmful effects.

Control of Raw Material Cell Population

The present invention is directed to control of glycosylation of cell populations to be used in therapy.

The present invention is specifically directed to control of glycosylation of cell materials, preferably when 1) there is difference between the origin of the cell material and the potential recipient of transplanted material. In a preferred embodiment there are potential inter-individual specific differences between the donor of cell material and the recipient of the cell material. In a preferred embodiment the invention is directed to animal or human, more preferably human specific, individual person specific glycosylation differences. The individual specific differences are preferably present in mononuclear cell populations of early human cells, early human blood cells and embryonal type cells. The invention is preferably not directed to observation of known individual specific differences such as blood group antigens changes on erythrocytes.

2) There is possibility in variation due to disease specific variation in the materials. The present invention is specifically directed to search of glycosylation differences in the early cell populations according to the present invention associated with infectious disease, inflammatory disease, or malignant disease. Part of the inventors have analysed numerous cancers and tumors and observed similar types glycosylations as certain glycosylation types in the early cells.

3) There is for a possibility of specific inter-individual biological differences in the animals, preferably humans, from which the cell are derived for example in relation to species, strain, population, isolated population, or race specific differences in the cell materials.

4) When it has been established that a certain cell population can be used for a cell therapy application, glycan analysis can be used to control that the cell population has the same characteristics as a cell population known to be useful in a clinical setting.

Time Dependent Changes During Cultivation of Cells

Furthermore during long term cultivation of cells spontaneous mutations may be caused in cultivated cell materials. It is noted that mutations in cultivated cell lines often cause harmful defects on glycosylation level.

It is further noticed that cultivation of cells may cause changes in glycosylation. It is realized that minor changes in any parameter of cell cultivation including quality and concentrations of various biological organic and inorganic molecules, any physical condition such as temperature, cell density, or level of mixing may cause difference in cell materials and glycosylation. The present invention is directed to monitoring glycosylation changes according to the present invention in order to observe change of cell status caused by any cell culture parameter affecting the cells.

The present invention is in a preferred embodiment directed to analysis of glycosylation changes when the density of cells is altered. The inventors noticed that This has a major impact of the glycosylation during cell culture.

It is further realized that if there is limitations in genetic or differentiation stability of cells, these would increase probability for changes in glycan structures. Cell populations in early stage of differentiation have potential to produce different cell populations. The present inventors were able to discover glycosylation changes in early human cell populations.

Differentiation of Cell Lines

The present invention is specifically directed to observe glycosylation changes according to the present invention when differentiation of a cell line is observed. In a preferred embodiment the invention is directed to methods for observation of differentiation from early human cell or another preferred cell type according to the present invention to mesodermal types of stem cell In case there is heterogeneity in cell material this may cause observable changes or harmful effects in glycosylation. Furthermore, the changes in carbohydrate structures, even non-harmful or functionally unknown, can be used to obtain information about the exact genetic status of the cells.

The present invention is specifically directed to the analysis of changes of glycosylation, preferably changes in glycan profiles, individual glycan signals, and/or relative abundancies of individual glycans or glycan groups according to the present invention in order to observe changes of cell status during cell cultivation.

Analysis of Supporting/feeder Cell Lines

The present invention is specifically directed to observe glycosylation differences according to the present invention, on supporting/feeder cells used in cultivation of stem cells and early human cells or other preferred cell type. It is known in the art that some cells have superior activities to act as a support/feeder cells than other cells. In a preferred embodiment the invention is directed to methods for observation of differences on glycosylation on these supporting/feeder cells. This information can be used in design of novel reagents to support the growth of the stem cells and early human cells or other preferred cell type.

Contaminations or Alterations in Cells Due to Process Conditions

Conditions and Reagents Inducing Harmful Glycosylation or Harmful Glycosylation Related Effects to Cells During Cell Handling The inventors further revealed conditions and reagents inducing harmful glycans to be expressed by cells with same associated problems as the contaminating glycans. The inventors found out that several reagents used in a regular cell purification processes caused changes in early human cell materials.

It is realized, that the materials during cell handling may affect the glycosylation of cell materials. This may be based on the adhesion, adsorption, or metabolic accumulation of the structure in cells under processing.

In a preferred embodiment the cell handling reagents are tested with regard to the presence glycan component being antigenic or harmful structure such as cell surface NeuGc, Neu-O-Ac or mannose structure. The testing is especially preferred for human early cell populations and preferred subpopulations thereof.

The inventors note effects of various effector molecules in cell culture on the glycans expressed by the cells if absorption or metabolic transfer of the carbohydrate structures have not been performed. The effectors typically mediate a signal to cell for example through binding a cell surface receptor.

The effector molecules include various cytokines, growth factors, and their signalling molecules and co-receptors. The effector molecules may be also carbohydrates or carbohydrate binding proteins such as lectins.

Controlled Cell Isolation/purification and Culture Conditions to Avoid Contaminations with Harmful Glycans or other Alteration In Glycome Level Stress Caused by Cell Handling It is realized that cell handling including isolation/purification, and handling in context of cell storage and cell culture processes are not natural conditions for cells and cause physical and chemical stress for cells. The present invention allows control of potential changes caused by the stress. The control may be combined by regular methods may be combined with regular checking of cell viability or the intactness of cell structures by other means.

Examples of Physical and/or Chemical Stress in Cell Handling Step

Washing and centrifuging cells cause physical stress which may break or harm cell membrane structures. Cell purifications and separations or analysis under non-physiological flow conditions also expose cells to certain non-physiological stress. Cell storage processes and cell preservation and handling at lower temperatures affects the membrane structure. All handling steps involving change of composition of media or other solution, especially washing solutions around the cells affect the cells for example by altered water and salt balance or by altering concentrations of other molecules effecting biochemical and physiological control of cells.

Observation and Control of Glycome Changes by Stress in Cell Handling Processes

The inventors revealed that the method according to the invention is useful for observing changes in cell membranes which usually effectively alter at least part of the glycome observed according to the invention. It is realized that this related to exact organization and intact structures cell membranes and specific glycan structures being part of the organization.

The present invention is specifically directed to observation of total glycome and/or cell surface glycomes, these methods are further aimed for the use in the analysis of intactness of cells especially in context of stressful condition for the cells, especially when the cells are exposed to physical and/or chemical stress. It is realized that each new cell handling step and/or new condition for a cell handling step is useful to be controlled by the methods according to the invention. It is further realized that the analysis of glycome is useful for search of most effectively altering glycan structures for analysis by other methods such as binding by specific carbohydrate binding agents including especially carbohydrate binding proteins (lectins, antibodies, enzymes and engineered proteins with carbohydrate binding activity).

Controlled Cell Preparation (Isolation or Purification) with Retard to Reagents

The inventors analysed process steps of common cell preparation methods. Multiple sources of potential contamination by animal materials were discovered.

The present invention is specifically directed to carbohydrate analysis methods to control of cell preparation processes. The present invention is specifically directed to the process of controlling the potential contaminations with animal type glycans, preferably N-glycolylneuraminic acid at various steps of the process.

The invention is further directed to specific glycan controlled reagents to be used in cell isolation The glycan-controlled reagents may be controlled on three levels:
1. Reagents controlled not to contain observable levels of harmful glycan structure, preferably N-glycolylneuraminic acid or structures related to it
2. Reagents controlled not to contain observable levels of glycan structures similar to the ones in the cell preparation
3. Reagent controlled not to contain observable levels of any glycan structures.

The control levels 2 and 3 are useful especially when cell status is controlled by glycan analysis and/or profiling methods. In case reagents in cell preparation would contain the indicated glycan structures this would make the control more difficult or prevent it. It is further noticed that glycan structures may represent biological activity modifying the cell status.

Cell Preparation Methods Including Glycan-Controlled Reagents

The present invention is further directed to specific cell purification methods including glycan-controlled reagents.

Preferred Controlled Cell Purification Process

The present invention is especially directed to controlled production of human early cells containing one or several following steps. It was realized that on each step using regular reagents in following process there is risk of contamination by extragenous glycan material. The process is directed to the use of controlled reagents and materials according to the invention in the steps of the process.

Preferred purification of cells includes at least one of the steps including the use of controlled reagent, more preferably at least two steps are included, more preferably at least 3 steps and most preferably at least steps 1, 2, 3, 4, and 6.
1. Washing cell material with controlled reagent.
2. When antibody based process is used cell material is in a preferred embodiment blocked with controlled Fc-receptor blocking reagent. It is further realized that part of glycosylation may be needed in a antibody preparation, in a preferred embodiment a terminally depleted glycan is used.
3. Contacting cells with immobilized cell binder material including controlled blocking material and controlled cell binder material. In a more preferred the cell binder material comprises magnetic beads and controlled gelatin material according the invention. In a preferred embodiment the cell binder material is controlled, preferably a cell binder antibody material is controlled. Otherwise the cell binder antibodies may contain even N-glycolylneuraminic acid, especially when the antibody is produced by a cell line producing N-glycolylneuraminic acid and contaminate the product.
4. Washing immobilized cells with controlled protein preparation or non-protein preparation.
   In a preferred process magnetic beads are washed with controlled protein preparation, more preferably with controlled albumin preparation.
5. Optional release of cells from immobilization.
6. Washing purified cells with controlled protein preparation or non-protein preparation.

In a preferred embodiment the preferred process is a method using immunomagnetic beads for purification of early human cells, preferably purification of cord blood cells.

The present invention is further directed to cell purification kit, preferably an immunomagnetic cell purification kit comprising at least one controlled reagent, more preferably at least two controlled reagents, even more preferably three controlled reagents, even preferably four reagents and most preferably the preferred controlled reagents are selected from the group: albumin, gelatin, antibody for cell purification and Fc-receptor blocking reagent, which may be an antibody.

Storage Induced Changes Causing Harmful Glycosylations or Change in the Status of Cells It was realized that storage of the cell materials may cause harmful changes in glycosylation or changes in cell status observable by glycosylation analysis according to the present invention.

Changes Observable in Context of Low Temperature Storage or Handling of Cells

The inventors discovered that keeping the cells in lower temperatures alters the status of cells and this observable analysing the chemical structures of cells, preferably the glycosylation of the cells. The lower temperatures usually vary between 0-36 degrees of Celsius including for example incubator temperature below about 36 degrees of Celsius more preferably below 35 degrees of Celsius, various room temperatures, cold room and fridge temperatures typically between 2-10 degrees of Celsius, and temperatures from incubation on ice close to 0 degrees of Celsius typically between 0-4 degrees of Celsius. The lowered temperatures are typically needed for processing of cells or temporary storage of the preferred cells.

The present invention is specifically directed to analysis of the status of cells kept in low temperatures in comparison to natural body temperatures. In a preferred embodiment the control is performed after certain time has passed from process in lower temperature in order to confirm the recovery of the cells from the lower temperature. In another preferred embodiment the present invention is directed to development of lower temperature methods by controlling the chemical structures of cells, preferably by controlling glycosylation according to the present invention.

Changes Observable in Context of Cryopreservation

The inventors discovered that cryopreservation alters the status of cells and this observable analysing the chemical structures of cells, preferably the glycosylation of the cells. The present invention is specifically directed to analysis of the status of cryopreserved cells. In a preferred embodiment the control is performed after certain time has passed from preservation in order to confirm the recovery of the cells from the cryopreservation. In another preferred embodiment the present invention is directed to development of cryopreservation methods by controlling the chemical structures of cells, preferably by controlling glycosylation according to the present invention.

Contaminations with Harmful Glycans Such as Antigenic Animal Type Glycans

Several glycans structures contaminating cell products may weaken the biological activity of the product.

The harmful glycans can affect the viability during handling of cells, or viability and/or desired bioactivity and/or safety in therapeutic use of cells.

The harmful glycan structures may reduce the in vitro or in vivo viability of the cells by causing or increasing binding of destructive lectins or antibodies to the cells. Such protein material may be included e.g. in protein preparations used in cell handling materials. Carbohydrate targeting lectins are also present on human tissues and cells, especially in blood and endothelial surfaces. Carbohydrate binding antibodies in human blood can activate complement and cause other immune responses in vivo. Furthermore immune defense lectins in blood or leukocytes may direct immune defense against unusual glycan structures.

Additionally harmful glycans may cause harmful aggregation of cells in vivo or in vitro. The glycans may cause unwanted changes in developmental status of cells by aggregation and/or changes in cell surface lectin mediated biological regulation.

Additional problems include allergenic nature of harmful glycans and misdirected targeting of cells by endothelial/cellular carbohydrate receptors in vivo.

Contaminations from Reagents

The present invention is specifically directed to control of the reagents used to prevent contamination by harmful glycan structures. The harmful glycan structures may originate from reagents used during cell handling processes such as cell preservation, cell preparation, and cell culture.

Preferred reagents to be controlled according to the present invention include cell culture reagents, cell blocking reagents, such as antibody receptor blocking reagents, washing solutions during cell processing, material blocking reagents, such as blocking reagents for materials like for example magnetic beads. Preferably the materials are controlled:

1. so that these would not contain a contaminating structure, preferably a NeuGc-structure according to the invention, or more specifically preferred glycan structure according to the invention
2. so that the materials contain very low amounts or do not contain any potentially harmful structures according to the invention.

ABBREVIATIONS AND DEFINITIONS

Modification Definitions

Ac=acetyl ester or acetyl amide modification ($C_2H_2O$).
S/P or SP=sulphate ($SO_3$) or phosphate ($PO_3H$) ester modification, or another modification of corresponding mass.

Other modifications (Mod)=any modification to the monosaccharide and modification compositions, either affecting the proposed structure and its molecular mass positively, such as H, $H_2$, or Pr (propyl, $C_3H_7$), or affecting the proposed structure and its molecular mass negatively, such as —$H_2O$ or —Ac (without acetyl, —$C_2H_2O$); the latter option corresponding to e.g. proposed elimination products.

Ionized Forms:

In mass spectrometry, glycans occur in ionized forms such as $[M+Na]^+$, $[M+K]^+$, $[M-H]^-$, or $[M-2H+Na]^-$. The present invention is directed to finding out proposed monosaccharide and modification compositions for mass spectrometric signals, based on most probable combinations of monosaccharides and modifications, typically according to definitions listed above and preferably based on sample type-specific monosaccharide and modification selections such as those listed in the Examples and Tables below. Single monosaccharide and modification compositions potentially give rise to multiple mass spectrometric signals, for example $[M+Na]^+$ and $[M+K]^+$ adduct ions, and the present invention is especially directed to taking this phenomenon into account in the analysis results.

Molecular Mass and m/z Calculations, and Abbreviations Used in the Text:

Molecular masses and m/z values for proposed monosaccharide compositions and ionized forms therefrom can be calculated from the corresponding atom compositions according to common knowledge of the art.

In the following text, figures, and tables the m/z values of proposed monosaccharide compositions may be expressed as the m/z value of the first isotope and rounded down for clarity.

The corresponding more precise expressions can be derived from the proposed compositions and/or experimental data, and they are optionally, especially when needed for interpretation of the analysis results, expressed with more precision in the text, tables, and/or figures.

Preferred Forms of Monosaccharide and Modification Compositions:

In analyses of human early cells or biological reagents or biological samples occurring in context of human early cell analysis, preferred monosaccharide and modification combinations according to the present inventions include those listed in the Examples and Tables below.

Structural Features Derived from the Glycome Compositions
Marker Structures and Glycomes The invention revealed individual glycan structures and structure groups, which are novel markers for the cell materials according to the invention. The present invention is directed to the use of the marker structures and their combinations for analysis, for labelling and for cell separation, as modification targets and for other methods according to invention.

The present invention revealed large groups of glycans, which can be derived from cells according to the invention The present invention is especially directed to release of various protein or lipid linked oligosaccharide and/or polysaccharide chains as free glycan, glycan reducing end derivative or glycopeptide fractions referred as glycomes from the cell material according to the invention The glycans can be released separately from differently linked glycan groups on proteins and or glycolipids or in combined process producing several isolated glycome fractions and/or combined glycome fractions, which comprise glycans released at least from two different glycomes. The relative amounts of various components/component groups observable in glycan profiling as peaks in mass spectra and in quantitative presentations of glycan based profiling information, especially in analysis of mass spectrometric and/or NMR-data were revealed to be characteristic for individual cell types. The glycomes was further revealed to contain glycan subgroups or subglycomes which are very useful for characterization of the cell materials according to the invention.

Glycome Types Based on Linkage Structures

The invention revealed four major glycome types based on the linkage structures. Two protein linked glycomes are N-linked glycomes and O-linked glycomes. The majority of the glycosaminoglycan (gag) glycomes (gagomes) are also linked to certain proteins by specific core and linkage structures. The glycolipid glycome is linked to lipids, usually sphingolipids.

Core Structures of Glycomes and Terminal Glycome Specific and Common Structures

The invention has revealed specific glycan core structures for the specific subglycomes studied. The various structures in specific glycomes were observed to contain common reducing end core structures such as N-glycan and O-glycan, Glycosaminoglycan and glycolipid cores. The cores are elongated with varying glycan chains usually comprising groups of glycans with different chain length. The presence of a core structures is often observably as a characteristic monosaccharide composition as monosaccharide composition of the core structure causing different relation of monosaccharide residues in specific glycan signals of glycomes when profiled by mass spectrometry according to the invention. The present invention further revealed specific non-reducing end terminal structures of specific marker glycans. Part of the non-reducing end terminal structures are characteristic for several glycomes, for example N-acetyllactosamine type terminal structures, including fucosylated and sialylated variants were revealed from complex N-glycans, O-glycan and Glycolipid glycomes. Part of the structures are specific for glycomes such terminal Man-structures in Low-mannose and High-mannose N-glycans.

Combined Analysis of Different Glycomes

The invention revealed similar structures on protein and lipid linked glycomes in the cell materials according to the invention. It was revealed that combined analysis of the different glycomes is useful characterization of specific cell materials according to the invention. The invention specifically revealed similar lactosamine type structures in glycolipid and glycoprotein linked glycomes.

The invention further revealed glycosaminoglycan glycome and glycome profile useful for the analysis of the cell status and certain synergistic characteristics glycosaminoglycan glycomes and other protein linked glycomes such as non-sialic acid containing acidic structures in N-liked glycomes. The biological roles of glycosaminoglycans and glycolipids in regulation of cell biology and their biosynthetic difference and distance revealed by glycome analysis make these a useful combination for analysis of cell status. It is further realized that combination of all glycomes including O-glycan and N-glycan glycomes, glycolipid glycome and glycosaminoglycan glycome are useful for analysis of cells according to the invention. The invention further revealed common chemical structural features in the all glycomes according invention supporting the effective combined production, purification and analysis of glycomes according to the invention.

In a preferred embodiment the invention is directed to combined analysis of following glycome combinations, more preferably the glycomes are analysed from same sample to obtain exact information about the status of the cell material:
1. Two protein linked glycomes: N-glycan and O-glycan glycomes
2. Glycolipid glycomes with protein linked glycomes, especially preferred glycolipid glycomes and N-glycan glycomes
3. Protein linked glycome or glycomes with glycosaminoglycan glycome, in preferred embodiment a glycosaminoglycan glycome and N-glycan glycome.
4. Lipid linked glycome or glycomes with glycosaminoglycan glycome
5. Protein linked O-glycan and N-glycan glycomes, glycolipid glycome and glycosaminoglycan glycome.

The invention further revealed effective methods for the analysis of different glycomes. It was revealed that several methods developed for sample preparation are useful for both lipid and protein linked glycomes, in a preferred embodiment proteolytic treatment is used for both production of protein linked glycome and a lipid linked glycome, especially for production of cell surface glycomes. For production of Total cell glycomes according to the invention the extraction of glycolipids is preferably used for degradation of cells and protein fraction obtained from the lipid extraction is used for protein linked glycome analysis. The invention is further directed to the chemical release of glycans, preferably for simultaneous release of both O-linked and N-linked glycans. Glycolipid and other glycomes, especially N-linked glycome, can be effectively released enzymatically, the invention is directed to sequential release of glycans by enzymes, preferably including step of inactivating enzymes between the treatments and using glycan controlled enzymes to avoid contamination or controlling contamination of glycans originating from enzymes.

Common Structural Features of All Glycomes and Preferred Common Subfeatures

The present invention reveals useful glycan markers for stem cells and combinations thereof and glycome compositions comprising specific amounts of key glycan structures. The invention is furthermore directed to specific terminal and core structures and to the combinations thereof.

The preferred glycome glycan structure(s) and/or glycomes from cells according to the invention comprise structure(s) according to the formula C0:

$$R_1Hex\beta z\{R_3\}_{n1}Hex(NAc)_{n2}XyR2,$$

Wherein X is glycosidically linked disaccharide epitope $\beta 4(Fuc\alpha 6)_n GN$, wherein n is 0 or 1, or X is nothing and Hex is Gal or Man or GlcA, HexNAc is GlcNAc or GalNAc, y is anomeric linkage structure α and/or β or linkage from derivatized anomeric carbon, z is linkage position 3 or 4, with the provision that when z is 4 then HexNAc is GlcNAc and then Hex is Man or Hex is Gal or Hex is GlcA, and when z is 3 then Hex is GlcA or Gal and HexNAc is GlcNAc or GalNAc;

n1 is 0 or 1 indicating presence or absence of R3;

n2 is 0 or 1, indicating the presence or absence of NAc, with the proviso that n2 can be 0 only when Hexβz is Galβ4, and n2 is preferably 0, n2 structures are preferably derived from glycolipids;

$R_1$ indicates 1-4, preferably 1-3, natural type carbohydrate substituents linked to the core structures or nothing;

$R_2$ is reducing end hydroxyl, chemical reducing end derivative or natural asparagine N-glycoside derivative such as asparagine N-glycosides including asparagine N-glycoside aminoacids and/or peptides derived from protein, or natural serine or threonine linked O-glycoside derivative such as serine or threonine linked O-glycosides including asparagine N-glycoside aminoacids and/or peptides derived from protein, or when n2 is 1 R2 is nothing or a ceramide structure or a derivative of a ceramide structure, such as lysolipid and amide derivatives thereof;

R3 is nothing or a branching structure representing a GlcNAcβ6 or an oligosaccharide with GlcNAcβ6 at its reducing end linked to GalNAc (when HexNAc is GalNAc); or when Hex is Gal and HexNAc is GlcNAc, and when z is 3 then R3 is Fucα4 or nothing, and when z is 4 R3 is Fucα3 or nothing.

The preferred disaccharide epitopes in the glycan structures and glycomes according to the invention include structures Galβ4GlcNAc, Manβ4GlcNAc, GlcAβ4GlcNAc, Galβ3GlcNAc, Galβ3GalNAc, GlcAβ3GlcNAc, GlcAβ3GalNAc, and Galβ4Glc, which may be further derivatized from reducing end carbon atom and non-reducing monosaccharide residues and is in a separate embodiment branched from the reducing end residue. Preferred branched epitopes include Galβ4(Fucα3)GlcNAc, Galβ3(Fucα4)GlcNAc, and Galβ3(GlcNAcβ6)GalNAc, which may be further derivatized from reducing end carbon atom and non-reducing monosaccharide residues.

Preferred Epitopes for Methods According to the Invention
N-acetyllactosamine Galβ3/4GlcNAc Terminal Epitopes The two N-acetyllactosamine epitopes Galβ4GlcNAc and/or Galβ3GlcNAc represent preferred terminal epitopes present on stem cells or backbone structures of the preferred terminal epitopes for example further comprising sialic acid or fucose derivatisations according to the invention. In a preferred embodiment the invention is directed to fucosylated and/or non-substituted glycan non-reducing end forms of the terminal epitopes, more preferably to fucosylated and non-substituted forms. The invention is especially directed to non-reducing end terminal (non-substituted) natural Galβ4GlcNAc and/or Galβ3GlcNAc-structures from human stem cell glycomes. The invention is in a specific embodiment directed to non-reducing end terminal fucosylated natural Galβ4GlcNAc and/or Galβ3GlcNAc-structures from human stem cell glycomes.

Preferred Fucosylated N-acetyllactosamines

The preferred fucosylated epitopes are according to the Formula TF:

$$(Fuc\alpha 2)_{n1}Gal\beta 3/4(Fuc\alpha 4/3)_{n2}GlcNAc\beta\text{-R}$$

Wherein
n1 is 0 or 1 indicating presence or absence of Fucα2;
n2 is 0 or 1, indicating the presence or absence of Fucα4/3 (branch), and
R is the reducing end core structure of N-glycan, O-glycan and/or glycolipid.

The preferred structures thus include type 1 lactosaamines (Galβ3GlcNAc based):
Galβ3(Fucα4)GlcNAc (Lewis a), Fucα2Galβ3GlcNAc H-type 1, structure and, Fucα2Galβ3(Fucα4)GlcNAc (Lewis b) and type 2 lactosamines (Galβ4GlcNAc based):
Galβ4(Fucα3)GlcNAc (Lewis x), Fucα2Galβ4GlcNAc H-type 2, structure and, Fucα2Galβ4(Fucα3)GkcNAc (Lewis y).

The type 2 lactosamines (fucosylated and/or terminal non-substituted) form an especially preferred group in context of embryonal-type stem cells and differentiated cells derived directly from these. Type 1 lactosamines (Galβ3GlcNAc— structures) are especially preferred in context of adult stem cells.

Lactosamines Galβ3/4GlcNAc and Glycolipid Structures Comprising Lactose Structures (Galβ4Glc)

The lactosamines form a preferred structure group with lactose-based glycolipids. The structures share similar features as products of β3/4Gal-transferases. The β3/4 galactose based structures were observed to produce characteristic features of protein linked and glycolipid glycomes.

The invention revealed that furthermore Galβ3/4GlcNAc-structures are a key feature of differentiation related structures on glycolipids of various stem cell types. Such glycolipids comprise two preferred structural epitopes according to the invention. The most preferred glycolipid types include thus lactosylceramide based glycosphingolipids and especially lacto-(Galβ3GlcNAc), such as
lactotetraosylceramide Galβ3GlcNAcβ3Galβ4GlcβCer, preferred structures further including its non-reducing terminal structures selected from the group: Galβ3(Fucα4)GlcNAc (Lewis a), Fucα2Galβ3GlcNAc (H-type 1), structure and, Fucα2Galβ3(Fucα4)GlcNAc (Lewis b) or sialylated structure SAα3Galβ3GlcNAc or SAα3Galβ3(Fucα4)GlcNAc, wherein SA is a sialic acid, preferably Neu5Ac preferably replacing Galβ3GlcNAc of lactotetraosylceramide and its fucosylated and/or elogated variants such as preferably according to the Formula:

$$(Sac\alpha 3)_{n5}(Fuc\alpha 2)_{n1}Gal\beta 3(Fuc\alpha 4)_{n3}GlcNAc\beta 3$$
$$[Gal\beta 3/4(Fuc\alpha 4/3)_{n2}GlcNAc\beta 3]_{n4}Gal\beta 4Glc\beta Cer$$

wherein
n1 is 0 or 1, indicating presence or absence of Fucα2;
n2 is 0 or 1, indicating the presence or absence of Fucα4/3 (branch),
n3 is 0 or 1, indicating the presence or absence of Fucα4 (branch)

n4 is 0 or 1, indicating the presence or absence of (fucosylated) N-acetyllactosamine elongation;

n5 is 0 or 1, indicating the presence or absence of Sacα3 elongation;

Sac is terminal structure, preferably sialic acid, with α3-linkage, with the proviso that when Sac is present, n5 is 1, then n1 is 0 and neolacto (Galβ4GlcNAc)-comprising glycolipids such as neolactoteraosylceramide Galβ4GlcNAcβ3Galβ4GlcβCer, preferred structures further including its non-reducing terminal Galβ4(Fucα3)GlcNAc (Lewis x), Fucα2Galβ4GlcNAc H-type 2, structure and, Fucα2Galβ4(Fucα3)GlcNAc (Lewis y) and its fucosylated and/or elogated variants such as preferably (Sacα3/6)$_{n5}$(Fucα2)$_{n1}$Galβ4(Fucα3)$_{n3}$GlcNAcβ3
[Galβ4(Fucα3)$_{n2}$GlcNAcβ3]$_{n4}$Galβ4GlcβCer n1 is 0 or 1 indicating presence or absence of Fucα2;

n2 is 0 or 1, indicating the presence or absence of Fucα3 (branch), n3 is 0 or 1, indicating the presence or absence of Fucα3 (branch)

n4 is 0 or 1, indicating the presence or absence of (fucosylated) N-acetyllactosamine elongation, n5 is 0 or 1, indicating the presence or absence of Sacα3/6 elongation;

Sac is terminal structure, preferably sialic acid (SA) with α3-linkage, or sialic acid with α6-linkage, with the proviso that when Sac is present, n5 is 1, then n1 is 0, and when sialic acid is bound by α6-linkage preferably also n3 is 0.

Preferred Stem Cell Glycosphingolipid Glycan Profiles, Compositions, and Marker Structures The inventors were able to describe stem cell glycolipid glycomes by mass spectrometric profiling of liberated free glycans, revealing about 80 glycan signals from different stem cell types. The proposed monosaccharide compositions of the neutral glycans were composed of 2-7 Hex, 0-5 HexNAc, and 0-4 dhex. The proposed monosaccharide compositions of the acidic glycan signals were composed of 0-2 NeuAc, 2-9 Hex, 0-6 HexNAc, 0-3 dhex, and/or 0-1 sulphate or phosphate esters. The present invention is especially directed to analysis and targeting of such stem cell glycan profiles and/or structures for the uses described in the present invention with respect to stem cells.

The present invention is further specifically directed to glycosphingolipid glycan signals specific to stem cell types as described in the Examples. In a preferred embodiment, glycan signals typical to hESC, preferentially including 876 and 892 are used in their analysis, more preferentially FucHexHexNAcLac, wherein α1,2-Fuc is preferential to α1,3/4-Fuc, and Hex$_2$HexNAc$_1$Lac, and more preferentially to Galβ3-[Hex$_1$HexNAc$_1$]Lac. In another preferred embodiment, glycan signals typical to MSC, especially CB MSC, preferentially including 1460 and 1298, as well as large neutral glycolipids, especially Hex$_{2-3}$HexNAc$_3$Lac, more preferentially poly-N-acetyllactosamine chains, even more preferentially β1,6-branched, and preferentially terminated with type II LacNAc epitopes as described above, are used in context of MSC according to the uses described in the present invention.

Terminal glycan epitopes that were demonstrated in the present experiments in stem cell glycosphingolipid glycans are useful in recognizing stem cells or specifically binding to the stem cells via glycans, and other uses according to the present invention, including terminal epitopes: Gal, Galβ4Glc (Lac), Galβ4GlcNAc (LacNAc type 2), Galβ3, Non-reducing terminal HexNAc, Fuc, α1,2-Fuc, α1,3-Fuc, Fucα2Gal, Fucα2Galβ4GlcNAc (H type 2), Fucα2Galβ4Glc (2'-fucosyllactose), Fucα3GlcNAc, Galβ4(Fucα3)GlcNAc (Lex), Fucα3Glc, Galβ4(Fucα3)Glc (3-fucosyllactose), Neu5Ac, Neu5Acα2,3, and Neu5Acα2,6. The present invention is further directed to the total terminal epitope profiles within the total stem cell glycosphingolipid glycomes and/or glycomes.

The inventors were further able to characterize in hESC the corresponding glycan signals to SSEA-3 and SSEA-4 developmental related antigens, as well as their molar proportions within the stem cell glycome. The invention is further directed to quantitative analysis of such stem cell epitopes within the total glycomes or subglycomes, which is useful as a more efficient alternative with respect to antibodies that recognize only surface antigens. In a further embodiment the present invention is directed to finding and characterizing the expression of cryptic developmental and/or stem cell antigens within the total glycome profiles by studying total glycan profiles, as demonstrated in the Examples for α1,2-fucosylated antigen expression in hESC in contrast to SSEA-1 expression in mouse ES cells.

The present invention revealed characteristic variations (increased or decreased expression in comparison to similar control cell or a contamination cell or like) of both structure types in various cell materials according to the invention. The structures were revealed with characteristic and varying expression in three different glycome types: N-glycans, O-glycans, and glycolipids. The invention revealed that the glycan structures are a characteristic feature of stem cells and are useful for various analysis methods according to the invention. Amounts of these and relative amounts of the epitopes and/or derivatives varies between cell lines or between cells exposed to different conditions during growing, storage, or induction with effector molecules such as cytokines and/or hormones.

The preferred glycome glycan structure(s) and/or glycomes from cells according to the invention comprise structure(s) according to the formula C1:

$R_1$Hexβz{$R_3$}$_{n1}$HexNAcXy$R_2$,

Wherein X is glycosidically linked disaccharide epitope β4(Fucα6)$_n$GN, wherein n is 0 or 1, or X is nothing and Hex is Gal or Man or GlcA, HexNAc is GlcNAc or GalNAc, y is anomeric linkage structure α and/or β or linkage from derivatized anomeric carbon, z is linkage position 3 or 4, with the provision that when z is 4 then HexNAc is GlcNAc and then Hex is Man or Hex is Gal or Hex is GlcA, and when z is 3 then Hex is GlcA or Gal and HexNAc is GlcNAc or GalNAc, $R_1$ indicates 1-4, preferably 1-3, natural type carbohydrate substituents linked to the core structures, $R_2$ is reducing end hydroxyl, chemical reducing end derivative or natural asparagine N-glycoside derivative such as asparagine N-glycosides including asparagines N-glycoside aminoacids and/or peptides derived from protein, or natural serine or threonine linked O-glycoside derivative such as serine or threonine linked O-glycosides including asparagines N-glycoside aminoacids and/or peptides derived from protein.

R3 is nothing or a branching structure representing a GlcNAcβ6 or an oligosaccharide with GlcNAcβ6 at its reducing end linked to GalNAc (when HexNAc is GalNAc) or when Hex is Gal and HexNAc is GlcNAc the then when z is 3 R3 is Fucα4 or nothing and when z is 4 R3 is Fucα3 or nothing.

The preferred disaccharide epitopes in the glycan structures and glycomes according to the invention include structures Galβ4GlcNAc, Manβ4GlcNAc, GlcAβ4GlcNAc, Galβ3GlcNAc, Galβ3GalNAc, GlcAβ3GlcNAc and GlcAβ3GalNAc, which may be further derivatized from reducing end carbon atom and non-reducing monosaccharide residues and is separate embodiment branched from the reducing end residue. Preferred branched epitopes include Galβ4(Fucα3)GlcNAc, Galβ3(Fucα4)GlcNAc, Galβ3 (GlcNAcβ6)GalNAc, which may be further derivatized from reducing end carbon atom and non-reducing monosaccharide residues.

The preferred disaccharide epitopes of glycoprotein or glycolipid structures present on glycans of human cells according to the invention comprise structures based on the formula C2:

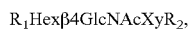

$R_1Hexβ4GlcNAcXyR_2$,

Wherein Hex is Gal OR Man and when Hex is Man then X is glycosidically linked disaccharide epitope β4(Fucα6)$_n$GN, wherein n is 0 or 1, or X is nothing and when Hex is Gal then X is β3GalNAc of O-glycan core or β2/4/6Manα3/6 terminal of N-glycan core (as in formula NC3)
y is anomeric linkage structure α and/or β or linkage from derivatized anomeric carbon,
$R_1$, indicates 1-4, preferably 1-3, natural type carbohydrate substituents linked to the core structures,
when Hex is Gal preferred R1 groups include structures SAα3/6, SAα3/6Galβ4GlcNAcβ3/6,
when Hex is Man preferred R1 groups include Manα3, Manα6, branched structure Manα3 {Manα6} and elongated variants thereof as described for low mannose, high-mannose and complex type N-glycans below,
$R_2$ is reducing end hydroxyl, chemical reducing end derivative or natural asparagine N-glycoside derivative such as asparagine N-glycosides including asparagines N-glycoside aminoacids and/or peptides derived from protein, or natural serine or threonine linked O-glycoside derivative such as serine or threonine linked O-glycosides including asparagines N-glycoside aminoacids and/or peptides derived from protein.

Structures of N-Linked Glycomes
Common Core Structure of N-Linked Glycomes

The inventors revealed that the N-glycans released by specific N-glycan release methods from the cells according to the invention, and preferred cells according to the invention, comprise mostly a specific type of N-glycan core structure.

The preferred N-glycan structure of each cell type is characterised and recognized by treating cells with a N-glycan releasing enzyme releasing practically all N-glycans with core type according to the invention. The N-glycan releasing enzyme is preferably protein N-glycosidase enzyme, preferably by protein N-glycosidase releasing effectively the N-glycomes according to the invention, more preferably protein N-glycosidase with similar specificity as protein N-glycosidase F, and in a specifically preferred embodiment the enzyme is protein N-glycosidase F from *F. meningosepticum*. Alternative chemical N-glycan release method was used for controlling the effective release of the N-glycomes by the N-glycan releasing enzyme.

The inventors used the NMR glycome analysis according to the invention for further characterization of released N-glycomes from small cell samples available. NMR spectroscopy revealed the N-glycan core signals of the preferred N-glycan core type of the cells according to the invention.

The Minimum Formula

The present invention is directed to glycomes derived from stem cells and comprising a common N-glycosidic core structures. The invention is specifically directed to minimum formulas covering both $GN_1$-glycomes and $GN_2$-glycomes with difference in reducing end structures.

The minimum core structure includes glycans from which reducing end GlcNAc or Fucα6GlcNAc has been released. These are referred as $GN_1$-glycomes and the components thereof as $GN_1$-glycans. The present invention is specifically directed to natural N-glycomes from human stem cells comprising $GN_1$-glycans. In a preferred embodiment the invention is directed to purified or isolated practically pure natural $GN_1$-glycome from human stem cells. The release of the reducing end GlcNAc-unit completely or partially may be included in the production of the N-glycome or N-glycans from stem cells for analysis.

The glycomes including the reducing end GlcNAc or Fucα6GlcNAc are referred as $GN_2$-glycomes and the components thereof as $GN_2$-glycans. The present invention is also specifically directed to natural N-glycomes from human stem cells comprising $GN_2$-glycans. In a preferred embodiment the invention is directed to purified or isolated practically pure natural $GN_2$-glycome from human stem cells.

The preferred N-glycan core structure(s) and/or N-glycomes from stem cells according to the invention comprise structure(s) according to the formula NC1:

$R_1Mβ4GNXyR_2$,

Wherein X is glycosidically linked disaccharide epitope β4(Fucα6)$_n$GN, wherein n is 0 or 1, or X is nothing and y is anomeric linkage structure α and/or β or linkage from derivatized anomeric carbon, and
R1 indicates 1-4, preferably 1-3, natural type carbohydrate substituents linked to the core structures,
$R_2$ is reducing end hydroxyl, chemical reducing end derivative or natural asparagine N-glycoside derivative such as asparagine N-glycosides including asparagines N-glycoside aminoacids and/or peptides derived from protein.

It is realized that when the invention is directed to a glycome, the formula indicates mixture of several or typically more than ten or even higher number of different structures according to the Formulas describing the glycomes according to the invention.

The possible carbohydrate substituents $R_1$ comprise at least one mannose (Man) residue, and optionally one or several GlcNAc, Gal, Fuc, SA and/GalNAc residues, with possible sulphate and or phosphate modifications.

When the glycome is released by N-glycosidase the free N-glycome saccharides comprise in a preferred embodiment reducing end hydroxyl with anomeric linkage A having structure α and/or β, preferably both α and β. In another embodiment the glycome is derivatized by a molecular structure which can be reacted with the free reducing end of a released glycome, such as amine, aminooxy or hydrazine or thiol structures. The derivatizing groups comprise typically 3 to 30 atoms in aliphatic or aromatic structures or can form terminal group spacers and link the glycomes to carriers such as solid phases or microparticles, polymeric carries such as oligosaccharides and/or polysaccharide, peptides, dendrimer, proteins, organic polymers such as plastics, polyethyleneglycol and derivatives, polyamines such as polylysines.

When the glycome comprises asparagine N-glycosides, A is preferably beta and R is linked asparagine or asparagine peptide. The peptide part may comprise multiple different aminoacid residues and typically multiple forms of peptide with different sequences derived from natural proteins carrying the N-glycans in cell materials according to the invention. It is realized that for example proteolytic release of glycans may produce mixture of glycopeptides. Preferably the peptide parts of the glycopeptides comprises mainly a low number of amino acid residues, preferably two to ten residues, more preferably two to seven amino acid residues and even more preferably two to five aminoacid residues and most preferably two to four amino acid residues when "mainly" indicates preferably at least 60% of the peptide part, more preferably at least 75% and most preferably at least 90% of the peptide part comprising the peptide of desired low number of aminoacid residues.

The Preferred $GN_2$-N-Glycan Core Structure(s)

The preferred $GN_2$-N-glycan core structure(s) and/or N-glycomes from stem cells according to the invention comprise structure(s) according to the formula NC2:

$$R_1M\beta4GN\beta4(Fuc\alpha6)_nGNyR_2,$$

wherein n is 0 or 1 and
wherein y is anomeric linkage structure α and/or β or linkage from derivatized anomeric carbon and
$R_1$ indicates 1-4, preferably 1-3, natural type carbohydrate substituents linked to the core structures,
$R_2$ is reducing end hydroxyl chemical reducing end derivative or natural asparagine N-glycoside derivative such as asparagine N-glycosides including asparagines N-glycoside aminoacid and/or peptides derived from protein.

The preferred compositions thus include one or several of the following structures
NC2a: $M\alpha3\{M\alpha6\}M\beta4GN\beta4\{Fuc\alpha6\}_{n1}GNyR_2$
NC2b: $M\alpha6M\beta4GN\beta4\{Fuc\alpha6\}_{n1}GNyR_2$
NC2c: $M\alpha3M\beta4GN\beta4\{Fuc\alpha6\}_{n1}GNyR_2$ More preferably compositions comprise at least 3 of the structures or most preferably both structures according to the formula NC2a and at least both fucosylated and non-fucosylated with core structure(s) NC2b and/or NC2c.

The Preferred $GN_1$—N-glycan Core Structure(s)

The preferred $GN_1$—N-glycan core structure(s) and/or N-glycomes from stem cells according to the invention comprise structure(s) according to the formula NC3:

$$R_1M\beta4GNyR_2,$$

wherein y is anomeric linkage structure α and/or β or linkage from derivatized anomeric carbon and
$R_1$ indicates 1-4, preferably 1-3, natural type carbohydrate substituents linked to the core structures,
$R_2$ is reducing end hydroxyl, chemical reducing end derivative or natural asparagine N-glycoside derivative such as asparagine N-glycosides including asparagine N-glycoside aminoacids and/or peptides derived from protein.

Multi-Mannose $GN_1$—N-Glycan Core Structure(s)

The invention is specifically directed glycans and/or glycomes derived from preferred cells according to the present invention when the natural glycome or glycan comprises Multi-mannose $GN_1$—N-glycan core structure(s) structure(s) according to the formula NC4:

$$[R_1M\alpha3]_{n3}\{R_3M\alpha6\}_{n2}M\beta4GNXyR_2,$$

$R_1$ and R3 indicate nothing or one or two, natural type carbohydrate substituents linked to the core structures, when the substituents are α-linked mannose monosaccharide and/or oligosaccharides and the other variables are as described above.

Furthermore common elongated $GN_2$—N-glycan core structures are preferred types of glycomes according to the invention The preferred N-glycan core structures further include differently elongated $GN_2$—N-glycan core structures according to the formula NC5:

$$[R_1M\alpha3]_{n3}\{R_3M\alpha6\}_{n2}M\beta4GN\beta4\{Fuc\alpha6\}_{n1}GNyR_2,$$

wherein n1, n2 and n3 are either 0 or 1 and
wherein y is anomeric linkage structure α and/or β or linkage from derivatized anomeric carbon and
$R_1$ and $R_3$ indicate nothing or 1-4, preferably 1-3, most preferably one or two, natural type carbohydrate substituents linked to the core structures,
$R_2$ is reducing end hydroxyl, chemical reducing end derivative or natural asparagine N-glycoside derivative such as asparagine N-glycosides including asparagine N-glycoside aminoacids and/or peptides derived from protein,
GN is GlcNAc, M is mannosyl-, [ ] indicate groups either present or absent in a linear sequence.
{ } indicates branching which may be also present or absent. with the provision that at least n2 or n3 is 1. Preferably the invention is directed to compositions comprising with all possible values of n2 and n3 and all saccharide types when R1 and/or are R1 are oligosaccharide sequences or nothing.

Preferred N-Glycan Types in Glycomes Comprising N-Glycans

The present invention is preferably directed to N-glycan glycomes comprising one or several of the preferred N-glycan core types according to the invention. The present invention is specifically directed to specific N-glycan core types when the compositions comprise N-glycan or N-glycans from one or several of the groups Low mannose glycans, High mannose glycans, Hybrid glycans, and Complex glycans, in a preferred embodiment the glycome comprise substantial amounts of glycans from at least three groups, more preferably from all four groups.

Major Subtypes of N-Glycans in N-Linked Glycomes

The invention revealed certain structural groups present in N-linked glycomes. The grouping is based on structural features of glycan groups obtained by classification based on the monosaccharide compositions and structural analysis of the structural groups. The glycans were analysed by NMR, specific binding reagents including lectins and antibodies and specific glycosidases releasing monosaccharide residues from glycans. The glycomes are preferably analysed as neutral and acidic glycomes.

The Major Neutral Glycan Types

The neutral glycomes mean glycomes comprising no acidic monosaccharide residues such as sialic acids (especially NeuNAc and NeuGc), HexA (especially GlcA, glucuronic acid) and acid modification groups such as phosphate and/or sulphate esters. There are four major types of neutral N-linked glycomes which all share the common N-glycan core structure: High-mannose N-glycans, low-mannose N-glycans, hydrid type and complex type N-glycans. These have characteristic monosaccharide compositions and specific substructures. The complex and hybrid type glycans may include certain glycans comprising monoantennary glycans.

The groups of complex and hybrid type glycans can be further analysed with regard to the presence of one or more fucose residues. Glycans containing at least one fucose units are classified as fucosylated. Glycans containing at least two fucose residues are considered as glycans with complex fucosylation indicating that other fucose linkages, in addition to the α1,6-linkage in the N-glycan core, are present in the structure. Such linkages include α1,2-, α1,3-, and α1,4-linkage.

Furthermore the complex type N-glycans may be classified based on the relations of HexNAc (typically GlcNAc or Gal- NAc) and Hex residues (typically Man, Gal). Terminal Hex-NAc glycans comprise at least three HexNAc units and at least two Hexose units so that the number of Hex Nac residues is at least larger or equal to the number of hexose units, with the provision that for non branched, monoantennary glycans the number of HexNAcs is larger than number of hexoses.

This consideration is based on presence of two GlcNAc units in the core of N-glycan and need of at least two Mannose units to for a single complex type N-glycan branch and three mannose to form a trimannosyl core structure for most complex type structures. A specific group of HexNAc N-Glycans contains the same number of HexNAcs and Hex units, when the number is at least 5.

Preferred Mannose Type Structures

The invention is further directed to glycans comprising terminal Mannose such as Mα6-residue or both Manα6- and Manα3-residues, respectively, can additionally substitute other Mα2/3/6 units to form a Mannose-type structures including hydrid, low-Man and High-Man structures according to the invention.

Preferred high- and low mannose type structures with GN2-core structure are according to the Formula M2:

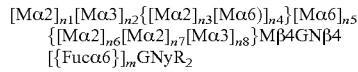

wherein p, n1, n2, n3, n4, n5, n6, n7, n8, and m are either independently 0 or 1; with the proviso that when n2 is 0, also n1 is 0; when n4 is 0, also n3 is 0; when n5 is 0, also n1, n2, n3, and n4 are 0; when n7 is 0, also n6 is 0; when n8 is 0, also n6 and n7 are 0;

y is anomeric linkage structure α and/or β or linkage from derivatized anomeric carbon, and $R_2$ is reducing end hydroxyl, chemical reducing end derivative or natural asparagine N-glycoside derivative such as asparagine N-glycosides including asparagines N-glycoside aminoacid and/or peptides derived from protein;

[ ] indicates determinant either being present or absent depending on the value of n1, n2, n3, n4, n5, n6, n7, n8, and m; and { } indicates a branch in the structure.

Preferred $yR_2$-structures include $[\beta\text{-N-Asn}]_p$, wherein p is either 0 or 1.

Preferred Mannose Type Glycomes Comprising GN1-Core Structures

As described above a preferred variant of N-glycomes comprising only single GlcNAc-residue in the core. Such structures are especially preferred as glycomes produced by endo-N-acetylglucosaminidase enzymes and Soluble glycomes. Preferred Mannose type glycomes include structures according to the Formula M2

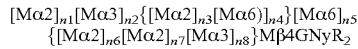

Fucosylated high-mannose N-glycans according to the invention have molecular compositions $Man_{5-9}GlcNAc_2Fuc_1$. For the fucosylated high-mannose glycans according to the formula, the sum of n1, n2, n3, n4, n5, n6, n7, and n8 is an integer from 4 to 8 and m is 0.

The low-mannose structures have molecular compositions $Man_{1-4}GlcNAc_2Fuc_{0-1}$. They consist of two subgroups based on the number of Fuc residues: 1) nonfucosylated low-mannose structures have molecular compositions $Man_{1-4}GlcNAc_2$ and 2) fucosylated low-mannose structures have molecular compositions $Man_{1-4}GlcNAc_2Fuc_1$. For the low mannose glycans the sum of n1, n2, n3, n4, n5, n6, n7, and n8 is less than or equal to (m+3); and preferably n1, n3, n6, and n7 are 0 when m is 0.

Low Mannose Glycans

The invention revealed a very unusual group of glycans in N-glycomes of the invention defined here as low mannose N-glycans. These are not clearly linked to regular biosynthesis of N-glycans, but may represent unusual biosynthetic midproducts or degradation products. The low mannose glycans are especially characteristics changing during the changes of cell status, the differentiation and other changes according to the invention, for examples changes associated with differentiation status of embryonal-type stem cells and their differentiated products and control cell materials. The invention is especially directed to recognizing low amounts of low-mannose type glycans in cell types, such as stem cells, preferably embryonal type stem cells with low degree of differentiation.

The invention revealed large differences between the low mannose glycan expression in the early human blood cell glycomes, especially in different preferred cell populations from human cord blood.

The invention is especially directed to the use of specific low mannose glycan comprising glycomes for analysis of early human blood glycomes especially glycomes from cord blood.

The invention further revealed specific mannose directed recognition methods useful for recognizing the preferred glycomes according to the invention. The invention is especially directed to combination of glycome analysis and recognition by specific binding agents, most preferred binding agent include enzymes and this derivatives. The invention further revealed that specific low mannose glycans of the low mannose part of the glycomes can be recognized by degradation by specific α-mannosidase ($Man_{2-4}GlcNAc_2Fuc_{0-1}$) or β-mannosidase ($Man_1GlcNAc_2Fuc_{0-1}$) enzymes and optionally further recognition of small low mannose structures, even more preferably low mannose structures comprising terminal Manβ4-structures according to the invention.

The low mannose N-glycans, and preferred subgroups and individual structures thereof, are especially preferred as markers of the novel glycome compositions of the cells according to the invention useful for characterization of the cell types.

The low-mannose type glycans includes a specific group of α3- and/or α6-linked mannose type structures according to the invention including a preferred terminal and core structure types according to the invention.

The inventions further revealed that low mannose N-glycans comprise a unique individual structural markers useful for characterization of the cells according to the invention by specific binding agents according to the invention or by combinations of specific binding agents according to the invention.

Neutral low-mannose type N-glycans comprise one to four or five terminal Man-residues, preferentially Manoα structures; for example $Man\alpha_{0-3}Man\beta4GlcNAc\beta4GlcNAc(\beta\text{-N-Asn})$ or $Man\alpha_{0-4}Man\beta4GlcNAc\beta4(Fuc\alpha6)GlcNAc(\beta\text{-N-Asn})$.

Low-mannose N-glycans are smaller and more rare than the common high-mannose N-glycans ($Man_{5-9}GlcNAc_2$). The low-mannose N-glycans detected in cell samples fall into two subgroups: 1) non-fucosylated, with composition $Man_nGlcNAc_2$, where $1 \le n \le 4$, and 2) core-fucosylated, with composition $Man_nGlcNAc_2Fuc_1$, where $1 \le n \le 5$. The largest of the detected low-mannose structure structures is $Man_5GlcNAc_2Fuc_1$ (m/z 1403 for the sodium adduct ion), which due to biosynthetic reasons most likely includes the structure below (in the figure the glycan is free oligosaccharide and β-anomer; in glycoproteins in tissues the glycan is N-glycan and β-anomer):

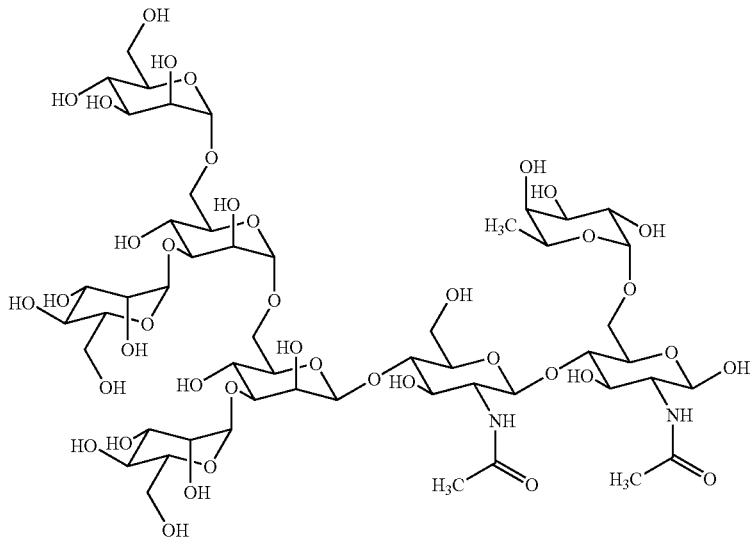 [SMILES: CC(=O)NC1C(O)OC(COC2OC(C)C(O)C(O)C2O)C(OC2OC(CO)C(OC3OC(COC4OC(COC5OC(CO)C(O)C(O)C5O)C(O)C(OC5OC(CO)C(O)C(O)C5O)C4O)C(O)C(OC4OC(CO)C(O)C(O)C4O)C3O)C(O)C2NC(C)=O)C1O]

Preferred General Molecular Structural Features of Low Man Glycans

According to the present invention, low-mannose structures are preferentially identified by mass spectrometry, preferentially based on characteristic $Hex_{1-4}HexNAc_2dHex_{0-1}$ monosaccharide composition. The low-mannose structures are further preferentially identified by sensitivity to exoglycosidase digestion, preferentially α-mannosidase ($Hex_{2-4}HexNAc_2dHex_{0-1}$) or β-mannosidase ($Hex_1HexNAc_2dHex_{0-1}$) enzymes, and/or to endoglycosidase digestion, preferentially N-glycosidase F detachment from glycoproteins, Endoglycosidase H detachment from glycoproteins (only $Hex_{1-4}HexNAc_2$ liberated as $Hex_{1-4}HexNAc_1$), and/or Endoglycosidase F2 digestion (only $Hex_{1-4}HexNAc_2dHex_1$ digested to $Hex_{1-4}HexNAc_1$). The low-mannose structures are further preferentially identified in NMR spectroscopy based on characteristic resonances of the Manβ4GlcNAcβ4GlcNAc N-glycan core structure and Manα residues attached to the Manβ4 residue.

Several preferred low Man glycans described above can be presented in a single Formula:

[Mα3]$_{n2}${[Mα6]$_{n4}$}[Mα6]$_{n5}${([Mα3]$_{n8}$}Mβ4GNβ4[{Fucα6}]$_m$GNyR$_2$ wherein p, n2, n4, n5, n8, and m are either independently 0 or 1; with the proviso that when n2 is 0, also n1 is 0; when n4 is 0, also n3 is 0; when n5 is 0, also n1, n2, n3, and n4 are 0; when n7 is 0, also n6 is 0; when n8 is 0, also n6 and n7 are 0; the sum of n1, n2, n3, n4, n5, n6, n7, and n8 is less than or equal to (m+3); [ ] indicates determinant either being present or absent depending on the value of n2, n4, n5, n8, and m; and { } indicates a branch in the structure; y and R2 are as indicated above.

Preferred non-fucosylated low-mannose glycans are according to the formula:

[Mα3]$_{n2}$([Mα6]$_{n4}$)[Mα6]$_{n5}${[Mα3]$_{n8}$}Mβ4GNβ4GNyR$_2$ wherein p, n2, n4, n5, n8, and m are either independently 0 or 1, with the provision that when n5 is 0, also n2 and n4 are 0, and preferably either n2 or n4 is 0, [ ] indicates determinant either being present or absent depending on the value of, n2, n4, n5, n8, { } and 0 indicates a branch in the structure, y and R2 are as indicated above.

Preferred Individual Structures of Non-Fucosylated Low-Mannose Glycans

Special Small Structures

Small non-fucosylated low-mannose structures are especially unusual among known N-linked glycans and characteristic glycans group useful for separation of cells according to the present invention. These include:

Mβ4GNβ4GNyR$_2$
Mα6Mβ4GNβ4GNyR$_2$
Mα3Mβ4GNβ4GNyR$_2$ and
Mα6{Mα3}Mβ4GNβ4GNyR$_2$.

Mβ4GNβ4GNyR$_2$ trisaccharide epitope is a preferred common structure alone and together with its mono-mannose derivatives Mα6Mβ4GNβ4GNyR$_2$ and/or Mα3Mβ4GNβ4GNyR$_2$, because these are characteristic structures commonly present in glycomes according to the invention. The invention is specifically directed to the glycomes comprising one or several of the small non-fucosylated low-mannose structures. The tetrasaccharides are in a specific embodiment preferred for specific recognition directed to α-linked, preferably α3/6-linked Mannoses as preferred terminal recognition element.

Special Large Structures

The invention further revealed large non-fucosylated low-mannose structures that are unusual among known N-linked glycans and have special characteristic expression features among the preferred cells according to the invention. The preferred large structures include

[Mα3]$_{n2}$([Mα6]$_{n4}$)Mα6{Mα3}Mβ4GNβ4GNyR$_2$ more specifically
Mα6Mα6{Mα3}Mβ4GNβ4GNyR$_2$
Mα3Mα6{Mα3}Mβ4GNβ4GNyR$_2$ and
Mα3(Mα6)Mα6{Mα3}Mβ4GNβ4GNyR$_2$.

The hexasaccharide epitopes are preferred in a specific embodiment as rare and characteristic structures in preferred cell types and as structures with preferred terminal epitopes. The heptasaccharide is also preferred as structure comprising a preferred unusual terminal epitope Mα3(Mα6)Mα useful for analysis of cells according to the invention.

Preferred fucosylated low-mannose glycans are derived according to the formula:

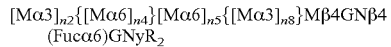
[Mα3]$_{n2}$\{[Mα6]$_{n4}$\}[Mα6]$_{n5}$\{[Mα3]$_{n8}$\}Mβ4GNβ4(Fucα6)GNyR$_2$ wherein p, n2, n4, n5, n8, and m are either independently 0 or 1, with the provisio that when n5 is 0, also n2 and n4 are 0,
[ ] indicates determinant either being present or absent depending on the value of n1, n2, n3, n4, ( ) indicates a branch in the structure; and wherein n1, n2, n3, n4 and m are either independently 0 or 1,
with the provisio that when n3 is 0, also n1 and n2 are 0,
[ ] indicates determinant either being present or absent depending on the value of n1, n2, n3, n4 and m,
{ } and ( ) indicate a branch in the structure.

Preferred Individual Structures of Fucosylated Low-Mannose Glycans

Small fucosylated low-mannose structures are especially unusual among known N-linked glycans and form a characteristic glycan group useful for separation of cells according to the present invention. These include:
Mβ4GNβ(Fucα6)GNyR$_2$
Mα6Mβ4GNβ4(Fucα6)GNyR$_2$
Mα3Mβ4GNβ4(Fucα6)GNyR$_2$ and
Mα6\{Mα3\}Mβ4GNβ4(Fucα6)GNyR$_2$.

Mβ4GNβ4(Fucα6)GNyR$_2$ tetrasaccharide epitope is a preferred common structure alone and together with its monomannose derivatives Mα6Mβ4GNβ4(Fucα6)GNyR$_2$ and/or Mα3Mβ4GNβ4(Fucα6)GNyR$_2$, because these are commonly present characteristics structures in glycomes according to the invention. The invention is specifically directed to the glycomes comprising one or several of the small non-fucosylated low-mannose structures. The tetrasaccharides are in a specific embodiment preferred for specific recognition directed to C-linked, preferably α3/6-linked Mannoses as preferred terminal recognition element.

Special Large Structures

The invention further revealed large fucosylated low-mannose structures are unusual among known N-linked glycans and have special characteristic expression features among the preferred cells according to the invention. The preferred large structure includes

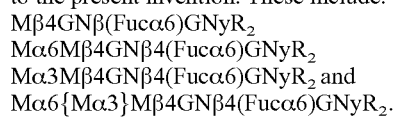
[Mα3]$_{n2}$([Mα6]$_{n4}$)Mα6\{Mα3\}Mβ4GNβ4(Fucα6)GNyR$_2$ more specifically
Mα6Mα6\{Mα3\}Mβ4GNβ4(Fucα6)GNyR$_2$
Mα3Mα6\{Mα3\}Mβ4GNβ4(Fucα6)GNyR$_2$ and
Mα3(Mα6)Mα6\{Mα3\}Mβ4GNβ4(Fucα6)GNyR$_2$.

The heptasaccharide epitopes are preferred in a specific embodiment as rare and characteristic structures in preferred cell types and as structures with preferred terminal epitopes. The octasaccharide is also preferred as structure comprising a preferred unusual terminal epitope Mα3(Mα6)Mα useful for analysis of cells according to the invention.

Preferred Non-Reducing End Terminal Mannose-Epitopes

The inventors revealed that mannose-structures can be labeled and/or otherwise specifically recognized on cell surfaces or cell derived fractions/materials of specific cell types. The present invention is directed to the recognition of specific mannose epitopes on cell surfaces by reagents binding to specific mannose structures from cell surfaces.

The preferred reagents for recognition of any structures according to the invention include specific antibodies and other carbohydrate recognizing binding molecules. It is known that antibodies can be produced for the specific structures by various immunization and/or library technologies such as phage display methods representing variable domains of antibodies. Similarly with antibody library technologies, including aptamer technologies and including phage display for peptides, exist for synthesis of library molecules such as polyamide molecules including peptides, especially cyclic peptides, or nucleotide type molecules such as aptamer molecules.

The invention is specifically directed to specific recognition high-mannose and low-mannose structures according to the invention. The invention is specifically directed to recognition of non-reducing end terminal Mα-epitopes, preferably at least disaccharide epitopes, according to the formula:

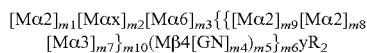
[Mα2]$_{m1}$[Mαx]$_{m2}$[Mα6]$_{m3}$\{\{[Mα2]$_{m9}$[Mα2]$_{m8}$[Mα3]$_{m7}$\}$_{m10}$(Mβ4[GN]$_{m4}$)$_{m5}$\}$_{m6}$yR$_2$ wherein m1, m2, m3, m4, m5, m6, m7, m8, m9 and m10 are independently either 0 or 1; with the proviso that when m3 is 0, then m1 is 0 and, when m7 is 0 then either m1-5 are 0 and m8 and m9 are 1 forming Mα2Mα2-disaccharide or both m8 and m9 are 0
y is anomeric linkage structure α and/or β or linkage from derivatized anomeric carbon, and
R$_2$ is reducing end hydroxyl, chemical reducing end derivative
and x is linkage position 3 or 6 or both 3 and 6 forming branched structure,
{ } indicates a branch in the structure.

The invention is further directed to terminal Mα2-containing glycans containing at least one Mα2-group and preferably Mα2-group on each, branch so that m1 and at least one of m8 or m9 is 1. The invention is further directed to terminal Mα3 and/or Mα6-epitopes without terminal Mα2-groups, when all m1, m8 and m9 are 1.

The invention is further directed in a preferred embodiment to the terminal epitopes linked to a Mβ-residue and for application directed to larger epitopes. The invention is especially directed to Mβ4GN-comprising reducing end terminal epitopes.

The preferred terminal epitopes comprise typically 2-5 monosaccharide residues in a linear chain. According to the invention short epitopes comprising at least 2 monosaccharide residues can be recognized under suitable background conditions and the invention is specifically directed to epitopes comprising 2 to 4 monosaccharide units and more preferably 2-3 monosaccharide units, even more preferred epitopes include linear disaccharide units and/or branched trisaccharide non-reducing residue with natural anomeric linkage structures at reducing end. The shorter epitopes may be preferred for specific applications due to practical reasons including effective production of control molecules for potential binding reagents aimed for recognition of the structures.

The shorter epitopes such as Mα2M-may is often more abundant on target cell surface as it is present on multiple arms of several common structures according to the invention.

Preferred Disaccharide Epitopes Includes

Manα2Man, Manα3Man, Manα6Man, and more preferred anomeric forms Manα2Manα, Manα3Manα, Manα6Manα, Manα3Manα and Manα6Manα.

Preferred branched trisaccharides includes Manα3(Manα6)Man, Manα3(Manα6)Manα, and Manα3(Manα6)Manα.

The invention is specifically directed to the specific recognition of non-reducing terminal Manα2-structures especially in context of high-mannose structures.

The invention is specifically directed to following linear terminal mannose epitopes:

a) preferred terminal Manα2-epitopes including following oligosaccharide sequences:
Manα2Man,
Manα2Manα,
Manα2Manα2Man,  Manα2Manα3Man,
Manα2Manα3Man,
Manα2Manα6Man,
Manα2Manα2Manα,  Manα2Manα3Manβ,
Manα2Manα6Manα,
Manα2Manα2Manα3Man,  Manα2Manα3Manα6Man,
Manα2Manα6Manα6Man
Manα2Manα2Manα3Manβ,  Manα2Manα3Manα6Manβ,
Manα2Manα6Manα6Manβ;

The invention is further directed to recognition of and methods directed to non-reducing end terminal Manα3- and/or Manα6-comprising target structures, which are characteristic features of specifically important low-mannose glycans according to the invention. The preferred structural groups includes linear epitopes according to b) and branched epitopes according to the c3) especially depending on the status of the target material.

b) preferred terminal Manα3- and/or Manα6-epitopes including following oligosaccharide sequences:
Manα3Man, Manα6Man, Manα3Manβ, Manα6Manβ, Manα3Manα, Manα6Manα, Manα3Manα6Man, Manα6Manα6Man, Manα3Manα6Manβ, Manα6Manα6Manβ and to following c) branched terminal mannose epitopes, are preferred as characteristic structures of especially high-mannose structures (c1 and c2) and low-mannose structures (c3), the preferred branched epitopes include:

c1) branched terminal Manα2-epitopes
Manα2Manα3(Manα2Manα6)Man,  Manα2Manα3
(Manα2Manα6)Manα,
Manα2Manα3(Manα2Manα6)Manα6Man, Manα2Manα3
(Manα2Manα6)Manα6Manβ,
Manα2Manα3(Manα2Manα6)Manα6(Manα2Manα3)
Man,
Manα2Manα3(Manα2Manα6)Manα6
(Manα2Manα2Manα3)Man,
Manα2Manα3(Manα2Manα6)Manα6(Manα2Manα3)
Manβ
Manα2Manα3(Manα2Manα6)Manα6
(ManαManα2Manα3)Manβ c2) branched terminal Manα2- and Manα3 or Manα6-epitopes according to formula when m1 and/or m8 and/m9 is 1 and the molecule comprise at least one nonreducing end terminal Manα3 or Manα6-epitope c3) branched terminal Manα3 or Manα6-epitopes
Manα3(Manα6)Man, Manα3(Manα6)Manβ, Manα3(Manα6)Manα,
Manα3(Manα6)Manα6Man, Manα3(Manα6)Manα6Manβ,
Manα3(Manα6)Manα6(Manα3)Man, Manα3(Manα6)Manα6(Manα3)Manβ

The present invention is further directed to increase of selectivity and sensitivity in recognition of target glycans by combining recognition methods for terminal Manα2 and Manα3 and/or Manα6-comprising structures. Such methods would be especially useful in context of cell material according to the invention comprising both high-mannose and low-mannose glycans.

Complex Type N-Glycans

According to the present invention, complex-type structures are preferentially identified by mass spectrometry, preferentially based on characteristic monosaccharide compositions, wherein HexNAc≥4 and Hex≥3. In a more preferred embodiment of the present invention, 4≤HexNAc≤20 and 3≤Hex≤21, and in an even more preferred embodiment of the present invention, 4≤HexNAc≤10 and 3≤Hex≤11. The complex-type structures are further preferentially identified by sensitivity to endoglycosidase digestion, preferentially N-glycosidase F detachment from glycoproteins. The complex-type structures are further preferentially identified in NMR spectroscopy based on characteristic resonances of the Manα3(Manα6)Manβ4GlcNAcβ4GlcNAc N-glycan core structure and GlcNAc residues attached to the Manα3 and/or Manα6 residues.

Beside Mannose-type glycans the preferred N-linked glycomes include GlcNAcβ2-type glycans including Complex type glycans comprising only GlcNAcβ2-branches and Hydrid type glycan comprising both Mannose-type branch and GlcNAcβ2-branch.

GlcNAcβ2-type Glycans

The invention revealed GlcNAcβ2Man structures in the glycomes according to the invention. Preferably GlcNAcβ2Man-structures comprise one or several of GlcNAcβ2Manα-structures, more preferably GlcNAcβ2Manα3 or GlcNAcβ2Manα6-structure.

The Complex type glycans of the invention comprise preferably two GlcNAcβ2Manα structures, which are preferably GlcNAcβ2Manα3 and GlcNAcβ2Manα6-. The Hybrid type glycans comprise preferably GlcNAcβ2Manα3-structure.

The present invention is directed to at least one of natural oligosaccharide sequence structures and structures truncated from the reducing end of the N-glycan according to the Formula GNβ2

$$[R_1GN\beta2]_{n1}[M\alpha3]_{n2}\{[R_3]_{n3}$$
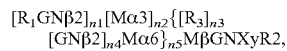
$$[GN\beta2]_{n4}M\alpha6\}_{n5}M\beta GNXyR_2,$$

with optionally one or two or three additional branches according to formula $[R_xGN\beta z]_{nx}$ linked to Mα6-, Mα3-, or Mβ4 and $R_x$ may be different in each branch wherein n1, n2, n3, n4, n5 and nx, are either 0 or 1, independently, with the proviso that when n2 is 0 then n1 is 0 and when n3 is 1 or/and n4 is 1 then n5 is also 1, and at least n1 or n4 is 1, or n3 is 1, when n4 is 0 and n3 is 1 then $R_3$ is a mannose type substituent or nothing and wherein X is glycosidically linked disaccharide epitope β4(Fucα6)$_n$GN, wherein n is 0 or 1, or X is nothing and y is anomeric linkage structure α and/or β or linkage from derivatized anomeric carbon, and $R_1$, $R_x$ and $R_3$ indicate independently one, two or three, natural substituents linked to the core structure, $R_2$ is reducing end hydroxyl, chemical reducing end derivative or natural asparagine N-glycoside derivative such as asparagine N-glycosides including asparagines N-glycoside aminoacids and/or peptides derived from protein.

[ ] indicate groups either present or absent in a linear sequence. { } indicates branching which may be also present or absent.

Elongation of GlcNAcβ2-Type Structures, Complex/hydrid Type Structures

The substituents $R_1$, $R_x$ and $R_3$ may form elongated structures. In the elongated structures $R_1$, and $R_x$ represent substituents of GlcNAc (GN) and $R_3$ is either substituent of GlcNAc or when n4 is 0 and n3 is 1 then R3 is a mannose type substituent linked to mannose a 6-branch forming a Hybrid type structure. The substituents of GN are monosaccharide Gal, GalNAc, or Fuc or and acidic residue such as sialic acid or sulfate or fosfate ester.

GlcNAc or GN may be elongated to N-acetyllactosaminyl also marked as GalβGN or di-N-acetyllactosdiaminyl GalNAcβGlcNAc preferably GalNAcβ4GlcNAc. LNβ2M can be further elongated and/or branched with one or several other monosaccharide residues such as by galactose, fucose, SA or LN-unit(s) which may be further substituted by SAα-structures, and/or Mα6 residue and/or Mα3 residues can be further substituted one or two β6-, and/or β4-linked additional branches according to the formula,
and/or either of Mα6 residue or Mα3 residue may be absent and/or Mα6-residue can be additionally substitutes other Manα units to form a hybrid type structures
and/or Manβ4 can be further substituted by GNβ4,
and/or SA may include natural substituents of sialic acid and/or it may be substituted by other SA-residues preferably by α8- or α9-linkages.

The SAα-groups are linked to either 3- or 6-position of neighboring Gal residue or on 6-position of GlcNAc, preferably 3- or 6-position of neighboring Gal residue. In separately preferred embodiments the invention is directed structures comprising solely 3-linked SA or 6-linked SA, or mixtures thereof.

Hybrid Type Structures

According to the present invention, hybrid-type or monoantennary structures are preferentially identified by mass spectrometry, preferentially based on characteristic monosaccharide compositions, wherein HexNAc=3 and Hex≥2. In a more preferred embodiment of the present invention 2≤Hex≤11, and in an even more preferred embodiment of the present invention 2≤Hex≤9. The hybrid-type structures are further preferentially identified by sensitivity to exoglycosidase digestion, preferentially α-mannosidase digestion when the structures contain non-reducing terminal α-mannose residues and Hex≥3, or even more preferably when Hex≥4, and to endoglycosidase digestion, preferentially N-glycosidase F detachment from glycoproteins. The hybrid-type structures are further preferentially identified in NMR spectroscopy based on characteristic resonances of the Manα3(Manα6)Manβ4GlcNAcβ4GlcNAc N-glycan core structure, a GlcNAcβ residue attached to a Manα residue in the N-glycan core, and the presence of characteristic resonances of non-reducing terminal α-mannose residue or residues.

The monoantennary structures are further preferentially identified by insensitivity to α-mannosidase digestion and by sensitivity to endoglycosidase digestion, preferentially N-glycosidase F detachment from glycoproteins. The monoantennary structures are further preferentially identified in NMR spectroscopy based on characteristic resonances of the Manα3Manβ4GlcNAcβ4GlcNAc N-glycan core structure, a GlcNAcβ residue attached to a Manα residue in the N-glycan core, and the absence of characteristic resonances of further non-reducing terminal α-mannose residues apart from those arising from a terminal α-mannose residue present in a ManαManβ sequence of the N-glycan core.

The present invention is directed to at least one of natural oligosaccharide sequence structures and structures truncated from the reducing end of the N-glycan according to the Formula HY1

$$R_1GN\beta 2M\alpha 3\{[R_3]_{n3}M\alpha 6\}M\beta 4GNXyR_2,$$

wherein n3, is either 0 or 1, independently,
AND
wherein X is glycosidically linked disaccharide epitope β4(Fucα6)$_n$GN, wherein n is 0 or 1, or X is nothing and y is anomeric linkage structure α and/or β or linkage from derivatized anomeric carbon, and $R_1$ indicate nothing or substituent or substituents linked to GlcNAc, $R_3$ indicates nothing or Mannose-substituent(s) linked to mannose residue, so that each of $R_1$, and $R_3$ may correspond to one, two or three, more preferably one or two, and most preferably at least one natural substituents linked to the core structure, $R_2$ is reducing end hydroxyl, chemical reducing end derivative or natural asparagine N-glycoside derivative such as asparagine N-glycosides including asparagines N-glycoside aminoacids and/or peptides derived from protein.

[ ] indicate groups either present or absent in a linear sequence. { } indicates branching which may be also present or absent.

Preferred Hybrid Type Structures

The preferred hydrid type structures include one or two additional mannose residues on the preferred core structure.

$$R_1GN\beta 2M\alpha 3\{[M\alpha 3]_{m1} ([M\alpha 6])_{m2}M\alpha 6\}M\beta 4GNXyR_2, \quad \text{Formula HY2}$$

wherein n3, is either 0 or 1, and m1 and m2 are either 0 or 1, independently,
{ } and ( ) indicates branching which may be also present or absent,
other variables are as described in Formula HY1.

Furthermore the invention is directed to structures comprising additional lactosamine type structures on GNβ2-branch. The preferred lactosamine type elongation structures includes N-acetyllactosamines and derivatives, galactose, GalNAc, GlcNAc, sialic acid and fucose.

Preferred structures according to the formula HY2 include:
Structures containing non-reducing end terminal GlcNAc
As a specific preferred group of glycans
GNβ2Mα3{Mα3Mα6}Mβ4GNXyR$_2$,
GNβ2Mα3{Mα6Mα6}Mβ4GNXyR$_2$,
GNβ2Mα3{Mα3(Mα6)Mα6)Mβ4GNXyR$_2$,
and/or elongated variants thereof
R$_1$GNβ2Mα3{Mα3Mα6}Mβ4GNXyR$_2$,
R$_1$GNβ2Mα3{Mα6Mα6}Mβ4GNXyR$_2$,
R$_1$GNβ2Mα3{Mα3(Mα6)Mα6}Mβ4GNXyR$_2$, $$[R_1Gal[NAc]_{o2}\beta z]_{o1}GN\beta 2M\alpha 3\{[M\alpha 3]_{m1} [(M\alpha 6)]_{m2}M\alpha 6\}_{n5}M\beta 4GNXyR_2, \quad \text{Formula HY3}$$

wherein n1, n2, n3, n5, m1, m2, o1 and o2 are either 0 or 1, independently,
z is linkage position to GN being 3 or 4 in a preferred embodiment 4,
$R_1$ indicates on or two a N-acetyllactosamine type elongation groups or nothing,
{ } and ( ) indicates branching which may be also present or absent,
other variables are as described in Formula HY1.

Preferred structures according to the formula HY3 include especially
structures containing non-reducing end terminal Galβ, preferably Galβ3/4 forming a terminal N-acetyllactosamine structure. These are preferred as a special group of Hybrid type structures, preferred as a group of specific value in characterization of balance of Complex N-glycan glycome and High mannose glycome:
GalβzGNβ2Mα3{Mα3Mα6}Mβ4GNXyR$_2$,
GalβzGNβ2Mα3{Mα6Mα6}Mβ4GNXyR$_2$,
GalβzGNβ2Mα3{Mα3(Mα6)Mα6}Mβ4GNXyR$_2$,
and/or elongated variants thereof preferred for carrying additional characteristic terminal structures useful for characterization of glycan materials
R$_1$GalβzGNβ2Mα3{Mα3Mα6}Mβ4GNXyR$_2$,
R$_1$GalβzGNβ2Mα3{Mα6Mα6}Mβ4GNXyR$_2$, $R_1Gal\beta zGN\beta 2M\alpha 3\{M\alpha 3(M\alpha 6)M\alpha 6\}M\beta 4GNXyR_2$. Preferred elongated materials include structures wherein $R_1$ is a sialic acid, more preferably NeuNAc or NeuGc.

Complex N-Glycan Structures

The present invention is directed to at least one of natural oligosaccharide sequence structures and structures truncated from the reducing end of the N-glycan according to the Formula CO1

$$[R_1GN\beta 2]_{n1}[M\alpha 3]_{n2}\{[R_3GN\beta 2]_{n4}M\alpha 6\}_{n5}M\beta 4GNXyR_2$$

with optionally one or two or three additional branches according to formula $[R_xGN\beta z]_{nx}$ linked to $M\alpha 6$-, $M\alpha 3$-, or $M\beta 4$ and $R_x$ may be different in each branch wherein n1, n2, n4, n5 and nx, are either 0 or 1, independently, with the proviso that when n2 is 0 then n1 is 0 and when n4 is 1 then n5 is also 1, and at least n1 is 1 or n4 is 1, and at least either of n1 and n4 is 1 and wherein X is glycosidically linked disaccharide epitope $\beta 4(Fuc\alpha 6)_nGN$, wherein n is 0 or 1, or X is nothing and y is anomeric linkage structure $\alpha$ and/or $\beta$ or linkage from derivatized anomeric carbon, and $R_1$, $R_x$ and $R_3$ indicate independently one, two or three, natural substituents linked to the core structure, $R_2$ is reducing end hydroxyl, chemical reducing end derivative or natural asparagine N-glycoside derivative such as asparagine N-glycosides including asparagines N-glycoside aminoacids and/or peptides derived from protein.

[ ] indicate groups either present or absent in a linear sequence. { } indicates branching which may be also present or absent.

Preferred Complex Type Structures

Incomplete Monoantennary N-Glycans

The present invention revealed incomplete Complex monoantennary N-glycans, which are unusual and useful for characterization of glycomes according to the invention. The most of the in complete monoantennary structures indicate potential degradation of biantennary N-glycan structures and are thus preferred as indicators of cellular status. The incomplete Complex type monoantennary glycans comprise only one $GN\beta 2$-structure.

The invention is specifically directed to structures are according to the Formula CO1 above when only n1 is 1 or n4 is one and mixtures of such structures.

The preferred mixtures comprise at least one monoantennary complex type glycans

A) with single branches from a likely degradative biosynthetic process:

$R_1GN\beta 2M\alpha 3\beta 4GNXyR_2$ $R_3GN\beta 2M\alpha 6M\beta 4GNXyR_2$ and B) with two branches comprising mannose branches B1) $R_1GN\beta 2M\alpha 3\{M\alpha 6\}_{n5}M\beta 4GNXyR_2$ B2) $M\alpha 3\{R_3GN\beta 2M\alpha 6\}_{n5}M\beta 4GNXyR_2$ The structure B2 is preferred with A structures as product of degradative biosynthesis, it is especially preferred in context of lower degradation of $M\alpha n\alpha 3$-structures. The structure B1 is useful for indication of either degradative biosynthesis or delay of biosynthetic process Biantennary and Multiantennary Structures The inventors revealed a major group of biantennary and multiantennary N-glycans from cells according to the invention, the preferred biantennary and multiantennary structures comprise two $GN\beta 2$ structures.

These are preferred as an additional characteristics group of glycomes according to the invention and are represented according to the Formula CO2:

$$R_1GN\beta 2M\alpha 3\{R_3GN\beta 2M\alpha 6\}M\beta GNXyR_2$$

with optionally one or two or three additional branches according to formula $[R_xGN\beta z]_{nx}$ linked to $M\alpha 6$-, $M\alpha 3$-, or $M\beta 4$ and $R_x$ may be different in each branch wherein nx is either 0 or 1, and other variables are according to the Formula CO1.

Preferred Biantennary Structure

A biantennary structure comprising two terminal $GN\beta$-epitopes is preferred as a potential indicator of degradative biosynthesis and/or delay of biosynthetic process. The more preferred structures are according to the Formula CO2 when $R_1$ and $R_3$ are nothing.

Elongated Structures

The invention revealed specific elongated complex type glycans comprising Gal and/or GalNAc-structures and elongated variants thereof. Such structures are especially preferred as informative structures because the terminal epitopes include multiple informative modifications of lactosamine type, which characterize cell types according to the invention. The present invention is directed to at least one of natural oligosaccharide sequence structure or group of structures and corresponding structure(s) truncated from the reducing end of the N-glycan according to the Formula CO3

$$[R_1Gal[NAc]_{o2}\beta z2]_{o1}GN\beta 2M\alpha 3\{[R_1Gal[NAc]_{o4}\beta z2]_{o3}GN\beta 2M\alpha 6\}M\beta 4GNXyR_2,$$

with optionally one or two or three additional branches according to formula $[R_xGN\beta z1]_{nx}$ linked to $M\alpha 6$-, $M\alpha 3$-, or $M\beta 4$ and $R_x$ may be different in each branch wherein nx, o1, o2, o3, and o4 are either 0 or 1, independently, with the provisio that at least o1 or o3 is 1, in a preferred embodiment both are 1 z2 is linkage position to GN being 3 or 4, in a preferred embodiment 4, z1 is linkage position of the additional branches.

$R_1$, Rx and $R_3$ indicate on or two a N-acetyllactosamine type elongation groups or nothing, { } and ( ) indicates branching which may be also present or absent other variables are as described in Formula CO1.

Galactosylated Structures

The inventors characterized especially directed to digalactosylated structure $Gal\beta zGN\beta 2M\alpha 3\{Gal\beta zGN\beta 2M\alpha 6\}M\beta 4GNXyR_2$, and monogalactosylated structures:

$Gal\beta zGN\beta 2M\alpha 3\{GN\beta 2M\alpha 6\}M\beta 4GNXyR_2$, $GN\beta 2M\alpha 3\{Gal\beta zGN\beta 2M\alpha 6\}M\beta 4GNXyR_2$, and/or elongated variants thereof preferred for carrying additional characteristic terminal structures useful for characterization of glycan materials $R_1Gal\beta zGN\beta 2M\alpha 3\{R_3Gal\beta zGN\beta 2M\alpha 6\}M\beta 4GNXyR_2$ $R_1Gal\beta zGN\beta 2M\alpha 3\{GN\beta 2M\alpha 6\}M\beta 4GNXyR_2$, and $GN\beta 2M\alpha 3\{R_3Gal\beta zGN\beta 2M\alpha 6\}M\beta 4GNXyR_2$.

Preferred elongated materials include structures wherein $R_1$ is a sialic acid, more preferably NeuNAc or NeuGc.

LacdiNAc-Structure Comprising N-Glycans

The present invention revealed for the first time LacdiNAc, GalNacbGlcNAc structures from the cell according to the invention. Preferred N-glycan lacdiNAc structures are included in structures according to the Formula CO1, when at least one the variable o2 and o4 is 1.

The Major Acidic Glycan Types

The acidic glycomes mean glycomes comprising at least one acidic monosaccharide residue such as sialic acids (especially NeuNAc and NeuGc) forming sialylated glycome, HexA (especially GlcA, glucuronic acid) and/or acid modification groups such as phosphate and/or sulphate esters.

According to the present invention, presence of phosphate and/or sulphate ester (SP) groups in acidic glycan structures is preferentially indicated by characteristic monosaccharide compositions containing one or more SP groups. The preferred compositions containing SP groups include those formed by adding one or more SP groups into non-SP group containing glycan compositions, while the most preferential compositions containing SP groups according to the present invention are selected from the compositions described in the acidic N-glycan fraction glycan group tables. The presence of phosphate and/or sulphate ester groups in acidic glycan structures is preferentially further indicated by the characteristic fragments observed in fragmentation mass spectrometry corresponding to loss of one or more SP groups, the insensitivity of the glycans carrying SP groups to sialidase digestion. The presence of phosphate and/or sulphate ester groups in acidic glycan structures is preferentially also indicated in positive ion mode mass spectrometry by the tendency of such glycans to form salts such as sodium salts as described in the Examples of the present invention. Sulphate and phosphate ester groups are further preferentially identified based on their sensitivity to specific sulphatase and phosphatase enzyme treatments, respectively, and/or specific complexes they form with cationic probes in analytical techniques such as mass spectrometry.

Complex N-Glycan Glycomes, Sialylated

The present invention is directed to at least one of natural oligosaccharide sequence structures and structures truncated from the reducing end of the N-glycan according to the Formula

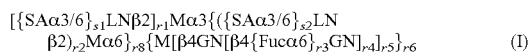

with optionally one or two or three additional branches according to formula

wherein r1, r2, r3, r4, r5, r6, r7 and r8 are either 0 or 1, independently, wherein s1, s2 and s3 are either 0 or 1, independently,
with the proviso that at least r1 is 1 or r2 is 1, and at least one of s1, s2 or s3 is 1.

LN is N-acetyllactosaminyl also marked as GalβGN or di-N-acetyllactosdiaminyl GalNAcβGlcNAc preferably GalNAcβ4GlcNAc, GN is GlcNAc, M is mannosyl-, with the proviso LNβ2M or GNβ2M can be further elongated and/or branched with one or several other monosaccharide residues such as by galactose, fucose, SA or LN-unit(s) which may be further substituted by SAα-structures,
and/or one LNβ can be truncated to GNβ
and/or Mα6 residue and/or Mα3 residues can be further substituted one or two β6-, and/or β4-linked additional branches according to the formula,
and/or either of Mα6 residue or Mα3 residue may be absent and/or Mα6-residue can be additionally substitutes other Manα units to form a hybrid type structures
and/or Manβ4 can be further substituted by GNβ4,
and/or SA may include natural substituents of sialic acid and/or it may be substituted by other SA-residues preferably by α8- or α9-linkages.
( ), { }, [ ] and [ ] indicate groups either present or absent in a linear sequence. { } indicates branching which may be also present or absent.

The SAα-groups are linked to either 3- or 6-position of neighboring Gal residue or on 6-position of GlcNAc, preferably 3- or 6-position of neighboring Gal residue. In separately preferred embodiments the invention is directed structures comprising solely 3-linked SA or 6-linked SA, or mixtures thereof. In a preferred embodiment the invention is directed to glycans wherein r6 is 1 and r5 is 0, corresponding to N-glycans lacking the reducing end GlcNAc structure.

The LN unit with its various substituents can in a preferred general embodiment represented by the formula:

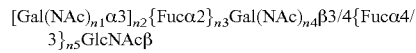

wherein n1, n2, n3, n4, and n5 are independently either 1 or 0, with the provisio that
the substituents defined by n2 and n3 are alternative to presence of SA at the non-reducing end terminal
the reducing end GlcNAc-unit can be further β3- and/or β6-linked to another similar LN-structure forming a poly-N-acetyllactosamine structure
with the provision that for this LN-unit n2, n3 and n4 are 0, the Gal(NAc)β and GlcNAcβ units can be ester linked a sulphate ester group,
( ), and [ ] indicate groups either present or absent in a linear sequence; { } indicates branching which may be also present or absent
LN unit is preferably Galβ4GN and/or Galβ3GN. The inventors revealed that early human cells can express both types of N-acetyllactosamine, the invention is especially directed to mixtures of both structures. Furthermore the invention is directed to special relatively rear type 1 N-acetyllactosamines, Galβ3GN, without any non-reducing end/site modification, also called lewis c-structures, and substituted derivatives thereof, as novel markers of early human cells.

Occurrence of Structure Groups in Preferred Cell Types

In the present invention, glycan signals with preferential monosaccharide compositions can be grouped into structure groups based on classification rules described in the present invention. The present invention includes parallel and overlapping classification systems that are used for the classification of the glycan structure groups.

Glycan signals isolated from the N-glycan fractions from the cell types studied in the present invention are grouped into glycan structure groups based on their preferential monosaccharide compositions according to the invention, in Table 46 for neutral N-glycan fractions and Table 47 for acidic N-glycan fractions. Taken together, the analyses revealed that all the structure groups according to the invention are present in the studied cell types.

The invention is specifically directed to terminal HexNAc groups and/or other structure groups and/or combinations thereof as shown in the Examples describing and analysis of stem cell including hESC glycan structure classification. Non-reducing terminal HexNAc residues could be liberated from the cell types studied in the present invention by specific combinations of β-hexosaminidase and β-glucosaminidase digestions, confirming the structural group classification of the present invention, and identifying terminal HexNAc residues as β-GlcNAc and/or β-GalNAc residues in the studied cell types. According to the present invention, specifically in hESC and cells differentiated therefrom the terminal HexNAc residues preferentially include both β-GlcNAc and β-GalNAc residues, more preferentially terminal β-GlcNAc linkages including bisecting GlcNAc linkages and other hybrid-type and complex-type GlcNAc linkages according to the present invention, and terminal GalNAc linkages including β4-linked GalNAc and most preferentially GalNAcβ4GlcNAcβ (LacdiNAc) structures according to the present invention.

Integrated Glycome Analysis Technology

The invention is directed to analysis of present cell materials based on single or several glycans (glycome profile) of cell materials according to the invention. The analysis of multiple glycans is preferably performed by physical analysis methods such as mass spectrometry and/or NMR.

The invention is specifically directed to integrated analysis process for glycomes, such as total glycomes and cell surface glycomes. The integrated process represent various novel aspects in each part of the process. The methods are especially directed to analysis of low amounts of cells. The integrated analysis process includes A) preferred preparation of substrate cell materials for analysis, including one or several of the methods: use of a chemical buffer solution, use of detergents, chemical reagents and/or enzymes.

B) release of glycome(s), including various subglycome type based on glycan core, charge and other structural features, use of controlled reagents in the process C) purification of glycomes and various subglycomes from complex mixtures D) preferred glycome analysis, including profiling methods such as mass spectrometry and/or NMR spectroscopy E) data processing and analysis, especially comparative methods between different sample types and quantitative analysis of the glycome data.

A. Preparation of Cell Materials

Cell substrate material and its preparation for total and cell surface glycome analysis. The integrated glycome analysis includes preferably a cell preparation step to increase the availability of cell surface glycans. The cell preparation step preferably degrades either total cell materials or cell surface to yield a glycome for more effective glycan release. The degradation step preferably includes methods of physical degradation and/or chemical degradation. In a preferred embodiment at least one physical and one chemical degradation methods are combined, more preferably at least one physical method is combined with at least two chemical methods, even more preferably with at least three chemical methods.

The physical degration include degration by energy including thermal and/or mechanical energy directed to the cells to degrade cell structures such as heating, freezing, sonication, and pressure. The chemical degradation include use of chemicals and specific concentrations of chemicals for disruption of cells preferably detergents including ionic and neutral detergents, chaotropic salts, denaturing chemicals such as urea, and non-physiological salt concentrations for distruption of the cells.

The glycome analysis according to the invention is divided to two methods including Total cell glycomes, and Cell surface glycomes. The production of Total cell glycomes involves degradation of cells by physical and/or chemical degradation methods, preferably at least by chemical methods, more preferably by physical and chemical methods. The Cell surface glycomes is preferably released from cell surface preserving cell membranes intact or as intact as possible, such methods involve preferably at least one chemical method, preferably enzymatic method. The cell surface glycomes may be alternatively released from isolated cell membranes, this method involves typically chemical and/or physical methods similarly as production of total cell glycomes, preferably at least use of detergents.

a. Total Cell Glycomes

The present invention revealed special methods for effective purification of released glycans from total cell derived materials so that free oligosaccharides can be obtained. In a preferred embodiment a total glycome is produced from a cell sample, which is degraded to form more available for release of glycans. A preferred degraded form of cells is detergent lysed cells optionally involving physical distruption of cell materials.

Preferred detergents and reaction conditions include, a1) ionic detergents, preferably SDS type anionic detergent comprising an anionic group such as sulfate and an alkyl chain of 8-16 carbon atoms, more preferably the anionic detergent comprise 10-14 carbon atoms and it is most preferably sodium dodecyl sulfate (SDS), and/or a2) non-ionic detergents such as alkylglycosides comprising a hexose and 4-12 carbon alkyl chain more preferably the alkyl chain comprises a hexoses being galactose, glucose, and/or mannose, more preferably glucose and/or mannose and the alkyl comprises 6-10 carbon atoms, preferably the non-ionic detergent is octylglucoside It is realized that various detergent combinations may be produced and optimized. The combined use of an ionic, preferably anionic, and non-ionic detergents according to the invention is especially preferred.

Preferred Cell Preparation Methods for Production of Total Cell Glycome

The preferred methods of cell degration for Total cell glycomes include physical degration including at least heat treatment heat and chemical degration by a detergent method or by a non-detergent method preferably enzymatic degradation, preferably heat treatment. Preferably two physical degradation methods are included.

A Preferred Non-Detergent Method Includes

A non-detergent method is preferred for avoiding detergent in later purification. The preferred non-detergent method involves physical degradation of cells preferably pressure and or by heat and a chemical degradation by protease. A preferred non-detergent method includes:

i) cell degradation by physical methods, for example by pressure methods such as by French press.

The treatment is preferably performed quickly in cold temperatures, preferably at 0-2 degrees of Celsius, and more preferably at about 0 or 1 degree of celsius and/or in the presence of glycosidase inhibitors.

ii) The degraded cells are further treated with chemical degradation, preferably by effective general protease, more preferably trypsin is used for the treatment. Preferred trypsin preparation according to the invention does not cause glycan contamination to the sample/does not contain glycans releasable under the reaction conditions.

iii) optionally the physical degradation and chemical degradation are repeated.

iv) At the end of protease treatment the sample is boiled for further denaturing the sample and the protease. The boiling is performed at temperature denaturing/degrading further the sample and the protease activity (conditions thus depend on the protease used) preferably about 100 degrees Celsius for time enough for denaturing protease activity preferably about 10-20 minutes for trypsin, more preferably about 15 minutes.

Preferred Detergent Method for Production of Total Glycomes

The invention is in another preferred embodiment directed to detergent based method for lysing cells. The invention includes effective methods for removal of detergents in later purification steps. The detergent methods are especially preferred for denaturing proteins, which may bind or degrade glycans, and for degrading cell membranes to increase the accessibility of intracellular glycans.

For the detergent method the cell sample is preferably a cell pellet produced at cold temperature by centrifuging cells but avoiding distruption of the cells, optionally stored frozed and melted on ice. Optionally glycosidase inhibitors are used during the process.

The method includes following steps:

i) production of cell pellet preferably by centrifugation, ii) lysis by detergent on ice, the detergent is preferably an anionic detergent according to the invention, more preferably SDS. The concentration of the detergent is preferably between about 0.1% and 5%, more preferably between 0.5%-3%, even more preferably between 0.5-1.5% and most preferably about 1% and the detergent is SDS (or between 0.9-1.1%). the solution is preferably produced in ultrapure water, iii) mixing by effective degradation of cells, preferably mixing by a Vortex-mixer as physical degradation step, iv) boiling on water bath, preferably for 3-10 min, most preferably about 5 min (4-6 min) as second physical degradation step, it is realized that even longer boiling may be performed for example up to 30 min or 15 min, but it is not optimal because of evaporation sample v) adding one volume of non-ionic detergent, preferably alkyl-glycoside detergent according to the invention, most preferably n-octyl-β-D-glucoside, the preferred amount of the detergent is about 5-15% as water solution, preferably about 10% of octyl-glucoside. The non-ionic detergent is especially preferred in case an enzyme sensitive to SDS, such as a N-glycosidase, is to be used in the next reaction step. and vi) incubation at room temperature for about 5 min to about 1-4 hours, more preferably less than half an hour, and most preferably about 15 min.

Preferred Amount of Detergents in the Detergent Method

Preferably the anionic detergent and cationic detergent solutions are used in equal volumes. Preferably the solutions are about 1% SDS and about 10% octyl-glucoside. The preferred amounts of the solutions are preferably from 0.1 µl to about 2 µl, more preferably 0.15 µl to about 1.5 µl per and most preferably from 0.16 µl to 1 µl per 100 000 cells of each solution. Lower amounts of the detergents are preferred if possible for reduction of the amount of detergent in later purification, highest amounts in relation to the cell amounts are used for practical reasons with lowest volumes. It is further realized that corresponding weight amounts of the detergents may be used in volumes of about 10% to about 1000%, or from about 20% to about 500% and even more effectively in volumes from 30% to about 300% and most preferably in volumes of range from 50% to about 150% of that described. It is realized that critical micellar concentration based effects may reduce the effect of detergents at lowest concentrations.

In a preferred embodiment a practical methods using tip columns as described in the invention uses about 1-3 µl of each detergent solution, more preferably 1.5-2.5 µl, and most preferably about 2 µl of the preferred detergent solutions or corresponding detergent amounts are used for about 200 000 or less cells (preferably between 2000 and about 250 000 cells, more preferably from 50 000 to about 250 000 cells and most preferably from 100 000 to about 200 000 cells). Another practical method uses about 2-10 µl of each detergent solution, more preferably 4-8 µl, and most preferably about 5 µl (preferably between 4 and 6 µl and more preferably between 4.5 and 5.5 µl) of detergent solutions or corresponding amount of the detergents for lysis of cell of a cell amount from about 200 000-3 million cells (preferred more exact ranges include 200 000-3.5 million, 200 000 to 3 million and 200 000 to 2.5 million cells), preferably a fixed amount (specific amount of microliters preferably with the accuracy of at least 0.1 microliter) in a preferred range such as of 5.0 µl is used for the wider range of cells 200 000-3 million. It was invented that is possible to handle similarity wider range of materials. It is further realized that the method can be optimized so that exact amount of detergent, preferably within the ranges described, is used for exact amount of cells, such method is preferably an automized when there is possible variation in amounts of sample cells.

b. Cell Surface Glycomes

In another preferred embodiment the invention is directed to release of glycans from intact cells and analysis of released cell surface glycomes. The present invention is directed to specific buffer and enzymatic cell pre-modification conditions that would allow the efficient use of enzymes for release and optionally modification and release of glycans.

B. The Glycan Release Methods

The invention is directed to various enzymatic and chemical methods to release glycomes. The release step is not needed for soluble glycomes according to the invention. The invention further revealed soluble glycome components which can be isolated from the cells using methods according to the invention.

C. Purification of Glycans from Cell Derived Materials

The purification of glycome materials form cell derived molecules is a difficult task. It is especially difficult to purify glycomes to obtain picomol or low nanomol samples for glycome profiling by mass spectrometry or NMR-spectrometry. The invention is especially directed to production of material allowing quantitative analysis over a wide mass range. The invention is specifically directed to the purification of non-derivatized or reducing end derivatized glycomes according to the invention and glycomes containing specific structural characteristics according to the invention. The structural characteristics were evaluated by the preferred methods according to the invention to produce reproducible and quantitative purified glycomes.

Glycan Purification Process Steps

The glycan purification method according to the present invention consists of at least one of purification options, preferably in specific combinations described below, including one or several of following the following purification process steps in varying order:

6) Precipitation-extraction;
7) Ion-exchange;
8) Hydrophobic interaction;
9) Hydrophilic interaction; and
10) Affinity to carbon materials especially graphitized carbon.

Prepurification and Purification Process Steps

In general the purification steps may be divided to two major categories:

Prepurification steps to remove major contaminations and purification steps usually directed to specific binding and optionally fractionation og glycomes a) Prepurification to Remove Non-Carbohydrate Impurities The need for prepurification depends on the type and amounts of the samples and the amounts of impurities present. Certain samples it is possible to omit all or part of the prepurification steps. The prepurification steps are aimed for removal of major non-carbohydrate impurities by separating the impurity and the glycome fraction(s) to be purified to different phases by precipitation/extraction or binding to chromatography matrix and the separating the impurities from the glycome fraction(s).

The prepurification steps include one, two or three of following major steps:

Precipitation-extraction, Ion-exchange, Hydrophobic interaction.

The precipitation and/or extraction is based on the high hydrophilic nature of glycome compositions and components, which is useful for separation from different cellular components and chemicals. The prepurification ion exchange chromatography is directed to removal of classes molecules with different charge than the preferred glycome or glycome fraction to be studied. This includes removal of salt ions and aminoacids, and peptides etc. The glycome may comprise only negative charges or in more rare case also only positive charges and the same charge is selected for the chromatography matrix for removal of the impurities for the same charge without binding the glycome at prepurification.

In a preferred embodiment the invention is directed to removal of cationic impurities from glycomes containing neutral and/or negatively charged glycans. The invention is further directed to use both anion and cation exchange for removal of charged impurities from non-charged glycomes. The preferred ion exchange and cation exchange materials includes polystyrene resins such as Dowex resins.

The hydrophilic chromatography is preferably aimed for removal of hydrophobic materials such as lipids detergents and hydrophobic protein materials.

It is realized that different combinations of the prepurification are useful depending on the cell preparation and sample type. Preferred combinations of the prepurification steps include: Precipitation-extraction and Ion-exchange; Precipitation-extraction and Hydrophobic interaction; and Ion-exchange and Hydrophobic interaction. The two prepurification steps are preferably performed in the given order.

Purification Steps Including Binding and Optionally Fractionation of Glycomes

The purification steps utilize two major concepts for binding to carbohydrates and combinations thereof: a) Hydrophilic interactions and b) Ion exchange a) Hydrophilic Interactions The present invention is specifically directed to use of matrices with repeating polar groups with affinity for carbohydrates for purification of glycome materials according to the invention in processes according to the invention. The hydrophilic interaction material may include additional ion exchange properties.

The preferred hydrophilic interaction materials includes carbohydrate materials such as carbohydrate polymers in presence of non-polar organic solvents. A especially preferred hydrophilic interaction chromatography matrix is cellulose.

A specific hydrophilic interaction material includes graphitized carbon. The graphitized carbon separates non-charged carbohydrate materials based mainly on the size on the glycan. There are also possible ion exchange effects. In a preferred embodiment the invention is directed to graphitized carbon chromatography of prepurified samples after desalting and removal of detergents.

The invention is specifically directed to purification of non-derivatized glycomes and neutral glycomes by cellulose chromatography. The invention is further directed to purification of non-derivatized glycomes and neutral glycomes by graphitized carbon chromatography. In a preferred embodiment the purification according to the invention includes both cellulose and graphitized carbon chromatography.

b) Ion Exchange

The glycome may comprise only negative charges or in more rare case also only positive charges. At purification stage the ion exchange material is selected to contain opposite charge than the glycome or glycome fraction for binding the glycome. The invention is especially directed to the use of anion exchange materials for binding of negatively charged Preferred ion exchange materials includes ion exchange and especially anion exchange materials includes polystyrene resins such as Dowex-resins, preferably quaternary amine resins anion exchange or sulfonic acid cation exchange resins It was further revealed that even graphitized carbon can be used for binding of negatively charged glycomes and the materials can be eluted from the carbon separately from the neutral glycomes or glycome fractions according to the invention.

The invention is specifically directed to purification of anionic glycomes by anion exchange chromatography.

The invention is specifically directed to purification of anionic glycomes by anion exchange chromatography.

The invention is further directed to purification of anionic glycomes by cellulose chromatography. The preferred anionic glycomes comprise sialic acid and/or sulfo/fosfo esters, more preferably both sialic acid and sulfo/fosfo esters. A preferred class of sulfo/fosfoester glycomes are complex type N-glycans comprising sulfate esters.

Prepurification and Purification Steps in Detail

1) Precipitation-Extraction may include precipitation of glycans or precipitation of contaminants away from the glycans. Preferred precipitation methods include:

1. Glycan material precipitation, for example acetone precipitation of glycoproteins, oligosaccharides, glycopeptides, and glycans in aqueous acetone, preferentially ice-cold over 80% (v/v) aqueous acetone; optionally combined with extraction of glycans from the precipitate, and/or extraction of contaminating materials from the precipitate;

2. Protein precipitation, for example by organic solvents or trichloroacetic acid, optionally combined with extraction of glycans from the precipitate, and/or extraction of contaminating materials from the precipitate;

3. Precipitation of contaminating materials, for example precipitation with trichloroacetic acid or organic solvents such as aqueous methanol, preferentially about ⅔ aqueous methanol for selective precipitation of proteins and other non-soluble materials while leaving glycans in solution;

2) Ion-Exchange may include ion-exchange purification or enrichment of glycans or removal of contaminants away from the glycans. Preferred ion-exchange methods include:

1. Cation exchange, preferably for removal of contaminants such as salts, polypeptides, or other cationizable molecules from the glycans; and 2. Anion exchange, preferably either for enrichment of acidic glycans such as sialylated glycans or removal of charged contaminants from neutral glycans, and also preferably for separation of acidic and neutral glycans into different fractions.

3) Hydrophilic Interaction may include purification or enrichment of glycans due to their hydrophilicity or specific adsorption to hydrophilic materials, or removal of contaminants such as salts away from the glycans. Preferred hydrophilic interaction methods include:

1. Hydrophilic interaction chromatography with specific organic or inorganic polar interaction materials, preferably for purification or enrichment of glycans and/or glycopeptides;

2. Preferably adsorption of glycans to carbohydrate materials, preferably to cellulose in hydrophobic solvents for their purification or enrichment, preferably to microcrystalline cellulose, and elution by polar solvents such as water and or alcohol, which is preferably ethanol or methanol. The solvent system for absorption comprise preferably i) a hydrophobic alcohol comprising about three to five carbon atoms, including propanols, butanols, and pentanols, more preferably being n-butanol;
　　ii) a hydrophilic alcohol such as methanol or ethanol, more preferably methanol, or a hydrophilic weak organic acid, preferably acetic acid and;
　　iii) water. The hydrophobic alcohol being the major constituent of the mixture with multifold excess to other components. The absorption composition is preferably using an n-butanol:methanol:water or similar solvent system for adsorption and washing the adsorbed glycans, in most preferred system n-butanol:methanol:water in relative volumes of 10:1:2. The preferred polar solvents for elution of the glycomes are water or water:ethanol or similar solvent system for elution of purified glycans from cellulose. Fractionation is possible by using first less polar elution solvent to elute a fraction of glycome compositions and the eluting rest by more polar solvent such as water 3. Affinity to carbon may include purification or enrichment of glycans due to their affinity or specific adsorption to specific carbon materials preferably graphitized carbon, or removal of contaminants away from the glycans. Preferred graphitized carbon affinity methods includes porous graphitized carbon chromatography.

Preferred purification methods according to the invention include combinations of one or more prepurification and/or purification steps. The preferred method include preferably at least two and more preferably at least three prepurification steps according to the invention. The preferred method include preferably at least one and more preferably at least two purification steps according to the invention. It is further realized that one prepurification step may be performed after a purification step or one purification step may be performed after a prepurification step. The method is preferably adjusted based on the amount of sample and impurities present in samples. Examples of the preferred combinations include the following combinations:

For neutral underivatized glycan purification:
A. 1. precipitation and/or extraction 2. cation exchange of contaminants, 3. hydrophobic adsorption of contaminants, and 4. hydrophilic purification, preferably by carbon, preferably graphitized carbon, and/or carbohydrate affinity purification of glycans.
B. 1. precipitation and/or extraction, 2. hydrophobic adsorption of contaminants 3. cation exchange of contaminants, 4. hydrophilic purification by carbon, preferably graphitized carbon, and/or carbohydrate affinity purification of glycans The preferred method variants further includes preferred variants when
　　1. both carbon and carbohydrate chromatography is performed in step 4,
　　2. only carbon chromatography is performed in step 4
　　3. only carbohydrate chromatography is performed in step 4
　　4. order steps three and four is exchanged
　　5. both precipitation and extraction are performed in prepurification step 2) For sialylated/acidic underivatized glycan purification:
The same methods are preferred but preferably both carbon and carbohydrate chromatography is performed in step 4. The carbohydrate affinity chromatography is especially preferred for acidic and/sialylated glycans. In a preferred embodiment for additional purification one or two last chromatography methods are repeated.

D. Analysis of the Glycomes

The present invention is specifically directed to detection various component in glycomes by specific methods for recognition of such components. The methods includes binding of the glycome components by specific binding agents according to the invention such as antibodies and/or enzymes, these methods preferably include labeling or immobilization of the glycomes. For effective analysis of the glycome a large panel of the binding agents are needed.

The invention is specifically directed to physicochemical profiling methods for exact analysis of glycomes. The preferred methods includes mass spectrometry and NMR-spectroscopy, which give simultaneously information of numerous components of the glycomes. In a preferred embodiment the mass spectrometry and NMR-spectroscopy methods are used in a combination.

E. Quantitative and Qualitative Analysis of Glycome Data

The invention revealed methods to create reproducible and quantitative profiles of glycomes over large mass ranges and degrees of polymerization of glycans. The invention further reveals novel methods for quantitative analysis of the glycomics data produced by mass spectrometry. The invention is specifically directed to the analysis of non-derivatized or reducing end derivatized glycomes according to the invention and the glycomes containing specific structural characteristics according to the invention.

The invention revealed effective means of comparison of glycome profiles from different cell types or cells with difference in cell status or cell types. The invention is especially directed to the quantitative comparison of relative amount of individual glycan signal or groups of glycan signals described by the invention.

The invention is especially directed to
i) calculating average value and variance values of signal or signals, which have obtained from several experiments/samples and which correspond to an individual glycan or glycan group according to the invention for a first cell sample and for a second cell sample
ii) comparing these with values derived for the corresponding signal(s)
iii) optionally calculating statistic value for testing the probability of similarity of difference of the values obtained for the cell types or estimating the similarity or difference based on the difference of the average and optionally also based on the variance values.
iv) preferably repeating the comparison one or more signals or signal groups, and further preferably performing combined statistical analysis to estimate the similarity and/or differences between the data set or estimating the difference or similarity
v) preferably use of the data for estimating the differences between the first and second cell samples indicating difference in cell status and/or cell type The invention is further directed to combining information of several quantitative comparisons of between corresponding signals by method of
i) calculating differences between quantitative values of corresponding most different glycan signals or glycan group signals, changing negative values to corresponding positive values, optionally multiplying selected signals by selected factors to adjust the weight of the signals in the calculation
ii) adding the positive difference values to a sum value
iii) comparing the sum values as indicators of cell status or type.

It was further revealed that there is characteristic signals that are present in certain cell types according to the invention but absent or practically absent in other cell types. The invention is therefore directed to the qualitative comparison of relative amount of individual glycan signal or groups of glycan signals described by the invention and observing signals present or absent/practically absent in a cell type. The invention is further directed to selection of a cut off value used for selecting absent or practically absent signals from a mass spectrometric data, for example the preferred cut off value may be selected in range of 0-3% of relative amount preferably the cut off value is less than 2%, or less than 1% or less than 0.5%. In a preferred embodiment the cut off value is adjusted or defined based on quality of the mass spectrum obtained, preferably based on the signal intensities and/or based on the number of signals observable.

The invention is further directed to automized qualitative and/or quantitative comparisons of data from corresponding signals from different samples by computer and computer programs processing glycome data produced according to the invention. The invention is further directed to raw data based analysis and neural network based learning system analysis as methods for revealing differences between the glycome data according to the invention.

Identification and Classification of Differences in Glycan Datasets

The present invention is specifically directed to analyzing glycan datasets and glycan profiles for comparison and characterization of different cell types. In one embodiment of the invention, glycan signals or signal groups associated with given cell type are selected from the whole glycan datasets or profiles and indifferent glycan signals are removed. The resulting selected signal groups have reduced background and less observation points, but the glycan signals most important to the resolving power are included in the selection. Such selected signal groups and their patterns in different sample types serve as a signature for the identification of the cell type and/or glycan types or biosynthetic groups that are typical to it. By evaluating multiple samples from the same cell type, glycan signals that have individual i.e. cell line specific variation can be excluded from the selection. Moreover, glycan signals can be identified that do not differ between cell types, including major glycans that can be considered as housekeeping glycans.

To systematically analyze the data and to find the major glycan signals associated with given cell type according to the invention, difference-indicating variables can be calculated for the comparison of glycan signals in the glycan datasets. Preferential variables between two samples include variables for absolute and relative difference of given glycan signal between the datasets from two cell types. Most preferential variables according to the invention are:
1. absolute difference $A=(S2-S1)$, and
2. relative difference $R=A/S1$,
wherein S1 and S2 are relative abundances of a given glycan signal in cell types 1 and 2, respectively.

It is realized that other mathematical solutions exist to express the idea of absolute and relative difference between glycan datasets, and the above equations do not limit the scope of the present invention. According to the present invention, after A and R are calculated for the glycan profile datasets of the two cell types, the glycan signals are thereafter sorted according to the values of A and R to identify the most significant differing glycan signals. High value of A or R indicates association with cell type 2, and vice versa. In the list of glycan data sorted independently by R and A, the cell-type specific glycans occur at the top and the bottom of the lists. More preferentially, if a given signal has high values of both A and R, it is more significant.

Preferred Representation of the Dataset when Comparing Two Cell Materials

Figure 41:
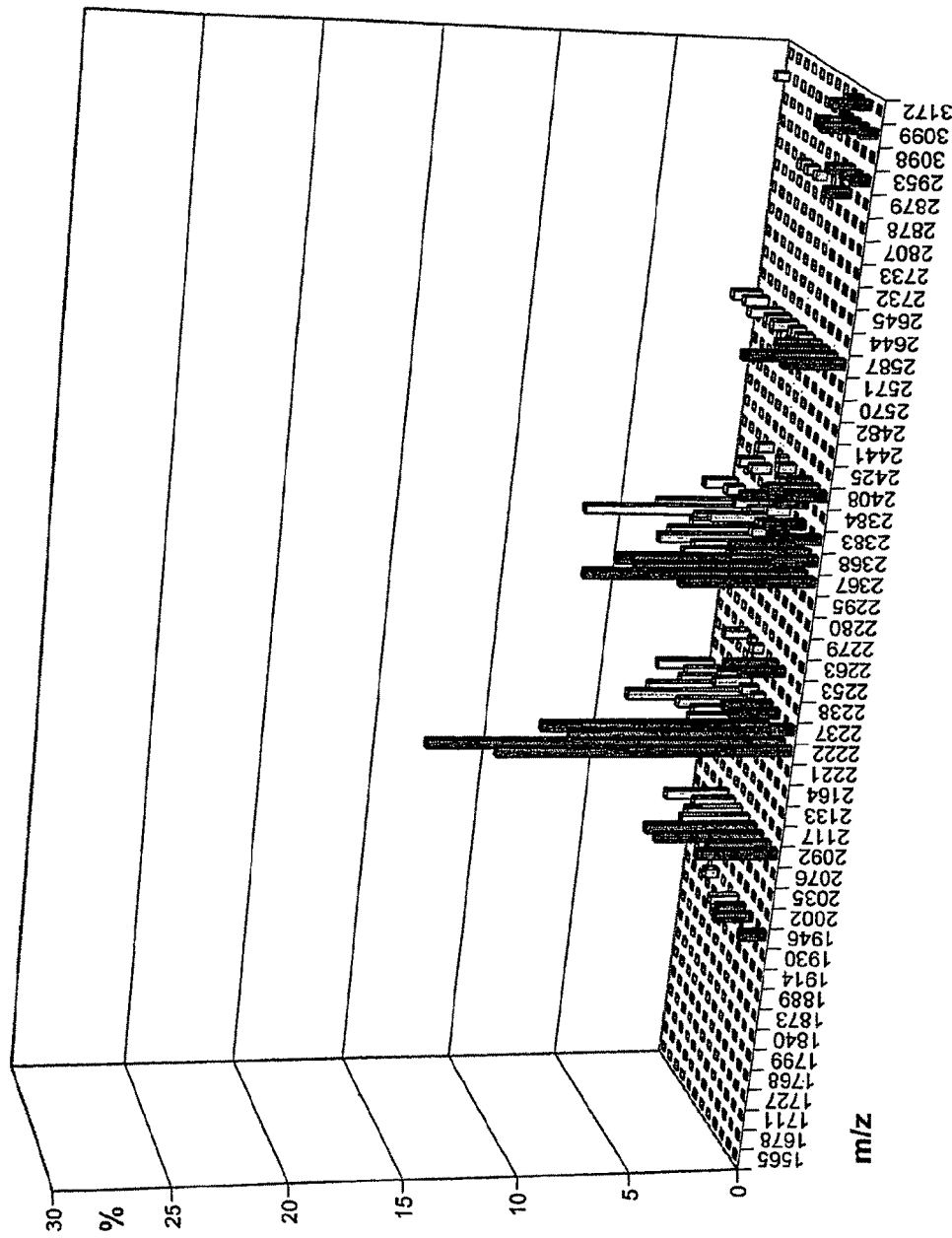
FIG. 41. hESC-associated glycan signals selected from the 50 most abundant sialylated N-glycan signals of the analyzed hESC, EB, and st3 samples (data taken from FIG. 39.B).
Figure 42:
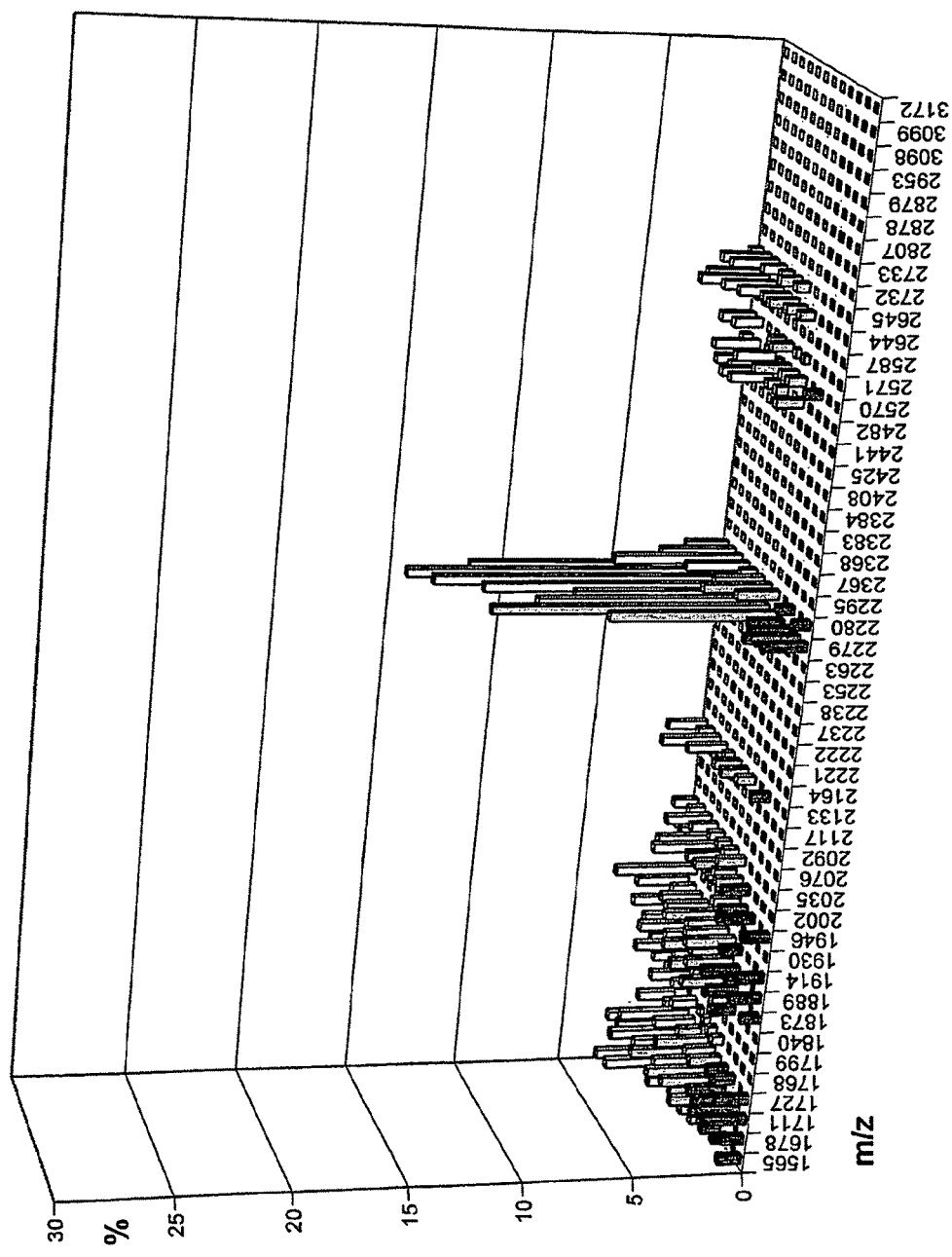
FIG. 42. Differentiated cell associated glycan signals selected from the 50 most abundant sialylated N-glycan signals of the analyzed hESC, EB, and st3 samples (data taken from FIG. 39.B)

The present invention is specifically directed to the comparative presentation of the quantitative glycome dataset as multidimensional graphs comparing the parallel data for example as shown in FIGS. 41 and 42 or as other three dimensional presentations or for example as two dimensional matrix showing the quantities with a quantitative code, preferably by a quantitative color code.

Released Glycomes

The invention is directed to methods to produce released, in a preferred enzymatically released glycans, also referred as glycomes, from embryonal type cells. A preferred glycome type is N-glycan glycome released by a N-glycosidase enzyme. The invention is further directed to profiling analysis of the released glycomes.

Low Amounts of Cells for Glycome Analysis from Stem Cells

The invention revealed that its possible to produce glycome from very low amount of cells. The preferred embodiments amount of cells is between 1000 and 10 000 000 cells, more preferably between 10 000 and 1 000 000 cells. The invention is further directed to analysis of released glycomes of amount of at least 0.1 pmol, more preferably of at least to 1 pmol more preferably at least of 10 pmol.

(a) Total asparagine-linked glycan (N-glycan) pool was enzymatically isolated from about 100 000 cells. (b) The total N-glycan pool (picomole quantities) was purified with microscale solid-phase extraction and divided into neutral and sialylated N-glycan fractions. The N-glycan fractions were analyzed by MALDI-TOF mass spectrometry either in positive ion mode for neutral N-glycans (c) or in negative ion mode for sialylated glycans (d). Over one hundred N-glycan signals were detected from each cell type revealing the surprising complexity of hESC glycosylation. The relative abundances of the observed glycan signals were determined based on relative signal intensities (Saarinen et al., 1999, *Eur. J. Biochem.* 259, 829-840).

Methods for Low Sample Amounts

The present invention is specifically directed to methods for analysis of low amounts of samples.

The invention further revealed that it is possible to use the methods according to the invention for analysis of low sample amounts. It is realized that the cell materials are scarce and difficult to obtain from natural sources. The effective analysis methods would spare important cell materials. Under certain circumstances such as in context of cell culture the materials may be available from large scale. The required sample scale depends on the relative abundancy of the characteristic components of glycome in comparison to total amount of carbohydrates. It is further realized that the amount of glycans to be measured depend on the size and glycan content of the cell type to be measured and analysis including multiple enzymatic digestions of the samples would likely require more material. The present invention revealed especially effective methods for free released glycans.

The picoscale samples comprise preferably at least about 1000 cells, more preferably at least about 50 000 cells, even more preferably at least 100 000 cells, and most preferably at least about 500 000 cells. The invention is further directed to analysis of about 1 000 000 cells. The preferred picoscale samples contain from at least about 1000 cells to about 10 000 000 cells according to the invention. The useful range of amounts of cells is between 50 000 and 5 000 000, even more preferred range of cells is between 100 000 and 3 000 000 cells. A preferred practical range for free oligosaccharide glycomes is between about 500 000 and about 2 000 000 cells. It is realized that cell counting may have variation of less than 20%, more preferably 10% and most preferably 5%, depending on cell counting methods and cell sample, these variations may be used instead of term about. It is further understood that the methods according to the present invention can be upscaled to much larger amounts of material and the pico/nanoscale analysis is a specific application of the technology.

The invention is specifically directed to use of microcolumn technologies according to the invention for the analysis of the preferred picoscale and low amount samples according to the invention, The invention is specifically directed to purification to level, which would allow production of high quality mass spectrum covering the broad size range of glycans of glycome compositions according to the invention.

Glycan Preparation and Purification for Glycome Analysis of Cell Materials According to the Invention, Especially for Mass Spectrometric Methods
Use of Microfluidistic Methods Including Microcolumn Chromatography The present invention is especially directed to use microfluidistic methods involving low sample volumes in handling of the glycomes in low volume cell preparation, low volume glycan release and various chromatographic steps. The invention is further directed to integrated cell preparation, glycan release, and purification and analysis steps to reduce loss of material and material based contaminations. It is further realized that special cleaning of materials is required for optimal results.

Low Volume Reaction in Cell Preparation and Glycan Release

The invention is directed to reactions of volume of 1-100 microliters, preferably about 2-50 microliters and even more preferably 3-20 microliters, most preferably 4-10 microliter. The most preferred reaction volumes includes 5-8 microliters+/−1 microliters. The minimum volumes are preferred to get optimally concentrated sample for purification. The amount of material depend on number of experiment in analysis and larger amounts may be produced preferably when multiple structural analysis experiments are needed.

It is realized that numerous low volume chromatographic technologies may be applied, such low volume column and for example disc based microfluidistic systems.

The inventors found that the most effective methods are microcolumns. Small column can be produced with desired volume. Preferred volumes of microcolumns are from about 2 Microliters to about 500 microliters, more preferably for routine sample sizes from about 5. microliter to about 100 microliters depending on the matrix and size of the sample. Preferred microcolumn volumes for graphitised carbon, cellulose chromatography and other tip-columns are from 2 to 20 µl, more preferably from 3 to 15 µl, even more preferably from 4 to 10 µl, For the microcolumn technologies in general the samples are from about 10 000 to about million cells. The methods are useful for production of picomol amounts of total glycome mixtures from cells according to the invention.

In a preferred embodiment microcolumns are produced in regular disposable usually plastic pipette tips used for example in regular "Finnpipette"-type air-piston pipettes. The pipette-tip microcolumn contain the preferred chromatographic matrix. In a preferred embodiment the microcolumn contains two chromatographic matrixes such as an anion and cation exchange matrix or a hydrophilic and hydrophobic chromatography matrix.

The pipette tips may be chosen to be a commercial tip contain a filter. In a preferred embodiment the microcolumn is produced by narrowing a thin tip from lower half so that the preferred matrix is retained in the tip. The narrowed tip is useful as the volume of filter can be omitted from washing steps The invention is especially directed to plastic pipette tips containing the cellulose matrix, and in an other embodiment to the pipette tip microcolumns when the matrix is graphitised carbon matrix. The invention is further directed to the preferred tip columns when the columns are narrowed tips, more preferably with column volumes of 1 microliter to 100 microliters.

The invention is further directed to the use of the tip columns containing any of the preferred chromatographic matrixes according to the invention for the purification of glycomes according to the invention, more preferably matrixes for ion exchange, especially polystyrene anion exchangers and cation exchangers according to the invention; hydrophilic chromatographic matrixes according to the invention, especially carbohydrate matrixes and most cellulose matrixes.

NMR-Analysis of Glycomes

The present invention is directed to analysis of released glycomes by spectrometric method useful for characterization of the glycomes. The invention is directed to NMR spectroscopic analysis of the mixtures of released glycans. The inventors showed that it is possible to produce a released glycome from human stem cells in scale large enough and of useful purity for NMR analysis of the glycome.

The invention is especially directed to methods of producing NMR from specific subglycomes, preferably N-linked glycome, O-linked glycome, glycosaminoglycan glycome and/or glycolipid glycome. The NMR-profiling according to the invention is further directed to the analysis of the novel and rare structure groups revealed from cell glycomes according to the invention. The general information about complex cell glycome material directed NMR-methods are limited.

Preferably the NMR-analysis is performed from an isolated subglycome. The preferred isolated subglycomes include acidic glycomes and neutral glycomes.

NMR-Glycome Analysis from Larger Amounts of Cells

It is realized that numerous methods have been described for purification of oligosaccharide mixtures useful for NMR from various materials, including usually purified individual proteins. It is realized that present methods are useful for NMR-profiling even for larger amounts of cells according to the invention, especially in combination with NMR-profiling according to the invention and/or when directed to the analysis specific and preferred structure groups according to the invention The preferred purification methods are effective and form an optimised process for purification of glycomes from even larger amounts of cells and tissues than described for nanoscale methods below. The methods are preferred also for any larger amount of cells.

Purification Method for Low Amount Nanoscale NMR-Profiling of Cell Samples

Moreover, when purification methods for larger amounts of carbohydrate materials exists, but very low and complex carbohydrate materials with very complex impurities such as cell-derived materials have been less studied as low amounts, especially when purity useful for NMR-analysis is needed.

Preferred Sample Amounts Allowing Effective NMR Analysis of Cell Glycomes

The invention specifically revealed that NMR-samples can be produced from very low amounts of cells according to the invention. Preferred sample amounts of cells for a one-dimensional proton-NMR profiling are from about 2 million to 100 million cells, more preferably 10-50 million cells. It is further realized that good quality NMR data can be obtained from samples containing at least about 10-20 million cells.

The preferred analysis methods is directed to high resolution NMR observing oligosaccharide/saccharide conjugate mixture from an amount of at least 4 nmol more preferably at least 1 nmol and the cell amount yielding the preferred amount of saccharide mixture. For nanoscale analysis according to the invention cell material is selected so that it would yield at least about 50 nmol of oligosaccharide mixture, more preferably at least about 5 nmol and most preferably at least about 1 nmol of oligosaccharide mixture. Preferred amounts of major components in glycomes to be observed effectively by the methods according to the invention include yield at least about 10 nmol of oligosaccharide component, more preferably at least about 1 nmol and most preferably at least about 0.2 mmol of oligosaccharide component.

The preferred cell amount for analysis of a subglycome from a cell type is preferably optimised by measuring the amounts of glycans produced from the cell amounts of preferred ranges.

It is realized that depending on the cell and subglycome type the required yield of glycans and the heterogeneity of the materials vary yielding different amounts of major components.

Preferred Purification Methods

For the production of sample for nanoscale NMR, the methods described for preparation of cell samples and release of oligosaccharides for mass spectrometric profiling according to the invention may be applied.

For the purification of sample for nanoscale NMR the methods described for purification mass spectrometry profiling samples according to the invention may be applied.

The preferred purification method for nanoscale NMR-profiling according to the invention include following general purification process steps:
1) Precipitation/extraction;
2) Hydrophobic interaction;
3) Affinity to carbon material, especially graphitized carbon.
4) Gel filtration chromatography The more preferred purification process includes precipitation/extraction aimed for removal of major non-carbohydrate impurities by separating the impurity and the glycome fraction(s) to be purified to different phases. Hydrophobic interaction step aims to purify the glycome components from more hydrophobic impurities as these are bound to hydrophobic chromatography matrix and the glycome components are not retained. Chromatography on graphitized carbon may include purification or enrichment of glycans due to their affinity or specific adsorption to graphitized carbon, or removal of contaminants from the glycans. The glycome components obtained by the aforementioned steps are then subjected to gel filtration chromatography, separating molecules according to their hydrodynamic volume, i.e. size in solution. The gel filtration chromatography step allows detection and quantitation of glycome components by absorption at low wavelengths (205-214 nm).

The most preferred purification process includes precipitation/extraction and hydrophobic interaction steps aimed for removal of major non-carbohydrate impurities and more hydrophobic impurities. Chromatography on graphitized carbon is used for removal of contaminants from the glycans, and to divide the glycome components to fractions of neutral glycome components and acidic glycome components. The neutral and acidic glycome component fractions are then subjected to gel filtration chromatography, separating molecules according to their size. Preferably, the neutral glycome component fraction is chromatographed in water and the acidic glycome component fraction is chromatographed in 50-200 mM aqueous ammonium bicarbonate solution. The gel filtration chromatography step allows detection and quantitation of glycome components by absorption at low wavelengths (205-214 nm). Fractions showing absorbance are subjected to MALDI-TOF mass spectrometry.

Preferred Methods for Producing Enriched Glycome Fractions for NMR

The fractionation can be used to enrich components of low abundance. It is realized that enrichment would enhance the detection of rare components. The fractionation methods may be used for larger amounts of cell material. In a preferred embodiment the glycome is fractionated based on the molecular weight, charge or binding to carbohydrate binding agents such as lectins and/or other binding agents according to the invention.

These methods have been found useful for specific analysis of specific subglycomes and enrichment more rare components. The present invention is in a preferred embodiment directed to charge based separation of neutral and acidic glycans. This method gives for analysis method, preferably mass spectroscopy material of reduced complexity and it is useful for analysis as neutral molecules in positive mode mass spectrometry and negative mode mass spectrometry for acidic glycans.

It is realized that preferred amounts of enriched glycome oligosaccharide mixtures and major component comprising fractions can be produced from larger glycome preparations.

In a preferred embodiment the invention is directed to size based fractionation methods for effective analysis of preferred classes of glycans in glycomes. The invention is especially directed to analysis of lower abundance components with lower and higher molecular weight than the glycomes according to the invention. The preferred method for size based fractionation is gel filtration. The invention is especially directed to analysis of enriched group glycans of N-linked glycomes preferably including lower molecular weight fraction including low-mannose glycans, and one or several preferred low mannose glycan groups according to the invention.

Preferred NMR-Methods

In a preferred embodiment the NMR-analysis of the stem cell glycome is one-dimensional proton-NMR analysis showing structural reporter groups of the major components in the glycome.

Combination of NMR- and Mass Spectrometry for Glycome Analysis

The present invention is further directed to combination of the mass spectrometric and NMR analysis of stem cells. The preferred method include production of any mass spectrometric profile from any glycome according to the invention from a cell sample according to the invention, optionally characterizing the glycome by other methods like glycosidase digestion, fragmentation mass spectrometry, specific binding agents, and production of NMR-profile from the same sample glycome or glycomes to compare these profiles.

The Binding Methods for Recognition of Structures from Cell Surfaces

Recognition of Structures from Glycome Materials and on Cell Surfaces by Binding Methods The present invention revealed that beside the physicochemical analysis by NMR and/or mass spectrometry several methods are useful for the analysis of the structures. The invention is especially directed to two methods:
  i) Recognition by enzymes involving binding and alteration of structures.

This method alters specific glycan structures by enzymes capable of altering the glycan structures. The preferred enzymes includes
a) glycosidase-type enzymes capable of releasing monosaccharide units from glycans
b) glycosyltransferring enzymes, including transglycosylating enzymes and glycosyltransferases
c) glycan modifying enzymes including sulfate and or fosfate modifying enzymes ii) Recognition by molecules binding glycans referred as the binders
These molecules bind glycans and include property allowing observation of the binding such as a label linked to the binder. The preferred binders include
a) Proteins such as antibodies, lectins and enzymes
b) Peptides such as binding domains and sites of proteins, and synthetic library derived analogs such as phage display peptides
c) Other polymers or organic scaffold molecules mimicking the peptide materials The peptides and proteins are preferably recombinant proteins or corresponding carbohydrate recognition domains derived thereof, when the proteins are selected from the group monoclonal antibody, glycosidase, glycosyl transferring enzyme, plant lectin, animal lectin or a peptide mimetic thereof and wherein the binder includes a detectable label structure.

Preferred Binder Molecules

The present invention revealed various types of binder molecules useful for characterization of cells according to the invention and more specifically the preferred cell groups and cell types according to the invention. The preferred binder molecules are classified based on the binding specificity with regard to specific structures or structural features on carbohydrates of cell surface. The preferred binders recognize specifically more than single monosaccharide residue.

It is realized that most of the current binder molecules such as all or most of the plant lectins are not optimal in their specificity and usually recognize roughly one or several monosaccharides with various linkages. Furthermore the specificities of the lectins are usually not well characterized with several glycans of human types.

The preferred high specificity binders recognize
A) at least one monosaccharide residue and a specific bond structure between those to another monosaccharides next monosaccharide residue referred as MS1B1-binder,
B) more preferably recognizing at least part of the second monosaccharide residue referred as MS2B1-binder,
C) even more preferably recognizing second bond structure and or at least part of third mono saccharide residue, referred as MS3B2-binder, preferably the MS3B2 recognizes a specific complete trisaccharide structure.
D) most preferably the binding structure recognizes at least partially a tetrasaccharide with three bond structures, referred as MS4B3-binder, preferably the binder recognizes complete tetrasaccharide sequences.

The preferred binders includes natural human and or animal, or other proteins developed for specific recognition of glycans. The preferred high specificity binder proteins are specific antibodies preferably monoclonal antibodies; lectins, preferably mammalian or animal lectins; or specific glycosyltransferring enzymes more preferably glycosidase type enzymes, glycosyltransferases or transglycosylating enzymes.

Target Structures for Specific Binders and Examples of the Binding Molecules
Combination of Terminal Structures in Combination with Specific Glycan Core Structures It is realized that part of the structural elements are specifically associated with specific glycan core structure. The recognition of terminal structures linked to specific core structures are especially preferred, such high specificity reagents have capacity of recognition almost complete individual glycans to the level of physicochemical characterization according to the invention. For example many specific mannose structures according to the invention are in general quite characteristic for N-glycan glycomes according to the invention. The present invention is especially directed to recognition terminal epitopes.

Common Terminal Structures on Several Glycan Core Structures

The present invention revealed that there are certain common structural features on several glycan types and that it is possible to recognize certain common epitopes on different glycan structures by specific reagents when specificity of the reagent is limited to the terminal without specificity for the core structure. The invention especially revealed characteristic terminal features for specific cell types according to the invention. The invention realized that the common epitopes increase the effect of the recognition. The common terminal structures are especially useful for recognition in the context with possible other cell types or material, which do not contain the common terminal structure in substantial amount.

Specific Preferred Structural Groups

The present invention is directed to recognition of oligosaccharide sequences comprising specific terminal monosaccharide types, optionally further including a specific core structure. The preferred oligosaccharide sequences classified based on the terminal monosaccharide structures.

1. Structures with Terminal Mannose Monosaccharide

Preferred mannose-type target structures have been specifically classified by the invention. These include various types of high and low-mannose structures and hybrid type structures according to the invention.

Low or Uncharacterised Specificity Binders
preferred for recognition of terminal mannose structures includes mannose-monosaccharide binding plant lectins.

Preferred High Specific High Specificity Binders
include
i) Specific mannose residue releasing enzymes such as linkage specific mannosidases, more preferably an α-mannosidase or β-mannosidase.

Preferred α-mannosidases includes linkage specific α-mannosidases such as α-Mannosidases cleaving preferably non-reducing end terminal
α2-linked mannose residues specifically or more effectively than other linkages, more preferably cleaving specifically Manα2-structures; or
α6-linked mannose residues specifically or more effectively than other linkages, more preferably cleaving specifically Manα6-structures;
Preferred β-mannosidases includes β-mannosidases capable of cleaving β4-linked mannose from non-reducing end terminal of N-glycan core Manβ4GlcNAc-structure without cleaving other β-linked monosaccharides in the glycomes.

ii) Specific binding proteins recognizing preferred mannose structures according to the invention. The preferred reagents include antibodies and binding domains of antibodies (Fab-fragments and like), and other engineered carbohydrate binding proteins. The invention is directed to antibodies recognizing MS2B1 and more preferably MS3B2-structures

2. Structures with Terminal Gal-Monosaccharide

Preferred galactose-type target structures have been specifically classified by the invention. These include various types of N-acetyllactosamine structures according to the invention.

Low or Uncharacterised Specificity Binders for Terminal Gal

Preferred for recognition of terminal galactose structures includes plant lectins such as ricin lectin (ricinus communis agglutinin RCA), and peanut lectin(/agglutinin PNA).

Preferred High Specific High Specificity Binders Include i) Specific galactose residue releasing enzymes such as linkage specific galactosidases, more preferably α-galactosidase or β-galactosidase.

Preferred α-galactosidases include linkage galactosidases capable of cleaving Galα3Gal-structures revealed from specific cell preparations Preferred β-galactosidases includes β-galactosidases capable of cleaving
β4-linked galactose from non-reducing end terminal Galβ4GlcNAc-structure without cleaving other β-linked monosaccharides in the glycomes and
β3-linked galactose from non-reducing end terminal Galβ3GlcNAc-structure without cleaving other C-linked monosaccharides in the glycomes ii) Specific binding proteins recognizing preferred galactose structures according to the invention. The preferred reagents include antibodies and binding domains of antibodies (Fab-fragments and like), and other engineered carbohydrate binding proteins and animal lectins such as galectins.

3. Structures with Terminal GalNAc-Monosaccharide

Preferred GalNAc-type target structures have been specifically revealed by the invention. These include especially LacdiNAc, GalNAcβGlcNAc-type structures according to the invention.

Low or Uncharacterised Specificity Binders for Terminal GalNAc

Several plant lectins has been reported for recognition of terminal GalNAc. It is realized that some GalNAc-recognizing lectins may be selected for low specificity recognition of the preferred LacdiNAc-structures.

Preferred High Specific High Specificity Binders Include i) The invention revealed that β-linked GalNAc can be recognized by specific β-N-acetylhexosaminidase enzyme in combination with β-N-acetylhexosaminidase enzyme. This combination indicates the terminal monosaccharide and at least part of the linkage structure.

Preferred β-N-acetylhexosaminidase, includes enzyme capable of cleaving β-linked GalNAc from non-reducing end terminal GalNAcβ4/3-structures without cleaving α-linked HexNAc in the glycomes; preferred N-acetylglucosaminidases include enzyme capable of cleaving β-linked GlcNAc but not GalNAc.

ii) Specific binding proteins recognizing preferred GalNAcβ4, more preferably GalNAcβ4GlcNAc, structures according to the invention. The preferred reagents include antibodies and binding domains of antibodies (Fab-fragments and like), and other engineered carbohydrate binding proteins, and a special plant lectin WFA (*Wisteria floribunda* agglutinin).

4. Structures with Terminal GlcNAc-Monosaccharide

Preferred GlcNAc-type target structures have been specifically revealed by the invention. These include especially GlcNAcβ-type structures according to the invention.

Low or Uncharacterised Specificity Binders for Terminal GlcNAc

Several plant lectins has been reported for recognition of terminal GlcNAc. It is realized that some GlcNAc-recognizing lectins may be selected for low specificity recognition of the preferred GlcNAc-structures.

Preferred High Specific High Specificity Binders Include i) The invention revealed that β-linked GlcNAc can be recognized by specific β-N-acetylglucosaminidase enzyme.

Preferred β-N-acetylglucosaminidase includes enzyme capable of cleaving β-linked GlcNAc from non-reducing end terminal GlcNAcβ2/3/6-structures without cleaving β-linked GalNAc or α-linked HexNAc in the glycomes;

ii) Specific binding proteins recognizing preferred GlcNAcβ2/3/6, more preferably GlcNAcβ2Manα structures according to the invention. The preferred reagents include antibodies and binding domains of antibodies (Fab-fragments and like), and other engineered carbohydrate binding proteins.

5. Structures with Terminal Fucose-Monosaccharide

Preferred fucose-type target structures have been specifically classified by the invention. These include various types of N-acetyllactosamine structures according to the invention.

Low or Uncharacterised Specificity Binders for Terminal Fuc

Preferred for recognition of terminal fucose structures includes fucose monosaccharide binding plant lectins. Lectins of *Ulex europeaus* and *Lotus tetragonolobus* has been reported to recognize for example terminal Fucoses with some specificity binding for α2-linked structures, and branching α3-fucose, respectively.

Preferred High Specific High Specificity Binders Include i) Specific fucose residue releasing enzymes such as linkage fucosidases, more preferably α-fucosidase.

Preferred α-fucosidases include linkage fucosidases capable of cleaving Fucα2Gal-, and Galβ4/3(Fucα3/4)GlcNAc-structures revealed from specific cell preparations.

ii) Specific binding proteins recognizing preferred fucose structures according to the invention. The preferred reagents include antibodies and binding domains of antibodies (Fab-fragments and like), and other engineered carbohydrate binding proteins and animal lectins such as selectins recognizing especially Lewis type structures such as Lewis x, Galβ4(Fucα3)GlcNAc, and sialyl-Lewis x, SAα3Galβ4(Fucα3)GlcNAc.

The preferred antibodies includes antibodies recognizing specifically Lewis type structures such as Lewis x, and sialyl-Lewis x. More preferably the Lewis x-antibody is not classic SSEA-1 antibody, but the antibody recognizes specific protein linked Lewis x structures such as Galβ4(Fucα3)GlcNAcβ2Manα-linked to N-glycan core.

6. Structures with Terminal Sialic Acid-Monosaccharide

Preferred sialic acid-type target structures have been specifically classified by the invention.

Low or Uncharacterised Specificity Binders for Terminal Fuc

Preferred for recognition of terminal sialic acid structures includes sialic acid monosaccharide binding plant lectins.

Preferred High Specific High Specificity Binders Include i) Specific sialic acid residue releasing enzymes such as linkage sialidases, more preferably α-sialidases.

Preferred α-sialidases include linkage sialidases capable of cleaving SAα3Gal- and SAα6Gal-structures revealed from specific cell preparations by the invention.

Preferred lectins, with linkage specificity include the lectins, that are specific for SAα3Gal-structures, preferably being *Maackia amurensis* lectin and/or lectins specific for SAα6Gal-structures, preferably being *Sambucus nigra* agglutinin.

ii) Specific binding proteins recognizing preferred sialic acid oligosaccharide sequence structures according to the invention. The preferred reagents include antibodies and binding domains of antibodies (Fab-fragments and like), and other engineered carbohydrate binding proteins and animal lectins such as selectins recognizing especially Lewis type structures such as sialyl-Lewis x, SAα3Galβ4(Fucα3)GlcNAc or sialic acid recognizing Siglec-proteins.

The preferred antibodies includes antibodies recognizing specifically sialyl-N-acetyllactosamines, and sialyl-Lewis x.

Preferred antibodies for NeuGc-structures includes antibodies recognizes a structure NeuGcα3Galβ4Glc(NAc)$_{0\ or\ 1}$ and/or GalNAcβ4[NeuGcα3]Galβ4Glc(NAc)$_{0\ or\ 1}$, wherein [ ] indicates branch in the structure and ( )$_{0\ or\ 1}$ a structure being either present or absent. In a preferred embodiment the invention is directed to recognition of the N-glycolyl-Neuraminic acid structures by antibody, preferably by a monoclonal antibody or human/humanized monoclonal antibody. A preferred antibody contains the variable domains of P3-antibody.

Binder-Label Conjugates

The present invention is specifically directed to the binding of the structures according to the present invention, when the binder is conjugated with "a label structure". The label structure means a molecule observable in a assay such as for example a fluorescent molecule, a radioactive molecule, a detectable enzyme such as horse radish peroxidase or biotin/streptavidin/avidin. When the labelled binding molecule is contacted with the cells according to the invention, the cells can be monitored, observed and/or sorted based on the presence of the label on the cell surface. Monitoring and observation may occur by regular methods for observing labels such as fluorescence measuring devices, microscopes, scintillation counters and other devices for measuring radioactivity.

Use of Binder and Labelled Binder-Conjugates for Cell Sorting

The invention is specifically directed to use of the binders and their labelled conjugates for sorting or selecting human stem cells from biological materials or samples including cell materials comprising other cell types. The preferred cell types includes cord blood, peripheral blood and embryonal stem cells and associated cells. The labels can be used for sorting cell types according to invention from other similar cells. In another embodiment the cells are sorted from different cell types such as blood cells or in context of cultured cells preferably feeder cells, for example in context of embryonal stem cells corresponding feeder cells such as human or mouse feeder cells. A preferred cell sorting method is FACS sorting. Another sorting methods utilized immobilized binder structures and removal of unbound cells for separation of bound and unbound cells.

Use of Immobilized Binder Structures

In a preferred embodiment the binder structure is conjugated to a solid phase. The cells are contacted with the solid phase, and part of the material is bound to surface. This method may be used to separation of cells and analysis of cell surface structures, or study cell biological changes of cells due to immobilization. In the analytics involving method the cells are preferably tagged with or labelled with a reagent for the detection of the cells bound to the solid phase through a binder structure on the solid phase. The methods preferably further include one or more steps of washing to remove unbound cells.

Preferred solid phases include cell suitable plastic materials used in contacting cells such as cell cultivation bottles, petri dishes and microtiter wells; fermentor surface materials Specific Recognition between Preferred Stem Cells and Contaminating Cells The invention is further directed to methods of recognizing stem cells from differentiated cells such as feeder cells, preferably animal feeder cells and more preferably mouse feeder cells. It is further realized, that the present reagents can be used for purification of stem cells by any fractionation method using the specific binding reagents.

Preferred fractionation methods includes fluorescence activated cell sorting (FACS), affinity chromatography methods, and bead methods such as magnetic bead methods.

Preferred reagents for recognition between preferred cells, preferably embryonal type cells, and contaminating cells, such as feeder cells, most preferably mouse feeder cells, include reagents according to the Table 49, more preferably proteins with similar specificity with lectins PSA, MAA, and PNA.

The invention is further directed to positive selection methods including specific binding to the stem cell population but not to contaminating cell population. The invention is further directed to negative selection methods including specific binding to the contaminating cell population but not to the stem cell population. In yet another embodiment of recognition of stem cells the stem cell population is recognized together with a homogenous cell population such as a feeder cell population, preferably when separation of other materials is needed. It is realized that a reagent for positive selection can be selected so that it binds stem cells as in the present invention and not to the contaminating cell population and a reagent for negative selection by selecting opposite specificity. In case of one population of cells according to the invention is to be selected from a novel cell population not studied in the present invention, the binding molecules according to the invention may be used when verified to have suitable specificity with regard to the novel cell population (binding or not binding). The invention is specifically directed to analysis of such binding specificity for development of a new binding or selection method according to the invention.

The preferred specificities according to the invention include recognition of:
  i) mannose type structures, especially alpha-Man structures like lectin PSA, preferably on the surface of contaminating cells
  ii) α3-sialylated structures similarity as by MAA-lectin, preferably for recognition of embryonal type stem cells
  iii) Gal/GalNAc binding specificity, preferably Gal1-3/GalNAc1-3 binding specificity, more preferably Galβ1-3/GalNAcβ1-3 binding specificity similar to PNA, preferably for recognition of embryonal type stem cells Manipulation of Cells by Binders The invention is specifically directed to manipulation of cells by the specific binding proteins. It is realized that the glycans described have important roles in the interactions between cells and thus binders or binding molecules can be used for specific biological manipulation of cells. The manipulation may be performed by free or immobilized binders. In a preferred embodiment cells are used for manipulation of cell under cell culture conditions to affect the growth rate of the cells.

Preferred Cell Population to be Produced by Glycomodification According to the Present Invention The present invention is directed to specific cell populations comprising in vitro enzymatically altered glycosylations according to the present invention. It is realized that special structures revealed on cell surfaces have specific targeting, and immune recognition properties with regard to cells carrying the structures. It is realized that sialylated and fucosylated terminal structures such as sialyl-lewis x structures target cells to selectins involved in bone marrow homing of cells and invention is directed to methods to produce such structures on cells surfaces. It is further realized that mannose and galactose terminal structures revealed by the invention target cells to liver and/or to immune recognition, which in most cases are harmful for effective cell therapy, unless liver is not targeted by the cells. NeuGc is target for immune recognition and has harmful effects for survival of cells expressing the glycans.

The invention revealed glycosidase methods for removal of the structures from cell surface while keeping the cells intact. The invention is especially directed to sialyltransferase methods for modification of terminal galactoses. The invention further revealed novel method to remove mannose residues from intact cells by alpha-mannosidase.

The invention is further directed to metabolic regulation of glycosylation to alter the glycosylation for reduction of potentially harmful structures.

The present invention is directed to specific cell populations comprising in vitro enzymatically altered sialylation according to the present invention. The preferred cell population includes cells with decreased amount of sialic acids on the cell surfaces, preferably decreased from the preferred structures according to the present invention. The altered cell population contains in a preferred embodiment decreased amounts of α3-linked sialic acids. The present invention is preferably directed to the cell populations when the cell populations are produced by the processes according to the present invention.

Cell Populations with Altered Sialylated Structures

The invention is further directed to novel cell populations produced from the preferred cell populations according to the invention when the cell population comprises altered sialylation as described by the invention. The invention is specifically directed to cell populations comprising decreased sialylation as described by the invention. The invention is specifically directed to cell populations comprising increased sialylation of specific glycan structures as described by the invention. Furthermore invention is specifically directed to cell populations of specifically altered α3- and or α6-sialylation as described by the invention These cells are useful for studies of biological functions of the cell populations and role of sialylated, linkage specifically sialylated and non-sialylated structures in the biological activity of the cells.

Preferred Cell Populations with Decreased Sialylation

The preferred cell population includes cells with decreased amount of sialic acids on the cell surfaces, preferably decreased from the preferred structures according to the present invention. The altered cell population contains in a preferred embodiment decreased amounts of α3-linked sialic or α6-linked sialic acid. In a preferred embodiment the cell populations comprise practically only α3-sialic acid, and in another embodiment only α6-linked sialic acids, preferably on the preferred structures according to the invention, most preferably on the preferred N-glycan structures according to the invention. The present invention is preferably directed to the cell populations when the cell populations are produced by the processes according to the present invention. The cell populations with altered sialylation are preferably mesenchymal stem cell, embryonal-type cells or cord blood cell populations according to the invention.

Preferred Cell Populations with Increased Sialylation

The preferred cell population includes cells with increased amount of sialic acids on the cell surfaces, preferably decreased from the preferred structures according to the present invention. The altered cell population contains in preferred embodiments increased amounts of α3-linked sialic or α6-linked sialic acid in a preferred embodiment the cell populations comprise practically only α3-sialic acid, and in another embodiment only α6-linked sialic acids, preferably on the preferred structures according to the invention, most preferably on the preferred N-glycan structures according to the invention. The present invention is preferably directed to the cell populations when the cell populations are produced by the processes according to the present invention. The cell populations with altered sialylation are preferably mesenchymal stem cells or embryonal-type cells or cord blood cell populations according to the invention.

Preferred Cell Populations with Altered Sialylation

The preferred cell population includes cells with altered linkage structures of sialic acids on the cell surfaces, preferably decreased from the preferred structures according to the present invention. The altered cell population contains in a preferred embodiments altered amount of α3-linked sialic and/or α6-linked sialic acid. The invention is specifically directed to cell populations having a sialylation level similar to the original cells but the linkages of structures are altered to α3-linkages and in another embodiment the linkages of structures are altered to α6-structures. In a preferred embodiment the cell populations comprise practically only α3-sialic acid, and in another embodiment only α6-linked sialic acids, preferably on the preferred structures according to the invention, most preferably on the preferred N-glycan structures according to the invention. The present invention is preferably directed to the cell populations when the cell populations are produced by the processes according to the present invention. The cell populations with altered sialylation are preferably mesenchymal stem cells or embryonal-type cells or cord blood cell populations according to the invention.

Cell Populations Comprising Preferred Cell Populations with Preferred Sialic Acid Types The preferred cell population includes cells with altered types of sialic acids on the cell surfaces, preferably on the preferred structures according to the present invention. The altered cell population contains in a preferred embodiment altered amounts of NeuAc and/or NeuGc sialic acid. The invention is specifically directed to cell populations having sialylation levels similar to original cells but the sialic acid structures altered to NeuAc and in another embodiment the sialic acid type structures altered to NeuGc. In a preferred embodiment the cell populations comprise practically only NeuAc, and in another embodiment only NeuGc sialic acids, preferably on the preferred structures according to the invention, most preferably on the preferred N-glycan structures according to the invention. The present invention is preferably directed to the cell populations when the cell populations are produced by the processes according to the present invention. The cell populations with altered sialylation are preferably mesenchymal stem cells or embryonal-type cells or cord blood cell populations according to the invention.

Methods to Alter (Remove or Reduce or Change) Glycosylation of Cells

Analysis and Degradative Removal of the Harmful Glycan Structure

The present invention is further directed to degradative removal of specific harmful glycan structures from cell, preferably from desired cell populations according to the invention.

The removal of the glycans or parts thereof occur preferably by enzymes such as glycosidase enzymes.

In some cases the removal of carbohydrate structure may reveal another harmful structure. In another preferred embodiment the present invention is directed to replacement of the removed structure by less harmful or better tolerated structure more optimal for the desired use.

Desilylation Methods
Preferred Special Target Cell Type

Effective and specific desilylation methods for the specific cell populations were developed. The invention is specifically directed to desilylation methods for modification of human cord blood cells. The cord blood cells are clearly different of other cell types and no desilylation methods have previously been developed for these cells. Due to cell specific differences any quantitative desilylation methods cannot be generalized from one cell population to another. Thus, any results and data demonstrated by other investigators using other cell types are not applicable to cord blood. The present invention is further directed to desilylation modifications of any human stem cell or cord blood cell subpopulation.

The present invention is specifically directed to methods for desilylation of the preferred structures according to the present invention from the surfaces of preferred cells. The present invention is further directed to preferred methods for the quantitative verification of the desilylation by the preferred analysis methods according to the present invention. The present invention is further directed to linkage specific desilylation and analysis of the linkage specific sialylation on the preferred carbohydrate structures using analytical methods according to the present invention The invention is preferably directed to linkage specific $\alpha$3-desilylation of the preferred structures according to the invention without interfering with the other sialylated structures according to the present invention. The invention is further directed to simultaneous desilylation $\alpha$3- and $\alpha$6-sialylated structures according to the present invention.

Furthermore the present invention is directed to desilylation when both NeuAc and NeuGc are quantitatively removed from cell surface, preferably from the preferred structures according to the present invention. The present invention is specifically directed to the removal of NeuGc from preferred cell populations, most preferably cord blood and stem cell populations and from the preferred structures according to the present invention. The invention is further directed to preferred methods according to the present invention for verification of removal of NeuGc, preferably quantitative verification and more preferably verification performed by mass spectrometry.

Modification of Cell Surfaces of the Preferred Cells by Glycosyltransferases

The inventors revealed that it is possible to produce controlled cell surface glycosylation modifications on the preferred cells according to the invention. The present invention is specifically directed to glycosyltransferase catalysed modifications of N-linked glycans on the surfaces of cells, preferably blood cells, more preferably leukocytes or stem cells or more preferably the preferred cells according to the present invention.

The present invention is directed to cell modifications by sialyltransferases and fucosyltransferases. Two most preferred transfer reactions according to the invention are $\alpha$3-modification reactions such as $\alpha$3-sialylation and $\alpha$3-fucosylations. When combined these reactions can be used to produce important cell adhesion structures which are sialylated and fucosylated N-acetyllactosamines such as sialyl-Lewis x (sLex).

Sialylation

Possible $\alpha$6-sialylation has been implied in bone marrow cells and in peripheral blood CD34+ cells released from bone marrow to circulation by growth factor administration, cord blood cells or other stem cell types have not been investigated. Furthermore, the previous study utilized an artificial sialic acid modification method, which may affect the specificity of the sialyltransferase enzyme and, in addition, the actual result of the enzyme reaction is not known as the reaction products were not analysed by the investigators. The reactions are likely to have been very much limited by the specificity of the $\alpha$6-sialyltransferase used and cannot be considered prior art in respect to the present invention.

The inventors of the present invention further revealed effective modification of the preferred cells according to the present inventions by sialylation, in a preferred embodiment by $\alpha$3-sialylation.

The prior art data cited above does not indicate the specific modifications according to the present invention to cells from early human blood, preferably cord blood, to cultured mesenchymal stem cells, or to cultured embryonal type cells. The present invention is specifically directed to sialyltransferase reactions towards these cell types. The invention is directed to sialyltransferase catalyzed transfer of a natural sialic acid, preferably NeuAc, NeuGc or Neu-O-Ac, from CMP-sialic acid to target cells.

Sialyltransferase catalyzed reaction according to Formula:

CMP-SA+target cell→SA-target cell+CMP,

Wherein SA is a sialic acid, preferably a natural sialic acid, preferably NeuAc, NeuGc or Neu-O-Ac and
the reaction is catalysed by a sialyltransferase enzyme preferably by an $\alpha$3-sialyltransferase
and
the target cell is a cultured stem cell or early human blood cell (cord blood cell).

Preferably the sialic acid is transferred to at least one N-glycan structure on the cell surface, preferably to form a preferred sialylated structure according to the invention Fucosyltransferase Reactions In the prior art fucosyltransferase reactions towards unspecified cell surface structures has been studied The prior art indicates that human cord blood cell populations may be $\alpha$3-fucosylated by human fucosyltransferase VI and such modified cell populations may be directed to bone marrow due to interactions with selecting.

Directing Cells and Selectin Ligands

The present invention describes reactions effectively modifying cord blood cells by fucosyltransferases, especially in order to produce sialylated and fucosylated N-acetyllactosamines on cell surfaces, preferably sLex and related structures. The present invention is further directed to the use of the increased sialylated and/or fucosylated structures on the cell surfaces for targeting the cells, in a preferred embodiment for selectin directed targeting of the cells.

The invention is further directed to $\alpha$3- and/or $\alpha$4-fucosylation of cultured stem cells, preferably embryonal stem cells and mesenchymal stem cells derived either from cord blood or bone marrow.

Fucosylation of Human Peripheral Blood Mononuclear Cell Populations

In a specific embodiment the present invention is directed to $\alpha$3-fucosylation of the total mononuclear cell populations from human peripheral blood. Preferably the modification is directed to at least to one protein linked glycan, more preferably to a N-linked glycan. The prior art reactions reported about cord blood did not describe reactions in such cell populations and the effect of possible reaction cannot be known. The invention is further directed to combined increased $\alpha$3-sialylation and fucosylation, preferably $\alpha$3-sialylation of human peripheral blood leukocytes. It is realized that the structures on the peripheral blood leukocytes can be used for targeting the peripheral blood leukocytes, preferably to selecting expressing sites such as selectin expressing malignant tissues.

Methods for Combined Increased α3-Sialylation and α3-Fucosylation

The invention is specifically directed to selection of a cell population from the preferred cell population according to the present invention, when the cell population demonstrate increased amount of α3-sialylation when compared with the baseline cell populations.

The inventors revealed that human cord blood in general is highly α6-sialylated and thus not a good target for α3/4-fucosylation reactions, especially for reactions directed to production of selectin ligand structures.

Use of Selected Cultured α3-Sialic Acid Expressing Cell Populations

The inventors revealed that specific subpopulations of native cord blood cells express increased amounts of α3-linked sialic acid. Preferred selected cell populations from cord blood for α3/4-fucosylation include CD133+ cells.

Furthermore it was found that cultured cells according to the invention have a high tendency to express α3-sialic acid instead to α6-linked sialic acids. The present invention is preferably directed to cultured mesenchymal stem cell lines, more preferably mesenchymal stem cells from bone marrow or from cord blood expressing increased amounts of α3-linked sialic acid

Fucosylation of α3-Sialylated Cells

The present invention is preferably directed to fucosylation after α3-sialylation of cells, preferably the preferred cells according to the invention. The invention describes for the first time combined reaction by two glycosyltransferases for the production of specific terminal epitopes comprising two different monosaccharide types on cell surfaces.

Fucosylation of Desilylated and α3-Sialylated Cells

The present invention is preferably directed to fucosylation after desilylation and β3-sialylation of cells, preferably the preferred cells according to the invention. The invention describes for the first time combined reaction by two glycosyltransferases and a glycosidase for the production of specific terminal epitopes comprised of two different monosaccharide types on cell surfaces.

Sialylation Methods

Preferred Special Target Cell Type

Early Human Blood

Effective specific sialylation methods for the specific cell populations were developed. The invention is specifically directed to sialylation methods for modification of human cord blood cells and subpopulations thereof and multipotent stem cell lines. The cord blood cells are clearly different from other cell types and no sialylation methods have been developed for the cell population. Due to cell specific differences any quantitative sialylation methods cannot be generalized from one cell population to another. The present invention is further directed to sialylation modifications of any human cord blood cell subpopulation.

Embryonal-Type Cells and Mesenchymal Stem Cells

The methods of present invention are further directed to the methods according to the invention for altering human embryonal-type and mesenchymal stem cells. In a preferred embodiment the modification technologies is directed to cultured cells according to the invention.

Production of Preferred Sialylated Structures

Present invention is specifically directed to methods for sialylation to produce preferred structures according to the present invention from the surfaces of preferred cells. The present invention is specifically directed to production preferred NeuGc- and NeuAc-structures. The invention is directed to production of potentially in vivo harmful structures on cells surfaces, e.g. for control materials with regard to cell labelling. The invention is further directed to production of specific preferred terminal structure types, preferably α3- and α6-sialylated structures, and specifically NeuAc- and NeuGc-structures for studies of biological activities of the cells.

The present invention is further directed to preferred methods for the quantitative verification of the sialylation by the preferred analysis methods according to the present invention. The present invention is further directed to linkage specific sialylation and analysis of the linkage specific sialylation on the preferred carbohydrate structures using analytical methods according to the present invention.

The invention is preferably directed to linkage specific α3-sialylation of the preferred structures according to the invention without interfering with the other sialylated structures according to the present invention. The invention is preferably directed to linkage specific α6-sialylation of the preferred structures according to the invention without interfering with the other sialylated structures according to the present invention.

The invention is further directed to simultaneous sialylation α3- and α6-sialylated structures according to the present invention. The present invention is further directed for the production of preferred relation of α3- and α6-sialylated structures, preferably in single reaction with two sialyl-transferases.

Furthermore the present invention is directed to sialylation when either NeuAc or NeuGc are quantitatively synthesized to the cell surface, preferably on the preferred structures according to the present invention. Furthermore the invention is directed to sialylation when both NeuAc and NeuGc are, preferably quantitatively, transferred to acceptor sites on the cell surface.

The present invention is specifically directed to the removal of NeuGc from preferred cell populations, most preferably cord blood cell populations and from the preferred structures according to the present invention, and resialylation with NeuAc.

The invention is further directed to preferred methods according to the present invention for verification of removal of NeuGc, and resialylation with NeuAc, preferably quantitative verification and more preferably verification performed by mass spectrometry with regard to the preferred structures.

Controlled Cell Modification

The present invention is further directed to cell modification according to the invention, preferably desilylation or sialylation of the cells according to the invention, when the sialidase reagent is a controlled reagent with regard of presence of carbohydrate material.

Purification of Cells with Regard to Modification Enzyme

The preferred processes according to the invention comprise of the step of removal of the enzymes from the cell preparations, preferably the sialyl modification enzymes according to the invention. Most preferably the enzymes are removed from a cell population aimed for therapeutic use. The enzyme proteins are usually antigenic, especially when these are from non-mammalian origin. If the material is not of human origin its glycosylation likely increases the antigenicity of the material. This is particularity the case when the glycosylation has major differences with human glycosylation, preferred examples of largely different glycosylations includes: procaryotic glycosylation, plant type glycosylation, yeast or fungal glycosylation, mammalian/animal glycosylation with Galα3Galβ4GlcNAc-structures, animal glycosylations with NeuGc structures. The glycosylation of a recombinant enzyme depends on the glycosylation in the production cell line, these produce partially non-physiological glycan structures. The enzymes are preferably removed from any cell populations aimed for culture or storage or therapeutic use. The presence of enzymes which have affinity with regard to cell surface may otherwise alter the cells as detectable by carbohydrate binding reagents or mass spectrometric or other analysis according to the invention and cause adverse immunological responses.

Under separate embodiment the cell population is cultured or stored in the presence of the modification enzyme to maintain the change in the cell surface structure, when the cell surface structures are recovering from storage especially at temperatures closer physiological or culture temperatures of the cells. Preferably the cells are then purified from trace amounts of the modification enzyme before use.

The invention is furthermore directed to methods of removal of the modification reagents from cell preparations, preferably the modification reagents are desilylation or resialylation reagents. It is realized that soluble enzymes can be washed from the modified cell populations. Preferably the cell material to be washed is immobilized on a matrix or centrifuged to remove the enzyme, more preferably immobilized on a magnetic bead matrix.

However, extraneous washing causes at least partial destruction of cells and their decreased viability. Furthermore, the enzymes have affinity with regard to the cell surface. Therefore the invention is specifically directed to methods for affinity removal of the enzymes. The preferred method includes a step of contacting the modified cells with an affinity matrix binding the enzyme after modification of the cells.

Under specific embodiment the invention is directed to methods of tagging the enzyme to be removed from the cell population. The tagging step is performed before contacting the enzyme with the cells. The tagging group is designed to bind preferably covalently to the enzyme surface, without reduction or without major reduction of the enzyme activity. The invention is further directed to the removal of the tagged enzyme by binding the tag to a matrix, which can be separated from the cells. Preferably the matrix comprises at least one matrix material selected from the group: polymers, beads, magnetic beads, or solid phase surface Enzymes Acceptable for Humans for Modification of Reagents or Cells Under specific embodiment the invention is directed to the use for modification of the cells according to the invention, or in a separate embodiment reagents for processes according to the invention, of a human acceptable enzyme, preferably a glycosidase according to the invention or in preferred embodiment sialidase or sialyltransferase, which is acceptable at least in certain amounts to human beings without causing harmful allergic or immune reactions. It is realized that the human acceptable enzymes may not be needed to be removed from reaction mixtures or less washing steps are needed for desirable level of the removal. The human acceptable enzyme is in preferred embodiment a human glycosyltransferase or glycosidase. The present invention is separately directed to human acceptable enzyme which is a sialyltransferase. The present invention is separately directed to human acceptable enzyme which is a sialidase, the invention is more preferably directed to human sialidase which can remove specific type of sialic acid from cells.

In a preferred embodiment the human acceptable enzyme is purified from human material, preferably from human serum, urine or milk. In another preferred embodiment the enzyme is recombinant enzyme corresponding to natural human enzyme. More preferably the enzyme corresponds to human natural enzyme corresponds to natural cell surface or a secreted from of the enzyme, more preferably serum or urine or human milk form of the enzyme. Even more preferably the present invention is directed to human acceptable enzyme which corresponds to a secreted form of a human sialyltransferase or sialidase, more preferably secreted serum/blood form of the human enzyme. In a preferred embodiment the human acceptable enzyme, more preferably recombinant human acceptable enzyme, is a controlled reagent with regard to potential harmful glycan structures, preferably NeuGc-structures according to the invention. The recombinant proteins may contain harmful glycosylation structures and inventors revealed that these kinds of structures are also present on recombinant glycosyltransferases, even on secreted (truncated) recombinant glycosyltransferases.

mRNA Corresponding to Glycosylation Enzymes

The present invention is further directed to correlation of specific messenger mRNA molecules with the preferred glycan structures according to the present invention. It is realized that glycosylation can be controlled in multiple levels and one of them is transcription. The presence of glycosylated structures may in some case correlate with mRNAs involved in the synthesis of the structures.

The present invention is especially directed to analysis of mRNA-species having correlation with expressed fucosylated glycan structures and "terminal HexNAc" containing structures preferred according to the present invention. The preferred mRNA-species includes mRNA corresponding to fucosyltransferases and N-acetylglucosaminyltransferase.

Observation of Glycan Binding Structures, Lectins, Corresponding mRNA-markers

The invention further revealed changes in mRNA-expression of glycosylation recognizing lectins such as galectins. The cells were further revealed to contain lactosamine receptors for lectins. The invention is especially directed to analysis of expression levels of human lectins and lactosamine galectin receptors, preferably analysis of galectins and selectins more preferably galectins for analysis of status of cells according to the present invention.

The invention specifically revealed novel NeuGc(N-glycolylneuraminic acid)-binding lectin activity from human embryonal stem cells. The lectin recognizes polyvalent NeuGc but does not bind effectively to polyvalent NeuNAc. The present invention is especially directed to labelling cells according to the invention by carbohydrate conjugates binding cells according to the invention, preferably labelled conjugates of NeuGc. The invention is further directed to sorting and selecting cells, and cell derived materials and purifying proteins from cells, using labelled carbohydrate conjugates, preferably, conjugates of NeuGc.

Specific Characteristic Marker Structures and Glycome Marker Components/compositions The N-glycan analysis of total profiles of released N-glycans revealed beside the glycans above, which were verified to comprise 1) complex biantennary N-glycans, such as Galβ4GlcNAcβ2Manα3(Galβ4GlcNAcβ2Manα6) Manβ4GlcNAcβ4(Fucα6)$_{0-1}$GlcNAcβ-, wherein the reminal N-acetyllactosamines can be elongated from Gal with NeuNAcα3 and/or NeuNAcα6 and 2) terminal mannose containing N-glycans such as Highmannose glycans with formula Hex$_{5-9}$HexNAc$_2$ and degradation products thereof comprising low number of mannose residues (Low mannose glycans) Hex$_{1-4}$HexNAc$_2$.

The Specific N-Glycan Core Marker Structure

The glycan share common core structure according to the Formula:

[Manα3]$_{n1}$(Manα6)$_{n2}$Manβ4GlcNAcβ4(Fucα6)$_{0-1}$ GlcNAcβAsn, wherein n1 and n2 are integers 0 or 1, independently indicating the presence or absence of the terminal Man-residue, and wherein the non-reducing end terminal Manα3/Manα6-residues can be elongated to the complex type, especially biantennry structures or to mannose type (high-Man and/or low Man) or to hybrid type structures as described in examples.

It was further analyzed that the N-glycan compositions contained only very minor amounts of glycans with additional HexNAx in comparison to monosaccharide compositions of the complex type glycan above, which could indicate presence of no or very low amounts of the N-glycan core linked GlcNAc-residues described by Stanley P M and Raju T S (JBC-(1998) 273 (23) 14090-8; JBC (1996) 271 (13) 7484-93) and/or bisecting GlcNAc. The NMR-analysis further indicated that stem cell N-glycans, such as the cord blood N-glycan structures are essentially devoid of GlcNAcα6 linked to reducing end subterminal GlcNAcβ4 of the N-glycan core. It is realized that part of the terminal HexNAc-type structures appear to represent bisecting GlcNAc-type type glycans, and quite low or non-existent amounts of the GlcNAcα6-branching and also low amounts of GlcNAcβ2-branch of Manβ4 described by Stanley and colleagues. Here, essentially devoid of indicates less than 10% of all the protein linked N-glycans, more preferably the additional HexNAc units are present in less than 8% of the stem cell N-glycans by mass spectrometric analysis.

The invention thus describes the major core structure of N-glycans in human stem cells verified by NMR-spectroscopy and by specific glycosidase digestions and was further quantitated to comprise a characteristic smaller structural group glycans comprising specific terminal HexNAc group and/or bisecting GlcNAc-type structures, which additionally modify part of the core structure. The invention further reveals that the core structure is a useful target structure for analysis of cells. The stem cells show characteristic binding with PSA-lectin, whose binding (and cytotoxic activity) is blocked by additional GlcNAc unit blocking the recognition of the N-glycan core (Raju and Stanley J B C (1994); JBC (1996) 271 (13) 7484-93). As an example very characteristic labelling with PSA-lectin is shown for embryonal stem cells in intracellular glycans in FIGS. 37 and 40.

The characteristic monosaccharide composition of the core structure will allow recognition of the major types of N-glycan structure groups present as additional modification of the core structure. Furthermore composition of the core structure is characteristic in mass spectrometric analysis of N-glycan and allow immediate recognition for example from $Hex_1HexNAc_1$-type (preferentially $Man_xGlcNAc_1$) glycans also present in total glycome composition.

Low-Molecular Weight Glycan Marker Structures and Stem Cell Glycome Components

The invention describes novel low-molecular weight acidic glycan components within the acidic N-glycan and/or soluble glycan fractions with characteristic monosaccharide compositions $SA_xHex_{1-2}HexNAc_{1-2}$, wherein x indicates that the corresponding glycans are preferentially sialylated with one or more sialic acid residues. The inventors realized that such glycans are novel and unusual with respect to N-glycan biosynthesis and described mammalian cell glycan components, as reveal also by the fact that they are classified as "other (N-)glycan types" in N-glycan classification scheme of the present invention. The invention is directed to analyzing, isolating, modifying, and/or binding to these novel glycan components according to the methods and uses of the present invention, and further to other uses of specific marker glycans as described here. As demonstrated in the Examples of the present invention, such glycan components were specific parts of total glycomes of certain cell types and preferentially to certain stem cell types, making their analysis and use beneficial with regard to stem cells. The invention is further directed to stem cell glycomes and subglycomes containing these glycan components.

Preferred Glycomes

The present invention is specifically directed to stem cell glycomes, which are essentially pure glycan mixtures comprising various glycans as described in the invention preferably in proportions shown by the invention. The essentially pure glycan mixtures comprise the key glycan components in proportions which are characteristics to stem cell glycomes. The preferred glycomes are obtained from human stem cells according to the invention.

The invention is further directed to glycomes as products of purification process and variations thereof according to the invention. The products purified from stem cell materials by the simple, quantitative and effective methods according to the invention are essentially pure. The essentially pure means that the mixtures are essentially devoid of contaminations disturbing analysis by MALDI mass spectrometry, preferably by MALDI-TOF mass spectrometry. The mass spectra produced by the present methods from the essentially pure glycomes reveal that there is essentially no non-carbohydrate impurities with weight larger than trisaccharide and very low amount of lower molecular weight impurities so that crystallization of MALDI matric is possible and the glycan signals can be observed for broad glycomes with large variations of monosaccharide compositions and ranges of molecular weight as described by the invention. It is realized that the purification of the materials from low amounts of stem cells comprising very broad range of cellular materials is very challenging task and the present invention has accomplished this.

Combination Compositions of the Preferred Glycome Mixtures with Matrix for Analysis Mass Spectrometric Matrix The invention further revealed that it is possible to combine the glycomes with matrix useful for a mass spectrometric analysis and to obtain combination mixture useful for spectrometric analysis. The preferred mass spectrometric matrix is matrix for MALDI (matrix assisted laser desorption ionization mass spectrometry) with mass spectrometric analysis (abbreviated as MALDI matrix), MALDI is preferably performed with TOF (time of flight) detection.

Preferred MALDI matrices include aromatic preferably benzene ring structure comprising molecules with following characteristic. The benzene ring structure molecules preferably comprises 1-4 substituents such as hydroxyl, carboxylic acid or ketone groups. Known MALDI matrixes have been reviewed in Harvey, Mass. Spec. Rev. 18, 349 (1999). The present invention is especially and separately directed to specific matrixes for analysis in negative ion mode of MALDI mass spectrometry, preferred for analysis of negatively charged (acidic, such as sialylated and/or sulfated and/or phosphorylated) subglycome, and in positive ion mode of MALDI mass spectrometry (preferred for analysis of neutral glycomes). It is realized that the matrices can be optimized for negative ion mode and positive ion mode.

The present invention is especially directed to glycome matrix composition optimized for the use in positive ion mode, and to the use of the MALDI-TOF matrix and matrix glycome composition, that is optimized for the use in the analysis in positive ion mode, for the analysis of glycome, preferably neutral glycome. The preferred matrices for positive ion mode are aromatic matrices, e.g. 2,5-dihydroxybenzoic acid, 2,5-dihydroxybenzoic acid/2-hydroxy-5-methoxybenzoic acid, 2,4,6-trihydroxyacetophenone or 6-aza-2-thiothymine, more preferably 2,5-dihydroxybenzoic acid. The present invention is especially directed to glycome matrix composition optimized for the use in negative ion mode, and to the use of the MALDI-TOF matrix and the matrix glycome compositions, that is optimized for the negative ion mode, for the analysis of glycome, preferably acidic glycome. The preferred matrices for negative ion mode are aromatic matrices, e.g. 2,4,6-trihydroxyacetophenone, 3-Hydroxypicolinic acid, 2,5-dihydroxybenzoic acid, 2,5-dihydroxybenzoic acid/2-hydroxy-5-methoxybenzoic acid, or 6-aza-2-thiothymine, more preferably 2,4,6-trihydroxyacetophenone. The invention is further directed to analysis method and glycome-matrix composition for the analysis of glycome compositions, wherein the glycome composition comprises both negative and neutral glycome components. Preferred matrices for analysis of negative and neutral glycome components comprising glycome are aromatic matrices, e.g. 2,4,6-trihydroxyacetophenone, 3-hydroxypicolinic acid, 2,5-dihydroxybenzoic acid, 2,5-dihydroxybenzoic acid/2-hydroxy-5-methoxybenzoic acid, or 6-aza-2-thiothymine, more preferably 2,4,6-trihydroxyacetophenone.

The MALDI-matrix is a molecule capable of
1) Specifically and effectively co-crystallizing with glycome composition with the matrix, crystallizing meaning here forming a solid mixture composition allowing analysis of glycome involving two steps below
2) absorbing UV-light typically provided by a laser in MALDI-TOF instrument, preferred wavelength of the light is 337 nm as defined by the manuals of MALDI-TOF methods
3) transferring energy to the glycome composition so that these will ionize and be analyzable by the MALDI-TOF mass spectrometry. The present invention is especially directed to compositions of glycomes in complex with MALDI mass spectrometry matrix.

The present invention is specifically directed to methods of searching novel MALDI-matrixes with the above characteristic, preferably useful for analysis by the method below. The method for searching novel MALDI-matrixes using the method in the next paragraph.

The present invention is specifically directed to methods of analysis of glycomes by MALDI-TOF including the steps:
1) Specifically and effectively co-crystallizing with glycome composition with the MALDI-TOF-matrix, crystallizing meaning here forming a solid mixture composition allowing analysis of glycome involving two steps below
2) Providing UV light to crystalline sample by a laser in MALDI-TOF instrument allowing the ionization of sample
3) Analysis of the ions produced by the MALDI mass spectrometer, preferably by TOF analysis. The invention is further directed to the combination of glycome purification methods and/or quantitative and qualitative data analysis methods according to the invention.

Crystalline Compositions of Glycomes

The present invention is further directed to essentially pure glycome compositions in solid co-crystalline form with MALDI matrix. The invention is preferably a neutral and/or acidic glycome as complex with a matrix optimized for analysis of the specific glycome type, preferably analysis in negative ion mode with a matrix such as 2,4,6-trihydroxyacetophenone. The invention is preferably a neutral (or non-acidic) glycome as complex with a matrix optimized for analysis in positive ion mode such as 2,5-dihydroxybenzoic acid.

The invention revealed that it is possible to analyze glycomes using very low amount of sample. The preferred crystalline glycome composition comprises between 0.1-100 pmol, more preferably 0.5-10 pmol more preferably 0.5-5 pmol and more preferably about 0.5-3 pmol more preferably about 0.5-2 pmol of sample co-crystallized with optimized amount of matrix preferably about 10-200 nmol, more preferably 30-150 nmol, and more preferably about 50-120 nmol and most preferably between 60-90 nmols of the matrix, preferably when the matrix is 2,5-dihydroxybenzoic acid. The matrix and analyte amounts are optimized for a round analysis spot with radius of about 1 mm and area of about 0.8 $mm^2$. It is realized that the amount of materials can be changed in proportion of the area of the spot, smaller amount for smaller spot. Examples of preferred amounts per area of spot are 0.1-100 pmol/0.8 $mm^2$ and 10-200 pmol/3 $mm^2$. Preferred molar excess of matrix is about 5000-1000000 fold, more preferably about 10000-500000 fold and more preferably about 15000 to 200 000 fold and most preferably about 20000 to 100000 fold excess when the matrix is 2,5-dihydroxybenzoic acid.

It is realized that the amount and relative amount of new matrix is optimized based on forming suitable crystals and depend on chemical structure of the matrix. The formation of crystals is observed by microscope and further tested by performing test analysis by MALDI mass spectrometry.

The invention is further directed to specific methods for crystallizing MALDI-matrix with glycome. Preferred method for crystallization in positive ion mode includes steps: (1) optionally, elimination of impurities, like salts and detergents, which interfere with the crystallization, (2) providing solution of glycome in $H_2O$ or other suitable solvent in the preferred concentration, (3) mixing the glycome with the matrix in solution or depositing the glycome in solution on a precrystallized matrix layer and (4) drying the solution preferably by a gentle stream of air.

Preferred method for crystallization in negative ion mode includes steps: (1) optionally, elimination of impurities, like salts and detergents, which interfere with the crystallization, (2) providing solution of glycome in $H_2O$ or other suitable solvent in the preferred concentration, (3) mixing the glycome with the matrix in solution or depositing the glycome in solution on a precrystallized matrix layer and (4) drying the solution preferably by vacuum.

Other Preferred Glycome Analysis Compostions
Binder Glycome Compositions

The invention is further directed to compositions of essentially pure glycome composition with specific glycan binding molecules such as lectins, glycosidases or glycosyltransferases and other glycosyl modifying enzymes such as sulfateses and/or phosphatases and antibodies. It is realized these composition are especially useful for analysis of glycomes.

The present invention revealed that the complex glycome compositions can be effectively and even quantitatively modified by glycosidases even in very low amounts. It was revealed that the numerous glycan structures similar to target structures of the enzymes do not prevent the degradation by competitive inhibition, especially by the enzymes used. The invention is specifically directed to preferred amounts directed to MALDI analysis for use in composition with a glycosyl modifying enzyme, preferably present in low amounts. Preferred enzymes suitable for analysis include enzymes according to the examples.

The invention is further directed to binding of specific component of glycome in solution with a specific binder. The preferred method further includes affinity chromatography step for purification of the bound component or analysis of the non-bound fraction and comparison it to the glycome solution without the binding substance. Preferred binders include lectins engineered to be lectins by removal of catalytic amino acids (methods published by Roger Laine, Anomeric, Inc., USA, and Prof Jukka Finne, Turku, Finland), lectins and antibodies or antibody fragments or minimal binding domains of the proteins.

Additional Data Analysis and Related Methods

The present invention is especially directed to the use of glycome data for production of mathematical formulas, or algorithms, for specific recognition or identification of specific cell types or cell groups. Data analysis methods are presented e.g. in Example 23.

The invention is especially directed to selecting specific "structural features" such as mass spectrometric signals (such as individual mass spectrometric signal corresponding to one or several monosaccharide compositions and/or glycan structures), or signal groups or subglycomes or signals corresponding to specific glycan classes, which are preferably according to the invention, preferably the signal groups or groups similar (preferably defined as specific structure group by the invention) to ones shown in Table 41, from quantitative glycome data, preferably from quantitative glycome data according to the invention, for the analysis of status of a stem cell population. The invention is furthermore directed to the methods of analysis of the cells by the methods involving the use of the specific signals or signal groups and a mathematical algorithm for analysis of cell status.

Preferred algorithm includes use of proportion (such as %-proportion) of the specific signals from total signals as specific values (structural features) and creating a "glycan score", which is algorithm showing characteristics/status of a cell type based on the specific proportional signal intensities (or quantitative presence of glycan structures measured by any quantitation method such as specific binding proteins or quantitative chromatographic or electrophoresis analysis such as HPLC analysis). Preferably signals which are, preferably most specifically, upregulated in a specific cell type(s) and signals which are, preferably most specifically, downregulated in the cell type in comparison to control cells (cell types) are selected to for the glycan score. In a preferred embodiment value(s) of downregulated signals are subtracted from upregulated signals when glycan score is calculated. The method yields largest score values for a specific cell type or types selected to be differentiated from other cell type(s).

The invention is specifically directed to methods for searching characteristic structural features (values) from glycome profiling data, preferably quantitative or qualitative glycome profiling data. The preferred methods include methods for comparing the glycome data sets obtained from different samples, or from average data sets obtained from a group of similar samples such as parallel samples from same or similar cell preparations. Methods for searching characteristic features are briefly described in the section: identification and classification of differences in glycan datasets. The comparison of datasets of the glycome data according to the invention preferably includes calculation of relative and/or absolute differences of signals, preferably each signal between two data sets, and in another preferred embodiment between three or more datasets. The method preferably further includes step of selecting the differing signals, or part thereof, for calculating glycan score.

It is further realized that the analyzed glycome data has other uses preferred by the invention such as use of the selected characteristic signals and corresponding glycan material:

1) for targets for structural analysis of glycans (preferably chemically by glycosidases, fragmentation mass spectrometry and/or NMR spectroscopy as shown by the present invention and/or structural analysis based on the presence of other signals and knowledge of biosynthesis of glycans). The preferred use for targets includes estimation of chemical characteristics of potential corresponding glycans for complete or partial purification/separation of the specific glycan(s). The preferred chemical characteristics to be analysed preferably include one or several of following properties: a) acidity (e.g. by presence of acidic residues such as sialic acid and/or sulfate and/or phosphate) for charge based separation, b) molecular weight or hydrodynamic volume affecting chromatographic separation, e.g. estimation of the elution volume in gel filtration methods (the effect of acidic residue can be estimated from effects of similar structures and the "size" of HexNAc (GaNAc/GlcNAc) is in general twice the size of Hex (such as Gal, Man or Gic), c) estimation (e.g. based on composition and biosynthetic knowledge of glycans) of presence of epitopes for specific binding reagents for labelling identification in a mixture or for affinity purification, d) estimation of presence of target epitopes for specific glycosyl modifying enzymes including glycosidases and/or glycosyltransferases (types of binding reagents) or for specific chemical modification reagents (such as periodate for specific oxidation or acid for specific acid hydrolysis), for modification of glycans and recognition of the modification by potential chemical change such as incorporation of radioactive label or by change of mass spectrometric signal of the glycan for labelling identification in a mixture.

2) use of the signals or partially or fully analysed glycan structures corresponding to the signals for searching specific binding reagents for recognition of cells which are preferably selected as described by the present invention (especially as described above) and in the methods for identification and classification of differences in glycan datasets and/or signals selected and/or tested by glycan score methods, are preferably selected for targets for structural analysis of glycans (preferably by glycosidases, fragmentation mass spectrometry and/or NMR spectroscopy as shown by the present invention) and/or for use of the signals or partially or fully analysed glycan structures corresponding to the signals for searching specific binding reagents for recognition of cells.

Figure 36:
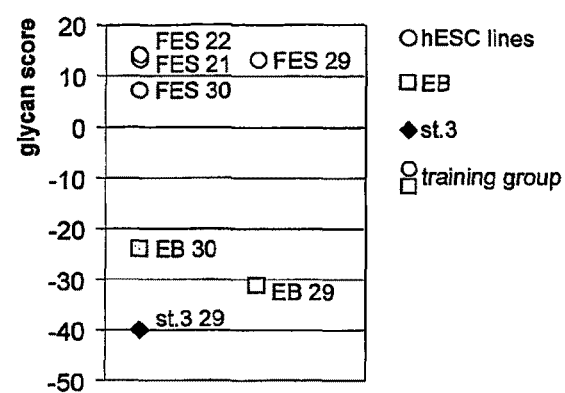
FIG. 36. Glycan fingerprinting analysis of the four hESC lines, embryoid bodies derived from FES 29 and FES 30 hESC lines (EB), and stage 3 differentiated cells derived from FES 29 (st3). The glycan score was calculated as described in the Examples.

The preferred method includes the step of comparing the values, and preferably presenting the score values in graphs such as ones shown in FIG. 36 (example 23), and preferably evaluating the statistic significance of the result by a statistic analysis methods such as a mathematical test for statistic significance such as Student's t-test or 2-tailed Mann-Whitney U test. Cell type refers here to cells with specific status and/or identity with possible individual variability.

It is realized that to differentiate a cell type from other(s) different characteristic signals may be selected than for another cell type. The invention however revealed that for stem cells and especially for embryonal stem cells preferred characteristic signals include ones selected in the Examples as described above. It is realized that a glycan score can be also created with less characteristic signals or with only part of signals and still relevant results can be obtained. The invention is further directed to methods for optimisation of glycan score algorithms and methods for selecting signals for glycan scores.

In case the specific proportion (value) of a characteristic signal is low in comparison to other values a specific factor can be selected for increase the relative "weight" of the value in the glycan scores to be calculated for the cell populations.

The preferred statuses of cells, to be analysed by mathematical methods such as algorithms using quantitative glycome profiling data according to the invention include differentiation status, individual characteristics and mutation, cell culture or storage conditions related status, effects of chemicals or biochemicals on cells, and other statuses described by the invention.

Stem Cell Nomenclature

Figure 44:
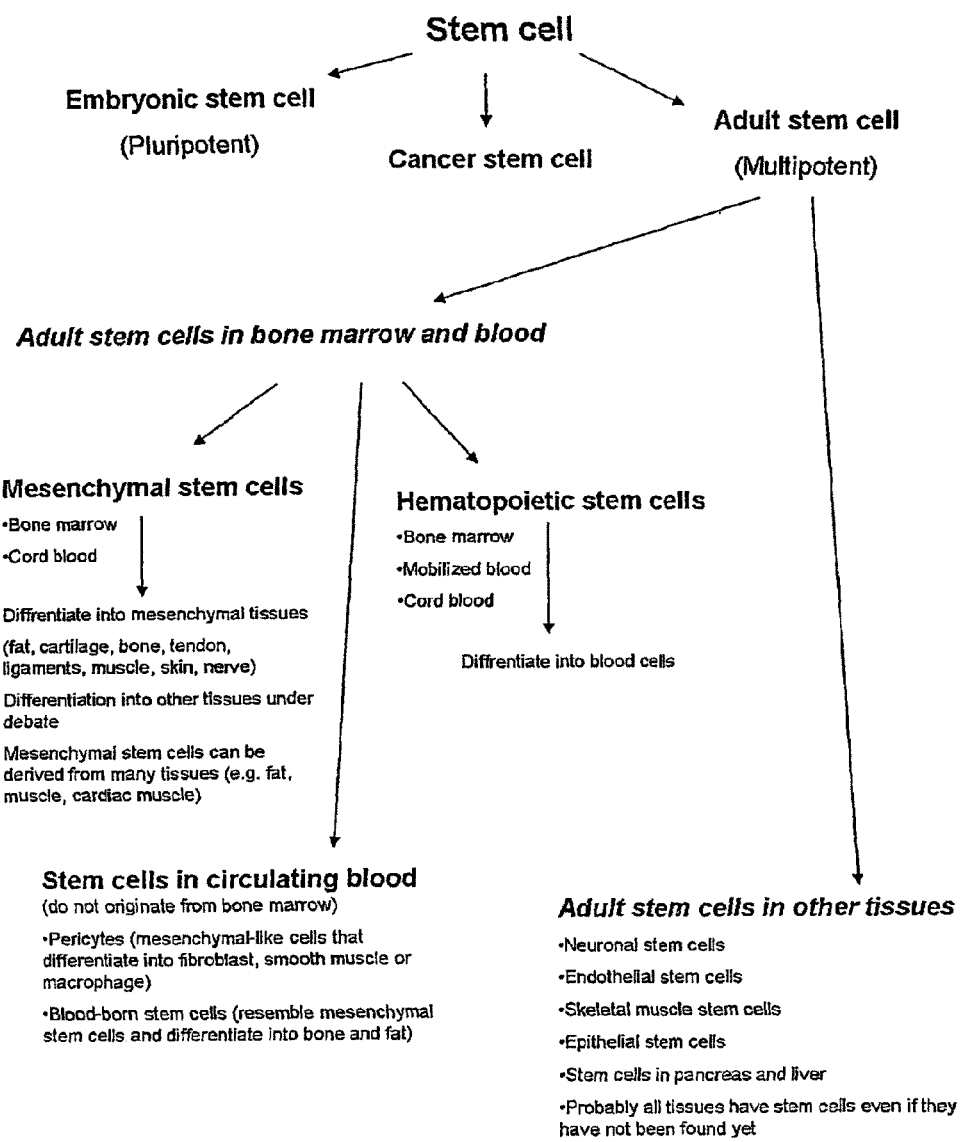
FIG. 44. Stem cell nomenclature used to describe the present invention.

The present invention is directed to analysis of all stem cell types, preferably human stem cells. A general nomenclature of the stem cells is described in FIG. 44. The alternative nomenclature of the present invention describe early human cells which are in a preferred embodiment equivalent of adult stem cells (including cord blood type materials) as shown in FIG. 44. Adult stem cells in bone marrow and blood is equivalent for stem cells from "blood related tissues".

Lectins for Manipulation of Stem Cells, Especially Under Cell Culture Conditions The present invention is especially directed to use of lectins as specific binding proteins for analysis of status of stem cells and/or for the manipulation of stems cells.

The invention is specifically directed to manipulation of stem cells under cell culture conditions growing the stem cells in presence of lectins. The manipulation is preferably performed by immobilized lectins on surface of cell culture vessels. The invention is especially directed to the manipulation of the growth rate of stem cells by growing the cells in the presence of lectins, as show in Table 50.

The invention is in a preferred embodiment directed to manipulation of stem cells by specific lectins recognizing specific glycan marker structures according to invention from the cell surfaces. The invention is in a preferred embodiment directed to use of Gal recognizing lectins such as ECA-lectin or similar human lectins such as galectins for recognition of galectin ligand glycans identified from the cell surfaces. It was further realized that there is specific variations of galectin expression in genomic levels in stem cells, especially for galectins-1, -3, and -8. The present invention is especially directed to methods of testing of these lectins for manipulation of growth rates of embryonal type stem cells and for adult stem cells in bone marrow and blood and differentiating derivatives thereof.

Sorting of Stem Cells by Specific Lectins

The invention revealed use of specific lectin types recognizing cell surface glycan epitopes according to the invention for sorting of stem cells, especially by FACS methods, most preferred cell types to be sorted includes adult stem cells in blood and bone marrow, especially cord blood cells. Preferred lectins for sorting of cord blood cells include GNA, STA, GS-II, PWA, HHA, PSA, RCA, and others as shown in Example 32. The relevance of the lectins for isolating specific stem cell populations was demonstrated by double labeling with known stem cells markers, as described in Example 32.

Preferred Structures of Glycan Glycomes of Stem Cells

The present invention is especially directed to following O-glycan marker structures of stem cells:

Core 1 type O-glycan structures following the marker composition NeuAc$_2$Hex$_1$HexNAc$_1$, preferably including structures SAα3Galβ3GalNAc and/or SAα3Galβ3(Saα6)GalNAc; and Core 2 type O-glycan structures following the marker composition NeuAc$_{0-2}$Hex$_2$HexNAc$_2$dHex$_{0-1}$, more preferentially further including the glycan series NeuAc$_{0-2}$Hex$_{2+n}$HexNAc$_{2+n}$dHex$_{0-1}$, wherein n is either 1, 2, or 3 and more preferentially n is 1 or 2, and even more preferentially n is 1;

more specifically preferably including R$_1$Galβ4(R$_3$)GlcNAcβ6(R$_2$Galβ3)GalNAc, wherein R$_1$ and R$_2$ are independently either nothing or sialic acid residue, preferably α2,3-linked sialic acid residue, or an elongation with Hex$_n$HexNAc$_n$, wherein n is independently an integer at least 1, preferably between 1-3, most preferably between 1-2, and most preferably 1, and the elongation may terminate in sialic acid residue, preferably α2,3-linked sialic acid residue; and R$_3$ is independently either nothing or fucose residue, preferably α1,3-linked fucose residue. It is realized that these structures correlate with expression of β6GlcNAc-transferases synthesizing core 2 structures.

Preferred Branched N-Acetyllactosamine Type Glycosphingolipids

The invention further revealed branched, I-type, poly-N-acetyllactosamines with two terminal Galβ4-residues from glycolipids of human stem cells. The structures correlate with expression of βGlcNAc-transferases capable of branching poly-N-acetyllactosamines and further to binding of lectins specific for branched poly-N-acetylalctosamines. It was further noticed that PWA-lectin had an activity in manipulation of stem cells, especially the growth rate thereof.

Preferred Qualitative and Quantitative Complete N-Glycomes of Stem Cells

High-Mannose Type and Glucosylated N-Glycans

The present invention is especially directed to glycan compositions (structures) and analysis of high-mannose type and glucosylated N-glycans according to the formula:

$$\text{Hex}_{n3}\text{HexNAc}_{n4},$$

wherein n3 is 5, 6, 7, 8, 9, 10, 11, or 12, and n4=2.

According to the present invention, within total N-glycomes of stem cells the major high-mannose type and glucosylated N-glycan signals include the compositions with 5≤n3≤10: Hex5HexNAc2 (1257), Hex6HexNAc2 (1419), Hex7HexNAc2 (1581), Hex8HexNAc2 (1743), Hex9HexNAc2 (1905), and Hex10HexNAc2 (2067);

and more preferably with 5≤n3≤9: Hex5HexNAc2 (1257), Hex6HexNAc2 (1419), Hex7HexNAc2 (1581), Hex8HexNAc2 (1743), and Hex9HexNAc2 (1905).

As demonstrated in the present invention by glycan structure analysis, preferably this glycan group in stem cells includes the molecular structure (Manα)$_8$Manβ4GlcNAcβ4GlcNAc within the glycan signal Hex9HexNAc2 (1905), and even more preferably Manα2Manα6(Manα2Manα3)Manα6 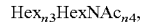(Manα2Manα2Manα3)Manβ4GlcNAcβ4GlcNAc.

Low-Mannose Type N-Glycans

The present invention is especially directed to glycan compositions (structures) and analysis of low-mannose type N-glycans according to the formula:

$$\text{Hex}_{n3}\text{HexNAc}_{n4}\text{dHex}_{n5},$$

wherein n3 is 1, 2, 3, or 4, n4=2, and n5 is 0 or 1.

According to the present invention, within total N-glycomes of stem cells the major low-mannose type N-glycan signals preferably include the compositions with 2≤n3≤4: Hex2HexNAc2 (771), Hex3HexNAc2 (933), Hex4HexNAc2 (1095), Hex2HexNAc2dHex (917), Hex3HexNAc2dHex (1079), and Hex4HexNAc2dHex (1241); and more preferably when n5 is 0: Hex2HexNAc2 (771), Hex3HexNAc2 (933), and Hex4HexNAc2 (1095).

As demonstrated in the present invention by glycan structure analysis of stem cells, preferably this glycan group in stem cells includes the molecular structures:

(Manα)$_{1-3}$Manβ4GlcNAcβ4(Fucα6)$_{0-1}$GlcNAc within the glycan signals 771, 917, 933, 1079, 1095, and 1095, and the preferred low-Man structures includes structures common all stem cell types, tri-Man and tetra-Man structures according as indicated in Table 46 (Manα)$_{0-1}$Manα6 (Manα3)Manβ4GlcNAcβ4(Fucα6)$_{0-1}$GlcNAc, more preferably the tri-Man structures:

Manα6(Manα3)Manβ4GlcNAcβ4(Fucα6)$_{0-1}$GlcNAc
even more preferably the abundant molecular structure:
Manα6(Manα3)Manβ4GlcNAcβGlcNAc within the glycan signal 933.

The invention is further directed to analysis of presence and/or absence of structures varying characteristically between stem cells.

These include fucosylated and nonfucosylated di-Man structures,
specifically associated with certain blood associated stem cells
[Manα6]$_{0-1}$(Manα3)$_{0-1}$Manβ4GlcNAcβ4(Fucα6)$_{0-1}$GlcNAc,
when either of the Mana-residues is present or absent.

The fucosylated structure was observed to be associated with specific blood related adult stem cells while the nonfucosylated structures was observed to have more varying expression in embryonal stem cells, embryoid bodies and more primitive cord blood stem cells (CD133+) and cord blood mesenchymal cells. It is realized that the both di-Man structures reflect have specific qualitative analytical value with regard to specific cell populations.

Quantitative Analysis Directed to the Low-Man Components

Beside the qualitative variations the low-Man glycans have specific value in quantitative analysis of stem cells. The present invention revealed that the low-Man glycans are especially useful for the analysis of status of the cells. For example the analysis in Table 38 revealed that the amounts of the glycans vary between individual embryonal stem cells and there was changes during differentiation. The qualitative analysis above revealed that actually there is even more characteristic changes of individual structures within the glycan group.

The group of low-Man glycans form a characteristic group among glycome compositions. The relative total amount of glycans is between 5-12% in embryonal cell derived materials of Table 38. The glycan group was revealed also to be characteristic in other stem cells and related materials with total relative amount of glycomes of 21 to 35%, notably the cells types, especially the more primitive LIN- and most effectively CD133+ cells differed clearly form the corresponding background cell populations, Table 5; and the two types feeder cells of the embryonal stem cells express the glycans in amounts of 7-8% of total neutral glycan glycomes, but the difference is again more pronounced within fucosylated structures, which are rare in the feeders, Table 44. Glycome analysis of feeder cells is especially useful for methods for development of binder reagents for separation of feeders and stem cells.

The invention is directed to analysis of relative amounts of low-Man glycans, and to the specific quantitative glycome compositions, especially neutral glycan compositions, comprising about 1 to 40% of low-Man glycans, more preferably between about 4 to 41% of the low-Man glycan for the analysis of stem cells according to the invention. 1 to 40% of low-Man glycans and use of the composition for the analysis of stem cells.

Fucosylated High-Mannose Type N-Glycans

The present invention is especially directed to glycan compositions (structures) and analysis of fucosylated high-mannose type N-glycans according to the formula:

$$Hex_{n3}HexNAc_{n4}dHex_{n5},$$

wherein n3 is 5, 6, 7, 8, or 9, n4=2, and n5=1.

According to the present invention, within total N-glycomes of stem cells the major fucosylated high-mannose type N-glycan signal preferentially is the composition Hex5HexNAc2dHex (1403). As demonstrated in the present invention by glycan structure analysis of stem cells, more preferably this glycan signal in stem cells includes the molecular structure (Manα)$_4$Manβ4GlcNAcβ4(Fucα6)GlcNAc.

Soluble Glycans

The present invention is especially directed to glycan compositions (structures) and analysis of neutral soluble N-glycan type glycans according to the formula:

$$Hex_{n3}HexNAc_{n4},$$

wherein n3 is 1, 2, 3, 4, 5, 6, 7, 8, or 9, and n4=1.

Within total N-glycomes of stem cells the major high-mannose type and glucosylated N-glycan signals include the compositions with 4≤n3≤8, more preferably 4≤n3≤7: Hex4HexNAc (892), Hex5HexNAc (1054), Hex6HexNAc (1216), Hex7HexNAc (1378). In the most preferred embodiment of the present invention, the major glycan signal in this group within total N-glycomes of stem cells is Hex5HexNAc (1054).

The inventors were able to determine the molecular structures of this glycan group with a combination of mass spectrometry, exoglycosidase digestions, and nuclear magnetic resonance spectroscopy. Therefore, in another embodiment of the present invention, preferably this glycan group in stem cells includes the N-glycan type molecular structures Hex$_h$[(Manα3)Manβ4GlcNAc], wherein h=n3−2, even more preferably when Hex are Manα.

Neutral Monoantennary or Hybrid-Type N-Glycans

The present invention is especially directed to glycan compositions (structures) and analysis of neutral monoantennary or hybrid-type N-glycans according to the formula:

$$Hex_{n3}HexNAc_{n4}dHex_{n5},$$

wherein n3 is an integer greater or equal to 2, n4=3, and n5 is an integer greater or equal to 0.

According to the present invention, within total N-glycomes of stem cells the major neutral monoantennary or hybrid-type N-glycan signals preferentially include the compositions with 2≤n3≤8 and 0≤n5≤2, more preferentially compositions with 3≤n3≤6 and 0≤n5≤1, with the proviso that when n3=6 also n5=0: Hex3HexNAc3 (1136), Hex3HexNAc3dHex (1282), Hex4HexNAc3 (1298), Hex4HexNAc3dHex (1444), Hex5HexNAc3 (1460), Hex5HexNAc3dHex (1606), and Hex6HexNAc3 (1622).

According to the present invention, the total N-glycomes of cultured human BM MSC, CB MSC, and cells differentiated from them preferentially additionally include the following structures: Hex2HexNAc3dHex (1120), Hex4HexNAc3dHex2 (1590), Hex5HexNAc3dHex2 (1752), Hex6HexNAc3dHex (1768), and Hex7HexNAc3 (1784).

In a preferred embodiment of the present invention, the N-glycan signal Hex5HexNAc3 (1460), more preferentially also Hex6HexNAc3 (1622), and even more preferentially also Hex5HexNAc3dHex (1606), contain non-reducing terminal Manα.

Neutral Complex-Type N-Glycans

The present invention is especially directed to glycan compositions (structures) and analysis of neutral complex-type N-glycans according to the formula:

$$Hex_{n3}HexNAc_{n4}dHex_{n5},$$

wherein n3 is an integer greater or equal to 3, n4 is an integer greater or equal to 4, and n5 is an integer greater or equal to 0.

Within the total N-glycomes of stem cells the major neutral complex-type N-glycan signals preferentially include the compositions with 3≤n3≤8, 4≤n4≤7, and 0≤n5≤4, more preferentially the compositions with 3≤n3≤5, n4=4, and 0≤n5≤1, with the proviso that when n3 is 3 or 4, then n5=1: Hex3HexNAc4dHex (1485), Hex4HexNAc4dHex (1647), Hex5HexNAc4 (1663), Hex5HexNAc4dHex (1809); and even more preferentially also including the composition Hex3HexNAc5dHex (1688).

In another embodiment of the present invention, the total N-glycomes of cultured human BM MSC, CB MSC, and cells differentiated from them preferentially include in the major neutral complex-type N-glycan signals the compositions with 3≤n3≤5, n3=4, and 0≤n5≤1, as well as the compositions with 5≤n4≤6, n3=n4+1, and 0≤n5≤1,
and even more preferentially also including the composition Hex3HexNAcSdHex: Hex3HexNAc4 (1339), Hex3HexNAc4dHex (1485), Hex4HexNAc4 (1501), Hex4HexNAc4dHex (1647), Hex5HexNAc4 (1663), Hex5HexNAc4dHex (1809), Hex6HexNAc5 (2028), Hex6HexNAc5dHex (2174), Hex7HexNAc6 (2393), Hex7HexNAc6dHex (2539), and Hex3HexNAc5dHex (1688).

In another embodiment of the present invention, the total N-glycomes of cultured hESC and cells differentiated from them preferentially further include in the major neutral complex-type N-glycan signal Hex4HexNAc5dHex (1850).

In another embodiment of the present invention, the N-glycan signal Hex3HexNAc4dHex (1485) contains non-reducing terminal GlcNAcβ, and more preferentially the total N-glycome includes the structure:
GlcNAcβ2Manα3(GlcNAcβ2Manα6)Manβ4GlcNAcβ4(Fucα6)GlcNAc (1485).

In yet another embodiment of the present invention, within the total N-glycome of stem cells, the N-glycan signal Hex5HexNAc4dHex (1809), more preferentially also Hex5HexNAc4 (1663), contain non-reducing terminal β1,4-Gal. Even more preferentially the total N-glycome includes the structure:
Galβ4GlcNAβ2Manα3(Galβ4GlcNAcβ2Manα6)Manβ4GlcNAcβ4GlcNAc (1663); and in a further preferred embodiment the total N-glycome includes the structure:
Galβ4GlcNAcβ2Manα3(Galβ4GlcNAcβ2Manα6)Manβ4GlcNAcβ4(Fucα6)GlcNAc (1809).

Neutral Fucosylated N-Glycans

The present invention is especially directed to glycan compositions (structures) and analysis of neutral fucosylated N-glycans according to the formula:

$$Hex_{n3}HexNAc_{n4}dHex_{n5},$$

wherein n5 is an integer greater than or equal to 1.

Within the total N-glycomes of stem cells the major neutral fucosylated N-glycan signals preferentially include glycan compositions wherein 1≤n5≤4, more preferentially 1≤n5≤3, even more preferentially 1≤n5≤2, and further more preferentially compositions Hex3HexNAc2dHex (1079), more preferentially also Hex2HexNAc2dHex (917), and even more preferentially also Hex5HexNAc4dHex (1809).

The inventors further found that within the total N-glycomes of stem cells a major fucosylation form is N-glycan core α1,6-fucosylation. In a preferred embodiment of the present invention, major fucosylated N-glycan signals contain GlcNAcβ4(Fucα6)GlcNAc reducing end sequence.

The inventors further found that stem cell total N-glycomes contain α1,2-Fuc, α1,3-Fuc, and/or α1,4-Fuc epitopes in a differentiation stage dependent manner. In a preferred embodiment of the present invention, major fucosylated N-glycan signals of stem cells contain α1,2-Fuc, α1,3-Fuc, and/or α1,4-Fuc epitopes, more preferentially in multifucosylated N-glycans, wherein 2≤n5≤4.

Within the total N-glycomes of BM and CB MSC the major neutral multifucosylated N-glycan signals preferentially include the composition Hex5HexNAc4dHex2 (1955), more preferentially also Hex5HexNAc4dHex3 (2101), even more preferentially also Hex4HexNAc3dHex2 (1590), and further more preferentially also Hex6HexNAc5dHex2 (2320).

Within the total N-glycomes of hESC the major neutral multifucosylated N-glycan signals preferentially include the composition Hex5HexNAc4dHex2 (1955), more preferentially also Hex5HexNAc4dHex3 (2101), even more preferentially also Hex4HexNAc5dHex2 (1996), and further more preferentially also Hex4HexNAc5dHex3 (2142).

Neutral N-Glycans with Non-Reducing Terminal HexNAc

The present invention is especially directed to glycan compositions (structures) and analysis of neutral N-glycans with non-reducing terminal HexNAc according to the formula:

$$Hex_{n3}HexNAc_{n4}dHex,$$

wherein n4≥n3.

Preferably these glycan signals include Hex3HexNAc4dHex (1485) in all stem cell types; additionally preferably including Hex3HexNAc4 (1339), Hex3HexNAc4 (1339), and/or Hex3HexNAc5 (1542) in CB and BM MSC as well as cells differentiated directly from them; additionally preferably including Hex4HexNAx5 (1704), Hex4HexNAc5dHex (1850), and/or Hex4HexNAc5dHex2 (1996) in hESC and cells differentiated directly from them; additionally preferably including Hex5HexNAc5 (1866) and/or Hex5HexNAc5dHex (2012) in EB and st.3 differentiated cells (from hESC), as well as adipocyte and osteoblast differentiated cells (from CB MSC and BM MSC, respectively).

Acidic Hybrid-Type or Monoantennary N-Glycans

The present invention is especially directed to glycan compositions (structures) and analysis of acidic hybrid-type or monoantennary N-glycans according to the formula:

$$NeuAc_{n1}NeuGc_{n2}Hex_{n3}HexNAc_{n4}dHex_{n5}SP_{n6},$$

wherein n1 and n2 are either independently 1, 2, or 3; n3 is an integer between 3-9; n4 is 3; n5 is an integer between 0-3; and n6 is an integer between 0-2; with the proviso that the sum n1+n2+n6 is at least 1.

Within the total N-glycomes of stem cells the major acidic hybrid-type or monoantennary N-glycan signals preferentially include glycan compositions wherein 3≤n3≤6, more preferentially 3≤n5≤5, and further more preferentially compositions NeuAcHex4HexNAc3dHex (1711), preferentially also NeuAcHex5HexNAc3dHex (1873).

Acidic Complex-Type N-Glycans

The present invention is especially directed to glycan compositions (structures) and analysis of acidic complex-type N-glycans according to the formula:

$$NeuAc_{n1}NeuGc_{n2}Hex_{n3}HexNAc_{n4}dHex_{n5}SP_{n6},$$

wherein n1 and n2 are either independently 1, 2, 3, or 4; n3 is an integer between 3-10; n4 is an integer between 4-9; n5 is an integer between 0-5; and n6 is an integer between 0-2; with the proviso that the sum n1+n2+n6 is at least 1.

Within the total N-glycomes of stem cells the major acidic complex-type N-glycan signals preferentially include glycan compositions wherein 4≤n4≤8, more preferentially 4≤n4≤6, more preferentially 4≤n4≤5 and further more preferentially compositions NeuAcHex5HexNAc4 (1930), NeuAcHex5HexNAc4dHex (2076), NeuAc2Hex5HexNAc4 (2221), NeuAcHex5HexNAc4dHex2 (2222), and NeuAc2Hex5HexNAc4dHex (2367); further more preferentially also NeuAc2Hex6HexNAc5dHex (2732), and more preferentially also NeuAcHex5HexNAc5dHex (2279);
and in BM and CB MSC as well as cells directly differentiated from them, further more preferentially also NeuAc2Hex6HexNAc5 (2586) and more preferentially also NeuAc2Hex7HexNAc6 (2952).

Modified Glycan Types

The inventors found that stem cell total N-glycomes; and soluble+N-glycomes further contain characteristic modified glycan signals, including sialylated fucosylated N-glycans, multifucosylated glycans, sialylated N-glycans with terminal HexNAc (the N>H and N=H subclasses), and sulphated or phosphorylated N-glycans, which are subclasses of the abovementioned glycan classes. According to the present invention, their quantitative proportions in different stem cell types have characteristic values as described in Table 51.

Phosphorylated and Sulphated Glycans

Specifically, major phosphorylated glycans typical to stem cells include Hex5HexNAc2($HPO_3$) (1313), Hex6HexNAc2($HPO_3$) (1475), and Hex7HexNAc2($HPO_3$) (1637);
and major sulphated glycans typical to stem cells include Hex5HexNAc4dHex($SO_3$) (1865) and more preferentially also Hex6HexNAc3($SO_3$) (1678).

According to the present invention, their quantitative proportions in different stem cell types preferentially have characteristic values as described in Table 51.

Preferred Combinations of Glycan Types in Complete Glycomes

The preferred complete glycomes of stem cells include glycan types of the four following types: 1) high-mannose type, 2) low-mannose type, 3) hybrid-type or monoantennary, and 3) complex-type N-glycans,
which more preferentially contain fucosylated glycans, even more preferentially also sialylated glycans, and further more preferentially also sulphated and/or phosphorylated glycans; and most preferentially also including soluble glycans as described in the present invention.

In a preferred embodiment of the preferred glycan type combinations within the stem cell complete glycomes, their relative abundances are as described in Table 51.

Preferred Binders for Stem Cell Sorting and Isolation

As described in the Examples, the inventors found that especially the mannose-specific and especially α1,3-linked mannose-binding lectin GNA was suitable for negative selection enrichment of CD34+ stem cells from CB MNC. In addition, the poly-LacNAc specific lectin STA and the fucose-specific and especially α1,2-linked fucose-specific lectin UEA were suitable for positive selection enrichment of CD34+ stem cells from CB MNC.

The present invention is specifically directed to stem cell binding reagents, preferentially proteins, preferentially mannose-binding or α1,3-linked mannose-binding, poly-LacNAc binding, LacNAc-binding, and/or fucose- or preferentially α1,2-linked fucose-binding; in a preferred embodiment stem cell binding or nonbinding lectins, more preferentially GNA, STA, and/or UEA; and in a further preferred embodiment combinations thereof; to uses described in the present invention taking advantage of glycan-binding reagents that selectively either bind to or do not bind to stem cells.

Preferred Uses for Stem Cell Type Specific Galectins and/or Galectin Ligands

As described in the Examples, the inventors also found that different stem cells have distinct galectin expression profiles and also distinct galectin (glycan) ligand expression profiles. The present invention is further directed to using galactose-binding reagents, preferentially galactose-binding lectins, more preferentially specific galectins; in a stem cell type specific fashion to modulate or bind to certain stem cells as described in the present invention to the uses described. In a further preferred embodiment, the present invention is directed to using galectin ligand structures, derivatives thereof, or ligand-mimicking reagents to uses described in the present invention in stem cell type specific fashion.

EXAMPLES

Example 1

Glycan Isolation and Analysis

Examples of Glycan Isolation Methods
Glycan Isolation.

N-linked glycans are preferentially detached from cellular glycoproteins by *F. meningosepticum* N-glycosidase F digestion (Calbiochem, USA) essentially as described previously (Nyman et al., 1998), after which the released glycans are preferentially purified for analysis by solid-phase extraction methods, including ion exchange separation, and divided into sialylated and non-sialylated fractions. For O-glycan analysis, glycoproteins are preferentially subjected to reducing alkaline O-elimination essentially as described previously (Nyman et al., 1998), after which sialylated and neutral glycan alditol fractions are isolated as described above. Free glycans are preferentially isolated by extracting them from the sample with water.

Example of a Glycan Purification Method.

Isolated oligosaccharides can be purified from complex biological matrices as follows, for example for MALDI-TOF mass spectrometric analysis. Optionally, contaminations are removed by precipitating glycans with 80-90% (v/v) aqueous acetone at −20° C., after which the glycans are extracted from the precipitate with 60% (v/v) ice-cold methanol. After glycan isolation, the glycan preparate is passed in water through a strong cation-exchange resin, and then through $C_{18}$ silica resin. The glycan preparate can be further purified by subjecting it to chromatography on graphitized carbon material, such as porous graphitized carbon (Davies, 1992). To increase purification efficiency, the column can be washed with aqueous solutions. Neutral glycans can be washed from the column and separated from sialylated glycans by elution with aqueous organic solvent, such as 25% (v/v) acetonitrile. Sialylated glycans can be eluted from the column by elution with aqueous organic solvent with added acid, such as 0.05% (v/v) trifluoroacetic acid in 25% (v/v) acetonitrile, which elutes both neutral and sialylated glycans. A glycan preparation containing sialylated glycans can be further purified by subjecting it to chromatography on microcrystalline cellulose in n-butanol:ethanol:water (10:1:2, v/v) and eluted by aqueous solvent, preferentially 50% ethanol:water (v/v). Preferentially, glycans isolated from small sample amounts are purified on miniaturized chromatography columns and small elution and handling volumes. An efficient purification method comprises most of the abovementioned purification steps. In an efficient purification sequence, neutral glycan fractions from small samples are purified with methods including carbon chromatography and separate elution of the neutral glycan fraction, and glycan fractions containing sialylated glycans are purified with methods including both carbon chromatography and cellulose chromatography.

MALDI-TOF Mass Spectrometry.

MALDI-TOF mass spectrometry is performed with a Voyager-DE STR BioSpectrometry Workstation or a Bruker Ultraflex TOF/TOF instrument, essentially as described previously (Saarinen et al., 1999; Harvey et al., 1993). Relative molar abundancies of both neutral (Naven & Harvey, 1996) and sialylated (Papac et al., 1996) glycan components are assigned based on their relative signal intensities. The mass spectrometric fragmentation analysis is done with the Bruker Ultraflex TOF/TOF instrument according to manufacturer's instructions.

Results

Examples of Analysis Sensitivity.

Protein-linked and free glycans, including N- and O-glycans, are typically isolated from as little as about $5 \times 10^4$ cells in their natural biological matrix and analyzed by MALDI-TOF mass spectrometry.

Examples of Analysis Reproducibility and Accuracy.

The present glycan analysis methods have been validated for example by subjecting a single biological sample, containing human cells in their natural biological matrix, to analysis by five different laboratory personnel. The results were highly comparable, especially by the terms of detection of individual glycan signals and their relative signal intensities, indicating that the reliability of the present methods in accurately describing glycan profiles of biological samples including cells is excellent. Each glycan isolation and purification phase has been controlled by its reproducibility and found to be very reproducible. The mass spectrometric analysis method has been validated by synthetic oligosaccharide mixtures to reproduce their molar proportions in a manner suitable for analysis of complex glycan mixtures and especially for accurate comparison of glycan profiles from two or more samples. The analysis method has also been successfully transferred from one mass spectrometer to another and found to reproduce the analysis results from complex glycan profiles accurately by means of calibration of the analysis.

Examples of Biological Samples and Matrices for Successful Glycan Analysis.

The method has been successfully implied on analysis of e.g. blood cells, cell membranes, aldehyde-fixated cells, glycans isolated from glycolipids and glycoproteins, free cellular glycans, and free glycans present in biological matrices such as blood. The experience indicates that the method is especially useful for analysis of oligosaccharide and similar molecule mixtures and their optional and optimal purification into suitable form for analysis.

Example 2

Glycan Profiling

Generation of Glycan Profiles from Mass Spectrometric Data

FIG. 1A shows a MALDI-TOF mass spectrum recorded in positive ion mode from a sample of neutral N-glycans. The profile includes multiple signals that interfere with the interpretation of the original sample's glycosylation, including non-glycan signals and multiple signals arising from single glycan signals. According to the present invention, the mass spectrometric data is transformed into a glycan profile (FIG. 1B), which represents better the original glycan profile of the sample. An exemplary procedure is briefly as follows, and it includes following steps: 1) The mass spectrometric signals are first assigned to proposed monosaccharide compositions e.g. according to Table 1. 2) The mass spectrometric signals of ions in the molecular weight are of glycan signals typically show isotopic patterns, which can be calculated based on natural abundancies of the isotopes of the elements in the Earth's crust. The relative signal intensities of mass spectrometric signals near each other can be overestimated or underestimated, if their isotopic patterns are not taken into account. According to the present method, the isotopic patterns are calculated for glycan signals near each other, and relative intensities of glycan signals corrected based on the calculations. 3) Glycan ions are predominantly present as [M+Na]+ ions in positive ion mode, but also as other adduct ions such as [M+K]+. The proportion of relative signal intensities of [M+Na]+ to [M+K]+ ions is deduced from several signals in the spectrum, and the proportion is used to remove the effect of [M+K]+ adduct ions from the spectrum. 4) Other contaminating mass spectrometric signals not arising from the original glycans in the sample can optionally be removed from the profile, such as known contaminants, products of elimination of water, or in a case of permethylated oligosaccharides, undermethylated glycan signals. 5) The resulting glycan signals in the profile are normalized, for example to 100%, for allowing comparison between samples.

Figure 2:
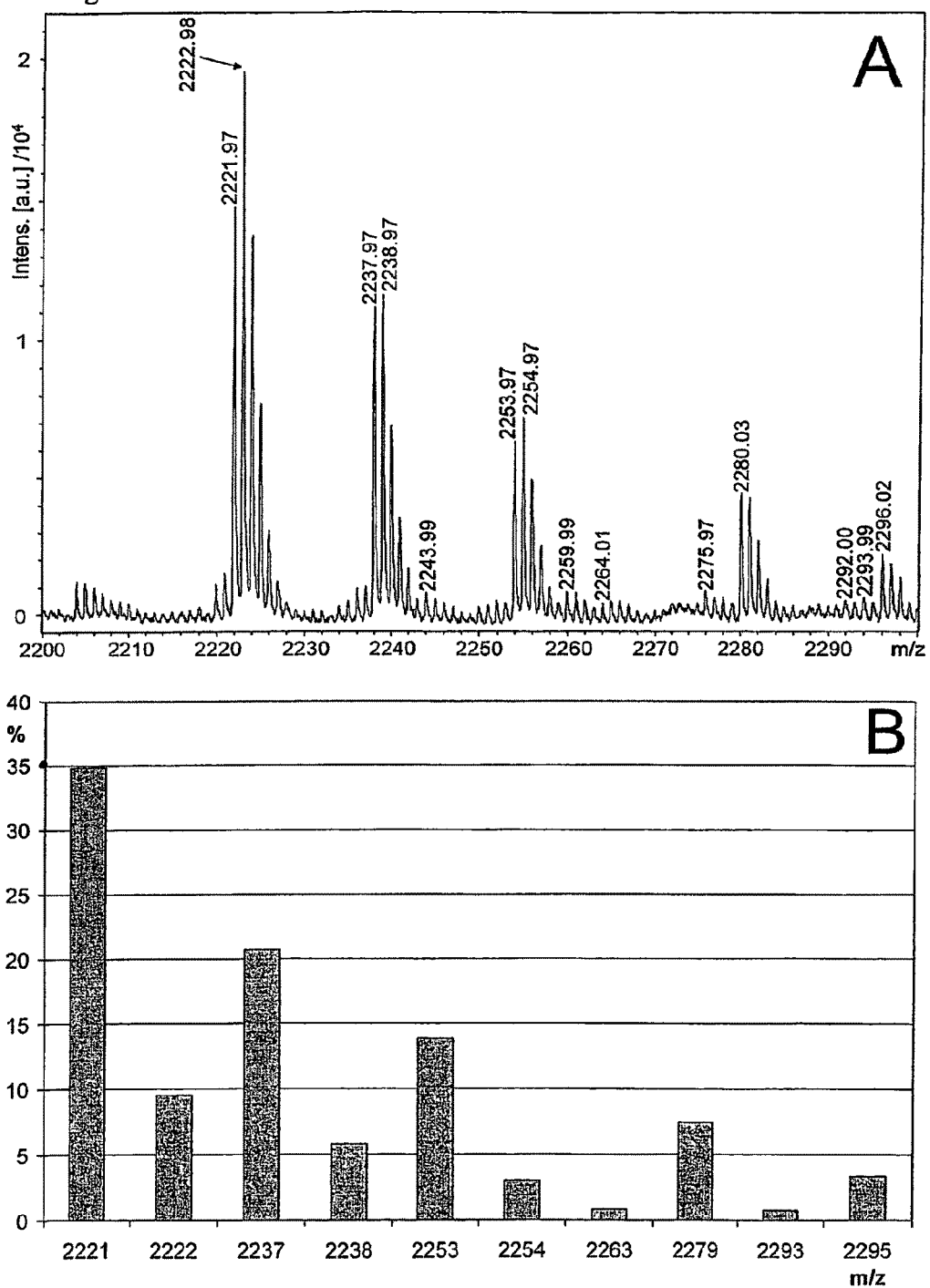
FIG. 2. Example of glycan signal analysis of MALDI-TOF mass spectrometric data. A. Mass spectrometric raw data showing a window of sialylated N-glycan mass spectrum in negative ion mode, B. Glycan profile generated from the data in A.

FIG. 2A shows a MALDI-TOF mass spectrum recorded in negative ion mode from a sample of neutral N-glycans. The profile includes multiple signals that interfere with the interpretation of the original sample's glycosylation, including non-glycan signals and multiple signals arising from single glycan signals. According to the present invention, the mass spectrometric data is transformed into a glycan profile (FIG. 2B), which represents better the original glycan profile of the sample. An exemplary procedure is briefly as follows, and it includes following steps: 1) The mass spectrometric signals are first assigned to proposed monosaccharide compositions e.g. according to Table 2. 2) The mass spectrometric signals of ions in the molecular weight are of glycan signals typically show isotopic patterns, which can be calculated based on natural abundancies of the isotopes of the elements in the Earth's crust. The relative signal intensities of mass spectrometric signals near each other can be overestimated or underestimated, if their isotopic patterns are not taken into account. According to the present method, the isotopic patterns are calculated for glycan signals near each other, and relative intensities of glycan signals corrected based on the calculations. 3) Glycan ions are predominantly present as [M-H]− ions in negative ion mode, but also as ions such as [M-2H+Na]− or [M-2H+K]−. The proportion of relative signal intensities of e.g. [M-H]− to [M-2H+Na]− and [M-2H+K]− ions is deduced from several signals in the spectrum, and the proportion is used to remove the effect of e.g. these adduct ions from the specs 4) Other contaminating mass spectrometric signals not arising from the original glycans in the sample can optionally be removed from the profile, such as known contaminants or products of elimination of water. 5) The resulting glycan signals in the profile are normalized, for example to 100%, for allowing comparison between samples.

Example 3

MALDI-TOF Mass Spectrometric N-glycan Profiling of Cord Blood Mononuclear Cell Populations and Peripheral Blood Mononuclear Cells Examples of Cell Material Production
Cord Blood Cell Populations Preparation of Mononuclear Cells.

Cord blood was diluted 1:4 with phosphate buffered saline (PBS)-2 mM EDTA and 35 ml of diluted cord blood was carefully layered over 15 ml of Ficoll-Paque® (Amersham Biosciences, Piscataway, USA). Tubes were centrifuged for 40 minutes at 400 g without brake. Mononuclear cell layer at the interphase was collected and washed twice in PBS-2 mM EDTA. Tubes were centrifuged for 10 minutes at 300 g.

Positive Selection of CD34+/CD133+ Cells.

The cord blood mononuclear cell pellet was resuspended in a final volume of 300 μl of PBS-2 mM EDTA-0.5% BSA (Sigma, USA) per $10^8$ total cells. To positively select CD34+ or CD133+ cells, 100 μl of FcR Blocking Reagent and 100 μl CD34 or CD133 Microbeads (Miltenyi Biotec, Bergisch Gladbach, Germany) were added per $10^8$ mononuclear cells. Suspension was incubated for 30 minutes at 6-12° C. Cells were washed with PBS-2 mM EDTA-0.5% BSA and resuspended in 500 μl of PBS-2 mM EDTA-0.5% BSA per $10^8$ cells.

The appropriate MACS affinity column type (Miltenyi Biotec, Bergisch Gladbach, Germany) was chosen according to the number of total cells: MS column for $<2\times10^8$ cells and LS column for $2\times10^8$-$2\times10^9$ cells. The column was placed in the magnetic field and rinsed with PBS-2 mM EDTA-0.5% BSA. Labeled cell suspension was applied to the column and the cells passing through the column were collected as the negative cell fraction (CD34− or CD133−). The column was then washed four times with PBS-2mM EDTA-0.5% BSA. The column was removed from the magnetic field and the retained positive cells (CD34+ or CD133$^+$) were eluted with PBS-2 mM EDTA-0.5% BSA using a plunger.

The eluted positive cells were centrifuged for 5 minutes at 300 g and resuspended in 300 μl PBS-2 mM EDTA-0.5% BSA. 25 μl of FcR Blocking Reagent and 25 μl CD34 or CD133 Microbeads were added. Suspension was incubated for 15 minutes at 6-12° C. Cells were washed with PBS-2 mM EDTA-0.5% BSA and resuspended in 500 μl of PBS-2 mM EDTA-0.5% BSA.

A MS column was placed in the magnetic field and rinsed with PBS-2mM EDTA-0.5% BSA. Labeled cell suspension was applied to the column. The column was washed four times with PBS-2 mM EDTA-0.5% BSA. The column was then removed from the magnetic field and the retained positive cells (CD34+ or CD133+) were eluted with PBS-2 mM EDTA-0.5% BSA using a plunger.

Negative Selection of Lin− Cells.

To deplete lineage committed cells, mononuclear cells ($8\times10^7$/ml) in PBS-0.5% BSA were labeled with 100 μl/ml cells with StemSep Progenitor Enrichment Cocktail containing antibodies against CD2, CD3, CD14, CD16, CD19, CD24, CD56, CD66b, Glycophorin A (StemCell Technologies, Vancouver, Canada) at room temperature for 15 minutes. Subsequently, 60 μl of colloidal magnetic iron particles were added per 1 ml cell suspension and incubated at room temperature for 15 minutes.

The labeled cell suspension was loaded into MACS LD column (Miltenyi Biotec) and unlabeled cells passing through the column were collected as the negative fraction (Lin−). LD column was washed twice with 1 ml PBS-0.5% BSA and effluents were collected into the same tube with unlabelled cells. The column was then removed from the magnetic field and the retained positive cells (Lin+) were eluted with PBS-0.5% BSA using a plunger.

Results

Glycan Isolation from Mononuclear Cell Populations.

Mononuclear cells were isolated from one sample of peripheral blood, as well as cord blood samples from multiple donors. The cord blood mononuclear cells were further affinity-purified into CD34+, CD34−, CD133+, CD133−, Lin+, and Lin− cell samples, as described under Experimental procedures. N-glycans were isolated from the samples, and glycan profiles were generated from MALDI-TOF mass spectrometry data of isolated neutral and sialylated N-glycan fractions as described in the preceding examples.

Neutral N-Glycan Profiles.

Neutral N-glycan profiles obtained from cord blood and peripheral blood mononuclear cells are presented in Table 3. The present results from cord blood cell populations are averaged from multiple experiments and multiple cord blood donors, while the peripheral blood cell results are exemplary results obtained from a single experiment. From the present results, it is evident that cord blood cell populations differ from each other and from peripheral blood cells with respect to their neutral N-glycan profiles. Differences in the glycan profiles between cell populations were consistent throughout multiple samples and experiments, and multiple individual glycan signals had consistently differing relative abundancies. The analysis revealed in each cell type the relative proportions of about 25-55 glycan signals that were assigned as non-sialylated N-glycan components.

Neutral N-Glycan Structural Features.

Neutral N-glycan groupings proposed for cord blood cell populations, cord blood mononuclear cells (CB MNC), and peripheral blood mononuclear cells (PB MNC) are presented in Table 5. In comparison of cord blood stem cell populations (CD34+, CD133+, and Lin−) and the corresponding stem cell depleted cord blood mononuclear cells, numerous cell-type specific features could be identified Identification of Soluble Glycan Components.

In the present analysis, neutral glycan components were identified in all the cell types that were assigned as soluble glycans based on their proposed monosaccharide compositions $Hex_{2-9}HexNAc_1$ and $Hex_{12}HexNAc_1$, and these glycan signals have been omitted from Table 3. The abundancies of these glycan components in relation to each other and in relation to the other glycan signals varied between individual samples and cell types. Indications for the presence of such glycans have previously been described in certain human cells (Moore, 1999). The relative proportions of $Hex_{2-9}HexNAc_1$ and $Hex_{12}HexNAc_1$ glycan signals are typically reduced if glycoprotein fractions are isolated from cord blood cell populations and washed, indicating that these glycan components are present in the soluble fraction of cells and not covalently bound to glycoproteins.

Sialylated N-Glycan Profiles.

Sialylated N-glycan profiles obtained from cord blood and peripheral blood mononuclear cells are presented in Table 4. From the present results, it is evident that cord blood cell populations differ from each other and from peripheral blood cells with respect to their sialylated N-glycan profiles. The analysis revealed in each cell type the relative proportions of about 45-125 glycan signals that were assigned as acidic N-glycan components.

Sialylated N-Glycan Structural Features.

Sialylated N-glycan groupings proposed for cord blood cell populations, cord blood mononuclear cells (CB MNC), and peripheral blood mononuclear cells (PB MNC) are presented in Table 6. In comparison of cord blood stem cell populations (CD34+) and the corresponding stem cell depleted cord blood mononuclear cells, numerous cell-type specific features could be identified.

Conclusions

Comparison of Neutral N-Glycan Profiles.

Differences in the glycan profiles between cell populations were consistent throughout multiple samples and experiments, indicating that the present method of glycan profiling and the differences in the present glycan profiles can be used to identify the presence of certain cell types in purified human cell populations, or their purity. The present method and the present results can also be used to identify cell-type specific glycan structural features or cell-type specific glycan profiles.

Comparison of Neutral N-Glycan Structural Features.

Differences in glycosylation profiles between analyzed cell types were identified based on proposed structural features, which can be used to identify cell-type specific glycan structural features. Identified cell-type specific features of neutral N-glycan profiles are concluded below:

CD34+:
1) Lower amounts of larger neutral N-glycans.

CD133+:
1) Lower amounts of larger neutral N-glycans;
2) Lower amounts of neutral N-glycans containing two or more deoxyhexose residues per chain, indicating reduced expression of neutral N-glycans containing α1,2-, α1,3-, or α1,4-linked fucose residues;
3) Increased amounts of terminal HexNAc residues; and
4) Lower amounts of hybrid-type and/or monoantennary neutral N-glycans.

Lin−:
1) Lower amounts of larger neutral N-glycans;
2) Lower amounts of neutral N-glycans containing two or more deoxyhexose residues per chain, indicating reduced expression of neutral N-glycans containing α1,2-, α1,3-, or α1,4-linked fucose residues; and
3) Increased amounts of terminal HexNAc residues.

Cord Blood Stem Cell Populations in General:

These neutral N-glycan profile features were common to all of the three cell types above when compared to corresponding stem cell depleted cord blood mononuclear cell samples. These features are more strongly expressed in CD133+ and Lin− cell populations than in CD34+ cell population.

1) Lower amounts of larger neutral N-glycans;
2) Lower amounts of neutral N-glycans containing two or more deoxyhexose residues per chain, indicating reduced expression of neutral N-glycans containing α1,2-, α1,3-, or α1,4-linked fucose residues;
3) Increased amounts of terminal HexNAc residues; and
4) Lower amounts of low-mannose type N-glycans compared to high-mannose type N-glycans.

Cord Blood Mononuclear Cells Compared to Peripheral Blood Mononuclear Cells:
1) Increased amounts of neutral N-glycans containing two or more deoxyhexose residues per chain, indicating increased expression of neutral N-glycans containing α1,2-, α1,3-, or α1,4-linked fucose residues.

Comparison of Sialylated N-Glycan Profiles.

Differences in the glycan profiles between cell populations were observed, indicating that the present method of glycan profiling and the differences in the present glycan profiles can be used to identify the presence of certain cell types in purified human cell populations, or their purity. The present method and the present results can also be used to identify cell-type specific glycan structural features or cell-type specific glycan profiles.

Comparison of Sialylated N-Glycan Structural Features.

Differences in glycosylation profiles between analyzed cell types were identified based on proposed structural features, which can be used to identify cell-type specific glycan structural features. Identified cell-type specific features of sialylated N-glycan profiles are concluded below:

CD34+:
1) Lower amounts of larger sialylated N-glycans; and
2) Lower amounts of potentially bisecting GlcNAc containing sialylated N-glycans.

Example 4

MALDI-TOF Mass Spectrometric O-glycan Profiling of Cord Blood and Peripheral Blood Mononuclear Cell Populations Experimental Procedures O-Glycan Isolation.

O-glycans were isolated from glycoproteins after enzymatic de-N-glycosylation by N-glycosidase F and extraction of soluble glycans as described in the preceeding Examples. O-glycans were liberated by reductive alkaline β-elimination essentially as described in (Nyman et al., 1998).

Results

O-Glycan Isolation.

O-glycans were isolated from de-N-glycosylated glycoproteins of Lin− and Lin+ cord blood mononuclear cells as described above, fractionated into sialylated and neutral glycan fractions, and analyzed by MALDI-TOF mass spectrometry as described in the preceeding Examples.

O-Glycan Profiles.

In the neutral O-glycan fraction, following O-glycan signals were detected: m/z 773, 919, 1138, and 1284, corresponding to sodium adduct ions of the O-glycan alditols $Hex_2HexNAc_2$, $Hex_2HexNAc_2dHex_1$, $Hex_3HexNAc_3$, and $Hex_2HexNAc_2dHex_1$, respectively. The relative amounts of the signals differed between cell types. In Lin− cells, the relationship of the amounts of $Hex_2HexNAc_2$ and $Hex_2HexNAc_2dHex_1$ signals was about 2:1, which is higher than in peripheral blood mononuclear cells. In the sialylated O-glycan fraction, following O-glycan signals were detected: m/z 675, 966, 1040, 1186, and 1331, corresponding to $[M-H]^-$ ions of the O-glycan alditols $NeuAc_1Hex_1HexNAc_1$, $NeuAc_2Hex_1HexNAc_1$, $NeuAc_1Hex_2HexNAc_2$, $NeuAc_1Hex_2HexNAc_2dHex_1$, and $NeuAc_2Hex_2HexNAc_2$, respectively. The relative amounts of the signals differed between cell types.

Example 5

MALDI-TOF Mass Spectrometric Glycolipid Glycan Profiling of Cord Blood and Peripheral Blood Mononuclear Cell Populations Experimental Procedures and Results Glycolipid and Glycan Isolation.

Glycolipids were isolated from peripheral blood and cord blood mononuclear cells essentially as described in (Karlsson, H. et al., 2000). Sphingoglycolipids were detached by digestion with endoglycoceramidase from *Macrobdella decora* (Calbiochem, USA). After the reaction, liberated glycans were purified, fractionated into sialylated and neutral glycan fractions, and analyzed by MALDI-TOF mass spectrometry as described in the preceding Examples.

Glycolipid Glycan Profiles.

Table 7 describes the detected glycan signals and their proposed monosaccharide compositions. Relative amounts of individual signals in the profile varied between the analyzed cell types. The monosaccharide compositions correlate with known glycolipid core structures, such as gangliosides, lacto- and neolactoglycolipids, and globosides, and extensions of the core structures, such as poly-N-acetyllactosamine chains. Several glycans show fucosylation and/or sialylation of the core and extended structures.

Example 6

Comparison of Freshly Isolated and Frozen-thawed cord blood cell glycan Profiles Results N-Glycan Isolation.

Several CD34+, CD34−, CD133+, and CD133− cell samples were isolated as described above from both fresh and frozen-thawed cord blood units. N-glycans were isolated from the samples, and glycan profiles were generated from MALDI-TOF mass spectrometry data of isolated neutral and sialylated N-glycan fractions as described in the preceding Examples.

Comparison of Glycan Profiles.

The analysis revealed significant differences in the N-glycan profiles between samples that were isolated from fresh cord blood units and units that were kept frozen and thawed before cell isolation. The differences in multiple signals in the glycan profiles were consistent in all the analyzed samples. The major difference in neutral N-glycan profiles was the signal at m/z 917, corresponding to $Hex_2HexNAc_2dHex_1$, which was the most abundant neutral N-glycan signal in the samples from frozen-thawed cord blood. The relative abundancies of the signal groups corresponding to $Hex_{1-4}HexNAc_2dHex_{0-1}$ and especially $Hex_{1-4}HexNAc_2dHex_1$ monosaccharide compositions, were elevated in the frozen-thawed cell samples in comparison to freshly isolated cell samples.

Conclusions

According to the present results, glycan profiling can effectively detect changes in glycan profiles, individual glycan signals, and glycan signal groups, which are associated with differential cell treatment conditions.

Example 7

Glycosidase Profiling of Cord Blood Mononuclear Cell N-glycans

Experimental Procedures

Exoglycosidase Digestions.

Neutral N-glycan fractions were isolated from cord blood mononuclear cell populations as described above. Exoglycosidase reactions were performed essentially after manufacturers' instructions and as described in (Saarinen et al., 1999). The different reactions were; α-Man: α-mannosidase from Jack beans (*C. ensiformis*; Sigma, USA); β1,4-Gal: β1,4-galactosidase from *S. pneumoniae* (recombinant in *E. coli*; Calbiochem, USA); β1,3-Gal: recombinant β1,3-galactosidase (Calbiochem, USA); GlcNAc: β-glucosaminidase from *S. pneumoniae* (Calbiochem, USA); α2,3-SA: α2,3-sialidase from *S. pneumoniae* (Calbiochem, USA). The analytical reactions were carefully controlled for specificity with synthetic oligosaccharides in parallel control reactions that were analyzed by MALDI-TOF mass spectrometry. The sialic acid linkage specificity of α2,3-SA was controlled with synthetic oligosaccharides in parallel control reactions, and it was confirmed that in the reaction conditions the enzyme hydrolyzed α2,3-linked but not α2,6-linked sialic acids. The analysis was performed by MALDI-TOF mass spectrometry as described in the preceding examples. Digestion results were analyzed by comparing glycan profiles before and after the reaction.

Results

Glycosidase Profiling of Neutral N-Glycans.

Neutral N-glycan fractions from affinity-purified CD34+, CD34−, CD133+, CD133−, Lin+, and Lin− cell samples from cord blood mononuclear cells were isolated as described above. The glycan samples were subjected to parallel glycosidase digestions as described under Experimental procedures. Profiling results are summarized in Table 8 (CD34+ and CD34− cells), Table 9 (CD133+ and CD133− cells), and Table 10 (Lin− and Lin+ cells). The present results show that several neutral N-glycan signals are individually sensitive towards all the exoglycosidases, indicating that in all the cell types several neutral N-glycans contain specific substrate glycan structures in their non-reducing termini. The results also show clear differences between the cell types in both the sensitivity of individual glycan signals towards each enzyme and also profile-wide differences between cell types, as detailed in the Tables cited above.

Glycosidase Profiling of Sialylated N-Glycans.

Figure 3:
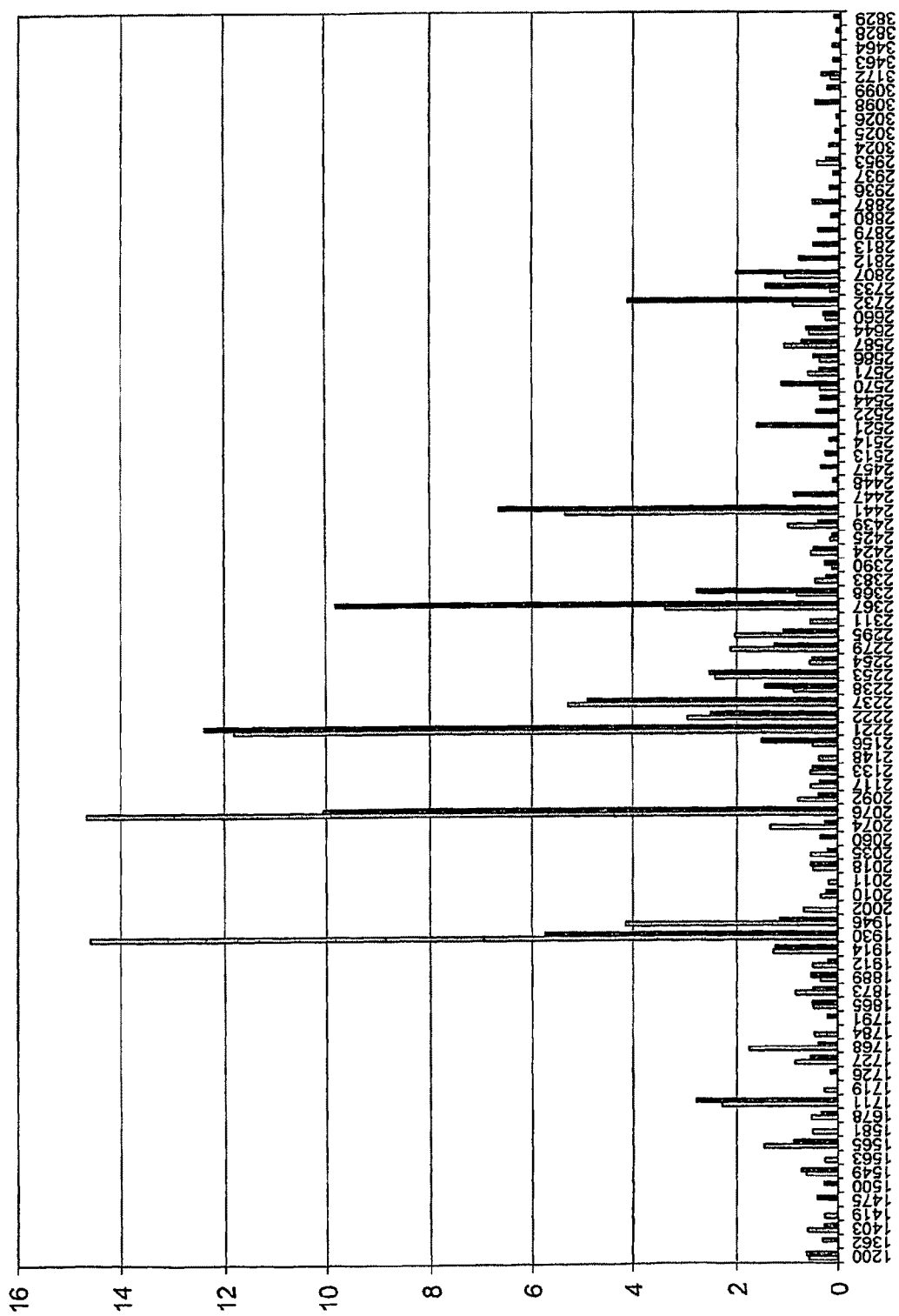
FIG. 3. α2,3-sialidase profiling analysis of cord blood CD133+ and CD133− cells. Sialylated glycan fractions isolated after the reaction, showing the sialylated N-glycans bearing sialic acid residues resistant to the action of α2,3-sialidase. Light columns: CD133+ cells; dark columns: CD133− cells.
Figure 4:
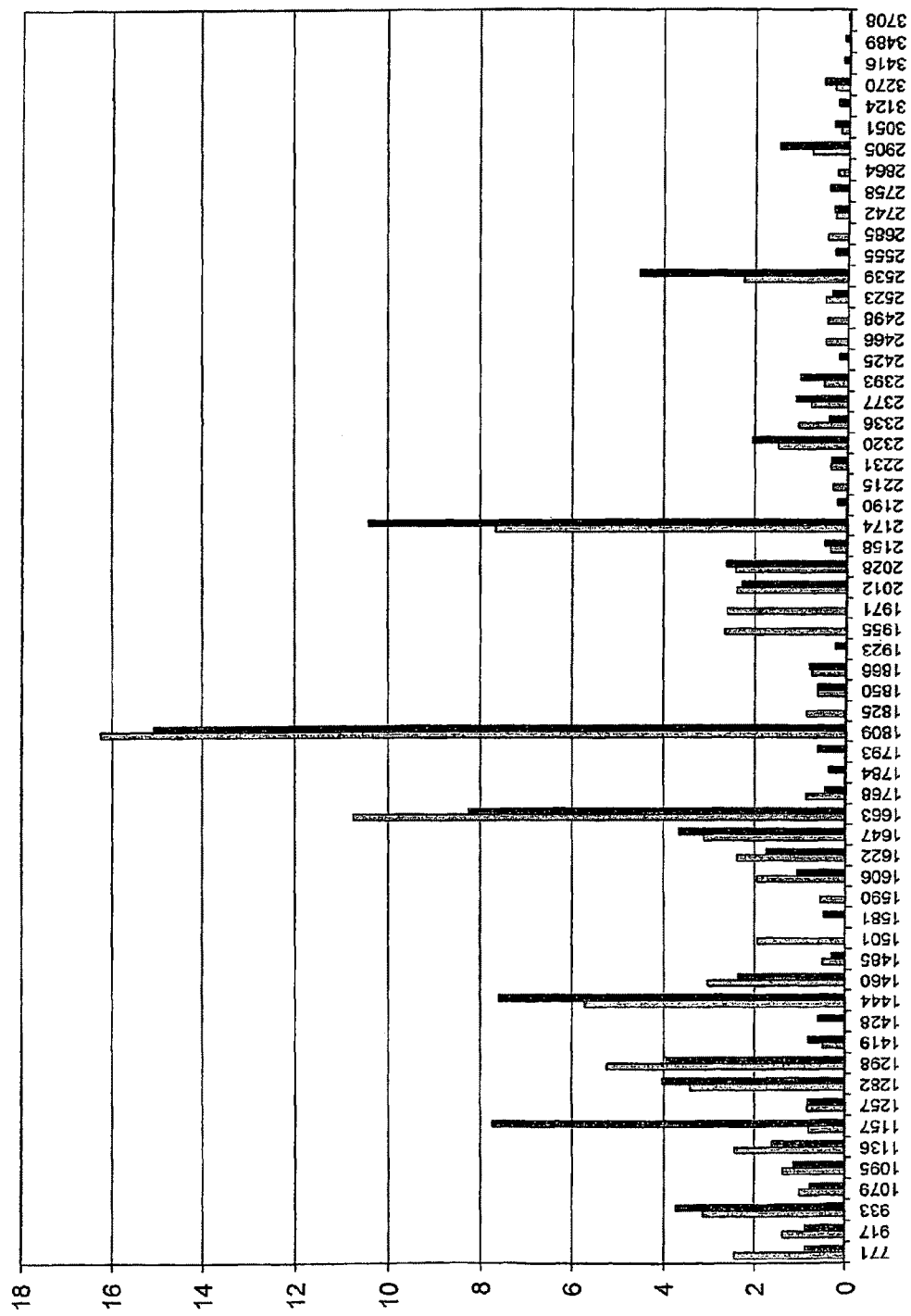
FIG. 4. α2,3-sialidase profiling analysis of cord blood CD133+ and CD133− cells. Neutral glycan fractions isolated after the reaction, showing the N-glycan core sequences of sialylated N-glycans that beared only α2,3-sialidase sensitive sialic acid residues. Light columns: CD133+ cells; dark columns: CD133− cells.

Sialylated N-glycan fractions from affinity-purified CD133+ and CD133− cell samples from cord blood mononuclear cells were isolated as described above. The glycan samples were subjected to parallel glycosidase digestions as described under Experimental procedures. Profiling results are summarized in FIGS. 3 and 4. The results show significant differences between the glycan profiles of the analyzed cell types in the sialylated and neutral glycan fractions resulting in the reaction. The present results show that differences are seen in multiple signals in a profile-wide fashion. Also individual signals differ between cell types, as discussed below.

Cord Blood $CD133^+$ and $CD133^-$ Cell N-Glycans are Differentially α2,3-Sialylated.

Figure 5:
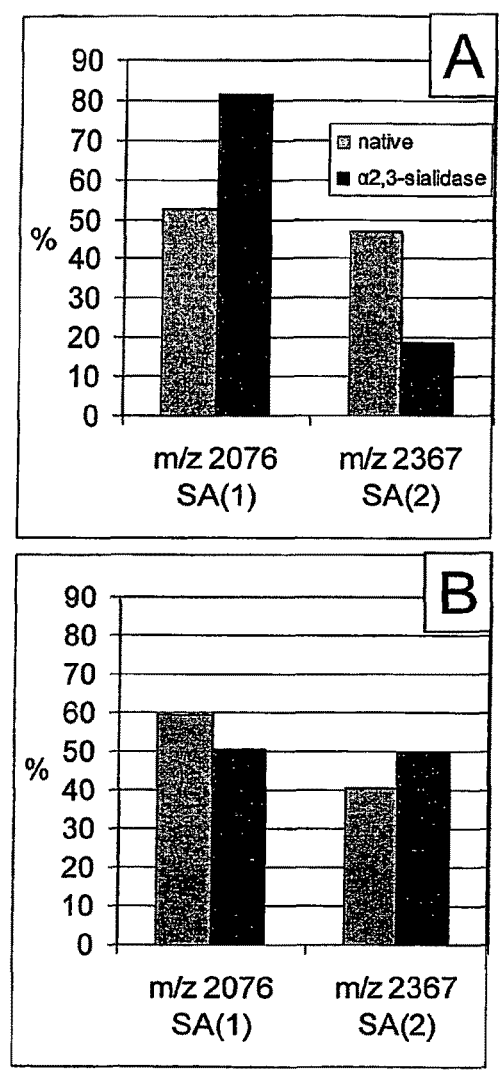
FIG. 5. α2,3-sialidase analysis of sialylated N-glycans isolated from A. cord blood CD133$^+$ cells and B. CD133$^-$ cells. The columns represent the relative proportions of a monosialylated glycan signal at m/z 2076 ($SA_1$) and the corresponding disialylated glycan signal at m/z 2367 ($SA_2$), as described in the text. In cord blood CD133$^-$ cells, the relative proportions of the $SA_1$ and $SA_2$ glycans do not change markedly upon α2,3-sialidase treatment (B), whereas in CD133$^+$ cells the proportion of α2,3-sialidase resistant $SA_2$ glycans is significantly smaller than α2,3-sialidase resistant $SA_1$ glycans (A).

Sialylated N-glycans from cord blood $CD133^+$ and $CD133^-$ cells were treated with α2,3-sialidase, after which the resulting glycans were divided into sialylated and non-sialylated fractions, as described under Experimental procedures. Both α2,3-sialidase resistant and sensitive sialylated N-glycans were observed, i.e. after the sialidase treatment sialylated glycans were observed in the sialylated N-glycan fraction and desialylated glycans were observed in the neutral N-glycan fraction. The results indicate that cord blood $CD133^+$ and $CD133^-$ cells are differentially α2,3-sialylated. For example, after α2,3-sialidase treatment the relative proportions of monosialylated ($SA_1$) glycan signal at m/z 2076, corresponding to the $[M-H]^-$ ion of $NeuAc_1Hex_5HexNAc_4dHex_1$, and the disialylated ($SA_2$) glycan signal at m/z 2367, corresponding to the $[M-H]^-$ ion of $NeuAc_2Hex_5HexNAc_4dHex_1$, indicate that α2,3-sialidase resistant disialylated N-glycans are relatively more abundant in $CD133^-$ than in $CD133^+$ cells, when compared to α2,3-sialidase resistant monosialylated N-glycans (FIG. 5). It is concluded that N-glycan α2,3-sialylation in relation to other sialic acid linkages including especially α2,6-sialylation, is more abundant in cord blood $CD133^+$ cells than in $CD133^-$ cells.

In cord blood $CD133^-$ cells, several sialylated N-glycans were observed that were resistant to α2,3-sialidase treatment, i.e. neutral glycans were not observed that would correspond to the desialylated forms of the original sialylated glycans. The results revealing differential α2,3-sialylation of individual N-glycan structures between cord blood $CD133^+$ and $CD133^-$ cells are presented in Table 11. The present results indicate that N-glycan α2,3-sialylation in relation to other sialic acid linkages is more abundant in cord blood CD133+ cells than in CD133− cells.

Sialidase Analysis.

Figure 6:
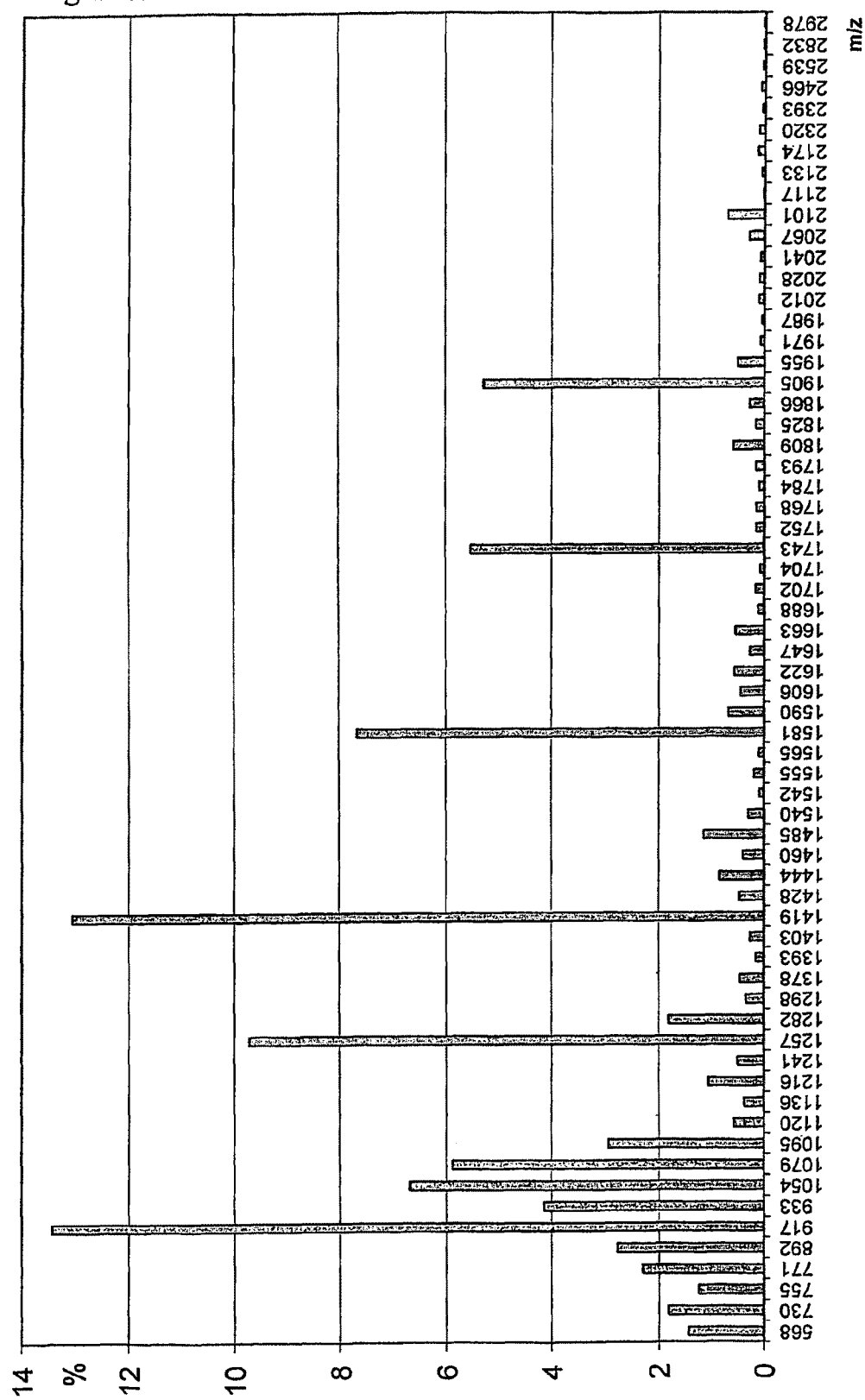
FIG. 6. Neutral N-glycan profiles of a cord blood mononuclear cell population.
Figure 7:
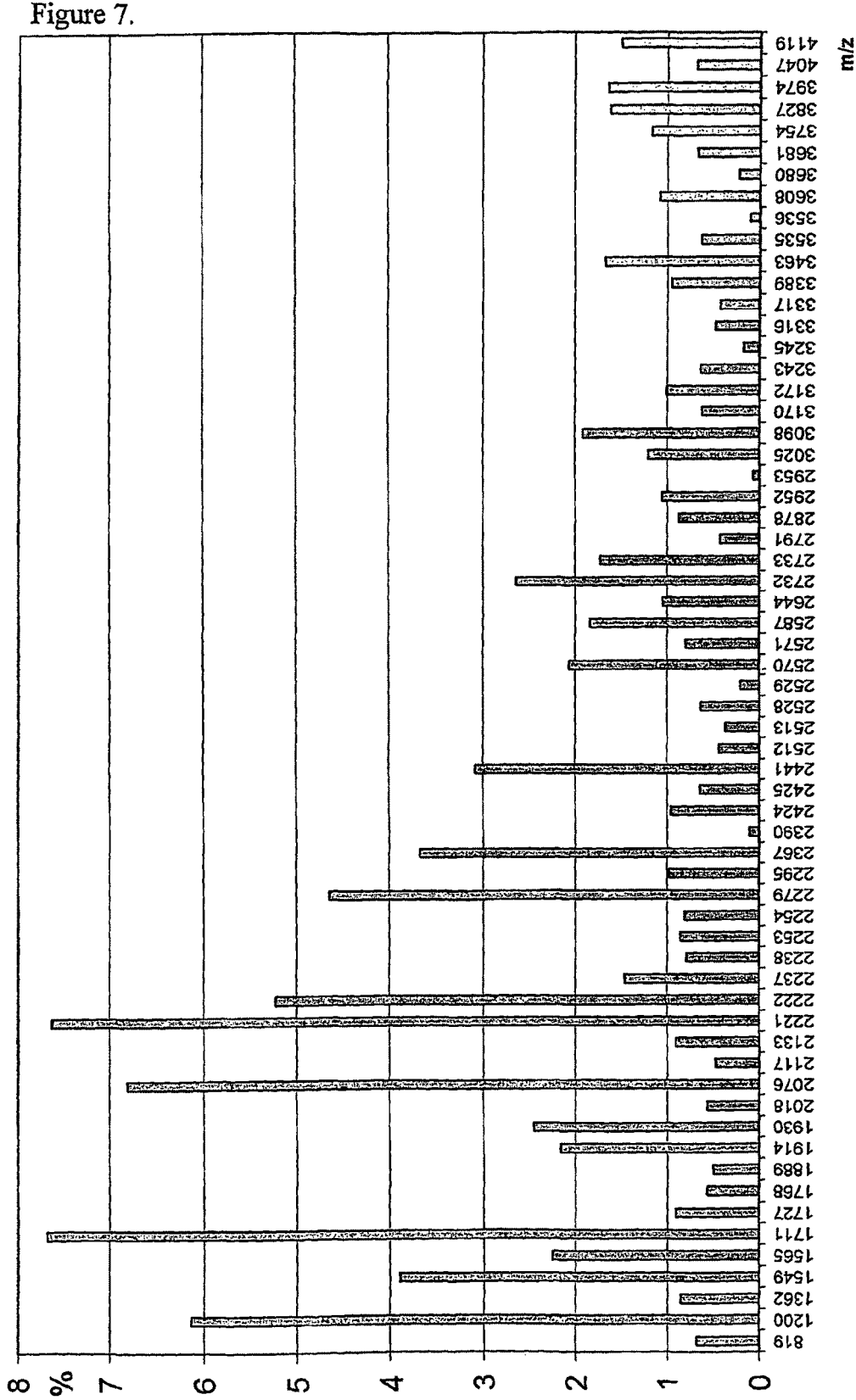
FIG. 7. Sialylated N-glycan profiles of a cord blood mononuclear cell population.
Figure 8:
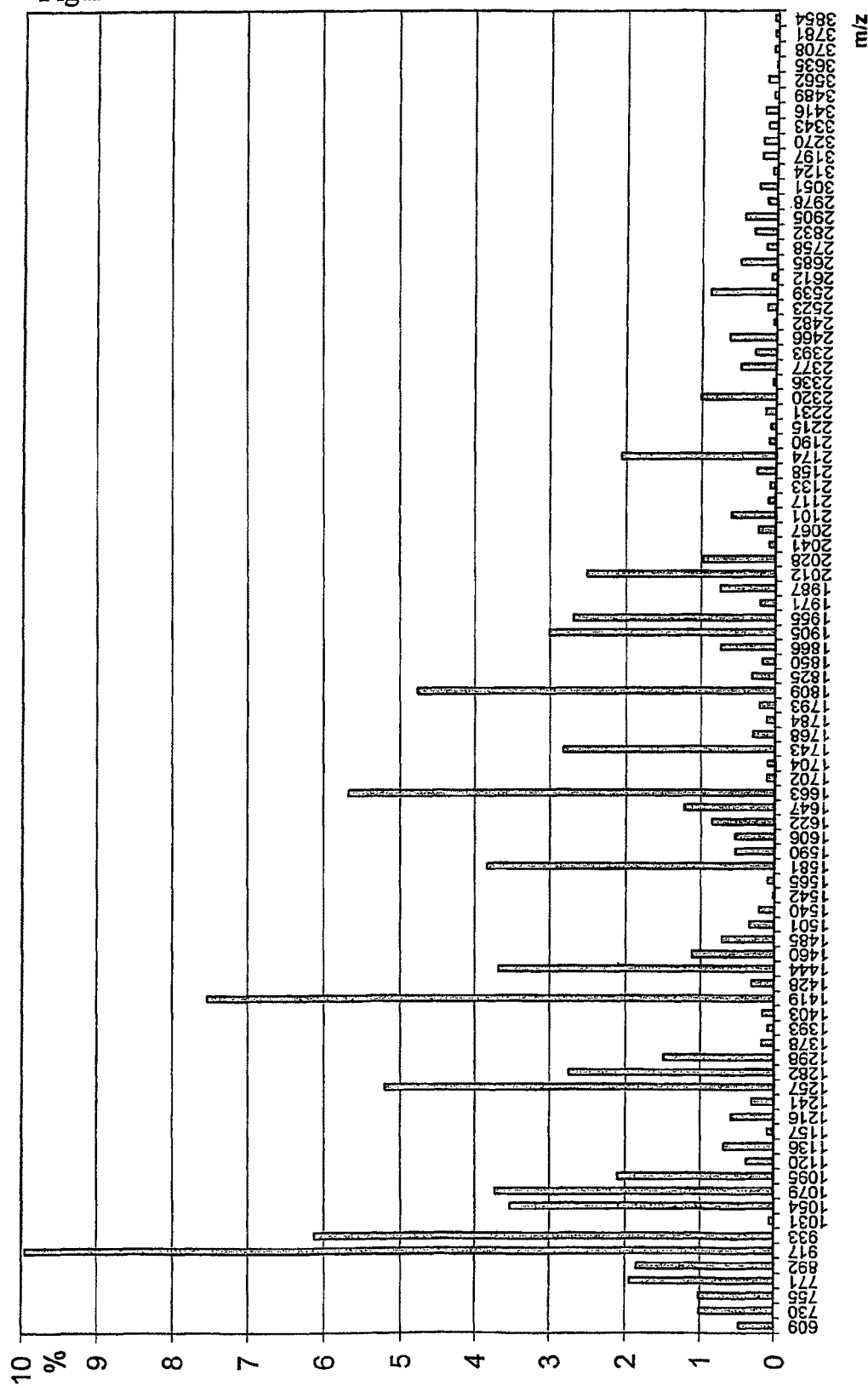
FIG. 8. Profiles of combined neutral and sialylated N-glycan fractions of a cord blood mononuclear cell population, after broad-range neuraminidase treatment of the sialylated fraction.

The sialylated N-glycan fraction isolated from a cord blood mononuclear cell population (CB MNC; FIG. 7) was digested with broad-range sialidase as described in the preceding Examples. After the reaction, it was observed by MALDI-TOF mass spectrometry that the vast majority of the sialylated N-glycans were desilylated and transformed into corresponding neutral N-glycans, indicating that they had contained sialic acid residues (NeuAc and/or NeuGc) as suggested by the proposed monosaccharide compositions. FIG. 8 shows the glycan profiles of combined neutral (FIG. 6) and desilylated (originally sialylated) N-glycan fractions of a CB MNC population. The profiles correspond to total N-glycan profiles isolated from the cell samples (in desilylated form). It is calculated that approximately 25% of the N-glycan signals correspond to high-mannose type N-glycan monosaccharide compositions, and 28% to low-mannose type N-glycans, 34% to complex-type N-glycans, and 13% to hybrid-type or monoantennary N-glycans monosaccharide compositions.

Conclusions

The present results suggest that 1) the glycosidase profiling method can be used to analyze structural features of individual glycan signals, as well as differences in individual glycans between cell types, 2) different cell types differ from each other with respect to both individual glycan signals' and glycan profiles' susceptibility to glycosidases, and 3) glycosidase profiling can be used as a further means to distinguish different cell types, and in such case the parameters for comparison are both individual signals and profile-wide differences.

Example 8

MALDI-TOF Mass Spectrometric N-glycan Profiling and Lectin Profiling of Cord Blood Derived and Bone Marrow Derived Mesenchymal Stem Cell Lines

Examples of Cell Sample Production

Cord Blood Derived Mesenchymal Stem Cell Lines
Collection of Umbilical Cord Blood.

Human term umbilical cord blood (UCB) units were collected after delivery with informed consent of the mothers and the UCB was processed within 24 hours of the collection. The mononuclear cells (MNCs) were isolated from each UCB unit diluting the UCB 1:1 with phosphate-buffered saline (PBS) followed by Ficoll-Paque Plus (Amersham Biosciences, Uppsala, Sweden) density gradient centrifugation (400 g/40 min). The mononuclear cell fragment was collected from the gradient and washed twice with PBS.

Umbilical Cord Blood Cell Isolation and Culture.

CD45/Glycophorin A (GlyA) negative cell selection was performed using immunolabeled magnetic beads (Miltenyi Biotec). MNCs were incubated simultaneously with both CD45 and GlyA magnetic microbeads for 30 minutes and negatively selected using LD columns following the manufacturer's instructions (Miltenyi Biotec). Both CD45/GlyA negative elution fraction and positive fraction were collected, suspended in culture media and counted CD45/GlyA positive cells were plated on fibronectin (FN) coated six-well plates at the density of $1 \times 10^6/cm^2$. CD45/GlyA negative cells were plated on FN coated 96-well plates (Nunc) about $1 \times 10^4$ cells/well. Most of the non-adherent cells were removed as the medium was replaced next day. The rest of the non-adherent cells were removed during subsequent twice weekly medium replacements.

The cells were initially cultured in media consisting of 56% DMEM low glucose (DMEM-LG, Gibco, http://www-.invitrogen.com) 40% MCDB-201 (Sigma-Aldrich) 2% fetal calf serum (FCS), 1× penicillin-streptomycin (both form Gibco), 1×ITS liquid media supplement (insulin-transfer-selenium), 1× linoleic acid-BSA, $5 \times 10^{-8}$ M dexamethasone, 0.1 mM L-ascorbic acid-2-phosphate (all three from Sigma-Aldrich), 10 nM PDGF (R&D systems, http://www.RnDSystems.com) and 10 nM EGF (Sigma-Aldrich). In later passages (after passage 7) the cells were also cultured in the same proliferation medium except the FCS concentration was increased to 10%.

Plates were screened for colonies and when the cells in the colonies were 80-90% confluent the cells were subcultured. At the first passages when the cell number was still low the cells were detached with minimal amount of trypsin/EDTA (0.25%/1 mM, Gibco) at room temperature and trypsin was inhibited with FCS. Cells were flushed with serum free culture medium and suspended in normal culture medium adjusting the serum concentration to 2%. The cells were plated about 2000-3000/cm². In later passages the cells were detached with trypsin/EDTA from defined area at defined time points, counted with hematocytometer and replated at density of 2000-3000 cells/cm².

Bone Marrow Derived Mesenchymal Stem Cell Lines
Isolation and Culture of Bone Marrow Derived Stem Cells.

Bone marrow (BM)-derived MSCs were obtained as described by Leskelä et al. (2003). Briefly, bone marrow obtained during orthopedic surgery was cultured in Minimum Essential Alpha-Medium (α-MEM), supplemented with 20 mM HEPES, 10% FCS, 1× penicillin-streptomycin and 2 mM L-glutamine (all from Gibco). After a cell attachment period of 2 days the cells were washed with $Ca^{2+}$ and $Mg^{2+}$ free PBS (Gibco), subcultured further by plating the cells at a density of 2000-3000 cells/cm2 in the same media and removing half of the media and replacing it with fresh media twice a week until near confluence.

Experimental Procedures

Flow Cytometric Analysis of Mesenchymal Stem Cell Phenotype.

Both UBC and BM derived mesenchymal stem cells were phenotyped by flow cytometry (FACSCalibur, Becton Dickinson). Fluorescein isothicyanate (FITC) or phycoerythrin (PE) conjugated antibodies against CD13, CD14, CD29, CD34, CD44, CD45, CD49e, CD73 and HLA-ABC (all from BD Biosciences, San Jose, Calif., i), CD105 (Abeam Ltd., Cambridge, UK, http://www.abcam.com) and CD133 (Miltenyi Biotec) were used for direct labeling. Appropriate FITC- and PE-conjugated isotypic controls (BD Biosciences) were used. Unconjugated antibodies against CD90 and HLA-DR (both from BD Biosciences) were used for indirect labeling. For indirect labeling FITC-conjugated goat anti-mouse IgG antibody (Sigma-aldrich) was used as a secondary antibody.

The UBC derived cells were negative for the hematopoietic markers CD34, CD45, CD14 and CD133. The cells stained positively for the CD13 (aminopeptidase N), CD29 (β1-integrin), CD44 (hyaluronate receptor), CD73 (SH3), CD90 (Thy1), CD105 (SH2/endoglin) and CD 49e. The cells stained also positively for HLA-ABC but were negative for HLA-DR. BM-derived cells showed to have similar phenotype.

They were negative for CD 14, CD34, CD45 and HLA-DR and positive for CD13, CD29, CD44, CD90, CD105 and HLA-ABC.

Adipogenic Differentiation.

To assess the adipogenic potential of the UCB-derived MSCs the cells were seeded at the density of $3 \times 10^3/cm^2$ in 24-well plates (Nunc) in three replicate wells. UCB-derived MSCs were cultured for five weeks in adipogenic inducing medium which consisted of DMEM low glucose, 2% FCS (both from Gibco), 10 μg/ml insulin, 0.1 mM indomethacin, 0.1 μM dexamethasone (Sigma-Aldrich) and penicillin-streptomycin (Gibco) before samples were prepared for glycome analysis. The medium was changed twice a week during differentiation culture.

Osteogenic Differentiation.

To induce the osteogenic differentiation of the BM-derived MSCs the cells were seeded in their normal proliferation medium at a density of $3 \times 10^3/cm^2$ on 24-well plates (Nunc). The next day the medium was changed to osteogenic induction medium which consisted of α-MEM (Gibco) supplemented with 10% FBS (Gibco), 0.1 μM dexamethasone, 10 mM β-glycerophosphate, 0.05 mM L-ascorbic acid-2-phosphate (Sigma-Aldrich) and penicillin-streptomycin (Gibco). BM-derived MSCs were cultured for three weeks changing the medium twice a week before preparing samples for glycome analysis.

Cell Harvesting for Glycome Analysis.

1 ml of cell culture medium was saved for glycome analysis and the rest of the medium removed by aspiration. Cell culture plates were washed with PBS buffer pH 7.2. PBS was aspirated and cells scraped and collected with 5 ml of PBS (repeated two times). At this point small cell fraction (10 μl) was taken for cell-counting and the rest of the sample centrifuged for 5 minutes at 400 g. The supernatant was aspirated and the pellet washed in PBS for an additional 2 times.

The cells were collected with 1.5 ml of PBS, transferred from 50 ml tube into 1.5 ml collection tube and centrifuged for 7 minutes at 5400 rpm. The supernatant was aspirated and washing repeated one more time. Cell pellet was stored at −70° C. and used for glycome analysis.

Lectin Stainings.

FITC-labeled *Maackia amurensis* agglutinin (MAA) was purchased from EY Laboratories (USA) and FITC-labeled *Sambucus nigra* agglutinin (SNA) was purchased from Vector Laboratories (UK). Bone marrow derived mesenchymal stem cell lines were cultured as described above. After culturing, cells were rinsed 5 times with PBS (10 mM sodium phosphate, pH 7.2, 140 mM NaCl) and fixed with 4% PBS-buffered paraformaldehyde pH 7.2 at room temperature (RT) for 10 minutes. After fixation, cells were washed 3 times with PBS and non-specific binding sites were blocked with 3% HSA-PBS (FRC Blood Service, Finland) or 3% BSA-PBS (>99% pure BSA, Sigma) for 30 minutes at RT. According to manufacturers' instructions cells were washed twice with PBS, TBS (20 mM Tris-HCl pH 7.5, 150 mM NaCl, 10 mM $CaCl_2$) or HEPES-buffer (10 mM HEPES, pH 7.5, 150 mM NaCl) before lectin incubation. FITC-labeled lectins were diluted in 1% HSA or 1% BSA in buffer and incubated with the cells for 60 minutes at RT in the dark. Furthermore, cells were washed 3 times 10 minutes with PBS/TBS/HEPES and mounted in Vectashield mounting medium containing DAPI-stain (Vector Laboratories, UK). Lectin stainings were observed with Zeiss Axioskop 2 plus—fluorescence microscope (Carl Zeiss Vision GmbH, Germany) with FITC and DAPI filters. Images were taken with Zeiss AxioCam MRc-camera and with AxioVision Software 3.1/4.0 (Carl Zeiss) with the 400× magnification.

Results

Glycan Isolation from Mesenchymal Stem Cell Populations.

The present results are produced from two cord blood derived mesenchymal stem cell lines and cells induced to differentiate into adipogenic direction, and two marrow derived mesenchymal stem cell lines and cells induced to differentiate into osteogenic direction. The characterization of the cell lines and differentiated cells derived from them are described above. N-glycans were isolated from the samples, and glycan profiles were generated from MALDI-TOF mass spectrometry data of isolated neutral and sialylated N-glycan fractions as described in the preceding examples.

Cord Blood Derived Mesenchymal Stem Cell (CB MSC) Lines

Neutral N-Glycan Profiles.

Figure 9:
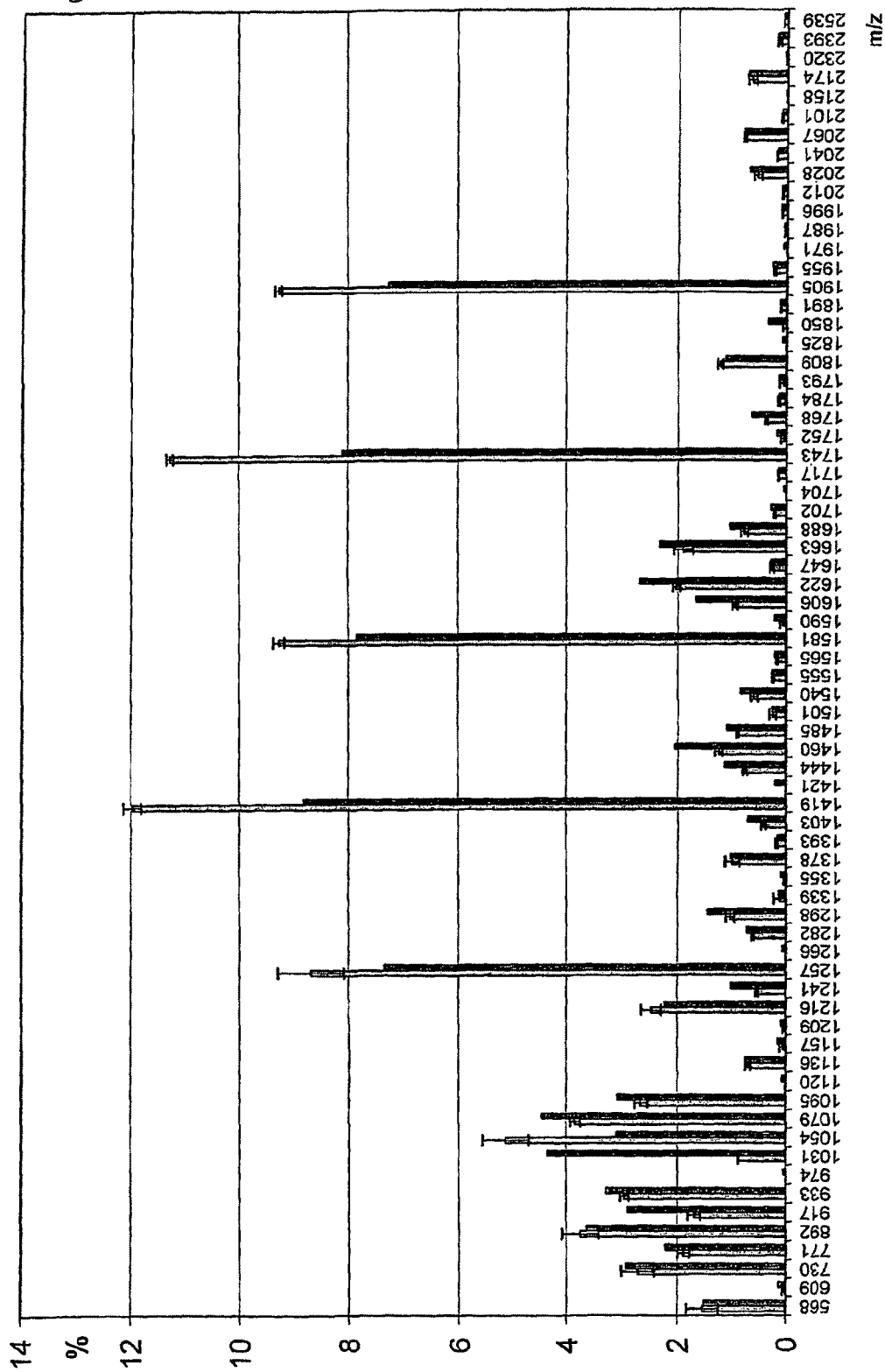
FIG. 9. Neutral N-glycan profiles of two cord blood derived mesenchymal stem cell lines. Light columns: cell line 1; dark columns: cell line 2.

Neutral N-glycan profiles obtained from two CB MSC lines are presented in FIG. 9. The two cell lines resemble closely each other with respect to their overall neutral N-glycan profiles. However, minor differences between the profiles are observed, and some glycan signals can only be observed in one cell line, indicating that the two cell lines have glycan structures that differ them from each other. The analysis revealed in each cell type the relative proportions of about 50-70 glycan signals that were assigned as non-sialylated N-glycan components. Typically, significant differences in the glycan profiles between cell populations are consistent throughout multiple experiments.

Neutral N-Glycan Structural Features.

Neutral N-glycan groupings proposed for the two CB MSC lines resemble each other closely, indicating that there are no major differences in their neutral N-glycan structural features. However, CB MSCs differ from the CB mononuclear cell populations, and they have for example relatively high amounts of neutral complex-type N-glycans, as well as hybrid-type or monoantennary neutral N-glycans, compared to other structural groups in the profiles.

Identification of Soluble Glycan Components.

Similarly to CB mononuclear cell populations, in the present analysis neutral glycan components were identified in all the cell types that were assigned as soluble glycans based on their proposed monosaccharide compositions including components from the glycan group $Hex_{2-12}HexNAc_1$ (see Figures). The abundancies of these glycan components in relation to each other and in relation to the other glycan signals vary between individual samples and cell types.

Sialylated N-Glycan Profiles.

Figure 10:
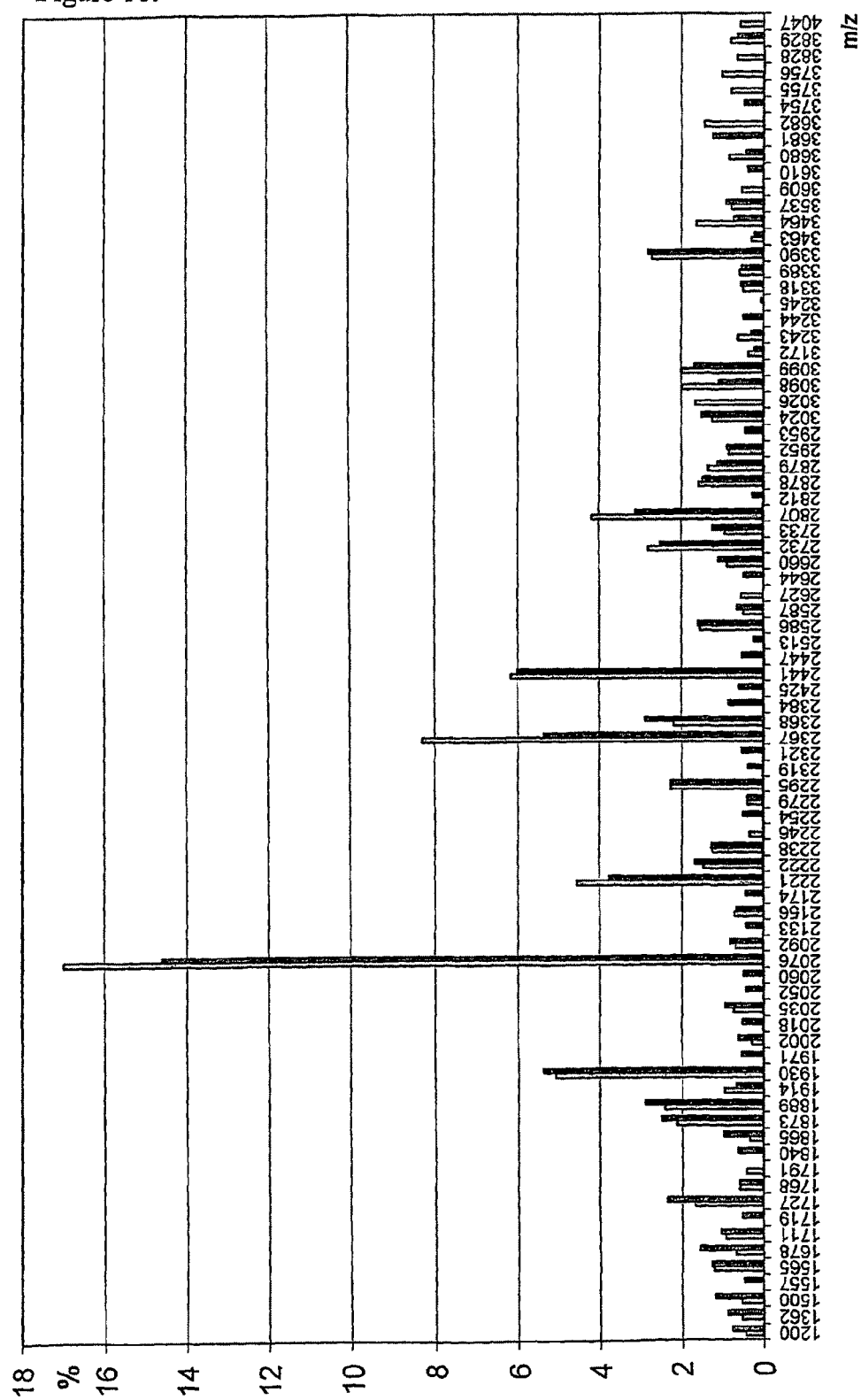
FIG. 10. Sialylated N-glycan profiles of two cord blood derived mesenchymal stem cell lines. Light columns: cell line 1; dark columns: cell line 2.

Sialylated N-glycan profiles obtained from two CB MSC lines are presented in FIG. 10. The two cell lines resemble closely each other with respect to their overall sialylated N-glycan profiles. However, minor differences between the profiles are observed, and some glycan signals can only be observed in one cell line, indicating that the two cell lines have glycan structures that differ them from each other. The analysis revealed in each cell type the relative proportions of about 50-70 glycan signals that were assigned as acidic N-glycan components. Typically, significant differences in the glycan profiles between cell populations are consistent throughout multiple experiments.

Differentiation-Associated Changes in Glycan Profiles.

Figure 11:
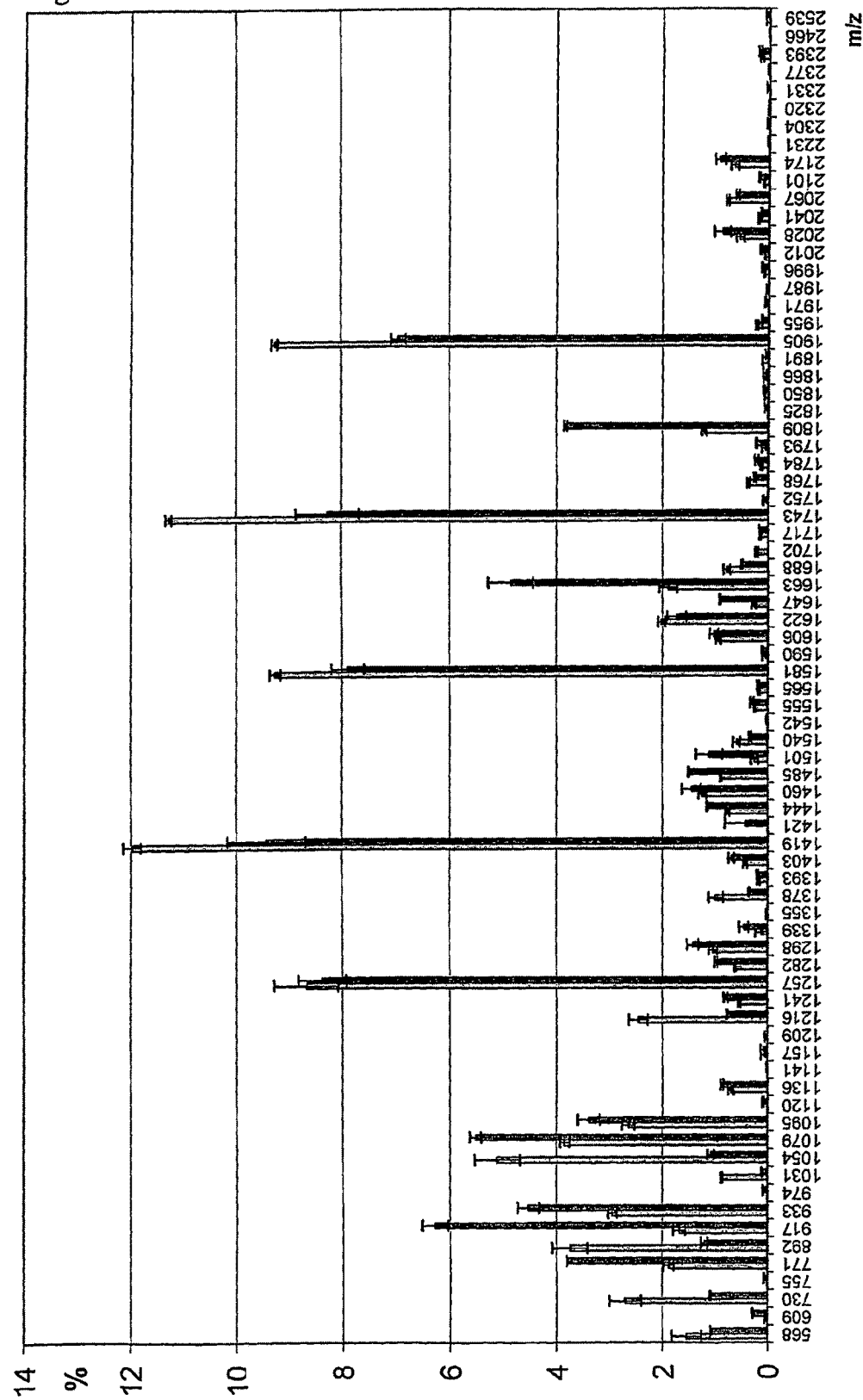
FIG. 11. Neutral N-glycan profiles of a cord blood derived mesenchymal stem cell line and cells differentiated into adipogenic direction. Light columns: mesenchymal stem cell line; dark columns: mesenchymal stem cell line in adipogenic medium.

FIG. 11 shows how neutral N-glycan profiles of CB MSCs change upon differentiation in adipogenic cell culture medium. The present results indicate that relative abundancies of several individual glycan signals as well as glycan signal groups change due to cell culture in differentiation medium. The major change in glycan structural groups associated with differentiation is increase in amounts of neutral complex-type N-glycans, such as signals at m/z 1663 and m/z 1809, corresponding to the $Hex_5HexNAc_4$ and $Hex_5HexNAc4dHex_1$ monosaccharide compositions, respectively. Changes were also observed in sialylated glycan profiles.

Glycosidase Analyses of Neutral N-Glycans.

Figure 12:
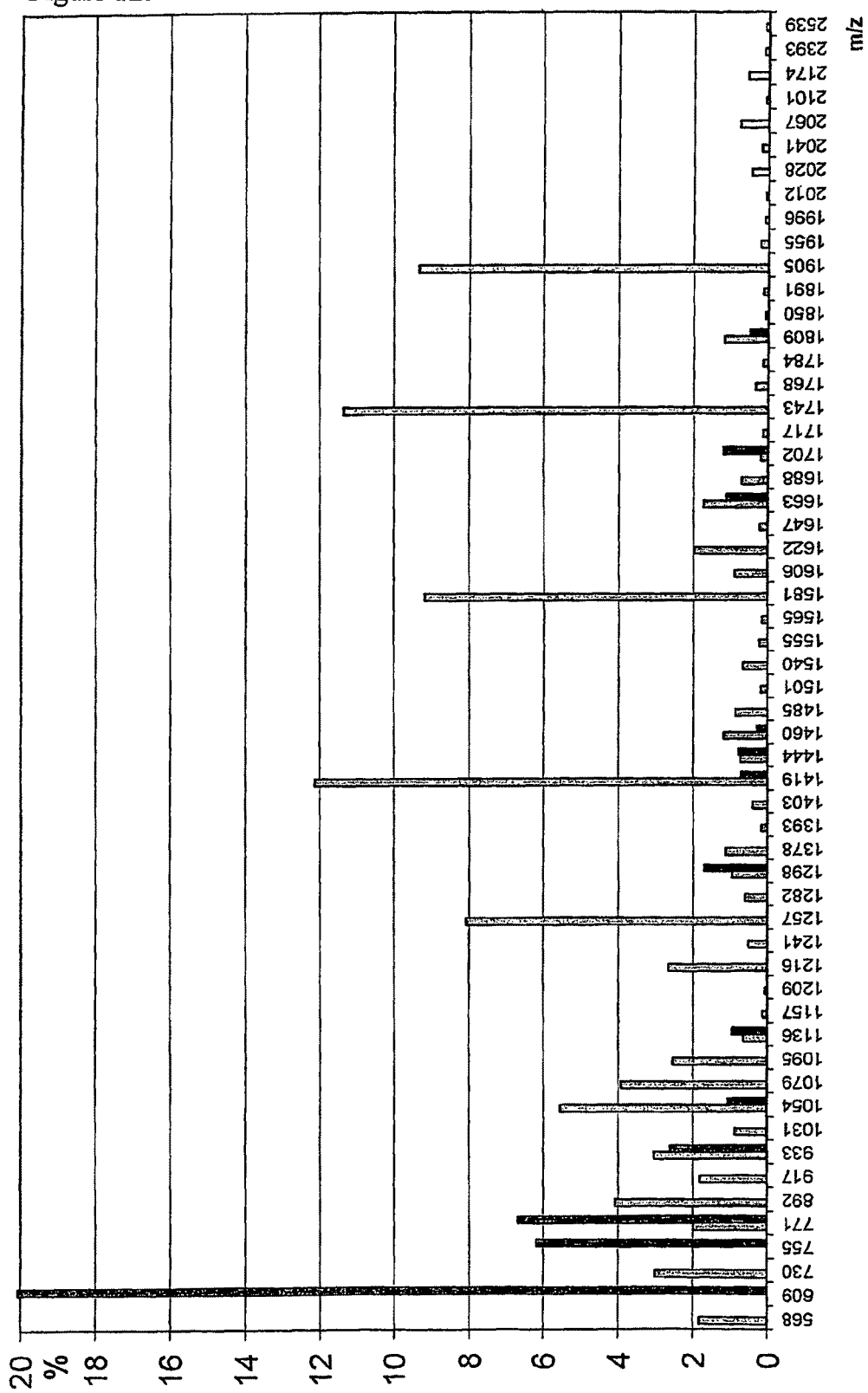
FIG. 12. Neutral N-glycan profiles of a cord blood derived mesenchymal stem cell line before (light columns) and after (dark columns) α-mannosidase digestion.
Figure 13:
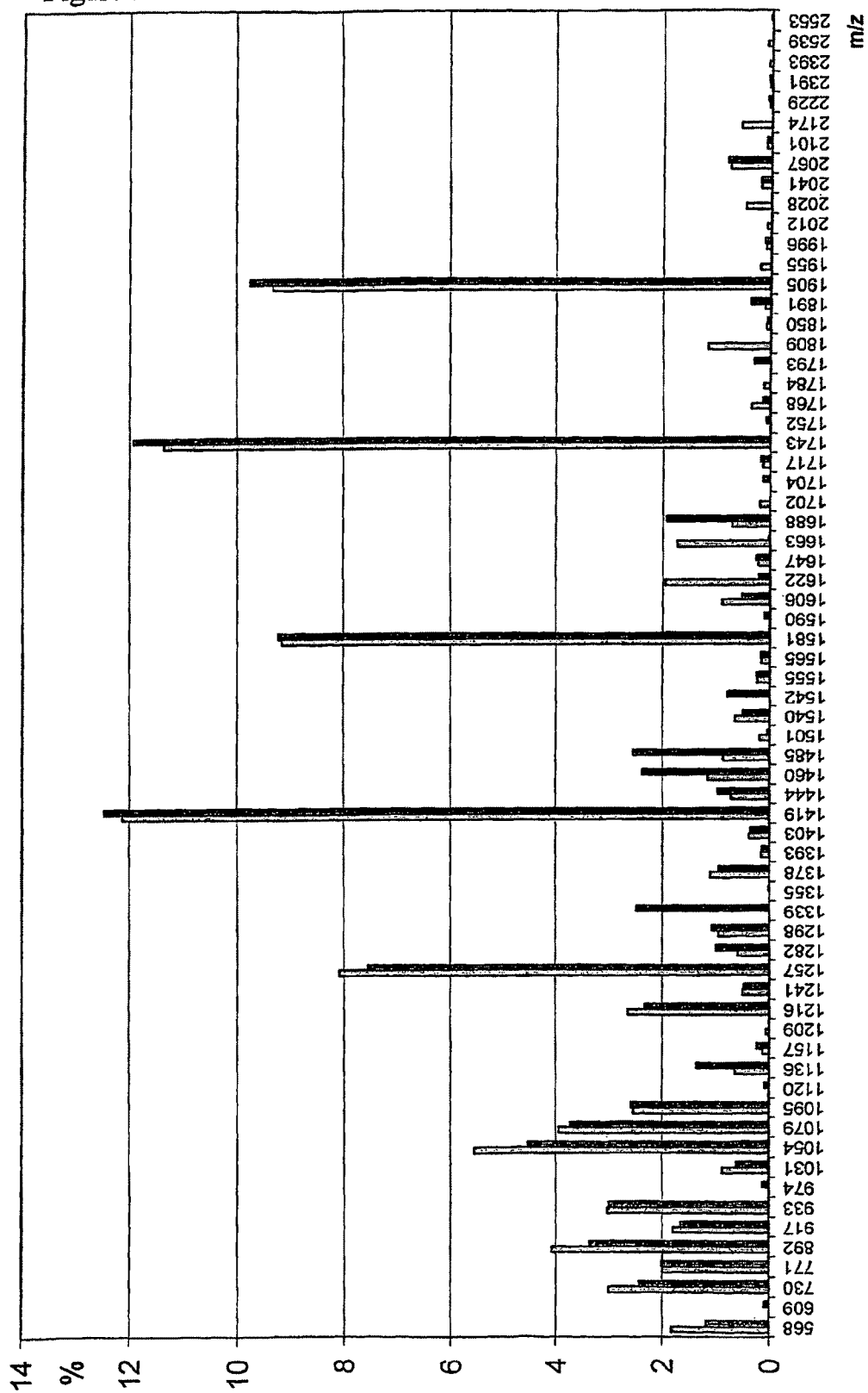
FIG. 13. Neutral N-glycan profiles of a cord blood derived mesenchymal stem cell line before (light columns) and after (dark columns) β1,4-galactosidase digestion.
Figure 14:
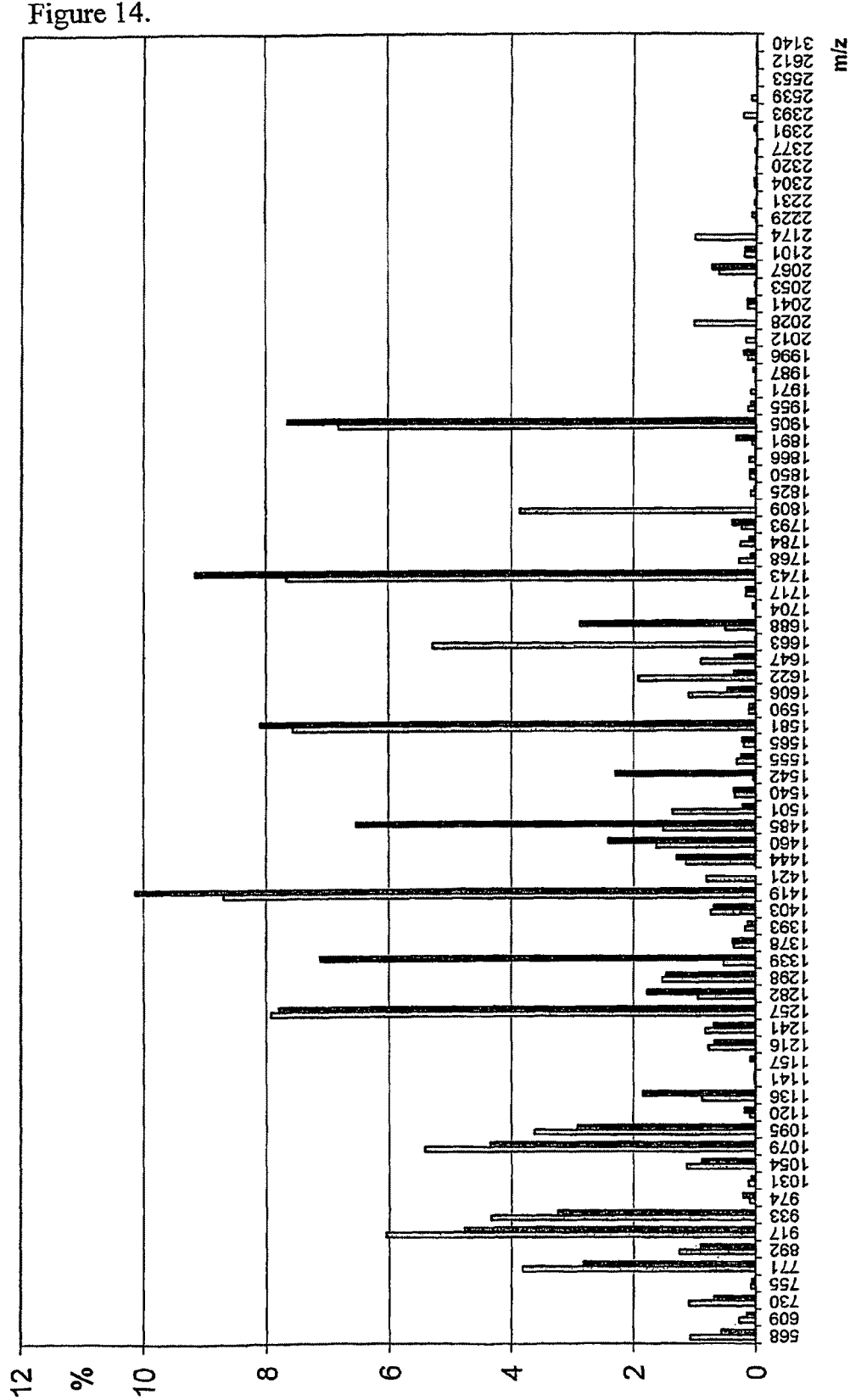
FIG. 14. Neutral N-glycan profiles of a cord blood derived mesenchymal stem cell line, grown in adipogenic medium, before (light columns) and after (dark columns) β1,4-galactosidase digestion.

Specific exoglycosidase digestions were performed on isolated neutral N-glycan fractions from CB MSC lines as described in the preceding Examples. The results of α-mannosidase analysis are described in FIG. 12, showing in detail which of the neutral N-glycan signals in the neutral N-glycan profiles of CB MNC lines are susceptible to α-mannosidase digestion, indicating for the presence of non-reducing terminal α-mannose residues in the corresponding glycan structures. As an example, the major neutral N-glycan signals at m/z 1257, 1419, 1581, 1743, and 1905, which were preliminarily assigned as high-mannose type N-glycans according to their proposed monosaccharide compositions $Hex_{5-9}HexNAc_2$, were shown to contain terminal α-mannose residues thus confirming the preliminary assignment. The results of β1,4-galactosidase analysis are described in FIG. 13 (for a CB MNC line) and FIG. 14 (for a CB MNC line cultured in adipogenic medium) showing in detail which of the neutral N-glycan signals in the neutral N-glycan profiles of CB MNC lines and differentiated CB MNCs are susceptible to β1,4-galactosidase digestion, indicating for the presence of non-reducing terminal β1,4-galactose residues in the corresponding glycan structures. As an example, the major neutral complex-type N-glycan signals at m/z 1663 and m/z 1809 were shown to contain terminal β1,4-linked galactose residues.

Bone Marrow Derived Mesenchymal Stem Cell (BM MSC) Lines

Neutral N-Glycan Profiles and Differentiation-Associated Changes in Glycan Profiles.

Figure 15:
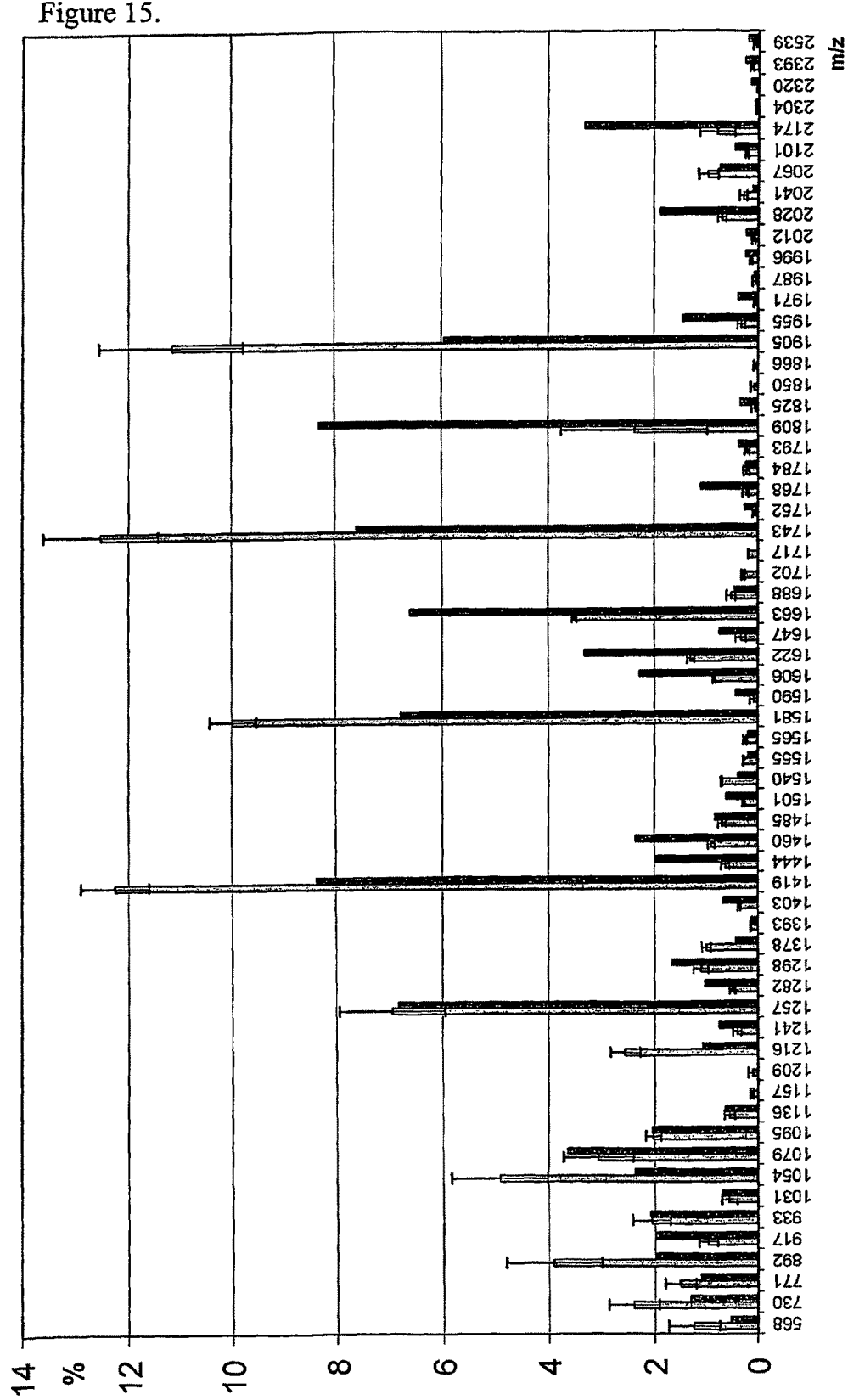
FIG. 15. Neutral N-glycan profiles of a bone marrow derived mesenchymal stem cell line and cells differentiated into osteogenic direction. Light columns: mesenchymal stem cell line in proliferation medium; dark columns: mesenchymal stem cell line in osteogenic medium.

Neutral N-glycan profiles obtained from a BM MSC line, grown in proliferation medium and in osteogenic medium are presented in FIG. 15. The BM MSCs resemble CB MSC lines with respect to their overall neutral N-glycan profiles. However, differences between cell lines derived from the two sources are observed, and some glycan signals can only be observed in one cell line, indicating that the cell lines have glycan structures that differ them from each other. The major characteristic structural feature of BM MSCs is even more abundant neutral complex-type N-glycans compared to CB MSC lines. Similarly to CB MSCs, these glycans were also the major increased glycan signal group upon differentiation of BM MSCs. The analysis revealed in each cell type the relative proportions of about 50-70 glycan signals that were assigned as non-sialylated N-glycan components. Typically, significant differences in the glycan profiles between cell populations are consistent throughout multiple experiments.

Sialylated N-Glycan Profiles.

Figure 16:
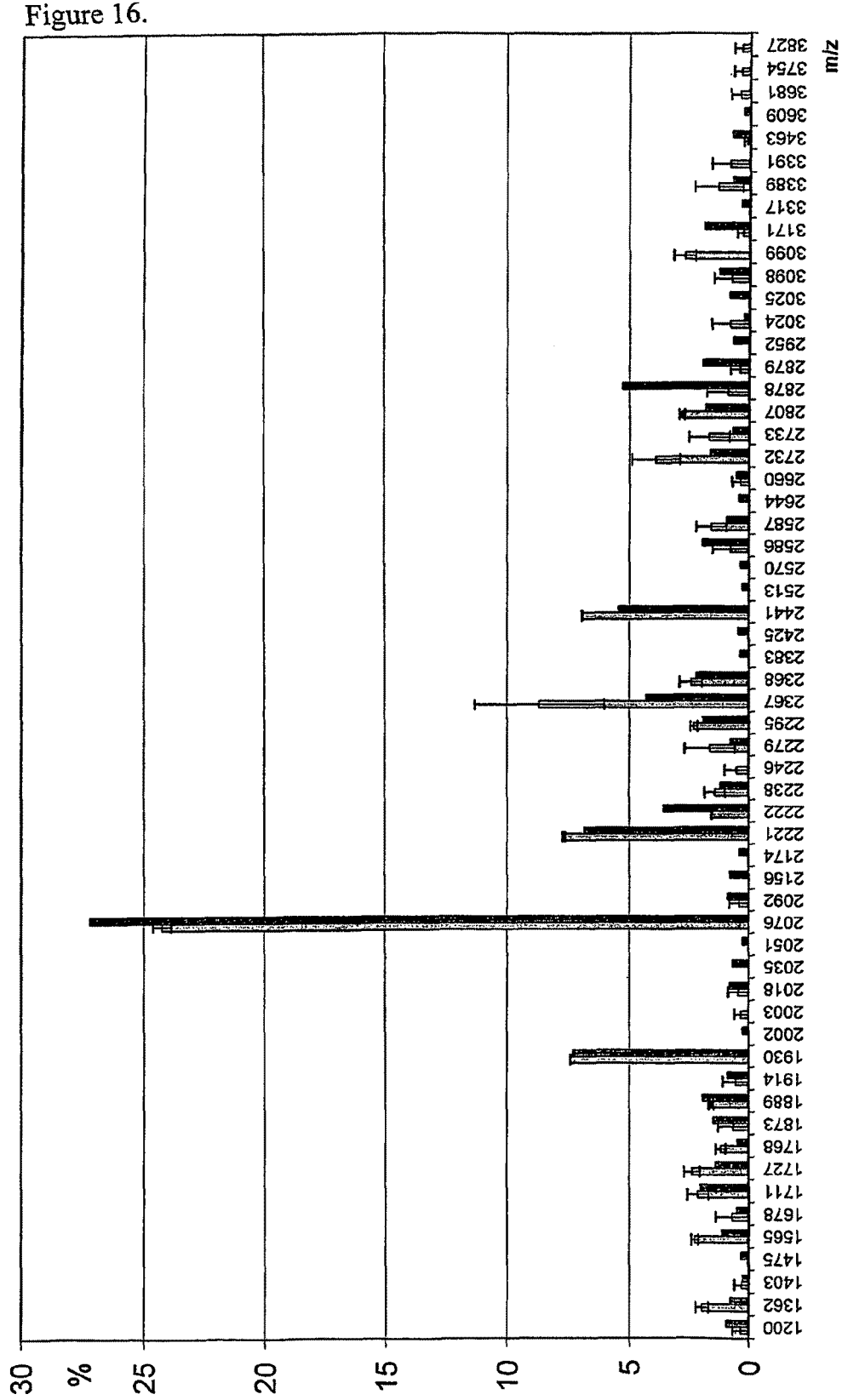
FIG. 16. Sialylated N-glycan profiles of a bone marrow derived mesenchymal stem cell line and cells differentiated into osteogenic direction. Light columns: mesenchymal stem cell line in proliferation medium; dark columns: mesenchymal stem cell line in osteogenic medium.

Sialylated N-glycan profiles obtained from a BM MSC line, grown in proliferation medium and in osteogenic medium are presented in FIG. 16. The undifferentiated and differentiated cells resemble closely each other with respect to their overall sialylated N-glycan profiles. However, minor differences between the profiles are observed, and some glycan signals can only be observed in one cell line, indicating that the two cell types have glycan structures that differ them from each other. The analysis revealed in each cell type the relative proportions of about 50 glycan signals that were assigned as acidic N-glycan components. Typically, significant differences in the glycan profiles between cell populations are consistent throughout multiple experiments.

Sialidase Analysis.

Figure 17:
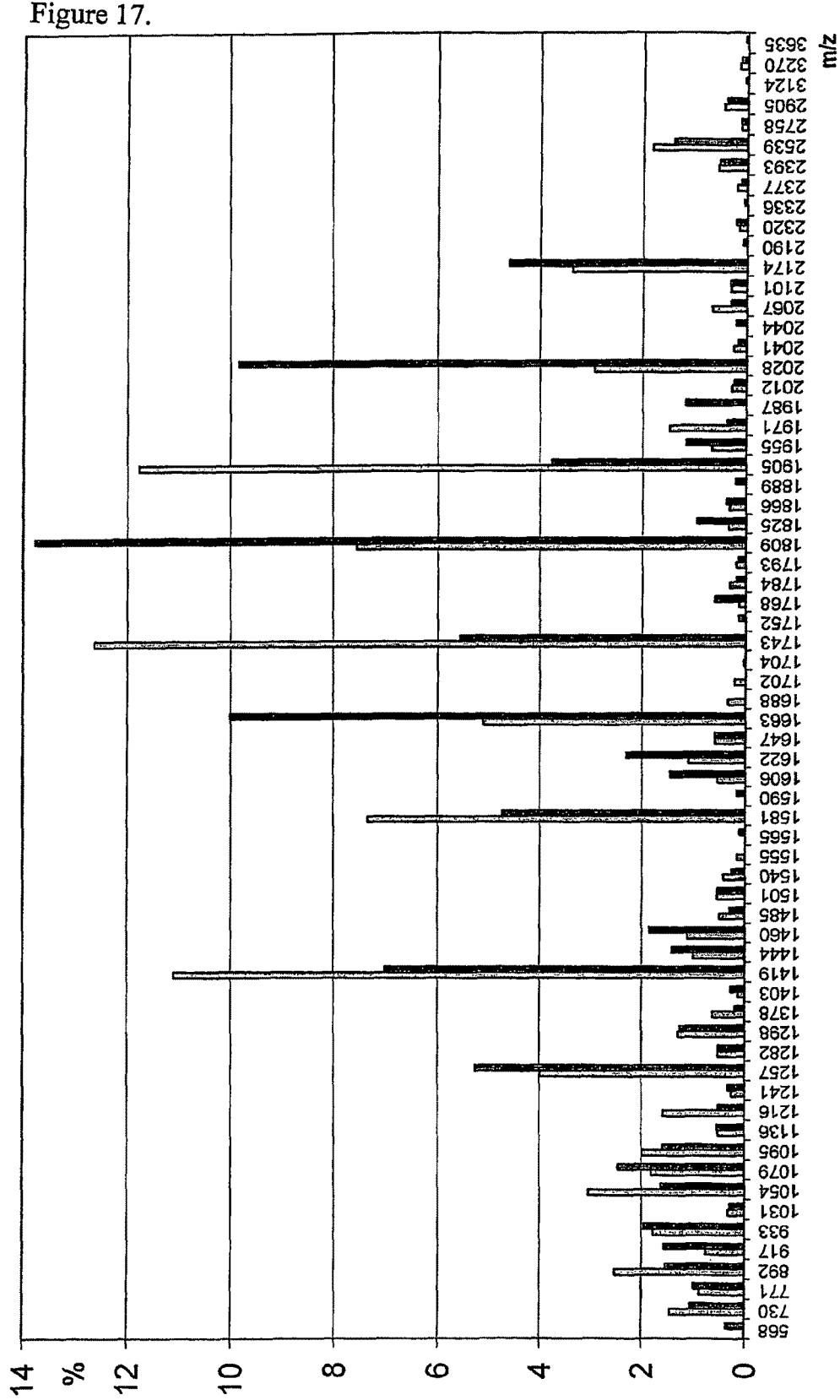
FIG. 17. Profiles of combined neutral and sialylated N-glycan fractions of a bone marrow derived mesenchymal stem cell line and cells differentiated into osteogenic direction, after broad-range neuraminidase treatment of the sialylated fraction. Light columns: mesenchymal stem cell line in proliferation medium; dark columns: mesenchymal stem cell line in osteogenic medium.

The sialylated N-glycan fraction isolated from BM MSCs was digested with broad-range sialidase as described in the preceding Examples. After the reaction, it was observed by MALDI-TOF mass spectrometry that the vast majority of the sialylated N-glycans were desilylated and transformed into corresponding neutral N-glycans, indicating that they had contained sialic acid residues (NeuAc and/or NeuGc) as suggested by the proposed monosaccharide compositions. FIG. 17 shows the glycan profiles of combined neutral and desilylated (originally sialylated) N-glycan fractions of BM MSCs grown in proliferation medium and in osteogenic medium. The profiles correspond to total N-glycan profiles isolated from the cell samples (in desilylated form). It is calculated that in undifferentiated BM MSCs (grown in osteogenic medium), approximately 53% of the N-glycan signals correspond to high-mannose type N-glycan monosaccharide compositions, 8% to low-mannose type N-glycans, 31% to complex-type N-glycans, and 7% to hybrid-type or monoantennary N-glycan monosaccharide compositions. In differentiated BM MSCs (grown in osteogenic medium), approximately 28% of the N-glycan signals correspond to high-mannose type N-glycan monosaccharide compositions, 9% to low-mannose type N-glycans, 50% to complex-type N-glycans, and 11% to hybrid-type or monoantennary N-glycan monosaccharide compositions.

Lectin Binding Analysis of Mesenchymal Stem Cells.

As described under Experimental procedures, bone marrow derived mesenchymal stem cells were analyzed for the presence of ligands of α2,3-linked sialic acid specific (MAA) and α2,6-linked sialic acid specific (SNA) lectins on their surface. It was revealed that MAA bound strongly to the cells whereas SNA bound weakly, indicating that in the cell culture conditions, the cells had significantly more α2,3-linked than α2,6-linked sialic acids on their surface glycoconjugates. The present results suggest that lectin staining can be used as a further means to distinguish different cell types and complements mass spectrometric profiling results.

Detection of Potential Glycan Contaminations from Cell Culture Reagents

In the sialylated N-glycan profiles of MSC lines, specific N-glycan signals were observed that indicated contamination of mesenchymal stem cell glycoconjugates by abnormal sialic acid residues. First, when the cells were cultured in cell culture media with added animal sera, such as bovine of equine sera, potential contamination by N-glycolylneuraminic acid (NeuSGc) was detected. The glycan signals at m/z 1946, corresponding to the $[M-H]^-$ ion of $NeuGc_1Hex_5HexNAc_4$, as well as m/z 2237 and m/z 2253, corresponding to the $[M-H]^-$ ions of $NeuGc_1NeuAc_1Hex_5HexNAC_4$ and $NeuGC_2Hex_5HexNAc_4$, respectively, were indicative of the presence of Neu5Gc, i.e. a sialic acid residue with 16 Da larger mass than N-acetylneuraminic acid (Neu5Ac). Moreover, when the cells were cultured in cell culture media with added horse serum, potential contamination by O-acetylated sialic acids was detected. Diagnostic signals used for detection of O-acetylated sialic acid containing sialylated N-glycans included $[M-H]^-$ ions of $Ac_1NeuAc_2Hex_5HexNAc_4$, $Ac_2NeuAC_2Hex_5HexNAc_4$, and $Ac_2NeuAc_2Hex_5HexNAc_4$, at calculated m/z 1972.7, 2263.8, and 2305.8, respectively.

Conclusions

Uses of the Glycan Profiling Method.

The results indicate that the present glycan profiling method can be used to differentiate CB MSC lines and BM MSC lines from each other, as well as from other cell types such as cord blood mononuclear cell populations. Differentiation-induced changes as well as potential glycan contaminations from e.g. cell culture media can also be detected in the glycan profiles, indicating that changes in cell status can be detected by the present method. The method can also be used to detect MSC-specific glycosylation features including those discussed below.

Differences in Glycosylation Between Cultured Cells and Native Human Cells.

The present results indicate that BM MSC lines have more high-mannose type N-glycans and less low-mannose type N-glycans compared to the other N-glycan structural groups than mononuclear cells isolated from cord blood. Taken together with the results obtained from cultured human embryonal stem cells in the following Examples, it is indicated that this is a general tendency of cultured stem cells compared to native isolated stem cells. However, differentiation of BM MSCs in osteogenic medium results in significantly increased amounts of complex-type N-glycans and reduction in the amounts of high-mannose type N-glycans.

Mesenchymal Stem Cell Line Specific Glycosylation Features.

The present results indicate that mesenchymal stem cell lines differ from the other cell types studied in the present study with regard to specific features of their glycosylation, such as:
1) Both CB MSC lines and BM MSC lines have unique neutral and sialylated N-glycan profiles;
2) The major characteristic structural feature of both CB and BM MSC lines is abundant neutral complex-type N-glycans;
3) An additional characteristic feature is low sialylation level of complex-type N-glycans.

Example 9

MALDI-TOF Mass Spectrometric N-glycan Profiling of Human Embryonic Stem Cell Lines Examples of Cell Material Production Human Embryonic Stem Cell Lines (hESC)
Undifferentiated hESC.
Processes for generation of hESC lines from blastocyst stage in vitro fertilized excess human embryos have been described previously (e.g. Thomson et al., 1998). Two of the analysed cell lines in the present work were initially derived and cultured on mouse embryonic fibroblasts feeders (MEF; 12-13 pc fetuses of the ICR strain), and two on human foreskin fibroblast feeder cells (HFF; CRL-2429 ATCC, Mananas, USA). For the present studies all the lines were transferred on HFF feeder cells treated with mitomycin-C (1 µg/ml; Sigma-Aldrich) and cultured in serum-free medium (Knockout™ D-MEM; Gibco® Cell culture systems, Invitrogen, Paisley, UK) supplemented with 2 mM L-Glutamin/Penicillin streptomycin (Sigma-Aldrich), 20% Knockout Serum Replacement (Gibco), 1× non-essential amino acids (Gibco), 0.1 mM β-mercaptoethanol (Gibco), 1×ITSF (Sigma-Aldrich) and 4 ng/ml bFGF (Sigma/Invitrogen).

Stage 2 Differentiated hESC (Embryoid Bodies).
To induce the formation of embryoid bodies (EB) the hESC colonies were first allowed to grow for 10-14 days whereafter the colonies were cut in small pieces and transferred on non-adherent Petri dishes to form suspension cultures. The formed EBs were cultured in suspension for the next 10 days in standard culture medium (see above) without bFGF.

Stage 3 Differentiated hESC.
For further differentiation EBs were transferred onto gelatin-coated (Sigma-Aldrich) adherent culture dishes in media consisting of DMEM/F12 mixture (Gibco) supplemented with ITS, Fibronectin (Sigma), L-glutamine and antibiotics. The attached cells were cultured for 10 days whereafter they were harvested.

Sample Preparation.
The cells were collected mechanically, washed, and stored frozen prior to glycan analysis.

Results

Neutral N-Glycan Profiles—Effect of Differentiation Status.

Figure 18:
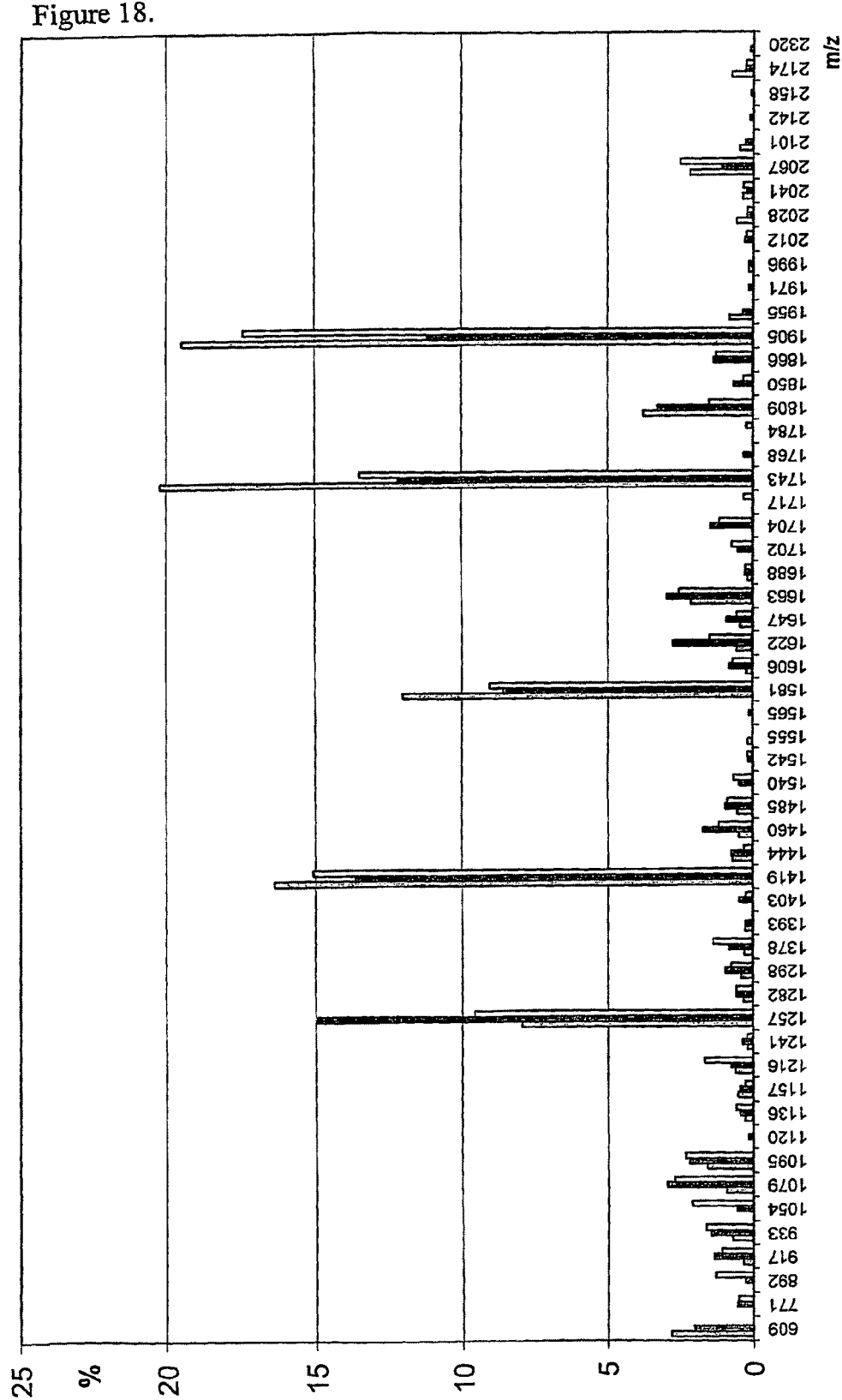
FIG. 18. Neutral N-glycan profiles of a human embryonic stem cell line (light columns), cells differentiated into embryoid bodies (dark columns), and st3 differentiated cells (blank columns).

Neutral N-glycan profiles obtained from a human embryonal stem cell (hESC) line, its embryoid body (EB) differentiated form, and its stage 3 (st.3) differentiated form are presented in FIG. 18. Although the cell types resemble each other with respect to the major neutral N-glycan signals, the neutral N-glycan profiles of the two differentiated cell forms differ significantly from the undifferentiated hESC profile. In fact, the farther differentiated the cell type is, the more its neutral N-glycan profile differs from the undifferentiated hESC profile. Multiple differences between the profiles are observed, and many glycan signals can only be observed in one or two out of three cell types, indicating that differentiation induces the appearance of new glycan types. The analysis revealed in each cell type the relative proportions of about 40-55 glycan signals that were assigned as non-sialylated N-glycan components. Typically, significant differences in the glycan profiles between cell populations are consistent throughout multiple experiments.

Figure 20:
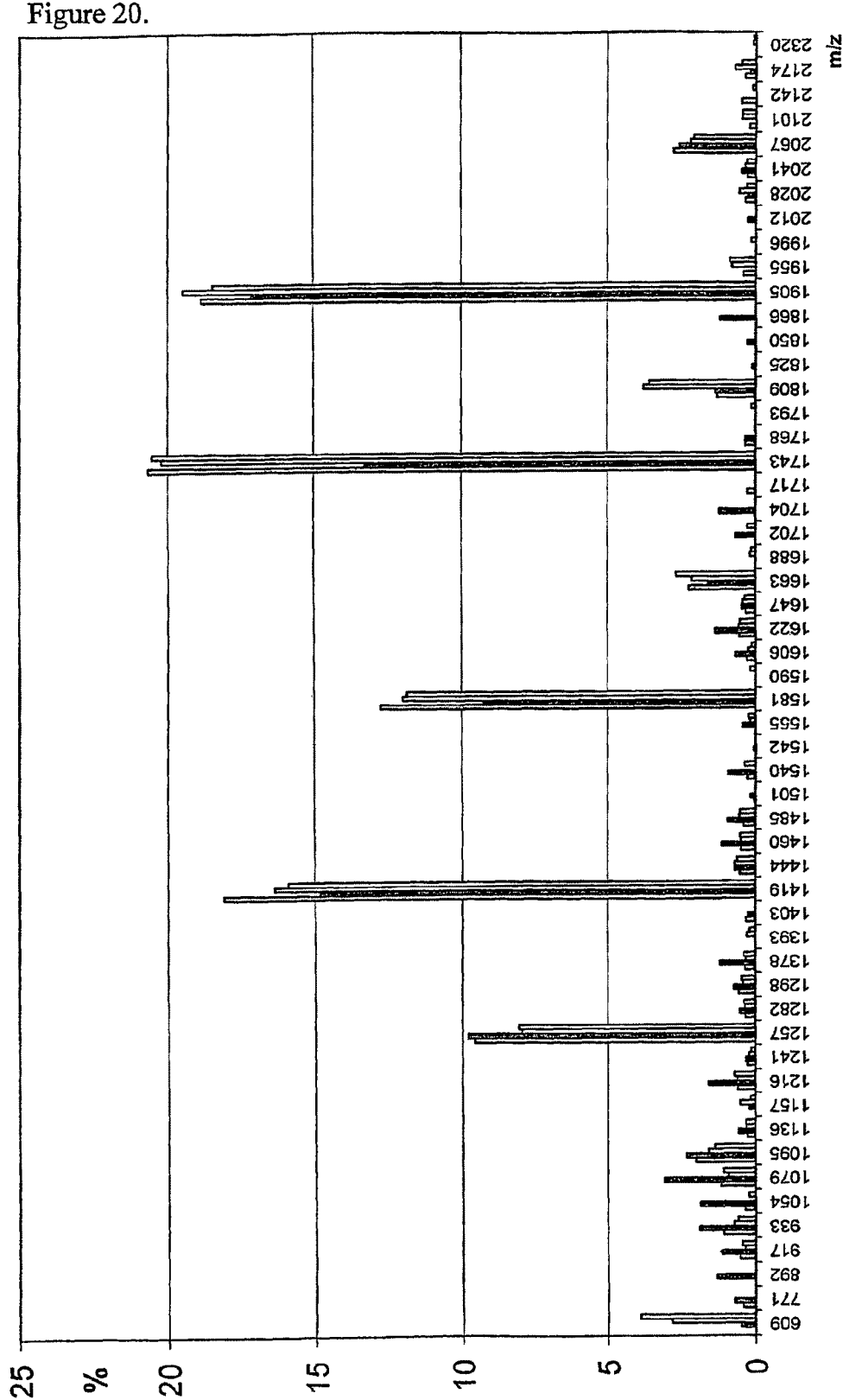
FIG. 20. Neutral N-glycan profiles of four human embryonic stem cell lines (differently shaded columns, BESC lines 1-4).

Neutral N-Glycan Profiles—Comparison of hESC Lines.
Neutral N-glycan profiles obtained from four hESC lines are presented in FIG. 20. The four cell lines closely resemble each other. Individual profile characteristics and cell line specific glycan signals are present in the glycan profiles, but it is concluded that hESC lines resemble more each other with respect to their neutral N-glycan profiles and are different from differentiated EB and st3 cell types. hESC lines 3 and 4 are derived from sibling embryos, and their neutral N-glycan profiles resemble more each other and are different from the two other cell lines, i.e. they contain common glycan signals. The analysis revealed in each cell type the relative proportions of about 40-55 glycan signals that were assigned as non-sialylated N-glycan components. Typically, significant differences in the glycan profiles between cell populations are consistent throughout multiple experiments.

Neutral N-Glycan Structural Features.
Neutral N-glycan groupings proposed for analysed cell types are presented in Table 12. Again, the analysed three major cell types, namely undifferentiated hESCs, differentiated cells, and human fibroblast feeder cells, differ from each other significantly. Within each cell type, however, there are minor differences between individual cell lines. Moreover, differentiation-associated neutral N-glycan structural features are expressed more strongly in st.3 differentiated cells than in EB cells. Cell-type specific glycosylation features are discussed below in Conclusions.

Glycosidase Analysis of Neutral N-Glycan Fractions.
Specific exoglycosidase digestions were performed on isolated neutral N-glycan fractions from hESC lines as described in the preceding Examples. In α-mannosidase analysis, several neutral glycan signals were shown to be susceptible to α-mannosidase digestion, indicating for potential presence of non-reducing terminal α-mannose residues in the corresponding glycan structures. In hESC and EB cells, these signals included m/z 917, 1079, 1095, 1241, 1257, 1378, 1393, 1403, 1444, 1555, 1540, 1565, 1581, 1606, 1622, 1688, 1743, 1768, 1905, 1996, 2041, 2067, 2158, and 2320 (the corresponding monosaccharide compositions are presented in for example Table 1). In β1,4-galactosidase analysis, several neutral glycan signals were shown to be susceptible to β1,4-galactosidase digestion, indicating for potential presence of non-reducing terminal β1,4-galactose residues in the corresponding glycan structures. In hESC and EB cells, these signals included m/z 609, 771, 892, 917, 1241, 1378, 1393, 1555, 1565, 1606, 1622, 1647, 1663, 1704, 1809, 1850, 1866, 1955, 1971, 1996, 2012, 2028, 2041, 2142, 2174, and 2320 (the corresponding monosaccharide compositions are presented in for example Table 1). In α1,3/4-fucosidase analysis, several neutral glycan signals were shown to be susceptible to α1,3/4-fucosidase digestion, indicating for potential presence of non-reducing terminal α1,3- and/or α1,4-fucose residues in the corresponding glycan structures. In hESC and EB cells, these signals included m/Z 1120, 1590, 1784, 1793, 1955, 1996, 2101, 2117, 2142, 2158, 2190, 2215, 2247, 2263, 2304, 2320, 2393, and 2466 (the corresponding monosaccharide compositions are presented in for example Table 1).

Identification of Soluble Glycan Components.

Similarly to the cell types described in the preceding examples, in the present analysis neutral glycan components were identified in all the cell types that were assigned as soluble glycans based on their proposed monosaccharide compositions including components from the glycan group $Hex_{2-12}HexNAc_1$ (see Figures). The abundances of these glycan components in relation to each other and in relation to the other glycan signals vary between individual samples and cell types.

Sialylated N-Glycan Profiles—Effect of Differentiation Status.

Figure 19:
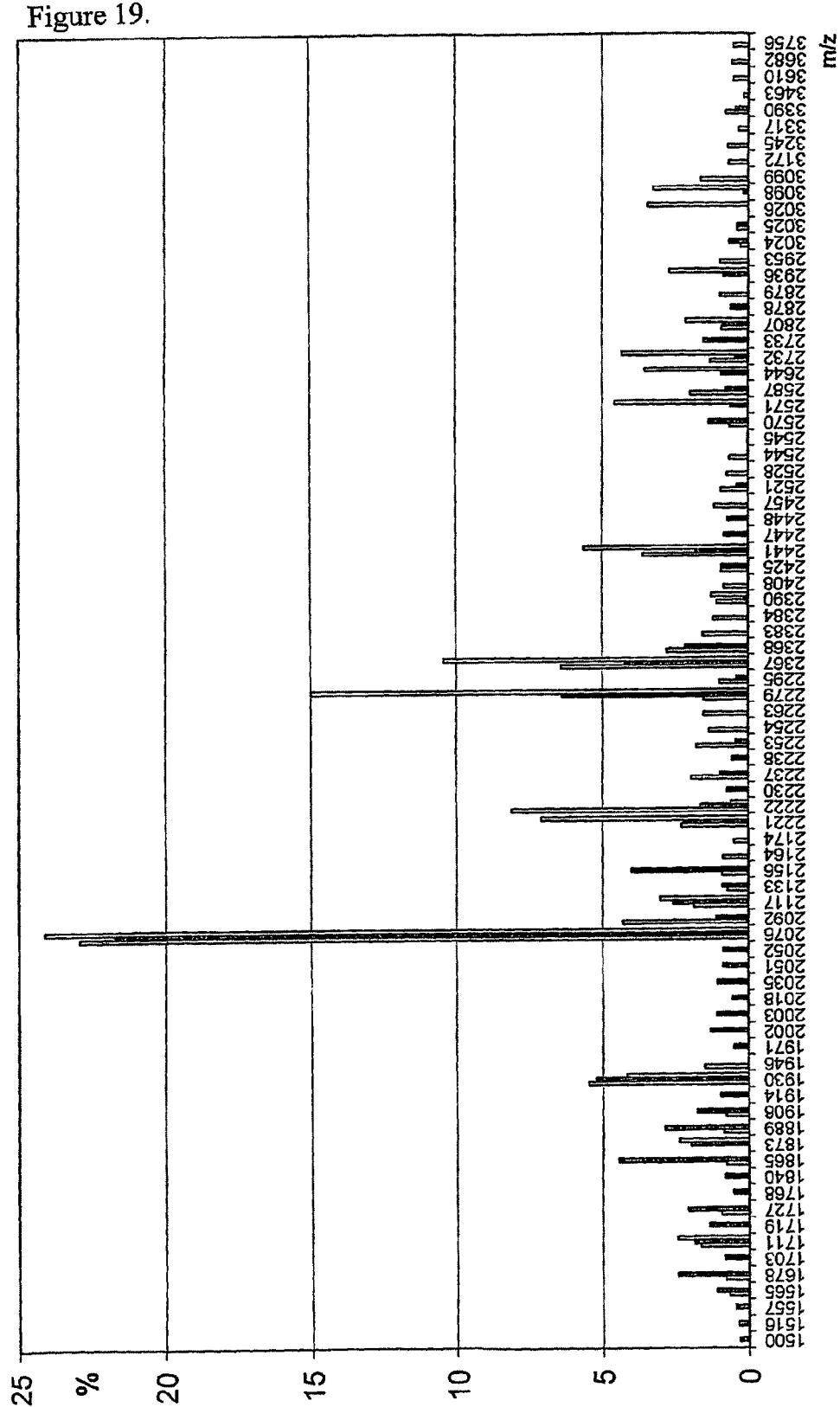
FIG. 19. Sialylated N-glycan profiles of a human embryonic stem cell line (light columns), cells differentiated into embryoid bodies (dark columns), and st.3 differentiated cells (blank columns).

Sialylated N-glycan profiles obtained from a human embryonal stem cell (hESC) line, its embryoid body (EB) differentiated form, and its stage 3 (st.3) differentiated form are presented in FIG. 19. Although the cell types resemble each other with respect to the major sialylated N-glycan signals, the sialylated N-glycan profiles of the two differentiated cell forms differ significantly from the undifferentiated hESC profile. In fact, the farther differentiated the cell type is, the more its sialylated N-glycan profile differs from the undifferentiated hESC profile. Multiple differences between the profiles are observed, and many glycan signals can only be observed in one or two out of three cell types, indicating that differentiation induces the appearance of new glycan types as well as decrease in amounts of stem cell specific glycan types. For example, there is significant differentiation-associated decrease in relative amounts of glycan signals at m/z 1946 and 2222, corresponding to monosaccharide compositions $NeuGc_1Hex_5HexNAc_4$ and $NeuAc_1Hex_5HexNAc_4dHex_2$, respectively. The analysis revealed in each cell type the relative proportions of about 50-70 glycan signals that were assigned as acidic N-glycan components. Typically, significant differences in the glycan profiles between cell populations are consistent throughout multiple experiments.

Sialylated N-Glycan Profiles—Comparison of hESC Lines.

Figure 21:
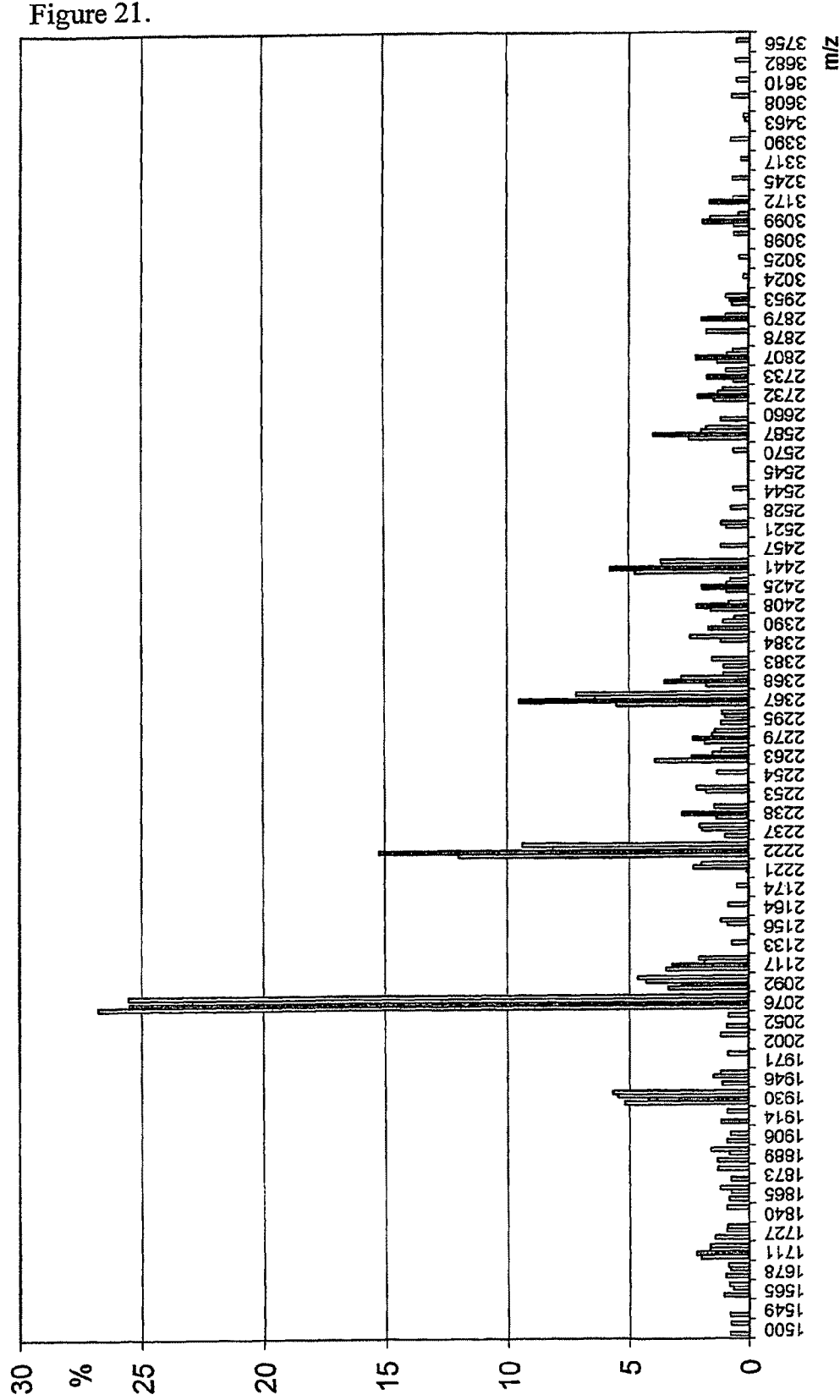
FIG. 21. Sialylated N-glycan profiles of four human embryonic stem cell lines (differently shaded columns, hESC lines 1-4).

Sialylated N-glycan profiles obtained from four hESC lines are presented in FIG. 21. The four cell lines closely resemble each other. Individual profile characteristics and cell line specific glycan signals are present in the glycan profiles, but it is concluded that hESC lines resemble more each other with respect to their sialylated N-glycan profiles and are different from differentiated EB and st.3 cell types. The analysis revealed in each cell type the relative proportions of about 50-70 glycan signals that were assigned as acidic N-glycan components. Typically, significant differences in the glycan profiles between cell populations are consistent throughout multiple experiments.

Human Fibroblast Feeder Cell Lines.

Figure 22:
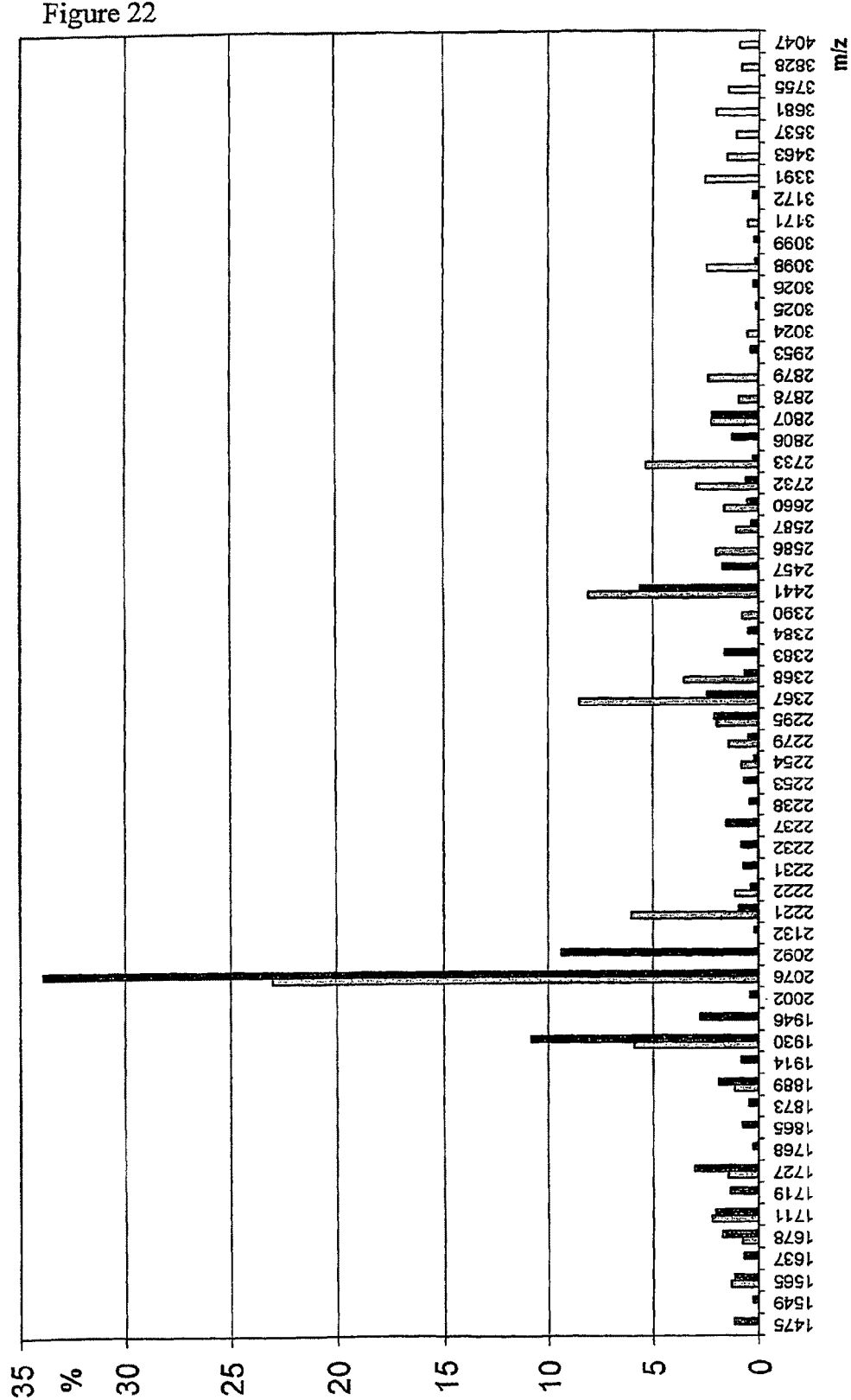
FIG. 22. Sialylated N-glycan profiles of two human fibroblast feeder cell samples: Light columns: cells grown separately from stem cells; dark columns: cells grown together with stem cells (feeder layer cells).

Sialylated N-glycan profiles obtained from human fibroblast feeder cell lines are presented in FIG. 22. The present results show that the feeder cells differ from hESC, EB, and st3 differentiated cells, and that feeder cells grown separately and with hESC cells differ from each other.

Sialylated N-Glycan Structural Features.

Sialylated N-glycan groupings proposed for analysed cell types are presented in Table 13. Again, the analysed three major cell types, namely undifferentiated hESCs, differentiated cells, and human fibroblast feeder cells, differ from each other significantly. Within each cell type, however, there are minor differences between individual cell lines. Moreover, differentiation-associated sialylated N-glycan structural features are expressed more strongly in st.3 differentiated cells than in EB cells. Cell-type specific glycosylation features are discussed below in Conclusions.

Conclusions

Comparison of Glycan Profiles.

Differences in the glycan profiles between cell types were consistent throughout multiple samples and experiments, indicating that the present method of glycan profiling and the differences in the present glycan profiles can be used to identify hESCs or cells differentiated therefrom, or other cells such as feeder cells, or to determine their purity, or to identify cell types present in a sample. The present method and the present results can also be used to identify cell-type specific glycan structural features or cell-type specific glycan profiles. The method proved especially useful in determination of differentiation stage, as demonstrated by comparing analysis results between hESC, EB, and st.3 differentiated cells. Furthermore, hESCs were shown to have unique glycosylation profiles, which can be differentiated from differentiated cell types as well as from other stem cell types such as MSCs, indicating that stem cells in general and also specific stem cell types can be identified by the present method. The present method could also detect glycan structures common to hESC lines derived from sibling embryos, indicating that related structural features can be identified in different cell lines or their similarity be estimated by the present method.

Comparison of Neutral N-Glycan Structural Features.

Differences in glycosylation profiles between analyzed cell types were identified based on proposed structural features, which can be used to identify cell-type specific glycan structural features. Identified cell-type specific features of neutral N-glycan profiles are concluded below:

hESC Lines:
1) Increased amounts of fucosylated neutral N-glycans, especially glycans with two or more deoxyhexose residues per chain, indicating increased expression of neutral N-glycans containing α1,2-, α1,3-, or α1,4-linked fucose residues; and
2) Increased amounts of larger neutral N-glycans.

EBs and st3 Differentiated Cells (st.3 Cells Expressing the Features More Strongly):
1) Lower amounts of neutral N-glycans containing two or more deoxyhexose residues per chain, indicating reduced expression of neutral N-glycans containing α1,2-, α1,3-, or α1,4-linked fucose residues;
2) Increased amounts of hybrid-type, monoantennary, and complex-type neutral N-glycans.
3) Increased amounts of terminal HexNAc residues; and 4) Potentially increased amounts of bisecting GlcNAc structures.

Human Fibroblast Feeder Cells:
1) Increased amounts of larger neutral N-glycans;
2) Lower amounts of neutral N-glycans containing two or more deoxyhexose residues per chain, indicating reduced expression of neutral N-glycans containing α1,2-, α1,3-, or α1,4-linked fucose residues;
3) Increased amounts of terminal HexNAc residues; and
4) Potentially no bisecting GlcNAc structures.

Comparison of sialylated N-glycan structural features. Differences in glycosylation profiles between analyzed cell types were identified based on proposed structural features, which can be used to identify cell-type specific glycan structural features. Identified cell-type specific features of sialylated N-glycan profiles are concluded below:

hESC Lines:
1) Increased amounts of fucosylated sialylated N-glycans, especially glycans with two or more deoxyhexose residues per chain, indicating increased expression of sialylated N-glycans containing α1,2-, α1,3-, or α1,4-linked fucose residues;
2) Increased amounts of terminal HexNAc residues; and
3) Increased amounts of Neu5Gc containing sialylated N-glycans.

EBs and st3 Differentiated Cells (st3 Cells Expressing the Features More Strongly):
1) Lower amounts of sialylated N-glycans containing two or more deoxyhexose residues per chain, indicating reduced expression of sialylated N-glycans containing α1,2-, α1,3-, or α1,4-linked fucose residues;
2) Increased amounts of hybrid-type or monoantennary sialylated N-glycans; and
3) Potentially increased amounts of bisecting GlcNAc structures.

Human Fibroblast Feeder Cells:
1) Increased amounts of larger sialylated N-glycans;
2) Lower amounts of terminal HexNAc residues; and
3) Potentially lower amounts of bisecting GlcNAc structures.

Example 10

Enzymatic Modification of Cell Surface Glycan Structures

Experimental Procedures

Enzymatic Modifications.

Sialyltransferase reaction: Human cord blood mononuclear cells ($3\times10^6$ cells) were modified with 60 mU α2,3-(N)-sialyltransferase (rat, recombinant in S. frugiperda, Calbiochem), 1.6 μmol CMP-Neu5Ac in 50 mM sodium 3-morpholinopropanesulfonic acid (MOPS) buffer pH 7.4, 150 mM NaCl at total volume of 100 μl for up to 12 hours. Fucosyltransferase reaction: Human cord blood mononuclear cells ($3\times10^6$ cells) were modified with 4 mU α1,3-fucosyltransferase VI (human, recombinant in S. frugiperda, Calbiochem), 1 μmol GDP-Fuc in 50 mM MOPS buffer pH 7.2, 150 mM NaCl at total volume of 100 μl for up to 3 hours. Broad-range sialidase reaction: Human cord blood mononuclear cells ($3\times10^6$ cells) were modified with 5 mU sialidase (A. ureafaciens, Glyko, UK) in 50 mM sodium acetate buffer pH 5.5, 150 mM NaCl at total volume of 100 μl for up to 12 hours. α2,3-specific sialidase reaction: Cells were modified with α2,3-sialidase (S. pneumoniae, recombinant in E. coli) in 50 mM sodium acetate buffer pH 5.5, 150 mM NaCl at total volume of 100 μl. α-mannosidase reaction: α-mannosidase was from Jack beans and reaction was performed essentially similarly as with other enzymes described above. Sequential enzymatic modifications: Between sequential reactions cells were pelleted with centrifugation and supernatant was discarded, after which the next modification enzyme in appropriate buffer and substrate solution was applied to the cells as described above. Washing procedure: After modification, cells were washed with phosphate buffered saline.

Glycan Analysis.

After washing the cells, total cellular glycoproteins were subjected to N-glycosidase digestion, and sialylated and neutral N-glycans isolated and analyzed with mass spectrometry as described above. For O-glycan analysis, the glycoproteins were subjected to reducing alkaline β-elimination essentially as described previously (Nyman et al., 1998), after which sialylated and neutral glycan alditol fractions were isolated and analyzed with mass spectrometry as described above.

Results

Sialidase Digestion.

Upon broad-range sialidase catalyzed desilylation of living cord blood mononuclear cells, sialylated N-glycan structures as well as O-glycan structures (data not shown) were desilylated, as indicated by increase in relative amounts of corresponding neutral N-glycan structures, for example $Hex_6HexNAc_3$, $Hex_5HexNAc_4dHex_{0-2}$, and $Hex_6HexNAc_5dHex_{0-1}$ monosaccharide compositions (Table 15). In general, a shift in glycosylation profiles towards glycan structures with less sialic acid residues was observed in sialylated N-glycan analyses upon broad-range sialidase treatment. The shift in glycan profiles of the cells upon the reaction served as an effective means to characterize the reaction results. It is concluded that the resulting modified cells contained less sialic acid residues and more terminal galactose residues at their surface after the reaction.

α2,3-Specific Sialidase Digestion.

Similarly, upon α2,3-specific sialidase catalyzed desilylation of living mononuclear cells, sialylated N-glycan structures were desilylated, as indicated by increase in relative amounts of corresponding neutral N-glycan structures (data not shown). In general, a shift in glycosylation profiles towards glycan structures with less sialic acid residues was observed in sialylated N-glycan analyses upon α2,3-specific sialidase treatment. The shift in glycan profiles of the cells upon the reaction served as an effective means to characterize the reaction results. It is concluded that the resulting modified cells contained less α2,3-linked sialic acid residues and more terminal galactose residues at their surface after the reaction.

Sialyltransferase Reaction.

Upon α2,3-sialyltransferase catalyzed sialylation of living cord blood mononuclear cells, numerous neutral (Table 15) and sialylated N-glycan (Table 14) structures as well as O-glycan structures (data not shown) were sialylated, as indicated by decrease in relative amounts of neutral N-glycan structures ($Hex_5HexNAc_4dHex_{0-3}$ and $Hex_6HexNAc_5dHex_{0-2}$ monosaccharide compositions in Table 15) and increase in the corresponding sialylated structures (for example the $NeuAc_2Hex_5HexNAc_4dHex$, glycan in Table 14). In general, a shift in glycosylation profiles towards glycan structures with more sialic acid residues was observed both in N-glycan and O-glycan analyses. It is concluded that the resulting modified cells contained more α2,3-linked sialic acid residues and less terminal galactose residues at their surface after the reaction.

Fucosyltransferase Reaction.

Upon α1,3-fucosyltransferase catalyzed fucosylation of living cord blood mononuclear cells, numerous neutral (Table 15) and sialylated N-glycan structures as well as O-glycan structures (see below) were fucosylated, as indicated by decrease in relative amounts of nonfucosylated glycan structures (without dhex in the proposed monosaccharide compositions) and increase in the corresponding fucosylated structures (with $n_{dHex}>0$ in the proposed monosaccharide compositions). For example, before fucosylation O-glycan alditol signals at m/z 773, corresponding to the $[M+Na]^+$ ion of $Hex_2HexNAc2$ alditol, and at m/z 919, corresponding to the $[M+Na]^+$ ion of $Hex_2HexNAc_2dHex_1$ alditol, were observed in approximate relative proportions 9:1, respectively (data not shown). After fucosylation, the approximate relative proportions of the signals were 3:1, indicating that significant fucosylation of neutral O-glycans had occurred. Some fucosylated N-glycan structures were even observed after the reaction that had not been observed in the original cells, for example neutral N-glycans with proposed structures $Hex_6HexNAc_5dHex_1$ and $Hex_6HexNAc_5dHex_2$ (Table 15), indicating that in α1,3-fucosyltransferase reaction the cell surface of living cells can be modified with increased amounts or extraordinary structure types of fucosylated glycans, especially terminal Lewis x epitopes in protein-linked N-glycans as well as in O-glycans.

Sialidase Digestion Followed by Sialyltransferase Reaction.

Figure 23:
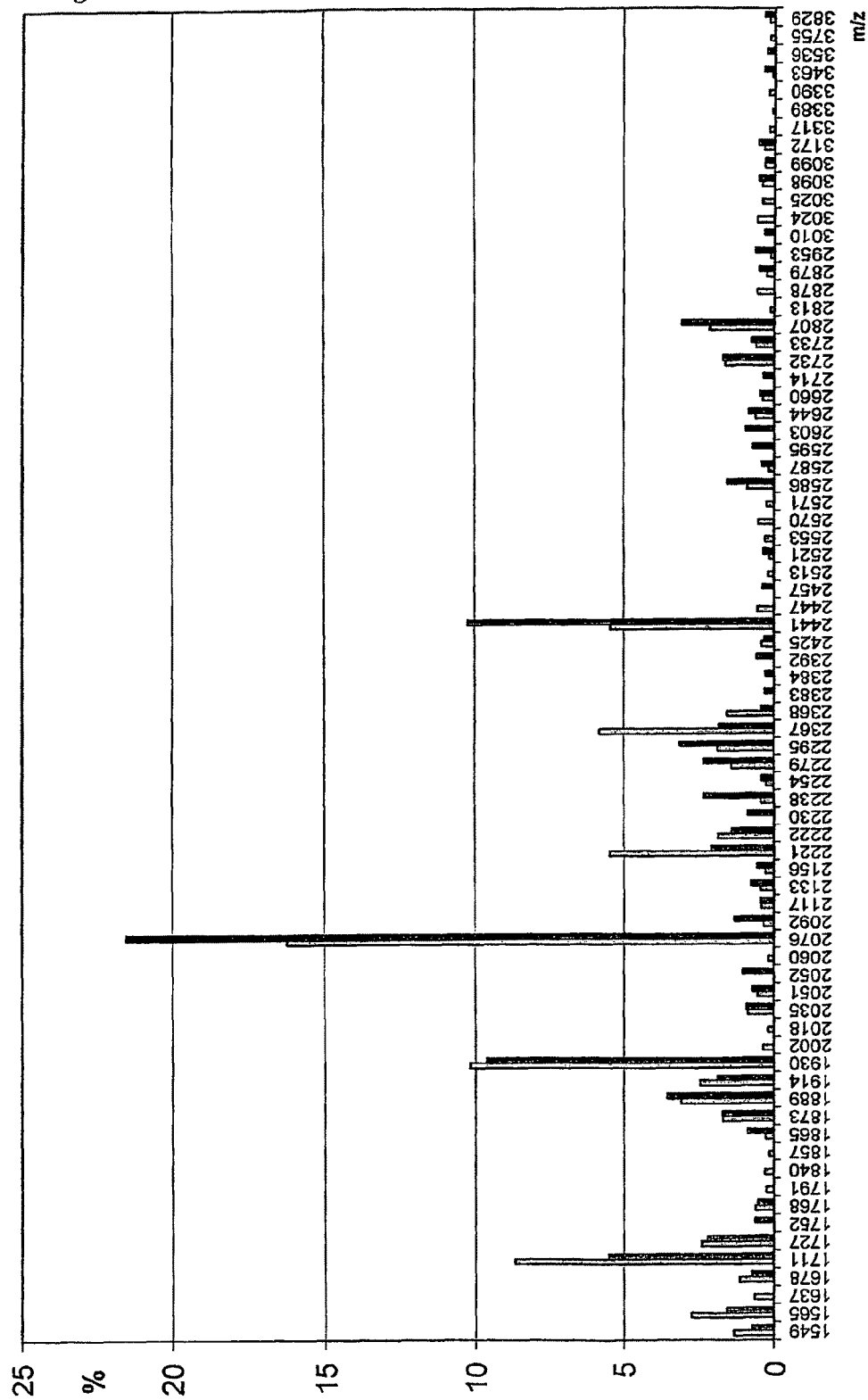
FIG. 23. Cord blood mononuclear cell sialylated N-glycan profiles before (light columns) and after (dark columns) subsequent broad-range sialidase and $\alpha 2,3$-sialyltransferase reactions. The m/z values refer to Table 16.

Cord blood mononuclear cells were subjected to broad-range sialidase reaction, after which α2,3-sialyltransferase and CMP-Neu5Ac were added to the same reaction, as described under Experimental procedures. The effects of this reaction sequence on the N-glycan profiles of the cells are described in FIG. 23. The sialylated N-glycan profile was also analyzed between the reaction steps, and the result clearly indicated that sialic acids were first removed from the sialylated N-glycans (indicated for example by appearance of increased amounts of neutral N-glycans), and then replaced by α2,3-linked sialic acid residues (indicated for example by disappearance of the newly formed neutral N-glycans; data not shown). It is concluded that the resulting modified cells contained more α2,3-linked sialic acid residues after the reaction.

Sialyltransferase Reaction Followed by Fucosyltransferase Reaction.

Figure 24:
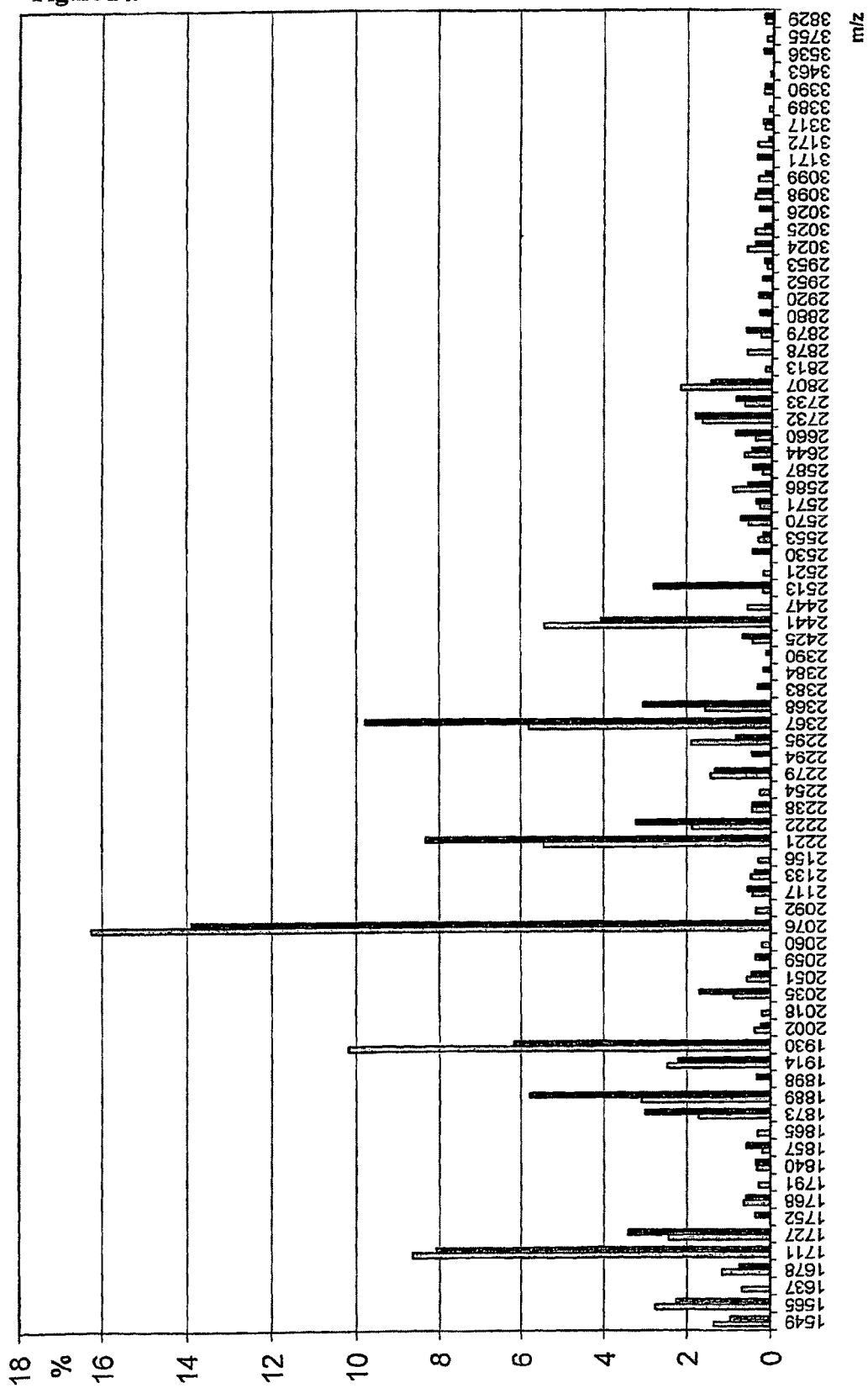
FIG. 24. Cord blood mononuclear cell sialylated N-glycan profiles before (light columns) and after (dark columns) subsequent $\alpha 2,3$-sialyltransferase and $\alpha 1,3$-fucosyltransferase reactions. The m/z values refer to Table 16.

Cord blood mononuclear cells were subjected to α2,3-sialyltransferase reaction, after which α1,3-fucosyltransferase and GDP-fucose were added to the same reaction, as described under Experimental procedures. The effects of this reaction sequence on the sialylated N-glycan profiles of the cells are described in FIG. 24. The results show that a major part of the glycan signals (detailed in Table 16) have undergone changes in their relative intensities, indicating that a major part of the sialylated N-glycans present in the cells were substrates of the enzymes. It was also clear that the combination of the enzymatic reaction steps resulted in different result than either one of the reaction steps alone.

Different from the α1,3-fucosyltransferase reaction described above, sialylation before fucosylation apparently sialylated the neutral fucosyltransferase acceptor glycan structures present on cord blood mononuclear cell surfaces, resulting in no detectable formation of the neutral fucosylated N-glycan structures that had emerged after α1,3-fucosyltransferase reaction alone (discussed above; Table 15).

α-mannosidase Reaction.

α-mannosidase reaction of whole cells showed a minor reduction of glycan signals including those indicated to contain α-mannose residues in the preceding examples.

Glycosyltransferase-Derived Glycan Structures.

We detected that glycosylated glycosyltransferase enzymes can contaminate cells in modification reactions. For example, when cells were incubated with recombinant fucosyltransferase or sialyltransferase enzymes produced in *S. frugiperda* cells, N-glycosidase and mass spectrometric analysis of cellular and/or cell-associated glycoproteins resulted in detection of an abundant neutral N-glycan signal at m/z 1079, corresponding to $[M+Na]^+$ ion of $Hex_3HexNAc_2dHex_1$ glycan component (calc. m/z 1079.38). Typically, in recombinant glycosyltransferase treated cells, this glycan signal was more abundant than or at least comparable to the cells' own glycan signals, indicating that insect-derived glycoconjugates are a very potent contaminant associated with recombinant glycan-modified enzymes produced in insect cells. Moreover, this glycan contamination persisted even after washing of the cells, indicating that the insect-type glycoconjugate corresponding to or associated with the glycosyltransferase enzymes has affinity towards cells or has tendency to resist washing from cells. To confirm the origin of the glycan signal, we analyzed glycan contents of commercial recombinant fucosyltransferase and sialyltransferase enzyme preparations and found that the m/z 1079 glycan signal was a major N-glycan signal associated with these enzymes. Corresponding N-glycan structures, e.g. Manα3(Manα6)Manβ4GlnNAc(Fucα3/6)GlcNAc(β-N-Asn), have been described previously from glycoproteins produced in *S. frugiperda* cells (Staudacher et al., 1992; Kretzchmar et al., 1994; Kubelka et al., 1994; Altmann et al., 1999). As described in the literature, these glycan structures, as well as other glycan structures potentially contaminating cells treated with recombinant or purified enzymes, especially insect-derived products, are potentially immunogenic in humans and/or otherwise harmful to the use of the modified cells. It is concluded that glycan-modifying enzymes must be carefully selected for modification of human cells, especially for clinical use, not to contain immunogenic glycan epitopes, non-human glycan structures, and/or other glycan structures potentially having unwanted biological effects.

Example 11

MALDI-TOF Mass Spectrometric Profiling of Cell Surface Glycans

Experimental Procedures and Results

Cells, Mononuclear cells were isolated from human peripheral blood by Ficoll-Hypaque density gradient (Amersham Biosciences, Piscataway, USA) essentially as described. The surface glycoprotein glycans were liberated by mild trypsin treatment (80 micrograms/ml in PBS) at +37 degrees Celsius for 2 hours. The intact cells were harvested by centrifugation, and the supernatant containing the liberated glycans (at this stage as cell surface glycoprotein glycopeptides) was taken for further analyses. The harvested cells and the supernatant were subjected to Glycan profiling by protein N-glycosidase as described in the preceding examples. The N-glycan profiles of the supernatant containing the cell surface glycoprotein glycopeptides, were compared against N-glycan profiles of the cells harvested from the trypsin treatment.

Results

N-Glycan analyses of HMC cell surface glycopeptide glycomes. HMC were isolated from peripheral blood, treated with trypsin to release the surface glycoprotein glycopeptides, followed by release of glycopeptide glycans, and subjected to glycome profiling as described under Experimental procedures. In MALDI-TOF mass spectrometry of the sialylated N-glycan fractions, several glycon signals were detected in these samples. When the resulting glycome profile was compared to a corresponding glycome isolated from the trypsin treated cells, it could be observed that many sialylated components were enriched in the surface glycoprotein glycopeptide fraction, whereas some structures appeared to have more intracellular localization. Examples or the former structures are (monosaccharide compositions in parenthesis): m/z [M-H]$^+$ 1930 (SaHex5HexNAc4), 2221 (Sa2Hex5HexNAc4), 2222 (SaHex5HexNAc4dHex2), 2367 (Sa2Hex5HexNAc4dHex), 2368(SaHex5HexNAc4dHex3), 2587 (SaHex6HexNAc5dHex2), and 3024 (Sa3Hex6HexNAc5dHex). Examples of the latter are m/z 1873(SaHex5HexNAc3dHex), and 2035 (SaHexHexNAc3dHex).

Example 12

Comparison of Human and Murine Fibroblast Feeder Cell N-glycan Profiles

Results

Figure 25:
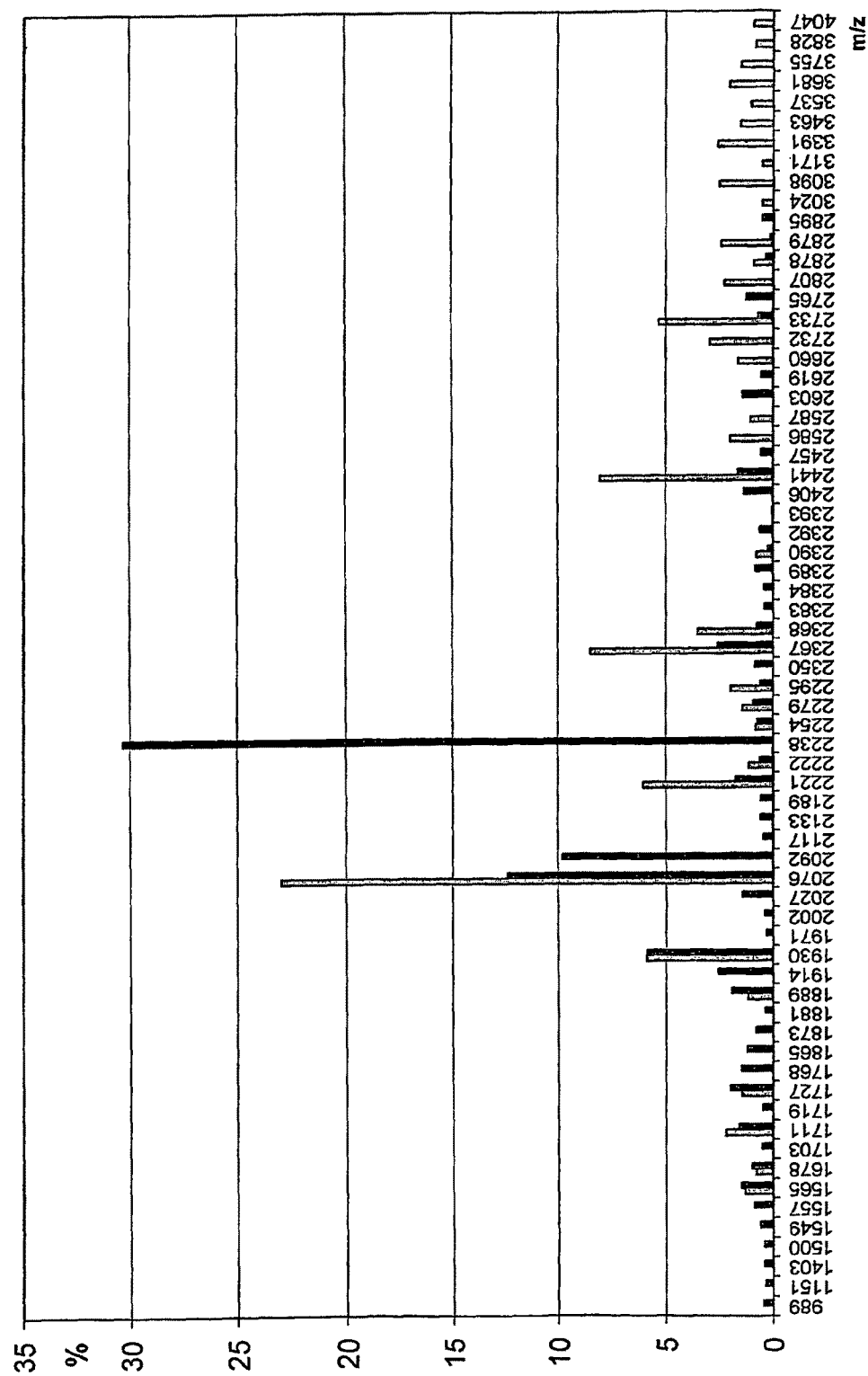
FIG. 25. Sialylated N-glycan profiles of human fibroblast feeder cells (light columns) and mouse fibroblast feeder cells (dark columns).

N-glycans were isolated, divided into sialylated and neutral fractions, and analysed by MALDI-TOF mass spectrometry as described in the preceding Examples. Comparison of sialylated N-glycan profiles of human fibroblast feeder cells and mouse fibroblast feeder cells is shown in FIG. 25. There are numerous differences in the glycan profiles and it is concluded that human and murine feeder cells differ from each other significantly with respect to their overall glycan profiles as well as many individual glycan signals. The major differences are 2092 and 2238, corresponding to the monosaccharide compositions NeuAc$_1$Hex$_6$HexNAc$_4$ and NeuAc$_1$Hex$_6$HexNAc$_4$dHex$_1$, respectively. These signals correspond to the major sialylated N-glycans that human embryonal stem cells interact with on the cell surfaces of their feeder cells. The present results indicate that the glycan analysis method can be used to study species-specific differences in stem cell to feeder cell interactions.

Example 13

Proton NMR Analysis of Human Embryonic Stem Cell N-glycan Fractions

Experimental Procedures

N-glycans were isolated from human embryonic stem cell (hESC) line (25 million cells) and fractionated into neutral and acidic N-glycan fractions as described above. The final purification prior to NMR analysis was performed by gel filtration high-performance liquid chromatography (HPLC) on a Superdex Peptide HR10/300 column in water or 50 mM ammonium bicarbonate for the neutral and acidic fractions, respectively. Fractions were collected and MALDI-TOF mass spectra were recorded from each fraction as described above (data not shown). All fractions containing N-glycans were pooled and prepared for the NMR experiment. The yields of neutral and acidic glycans were 4.0 and 6.6 nmol, respectively.

Prior to NMR analysis the purified glycome fractions were repeatedly dissolved in 99.996% deuterium oxide and dried to omit H$_2$O and to exchange sample protons. The $^1$H-NMR spectra at 800 MHz were recorded using a cryo-probe for enhanced sensitivity. Chemical shifts are expressed in parts per million (ppm) by reference to internal standard acetone (2.225 ppm).

Results And Discussion

Neutral N-Glycan Fraction.

The identified signals in the neutral N-glycan spectrum are described in Table 17. The identified signals were consistent with N-glycan structures, more specifically high-mannose type N-glycan structures such as the structures A-D in FIG. 26 that have the proposed monosaccharide compositions Man$_{7-9}$GlcNAc$_2$. In the mass spectrum recorded from the pooled neutral N-glycan fraction, the signals with the Hex$_{7-9}$HexNAc$_2$ composition together accounted for more than a half of the total signal intensity, which is consistent with the NMR result that these signals were the major glycans in the sample. The NMR spectrum contained the characteristic signals of the glycan structures A-D (Fu et al., 1994; Hård et al., 1991) and the significant signals in the NMR spectrum can be explained by the following glycan structure combinations: A+D, B+C, A+B+D, A+C+D, B+C+D, and A+B+C+D.

Neutral N-Glycan Core Sequences.

The identified N-glycan core structure common to all the identified glycan structures in the NMR spectrum includes the following glycan sequences: the internal core sequences Manβ4GlcNAc, Manα3Manβ4GlcNAc, Manα6Manβ4GlcNAc, and Manα3(Manα6)Manβ4GlcNAc, and the reducing terminal glycan core sequences GlcNAcβ4GlcNAc, Manβ4GlcNAcβ4GlcNAc, Manα3Manβ4GlcNAcβ4GlcNAc, Manα6Manβ4GlcNAcβ4GlcNAc, and Manα3(Manα6)Manβ4GlcNAcβ4GlcNAc. The N-glycans in the sample were liberated by N-glycosidase F enzyme indicating that the reducing terminal core sequences were β-N-linked to asparagine residues in the original sample glycoproteins. Other glycan core structures could not be identified in the spectrum.

Neutral N-Glycan Antennae.

In the identified structures A-D, the common reducing terminal N-glycan core sequence Manα3(Manα6)Manβ4GlcNAcβ4GlcNAc is further elongated by the following antennae: Manα2Manα2 or Manα2 to the α3-linked Man; and/or Manα2Manα3, Manα2Manα6, Manα3, and/or Manα6 to the α6-linked Man. Other glycan antennae could not be identified in the spectrum.

Acidic N-Glycan Fraction.

The identified signals in the acidic N-glycan spectrum are described in Table 18. The identified signals were consistent with N-glycan structures, more specifically complex type N-glycan structures such as the reference structures A-E in FIG. 27 (Hård et al., 1992; Helin et al., 1995). In the mass spectrum recorded from the pooled acidic N-glycan fraction, the signals containing exactly five hexoses and four N-acetylhexosamines in their proposed composition i.e. containing the Hex$_5$HexNAc$_4$ structural feature (like structures B-E) together accounted for approximately 45% of the total signal intensity, which is consistent with the NMR result that the corresponding glycans were the major glycans in the sample. The NMR spectrum contained the characteristic signals of the structures A-E, and the significant signals in the NMR spectrum can be explained by the structural components of these reference structures.

Acidic N-Glycan Core Sequences.

The identified N-glycan core structure common to all the identified glycan structures in the NMR spectrum includes the following glycan sequences: the reducing terminal glycan core sequences GlcNAcβ4(±Fucα6)GlcNAc, Manβ4GlcNAcβ4(±Fucα6)GlcNAc, Manα3Manβ4GlcNAcβ4(±Fucα6)GlcNAc, Manα6Manβ4GlcNAcβ4(±Fucα6)GlcNAc, and Manα3(Manα6)Manβ4GlcNAcβ4(±Fucα6)GlcNAc, wherein ±Fucα6 indicates the site of N-glycan core fucosylation. The N-glycans in the sample were liberated by N-glycosidase F enzyme indicating that the reducing terminal core sequences were β-N-linked to asparagine residues in the original sample glycoproteins. Other glycan core structures could not be identified in the spectrum.

Acidic N-Glycan Antennae.

In the reference structures A-D, the reducing terminal N-glycan core sequences are further elongated by the following antennae, which were also identified in the recorded spectrum: Neu5Acα3Galβ4GlcNAcβ2, Neu5Acα6Galβ4GlcNAcβ2, Galβ4GlcNAcβ2, and/or Galα3Galβ4GlcNAcβ2 to either α3-linked Man or α6-linked Man. The identified antennae in the NMR spectrum include the internal glycan sequence GlcNAc β-linked or more specifically β2-linked to the N-glycan core structure. Other glycan antennae could not be identified in the spectrum, indicating that these antennae were the most abundant antenna structures in the sample.

Gala3Gal Sequences.

In the mass spectrum recorded from the pooled acidic N-glycan fraction, the signals corresponding to glycan structures containing the $Hex_6HexNAc_4$ composition feature together accounted for about 16% of the total signal intensity, which is consistent with the NMR result that these signals correspond to major glycans in the sample.

Comparison of NMR Profiling and Mass Spectrometric Profiling Results.

As described above, the $^1$H-NMR spectra were consistent with the mass spectra recorded from the hESC samples and support the quantitative and structural assignments made based on the mass spectrometric profiles in the preceding Examples.

NMR REFERENCES

Fu D., Chen L. and O'Neill R. A. (1994) *Carbohydr. Res.* 261, 173-186

Helin J., Maaheimo H., Seppo A., Keane A. and Renkonen O. (1995) *Carbohydr. Res.* 266, 191-209

Hard K., Mekking A., Kamerling J. P., Dacremont G. A. A. and Vliegenthart J. F. G. (1991) *Glycoconjugate J.* 8, 17-28

Hård K., Van Zadelhoff G., Moonen P., Kamerling J. P. and Vliegenthart J. F. G. (1992) *Eur. J. Biochem.* 209, 895-915

Example 14

O-glycan Profiling of Human Stem Cells

Methods

Reductive β-Elimination.

The procedure has been described (Nyman et al., 1998). Briefly, glycoproteins were dissolved in 1 M NaBH in 0.1 M NaOH and incubated at 37° C. for two days. Borohydride was destroyed by repeated evaporation from mild acetic acid in methanol. The resulting glycan alditols were purified by solid-phase extraction methods as described above.

Non-Reductive β-Elimination.

The procedure has been described (Huang et al., 2001). Briefly, glycoproteins were dissolved in ammonium carbonate in concentrated ammonia and incubated at 60° C. for two days. The reagents were removed by evaporation and glycosylamines by brief incubation and evaporation from mild aqueous acetic acid. The resulting reducing glycans were purified by solid-phase extraction methods as described above.

Mass spectrometry and data analysis were performed as described in the preceding Examples.

Results and Discussion

O-Glycans in Cord Blood Mononuclear Cells.

Figure 28:
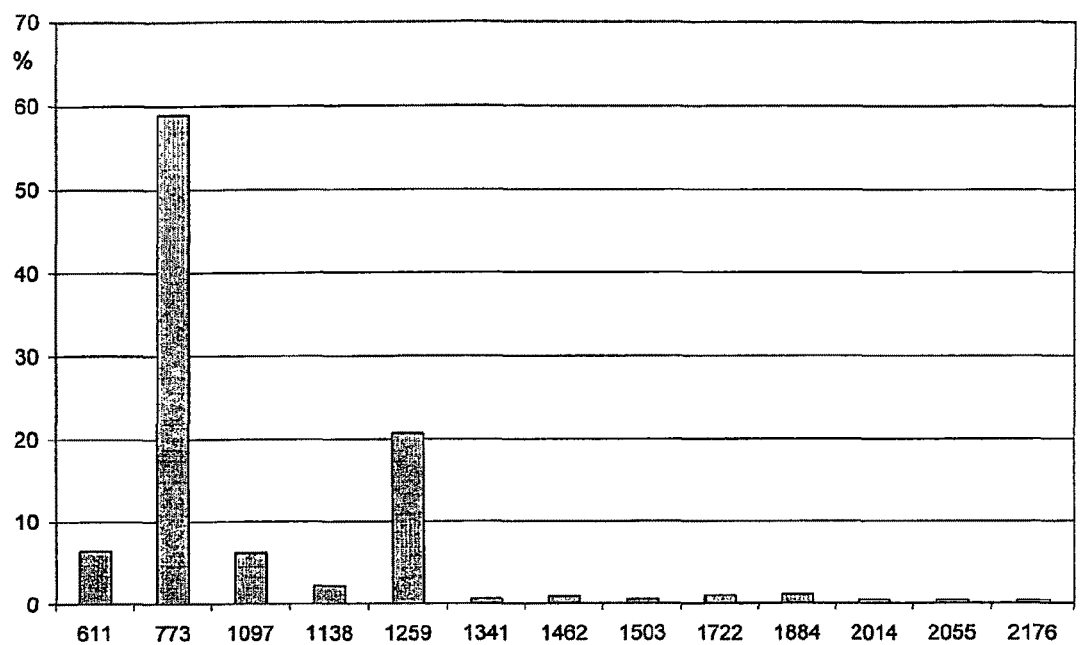
FIG. 28. Neutral O-glycan fraction glycan signals of cord blood mononuclear cells (CB MNC).
Figure 29:
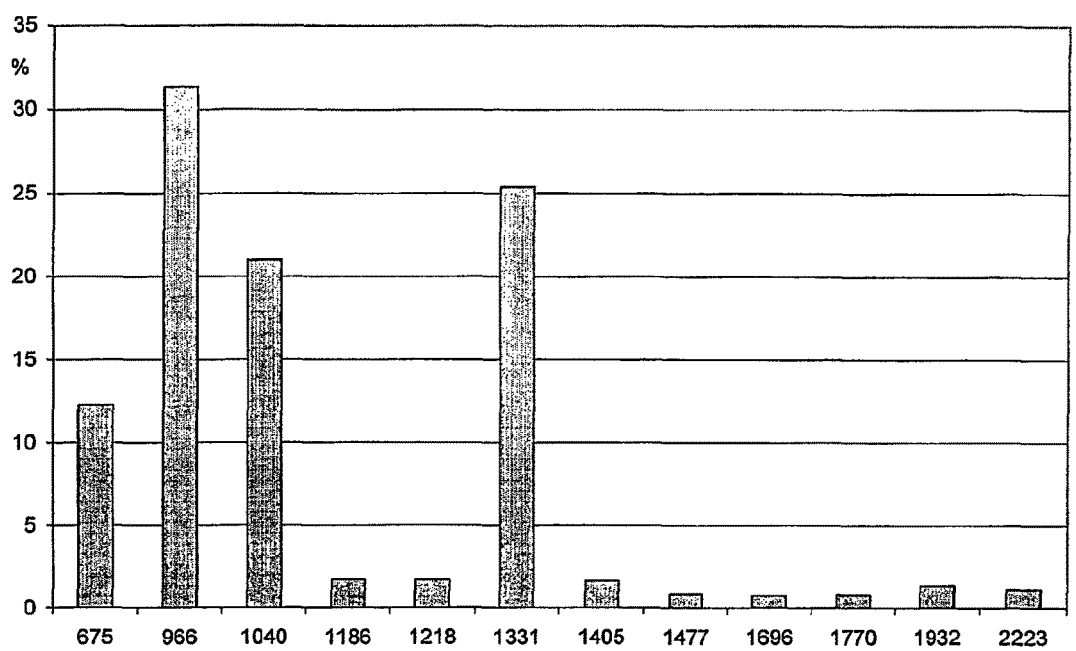
FIG. 29. Acidic O-glycan fraction glycan signals of cord blood mononuclear cells (CB MNC).

O-glycan fraction was isolated by reductive β-elimination from total glycoprotein fractions of cord blood mononuclear cells. The glycan alditols were divided into neutral and acidic fractions and analyzed by MALDI-TOF mass spectrometry as described above. The identified neutral and acidic glycan alditol signals are presented in Table 19 and Table 20, respectively, and their relative abundances are described in FIG. 28 and FIG. 29. The glycan signals in the present example include both N- and O-glycan alditol signals.

O-Glycans in Human Embryonic Stem Cells.

O-glycans were isolated by non-reductive β-elimination from total glycoprotein fractions of human embryonic stem cells (hESC) grown on mouse feeder cell layers. The glycans were divided into neutral and acidic fractions and analyzed by MALDI-TOF mass spectrometry as described above. The identified glycan signals in the neutral and acidic glycans fractions are presented in Table 21 and Table 22, respectively. The most abundant potential O-glycan signals were $Hex_1HexNAc_2$, $Hex_2HexNAc_2$, $Hex_2HexNAc_2dHex_1$, $Hex_3HexNAc_3$, $Hex_3HexNAc_3dHex_1$, $NeuAc_2Hex_1HexNAc_1$, $NeuAc_1Hex_2HexNAc_2$, $NeuAc_1Hex_2HexNAc_2dHex_1$, $NeuAc_2Hex_2HexNAc_2$, $NeuAc_1Hex_3HexNAc_3$, $NeuAc_2Hex_2HexNAc_2dHex_1$, $NeuAc_1Hex_3HexNAc_3$, $Hex_3HexNAc_3SP$, $Hex_4HexNAc_4SP$, and $Hex_4HexNAc_4dHex_1SP$, wherein SP corresponds to a charged group with a mass of sulphate or phosphate such as sulphate ester linked to an N-acetyllactosamine structure.

Example 15

Glycosaminoglycan Fragment Analyses from Human Stem Cells

N-glycan and soluble glycan fractions were prepared from human cord blood cell populations as described in the preceding Examples. In cord blood mononuclear cells as well as affinity-purified cord blood CD34+, CD34−, CD133−, and LIN+ cell populations, following glycan fragments were identified (approximate experimental m/z for [M-H]$^-$ ions in parenthesis): $R^1$ (816), $R^1HexNAc_1$ (1019), $R^2$ (1058), $R^1HexNAc_1HexA_1$ (1195), $R^2HexA_1$ (1234), $R^1HexNAc_2HexA_1$ (1398), $R^2HexNAc_1HexA_1$ (1437), $R^1HexNAc_2HexA_2$ (1574), $R^2HexNAc_1HexA_2$ (1613), $R^1HexNAc_3HexA_2$ (1777), $R^2HexNAc_2HexA_2$ (1816), $R^2HexNAc_2HexA_3$ (1992), and $R^2HexNAc_3HexA_3$ (2195), wherein $R^1$ is preferentially $HexA_1Hex_2Pen_1R^3$, $R^2$ is preferentially $HexA_1Hex_3Pen_1R^4$, $R^3$ is preferentially $SO_3Ser_1$ or $HPO_3Ser_1$, $R^4$ is preferentially $(SO_3)_2Ser_1$, $SO_3HPO_3Ser_1$, or $(HPO_3)_2Ser_1$. The identified glycans are indicated as being glycosaminoglycan fragments present in stem cell and mononuclear cell populations in human cord blood.

Example 16

Exoglycosidase Analysis of Human Embryonic Stem Cells

Experimental Procedures hESC and Differentiated Cell Samples.

The human embryonic stem cell (hESC) and embryoid body (EB) samples were prepared from hESC line FES 29 (Skottman et al., 2005) essentially as described in the preceding Examples, however in the present Example the hESCs were propagated on murine fibroblast feeder cells (mEF) and the hESC samples contained some mEF cells.

Exoglycosidase digestions were performed essentially as described (Saarinen et al., 1999) and as described in the preceding Examples. The enzymes used were α-mannosidase and β-hexosaminidase from Jack beans (*C. ensiformis*, Sigma, USA), β-glucosaminidase and β1,4-galactosidase from *S. pneumoniae* (rec. in *E. coli*, Calbiochem, USA), α2,3-sialidase from *S. pneumoniae* (Glyko, UK), α1,3/4-fucosidase from *Xanthomonas* sp. (Calbiochem, USA), α1,2-fucosidase from *X. manihotis* (Glyko), β1,3-galactosidase (rec. in *E. coli*, Calbiochem), and α2,3/6/8/9-sialidase from *A. ureafaciens* (Glyko). The specific activities of the enzymes were controlled in parallel reactions with purified oligosaccharides or oligosaccharide mixtures, and analyzed similarly as the analytic reactions. The changes in the exoglycosidase digestion result Tables are relative changes in the recorded mass spectra and they do not reflect absolute changes in the glycan profiles resulting from glycosidase treatments.

Results and Discussion hESC

Neutral and acidic N-glycan fractions were isolated from hESC grown on both murine and human fibroblast feeder cells as described in the preceding Examples. The results of parallel exoglycosidase digestions of the neutral (Tables 23 and 24) and acidic (Table 25) glycan fractions are discussed below. In the following chapters, the glycan signals are referred to by their proposed monosaccharide compositions according to the Tables of the present invention and the corresponding m/z values can be read from the Tables.

α-Mannosidase Sensitive Structures.

All the glycan signals that showed decrease upon α-mannosidase digestion of the neutral N-glycan fraction (Tables 23 and 24) are indicated to correspond to glycans that contain terminal α-mannose residues. The present results indicate that the majority of the neutral N-glycans of hESC contain terminal α-mannose residues. On the other hand, increased signals correspond to their reaction products. Structure groups that form series of α-mannosylated glycans in the neutral N-glycan fraction as well as individual α-mannosylated glycans are discussed below in detail.

The $Hex_{1-9}HexNAc_1$ glycan series was digested so that $Hex_{3-9}HexNAc_1$ were digested and transformed into $Hex_1HexNAc_1$ (data not shown), indicating that they had contained terminal α-mannose residues. Because they were transformed into $Hex_1HexNAc_1$, their experimental structures were $(Man\alpha)_{1-8}Hex_1HexNAc_1$.

The $Hex_{1-12}HexNAc_2$ glycan series was digested so that $Hex_{3-12}HexNAc_2$ were digested and transformed into $Hex_{1-7}HexNAc_2$ and especially into $Hex_1HexNAc_2$ that had not existed before the reaction and was the major reaction product. This indicates that 1) glycans $Hex_{3-12}HexNAc_2$ include glycans containing terminal α-mannose residues, 2) glycans $Hex_{3-7}HexNAc_2$ could be formed from larger α-mannosylated glycans, and 3) majority of the glycans $Hex_{3-12}HexNAc_2$ were transformed into newly formed $Hex_1HexNAc_2$ and therefore had the experimental structures $(Man\alpha)_n Hex_1HexNAc_2$, wherein n≥1. The fact that the α-mannosidase reaction was only partially completed for many of the signals suggests that also other glycan components are included in the $Hex_{1-12}HexNAc_2$ glycan series. In particular, the $Hex_{10-12}HexNAc_2$ components contain 1-3 hexose residues more than the largest typical mammalian high-mannose type N-glycan, suggesting that they contains glucosylated structures including $(Glc\alpha)_{1-3}Hex8HexNAc_2$, preferentially α2- and/or α3-linked Glc and even more preferentially present in the glucosylated N-glycans $Glc\alpha3 \rightarrow Man_9GlcNAc_2$, $Glc\alpha2Glc\alpha3 \rightarrow Man_9GlcNAc_2$, and/or $Glc\alpha2Glc\alpha2Glc\alpha3 \rightarrow Man_9GlcNAc_2$. The corresponding glucosylated fragments were observed after the α-mannosidase digestion, preferentially corresponding to $Glc_{1-3}Man_4GlcNAc_2$ ($Hex_{5-7}HexNAc_2$).

The $Hex_{1-6}HexNAc_1dHex_1$ glycan series was digested so that $Hex_{3-9}HexNAcdHex_1$ were digested and transformed into $Hex_1HexNAc_1dHex_1$, indicating that they had contained terminal α-mannose residues and their experimental structures were $(Man\alpha)_{2-5}Hex_1HexNAc_1dHex_1$. $Hex_1HexNAc_1dHex_1$ appeared as a new signal indicating that glycans with structures $(Man\alpha)_n Hex_1HexNAc_1dHex_1$, wherein n≥1, had existed in the sample.

The $Hex_{2-7}HexNAc_3$ glycan series was digested so that $Hex_{5-7}HexNAc_3$ were digested and transformed into other glycans in the series, indicating that they had contained terminal α-mannose residues. $Hex_2HexNAc_3$ appeared as a new signal indicating that glycans with structures $(Man\alpha)_n Hex_2HexNAc_3$, wherein n≥1, had existed in the sample.

The $Hex_{2-7}HexNAc_3dHex_1$ glycan series was digested so that $Hex_{5-7}HexNAc_3dHex_1$ were digested and transformed into other glycans in the series, indicating that they had contained terminal α-mannose residues. $Hex_2HexNAc_3dHex_1$ was increased significantly indicating that glycans with structures $(Man\alpha)_n Hex_2HexNAc_3dHex_1$, wherein n≥1, had existed in the sample.

$Hex_3HexNAc_3dHex_2$ appeared as a new signal indicating that glycans with structures $(Man\alpha)_n Hex_3HexNAc_3dHex_2$, wherein n≥1, had existed in the sample.

β-Glucosaminidase Sensitive Structures.

The $Hex_3HexNAC_{2-5}$ and $Hex_3HexNAc_{2-5}dHex_1$-glycan series were digested so that $Hex_{3-5}HexNAc_1dHex_{0-1}$ were digested and transformed into $Hex_3HexNAc_2dHex_{0-1}$, indicating that they had contained terminal β-GlcNAc residues and their experimental structures were $(GlcNAc\beta \rightarrow)_{1-3}Hex_3HexNAc_2$ and $(GlcNAc\beta \rightarrow)_{1-3}Hex_3HexNAc_2dHex_1$, respectively.

$Hex_4HexNAc_4$, $Hex_4HexNAc_4dHex_1$, $Hex_4HexNAc_4dHex_2$, and $Hex_5HexNAc_5dHex_1$ were also digested indicating they contained structures including $(GlcNAc\beta \rightarrow)Hex_4HexNAc_3$, $(GlcNAc\beta \rightarrow)Hex_4HexNAc_3dHex_1$, $(GlcNAc\beta \rightarrow)Hex_4HexNAc_3dHex_2$, and $(GlcNAc\beta \rightarrow)Hex_5HexNAc_4dHex_1$, respectively.

$Hex_4HexNAc_5dHex_1$ and $Hex_4HexNAc_5dHex_2$ were digested by β-glucosaminidase and indicated to contain two β-GlcNAc residues each. In contrast, $Hex_4HexNAc_5$ was not digested with β-glucosaminidase.

β-Hexosaminidase Sensitive Structures.

The $Hex_4HexNAc_5$ glycan signal was sensitive to β-hexosaminidase but not to β-glucosaminidase indicating that it corresponded to glycan structures containing terminal β-N-acetylhexosamine residues other than β-GlcNAc, preferentially β-GalNAc. Upon β-hexosaminidase digestion, the signal was transformed into, $Hex_4HexNAc_3$ indicating that the enzyme liberated two HexNAc residues from the corresponding glycan structures.

β1,4-Galactosidase Sensitive Structures.

Glycan signals that were sensitive to β1,4-galactosidase comprised a major proportion of hESC glycans, indicating that β1,4-linked galactose is a common terminal epitope in hESC neutral N-glycans.

$Hex_5HexNAc_4$ and $Hex_5HexNAc_4dHex_1$ were digested into $Hex_3HexNAc_4$ and $Hex_3HexNAc_4dHex_1$ indicating they had the structures $(Gal\beta4GlcNAc\beta \rightarrow)_2Hex_3HexNAc_2$ and $(Gal\beta4GlcNAc\beta \rightarrow)_2Hex_3HexNAc_2dHex_1$, respectively. In contrast, $Hex_5HexNAc_4dHex_2$ was digested into $Hex_4HexNAc_4dHex_2$ indicating that it had the structure (Galβ4GlcNAcβ→)Hex$_4$HexNAc$_3$dHex$_2$, and Hex$_5$HexNAc$_4$dHex$_3$ was not digested at all. Taken together, in hESC, hexose residues are protected by deoxyhexose residues from the action of β1,4-galactosidase in the N-glycan structures. Such dHex-protected structures containing β1,4-linked galactose include Galβ4(Fucα3)GlcNAc and Fucα2Galβ4GlcNAc.

Hex$_4$HexNA$_5$ that also included a β-hexosaminidase sensitive component was digested by β1,4-galactosidase. Taken together, the results suggest that the Hex$_4$HexNAc$_5$ glycan signal includes glycan structures including Galβ4GlcNAc (GalNAcβHexNAcβ)Hex$_3$HexNAc$_2$.

β1,3-Galactosidase Sensitive Structures.

Because only few structures in hESC neutral N-glycan fraction were sensitive to the action of β1,3-galactosidase, the majority of terminal galactose residues appear to be β1,4-linked.

Glycosidase Resistant Structures.

In the present experiments, Hex$_4$HexNAc$_3$, Hex$_4$HexNAc$_3$dHex$_2$, and Hex$_5$HexNAc$_5$ were resistant to the tested exoglycosidases. The second monosaccharide composition contains more than one deoxyhexose residues suggesting that it is protected from glycosidase digestions by dHex residues such as α2-, α3-, or α4-linked fucose residues, preferentially present in Fucα2Gal, Fucα3GlcNAc, and/or Fucα4GlcNAc epitopes.

The compiled neutral N-glycan fraction glycan structures based on the exoglycosidase digestions of hESC are presented in Table 26.

Acidic N-Glycan Fraction.

The acidic N-glycan fraction of hESC grown on mEF cell layers were characterized by parallel α2,3-sialidase and *A. ureafaciens* sialidase treatments as well as sequential digestions with α1,3/4-fucosidase and α1,2-fucosidase. The results from these reactions as analyzed by MALDI-TOF mass spectrometry are described in Table 25. The results suggest that multiple N-glycan components in the hESC sample contain the specific glycan substrates for these enzymes, namely α2,3-linked and other sialic acid residues, and both α1,2- and α1,3/4-linked fucose residues. Some glycan signals showed the presence of many of these epitopes, such as the glycan signal at m/z 2222 (corresponding to NeuAc$_1$Hex$_5$HexNAc$_4$dHex$_2$) that was suggested to contain all these epitopes, preferentially in multiple glycan structures. The compiled acidic N-glycan fraction glycan structures based on the exoglycosidase digestions of hESC are presented in Table 27.

EB

Differentiation specific changes between embryoid bodies (EB; FES 29 st 2 in Table 23) and hESC (FES 29 st 1 in Table 23) were reflected in their neutral N-glycan fraction exoglycosidase digestion profiles, as described in Table 23. Differential exoglycosidase digestion results were observed in glycan signals including m/z 1688, 1704, 1793, 1866, 1955, 1971, 2012, 2028, 2142, 2158, and 2320, corresponding to different neutral N-glycan fraction glycan profiles.

meF

By comparison of Table 22 and Table 23, murine feeder cell (mEF) specific neutral N-glycan fraction glycan components were identified and they are listed in Table 28. These glycan components are characterized by additional hexose residues compared to hESC or hEF specific structures according to the present invention. The exoglycosidase experiments also suggest that β1,4-linked galactose epitopes are protected from β1,4-galactosidase digestion by any additional hexose residues in the monosaccharide compositions. Taken together with the NMR analysis results of the present invention, the additional hexose residues are suggested to be α-linked galactose residues, more specifically including Galα3Gal epitopes in the N-glycan antennae, as described in Table 28.

Example 17

Exoglycosidase Analysis of Human Mesenchymal Stem Cells

The changes in the exoglycosidase digestion result Tables are relative changes in the recorded mass spectra and they do not reflect absolute changes in the glycan profiles resulting from glycosidase treatments. The experimental procedures are described in the preceding Example.

Results

Undifferentiated BM MSC

Neutral and acidic N-glycan fractions were isolated from BM MSC as described. The results of parallel exoglycosidase digestions of the neutral (Table 29) and acidic (data not shown) glycan fractions are discussed below. In the following chapters, the glycan signals are referred to by their proposed monosaccharide compositions according to the Tables of the present invention and the corresponding m/z values can be read from the Tables.

α-Mannosidase Sensitive Structures.

All the glycan signals that showed decrease upon α-mannosidase digestion of the neutral N-glycan fraction (Table 29) are indicated to correspond to glycans that contain terminal α-mannose residues. The present results indicate that the majority of the neutral N-glycans of BM MSC contain terminal α-mannose residues. On the other hand, increased signals correspond to their reaction products. Structure groups that form series of α-mannosylated glycans in the neutral N-glycan fraction as well as individual α-mannosylated glycans are discussed below in detail.

The Hex$_{1-9}$HexNAc$_1$ glycan series was digested so that Hex$_{3-9}$HexNAc$_1$ were digested and transformed into Hex$_1$HexNAc$_1$ (data not shown), indicating that they had contained terminal α-mannose residues. Because they were transformed into Hex$_1$HexNAc$_1$, their experimental structures were (Manα)$_{1-8}$Hex$_1$HexNAc$_1$.

The Hex$_{1-10}$HexNAc$_2$ glycan series was digested so that Hex$_{4-10}$HexNAc$_2$ were digested and transformed into Hex$_1$HexNAc$_2$ and especially into Hex$_1$HexNAC$_2$ that had not existed before the reaction and was the major reaction product. This indicates that 1) glycans Hex$_{4-10}$HexNAc$_2$ include glycans containing terminal α-mannose residues, 2) glycans Hex$_{1-4}$HexNAc$_2$ could be formed from larger α-mannosylated glycans, and 3) majority of the glycans Hex$_{4-10}$HexNAc$_2$ were transformed into newly formed Hex$_1$HexNAc$_2$ and therefore had the experimental structures (Manα)$_n$Hex$_1$HexNAc$_2$, wherein n≥1. The fact that the α-mannosidase reaction was only partially completed for many of the signals suggests that also other glycan components are included in the Hex$_{1-10}$HexNAc$_2$ glycan series. In particular, the Hex$_{10}$HexNAc$_2$ component contains one hexose residue more than the largest typical mammalian high-mannose type N-glycan, suggesting that it contains glucosylated structures including (Glcα→)Hex$_8$HexNAc$_2$, preferentially α3-linked Glc and even more preferentially present in the glucosylated N-glycan (Glcα3→)Man$_9$GlcNAc$_2$.

The Hex$_{1-6}$HexNAc$_1$dHex$_1$ glycan series was digested so that Hex$_{3-9}$HexNAc$_1$dHex$_1$ were digested and transformed into Hex$_1$HexNAc$_1$dHex$_1$, indicating that they had contained terminal α-mannose residues and their experimental structures were (Manα)$_{2-5}$Hex$_1$HexNAc$_1$dHex$_1$.

Hex$_1$HexNAc$_1$dHex$_1$ appeared as a new signal indicating that glycans with structures (Manα)$_n$Hex$_1$HexNAc$_1$dHex$_1$, wherein n≥1, had existed in the sample.

The Hex$_{2-7}$HexNAc$_3$ glycan series was digested so that Hex$_{6-7}$HexNAc$_3$ were digested and transformed into other glycans in the series, indicating that they had contained terminal α-mannose residues. Hex$_2$HexNAc$_3$ appeared as a new signal indicating that glycans with structures (Manα)$_n$Hex$_2$HexNAc$_3$, wherein n≥1, had existed in the sample.

The Hex$_{2-7}$HexNAc$_3$dHex$_1$ glycan series was digested so that Hex$_{6-7}$HexNAc$_3$dHex$_1$ were digested and transformed into other glycans in the series, indicating that they had contained terminal α-mannose residues. Hex$_2$HexNAc$_3$dHex$_1$ appeared as a new signal indicating that glycans with structures (Manα)$_n$Hex$_2$HexNAc$_3$dHex$_1$, wherein n≥1, had existed in the sample.

Hex$_3$HexNAc$_3$dHex$_2$ and Hex$_3$HexNAc$_4$ appeared as new signals indicating that glycans with structures (Manα)$_n$Hex$_3$HexNAc$_3$dHex$_2$ and (Manα)$_n$Hex$_3$HexNAc$_4$, respectively, wherein n≥1, had existed in the sample.

β-Glucosaminidase Sensitive Structures.

The Hex$_3$HexNAc$_{2-5}$dHex$_1$ glycan series was digested so that Hex$_{3-9}$HexNAc$_1$dHex$_1$ were digested and transformed into Hex$_1$HexNAc$_1$dHex$_1$, indicating that they had contained terminal α-mannose residues and their experimental structures were (Manα)$_{2-5}$Hex$_1$HexNAc$_1$dHex$_1$. Hex$_1$HexNAc$_1$dHex$_1$, appeared as a new signal indicating that glycans with structures (Manα)$_n$Hex$_1$HexNAc$_1$dHex$_1$, wherein n≥1, had existed in the sample. However, Hex$_3$HexNAc$_6$dHex$_1$ was not digested indicating that it contained other terminal HexNAc residues than β-linked GlcNAc residues.

Hex$_2$HexNAc$_3$ and Hex$_2$HexNAc$_3$dHex$_1$ were digested into Hex$_2$HexNAc$_2$ and Hex$_2$HexNAc$_2$dHex$_1$ indicating they had the structures (GlcNAcβ→)Hex$_2$HexNAc$_2$ and (GlcNAcβ→)Hex$_2$HexNAc$_2$dHex$_1$, respectively.

Hex$_4$HcxNAc$_4$dHex$_1$, Hex$_4$HexNAc$_4$dHex$_2$, Hex$_4$HexNAc$_5$dHex$_2$, and Hex$_5$HexNAc$_5$dHex$_1$ were also digested indicating they contained structures including (GlcNAcβ→)Hex$_4$HexNAc$_3$dHex$_1$, (GlcNAcβ→)Hex$_4$HexNAc$_3$dHex$_2$, (GlcNAcβ→)Hex$_4$HexNAc$_4$dHex$_2$, and (GlcNAcβ→)Hex$_5$HexNAc$_4$dHex$_1$, respectively.

β1,4-Galactosidase Sensitive Structures.

Glycan signals that were sensitive to β1,4-galactosidase comprised a major proportion of BM MSC glycans, indicating that β1,4-linked galactose is a common terminal epitope in BM MSC neutral N-glycans.

Hex$_5$HexNAc$_4$ and Hex$_5$HexNAc$_4$dHex$_1$ were digested into Hex$_3$HexNAc$_4$ and Hex$_3$HexNAc$_4$dHex$_1$ indicating they had the structures (Galβ4GlcNAcβ→)$_2$Hex$_3$HexNAc$_2$ and (Galβ4GlcNAcβ→)$_2$Hex$_3$HexNAc$_2$dHex$_1$, respectively. In contrast, Hex$_5$HexNAc$_4$dHex$_2$ was digested into Hex$_4$HexNAc$_4$dHex$_2$ indicating that it had the structure (Galβ4GlcNAcβ→)Hex$_4$HexNAc$_3$dHex$_2$, respectively, and Hex$_5$HexNAc$_4$dHex$_3$ was not digested at all. Taken together, in BM MSC, n−1 hexose residues are protected by deoxyhexose residues from the action of β1,4-galactosidase in the N-glycan structures Hex$_5$HexNAc$_4$dHex$_n$, wherein 0≤n≤3. Such dHex-protected structures containing β1,4-linked galactose include Galβ4(Fucα3)GlcNAc and Fucα2Galβ4GlcNAc.

Similarly, Hex$_6$HexNAc$_5$, Hex$_5$HexNAc$_5$dHex$_1$, Hex$_6$HexNAc$_5$, and Hex$_5$HexNAc$_5$dHex$_1$ were digested into Hex$_3$HexNAc$_5$, Hex$_3$HexNAc$_5$dHex$_1$, and Hex$_3$HexNAc$_6$dHex$_1$ indicating they had the structures (Galβ4GlcNAcβ→)$_3$Hex$_3$HexNAc$_2$, (Galβ4GlcNAcβ→)$_2$Hex$_3$HexNAc$_3$dHex$_1$, and (Galβ4GlcNAcβ→)$_3$Hex$_3$HexNAc$_3$dHex$_1$, respectively. In contrast, Hex$_4$HexNAc$_5$dHex$_2$, Hex$_5$HexNAc$_5$dHex$_3$, Hex$_6$HexNAc$_5$dHex$_2$, and Hex$_6$HexNAc$_5$dHex$_3$ were not digested, indicating that hexose residues in these structures were protected by deoxyhexose residues. Such dHex-protected structures containing β1,4-linked galactose include Galβ4(Fucα3)GlcNAc and Fucα2Galβ4GlcNAc. However, Hex$_4$HexNAc$_5$dHex$_3$ was digested indicating that it contained one or more terminal β1,4-linked galactose residues.

Hex$_7$HexNAc$_3$, Hex$_6$HexNAc$_3$dHex$_1$, Hex$_6$HexNAc$_3$, and HeX$_5$HexNAc$_3$dHex$_1$ were digested into products including Hex$_5$HexNAc$_3$ and Hex$_4$HexNAc$_3$dHex$_1$, indicating they had the structures (Galβ4GlcNAcβ→)Hex$_5$HexNAc$_2$ and (Galβ4GlcNAcβ→)Hex$_{4-5}$HexNAc$_3$dHex$_1$, respectively. The relative amounts of Hex$_3$HexNAc$_3$, and Hex$_3$HexNAc$_3$dHex$_1$ were increased indicating that they were products of (Galβ4GlcNAcβ→)Hex$_3$HexNAc$_2$ and (Galβ4GlcNAcβ→)Hex$_3$HexNAc$_2$dHex$_1$, respectively.

β1,3-Galactosidase Sensitive Structures.

Because only few structures in BM MSC neutral N-glycan fraction are sensitive to the action of β1,3-galactosidase, the majority of terminal galactose residues appear to be β1,4-linked. The glycan signals corresponding to β1,3-galactosidase sensitive glycans include Hex$_5$HexNAc$_5$dHex$_1$ and Hex$_4$HexNAc$_5$dHex$_3$.

Glycosidase Resistant Structures.

In the present experiments, Hex$_2$HexNAc$_3$dHex$_2$, Hex$_4$HexNAc$_3$dHex$_2$, and Hex$_{11}$HexNAc$_2$ were resistant to the tested exoglycosidases. The first two proposed monosaccharide compositions contain more than one deoxyhexose residues suggesting that they are protected from glycosidase digestions by the second dHex residues such as α2-, α3-, or α4-linked fucose residues, preferentially present in Fucα2Gal, Fucα3GlcNAc, and/or Fucα4GlcNAc epitopes. The last proposed monosaccharide composition contains two hexose residues more than the largest typical mammalian high-mannose type N-glycan, suggesting that it contains glucosylated structures including (Glcα→)$_2$Hex$_9$HexNAc$_2$, preferentially α2- and/or α3-linked Glc and even more preferentially present in the deglucosylated N-glycan (Glcα-Glcα→)Man$_9$GlcNAc$_2$.

The compiled neutral N-glycan fraction glycan structures based on the exoglycosidase digestions of BM MSC are presented in Table 30.

Osteoblast-Differentiated BM MSC

The analysis of osteoblast differentiated BM MSC are presented in Table 31, allowing comparison of differentiation specific changes in CB MSC. The exoglycosidase profiles produced for BM MSC and osteoblast differentiated BM MSC are characteristic for the two cell types. For example, signals at m/z 1339, 1784, and 2466 are digested differentially in the two experiments. Specifically, the presence of β1,3-galactosidase sensitive neutral N-glycan signals in osteoblast differentiated BM MSC indicate that the differentiated cells contain more β1,3-linked galactose residues than the undifferentiated cells.

The sialidase analysis performed for the acidic N-glycan fraction of BM MSC supported the proposed monosaccharide compositions based on sialylated (NeuAc or NeuGc containing) N-glycans in the acidic N-glycan fraction.

Analysis of CB MSC Neutral Glycan Fraction by Exoglycosidases

The results of the analysis by β1,4-galactosidase and 0-glucosaminidase are presented in Table 32. The results suggest that also in CB MSC neutral N-glycans containing non-reducing terminal β1,4-linked galactose residues are abundant, and they suggest the presence of characteristic non-reducing terminal epitopes for most of the observed glycan signals. The analysis of adipocyte differentiated CB MSC are presented in Table 33, allowing comparison of differentiation specific changes in CB MSC, similarly as described above for BM MSC.

The sialidase analysis performed for the acidic N-glycan fraction of CB MSC supported the proposed monosaccharide compositions based on sialylated (NeuAc or NeuGc containing) N-glycans in the acidic N-glycan fraction.

Example 18

Analysis of Acidic Glycans

Results and Discussion

Acidic Glycans Containing Sulphate or Phosphate Ester Groups.

The cell type specific occurrence of glycan signals corresponding to monosaccharide compositions containing sulphate or phosphate ester groups are listed in Table 46.

Acidic Glycans Containing Sialidase-Resistant Sulphate or Phosphate Ester Groups.

The glycan signals in hESC and CB MNC corresponding to monosaccharide compositions containing sulphate or phosphate ester groups (SP) were studied by treating the acidic N-glycan fractions isolated from these cells by *A. ureafaciens* sialidase as described above, and analyzing the sialidase-resistant glycan signals after the treatment as described above. In both these cell types, specific glycan signals had resisted the action of sialidase and were assigned either as native SP-containing glycan signals or desilylated SP-containing glycan signals. Such signals are indicated for hESC in Table 26 as signals containing SP in their monosaccharide compositions (marked with +, ++, or +++ in Table 26), and selected in a separate table (Table 34) for CB MNC.

Fragmentation Mass Spectrometry of Stem Cell N-Glycans.

Figure 30:
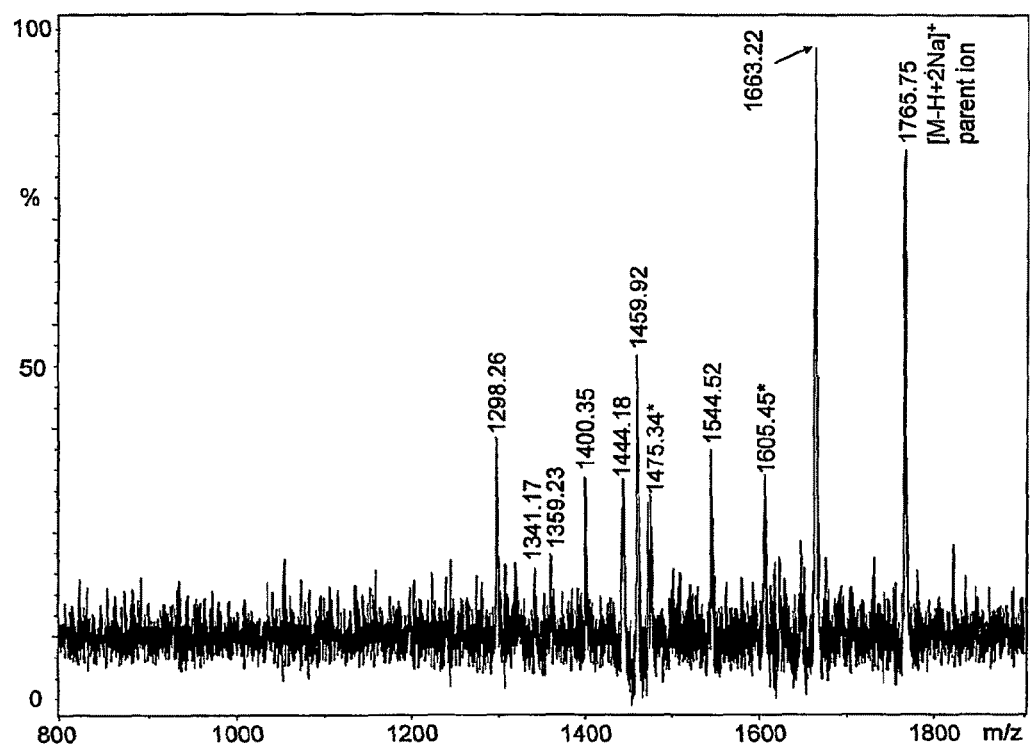
FIG. 30. Fragmentation mass spectrometry of parent ion at m/z 1765.75 corresponding to $[M-H+2Na]^+$ adduct ion of Hex5HexNAc4SP1. Fragment ions corresponding to loss of SPNa (m/z 166322), HexNAcSPNa (m/z 1459.92), or Hex-HexNAcSPNa (m/z 1298.26) are the major fragmentation products. x-axis: mass-to-charge ratio (m/z); y-axis: relative signal intensity (%).

Acidic N-glycans isolated from a bone marrow derived mesenchymal stem cell line were analyzed by MALDI-TOF mass spectrometry in negative ion mode. The spectrum showed the presence of glycan signals containing sulphate or phosphate ester (SP) in their proposed monosaccharide compositions, as described in the Tables of the present invention. One such glycan signal was at m/z 1719, corresponding to the [M-H]$^-$ ion of Hex$_5$HexNAc$_4$SP$_1$. When the same sample was analyzed by MALDI-TOF mass spectrometry in positive ion mode, a corresponding signal was detected at m/z 1765 for the ion [M-H+2Na]$^+$, but not at m/z 1743 for the ion [M+Na]$^+$, suggesting that the molecule contained an acidic group that was ionized and present as sodium salt in positive ion mode mass spectrometry. When the ion at m/z 1765 was subjected to fragmentation, a fragmentation mass spectrum in FIG. 30 was recorded. The fragmentation spectrum showed the major fragment at m/z 1663 corresponding to the [M+Na]$^+$ ion of Hex$_5$HexNAc$_4$ (resulting from elimination of SPNa, sodium salt of sulphate or phosphate ester). However, no fragmentation products were observed at m/z 1452 that would have corresponded to elimination of sialic acid from the parent ion. Taken together, the results of the fragmentation experiment supported the presence of sulphate or phosphate ester in the glycan signal at m/z 1719 in the negative ion mode mass spectrum and at m/z 1765 in the positive ion mode mass spectrum. The observed fragment ions and their proposed monosaccharide compositions were: m/z 1765.75, [M-H+2Na]$^+$/Hex$_5$HexNAc$_4$SP$_1$ (parent ion); m/z 1663.22, [M+Na]$^+$/Hex$_5$HexNAc$_4$; m/z 1605.45, unidentified fragment; m/z 1544.52, [M-H+2Na—H$_2$O]$^+$/Hex$_5$HexNAc$_3$SP$_1$-H$_2$O; m/z 1475.34, unidentified fragment; m/z 1459.92, [M+Na]$^+$/Hex$_5$HexNAc$_3$; m/z 1444.18, [M-H+2Na—H$_2$O]$^+$/Hex$_5$HexNAc$_3$-H$_2$O; m/z 1400.35, [M-H+2Na]$^+$/Hex$_4$HexNAc$_3$SP$_1$; m/z 1539.23, [M-H+2Na]$^+$/Hex$_5$HexNAc$_2$SP$_1$; m/z 1341.17, [M-H+2Na—H$_2$O]$^+$/Hex$_5$HexNAc$_2$SP$_1$-H$_2$O; m/z 1298.26, [M+Na]$^+$/Hex$_4$HexNAc$_3$.

Fragmentation Mass Spectrometry of Mouse Fibroblast Feeder Cell N-Glycans.

Acidic N-glycans isolated from a mouse fibroblast feeder cell line were analyzed by MALDI-TOF mass spectrometry in negative ion mode. The spectrum showed the presence of glycan signals containing an additional hexose in their proposed monosaccharide compositions ($n_{Hex}=n_{HexNAc}+2$), as described in the preceding Examples. One such glycan signal was at m/z 2238, corresponding to the [M-H]$^-$ ion of NeuAc$_1$Hex$_6$HexNAc$_4$dHex$_1$. When the same sample was analyzed by MALDI-TOF mass spectrometry in positive ion mode, a corresponding signal was detected at m/z 2284 for the ion [M-H+2Na]$^+$. When glycans at m/z 2284 were subjected to fragmentation (data not shown), the fragmentation spectrum showed the major fragment at m/z 1971.30 corresponding to the [M+Na]$^+$ ion of Hex$_6$HexNAc$_4$dHex$_1$ (resulting from elimination of NeuAcNa, or sodium salt of an acetylneuraminic acid residue). Other observed fragment ions and their proposed monosaccharide compositions were: m/z 2122.12 corresponding to the [M-H+2Na]$^+$ ion of NeuAc$_1$Hex$_5$HexNAc$_4$dHex$_1$, m/z 1808.96 corresponding to the [M+Na]$^+$ ion of Hex$_5$HexNAc4dHex$_1$, and m/z 1606.23 corresponding to the [M+Na]$^+$ ion of Hex$_5$HexNAc$_3$dHex$_1$.

Example 19

Lectin and Antibody Profiling of Human Embryonic Stem Cells

Experimental Procedures

Cell Samples.

Human embryonic stem cell (hESC) lines FES 22 and FES 30 (Family Federation of Finland) were propagated on mouse feeder cell (mEF) layers as described above.

FITC-Labeled Lectins.

Fluorescein isothiocyanate (FITC) labeled lectins were purchased from several manufacturers: FITC-GNA, -HRA, -MAA, -PWA, -STA and -LTA were from EY Laboratories (USA); FITC-PSA and -UEA and biotin-labelled WFA were from Sigma (USA); and FITC-RCA, -PNA and -SNA were from Vector Laboratories (UK).

Fluorescence Microscopy Labeling Experiments were conducted essentially as described in the preceding Examples. Biotin label was visualized by fluorescein-conjugated streptavidin.

Results

Table 35 shows the tested FITC-labelled lectins, examples of their target saccharide sequences, and the graded lectin binding intensities as described in the Table legend, in fluorescence microscopy of fixed cells grown on microscopy slides. Multiple binding specificities for the used lectins are described in the art and in general the binding of a lectin in the present experiments means that the cells express specific ligands for the lectin on their surface, but does not exclude the presence of also other ligands that are recognized by the lectin.

α-Linked Mannose.

Abundant labelling of mEF by *Pisum sativum* (PSA) lectins suggests that they express mannose, more specifically α-linked mannose residues on their surface glycoconjugates such as N-glycans. The results further suggest that the both hESC lines do not express these ligands at as high concentrations as mEF on their surface.

β-Linked Galactose.

Abundant labelling of hESC by peanut lectin (PNA) and less intense labelling by *Ricinus communis* lectin I (RCA-I) suggests that hESC express β-linked non-reducing terminal galactose residues on their surface glycoconjugates such as N- and/or O-glycans. More specifically, RCA-I binding suggests that the cells contain high amounts of unsubstituted Galβ epitopes on their surface. PNA binding suggests for the presence of unsubstituted Galβ, and the absence of specific binding of PNA to mEF suggests that the binding epitopes for this lectin are less abundant in mEF.

Sialic Acids.

Specific labelling of hESC by both *Maackia amurensis* (MAA) and *Sambucus nigra* (SNA) lectins suggests that the cells express sialic acid residues on their surface glycoconjugates such as N- and/or O-glycans and/or glycolipids. More specifically, the specific MAA binding of hESC suggests that the cells contain high amounts of α2,3-linked sialic acid residues. In contrast, the results suggest that these epitopes are less abundant in mEF. SNA binding in both cell types suggests for the presence of also α2,6-linkages in the sialic acid residues on the cell surface.

Poly-N-Acetyllactosamine Sequences.

Labelling of the cells by pokeweed (PWA) and less intense labelling by *Solanum tuberosum* (STA) lectins suggests that the cells express poly-N-acetyllactosamine sequences on their surface glycoconjugates such as N- and/or O-glycans and/or glycolipids. The results further suggest that cell surface poly-N-acetyllactosamine chains contain both linear and branched sequences.

β-Linked N-Acetylgalactosamine.

Abundant labelling of hESC by *Wisteria floribunda* lectin (WFA) suggests that hESC express β-linked non-reducing terminal N-acetylgalactosamine residues on their surface glycoconjugates such as N- and/or O-glycans. The absence of specific binding of WFA to mEF suggests that the lectin ligand epitopes are less abundant in mEF.

Fucosylation.

Labelling of the cells by *Ulex europaeus* (UEA) and less intense labelling by *Lotus tetragonolobus* (LTA) lectins suggests that the cells express fucose residues on their surface glycoconjugates such as N- and/or O-glycans and/or glycolipids. More specifically, the UEA binding suggests that the cells contain α-linked fucose residues including α1,2-linked fucose residues. LTA binding suggests for the presence of α-linked fucose residues including α1,3- or α1,4-linked fucose residues on the cell surface.

The specific antibody anti-Lex and anti-sLex antibody binding results indicate that the hESC samples contain Galβ4(Fucα3)GlcNAcβ and SAα3Galβ4(Fucα3)GlcNAcβ carbohydrate epitopes on their surface, respectively.

Taken together, in the present experiments the lectins PNA, MAA, and WFA as well as the antibodies anti-Lex and anti-sLex bound specifically to hESC but not to mEF. In contrast, the lectin PSA bound specifically to mEF but not to hESC. This suggests that the glycan epitopes that these reagents recognize have hESC or mEF specific expression patterns. On the other hand, other reagents in the tested reagent panel bound differentially to the two hESC lines FES 22 and FES 30, indicating cell line specific glycosylation of the hESC cell surfaces (Table 35).

Discussion

Venable, A., et al. (2005 BMC Dev. Biol.) have previously described lectin binding profiles of SSEA-4 enriched human embryonic stem cells (hESC) grown on mouse feeder cells. The lectins used were *Lycopersicon esculentum* (LEA, TL), RCA, Concanavalin A (ConA), WFA, PNA, SNA, *Hippeastrum* hybrid (HHA, HHL), *Vicia villosa* (VVA), UEA, *Phaseolus vulgaris* (PHA-L and PHA-E), MAA, LTA (LTL), and *Dolichos biflorus* (DBA) lectins. In FACS and cytochemistry analysis, four lectins were found to have similar binding percentage as SSEA-4 (LEA, RCA, ConA, and WFA) and in addition two lectins also had high binding percentage (PNA and SNA). Two lectins did not bind to hESCs (DBA and LTA). Six lectins were found to partially bind to hESC(PHA-E, VVA, UEA, PHA-L, MAA, and HHA). The authors suggested that the differential lectin binding specificities can be used to distinguish hESC and differentiated hESC types based on carbohydrate presentation.

Venable et al. (2005) discuss some carbohydrate structures that they claim to have high expression on the surface of pluripotent SSEA-4 hESC (corresponding lectins according to Venable et al. in parenthesis): α-Man (ConA, HHA), Glc (ConA), Galβ3GalNAcβ(PNA), non-reducing terminal Gal (RCA), non-reducing terminal β-GalNAc (RCA), GalNAcp4Gal (WFA), GlcNAc (LEA), and SAα6GalNAc (SNA). In addition, Venable et al., discuss some carbohydrate structures that they claim to have expression on surface of a proportion of pluripotent SSEA-4 hESC (corresponding lectins according to Venable et al. in parenthesis): Gal (PHA-L, PHA-E, MAA), GalNAc (VVA) and Fuc (UEA). However, ConA is not especially specific to Glc and MAA has no specificity to Gal residues.

In the present experiments, RCA binding was observed on both hESC line FES 22 and mEF, but not on FES 30. This suggests that RCA binding specificity in hESC varies from cell line to another. The present experiments also show other lectins to be expressed on only one out of the two hESC lines (Table 35), suggesting that there is individual variation in binding of some lectins.

Based on LTA not binding to hESC in their experiments, Venable et al. (2005) suggest that on hESC surface there are no non-modified fucose residues that are α-linked to GlcNAc. However, in the present experiments LTA as well as anti-Lex and anti-sLex monoclonal antibodies were found to bind to the hESC line FES 22. The present antibody binding results indicate that FucαGlcNAc epitopes, specifically Galβ4(Fucα3)GlcNAc sequences, are present on hESC surface.

Venable et al. (2005) describe that PNA recognizes in their hESC samples specifically Galβ3GalNAc structures, wherein the GalNAc residue is β-linked. In the present experiments, PNA was used to recognize carbohydrate structures generally including β-linked galactose residues and without β-linkage requirement for the GalNAc residue.

Venable et al. (2005) describe that SNA recognizes in their hESC samples specifically SAα6GalNAc structures. In the present experiments, SNA was used to recognize α2,6-linked sialic acids in general and its ligands were also found on mEF.

Inhibition of MAA binding by 200 mM lactose in the experiments described by Venable et al. (2005) suggests non-specific binding of MAA with respect to sialic acids. According to the present experiments, MAA can recognize α2,3-linked sialic acid residues on hESC surface and differentiate between hESC and mEF.

Example 20

Lectin and Antibody Profiling of Human Mesenchymal Stem Cells

Experimental Procedures

Cell Samples.

Bone marrow derived human mesenchymal stem cell lines (MSC) were generated and cultured in proliferation medium as described above.

FITC-Labeled Lectins.

Fluorescein isothiocyanate (FITC) labelled lectins were purchased from several manufacturers: FITC-GNA, -HHA, -MAA, -PWA, -STA and -LTA were from EY Laboratories (USA); FITC-PSA and -UEA were from Sigma (USA); and FITC-RCA, -PNA and -SNA were from Vector Laboratories (UK). Lectins were used in dilution of 5 µg/$10^5$ cells in 1% human serum albumin (HSA; FRC Blood Service, Finland) in phosphate buffered saline (PBS).

Flow Cytometry.

Flow cytometric analysis of lectin binding was used to study the cell surface carbohydrate expression of MSC. 90% confluent MSC layers on passages 9-11 were washed with PBS and harvested into single cell suspensions by 0.25% trypsin-1 mM EDTA solution (Gibco). Detached cells were centrifuged at 600 g for five minutes at room temperature. Cell pellet was washed twice with 1% HSA-PBS, centrifuged at 600 g and resuspended in 1% HSA-PBS. Cells were placed in conical tubes in aliquots of 70000-83000 cells each. Cell aliquots were incubated with one of the FITC labelled lectin for 20 minutes at room temperature. After incubation cells were washed with 1% HSA-PBS, centrifuged and resuspended in 1% HSA-PBS. Untreated cells were used as controls. Lectin binding was detected by flow cytometry (FACSCalibur, Becton Dickinson). Data analysis was made with Windows Multi Document Interface for Flow Cytometry (WinMDI 2.8). Two independent experiments were carried out.

Fluorescence Microscopy Labeling Experiments were conducted as described in the preceding Examples.

Results and Discussion

Table 36 shows the tested FITC-labelled lectins, examples of their target saccharide sequences, and the amount of cells showing positive lectin binding (%) in FACS analysis after mild trypsin treatment. Table 37 shows the tested FITC-labelled lectins, examples of their target saccharide sequences, and the graded lectin binding intensities as described in the Table legend, in fluorescence microscopy of fixed cells grown on microscopy slides. Binding specificities of the used lectins are described in the art and in general the binding of a lectin in the present experiments means that the cells express specific ligands for the lectin on their surface. The examples of some of the specificities discussed below and those marked in the Tables are therefore non-exclusive in nature.

α-Linked Mannose.

Abundant labelling of the cells by both *Hippeastrum hybrid* (RHA) and *Pisum sativum* (PSA) lectins suggests that they express mannose, more specifically α-linked mannose residues on their surface glycoconjugates such as N-glycans. Possible α-mannose linkages include α1→2, α1→3, and α1→6. The lower binding of *Galanthus nivalis* (GNA) lectin suggests that some α-mannose linkages on the cell surface are more prevalent than others.

β-Linked Galactose.

Abundant labelling of the cells by *Ricinus communis* lectin I (RCA-I) and less intense labelling by peanut lectin (PNA) suggests that the cells express β-linked non-reducing terminal galactose residues on their surface glycoconjugates such as N- and/or O-glycans. More specifically, the intense RCA-I binding suggests that the cells contain high amounts of unsubstituted Galβ epitopes on their surface. The binding of RCA-I was increased by sialidase treatment of the cells before lectin binding, indicating that the ligands of RCA-I on MSC were originally partly covered by sialic acid residues. PNA binding suggests for the presence of another type of unsubstituted Galβ epitopes such as Core 1 O-glycan epitopes on the cell surface. The binding of PNA was also increased by sialidase treatment of the cells before lectin binding, indicating that the ligands of PNA on MSC were originally mostly covered by sialic acid residues. These results suggest that both RCA-I and PNA can be used to assess the amount of their specific ligands on the cell surface of BM MSC, and with or without conjunction with sialidase treatment to assess the sialylation level of their specific epitopes.

Sialic acids.

Abundant labelling of the cells by *Maackia amurensis* (MAA) and less intense labelling by *Sambucus nigra* (SNA) lectins suggests that the cells express sialic acid residues on their surface glycoconjugates such as N- and/or O-glycans and/or glycolipids. More specifically, the intense MAA binding suggests that the cells contain high amounts of α2,3-linked sialic acid residues on their surface. SNA binding suggests for the presence of also α2,6-linked sialic acid residues on the cell surface, however in lower amounts than α2,3-linked sialic acids. Both of these lectin binding activities could be reduced by sialidase treatment, indicating that the specificities of the lectins in BM MSC are mostly targeted to sialic acids.

Poly-N-Acetyllactosamine Sequences.

Labelling of the cells by *Solanum tuberosum* (STA) and less intense labelling by pokeweed (PWA) lectins suggests that the cells express poly-N-acetyllactosamine sequences on their surface glycoconjugates such as N- and/or O-glycans and/or glycolipids. Higher intensity labelling with STA than with PWA suggests that most of the cell surface poly-N-acetyllactosamine sequences are linear and not branched or substituted chains.

Fucosylation.

Labelling of the cells by *Ulex europaeus* (UEA) and less intense labelling by *Lotus tetragonolobus* (LTA) lectins suggests that the cells express ficose residues on their surface glycoconjugates such as N- and/or O-glycans and/or glycolipids. More specifically, the UEA binding suggests that the cells contain α-linked fucose residues, including α1,2-linked fucose residues, on their surface. LTA binding suggests for the presence of also α-linked fucose residues, including α1,3-linked fucose residues on the cell surface, however in lower amounts than UEA ligand fucose residues.

Mannose-Binding Lectin Labelling.

Low labelling intensity was also detected with human serum mannose-binding lectin (MBL) coupled to fluorescein label, suggesting that ligands for this innate immunity system component may be expressed on in vitro cultured BM MSC cell surface.

Binding of a NeuGc polymeric probe (Lectinity Ltd., Russia) to non-fixed hESC indicates the presence of NeuGc-specific lectin on the cell surfaces. In contrast, polymeric NeuAc probe did not bind to the cells with same intensity in the present experiments.

The binding of the specific antibodies to hESC indicates the presence of Lex and sialyl-Lewis x epitopes on their surfaces, and binding of NeuGc-specific antibody to hESC indicates the presence of NeuGc epitopes on their surfaces.

Example 21

Lectin and Antibody Profiling of Human Cord Blood Cell Populations

Results and Discussion

Figure 31:
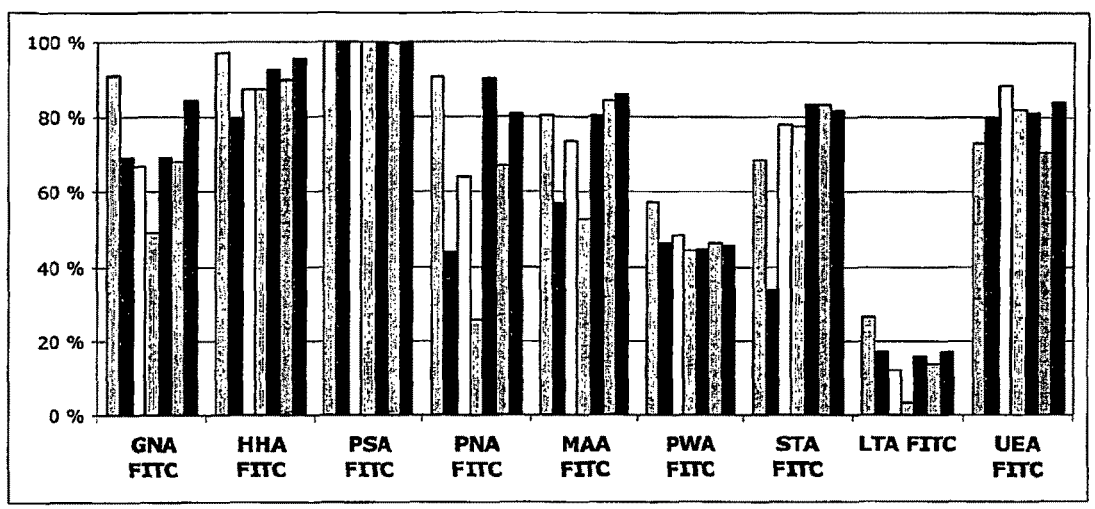
FIG. 31. FACS analysis of seven cord blood mononuclear cell samples (parallel columns) by FITC-labelled lectins. The percentages refer to proportion of cells binding to lectin. For abbreviations of FITC-labelled lectins see text.

FIG. 31 shows the results of FACS analysis of FITC-labelled lectin binding to seven individual cord blood mononuclear cell (CB MNC) preparations (experiments performed as described above). Strong binding was observed in all samples by GNA, HHA, PSA, MAA, STA, and UEA FITC-labelled lectins, indicating the presence of their specific ligand structures on the CB MNC cell surfaces. Also mediocre binding (PWA), variable binding between CB samples (PNA), and low binding (LTA) was observed, indicating that the ligands for these lectins are either variable or more rare on the CB MNC cell surfaces as the lectins above.

Example 22

Analysis of Total N-glycomes of Human Stem Cells and Cell Populations

Experimental Procedures

Cell and glycan samples were prepared as described in the preceding Examples.

Relative proportions of neutral and acidic N-glycan fractions were studied by desialylating isolated acidic glycan fraction with *A. ureafaciens* sialidase as described in the preceding Examples and then combining the desilylated glycans with neutral glycans isolated from the same sample. Then the combined glycan fractions were analyzed by positive ion mode MALDI-TOF mass spectrometry as described in the preceding Examples. The proportion of sialylated N-glycans of the combined N-glycans was calculated by calculating the percentual decrease in the relative intensity of neutral N-glycans in the combined N-glycan fraction compared to the original neutral N-glycan fraction, according to the equation:

$$\text{proportion} = \frac{I^{neutral} - I^{combined}}{I^{neutral}} \times 100\%,$$

wherein $I^{neutral}$ and $I^{combined}$ correspond to the sum of relative intensities of the five high-mannose type N-glycan $[M+Na]^+$ ion signals at m/z 1257, 1419, 1581, 1743, and 1905 in the neutral and combined N-glycan fractions, respectively.

Results and Discussion

The relative proportions of acidic N-glycan fractions in studied stem cell types were as follows: in human embryonic stem cells (hESC) approximately 35% (proportion of sialylated and neutral N-glycans is approximately 1:2), in human bone marrow derived mesenchymal stem cells (BM MSC) approximately 19% (proportion of sialylated and neutral N-glycans is approximately 1:4), in osteoblast-differentiated BM MSC approximately 28% (proportion of sialylated and neutral N-glycans is approximately 1:3), and in human cord blood (CB) CD133+ cells approximately 38% (proportion of sialylated and neutral N-glycans is approximately 2:3).

In conclusion, BM MSC differ from hESC and CB CD133+ cells in that they contain significantly lower amounts of sialylated N-glycans compared to neutral N-glycans. However, after osteoblast differentiation of the BM MSC the proportion of sialylated N-glycans increases.

Example 23

Analysis of the Human Embryonic Stem Cell N-glycome

Experimental Procedures

Human Embryonic Stem Cell Lines (hESC).

Four Finnish hESC lines, FES 21, FES 22, FES 29, and FES 30, were used in the present study. Generation of the lines has been described (Skotaan et al., 2005, and M.M., C.O., T.T., and T.O., manuscript submitted for publication). Two of the analysed cell lines in the present work were initially derived and cultured on mouse embryonic fibroblast feeders, and two on human foreskin fibroblast feeder cells. For the mass spectrometry studies all of the lines were transferred on HFF feeder cells treated with mitomycin-C (1 μg/ml, Sigma-Aldrich, USA) and cultured in serum-free medium (Knockout™ D-MEM; Gibco® Cell culture systems, Invitrogen, UK) supplemented with 2 mM L-Glutamin/Penicillin streptomycin (Sigma-Aldrich), 20% Knockout Serum Replacement (Gibco), 1× non-essential amino acids (Gibco), 0.1 mM β-mercaptoethanol (Gibco), 1×ITS (Sigma-Aldrich) and 4 ng/ml bFGF (Sigma/Invitrogen). To induce the formation of embryoid bodies (EB) the hESC colonies were first allowed to grow for 10-14 days whereafter the colonies were cut in small pieces and transferred on non-adherent Petri dishes to form suspension cultures. The formed EBs were cultured in suspension for the next 10 days in standard culture medium (see above) without bFGF. For further differentiation (into stage 3 differentiated cells) EBs were transferred onto gelatin-coated (Sigma-Aldrich) adherent culture dishes in media consisting of DMEM/F12 mixture (Gibco) supplemented with ITS, Fibronectin (Sigma), L-glutamine and antibiotics. The attached cells were cultured for 10 days whereafter they were harvested. For glycan analysis, the cells were collected mechanically, washed, and stored frozen until the analysis. In FACS analyses 70-90% of cells from mechanically isolated hESC colonies were typically Tra 1-60 and Tra 1-81 positive (not shown). Cells differentiated into embryoid bodies (EB) and further differentiated cells grown out of the EB as monolayers (stage 3 differentiated) were used for comparison against hESC. The differentiation protocol favors the development of neuroepithelial cells while not directing the differentiation into distinct terminally differentiated cell types (Okabe et al., 1996). Stage 3 cultures consisted of a heterogenous population of cells dominated by fibroblastoid and neuronal morphologies.

Glycan Isolation.

Asparagine-linked glycans were detached from cellular glycoproteins by *F. meningosepticum* N-glycosidase F digestion (Calbiochem, USA) essentially as described (Nyman et al., 1998). The detached glycans were divided into sialylated and non-sialylated fractions based on the negative charge of sialic acid residues. Cellular contaminations were removed by precipitating the glycans with 80-90% (v/v) aqueous acetone at −20° C. and extracting them with 60% (v/v) ice-cold methanol essentially as described previously (Verostek et al., 2000). The glycans were then passed in water through $C_{18}$ silica resin (BondElut, Varian, USA) and adsorbed to porous graphitized carbon (Carbograph, Alltech, USA) based on previous method (Davies et al., 1993). The carbon column was washed with water, then the neutral glycans were eluted with 25% acetonitrile in water (v/v) and the sialylated glycans with 0.05% (v/v) trifluoroacetic acid in 25% acetonitrile in water (v/v). Both glycan fractions were additionally passed in water through strong cation-exchange resin (Bio-Rad, USA) and $C_{18}$ silica resin (ZipTip, Millipore, USA). The sialylated glycans were further purified by adsorbing them to microcrystalline cellulose in n-butanol:ethanol:water (10:1:2, v/v), washing with the same solvent, and eluting by 50% ethanol: water (v/v). All the above steps were performed on miniaturized chromatography columns and small elution and handling volumes were used. The glycan analysis method was validated by subjecting human cell samples to analysis by five different persons. The results were highly comparable, especially by the terms of detection of individual glycan signals and their relative signal intensities, showing that the reliability of the present methods is suitable for comparing analysis results from different cell types.

Mass Spectrometry and Data Analysis.

MALDI-TOF mass spectrometry was performed with a Bruker Ultraflex TOF/TOF instrument (Bruker, Germany) essentially as described (Saarinen et al., 1999). Relative molar abundancies of both neutral and sialylated glycan components can be accurately assigned based on their relative signal intensities in the mass spectra (Naven and I-Harvey, 1996; Papac et al., 1996; Saarinen et al., 1999; Harvey, 1993). Each step of the mass spectrometric analysis methods were controlled for their reproducibility by mixtures of synthetic glycans or glycan mixtures extracted from human cells. The mass spectrometric raw data was transformed into the present glycan profiles by carefully removing the effect of isotopic pattern overlapping, multiple alkali metal adduct signals, products of elimination of water from the reducing oligosaccharides, and other interfering mass spectrometric signals not arising from the original glycans in the sample. The resulting glycan signals in the presented glycan profiles were normalized to 100% to allow comparison between samples. Quantitative difference between two glycan profiles (%) was calculated according to the equation:

$$\text{difference} = \frac{1}{2}\sum_{i=1}^{n}|p_{i,a} - p_{i,b}|, \quad (2)$$

wherein p is the relative abundance (%) of glycan signal i in profile a or b, and n is the total number of glycan signals.

Glycosidase Analysis.

The neutral N-glycan fraction was subjected to digestion with Jack bean α-mannosidase (*Canavalia ensiformis*; Sigma, USA) essentially as described (Saarinen et al., 1999). The specificity of the enzyme was controlled with glycans isolated from human tissues as well as purified oligosaccharides.

NMR Methods.

For NMR analysis, larger amounts of hESC were grown on mouse feeder cell (MEF) layers. The purity of the collected hESC sample (about 70%), was lower than in the mass spectrometry samples grown on HFF. However, the same $H_{5-9}N_2$ glycans were the major neutral N-glycan signals in both MEF and hESC. The isolated glycans were further purified for the analysis by gel filtration high-pressure liquid chromatography in a column of Superdex peptide HR 10/30 (Amersham), with water (neutral glycans) or 50 mM $NH_4HCO_3$ (sialylated glycans) as the eluant at a flow rate of 1 ml/min. The eluant was monitored at 214 nm, and oligosaccharides were quantified against external standards. The amount of N-glycans in NMR analysis was below five nanomoles.

Statistical Procedures.

Glycan score distributions of all three differentiation stages (hESC, EB, and st.3) were analyzed by the Kruskal-Wallis test. Parise comparisons were performed by the 2-tailed Student's t-test with Welch's approximation and 2-tailed Mann-Whitney U test. A p value less than 0.05 was considered significant.

Lectin Staining.

Fluorescein-labeled lectins were from EY Laboratories (USA) and the stainings were performed essentially after manufacturer's instructions. The specificity of the staining was controlled in parallel experiments by inhibiting lectin binding with specific oligo- and monosaccharides.

Results

Mass Spectrometric Profiling of the hESC N-glycome

Figure 32:
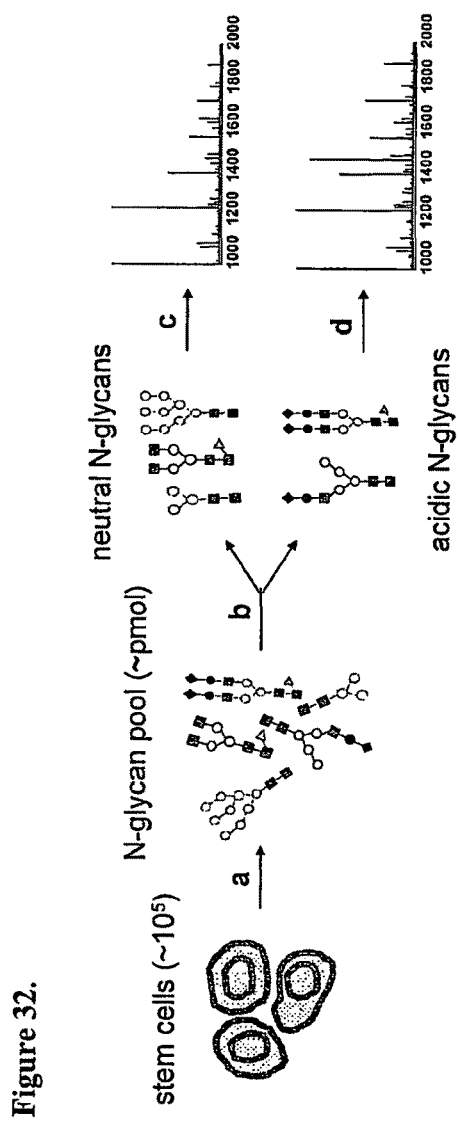
FIG. 32. Schematic representation of the analysis method of the present Example. a N-glycans were detached from stem cell glycoproteins by N-glycosidase enzyme digestion. b The total N-glycan pool was purified with microscale solid-phase extraction and divided into neutral and acidic N-glycan fractions. c and d The N-glycan fractions were analyzed by MALDI-TOF mass spectrometry either in positive ion mode as alkali metal adduct ions (c) or in negative ion mode as deprotonated ions (d).

In order to generate glycan profiles of hESC, embryonic bodies, and further differentiated cells, a MALDI-TOF mass spectrometry based analysis was performed as outlined in FIG. 32. We focused on the most common type of protein post-translational modifications, the asparagine-linked glycans (N-glycans), which were enzymatically released from cellular glycoproteins. During glycan isolation and purification, the total N-glycan pool was separated by an ion-exchange step into neutral N-glycans and sialylated N-glycans. These two glycan fractions were then analyzed separately by mass spectrometric profiling (FIG. 33), which yielded a global view of the N-glycan repertoire of the samples. The relative abundances of the observed glycan signals were determined based on their relative signal intensities (Naven and Harvey, 1996; Papac et al., 1996; Saarinen et al., 1999), which allowed quantitative comparison of glycome differences between samples. Over one hundred N-glycan signals were detected from each cell type.

Figure 33:
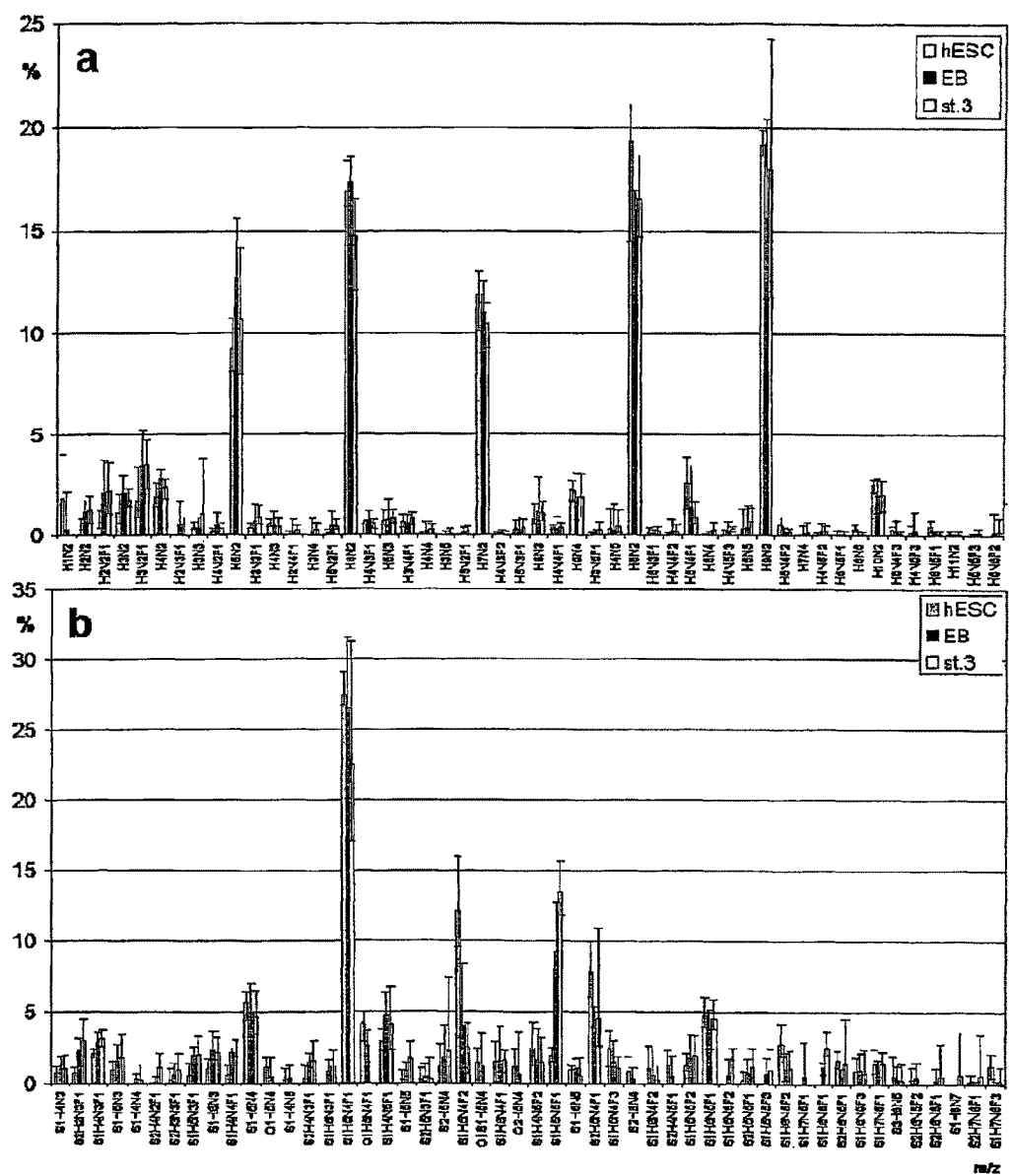
FIG. 33. Mass spectrometric profiling of human embryonic stem cell and differentiated cell N-glycans. a Neutral N-glycans and b 50 most abundant acidic N-glycans of the four hESC lines (white columns), embryoid bodies derived from FES 29 and FES 30 hESC lines EB, light columns), and stage 3 differentiated cells derived from FES 29 (st3, black columns). The columns indicate the mean abundance of each glycan signal (% of the total detected glycan signals). Error bars indicate the range of detected signal intensities. Proposed monosaccharide compositions are indicated on the x-axis. H: hexose, N: N-acetylhexosamine, F: deoxyhexose, S: N-acetylneuraminic acid, G: N-glycolylneuraminic acid, P: sulphate/phosphate ester.

The proposed monosaccharide compositions corresponding to the detected masses of each individual signal in FIG. 33 is indicated by letter code. However, it is important to realize that many of the mass spectrometric signals in the present analyses include multiple isomeric structures and the 100 most abundant signals very likely represent hundreds of different molecules. For example, the common hexoses (H) occurring in human N-glycans include D-mannose, D-galactose, and D-glucose (which all have a residue mass of 162.05 Da), and common N-acetylhexosamines (N) include both N-acetyl-D-glucosamine and N-acetyl-D-galactosamine (203.08 Da); deoxyhexoses (F) are typically L-fucose residues (146.06 Da).

In most of the previous glycomic studies of other mammalian tissues the isolated glycans have been derivatized (permethylated) prior to mass spectrometric profiling (Sutton-Smith et al., 2002; Dell and Morris, 2001; Consortium for Functional Glycomics, http://www.functionalglycomics.org) or chromatographic separation (Callewaert et al., 2004). However, in the present study we chose to directly analyze picomolar quantities of unmodified glycans and increased sensitivity was attained by omitting the derivatization and the subsequent additional purification steps. Further, instead of studying the glycan signals one at a time, we were able to simultaneously study all the glycans present in the unmodified glycomes by nuclear magnetic resonance spectroscopy (NM) and specific glycosidase enzymes. The present data demonstrate that mass spectrometric profiling can be used in the quantitative analysis of total glycomes, especially to pinpoint the major glycosylation differences between related samples.

Overview of the hESC N-Glycome: Neutral N-Glycans

Neutral N-glycans comprised approximately two thirds of the combined neutral and sialylated N-glycan pools. The 50 most abundant neutral N-glycan signals of the hESC lines are presented in FIG. 33a (grey columns). The similarity of the profiles, which is indicated by the minor variation in the glycan signals, suggest that the four cell lines closely resemble each other. For example, 15 of the 20 most abundant glycan signals were the same in every hESC line. These 15 neutral N-glycan signals typical for the hESC N-glycome are listed in Table 38. The five most abundant signals comprised 76% of the neutral N-glycans of hESC and dominated the profile.

Sialylated N-Glycans

Figure 35:
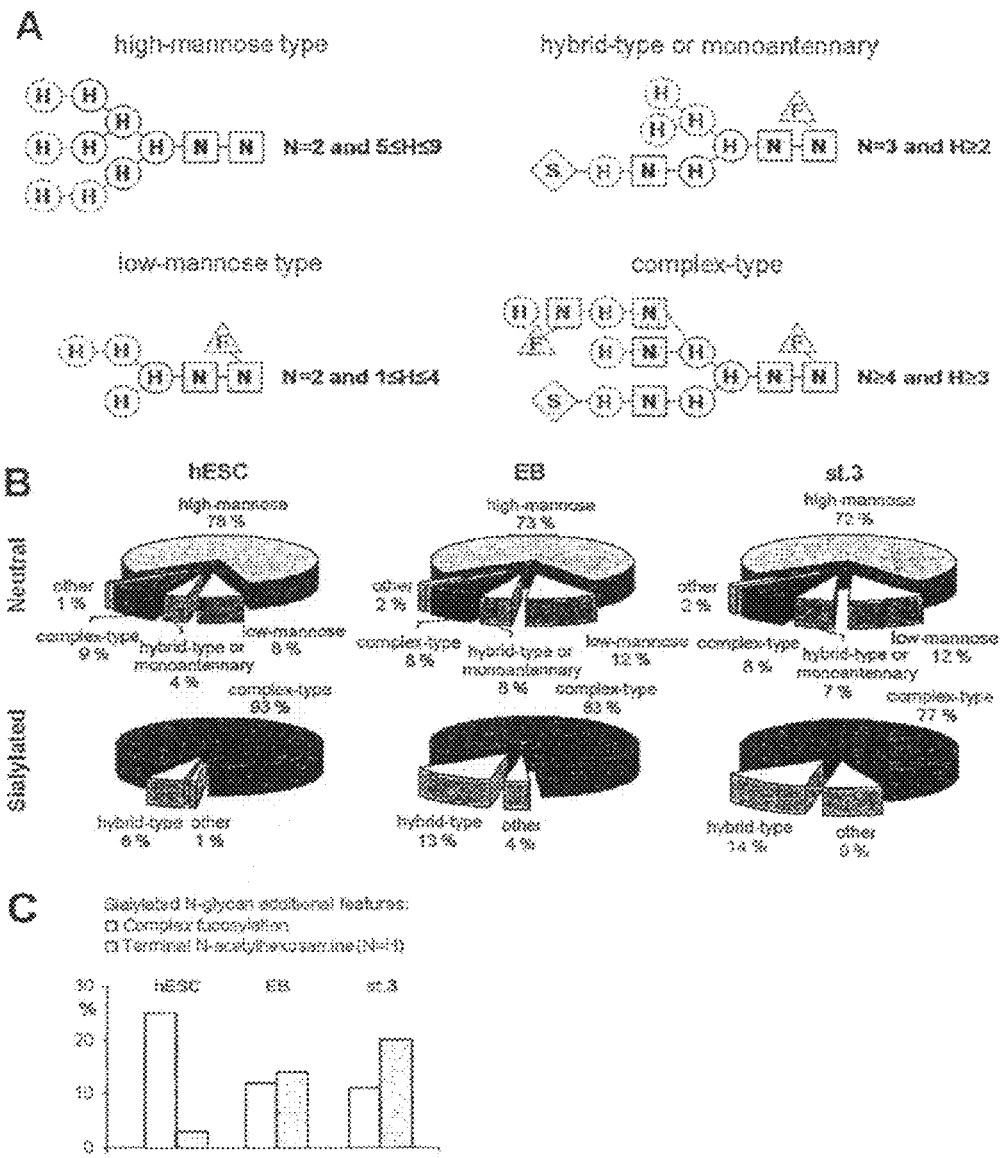
FIG. 35. a Classification rules for major human N-glycan biosynthetic groups. The minimal structures of each biosynthetic group (solid lines) form the basis for the classification rules. Variation of the basic structures by additional monosaccharide units (dashed lines) generates complexity to stem cell glycosylation as revealed in the present study. H: hexose, N: N-acetylhexosamine, F: deoxyhexose, S: N-acetylneuraminic acid. b Pie diagrams showing the classification of human embryonic stem cells (WESC), embryoid bodies (EB), and stage 3 differentiated cells (st3) data as described in the Examples. c Proportions of the two major identified differentiation stage associated glycan features within the complex-type sialylated N-glycans according to Table 41.

All N-glycan signals in the sialylated N-glycan fraction (FIG. 33b, grey columns) contain sialic acid residues (S: N-acetyl-D-neuraminic acid, or G: N-glycolyl-D-neuraminic acid). The 50 most abundant sialylated N-glycans in the four hESC lines showed more variation between individual cell lines than the neutral N-glycans. However, the four cell lines again resembled each other. The group of five most abundant sialylated N-glycan signals was the same in every cell line: $S_1H_5N_4F_1$, $S_1H_5N_4F_2$, $S_2H_5N_4F_1$, $S_1H_5N_4$, and $S_1H_6N_5F_1$ (for abbreviations see FIG. 33). The 15 sialylated N-glycan signals common to all the hESC lines are listed in Table 39. The majority (61%, in eight signals) of the sialylated glycan signals contained the $H_5N_4$ core composition and differed only by variable amounts of sialic acid (S or G) and deoxyhexose (F) residues. Similarly, another common core structure was $H_6N_5$ (12%, in seven signals). This highlights the biosynthetic mechanisms leading to the total spectrum of N-glycan structures in cells: N-glycans typically consist of common core structures that are modified by the addition of variable epitopes (FIG. 35).

Importantly, we were able to detect N-glycans containing N-glycolylneuraminic acid (G), for example glycans $G_1H_5N_4$, $G_1S_1H_5N_4$, and $G_2H_5N_4$, in the hESC samples. N-glycolylneuraminic acid has previously been reported in hESC as an antigen transferred from culture media containing animal-derived materials (Martin et al., 2005). Accordingly, the serum replacement medium used in the present experiments contained bovine serum proteins.

Variation Between Individual Cell Lines

Although the four hESC lines shared the same overall N-glycan profile, there was cell line specific variation within the profiles. Individual glycan signals unique to each cell line were detected, indicating that every cell line was slightly different from each other with respect to the approximately one hundred most abundant N-glycan structures they synthesized.

In general, the 30 most common N-glycan signals in each hESC line accounted for circa 85% of the total detected N-glycans, and represent a useful approximation of the hESC N-glycome (Tables 38 and 39). In other words, more than five out of six glycoprotein molecules isolated from any of the present hESC lines would carry such N-glycan structures.

Transformation of the N-Glycome During hESC Differentiation

A major goal of the present study was to identify glycan structures that would be specific to either stem cells or differentiated cells, and could therefore serve as differentiation stage markers. In order to determine whether the hESC N-glycome undergoes changes during differentiation, the N-glycan profiles obtained from hESC, EB, and stage 3 differentiated cells were compared (FIG. 33). The profiles of the differentiated cell types (EB and st.3) were significantly different from the profiles of undifferentiated hESC, indicated by non-overlapping distribution bars in many glycan signals. Further, there were many signals present in both hESC and EB that were not detected in stage 3 differentiated cells. Overall, 10% of the glycan signals present in hESC had disappeared in stage 3 differentiated cells. Simultaneously numerous new signals appeared in EB and stage 3 differentiated cells. Their proportion in EB and stage 3 differentiated cells was 14% and 16%, respectively. The glycan signals that were characteristic for hESC were typically decreased in the EB and had further decreased or totally disappeared in stage 3 differentiated cells. However, among the most common one hundred glycan signals there were no hESC signals that would not have been expressed in EB, suggesting that the EB N-glycome is an intermediate between hESC and stage 3 differentiated cells.

Taken together, differentiation induced the appearance of new N-glycan types while earlier glycan types disappeared. Further, we found that the major hESC-specific N-glycosylation features were not expressed as discrete glycan signals, but instead as glycan signal groups that were characterized by a specific monosaccharide composition feature (see below). In other words, differentiation of hESC into EB induced the disappearance of not only one but multiple glycan signals with hESC-associated features, and simultaneously also the appearance of glycan signal groups with other features associated with the differentiated cell types.

The N-glycan profiles of the differentiated cells were also quantitatively different from the undifferentiated hESC profiles. A practical way of quantifying the differences between individual glycan profiles is to calculate the sum of the signal intensity differences between two cell profiles (see Methods). According to this method, the EB neutral and sialylated N-glycan profiles had undergone a quantitative change of 14% and 29% from the hESC profiles, respectively. Similarly, the stage 3 differentiated cell neutral and sialylated N-glycan profiles had changed by 15% and 43% from the hESC profiles, respectively. This indicates that upon differentiation of hESC into stage 3 differentiated cells, nearly half of the total sialylated N-glycans present in the cells were transformed into different molecular structures, while significantly smaller proportion of the neutral N-glycan molecules were changed during the differentiation process. Taking into account that the proportion of sialylated to neutral N-glycans in hESC was approximately 1:2, the total N-glycome change was approximately 25% during the transition from hESC to stage 3 differentiated cells. Again, the N-glycan profile of EB appeared to lie between hESC and stage 3 differentiated cells.

The data indicated that the hESC N-glycome consisted of two discrete parts regarding propensity to change during hESC differentiation—a constant part of circa 75% and a changing part of circa 25%. In order to characterize the associated N-glycan structures, and to identify the potential biological roles of the constant and changing parts of the N-glycome, we performed structural analyses of the isolated hESC N-glycan samples.

Structural Analyses of the Major hESC N-Glycans: Preliminary Structure Assignment Based on Monosaccharide Compositions Human N-glycans can be divided into the major biosynthetic groups of high-mannose type, hybrid-type, and complex-type N-glycans. To determine the presence of these N-glycan groups in hESC and their progeny, assignment of probable structures matching the monosaccharide compositions of each individual signal was performed utilizing the established pathways of human N-glycan biosynthesis (Kornfeld and Kornfeld, 1985; Schachter, 1991). Here, the detected N-glycan signals were classified into four N-glycan groups according to the number of N and H residues in the proposed compositions as shown in FIG. 35a: 1) high-mannose type and 2) low-mannose type N-glycans, which are both characterized by two N residues (N=2), 3) hybrid-type or monoantennary N-glycans, which are classified by three N residues (N=3), and 4) complex-type N-glycans, which are characterized by four or more N residues (N≥4) in their proposed monosaccharide compositions. This is an approximation: for example, in addition to complex-type N-glycans also hybrid-type and monoantennary N-glycans may contain more than three N residues.

The data was analyzed quantitatively by calculating the percentage of glycan signals in the total N-glycome belonging to each structure group (Table 41, rows A-E and J-L; FIG. 35b). The quantitative changes in the structural groups reflect the relative activities of different biosynthetic pathways in each cell type. For example, the proportion of hybrid-type or monoantennary N-glycans was increased when hESC differentiated into EB. In general, the relative proportions of most glycan structure classes remained approximately constant through the hESC differentiation process, which indicated that both hESC and the differentiated cell types were capable of equally sophisticated N-glycosylation. The high proportion of N-glycans classified as low-mannose N-glycans in all the studied cell types was somewhat surprising in the light of earlier published studies of human N-glycosylation. However, previous studies had not explored the total N-glycan profiles of living cells. We have detected significant amounts of low-mannose N-glycans also in other human cells and tissues, and they are not specific to hESC (T.S., A.H., M.B., A.O., J.H., J.N, J. S. et al., unpublished results).

Verification of Structure Assignments by Enzymatic Degradation and Nuclear Magnetic Resonance Spectroscopy In order to verify the validity of the glycan structure assignments made based on the detected mass and the probable monosaccharide compositions we performed enzymatic degradation and proton nuclear magnetic resonance spectroscopic analyses ($^1$H-NMR) of selected neutral and sialylated N-glycans.

For the validation of neutral N-glycans we chose glycans with 5-9 hexose (H) and two N-acetylhexosamine (N) residues in their monosaccharide compositions ($H_5N_2$, $H_6N_2$, $H_7N_2$, $H_8N_2$, and $H_9N_2$) which were the most abundant N-glycans in all studied cell types (FIG. 33a). The monosaccharide compositions suggested (FIG. 35a) that these glycans were high-mannose type N-glycans (Kornfeld and Kornfeld, 1985). To test this hypothesis, neutral N-glycans from stem cell and differentiated cell samples were treated with α-mannosidase, and analyzed both before and after the enzymatic treatment (data not shown). The glycans in question were degraded and the corresponding signals disappeared from the mass spectra, indicating that they contained α-linked mannose residues.

The neutral N-glycan fraction was further analyzed by nanoscale proton nuclear magnetic resonance spectroscopic analysis ($^1$H-NMR). In the obtained $^1$H-NMR spectrum of the hESC neutral N-glycans signals consistent with high-mannose type N-glycans were detected, supporting the conclusion that they were the major glycan components in the sample.

Both α-mannosidase and NMR experiments indicated that the $H_{5-9}N_2$ glycan signals corresponded to high-mannose type N-glycans. From the data in FIG. 33a it could be estimated that they constituted half of all the detected glycoprotein N-glycans in hESC. This is in accordance with the established role of high-mannose type N-glycans in human cells (Helenius and Aebi, 2001, 2004). The presence of such constitutively expressed N-glycans also explained why the neutral N-glycan profiles did not change to the same extent as the sialylated N-glycan profiles during differentiation.

For the validation of structure assignments among the sialylated N-glycans we noted that the majority of the sialylated N-glycan signals isolated from hESC were characterized by the N≥4 monosaccharide composition (FIG. 33a), which suggested that they were complex-type N-glycans (FIG. 35). In the $^1$H-NMR analysis N-glycan backbone signals consistent with biantennary complex-type N-glycans were the major detected signals, in line with the assignment made based on the experimental monosaccharide compositions. The present results indicated that the classification of the glycan signals within the total N-glycome data could be used to construct an approximation of the whole N-glycome. However, such classification should not be applied to the analysis of single N-glycan signals.

Differentiation Stage Associated Structural Glycosylation Features

The glycan signal classification described above indicated changes in the core sequences of N-glycans. The present data also suggested that there were differences in variable epitopes added to the N-glycan core structures i.e. glycan features present in many individual glycan signals. In order to quantify such glycan structural features, the N-glycome data were further classified into glycan signal groups that share similar features in their proposed monosaccharide compositions (Table 41, rows F-I and M-P). As a result, the majority of the differentiation-associated glycan signals in the EB and stage 3 differentiated cell samples fell into different groups than the hESC specific glycans. Glycan signals with complex fucosylation (Table 41, row N) were associated with undifferentiated hESC, whereas glycan signals with potential terminal N-acetylhexosamine (Table 41, rows H and P) were associated with the differentiated cells.

Complex Fucosylation of N-Glycans is Characteristic of hESC

Differentiation stage associated changes in the sialylated N-glycan profile were more drastic than in the neutral N-glycan fraction and the group of five most abundant sialylated N-glycan signals was different at every differentiation stage (FIG. 33b). In particular, there was a significant differentiation-associated decrease in the relative amounts of glycans $S_1H_5N_4F_2$ and $S_1H_5N_4F_3$ as well as other glycan signals that contained at least two deoxyhexose residues (F≥2) in their proposed monosaccharide compositions. In contrast, glycan signals such as $S_2H_5N_4$ that contained no F were increased in the differentiated cell types. The results suggested that sialylated N-glycans in undifferentiated hESC were subject to more complex fucosylation than in the differentiated cell types (Table 41, row N).

The most common fucosylation type in human N-glycans is α1,6-fucosylation of the N-glycan core structure. The NMR analysis of the sialylated N-glycan fraction of hESC also revealed α1,6-fucosylation of the N-glycan core as the most abundant type of fucosylation. In the N-glycans containing more than one fucose residue, there must have been other fucose linkages in addition to the α1,6-linkage (Staudacher et al., 1999). The F≥2 structural feature decreased as the cells differentiated, indicating that complex fucosylation was characteristic of undifferentiated hESC.

N-Glycans with Terminal N-Acetylhexosamine Residues Become More Common with Differentiation A group of N-glycan signals which increased during differentiation contained equal amounts of N-acetylhexosamine and hexose residues (N=H) in their monosaccharide composition, e.g. $S_1H_5N_5F_1$. This was consistent with structures containing non-reducing terminal N-acetylhexosamine residues. Usually N-glycan core structures contain more hexose than N-acetylhexosamine residues. However, if complex-type N-glycans contain terminal N-acetylhexosamine residues that are not capped by hexoses, their monosaccharide compositions change to either the N=H or the N>H (FIG. 35a). EB and stage 3 differentiated cells showed increased amounts of potential terminal N-acetylhexosamine structures, of which the N=H structural feature was increased in both neutral and sialylated N-glycan pools (Table 41, rows I and P), whereas the N>H structural feature was elevated in the neutral N-glycan pool, but decreased in the sialylated N-glycan pool during differentiation (Table 41, rows H and O).

Glycome Profiling can Identify the Differentiation Stage of hESC

The analysis of glycome profiles indicated that the studied hESC lines and differentiated cells had differentiation stage specific N-glycan features. However, the data also demonstrated that N-glycan profiles of the individual hESC lines were different from each other and in particular the hESC line FES 22 was different from the other three stem cell lines (Table 41, rows C and I). To test whether the obtained N-glycan profiles could be used to generate an algorithm that would discriminate between hESC and differentiated cells even taking into account cell line specific variation, an analysis was performed using the data of Table 41. The hESC line FES 29 and embryoid bodies derived from it (EB 29) were selected as the training group for the calculation. The algorithm glycan score (Equation 1) was defined as the sum of those structural features that were at least two times greater in FES 29 than in EB 29 (row N in Table 41), from which the sum of the structural feature percentages that were at least two times greater in EB 29 than in FES 29 was subtracted (rows C, I, J, and P in Table 41):

$$\text{glycan score} = N - (C + I + J + P), \quad (1)$$

wherein the letters refer to the row numbering of Table 41.

The algorithm was then applied to the other samples that served as the test group in the analysis and the results are described graphically in FIG. 36. The differentiated cell samples (EB and stage 3) were significantly discriminated from hESC with $p<0.01$ (2-tailed Student's t-test with Welch's approximation, $p=0.0018$). The stage 3 differentiated cell samples were also significantly separated from the EB samples with $p<0.01$ (2-tailed Marm-Whitney U test, $p=0.0022$). This suggested that the hESC N-glycan profiles were similar at the glycome level despite of individual differences at the level of distinct glycan signals. The result also suggested that glycome profiling is a potential tool for monitoring the differentiation status of stem cells.

The Identified hESC Glycans can be Targeted at the Cell Surface

Figure 37:
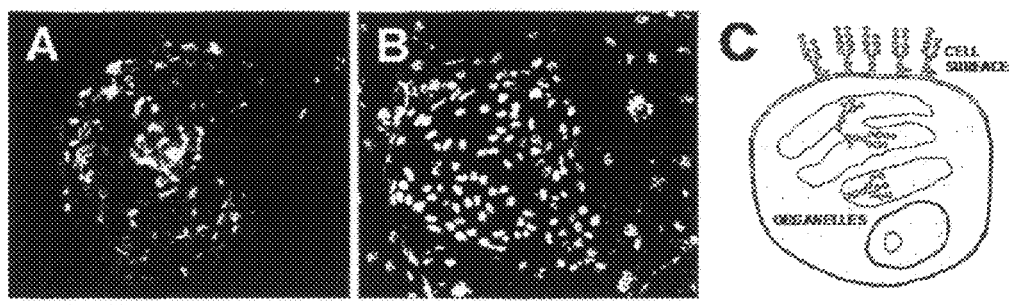
FIG. 37. Latin staining of hESC colonies grown on mouse feeder cell layers, with (A) *Maackia amuriensis* agglutinin (MAA) that recognizes $\alpha 2,3$-sialylated glycans, and with (B) *Pisum sativum* agglutinin (PSA) that recognizes $\alpha$-mannosylated glycans. Lectin binding to hESC was inhibited by $\alpha 3'$-sialyllactose and D-mannose for MAA and PSA, respectively, and PSA recognized hESC only after cell permeabilization (data not shown). Mouse fibroblasts had complementary staining patterns with both lectins, indicating that their surface glycans differed from hESC. C. The results indicate that mannosylated N-glycans are localized in the intracellular compartments in hESC, whereas $\alpha 2,3$-sialylated glycans occur on the cell surface.

From a practical perspective stem cell research would be best served by the identification of target structures on cell surface. To investigate whether individual glycan structures we had identified would be accessible to reagents targeting them at the cell surface we performed lectin labelling of two candidate structure types. Lectins are proteins that recognize glycans with specificity to certain glycan structures also in hESC (Venable et al., 2005). To study the localization of glycan components in hESC, stem cell colonies grown on mouse feeder cell layers were labeled in vitro by fluorescein-labelled lectins (FIG. 37). The hESC cell surfaces were clearly labeled by *Maackia amurensis* agglutinin (MAA) that recognizes structures containing α2,3-linked sialylation, indicating that sialylated glycans are abundant on the hESC cell surface (FIG. 37a). Such glycans would thus be available for recognition by more specific glycan-recognizing reagents such as antibodies. In contrast, the cell surfaces were not labelled by *Pisum sativum* agglutinin (PSA) that recognizes α-mannosylated glycans (FIG. 37b). However, PSA labelled the cells after permeabilization (data not shown), suggesting that the mannosylated N-glycans in hESC were localized in intracellular cell compartments such as the endoplasmic reticulum (ER) or the Golgi complex (FIG. 37c). Interestingly, the mouse fibroblast cells showed complementary staining patterns, suggesting that these lectin reagents efficiently discriminated between hESC and feeder cells. Together the results suggested that the glycan structures we identified could be utilized to design specific reagents targeting hESC.

Comparative Analysis of the N-Glycome

Figure 34:
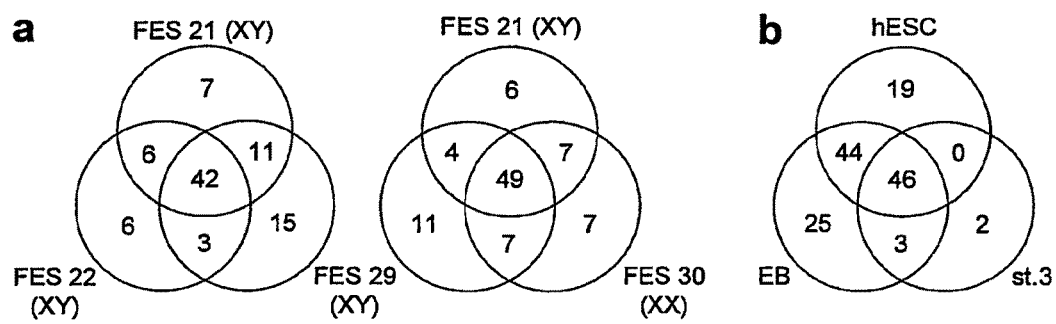
FIG. 34. Venn diagram showing distribution of the detected neutral and acidic N-glycan signals a between the four hESC lines (FES) and b between hESC, embryoid bodies derived from FES 29 and FES 30 hESC lines (EB), and stage 3 differentiated cells derived from FES 29 (st.3).

Although the N-glycan profiles of the four hESC lines share a similar overall profile shape, there was cell line specific variation in the N-glycan profiles. Individual glycan signals unique to each cell line were found, indicating that every cell line was slightly different from each other with respect to the approximately one hundred most abundant glycan structures they synthesize. This is represented in FIG. 34a as Venn diagrams combining all the detected glycan signals from both the neutral and the acidic N-glycan fractions. FES 29 and FES 30 were derived from sibling embryos, but their N-glycan profiles did not resemble each other more than they resembled FES 21 in the Venn diagram. Furthermore, FES 30 that has the karyotype XX did not differ significantly from the three XY hESC lines.

In order to determine whether the hESC N-glycome undergoes changes during differentiation, N-glycan profiles obtained from hESC, EB, and stage 3 differentiated cells were compared (FIG. 33). The N-glycan profiles of the differentiated cell types (EB and st.3) differed significantly from the profiles of undifferentiated hESC, which is indicated by non-overlapping distribution bars in many glycan signals. There were many signals in common between hESC and EB that disappeared in stage 3 differentiated cells, as described in the Venn diagram (FIG. 34b). Overall, 17% of the glycan signals present in hESC disappeared in EB, and in stage 3 differentiated cells 58% of the original N-glycan signals disappeared. Simultaneously numerous new signals appeared in EB and stage 3 differentiated cells. Their proportion in EB and stage 3 differentiated cells was 24% and 10%, respectively. This indicates that differentiation induced the appearance of new N-glycan types while earlier glycan types disappeared. The 19 N-glycan signals specific to the hESC samples are listed in Table 40.

Discussion

In the present study, novel mass spectrometric methods were applied to the first structural analysis of human embryonic stem cell N-glycan profiles. Previously, such investigation of whole cell glycosylation has not been feasible due to the lack of methods with sufficiently high sensitivity to analyze the scarce stem cells. The present method was validated for samples of approximately 100 000 cells and the glycan profiles of the analyzed cell types were consistent throughout multiple samples. The objective in the use of the present method was to provide a global view on the glycome profile, or a "fingerprint" of hESC glycosylation, rather than to present the stem cell glycome in terms of the molecular structures of each glycan component. However, changes observed in the N-glycan profiles provide vast amount of information regarding hESC glycosylation and its changes during differentiation, and allows rational design of detailed structural studies of selected glycan components or glycan groups.

The results indicate that a defined group of N-glycan signals dominate the hESC N-glycome and form a unique stem cell glycan profile. It seems that specific monosaccharide compositions were favored over the possible alternatives by the hESC N-glycan biosynthetic machinery. For example, the fifteen most abundant neutral N-glycan signals and fifteen most abundant sialylated N-glycan signals in hESC together comprised over 85% of the N-glycome. Further, different glycan structures were favored during the differentiation of the cells. This suggests that N-glycan biosynthesis in hESC is a controlled and predetermined process. As hundreds of genes, consisting of up to 1% of the human genome, are involved in glycan biosynthesis (Haltiwanger and Lowe, 2004), a future challenge is to characterize the regulatory processes that control hESC glycosylation during differentiation into specialized cell types.

Based on our results the hESC N-glycome seems to contain both a constant part consisting of "housekeeping glycans", and a changeable part that was altered when the hESC differentiated (FIG. 33). The constant part seemed to contain mostly high-mannose type and biantennary complex-type N-glycans. Such "housekeeping" glycans may need to be present at all times for the maintenance of basic cellular processes. Significantly, 25% (50% if high-mannose glycans are excluded) of the total N-glycan profile of hESC changed during their differentiation. This indicates that during differentiation hESC dramatically change both their appearance towards their environment and possibly also their own capability to sense and respond to exogenous signals.

Our data show that the differentiation-associated change in the N-glycome was generated by addition of variable epitopes on similar N-glycan core compositions. For example, the present lectin staining experiments demonstrated that sialylated glycans were abundant on the cell surface of hESC, indicating that they are potential targets for development of more specific recognition reagents. In contrast, the constantly expressed mannosylated glycans were found to reside mainly inside the cells. It seems plausible that knowledge of the changing surface glycan epitopes could be utilized as a basis in developing reagents and culture systems that would allow improved identification, selection, manipulation, and culture of hESC and their progeny. We are currently characterizing the stem cell specific glycosylation changes at the level of individual molecular structures.

The specific cellular glycan structures perform their functions mainly by 1) acting as ligands for specific glycan receptors (Kilpatrick, 2002; Zanetta and Vergoten, 2003), 2) functioning as structural elements of the cell (Imperiali and O'Connor, 1999), and 3) modulating the activity of their carrier proteins and lipids (Varki, 1993;). More than half of all proteins are glycosylated. Consequently, a global change in protein-linked glycan biosynthesis can simultaneously modulate the properties of multiple proteins. It is likely that the large changes in N-glycans during hESC differentiation have major influences on a number of cellular signaling cascades and affect in profound fashion biological processes within the cells. Our data may provide insight into the regulation of some of these processes.

The major hESC specific glycosylation feature we identified was the presence of more than one deoxyhexose residue in N-glycans, indicating complex fucosylation. Fucosylation is known to be important in cell adhesion and signalling events (Becker and Lowe, 2003) as well as essential for embryonic development. Knock-out of the N-glycan core $\alpha 1,6$-fucosyltransferase gene FUT8 leads to postnatal lethality in mice (Wang et al., 2005), and mice completely deficient in fucosylated glycan biosynthesis do not survive past early embryonic development (Smith et al., 2002). Fucosylation defects in humans cause a disease known as leukocyte adhesion deficiency (LAD; Luhn et al., 2001).

Fucosylated glycans such as the SSEA-1 antigen have previously been associated with both mouse embryonic stem cells (mESC) and human embryonic carcinoma cells (EC; Muramatsu and Muramatsu, 2004), but not with hESC. In addition, structurally related $Le^x$ oligosaccharides are able to inhibit embryonic compaction (Fenderson et al., 1984), suggesting that fucosylated glycans are directly involved in cell-to-cell contacts during embryonic development. The $\alpha 1,3$-fucosyltransferase genes indicated in the synthesis of the embryonic $Le^x$ and SSEA-1 antigens are FUT4 and FUT9 (Nakayama et al., 2001; Kudo et al., 2004). Interestingly, the published gene expression profiles for the same hESC lines as studied here (Skottman et al., 2005) have demonstrated that three human fucosyltransferase genes, FUT1, FUT4, and FUT8 are expressed in hESC, and that FUT1 and FUT4 are overexpressed in hESC when compared to EB. The known specificities of these fucosyltransferases (Mollicone et al., 1995) correlate with our findings of simple fucosylation in EB and complex fucosylation in hESC (FIG. 38). Taken together, although hESC do not express the specific glycolipid antigen recognized by the SSEA-1 antibody, they share with mESC the characteristic feature of complex fucosylation and may have conserved the biological functions of fucosylated glycan epitopes.

New N-glycan forms emerged in EB and stage 3 differentiated cells. These structural features included additional N-acetylhexosamine residues, potentially leading to new N-glycan terminal epitopes. Another differentiation-associated feature was an increase in the molar proportions of hybrid-type or monoantennary N-glycans. Biosynthesis of hybrid-type and complex-type N-glycans has been demonstrated to be biologically significant for embryonic and postnatal development in the mouse (Ioffe and Stanley, 1994 PNAS; Metzler et al., 1994 EMBO J; Wang et al., 2001 Glycobiology; Akama et al., 2006 PNAS). The preferential expression of complex-type N-glycans in hESC and then the change in the differentiating EB to express more hybrid-type or monoantennary N-glycans may thus be significant for the process of stem cell differentiation.

Human embryonic stem cell lines have previously been demonstrated to have a common genetic stem cell signature that can be identified using gene expression profiling techniques (Skottman et al., 2005; Sato et al., 2003; Abeyta et al., 2004; Bhattacharya et al., 2004). Such signatures have been proposed to be utilized in the characterization of cell lines. The present report provides the first glycomic signatures for hESC. The profile of the expressed N-glycans might be a useful tool for analyzing and classifying the differentiation stage in association with gene and protein expression analyses. Here we demonstrate that the glycan score algorithm was able to reliably differentiate cell samples of separate differentiation stage (FIG. 37). Glycome profiling may be a more sensitive measure of the cell status than any single cell surface marker. Such a method might be especially useful for the quality control of hESC-based cell products. However, further analysis of the hESC glycome may also lead to discovery of novel glycan antigens that could be used as stem cell markers in addition to the commonly used SSEA and Tra glycan antigens.

In conclusion, hESC have a unique glycome which undergoes major changes when the cells differentiate. Information regarding the specific glycome may be utilized in developing reagents for the targeting of these cells and their progeny. Future studies investigating the developmental and molecular regulatory processes resulting in the observed glycan profiles may provide significant insight into mechanisms of human development and regulation of glycosylation.

REFERENCES

Abeyta, M. J., Clark, A. T., Rodriguez, R. T., Bodnar, M. S., Pera, R. A., and Firpo, M. T. (2004). Unique gene expression signatures of independently-derived human embryonic stem cell lines. Hum. Mol. Genet. 13, 601-608.

Apweiler, R., Hermjakob, H., and Sharon, N. (1999). On the frequency of protein glycosylation, as deduced from analysis of the SWISS-PROT database. Biochim. Biophys. Acta 1473, 4-8.

Badcock, G., Pigott, C., Goepel, J., and Andrews, P. W. (1999). The human embryonal carcinoma marker antigen TRA-1-60 is a sialylated keratan sulfate proteoglycan. Cancer Res. 59, 4715-4719.

Becker, D. J., and Lowe, J. B. (2003). Fucose: biosynthesis and biological function in mammals. Glycobiology. 13:41 R-5R.

Bhattacharya, B., Miura, T., Brandenberger, R., Mejido, J., Luo, Y., Yang, A. X., Joshi, B. H., Ginis, I., Thies, R. S., Amit, M., Lyons, I., Condie, B. G., Itskovitz-Eldor, J., Rao, M. S., and Pur, R. K. (2004). Gene expression in human embryonic stem cell lines: Unique molecular signature. Blood 103, 2956-2964.

Callewaert, N., Van Vlierberghe, H., Van Hecke, A., Laroy, W., Delanghe, J., and Contreras, R. (2004). Noninvasive diagnosis of liver cirrhosis using DNA sequencer-based total serum protein glycomics. Nat. Med. 10:429-34.

Carson, D. D., and Lennarz, W. J. (1979). Inhibition of poly-isoprenoid and glycoprotein biosynthesis causes abnormal embryonic development. Proc. Natl. Acad. Sci. U.S.A. 76, 5709-5713.

Cooper, D. K. (1998). Xenoantigens and xenoantibodies. Xenotransplantation 5, 6-17.

Davies, M. J., Smith, K. D., Carruthers, R. A., Chai, W., Lawson, A. M., and Hounsell, E. F. (1993). Use of a porous graphitised carbon column for the high-performance liquid chromatography of oligosaccharides, alditols and glycopeptides with subsequent mass spectrometry analysis. J. Chromatogr. 646, 317-326.

Dell A., and Morris, H. R. (2001). Glycoprotein structure determination by mass spectrometry. Science 291, 2351-2356.

Fenderson, B. A., Zehavi, U., and Hakomori, S. (1984). A multivalent lacto-N-fucopentaose III lysyllysine conjugate decompacts preimplantation mouse embryos, while the free oligosaccharide is ineffective. J. Exp. Med. 160, 1591-1596.

Goldberg, D., Sutton-Smith, M., Paulson, J., and Dell, A. (2005). Automatic annotation of matrix-assisted laser desorption/ionization N-glycan spectra. Proteomics 5, 865-875.

Good H. C., Feizi, T., Kapadia, A., Knowles, B. B., Solter, D., and Evans, M. J. (1981). Stage-specific embryonic antigen involves α1→3 fucosylated type 2 blood group chains. Nature 292, 156-158.

Haltiwanger, R. S., and Lowe, J. B. (2004). Role of glycosylation in development. Annu. Rev. Biochem. 73, 491-537.

Handel, T. M., Johnson, Z., Crown, S. E., Lau, E. K., and Proudfoot, A. E. (2005). Regulation of protein function by glycosaminoglycans—as exemplified by chemokines. Annu. Rev. Biochem. 74:385-410.

Harvey, D. J. (1993). Quantitative aspects of the matrix-assisted laser desorption mass spectrometry of complex oligosaccharides. Rapid Commun. Mass Spectrom. 7, 614-619.

Helenius, A., and Aebi, M. (2001). Intracellular functions of N-linked glycans. Science 291, 2364-2369.

Helenius, A., and Aebi, M. (2004). Roles of N-linked glycans in the endoplasmic reticulum. Annu. Rev. Biochem. 73, 1019-1049.

Homeister, J. W., Thall, A. D., Petryniak, B., Maly, P., Rogers, C. E., Smith, P. L., Kelly, R. J., Gersten, K. M., Askari, S. W., Cheng, G., Smithson, G., Marks, P-M., Misra, A. K., Hindsgaul, O., von Andrian, U. H., and Lowe, J. B. (2001). The α(1,3)fucosyltransferases FucT-IV and FucT-VII exert collaborative control over selectin-dependent leukocyte recruitment and lymphocyte homing. Immunity. 15:115-26.

Imperiali, B., and O'Connor, S. E. (1999). Effect of N-linked glycosylation on glycopeptide and glycoprotein structure. Curr. Opin. Chem. Biol. 3, 643-649.

Kannagi, R., Cochran, N. A., Ishigami, F., Hlakomori, S., Andrews, P. W., Knowles, B. B., and Softer, D. (1983). Stage-specific embryonic antigens (SSEA-3 and -4) are epitopes of a unique globo-series ganglioside isolated from human teratocarcinoma cells. EMBO J. 2, 2355-2361.

Kilpatrick, D. C. (2002). Animal lectins: A historical introduction and overview. Biochim. Biophys. Acta 1572, 187-197.

Kornfeld, R., and Kornfeld, S. (1985). Assembly of asparagine-linked oligosaccharides. Annu. Rev. Biochem. 54, 631-664.

Kornfeld, S. (1986). Trafficking of lysosomal enzymes in normal and disease states. J. Clin. Invest. 77:1-6.

Kudo, T., Kaneko, M., Iwasaki, H., Togayachi, A., Nishihara, S., Abe, K., and Narimatsu, H. (2004). Normal embryonic and germ cell development in mice lacking α1,3-fucosyltransferase IX (Fut9) which show disappearance of stage-specific embryonic antigen 1. Mol. Cell. Biol. 24:4221-4228.

Lowe, J. B. (2002). Glycosylation in the control of selectin counter-receptor structure and function. Immunol. Rev. 186:19-36.

Luhn, K, Wild, M. K., Eckhardt, M., Gerardy-Schahn, R., and Vestweber, D. (2001). The gene defective in leukocyte adhesion deficiency II encodes a putative GDP-fucose transporter. Nat. Genet. 28:69-72.

Martin, M. J., Muotri, A., Gage, F., and Varki, A. (2005). Human embryonic stem cells express an immunogenic nonhuman sialic acid. Nat. Med. 11, 228-232.

Mollicone, R, Cailleau, A., and Oriol, R. (1995). Molecular genetics of H, Se, Lewis, and other fucosyltransferase genes. Transfusion Clin. Biol. 4:235-242.

Muramatsu, T., and Muramatsu, H. (2004). Carbohydrate antigens expressed on stem cells and early embryonic cells. Glycoconj. J. 21, 41-45.

Nakayama, F., Nishihara, S., Iwasaki, H., Kudo, T., Okubo, R., Kaneko, M., Nakamura, M., Karube, M., Sasaki, K., and Narimatsu, H. (2001). CD15 expression in mature granulocytes is determined by α1,3-fucosyltransferase IX, but in promyelocytes and monocytes by α1,3-fucosyltransferase IV. J. Biol. Chem. 276:16100-16106.

Naven, T. J., and Harvey, D. J. (1996). Effect of structure on the signal strength of oligosaccharides in matrix-assisted laser desorption/ionization mass spectrometry on time-of-flight and magnetic sector instruments. Rapid Commun. Mass Spectrom. 10, 1361-1366.

Nguyen, D. H., Tangvoranuntakul, P., and Varki, A. (2005). Effects of natural human antibodies against a nonhuman sialic acid that metabolically incorporates into activated and malignant immune cells J. Immunol. 175, 228-236.

Nyman, T. A., Kaiinen, N., Tölö, H., and Helin, J. (1998). Structural characterisation of N-linked and O-linked oligosaccharides derived from interferon-α2b and interferon-α14c produced by Sendai-virus-induced human peripheral blood leukocytes. Eur. J. Biochem. 253, 485-493.

Okabe, S., Forsberg-Nilsson, K., Spiro, A. C., Segal, M., and McKay, R. D. (1996). Development of neuronal precursor cells and functional postmitotic neurons from embryonic stem cells in vitro. Mech. Dev. 59:89-102.

Papac, D. I., Wong, A., and Jones, A. J. (1996). Analysis of acidic oligosaccharides and glycopeptides by matrix-assisted laser desorption/ionization time-of-flight mass spectrometry. Anal. Chem. 68, 3215-3223.

Saarinen, J., Welgus, H. G., Flizar, C. A., Kalkinen, N., and Helin, J. (1999). N-glycan structures of matrix metalloproteinase-1 derived from human fibroblasts and from HT-1080 fibrosarcoma cells. Eur. J. Biochem. 259, 829-840.

Sato, N., Sanjuan, I. M., Heke, M., Uchida, M., Naef, F., and Brivanlou, A. H. (2003). Molecular signature of human embryonic stem cells and its comparison with the mouse. Dev. Biol. 260, 404-413.

Schachter, H. (1991). The 'yellow brick road' to branched complex N-glycans. Glycobiology 1, 453-461.

Schneider, E. G., Nguyen, H. T., and Lennarz, W. J. (1978). The effect of tunicamycin, an inhibitor of protein glycosylation, on embryonic development in the sea urchin. J. Biol. Chem. 253, 2348-2355.

Shriver, Z., Raguram, S., and Sasisekharan, R. (2004). Glycomics: A pathway to a class of new and improved therapeutics. Nat. Rev. Drug Disc. 3, 863-873.

Skottman, H., Mikkola, M., Lundin, K., Olsson, C., Strömberg, A. M., Tuuri, T., Otonkoski, T., Hovatta, O., and Lahesmaa, R. (2005). Gene expression signatures of seven individual human embryonic stem cell lines. Stem cells 23, 1343-1356.

Smith, P. L., Myers, J. T., Rogers, C. E., Zhou, L., Petryniak, B., Becker, D. J., Homeister, J. W., and Lowe, J. B. (2002). Conditional control of selectin ligand expression and global fucosylation events in mice with a targeted mutation at the FX locus. J. Cell Biol. 158:801-815.

Solter, D., and Knowles, B. B. (1978). Monoclonal antibody defining a stage-specific mouse embryonic antigen (SSEA-1). Proc. Natl. Acad. Sci. U.S.A. 75, 5565-5569.

Staudacher, E., Altmann, F., Wilson, I. B. H., and März, L. (1999). Fucose in N-glycans: From plant to man. Biochim. Biophys. Acta 1473, 216-346.

Sutton-Smith, M., Morris, H. R., Grewal, P. K., Hewitt, J. E., Bittner, R. E., Goldin, E., Schiffmann, R., and Dell, A. (2002). MS screening strategies: Investigating the glycomes of knockout and myodystrophic mice and leukodystrophic human brains. Biochem. Soc. Symp. 69, 105-115.

Thomson, J. A., Itskovitz-Eldor, J., Shapiro, S. S., Waknitz, M. A., Swiergiel, J. J., Marshall, V. S., and Jones, J. M. (1998). Embryonic stem cell lines derived from human blastocysts. Science 282, 1145-1147.

Varki A. (1993). Biological roles of oligosaccharides: All of the theories are correct. Glycobiology 3, 97-130.

Venable, A., Mitalipova, M., Lyons, I., Jones, K., Shin, S., Pierce, M., and Stice, S. (2005). Lectin binding profiles of SSEA-4 enriched, pluripotent human embryonic stem cell surfaces. BMC Dev. Biol. 2005 5, 15.

Verostek, M. F., Lubowski, C., and Trimble, R. B. (2000). Selective organic precipitation/extraction of released N-glycans following large-scale enzymatic deglycosylation of glycoproteins. Anal. Biochem. 278, 111-122.

Wang, X., Inoue, S., Gu, J., Miyoshi E., Noda, K., Li, W., Mizuno-Horikawa, Y., Nakano, M., Asahi, M., Takahashi, M., Uozumi, N., Ihara, S., Lee, S. H., Ikeda, Y., Yamaguchi, Y., Aze, Y., Tomiyama, Y., Fujii, J., Suzuli, K., Kondo, A., Shapiro, S. D., Lopez-Otin, C., Kuwaki, T., Okabe, M., Honke, K., and Taniguchi, N. (2005). Dysregulation of TGF-β1 receptor activation leads to abnormal lung development and emphysema-like phenotype in core fucose-deficient mice. Proc. Natl. Acad. Sci. U.S.A. 102:15791-15796.

Wobus, A. M., and Boheler, K. R. (2005). Embryonic stem cells: Prospects for developmental biology and cell therapy. Physiol. Rev. 85, 635-678.

Zanetta, J. P., and Vergoten, G. (2003). Lectin domains on cytokines. Adv. Exp. Med. Biol. 535, 107-124.

Example 24

Gene Expression and Glycome Profiling of Human Embryonic Stem Cells

Results and Discussion

Obtaining of the gene expression data from the hESC lines FES 21, 22, 29, and 30 has been described (Skottnan et al., 2005) and the present data was produced essentially similarity. The results of the gene expression profiling analysis with regard to a selection of potentially glycan-processing and accessory enzymes are presented in Table 42, where gene expression is both qualitatively determined as being present (P) or absent (A) and quantitatively measured in comparison to embryoid bodies (EB) derived from the same cell lines.

Fucosyltransferase Expression Levels.

Three fucosyltransferase transcripts were detected in hESC: FUT1 (α1,2-fucosyltmmsferase; increased in all FES cell lines), FUT4 (α1,3-fucosyltransferase IV; increased in all FES cell lines), and FUT8 (N-glycan core α1,6-fucosyltransferase).

Hexosaminyltransferase Expression Levels.

The following transcripts in the selection of Table 42 were detected in hESC: MGAT3, MGAT2 (increased in three FES cell lines), MGAT1, GNT4b, β3GlcNAc-T5, β3GlcNAc-T7, β3GlcNAc-T4 (present in two FES cell lines), β6GlcNAcT (increased in one FES cell line), iβ3GlcNAcT, globosideT, and α4GlcNAcT (present in two FES cell lines).

Other Gene Expression Levels.

The following transcripts in the selection of Table 42 were detected in hESC: AER1 (increased in all FES cell lines), AGO61, β3GALT3, MAN1C1, and LGALS3.

Example 25

Analysis of Human and Murine Fibroblast Feeder Cells

Murine (mEF) and human (hEF) fibroblast feeder cells were prepared and their N-glycan fractions analyzed as described in the preceding Examples.

Results and Discussion

Figure 43:
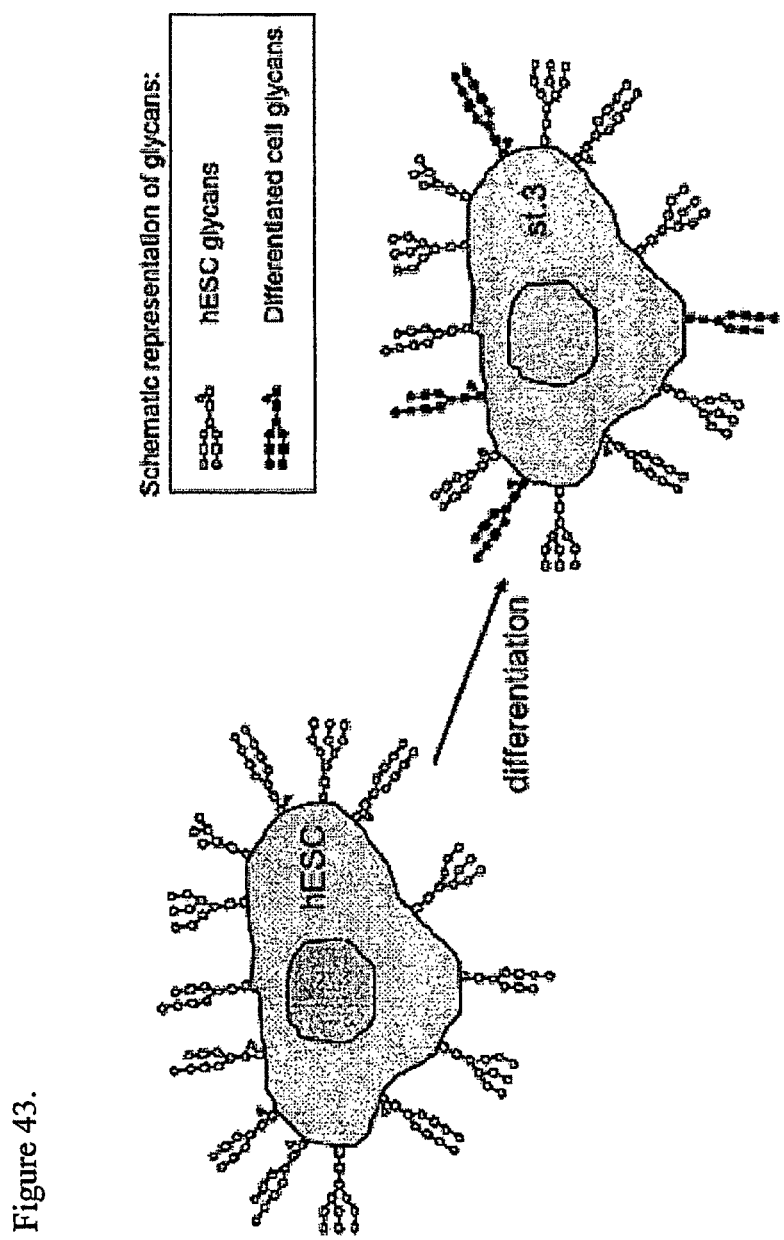
FIG. 43. Schematic representation of the N-glycan change during differentiation (details do not necessarily refer to actual structures). According to characterization of the Finnish hESC lines FES 21, 22, 29, and 30, hESC differentiation leads to a major change in hESC surface molecules. St3 means differentiation stage after EB stage.
Figure 45:
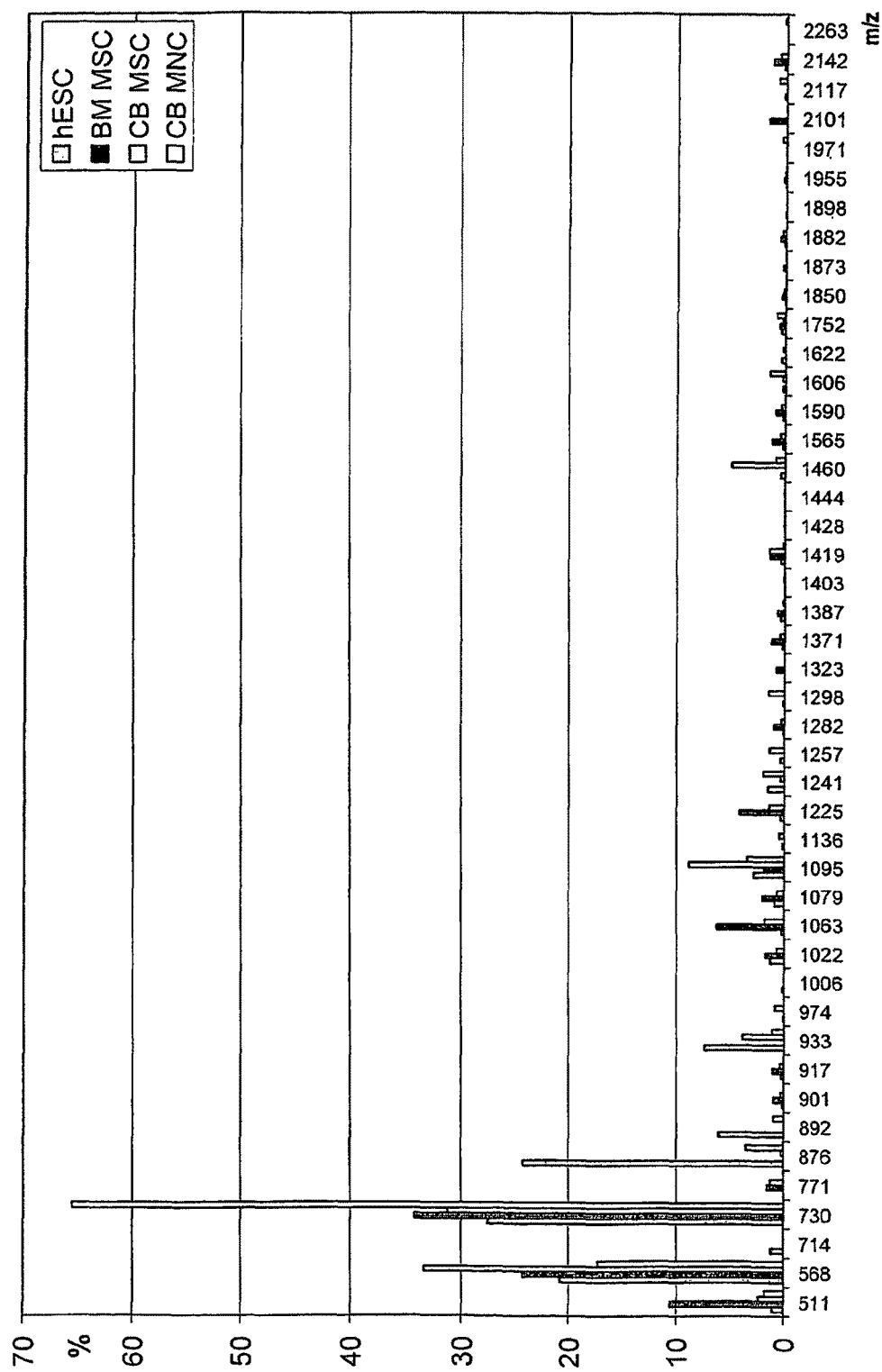
FIG. 45. MALDI-TOF mass spectrometric profile of isolated human stem cell neutral glycosphingolipid glycans. x-axis: approximate m/z values of $[M+Na]^+$ ions as described in Table. y-axis: relative molar abundance of each glycan component in the profile. hESC, BM MSC, CB MSC, CB MNC: stem cell samples as described in the text.

FIG. 43 shows the major neutral N-glycan fraction glycan signals of hEF and mEF. FIG. 44 shows the glycan grouping of neutral N-glycan fraction glycan signals of hEF and mEF. FIG. 45 shows the glycan grouping of acidic N-glycan fraction glycan signals of hEF and mEF. The mEF and hEF cells differed significantly from each other in their glycan profiles.

The results showed that mEF and hEF cellular N-glycan fractions differ significantly from each other. The differencies include differential proportions of glycan groups, major glycan signals, and the glycan profiles obtained from the cell samples. In addition, the major difference is the presence of Galα3Gal epitopes in the mEF cells, as discussed in the preceding Examples of the present invention.

Example 26

The glycome of Human Embryonic Stem Cells Reflects Their Differentiation Stage

Summary

Complex carbohydrate structures, glycans, are elementary components of glycoproteins, glycolipids, and proteoglycans. These glycoconjugates form a layer of glycans that covers all human cell surfaces and forms the first line of contact towards the cell's environment. Glycan structures called stage specific embryonic antigens (SSEA) are used to assess the undifferentiated stage of embryonic stem cells. However, the whole spectrum of stem cell glycan structures has remained unknown, largely due to lack of suitable analysis technology. We describe the first global study of glycoprotein glycans of human embryonic stem cells, embryoid bodies, and further differentiated cells by MALDI-TOF mass spectrometric profiling. The analysis reveals how certain asparagine-linked glycan structures characteristic to stem cells are lost during differentiation while new structures emerge in the differentiated cells. The results indicate that human embryonic stem cells have a unique glycome and that their differentiation stage can be identified by glycome analysis. We suggest that knowledge about stem cell specific glycan structures can be used for e.g. purification, manipulation, and quality control of stem cells.

Materials & Methods

Human Embryonic Stem Cell Lines.

Four Finnish hESC lines, FES 21, FES 22, FES 29, and FES 30 (Skottman et al., 2005. *Stem cells* 23:1343-56) were used in the present study. These lines are included in the International Stem Cell Initiative (Andrews et al., 2005. *Nat. Biotechnol.* 23:795-7). The cells were propagated on human foreskin fibroblast (hFF) feeder cells in serum-free medium (Knockout™, Gibco/Invitrogen). In FACS analyses 70-90% of cells from mechanically isolated colonies were typically Tra 1-60 and Tra 1-81 positive (not shown). Cells differentiated into embryoid bodies (EB, stage 2 differentiated) and further differentiated cells grown out of the EB as monolayers (stage 3 differentiated) were used for comparison against hESC. The differentiation protocol favors the development of neuroepithelial cells while not directing the differentiation into distinct terminally differentiated cell types (Okabe et al., 1996. *Mech. Dev.* 59:89-102). EB derived from FES 30 had less differentiated cell types than the other three EB. Stage 3 cultures consisted of a heterogenous population of cells dominated by fibroblastoid and neuronal morphologies. For the glycome studies the cells were collected mechanically, washed, and stored frozen until analysis.

In a preferred embodiment the invention is directed to the use of data obtained embryoid bodies or ESC-cell line cultivated under conditions favouring neuroepithelial cells for search of specific structures indicating neuroepithelial development, preferably by comparing the material with cell materials comprising neuronal and/or epithelial type cells.

Asparagine-Linked Glycome Profiling.

Total asparagine-linked glycan (N-glycan) pool was enzymatically isolated from about 100 000 cells. The total N-glycan pool (picomole quantities) was purified with microscale solid-phase extraction and divided into neutral and sialylated N-glycan fractions. The N-glycan fractions were analyzed by MALDI-TOF mass spectrometry either in positive ion mode for neutral N-glycans or in negative ion mode for sialylated glycans (Saarinen et al., 1999, *Eur. J. Biochem.* 259, 829-840). Over one hundred N-glycan signals were detected from each cell type revealing the surprising complexity of hESC glycosylation. The relative abundances of the observed glycan signals were determined based on relative signal intensities (Harvey, 1993. *Rapid Commun. Mass Spectrom.* 7:614-9; Papac et al., 1996. *Anal. Chem.* 68:3215-23).

Results

Figure 39:
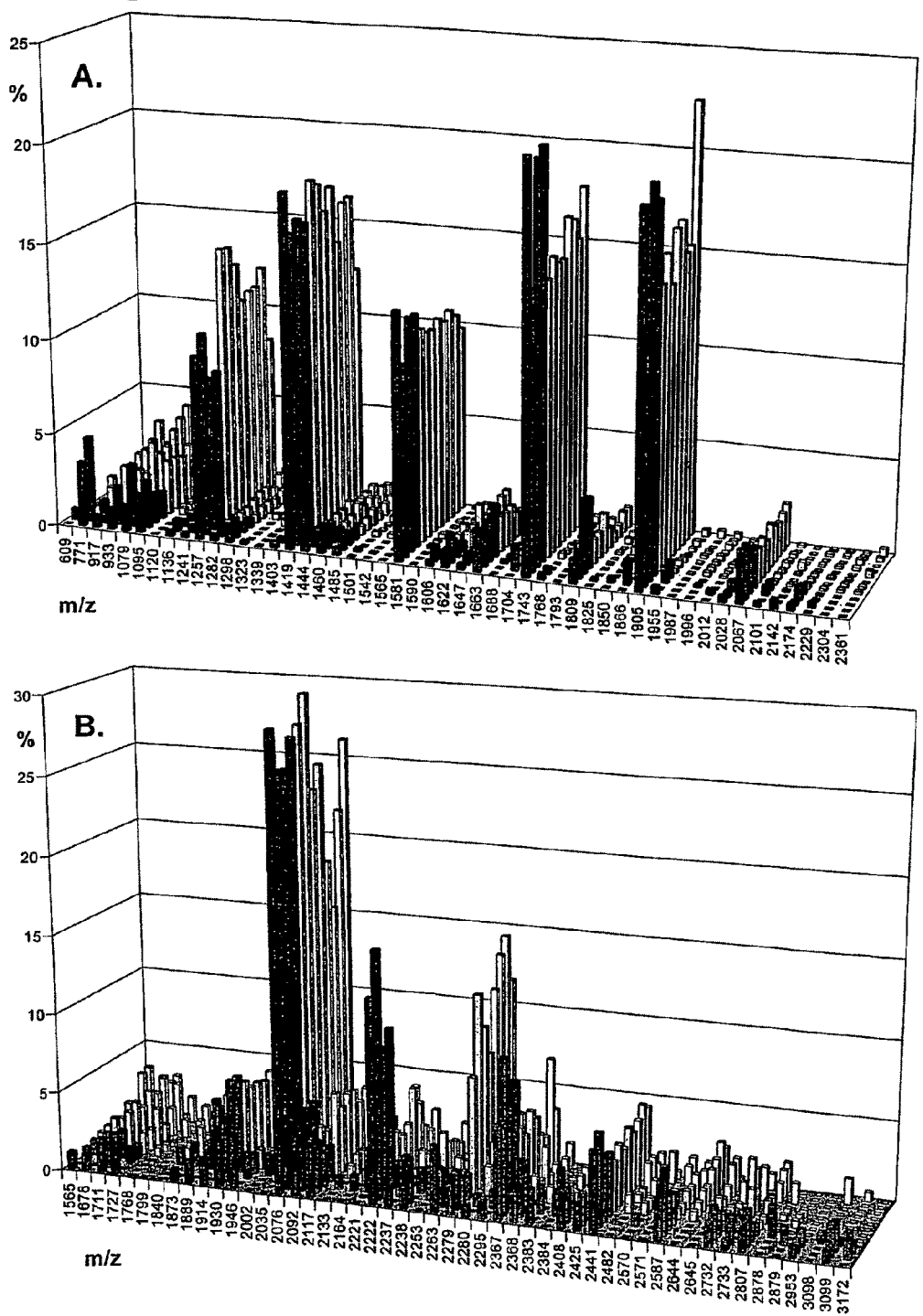
FIG. 39. Portrait of the hESC N-glycome MALDI-TOF mass spectrometric profiling of the most abundant 50 neutral N-glycans (A.) and 50 sialylated N-glycans (B.) of the four bESC lines FES 21, 22, 29, and 30 (black columns), four EB samples (gray columns), and four st3 differentiated cell samples (white columns) derived from the four hESC lines, respectively. The columns indicate the mean abundance of each glycan signal (% of the total glycan signals). The observed m/z values for either [M+Na]+ or [M-H]− ions for the neutral and sialylated N-glycan fractions, respectively, are indicated on the x-axis. Proposed monosaccharide compositions and N-glycan types are presented in Table 48.

In the present study, we analyzed the N-glycome profiles of hESC, EB, and st.3 differentiated cells (FIG. 39).

The similarity of the N-glycan profiles within the group of four hESC lines suggested that the obtained N-glycan profiles are a description of the characteristic N-glycome of hESC. Overall, 10% of the 100 most abundant N-glycan signals present in hESC disappeared in st.3 differentiated cells, and 16% of the most abundant signals in st.3 differentiated cells were not present in hESC. This indicates that differentiation induced the appearance of new N-glycan types while earlier glycan types disappeared. In quantitative terms, the differences between the glycan profiles of hESC, EB, and st.3 differentiated cells were: hESC vs. EB 19%, hESC vs. st.3 24%, and EB vs. st.3 12%.

Figure 40:
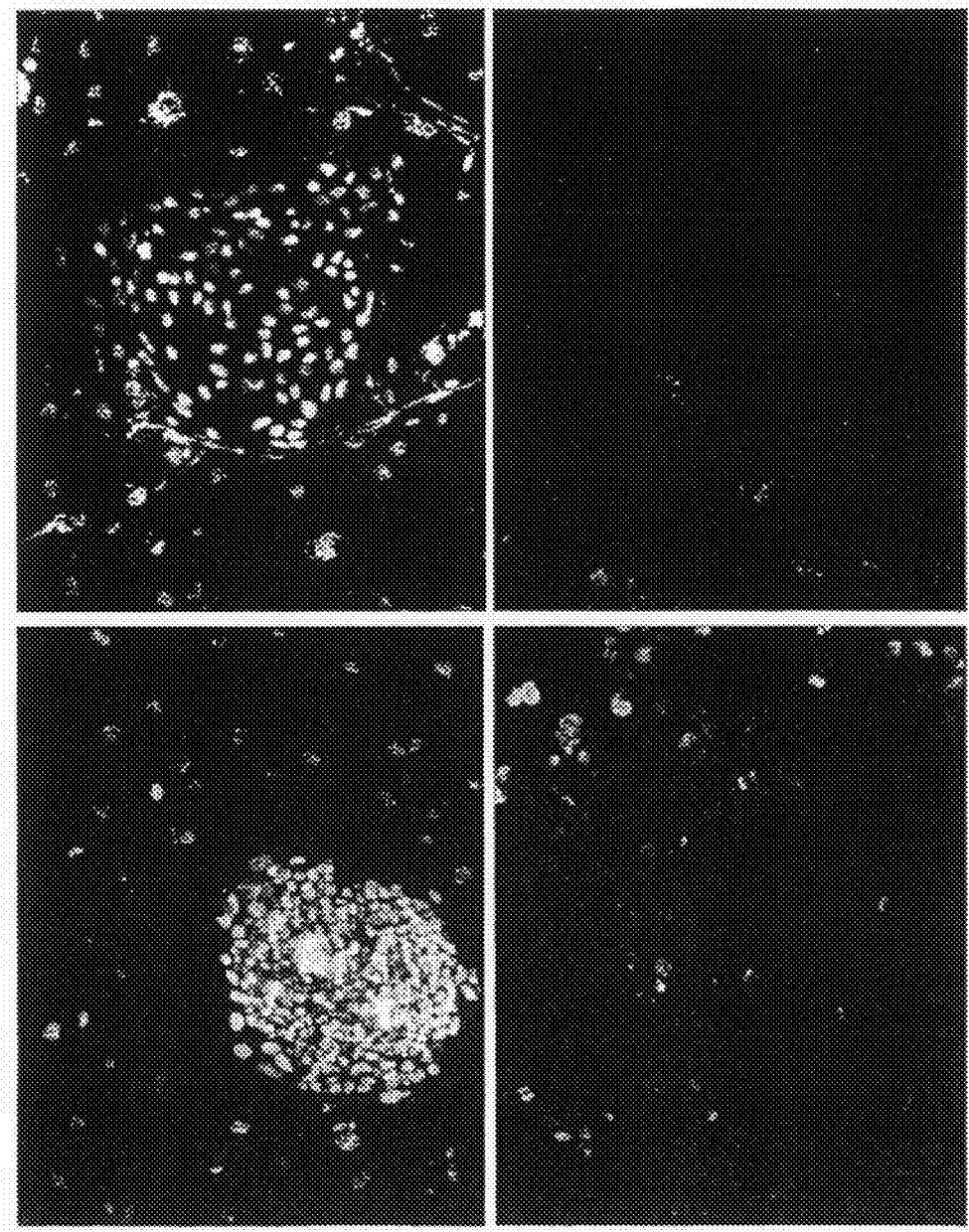
FIG. 40. Detection of hESC glycans by structure-specific reagents. To study the localization of the detected glycan components in hESC, stem cell colonies grown on mouse feeder cell layers were labeled by fluoresceinated glycan-specific reagents selected based on the analysis results (FIG. 36). A. The hESC surfaces were stained by *Maackia amurensis* agglutinin (MAA), indicating that α2,3-sialylated glycans are abundant on hESC but not on feeder cells (MEF, mouse feeder cells). B. In contrast, the hESC cell surfaces were not stained by *Pisum sativum* agglutinin (PSA) that recognized mouse feeder cells, indicating that α-mannosylated glycans are not abundant on hESC surfaces but are present on mouse feeder cells. C. Addition of 3'-sialyllactose blocks MAA binding, and D. addition of D-mannose blocks PSA binding.

The glycome profile data was used to design glycan-specific labeling reagents for hESC. The most interesting glycan types were chosen to study their expression profiles by lectin histochemistry as exemplified in FIG. 40 for the lectins that recognize either α2,3-sialylated (MAA-lectin, FIG. 40A.) binding to the hESC cells or α-mannosylated glycans (PSA-lectin, FIG. 40B.) binding to the surfaces of feeder cells (MEF). The binding of the lectin reagents was inhibited by specific carbohydrate inhibitors, sialylα2-lactose and mannose, respectively (FIG. 40C. and 40D.). The results are summarized in Table 49.

Table 49 further represent differential recognition feeder and stem cells by two other lectins, *Ricinus communis* agglutinin (RCA, ricin lectin), known to recognize especially terminal Galβ-structures, especially GalβAGlc(NAc)-type structures and peanut agglutinin (PNA) reconnizing Gal/GalNAc structures. The cell surface expression of ligand for two other lectin RCA and PNA on hESC cells, but only RCA ligands of feeder cells.

The present results indicate and the invention is directed to the hESC glycans are potential targets for recognition by stem cell specific reagents. The invention is further directed to methods of specific recognition and/or separation of hESC and differentiated cells such as feeder cells by glycan structure specific reagents such as lectins. Human embryonic stem cells have a unique glycome that reflects their differentiation stage. The invention is specifically directed to analysis of cells according to the invention with regard to differentiation stage.

The results were also used to generate an algorithm for identification of hESC differentiation stage (FIG. 36). To test whether the obtained N-glycan profiles could be used for reliable identification of hESC and differentiated cells even with the presence of sanple-to-sample variation, a discrimination analysis was performed on the data The hESC line FES 29 and embryoid bodies derived from it (EB 29) were selected as the training group for the calculation that effectively discriminated the two samples (FIG. 36):

glycan score=a−b−c, wherein a is the sum of the relative abundances (%) of all signals with proposed compositions with two or more dHex (F≥2) in the sialylated N-glycan fraction, b is the sum of the relative abundances (%) of all signals with hybrid-type structures (ST=H), and c is the sum of the relative abundances (%) of all signals with proposed compositions with five or more HexNAc and equal amounts of Hex and HexNAc (H=N≥5); see Table 48 for structure codes and FIG. 39 for the dataset.

The resulting equation was applied to the other samples that served as the test group in the analysis and the results are described graphically in FIG. 36. hESC and the differentiated cell samples were clearly discriminated from each other (p<0.01, Student's t test). Furthermore, the st.3 differentiated cell samples were separated from the EB samples (p<0.05, Mann-Whitney test). The predicted 95% confidence intervals (assuming normal distribution of glycan scores within each cell type) are shown for the three cell types, indicating that a calculated glycan score has potential to discriminate all three cell types. At 96% confidence interval, hESC and the differentiated cell types (EB and st.3) were still discriminated from each other (not shown in the figure). The results indicate that glycome profiling is a tool for monitoring the differentiation status of stem cells.

Conclusions
  The present data represent the glycome profiling of hESC:
    hESC have a unique N-glycome comprising of over 100 glycan components
    Differentiation induces a major change in the N-glycome and the cell surface molecular landscape of hESC
  Utility of hESC glycome data:
    Identification of new stem cell markers for e.g. antibody development
    Quality control of stem cell products
    Identification of hESC differentiation stage
    Control of variation between hESC lines
    Effect of external factors and culture conditions on hESC status Especially Preferred Uses of the Data are
  Use of the hESC glycome for identification of specific cell surface markers characteristic for the pluripotent hESCs.
  The invention is directed to further analysis and production of present and analogous glycome data and use of the methods for further indentification of novel stem cell specific glycosylation features and form the basis for studies of hESC glycobiology and its eventual applications according to the invention Example 27

Identification of Specific Glycosylation Signatures from Glycan Profiles in Various Steps of Human Embryonic Stem Cell Differentiation To identify differentiation stage specific N-glycan signals in sialylated N-glycan profiles of hESC, EB, and stage 3 differentiated cells (see Example 26 above), major signals specific to either the undifferentiated (FIG. 41) or differentiated cells (FIG. 42) were selected based on their relative abundances in the database of the four hESC lines, and the four EB and st.3 cell samples derived from the four hESC lines, respectively. The selected glycan signal groups, from where indifferent glycan signals have been removed, have reduced noise or background and less observation points, but have the resolving power. Such selected signal groups and their patterns in different sample types serve as a signature for the identification of for example 1) undifferentiated hESC (FIG. 41), 2) differentiated cells, preferentially their differentiation stage relative to hESC (FIG. 42), 3) differentiation lineage, such as the neuroectodermally enriched st3 cells compared to the mixed cell population of EB (e.g. 1799), 4) glycan signals that are specific to hESC (e.g. 2953), 5) glycan signals that are specific to differentiated cells (e.g. 2644), or 6) glycan signals that have individual i.e. cell line specific variation (e.g. 1946 in cell line FES 22, 2133 in cell line FES 29, and 2222 in cell line FES 30). Moreover, glycan signals can be identified that do not change during hESC differentiation, including major glycans that can be considered as housekeeping glycans in hESC and their progeny (e.g. 1257, 1419, 1581, 1743, 1905 in FIG. 39A, and 2076 in FIG. 39.B). Proposed glycan compositions and structure groups for the signals are presented in Table 48.

To further analyze the data and to find the major glycan signals associated in given hESC differentiation stage, two variables were calculated for the comparison of glycan signals in the N-glycan profile dataset described above, between two samples:
1. absolute difference A=(S2−S1), and
2. relative difference R=A/S1,
wherein S1 and S2 are relative abundances of a given glycan signal in samples 1 (the four EB samples) and 2 (the four st.3 cell samples), respectively.

When A and R were calculated for the glycan profile datasets of the two cell types, and the glycan signals thereafter sorted according to the values of A and R, the most significant differing glycan signals between the two samples could be identified. Among the fifty most abundant neutral N-glycan signals in the data (FIG. 39A), the following five signals experienced the highest relative change R in the transition from EB to st3 differentiated cells in the dataset of four EB and four st.3 cell samples: 1825 (R=5.8, corresponding to 6.8-fold increase), 1136 (R=1.4, corresponding to 2.4 fold increase), 1339 (R=0.9, corresponding to 1.9 fold increase), 2142 (R=0.87, corresponding to 87% decrease), and 2174 (R=0.56, corresponding to 56% decrease). Four of these signals corresponded to complex-type structures (Table 48), indicating that the major differing glycan structures were included in the complex-type glycan group. However, the majority of the other complex-type glycan signals in the dataset were not observed to differ as significantly between the two cell types (i.e. they did not have large values of A and/or R), indicating that the procedure was able to identify st.3 cell and EB associated glycan subgroups within the whole complex-type glycan group. The one signal corresponding to hybrid-type structures (1136) had the highest value of the absolute differences A among all the glycan signals in the neutral N-glycan profiles (A=0.48), indicating that also this signal had significance in the discrimination between the EB and st.3 cell samples in the studied dataset.

EB derived from the hESC line FES 30 were different in their overall N-glycan profiles compared to the other three EB samples (FIG. 39) and had the differentiation-specific glycan score value closer to the hESC samples (FIG. 36), correlating with the property of EB 30 having less differentiated cell types than the other three EB. This was also seen in distinct glycan signals, e.g. 2222 in FIG. 39.B.

Example 28

Schematic Concepts of Glycome Change and Mass Spectrometric Screening

Introduction to Glycomics

All human cell types have unique glycome—an entity of all glycans of the cell, present mainly on cell surface (FIG. 43) glycoproteins and glycolipids, including the SSEA and Tra glycan antigens. However, the whole spectrum of hESC glycan structures (the stem cell glycome) is still unknown. Glycans, the complex carbohydrate structures, are capable of great structural variation and their specific molecular structures carry diverse biological information.

FIG. 43 represents schematically the changes of glycomes observed during the differentiation according to the invention. FIG. 32 represents schematically the glycome analysis, that was performed by MALDI-TOF mass spectrometry of glycans released from cells.

Example 29

Influence of Lectins on Stem Cell Proliferation Rate

Experimental Procedures

Lectins (EY laboratories, USA) were passively adsorbed on 48-well plates (Nunclon surface, catalog No 150687, Nunc, Denmark) by overnight incubation in phosphate buffered saline.

Human bone marrow derived mesenchymal stem cells (BM MSC) were cultured in minimum essential α-medium (α-MEM) supplemented with 20 mM HEPES, 10% FCS, penicillin-streptomycin, and 2 mM L-glutamine (all from Gibco) on 48-well plates coated with different lectins. Cells were cultivated in Cell IQ (ChipMan Technologies, Tampere, Finland) at +37° C. with 5% $CO_2$. Images were taken every 15 minutes. Data were analyzed with Cell IQ Analyzer software by analyzer protocol built by Dr. Ulla Impola (Finnish Red Cross Blood Service, Helsinki, Finland).

Results and Discussion

The growth rates of BM MSC varied on different lectin-coated surfaces compared to each other and uncoated plastic surface (Table 50), indicating that proteins with different glycan binding specificities binding to stem cell surface glycans specifically influence their proliferation rate.

Lectins that had an enhancing effect on BM MSC growth rate included in order of relative efficacy:
GS II (β-GlcNAc)>ECA (LacNAc/β-Gal)>PWA (I-branched poly-LacNAc)>LTA (α1,3-Fuc)>PSA (α-Man),
wherein the preferred oligosaccharide specificities of the lectins are indicated in parenthesis. However, PSA was nearly equal to plastic in the present experiments.

Lectins that had an inhibitory effect on BM MSC growth rate included in order of relative efficacy:
RCA (β-Gal/LacNAc)>>UEA (α1,2-Fuc)>WFA (β-GalNAc)>STA (linear poly-LacNAc)>NPA (α-Man)>SNA (α2,6-linked sialic acids)=MAA (α2,3-linked sialic acids/α3'-sialyl LacNAc),
wherein the preferred oligosaccharide specificities of the lectins are indicated in parenthesis. However, NPA, SNA, and MAA were nearly equal to plastic in the present experiments.

Example 30

Glycosphingolipid Glycans of Human Stem Cells

Experimental Procedures

Samples from MSC, CB MNC, and hESC grown on mouse fibroblast feeder cells were produced as described in the preceding Examples. Neutral and acidic glycosphingolipid fractions were isolated from cells essentially as described (Miller-Podraza et al., 2000). Glycans were detached by *Macrobdella decora* endoglycoceramidase digestion (Calbiochem, USA) essentially according to manuacturer's instructions, yielding the total glycan oligosaccharide fractions from the samples. The oligosaccharides were purified and analyzed by MALDI-TOF mass spectrometry as described in the preceding Examples for the protein-linked oligosaccharide fractions. Proposed compositions for the oligosaccharides and signal nomenclature are presented in Tables 52 and 53 for the neutral and acidic glycan fractions, respectively.

Results and Discussion

Human Embryonic Stem Cells (hESC)

hESC Neutral Lipid Glycans.

The analyzed mass spectrometric profile of the hESC glycosphingolipid neutral glycan fraction is shown in FIG. 45.

Structural Analysis of the Major Neutral Lipid Glycans.

The six major glycan signals, together comprising more than 90% of the total glycan signal intensity, corresponded to monosaccharide compositions $Hex_3HexNAc_1$ (730), $Hex_3HexNAc_1dHex_1$ (876), $Hex_2HexNAc_1$ (568), $Hex_3HexNAc_2$ (933), $Hex_4HexNAc_1$ (892), and $Hex_4HexNAc_2$ (1095).

In β1,4-galactosidase digestion, the relative signal intensities of 1095 and 730 were reduced by about 30% and 10%, respectively. This suggests that 730 and 1095 contain minor components with non-reducing terminal β1,4-Gal epitopes, preferably including the structures Galβ4GlcNAcLac and GalβGlcNAc[$Hex_1HexNAc_1$]Lac. The other major components were thus shown to contain other terminal epitopes. Further, the glycan signal $Hex_5HexNAc_3$ (1460) was digested to $Hex_3HexNAc_3$ (1136), indicating that the original signal contained glycan structures containing two β1,4-Gal.

The major glycan signals were not sensitive to α-galactosidase digestion.

In α1,3/4-fucosidase digestion, the signal intensity of 876 was reduced by about 10%, indicating that only a minor proportion of the glycan signal corresponded to glycans with α1,3- or α1,4-linked fucose residue. The major affected signal in the total profile was $Hex_3HexNAc_1dHex_2$ (1022), indicating that it included glycans with either α1,3-Fuc or α1,4-Fuc. 511 was reduced by about 30%, indicating that the signal contained a minor component with α1,2-Fuc, preferentially including Fucα2Galβ4Glc (Fucα2'Lac, 2'-fucosyllactose).

When the α1,3/4-fucosidase reaction product was further digested with α1,2-fucosidase, 876 was completely digested into 730, indicating that the structure of the majority of the signal intensity contained non-reducing terminal α1,2-Fuc, preferably including the structure Fucα2[$Hex_1HexNAc_1$]Lac, more preferably including Fucα2GalHexNAcLac. Another partly digested glycan signal was $Hex_4HexNAc_2dHex_1$ (1241) that was thus indicated to contain α1,2-Fuc, preferably including the structure Fucα2-[$Hex_2HexNAc_2$]Lac, more preferably including Fucα2Gal[$Hex_1HexNAc_2$]Lac. 511 was completely digested, indicating that the original signal contained a major component with α1,3/4-Fuc, preferentially including Galβ4(Fucα3)Glc (3-fucosyllactose).

When the α1,3/4-fucosidase and α1,2-fucosidase reaction product was further digested with β1,4-galactosidase, the majority of the newly formed 730 was not digested, i.e. the relative proportion of 568 was not increased compared to β1,4-galactosidase digestion without preceding fucosidase treatments. This indicated that the majority of 876 did not contain β1,4-Gal subterminal to Fuc. Further, 892 was not digested, indicating that it did not contain non-reducing terminal β1,4-Gal.

When the α1,3/4-fucosidase, α1,2-fucosidase, and β1,4-galactosidase reaction product was further digested with β1,3-galactosidase, the signal intensity of 892 was reduced, indicating that it included glycans with terminal β1,3-Gal. The signal intensity of 568 was increased relative to 730, indicating that also 730 included glycans with terminal β1,3-Gal.

The experimental structures of the major hESC glycosphingolipid neutral glycan signals were thus determined ('>' indicates the order of preference among the lipid glycan structures of hESC; '[ ]' indicates that the oligosaccharide sequence in brackets may be either branched or unbranched; '( )' indicates a branch in the structure):

| | |
|---|---|
| 730 | Hex$_3$HexNAc$_1$ > Hex$_1$HexNAc$_1$Lac > Galβ4GlcNAcLac |
| 876 | Hex$_3$HexNAc$_1$dHex$_1$ > Fucα2[Hex$_1$HecNAc$_1$]Lac > Fucα2Galβ4GlcNAcLac > Fucα3/4[Hex$_1$HecNAc$_1$]Lac |
| 568 | Hex$_2$HexNAc$_1$ > HecNAcLac |
| 933 | Hex$_3$HexNAc$_2$ > [Hex$_1$HecNAc$_2$]Lac |
| 892 | Hex$_4$HexNAc$_1$ > [Hex$_2$HecNAc$_1$]Lac > Galβ3[Hex$_1$HecNAc$_1$]Lac |
| 1095 | Hex$_4$HexNAc$_2$ > [Hex$_2$HecNAc$_2$]Lac > Galβ3HexNAc[Hex$_1$HecNAc$_1$]Lac > Galβ4GlcNAc[Hex$_1$HecNAc$_1$]Lac |
| 1460 | Hex$_5$HexNAc$_3$ > [Hex$_3$HecNAc$_3$]Lac > Galβ4GlcNAc(Galβ4GlcNAc)[Hex$_1$HecNAc$_1$]Lac |

Acidic Lipid Glycans.

Figure 46:
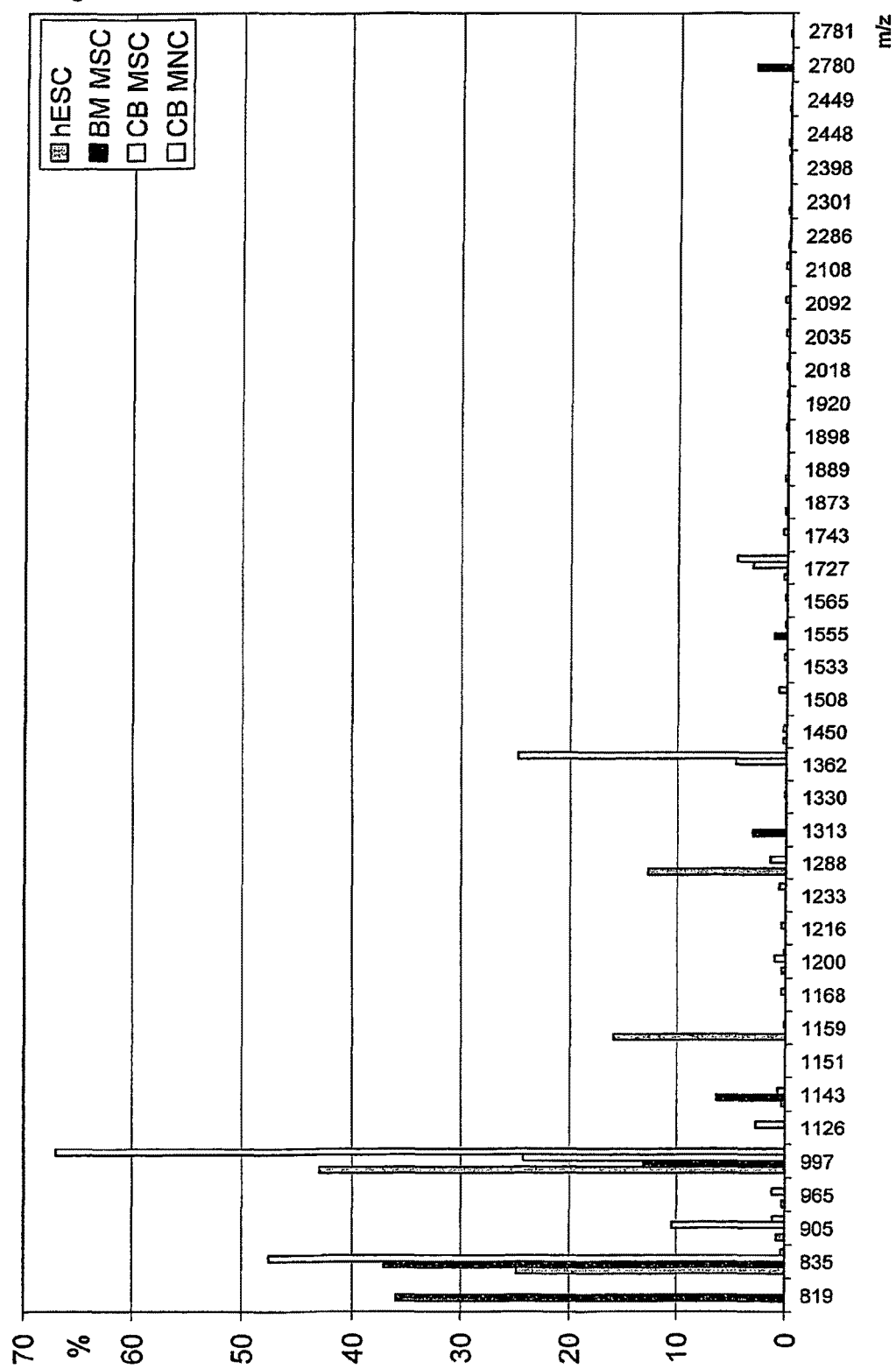
FIG. 46. MALDI-TOF mass spectrometric profile of isolated human stem cell acidic glycosphingolipid glycans. x-axis: approximate m/z values of $[M-H]^-$ ions as described in Table. y-axis: relative molar abundance of each glycan component in the profile. hESC, BM MSC, CB MSC, CB MNC: stem cell samples as described in the text.

The analyzed mass spectrometric profile of the hESC glycosphingolipid sialylated glycan fraction is shown in FIG. 46. The four major glycan signals, together comprising more than 96% of the total glycan signal intensity, corresponded to monosaccharide compositions NeuAc$_1$Hex$_3$HexNAc$_1$ (997), NeuAc$_1$Hex$_2$HexNAc$_1$ (835), NeuAc$_1$Hex$_4$HexNAc$_1$ (1159), and NeuAc$_2$Hex$_3$HexNAc$_1$ (1288).

The acidic glycan fraction was subjected to α2,3-sialidase digestion and the resulting neutral and acidic glycan fractions were purified and analyzed separately. In the acidic fraction, signals 1159 and 1288 were digested and 835 was partly digested. In the neutral fraction, signals 730 and 892 were the major appeared signals. These results indicated that: 1159 consisted mainly of glycans with α2,3-NeuAc, 1288 contained at least one α2,3-NeuAc, a major proportion of glycans in 835 contained α2,3-NeuAc, and in the original sample a major proportion of NeuAc$_{1-2}$Hex$_3$HexNAc$_1$ contained solely α2,3-linked NeuAc.

Human Mesenchymal Stem Cells (MSC)

Bone Marrow Derived (BM) MSC Neutral Lipid Glycans.

The analyzed mass spectrometric profile of the BM MSC glycosphingolipid neutral glycan fraction is shown in FIG. 45. The six major glycan signals, together comprising more than 94% of the total glycan signal intensity, corresponded to monosaccharide compositions Hex$_3$HexNAc$_1$ (730), Hex$_2$HexNAc$_1$ (568), Hex$_2$dHex$_1$ (511), Hex$_2$HexNAc$_2$dHex$_2$ (1063), Hex$_3$HexNAc$_2$dHex$_2$ (1225), and Hex$_3$HexNAc$_2$dHex$_1$ (1079). The four most abundant signals (730, 568, 511, and 1063) together comprised more than 75% of the total intensity.

Cord Blood Derived (CB) MSC Neutral Lipid Glycans.

The analyzed mass spectrometric profile of the CB MSC glycosphingolipid neutral glycan fraction is shown in FIG. 45. The ten major glycan signals, together comprising more than 92% of the total glycan signal intensity, corresponded to monosaccharide compositions Hex$_2$HexNAc$_1$ (568), Hex$_3$HexNAc$_1$ (730), Hex$_4$HexNAc$_2$ (1095), Hex$_5$HexNAc$_3$ (1460), Hex$_3$HexNAc$_2$ (933), Hex$_2$dHex$_1$ (511), Hex$_2$HexNAc$_2$dHex$_2$ (1063), Hex$_4$HexNAc$_3$ (1298), Hex$_3$HexNAc$_2$dHex$_2$ (1225), and Hex$_2$HexNAc$_2$ (771). The five most abundant signals (568, 730, 1095, 1460, and 933) together comprised more than 82% of the total intensity.

In β1,4-galactosidase digestion, the relative signal intensities of 1095, 1460, and 730 were reduced by about 90%, 95%, and 20%, respectively. This suggests that CB MSC contained major glycan components with non-reducing terminal β1,4-Gal epitopes, preferably including the structures Galβ4GlcNAcβ[Hex$_1$HexNAc$_1$]Lac, Galβ4GlcNAc[Hex$_2$HexNAc$_2$]Lac, and Galβ4GlcNAcLac. Further, the glycan signal Hex$_5$HexNAc$_3$ (1460) was digested into Hex$_4$HexNAc$_3$ (1298) and mostly into Hex$_3$HexNAc$_3$ (1136), indicating that the original signal contained glycan structures containing either one or two β1,4-Gal, and that the majority of the original glycans contained two β1,4-Gal, preferentially including the structure Galβ4GlcNAc(Galβ4GlcNAc)[Hex$_1$HexNAc$_1$]Lac. Similarly, 1095 was digested into Hex$_2$HexNAc$_2$ (771) in addition to 933, indicating that the original signal contained glycan structures containing either one or two β1,4-Gal, and that the minority of the original glycans contained two β1,4-Gal, preferentially including the structure Galβ4GlcNAc(Galβ4GlcNAc)Lac.

The experimental structures of the major CB MSC glycosphingolipid neutral glycan signals were thus determined ('>' indicates the order of preference among the lipid glycan structures of hESC; '[ ]' indicates that the oligosaccharide sequence in brackets may be either branched or unbranched; '( )' indicates a branch in the structure):

| | |
|---|---|
| 568 | Hex$_2$HexNAc$_1$ > HecNAcLac |
| 730 | Hex$_3$HexNAc$_1$ > Hex$_1$HexNAc$_1$Lac > Galβ4GlcNAcLac |
| 1095 | Hex$_4$HexNAc$_2$ > [Hex$_2$HecNAc$_2$]Lac > Galβ4GlcNAc[Hex$_1$HecNAc$_1$]Lac > Galβ4GlcNAc(Galβ4GlcNAc)Lac |
| 1460 | Hex$_5$HexNAc$_3$ > [Hex$_3$HecNAc$_3$]Lac > Galβ4GlcNAc[Hex$_2$HecNAc$_2$]Lac > Galβ4GlcNAc(Galβ4GlcNAc)[Hex$_1$HecNAc$_1$]Lac |
| 933 | Hex$_3$HexNAc$_2$ > Hex$_1$HexNAc$_2$Lac |

Sialylated Lipid Glycans.

The analyzed mass spectrometric profile of the hESC glycosphingolipid sialylated glycan fraction is shown in FIG. 46. The five major glycan signals of BM MSC, together comprising more than 96% of the total glycan signal intensity, corresponded to monosaccharide compositions NeuAc$_1$Hex$_2$HexNAc$_1$ (835), NeuAc$_1$Hex$_1$HexNAc$_1$dHex$_1$ (819), NeuAc$_1$Hex$_3$HexNAc$_1$ (997), NeuAc$_1$Hex$_3$HexNAc$_1$dHex$_1$ (1143), and NeuAc$_2$Hex$_1$HexNAc$_2$dHex$_1$ (1313). The six major glycan signals of CB MSC, together comprising more than 92% of the total glycan signal intensity, corresponded to monosaccharide compositions NeuAc$_1$Hex$_2$HexNAc$_1$ (835), NeuAc$_1$Hex$_3$HexNAc$_1$ (997), NeuAc$_2$Hex$_2$ (905), NeuAc$_1$Hex$_4$HexNAc$_2$ (1362), NeuAc$_1$Hex$_5$HexNAc$_3$ (1727), and NeuAc$_2$Hex$_2$HexNAc$_1$ (1126).

Human Cord Blood Mononuclear Cells (CB MNC)

CB MNC Neutral Lipid Glycans.

The analyzed mass spectrometric profile of the CB MNC glycosphingolipid neutral glycan fraction is shown in FIG. 45. The five major glycan signals, together comprising more than 91% of the total glycan signal intensity, corresponded to monosaccharide compositions $Hex_3HexNAc_1$ (730), $Hex_2HexNAc_1$ (568), $Hex_3HexNAc_1dHex_1$ (876), $Hex_4HexNAc_2$ (1095), and $Hex_4HexNAc_2dHex_1$ (1241).

In β1,4-galactosidase digestion, the relative signal intensities of 730 and 1095 were reduced by about 50% and 90%, respectively. This suggests that the signals contained major components with non-reducing terminal β1,4-Gal epitopes, preferably including the structures Galβ4GlcNAcβLac and Galβ4GlcNAcβ[$Hex_1HexNAc_1$]Lac. Further, the glycan signal $Hex_5HexNAc_3$ (1460) was digested to Hex4HexNAc3 (1298) and $Hex_3HexNAc_3$ (1136), indicating that the original signal contained glycan structures containing either one or two β1,4-Gal.

The experimental structures of the major CB MNC glycosphingolipid neutral glycan signals were thus determined ('>' indicates the order of preference among the lipid glycan structures of hESC; '[ ]' indicates that the oligosaccharide sequence in brackets may be either branched or unbranched; '( )' indicates a branch in the structure):

| | |
|---|---|
| 730 | $Hex_3HexNAc_1$ > $Hex_1HexNAc_1$Lac > Galβ4GlcNAcLac |
| 568 | $Hex_2HexNAc_1$ > HecNAcLac |
| 876 | $Hex_3HexNAc_1dHex_1$ > [$Hex_1HecNAc_1dHex_1$]Lac > Fuc[$Hex_1HecNAc_1$]Lac |
| 1095 | $Hex_4HexNAc_2$ > [$Hex_2HecNAc_2$]Lac > Galβ4GlcNAc[$Hex_1HecNAc_1$]Lac |
| 1241 | $Hex_4HexNAc_2dHex_1$ > [$Hex_2HecNAc_2dHex_1$]Lac > Fuc[$Hex_2HecNAc_2$]Lac |
| 1460 | $Hex_5HexNAc_3$ > [$Hex_3HecNAc_3$]Lac > Galβ4GlcNAc[$Hex_2HecNAc_2$]Lac > Galβ4GlcNAc(Galβ4GlcNAc)[$Hex_1HecNAc_1$]Lac |

Sialylated Lipid Glycans.

The analyzed mass spectrometric profile of the CB MNC glycosphingolipid sialylated glycan fraction is shown in FIG. 46. The three major glycan signals of CB MNC, together comprising more than 96% of the total glycan signal intensity, corresponded to monosaccharide compositions $NeuAc_1Hex_3HexNAc_1$ (997), $NeuAc_1Hex_4HexNAc_2$ (1362), and $NeuAc_1Hex_5HexNAc_3$ (1727).

Overview of Human Stem Cell Glycosphingolipid Glycan Profiles

The neutral glycan fractions of all the present sample types altogether comprised 45 glycan signals. The proposed monosaccharide compositions of the signals were composed of 2-7 Hex, 0-5 HexNAc, and 0-4 dHex. Glycan signals were detected at monoisotopic m/z values between 511 and 2263 (for [M+Na]$^+$ ion).

Major neutral glycan signals common to all the sample types were 730, 568, 1095, and 933, corresponding to the glycan structure groups $Hex_{0-1}HexNAc_1$Lac (568 or 730) and $Hex_{1-2}HexNAc_2$Lac (933 or 1095), of which the former glycans were more abundant and the latter less abundant. A general formula of these common glycans is $Hex_mHexNAc_n$-Lac, wherein m is either n or n−1, and n is either 1 or 2.

Neutral Glycolipid Profiles of Human Stem Cell Types:

Glycan signals typical to hESC preferentially include 876 and 892 (especially compared to MSC); the former preferentially corresponds to FucHexHexNAcLac, wherein α1,2-Fuc is preferential to α1,3/4-Fuc, and the latter preferentially corresponds to $Hex_2HexNAcLac$, and more preferentially to Galβ3[$Hex_1HexNAc_1$]Lac; the glycan core composition $Hex_4HexNAc_1$ was especially characteristic of hESC compared to other human stem cell types, in addition to fucosylation and more preferentially α1,2-linked fucosylation.

Glycan signals typical to both CB and BM MSC preferentially include 771, 1063, 1225; more preferentially including compositions $dHex_{0/2}Hex_{0-1}HexNAc_2Lac$.

Glycan signals typical to especially BM MSC preferentially include 511 and fucosylated structures, preferentially multifucosylated structures.

Glycan signals typical to especially CB MSC preferentially include 1460 and 1298, as well as large neutral glycolipids, especially $Hex_{2-3}HexNAc_3Lac$. In addition, low fucosylation and/or high expression of terminal β1,4-Gal was typical to especially CB MSC.

Glycan signals typical to CB MNC preferentially include compositions $dHex_{0-1}[HexHexNAc]_{1-2}Lac$, more preferentially high relative amounts of 730 compared to other signals; and fucosylated structures; and glycan profiles with less variability and/or complexity than other stem cell types.

The acidic glycan fractions of all the present sample types altogether comprised 38 glycan signals. The proposed monosaccharide compositions of the signals were composed of 0-2 NeuAc, 2-9 Hex, 0-6 HexNAc, 0-3 dHex, and/or 0-1 sulphate or phosphate esters. Glycan signals were detected at monoisotopic m/z values between 786 and 2781 (for [M-H]$^-$ ion).

The acidic glycosphingolipid glycans of CB MNC were mainly composed of $NeuAc_1Hex_{n+2}HexNAc_n$, wherein 1≤n≤3, indicating that their structures were NeuAc$_1$ [HexHexNAc]$_{1-3}$Lac.

Terminal glycan epitopes that were demonstrated in the present experiments in stem cell glycosphingolipid glycans include:

Gal
Galβ4Glc (Lac)
Galβ4GlcNAc (LacNAc type 2)
Galβb 3
Non-reducing terminal HexNAc
Fuc
α1,2-Fuc
α1,3-Fuc
Fucα2Gal
Fucα2Galβ4GlcNAc (H type 2)
Fucα2Galβ4Glc (2'-fucosyllactose)
Fucα3GlcNAc
Galβ4(Fucα3)GlcNAc (Lex)
Fucα3Glc
Galβ4(Fucα3)Glc (3-fucosyllactose)
Neu5Ac
Neu5Acα2,3
Neu5Acα2,6

Development-Related Glycan Epitope Expression.

According to the present invention, the glycosphingolipid glycan composition $Hex_4HexNAc_1$ preferentially corresponds to (iso)globo structures. The glycan sequence of the SSEA-3 glycolipid antigen has been determined to be Galβ3GalNAcβ3Galα4Galβ4Glc, which corresponds to the glycan signal $Hex_4HexNAc_1$ (892) detected in the present experiments only in hESC. Similarly, the glycan sequence of the SSEA-4 glycolipid antigen has been determined to be NeuAcα3Galβ3GalNAcβ3Galα4Galβ4Glc, which corresponds to the glycan signal $NeuAc_1Hex_4HexNAc_1$ (1159) detected in the present experiments only in hESC. Consistent with the present glycan structure analyses, the hESC samples were determined to be SSEA-3 and SSEA-4 positive by monoclonal antibody staining as described in the preceding Examples. In contrast to mouse ES cells, hESC do not express the SSEA-1 antigen; consistent with this we found only low expression levels of α1,3/4-fucosylated neutral glycolipid glycans. In contrast, we were able to show that the major fucosylated structures of hESC glycosphingolipid glycans contain α1,2-Fuc, which is a molecular level explanation to the mouse-human difference in SSEA-1 reactivity.

Example 31

Stem Cell O-glycan Structural Analysis

Results and Discussion

Total de-N-glycosylated protein pool of the hESC line FES 29, which was already treated with N-glycosidase F to get rid of N-glycans, was subjected to non-reductive β-elimination to harvest the total hESC O-glycan pool as described in the preceding Examples. The liberated glycans were purified, divided into neutral and acidic fractions, and analyzed by MALDI-TOF mass spectrometry as described.

Structural Analysis of the Major Neutral O-Glycans.

The two major [M+Na]+ glycan signals emerging from the O-glycan pool were m/z 771 (Hex2HexNAc2) and 917 (Hex2HexNAc2dHex1). O-glycans were then treated with β1,4-galactosidase as described in the preceding Examples. The m/z 771 glycan signal was sensitive to this treatment, indicating that the corresponding hESC neutral O-glycans had preferentially contained non-reducing terminal β1,4-linked Gal.

Structural Analysis of the Major Acidic O-Glycans.

The five major [M-H]− glycan signals emerging from the O-glycan pool were 964.35 (NeuAc2HexHexNAc), 1038.49 (NeuAc1Hex2HexNAc2), 1329.56 (NeuAc2Hex2HexNAc2), 1403.62 (NeuAc1Hex3HexNAc3), and 1768.75 (NeuAc1Hex4HexNAc4).

O-glycans were then treated with α2,3-sialidase as described in the preceding Examples. All these major peaks were absent in the mass spectrum recorded after this treatment. The loss of this glycan series consisting of sialic acid with varying number of HexHexNAc disaccharide indicated that the corresponding hESC acidic O-glycans had contained preferentially α2,3-linked sialic acids. In addition, the signal at m/z 1329.56 containing two sialic acids disappeared, indicating that both sialic acids were preferentially α2,3-linked.

The substrate specificity of α2,3-sialidase was tested in parallel experiments using two synthetic oligosaccharides, namely NeuAcα2,3Galβ1,4GlcNAcβ1,3Galβ1,4Glc and NeuAcα2,6[Galβ1,4GlcNAβ1,3(Galβ1,4GlcNAcβ1,6)] Galβ1,4Glc. The enzyme specifically hydrolyzed α2,3-linked sialic acids and left α2,6-linked sialic acids intact.

Example 32

Lectin Based Selection of CB MNC Cell Populations

The FACS experiments with fluorescein-labeled lectins and CB MNC were performed essentially similarly to Example 20. Double stainings were performed with CD34 specific monoclonal antibody (Jaatinen et al., 2006) with complementary fluorescent dye. Erythroblast depletion from CD MNC fraction was performed by anti-glycophorin A (GlyA) monoclonal antibody negative selection.

Results and Discussion

Compared to the CB MNC fraction, GlyA depleted CB MNC showed decreased staining in FACS with the following lectins (the decrease in % in parenthesis): PWA (48%), LTA (59%), UEA (34%), STA, MAA, and PNA (all latter three less than 23%); indicating that GlyA depletion increased the resolving power of the lectins in cell sorting.

In FACS double staining with both fluorescein-labeled lectins and anti-CD34 antibody, the following lectins colocalized with CD34+ cells: STA (3/3 samples), HHA (3/3 samples), PSA (3/3 samples), RCA (3/3 samples), and partly also NPA (2/3 samples). In contrast, the following lectins did not colocalize with CD34+ cells: GNA (3/3 samples) and PWA (3/3 samples), and partly also LTA (2/3 samples), WFA (2/3 samples), and GS-II (2/3 samples).

Taken together with the results of Example 21, the present results indicate that lectins can enrich CD34+ cells from CB MNC by both negative and positive selection, for example:
1) GNA binds to about 70% of CB MNC but not to CD34+ cells, leading to about 3× enrichment in negative selection of CB MNC in CD34+ cell isolation.
2) STA binds to about 50% of CB MNC and also to CD34+ cells, leading to about 2× enrichment in positive selection of CB MNC in CD34+ cell isolation.
3) UEA binds to about 50% of CB MNC and also to CD34+ cells, leading to about 2× enrichment in positive selection of CB MNC in CD34+ cell isolation.

Example 33

Galectin Gene Expression Profiles of Stem Cells

Experimental Procedures

Gene expression analysis of CB CD133+ cells has been described (Jaatinen et al., 2006) and the present analysis was performed essentially similarly. The galectins whose gene expression profile was analyzed included (corresponding Affymetrix codes in parenthesis): Galectin-1 (201105_at), galectin-2 (208450_at), galectin-3 (208949_s_at), galectin-4 (204272_at), galectin-6 (200923_at), galectin-7 (206400_at), galectin-8 (208933_sat), galectin-9 (203236_s_at), galectin-10 (206207_at), galectin-13 (220158_at).

Results and Discussion

In CB CD133+ versus CD133−, as well as CD34+ versus CD34− CB MNC cells, the galectin gene expression profile was as follows: Overall, galectins 1, 2, 3, 6, 8, 9, and 10 showed gene expression in both CD34+/CD133+ cells. Galectins 1, 2, and 3 were downregulated in both CD34+/CD133+ cells with respect to CD34−/CD133− cells, and in addition galectin 10 was downregulated in CD133+ cells with respect to CD133− cells. In contrast, in both CD34+/CD133+ cells galectin 8 was upregulated with respect to CD34−/CD133− cells.

In hESC versus EB samples, the galectin gene expression profile was as follows: Overall, galectins 1, 3, 6, 8, and 13 showed gene expression in hESC. Galectin 3 was clearly downregulated with respect to EB, and in addition galectin 13 was downregulated in 2 out of 4 hESC lines. In contrast, galectin 1 was clearly upregulated in all hESC lines.

The results indicate that both CB CD34+/CD133+ stem cell populations and hESC have an interesting and distinct galectin expression profiles, leading to different galectin ligand affinity profiles (Hirabayashi et al., 2002). The results further correlate with the glycan analysis results showing abundant galectin ligand expression in these stem cells, especially non-reducing terminal β-Gal and type II LacNAc, poly-LacNAc, β1,6-branched poly-LacNAc, and complex-type N-glycan expression.

TABLE 1

Preferred neutral glycan compositions. Calculated mass-to-charge ratios (calc. m/z) refer to the first isotope signal of [M + Na]$^+$ ion.

| Proposed composition | calc. m/z |
|---|---|
| HexHexNAc | 406.13 |
| Hex3 | 527.16 |
| HexHexNAcdHex | 552.19 |
| Hex2HexNAc | 568.19 |
| HexHexNAc2 | 609.21 |
| Hex4 | 689.21 |
| Hex2HexNAcdHex | 714.24 |
| Hex3HexNAc | 730.24 |
| HexHexNAc2dHex | 755.27 |
| Hex2HexNAc2 | 771.26 |
| HexHexNAc3 | 812.29 |
| Hex5 | 851.26 |
| Hex2HexNAcdHex2 | 860.30 |
| Hex4HexNAc | 892.29 |
| HexHexNAc2dHex2 | 901.33 |
| Hex2HexNAc2dHex | 917.32 |
| Hex3HexNAc2 | 933.32 |
| HexHexNAc3dHex | 958.35 |
| Hex2HexNAc3 | 974.34 |
| Hex2HexNAcdHex3 | 1006.36 |
| Hex6 | 1013.32 |
| HexHexNAc4 | 1015.37 |
| Hex3HexNAcdHex2 | 1022.35 |
| Hex5HexNAc | 1054.34 |
| Hex2HexNAc2dHex2 | 1063.38 |
| Hex3HexNAc2dHex | 1079.38 |
| Hex4HexNAc2 | 1095.37 |
| HexHexNAc3dHex2 | 1104.41 |
| Hex2HexNAc3dHex | 1120.40 |
| Hex3HexNAc3 | 1136.40 |
| Hex2HexNAcdHex4 | 1152.42 |
| HexHexNAc4dHex | 1161.43 |
| Hex7 | 1175.37 |
| Hex2HexNAc4 | 1177.42 |
| Hex2HexNAc2dHex3 | 1209.44 |
| Hex6HexNAc | 1216.40 |
| HexHexNAc5 | 1218.45 |
| Hex3HexNAc2dHex2 | 1225.43 |
| Hex4HexNAc2dHex | 1241.43 |
| Hex5HexNAc2 | 1257.42 |
| Hex2HexNAc3dHex2 | 1266.46 |
| Hex3HexNAc3dHex | 1282.45 |
| Hex4HexNAc3 | 1298.45 |
| HexHexNAc4dHex2 | 1307.49 |
| Hex2HexNAc4dHex | 1323.48 |
| Hex8 | 1337.42 |
| Hex3HexNAc4 | 1339.48 |
| Hex2HexNAc2dHex4 | 1355.50 |
| HexHexNAc5dHex | 1364.51 |
| Hex3HexNAc2dHex3 | 1371.49 |
| Hex7HexNAc | 1378.45 |
| Hex4HexNAc2dHex2 | 1387.49 |
| Hex2HexNAc5 | 1380.50 |
| Hex5NexNAc2dHex | 1403.48 |
| Hex2HexNAc3dHex3 | 1412.52 |
| Hex6HexNAc2 | 1419.48 |
| HexHexNAc6 | 1421.53 |
| Hex3HexNAc3dHex2 | 1428.51 |
| Hex4HexNAc3dHex | 1444.51 |
| HexHexNAc4dHex3 | 1453.54 |
| Hex5HexNAc3 | 1460.50 |
| Hex2HexNAc4dHex2 | 1469.54 |
| Hex3HexNAc4dHex | 1485.53 |
| Hex9 | 1499.48 |
| Hex4HexNAc4 | 1501.53 |
| HexHexNAc5dHex2 | 1510.57 |
| Hex3HexNAc2dHex4 | 1517.55 |
| Hex3HexNAc5dHex | 1526.56 |
| Hex4HexNAc2dHex3 | 1533.54 |
| Hex8HexNAc | 1540.50 |
| Hex3HexNAc5 | 1542.56 |
| Hex5HexNAc2dHex2 | 1549.54 |
| Hex6HexNAc2dHex | 1565.53 |
| Hex3HexNAc3dHex3 | 1574.57 |
| Hex7HexNAc2 | 1581.53 |
| Hex2HexNAc6 | 1583.58 |
| Hex4HexNAc3dHex2 | 1590.57 |
| Hex5HexNAc3dHex | 1606.56 |
| Hex2HexNAc4dHex3 | 1615.60 |
| Hex6HexNAc3 | 1622.56 |
| Hex3HexNAc4dHex2 | 1631.59 |
| Hex4HexNAc4dHex | 1647.59 |
| Hex10 | 1661.53 |
| Hex5HexNAc4 | 1663.58 |
| Hex2HexNAc5dHex2 | 1672.62 |
| Hex3HexNAc5dHex | 1688.61 |
| Hex5HexNAc2dHex3 | 1695.60 |
| Hex9HexNAc | 1702.56 |
| Hex4HexNAx5 | 1704.61 |
| Hex6HexNAc2dHex2 | 1711.59 |
| Hex3HexNAc2dHex4 | 1720.63 |
| Hex7HexNAc2dHex | 1727.59 |
| Hex2HexNAc6dHex | 1729.64 |
| Hex4HexNAc3dHex3 | 1736.62 |
| Hex8HexNAc2 | 1743.58 |
| Hex3HexNAc6 | 1745.64 |
| Hex5HexNAc3dHex2 | 1752.62 |
| Hex6HexNAc3dHex | 1768.61 |
| Hex3HexNAc4dHex3 | 1777.65 |
| Hex7HexNAc3 | 1784.61 |
| Hex4HexNAc4dHex2 | 1793.64 |
| Hex5HexNAc4dHex | 1809.64 |
| Hex2HexNAc5dHex3 | 1818.68 |
| Hex11 | 1823.58 |
| Hex6HexNAc4 | 1825.63 |
| Hex3HexNAc5dHex2 | 1834.67 |
| Hex4HexNAc5dHex | 1850.67 |
| Hex6HexNAc2dHex3 | 1857.65 |
| Hex10HexNAc | 1864.61 |
| Hex5HexNAc5 | 1866.66 |
| Hex7HexNAc2dHex2 | 1873.64 |
| Hex2HexNAc6dHex2 | 1875.70 |
| Hex4HexNAc3dHex4 | 1882.68 |
| Hex8HexNAc2dHex | 1889.64 |
| Hex3HexNAc6dHex | 1891.69 |
| Hex5HexNAc3dHex3 | 1898.68 |
| Hex9HexNAc2 | 1905.63 |
| Hex4HexNAc6 | 1907.69 |
| Hex6HexNAc3dHex2 | 1914.67 |
| Hex3HexNAc4dHex4 | 1923.71 |
| Hex7HexNAc3dHex | 1930.67 |
| Hex2HexNAc7dHex | 1932.72 |
| Hex4HexNAc4dHex3 | 1939.70 |
| Hex8HexNAc3 | 1946.66 |
| Hex5HexNAc4dHex2 | 1955.70 |
| Hex6HexNAc4dHex | 1971.69 |
| Hex3HexNAc5dHex3 | 1980.73 |
| Hex12 | 1985.63 |
| Hex7HexNAc4 | 1987.69 |
| Hex4HexNAc5dHex2 | 1996.72 |
| Hex5HexNAc5dHex | 2012.72 |
| Hex7HexNAc2dHex3 | 2019.70 |
| Hex2HexNAc6dHex3 | 2021.76 |
| Hex11HexNAc | 2026.66 |
| Hex6HexNAc5 | 2028.71 |
| Hex8HexNAc2dHex2 | 2035.70 |
| Hex3HexNAc6dHex2 | 2037.75 |
| Hex5HexNAc3dHex4 | 2044.73 |
| Hex4HexNAc6dHex | 2053.75 |
| Hex6HexNAc3dHex3 | 2060.73 |
| Hex10HexNAc2 | 2067.69 |
| Hex5HexNAc6 | 2069.74 |
| Hex7HexNAc3dHex2 | 2076.72 |
| Hex2HexNAc7dHex2 | 2078.78 |
| Hex4HexNAc4 | 2085.76 |
| Hex8HexNAc3dHex | 2092.72 |
| Hex3HexNAc7dHex | 2094.77 |
| Hex5HexNAc4dHex3 | 2101.76 |
| Hex9HexNAc3 | 2108.71 |
| Hex4HexNAc7 | 2110.77 |

TABLE 1-continued

Preferred neutral glycan compositions. Calculated mass-to-charge ratios (calc. m/z) refer to the first isotope signal of [M + Na]⁺ ion.

| Proposed composition | calc. m/z |
|---|---|
| Hex6HexNAc4dHex2 | 2117.75 |
| Hex3HexNAc5dHex4 | 2126.79 |
| Hex7HexNAc4dHex | 2133.75 |
| Hex4HexNAc5dHex3 | 2142.78 |
| Hex13 | 2147.69 |
| Hex8HexNAc4 | 2149.74 |
| Hex5HexNAc5dHex2 | 2158.78 |
| Hex6HexNAc5dHex | 2174.77 |
| Hex8HexNAc2dHex3 | 2181.76 |
| Hex3HexNAc6dHex3 | 2183.81 |
| Hex12HexNac | 2188.71 |
| Hex7HexNAc5 | 2190.77 |
| Hex4HexNAc6dHex2 | 2199.80 |
| Hex5HexNAc6dHex | 2215.80 |
| Hex7HexNAc3dHex3 | 2222.78 |
| Hex2HexNAc7dHex3 | 2224.84 |
| Hex11HexNAc2 | 2229.74 |
| Hex6HexNAc6 | 2231.79 |
| Hex8HexNAc3dHex2 | 2238.78 |
| Hex3HexNAc7dHex2 | 2240.83 |
| Hex5HexNAc4dHex4 | 2247.81 |
| Hex4HexNAc7dHex | 2256.83 |
| Hex6HexNAc4dHex3 | 2263.81 |
| Hex5HexNAc7 | 2272.82 |
| Hex7HexNAc4dHex2 | 2279.80 |
| Hex4HexNAc5dHex4 | 2288.84 |
| Hex5HexNAc5dHex3 | 2304.84 |
| Hex14 | 2309.74 |
| Hex9HexNAc4 | 2311.79 |
| Hex6HexNAc5dHex2 | 2320.83 |
| Hex7HexNAc5dHex | 2336.82 |
| Hex4HexNAc6dHex3 | 2345.86 |
| Hex8HexNAc5 | 2352.82 |
| Hex5HexNAc6dHex2 | 2361.86 |
| Hex6HexNAc6dHex | 2377.85 |
| Hex8HexNAc3dHex3 | 2384.83 |
| Hex3HexNAc7dHex3 | 2386.89 |
| Hex12HexNac2 | 2391.79 |
| Hex7HexNAc6 | 2393.85 |
| Hex4HexNAc7dHex2 | 2402.88 |
| Hex6HexNAc4dHex4 | 2409.87 |
| Hex5HexNAc7dHex | 2418.88 |
| Hex7HexNAc4dHex3 | 2425.86 |
| Hex6HexNAc7 | 2434.87 |
| Hex5HexNAc5dHex4 | 2450.89 |
| Hex6HexNAc5dHex3 | 2466.89 |
| Hex15 | 2471.79 |
| Hex7HexNAc5dHex2 | 2482.88 |
| Hex8HexNAc5dHex | 2498.88 |
| Hex5HexNAc6dHex3 | 2507.91 |
| Hex6HexNAc6dHex2 | 2523.91 |
| Hex7HexNAc6dHex | 2539.90 |
| Hex4HexNAc7dHex3 | 2548.94 |
| Hex13HexNAc2 | 2553.85 |
| Hex8HexNAc6 | 2555.90 |
| Hex5HexNAc7dHex2 | 2564.94 |
| Hex6HexNAc7dHex | 2580.93 |
| Hex6HexNAc5dHex4 | 2612.95 |
| Hex7HexNAc5dHex3 | 2628.94 |
| Hex16 | 2633.85 |
| Hex8HexNAc5dHex2 | 2644.94 |
| Hex6HexNAc6dHex3 | 2669.97 |
| Hex7HexNAc6dHex2 | 2685.96 |
| Hex5HexNAc7dHex3 | 2710.99 |
| Hex14HexNAc2 | 2715.90 |
| Hex6HexNAc7dHex2 | 2726.99 |
| Hex7HexNAc7dHex | 2742.98 |
| Hex8HexNAc7 | 2758.98 |
| Hex7Hexnac5dHex4 | 2775.00 |
| Hex8HexNAc5dHex3 | 2790.99 |
| Hex17 | 2795.90 |
| Hex7HexNAc6dHex3 | 2832.02 |
| Hex16HexNAc | 2836.92 |
| Hex9HexNAc6dHex | 2864.01 |
| Hex6HexNAc7dHex3 | 2873.05 |
| Hex15HexNAc2 | 2877.95 |
| Hex8HexNAc7dHex | 2905.04 |
| Hex8Hexnac5dHex4 | 2937.05 |
| Hex18 | 2957.95 |
| Hex7HexNAc6dHex4 | 2978.08 |
| Hex17HexNAc | 2998.98 |
| Hex8HexNAc7dHex2 | 3051.09 |
| Hex9HexNAc8 | 3124.11 |
| Hex8HexNAc6dHex4 | 3140.13 |
| Hex8HexNAc7dHex3 | 3197.15 |
| Hex9HexNAc8dHex/ Hex7HexNAc6dHex6 | 3270.17 |
| Hex9HexNAc6dHex4 | 3302.18 |
| Hex8HexNAc7dHex4 | 3343.21 |
| Hex9HexNAc8dHex2 | 3416.23 |
| Hex10HexNAc6dHex4 | 3464.24 |
| Hex10HexNAc9 | 3489.24 |
| Hex9HexNAc8dHex3 | 3562.28 |
| Hex11HexNAc6dHex4 | 3626.29 |
| Hex10HexNAc9dHex | 3635.30 |
| Hex9HexNAc8dHex4 | 3708.34 |
| Hex10HexNAc9dHex2/ Hex8HexNAc7dHex7 | 3781.36 |
| Hex9HexNAc8dHex5/ Hex7HexNAc6dHex10 | 3854.40 |

TABLE 2

Preferred acidic glycan compositions. Calculated mass-to-charge ratios (calc. m/z) refer to the first isotope signal of [M – H]⁻ ion.

| Proposed composition | calc. m/z |
|---|---|
| NeuAcHexHexNAc | 673.23 |
| NeuAcHexHexNAcdHex | 819.29 |
| NeuAcHex2HexNAc | 835.28 |
| NeuAcHexHexNAc2 | 876.31 |
| NeuAc2HexHexNAc | 964.33 |
| NeuAcHexHexNAcdHex2 | 965.35 |
| NeuAcHex2HexNAcdHex | 981.34 |
| Hex3HexNAc2SP | 989.28 |
| NeuAcHex3HexNAc | 997.34 |
| NeuAcHexHexNAc2dHex | 1022.37 |
| NeuAcHex2HexNAc2 | 1038.36 |
| NeuAcHexHexNAc3 | 1079.39 |
| NeuAc2HexHexNAcdHex | 1110.38 |
| NeuAc2Hex2HexNAc | 1126.38 |
| NeuAcHex2HexNAcdHex2 | 1127.40 |
| NeuAcHex3HexNAcdHex | 1143.39 |
| Hex4HexNAc2SP | 1151.33 |
| NeuAcHex4HexNAc | 1159.39 |
| NeuAc2HexHexNAc2 | 1167.41 |
| NeuAcHexHexNAc2dHex2 | 1168.43 |
| NeuAcHex2HexNAc2dHex | 1184.42 |
| Hex3HexNAc3SP | 1192.36 |
| NeuAcHex3HexNAc2/ NeuGcHex2HexNAc2dHex | 1200.42 |
| NeuGcHex3HexNAc2 | 1216.41 |
| NeuAcHexHexNAc3dHex | 1225.45 |
| NeuAcHex2HexNAc3 | 1241.44 |
| NeuAc2Hex2HexNAcdHex | 1272.44 |
| NeuAcHexHexNAc4 | 1282.47 |
| NeuAc2Hex3HexNAc | 1288.43 |
| NeuAcHex4HexNAcdHex | 1305.45 |
| NeuAc2HexHexNAc2dHex | 1313.46 |
| NeuAcHex5HexNAc/ NeuAcHex2HexNAc3SP | 1321.44/ 1321.40 |
| NeuAc2Hex2HexNAc2/ NeuGcNeuAcHexHexNAc2dHex | 1329.46 |
| NeuAcHex2HexNAc2dHex2 | 1330.48 |
| Hex3HexNAc3dHexSP | 1338.41 |

TABLE 2-continued

Preferred acidic glycan compositions. Calculated mass-to-charge ratios (calc. m/z) refer to the first isotope signal of [M − H]⁻ ion.

| Proposed composition | calc. m/z |
|---|---|
| NeuAcHex3HexNAc2dHex | 1346.47 |
| Hex4HexNAc3SP | 1354.41 |
| NeuAcHex4HexNAc2 | 1362.47 |
| NeuAc2HexHexNAc3 | 1370.48 |
| NeuAcHex2HexNAc3dHex | 1387.50 |
| NeuAcHex2HexNAc3 | 1403.49 |
| NeuGcHex3HexNAc3 | 1419.49 |
| NeuAcHexHexNAc4dHex | 1428.53 |
| NeuAc2Hex3HexNAcdHex | 1434.49 |
| NeuAcHex2HexNAc4 | 1444.52 |
| NeuAcHex3HexNAc3Ac | 1445.51 |
| NeuAc2Hex4HexNAc | 1450.48 |
| Hex5HexNAc2dHexSP | 1459.44 |
| NeuAc2Hex2HexNAc2dHex | 1475.52 |
| NeuAcHex6HexNAc/ | 1483.49/ |
| NeuAcHex3HexNAc3SP | 1483.45 |
| NeuAc2Hex3HexNAc2 | 1491.51 |
| NeuAcHex3HexNAc2dHex2 | 1492.53 |
| Hex4HexNAc3dHexSP | 1500.47 |
| NeuAcHex4HexNAc2dHex | 1508.53 |
| NeuAc2HexHexNAc3dHex/ | 1516.54/ |
| Hex5HexNAc3SP | 1516.46 |
| NeuAcHex5HexNAc2 | 1524.52 |
| NeuAc2Hex2HexNAc3 | 1532.54 |
| NeuAcHex2HexNAc3dHex2 | 1533.56 |
| NeuAcHex3HexNAc3dHex | 1549.55 |
| NeuAc2Hex2HexNAc2dHexSP | 1555.47 |
| Hex4HexNAc4SP | 1557.49 |
| NeuAcHex3HexNAc3(SP)2 | 1563.41 |
| NeuAcHex4HexNAc3 | 1565.55 |
| NeuAc2HexHexNAc4 | 1573.56 |
| NeuGcHex4HexNAc3 | 1581.54 |
| NeuAcHex2HexNac4dHex | 1590.58 |
| NeuAc2Hex4HexNAcdHex | 1596.54 |
| NeuAcHex3HexNAc4 | 1606.57 |
| NeuAc2Hex2HexNAc2dHex2/ | 1621.57/ |
| Hex6HexNAc2dHexSP | 1621.49 |
| NeuAc2Hex3HexNAc2dHex | 1637.57 |
| NeuAcHex4HexNAc3SP | 1645.50 |
| NeuAcHex2HexNAc5 | 1647.60 |
| NeuAcHex4HexNAc2dHex2 | 1654.58 |
| Hex5HexNAc3dHexSP | 1662.52 |
| NeuAcHex5HexNAc2dHex | 1670.58 |
| NeuAc2Hex2HexNAc3dHex | 1678.60 |
| NeuAcHex2HexNAc3dHex3 | 1679.62 |
| NeuAcHex6HexNAc2 | 1686.57 |
| NeuAc2Hex3HexNAc3 | 1694.59 |
| Hex4HexNAc4dHexSP | 1703.55 |
| NeuAcHex3HexNAc3dHex(SP)2 | 1709.47 |
| NeuGcNeuAcHex3HexNAc3 | 1710.59 |
| NeuAcHex4HexNAc3dHex | 1711.61 |
| Hex5HexNAc4SP | 1719.54 |
| NeuAcHex4HexNAc3(SP)2 | 1725.46 |
| Hex4HexNAc3dHex2(SP)2/ | 1726.48/ |
| NeuGc2Hex3HexNAc3 | 1726.58 |
| NeuAcHex5HexNAc3/ | 1727.60 |
| NeuAcHex2HexNAc3dHex | |
| NeuAc2Hex2HexNAc4 | 1735.62 |
| NeuAcHex2HexNAc4dHex2 | 1736.64 |
| NeuGcHex5HexNAc3 | 1743.60 |
| NeuAcHex4HexNAc4dHex | 1752.63 |
| NeuAc2Hex2HexNAc3dHexSP | 1758.55 |
| NeuAcHex3HexNAc4(SP)2/ | 1766.49/ |
| NeuAcHex6HexNAc2SP | 1766.53 |
| Hex6HexNAc2dHex2SP/ | 1767.55/ |
| Hex3HexNAc4dHex2(SP)2/ | 1767.51 |
| NeuAc2Hex2HexNAc2dHex3 | |
| NeuAcHex4HexNAc4 | 1768.63 |
| NeuAc2Hex6HexNAc/ | 1774.59/ |
| NeuAc2Hex3HexNAc3SP | 1774.55 |
| Hex7HexNAc2dHexSP | 1783.55 |
| NeuGcHex4HexNac4 | 1784.62 |
| NeuAcHex4HexNAc3dHexSP | 1791.56 |
| NeuAcHex2HexNAc5dHex | 1793.66 |
| NeuAc2Hex4HexNAc2dHex/ | 1799.62 |
| Hex5HexNAc4(SP)2 | |
| NeuAcHex3HexNac5 | 1809.65 |
| NeuAc2Hex5HexNAc2/ | 1815.62 |
| NeuAc2Hex2HexNAc4SP | |
| NeuAcHex5HexNAc2dHex2/ | 1816.64 |
| NeuAcHex2HexNAc4dHex2SP | |
| Hex6NexNAc3dHexSP | 1824.57 |
| NeuGcHex3HexNAc5 | 1825.65 |
| NeuAcHex6HexNAc2dHex | 1832.63 |
| NeuAc2Hex3HexNAc3dHex | 1840.65 |
| NeuAcHex3HexNAc3dHex3 | 1841.67 |
| NeuAc2Hex4HexNAc3 | 1856.64 |
| NeuAcHex4HexNAc3dHex2 | 1857.66 |
| Hex5HexNAc4dHexSP | 1865.60 |
| NeuAcHex4HexNAc4dHex(SP)2 | 1871.52 |
| NeuAcHex5HexNAc3dHex/ | 1873.66 |
| NeuGcHex4HexNAc3dHex2 | |
| Hex6HexNAc4SP | 1881.65 |
| NeuAcHex5HexNAC3(SP)2 | 1887.51 |
| NeuAcHex6HexNAc3 | 1889.65 |
| NeuAcHex3HexNAc4dHex2 | 1898.69 |
| Hex4HexNAc5dHexSP | 1906.63 |
| NeuAcHex6HexNAc2dHexSP/ | 1912.59 |
| NeuAcHex3HexNAc4dHex(SP)2 | |
| NeuAcHex4HexNAc4dHex | 1914.68 |
| NeuAc2Hex3HexNAc3dHexSP | 1920.60 |
| Hex5HexNAc5SP | 1922.62 |
| NeuAcHex4HexNAc4(SP)2 | 1928.54 |
| NeuAcHex5HexNAc4 | 1930.68 |
| NeuGcHex5HexNAc4 | 1946.67 |
| NeuAcHex5HexNAc3dHexSP | 1953.62 |
| NeuAcHex3HexNAc5dHex | 1955.71 |
| NeuAc2Hex5HexNAc2dHex/ | 1961.67/ |
| Hex6HexNAc4(SP)2 | 1961.55 |
| NeuAcHex4HexNAc5 | 1971.71 |
| NeuAcHex5HexNAc4Ac | 1972.69 |
| NeuAcHex6HexNAc2dHex2/ | 1978.69/ |
| NeuAcHex3HexNAc4dHex2SP | 1978.65 |
| NeuAc2Hex4HexNAc3dHex/ | 2002.70/ |
| Hex8HexNAc3SP | 2002.62 |
| NeuAcHex4HexNAc3dHex3 | 2003.72 |
| NeuAcHex5HexNAc4SP | 2010.64 |
| Hex5HexNAc4dHex2SP | 2011.66 |
| NeuAc2Hex5HexNAc3/ | 2018.70 |
| NeuGcNeuAcHex4HexNAc3dHex | |
| NeuAcHex5HexNAc3dHex2 | 2019.72 |
| NeuGcHex5HexNAc4SP | 2026.63 |
| Hex6HexNAc4dHexSP | 2027.65 |
| NeuAcHex6HexNAc3dHex | 2035.71 |
| NeuAc2Hex3HexNAc4dHex/ | 2043.73/ |
| Hex7HexNAc4SP | 2043.65 |
| NeuAcHex7HexNAc3 | 2051.71 |
| Hex4HexNAc5dHex2SP | 2052.68 |
| NeuAc2Hex4HexNAc4 | 2059.72 |
| NeuAcHex4HexNAc4dHex2 | 2060.74 |
| Hex5HexNAc5dHexSP | 2068.68 |
| NeuAcHex4HexNAc4dHex(SP)2 | 2074.60 |
| NeuAcHex5HexNAc4dHex | 2076.74 |
| NeuAc2Hex4HexNAc3dHexSP | 2082.66 |
| NeuGc2Hex4HexNAc4 | 2091.71 |
| NeuAcHex6HexNAc4/ | 2092.73 |
| NeuGcHex5HexNAc4dHex | |
| NeuAc2Hex5HexNAc3SP/ | 2098.65 |
| NeuGcNeuAcHex4HexNAc3dHexSP | |
| NeuAcHex5HexNAc3dHex2SP/ | 2099.67 |
| NeuGcHex4HexNAc3dHex3SP | |
| NeuAc2Hex3HexNAc5 | 2100.75 |
| NeuAc2Hex3HexNAc5dHex2/ | 2101.77/ |
| NeuAc2Hex4HexNAc4Ac | 2101.73 |
| NeuAcHex6HexNAc3dHexSP | 2115.67 |
| NeuAcHex4HexNAc5dHex | 2117.76 |
| Hex7HexNAc3dHex2SP/ | 2132.68/ |
| NeuAc2Hex3HexNAc3dHex3 | 2132.76 |

TABLE 2-continued

Preferred acidic glycan compositions. Calculated mass-to-charge ratios (calc. m/z) refer to the first isotope signal of [M − H]⁻ ion.

| Proposed composition | calc. m/z |
|---|---|
| NeuAcHex5HexNAc5 | 2133.76 |
| Hex8HexNAc3dHexSP/ | 2148.68 |
| NeuAc2Hex4HexNAc3dHex2 | |
| NeuAcHex8Hexnac2dHex/ | 2156.74/ |
| NeuAcHex5HexNAc4dHexSP | 2156.69 |
| Hex5HexNAC4dHex3SP | 2157.71 |
| NeuAc2Hex5HexNAc3dHex | 2164.75 |
| NeuAcHex5HexNAc3dHex3 | 2165.77 |
| NeuAcHex9HexNAc2/ | 2172.73/ |
| NeuAcHex6HexNAc4SP/ | 2172.69 |
| NeuGcNeuAcHex4dHexSP | |
| NeuAcHex4Hexnac6 | 2174.79 |
| NeuAc2Hex6HexNAc3/ | 2180.75 |
| NeuGc2Hex4HexNAc3dHex2 | |
| NeuAcHex6HexNAc3dHex2 | 2181.77 |
| NeuAc3Hex3HexNAc4/ | 2188.76/ |
| NeuGcHex6HexNAc4SP/ | 2188.68 |
| NeuAc2NeuGcHex2HexNAc4dHex | |
| NeuAcHex3HexNAc4dHex2/ | 2189.79/ |
| Hex7HexNAc4dHexSP | 2189.70 |
| NeuAcHex3HexNAc4dHex4 | 2190.81 |
| NeuGcNeuAcHex6HexNAc3/ | 2196.74 |
| NeuGc2Hex5HexNAc3dHex | |
| Hex4HexNAc5dHex3SP | 2198.74 |
| NeuAc2Hex4HexNAc4dHex | 2205.78 |
| NeuAcHex4HexNAc4dHex3 | 2206.80 |
| NeuAc2Hex4HexNAc4(SP)2 | 2219.64 |
| NeuAc2Hex5HexNAc4 | 2221.78 |
| NeuAcHex5HexNAc4dHex2 | 2222.80 |
| Hex6HexNAc5dHexSP | 2230.73 |
| NeuGcNeuAcHex5HexNAc4 | 2237.77 |
| NeuAcHex6HexNAc4dHex/ | 2238.79 |
| NeuGCHex5HexNAc4dHex2 | |
| NeuAc2Hex3HexNAc5dHex | 2246.81 |
| NeuAcHex3HexNAc5dHex3 | 2247.83 |
| NeuGc2Hex5Hexnac4 | 2253.76 |
| NeuAcHex7HexNAc4/ | 2254.79 |
| NeuGcHex6HexNAc4dHex | |
| NeuAc2Hex4HexNAc5 | 2262.80 |
| NeuAcHex4HexNAc5dHex2/ | 2263.82/ |
| NeuAc2Hex5HexNAc4Ac | 2263.79 |
| NeuAcHex5HexNAc5dHex | 2279.82 |
| NeuAc2Hex4HexNAc4dHexSP | 2285.74 |
| NeuAcHex4HexNAc4dHex3SP | 2286.76 |
| NeuAcHex8HexNAc3SP/ | TC2293.72/ |
| NeuAc3Hex4HexNAc3dHex | 2293.80 |
| NeuAc2Hex4HexNAc3dHex3 | 2294.82 |
| NeuAcHex6HexNAc5 | 2295.81 |
| NeuAc2Hex5HexNAc4SP | 2301.73 |
| NeuAcHex5HexNAc4dHex2SP | 2302.75 |
| NeuAc2Hex5HexNAc4Ac2 | 2305.80 |
| NeuAc2Hex5HexNAc3dHex2/ | 2310.81 |
| NeuGcNeuAcHex4HexNAc3dHex3 | |
| NeuAcHex5HexNAc3dHex4/ | 2311.83 |
| NeuGcHex6HexNAc5 | |
| NeuAcHex6HexNAc4dHexSP | 2318.75 |
| Hex6HexNAc4dHex3SP/ | 2319.77 |
| NeuGcNeuAcHex3HexNAc6 | |
| NeuAcHex4HexNAc6dHex | 2320.84 |
| NeuAcHex5HexNAc5dHexAc | 2321.83 |
| NeuAc2Hex6HexNAc3dHex | 2326.81 |
| NeuAcHex6HexNAc3dHex3 | 2327.83 |
| NeuAcHex7HexNAc4SP/ | 2334.74/ |
| NeuGcHex6HexNAc4dHexSP/ | 2334.79 |
| NeuAcHex10HexNAc2 | |
| NeuAcHex5HexNAc6 | 2336.84 |
| NeuAc3Hex4HexNac4 | 2350.82 |
| NeuAc2Hex4HexNAc4dHex2/ | 2351.84/ |
| Hex8HexNAc4dHexSP | 2351.76 |
| NeuGcNeuAc2Hex4HexNAc4 | 2366.81 |
| NeuAc2Hex5HexNAc4dHex | 2367.83 |
| NeuAcHex5HexNAc4dHex3 | 2368.85 |
| NeuAcHex5HexNAc4dHex2(SP)2 | 2382.71 |
| NeuAc2Hex6HexNAc4/ | 2383.83 |
| NeuGcNeuAcHex5HexNAc4dHex | |
| NeuAcHex6HexNAc4dHex2/ | 2384.85 |
| NeuGcHex5HexNAc4dHex3 | |
| NeuAc3Hex5HexNAc3SP/ | 2389.75/ |
| NeuAc2Hex5HexNAc4Ac4 | 2389.82 |
| NeuAc2Hex5HexNAc5dHex2SP | 2390.77 |
| NeuAcHex5HexNAc3dHex4SP/ | 2391.79/ |
| NeuAc3Hex3HexNAc5 | 2391.84 |
| NeuAc2Hex3HexNAc5dHex2 | 2392.86 |
| NeuAcHex3HexNAc5dHex4 | 2393.89 |
| NeuGc2Hex5HexNAc4dHex | 2399.82 |
| Hex4HexNAc6dHex3SP | 2401.82 |
| NeuAc2Hex6HexNAc3dHexSP | 2406.76 |
| NeuAcHex4HexNAc5dHex | 2408.86 |
| NeuAcHex4HexNAc5dHex3/ | 2409.88/ |
| NeuAc2Hex5HexNAc4dHexAc | 2409.84 |
| NeuAc2Hex5HexNAc5 | 2424.85 |
| NeuAcHex5HexNAc5dHex2 | 2425.87 |
| NeuAcHex8HexNAc3dHexSP/ | 2439.77 |
| NeuAc3Hex4HexNAc3dHex2 | |
| NeuAcHex6HexNAc5dHex | 2441.87 |
| NeuAc2Hex8HexNAc2dHex/ | 2447.83/ |
| NeuAc2Hex5HexNAc4dHexSP | 2447.79 |
| NeuAcHex8HexNAc2dHex3/ | 2448.85/ |
| NeuAcHex5HexNAc4dHex3SP | 2448.81 |
| NeuAc3Hex6dHex3 | 2450.91 |
| NeuAc2Hex5HexNAc4dHexAc2 | 2451.85 |
| NeuAc2Hex5HexNAc3dHex3 | 2456.87 |
| NeuAcHex7HexNAc5 | 2457.86 |
| NeuAcHex5HexNAc5dHex2Ac | 2467.89 |
| NeuAc2Hex6HexNAc3dHex2 | 2472.86 |
| NeuAcHex6HexNAc3dHex4/ | 2473.88 |
| NeuGcHex7HexNAc5 | |
| NeuAcHex5HexNAc6dHex | 2482.90 |
| NeuAcHex6HexNAc5Ac | 2483.88 |
| NeuAc2Hex7HexNAc3dHex | 2488.86 |
| NeuAcHex7HexNAc3dHex3 | 2489.88 |
| NeuAcHex6HexNAc6/ | 2498.89 |
| NeuGcHex5hexNAc6dHex | |
| NeuAc3Hex5HexNAc4 | 2512.87 |
| NeuAc2Hex5HexNAc4dHex2 | 2513.89 |
| NeuAcHex5HexNAc4dHex4 | 2514.91 |
| NeuAcHex6HexNAc4dHexSP/ | 2521.83/ |
| NeuAcHex9HexNAc3dHex/ | 2521.87 |
| NeuAc3Hex2HexNAc5dHex2 | |
| Hex6HexNAc5dHex3SP | 2522.85 |
| NeuGcNeuAc2Hex5HexNAc4 | 2528.87 |
| NeuAc2Hex6HexNAc4dHex/ | 2529.89 |
| NeuGcNeuAcHex5HexNAc4dHex2 | |
| NeuAcHex6HexNAc4dHex3 | 2530.91 |
| NeuAc3Hex3HexNAc5dHex/ | 2537.90/ |
| NeuGcHex6HexNAc5dHexSP/ | 2537.82 |
| NeuAcHex7HexNAc5SP | |
| NeuAc2Hex3HexNAc5dHex3 | 2538.92 |
| NeuAcHex5HexNAc7/ | 2539.92 |
| NeuAcHex5HexNAc5dHex5 | |
| NeuGc2NeuAcHex5HexNAc4 | 2544.86 |
| NeuGc2Hex5Hexnac4dHex2/ | 2545.88 |
| NeuGcNeuAcHex6HexNAc4dHex | |
| NeuAc3Hex4HexNAc5 | 2553.90 |
| NeuAc2Hex4HexNAc5dHex2 | 2554.92 |
| NeuAcHex4HexNAc5dHex4 | 2555.94 |
| NeuGc3Hex5HexNAc4 | 2560.86 |
| NeuAc2Hex5HexNAc5dHex | 2570.91 |
| NeuAcHex5HexNAc5dHex3 | 2571.93 |
| NeuAc2Hex6HexNAc5 | 2586.91 |
| NeuAcHex6HexNAc5dHex2 | 2587.93 |
| Hex7HexNAc6dHexSP | 2595.86 |
| NeuGcNeuAcHex6HexNAc5 | 2602.90 |
| NeuAcHex7HexNAc5dHex/ | 2603.92/ |
| NeuGcHex6HexNAc5dHex2 | 603.92 |
| NeuGc2Hex6HexNac5 | 2618.90 |
| NeuAcHex8HexNAc5/ | 2619.92 |
| NeuGcHex7HexNAc5dHex | |

TABLE 2-continued

Preferred acidic glycan compositions. Calculated mass-to-charge ratios (calc. m/z) refer to the first isotope signal of [M − H]⁻ ion.

| Proposed composition | calc. m/z |
| --- | --- |
| NeuAc2Hex5HexNAc6 | 2627.93 |
| NeuAcHex5HexNAc6dHex2 | 2628.95 |
| NeuGcHex8HexNAc5/ | 2635.91/ |
| NeuAcHex4HexNAc5dHex4SP | 2635.89 |
| NeuAcHex6HexNAc6dHex | 2644.95 |
| NeuAc2Hex5HexNAc5dHexSP | 2650.87 |
| NeuAc2Hex5HexNAc4dHex3 | 2659.95 |
| NeuAcHex7HexNAc6 | 2660.94 |
| NeuGcNeuAc2Hex5HexNAc4dHex | 2674.92 |
| NeuAc3Hex6HexNAc4 | |
| NeuGcHex6HexNAc5dHexSP/ | 2683.88 |
| NeuAcHex7HexNAc5dHexSP | |
| NeuAcHex5HexNAc7dHex | 2685.98 |
| NeuAc2Hex7HexNAc4dHex | 2691.94 |
| NeuAcHex7HexNAc4dHex3 | 2692.96 |
| NeuAc2Hex4HexNAc5dHex2(SP)2 | 2714.83 |
| NeuAcHex4HexNAc5dHex4(SP)2/ | 2715.85/ |
| NeuAc3Hex5HexNAc5 | 2715.95 |
| NeuAc2Hex5HexNAc5dHex2 | 2716.97 |
| NeuAcHex5HexNAc5dHex4 | 2717.99 |
| NeuAc2Hex6HexNAc5dHex | 2732.97 |
| NeuAcHex6HexNAc5dHex3 | 2733.99 |
| NeuAcHex6HexNAc5dHex2(SP)2 | 2747.84 |
| NeuGcNeuAcHex6HexNAc5dHex | 2748.96 |
| NeuAc3Hex4HexNAc6 | 2756.98 |
| NeuAc2Hex4HexNAc6dHex2 | 2758.00 |
| NeuAcHex7HexNAc4dHex4 | 2759.02 |
| NeuAc3Hex6HexNAc3dHex2 | 2763.96 |
| NeuAc2Hex6HexNAc3dHex4/ | 2764.98/ |
| NeuGc2Hex6HexNAc5dHex/ | 2764.96 |
| NeuGcHex7HexNAc5 | |
| NeuAcHex8HexNAc5dHex | 2765.98 |
| NeuAc2Hex5HexNAc6dHex | 2773.99 |
| NeuAcHex5HexNAc6dHex3 | 2775.01 |
| NeuGc2Hex7HexNAc5 | 2780.95 |
| NeuGcHex8HexNAc5dHex/ | 2781.97 |
| NeuAcHex9HexNac5 | |
| NeuAc2Hex6HexNAc6 | 2789.99 |
| NeuAc4Hex6HexNAc6dHex2 | 2791.01 |
| NeuAc4Hex5HexNAc4 | 2803.97 |
| NeuAc3Hex5HexNAc4dHex2/ | 2804.99/ |
| NeuAcHex6HexNAc6dHex(SP)2 | 2804.86 |
| Hex6HexNAc6dHex3SP2 | 2805.88 |
| NeuAc2Hex5HexNAc4dHex4 | 2806.01 |
| NeuAcHex7Hexnac6dHex | 2807.00 |
| NeuAc2Hex6HexNAc5dHexSP | 2812.92 |
| NeuAcHex6HexNAc5dHex3SP | 2813.94 |
| NeuGcNeuAc3Hex5HexNAc4 | 2819.96 |
| NeuAc3Hex6HexNAc4dHex/ | 2820.98 |
| NeuGcNeuAc2Hex5HexNAc4dHex2 | |
| NeuAc2Hex6HexNAc4dHex3 | 2822.00 |
| NeuAcHex8HexNAc6 | 2823.00 |
| NeuGc2NeuAc2Hex5HexNAc4 | 2835.96 |
| NeuGc2NeuAcHex5HexNAc4dHex2 | 2836.98 |
| NeuAc3Hex6HexNAc5 | 2878.00 |
| NeuAc2Hex6HexNAc5dHex2 | 2879.02 |
| NeuAcHex6HexNAc5dHex4 | 288.04 |
| NeuAcHex7HexNAc6dHexSP/ | 2886.96/ |
| NeuAcHex10HexNAc4dHex | 2887.00 |
| NeuGcNeuAc2Hex6HexNAc5 | 2894.00 |
| NeuAc2Hex7HexNAc5dHex/ | 2895.02 |
| NeuGcNeuAcHex6HexNAc5dHex2 | |
| NeuAc3Hex6HexNAc4dHexSP/ | 2900.94 |
| NeuGcNeuAc2Hex5HexNAc4dHex2SP | |
| NeuGc2NeuAcHex6HexNAc5 | 2909.99 |
| NeuGc2Hex6HexNAc5dHex2 | 2911.01 |
| NeuAc3Hex5HexNAc6 | 2919.03 |
| NeuAc2Hex5HexNAc6dHex2 | 2920.05 |
| NeuAcHex5HexNAc6dHex4 | 2921.07 |
| NeuGc3Hex6HexNAc5 | 2925.99 |
| NeuGcNeuAc2Hex5HexNAc6 | 2935.02 |
| NeuAc2Hex6HexNAc6dHex/ | 2936.04 |
| NeuGcNeuAcHex5HexNAc6dHex2 | |
| NeuAcHex6HexNAc6dHex3 | 2937.07 |
| NeuGc2NeuAcHex5HexNAc6/ | 2951.02/ |
| NeuAc3Hex5HexNAc4dHex3 | 2951.04 |
| NeuAc2Hex7HexNAc6 | 2952.04 |
| NeuAcHex7HexNAc6dHex2 | 2953.06 |
| NeuAc2Hex6HexNAc5dHex2SP | 2958.98 |
| NeuAcHex6HexNAc5dHex4SP | 2960.00 |
| NeuAc2Hex4HexNAc7dHex2 | 2961.08 |
| NeuAc2Hex4HexNAc7dHex4 | 2962.10 |
| NeuAcHex6HexNAc7dHex2 | 2994.09 |
| NeuAcHex7HexNAc7dHex | 3010.08 |
| NeuAc3Hex6HexNAc5dHex | 3024.06 |
| NeuAc2Hex6HexNAc5dHex3 | 3025.08 |
| NeuAcHex8HexNAc7 | 3026.08 |
| NeuAc3Hex5HexNAc6dHex | 3065.09 |
| NeuAc2Hex5HexNAc6dHex3 | 3066.11 |
| NeuAcHex7HexNAc8 | 3067.10 |
| NeuAc3Hex6HexNAc6 | 3081.08 |
| NeuAc2Hex6HexNAc6dHex2 | 3082.10 |
| NeuAc2Hex7HexNAc6dHex | 3098.10 |
| NeuAcHex7HexNAc6dHex3 | 3099.12 |
| NeuAc3Hex6HexNAc5dHexSP | 3104.02 |
| NeuAc2Hex6HexNAc5dHex3SP | 3105.04 |
| NeuAcHex8HexNAc7SP/ | 3106.03/ |
| NeuAc3Hex4HexNAc7dHex | 3106.11 |
| Hex8HexNAc7dHex2SP/ | 3107.05/ |
| NeuAc2Hex4HexNAc7dHex3 | 3107.13 |
| NeuAcHex7HexNAc7dHex2 | 3156.14 |
| NeuAc3Hex6HexNAc5dHex2 | 3170.12 |
| NeuAc2Hex6HexNAc5dHex4 | 3171.14 |
| NeuAcHex8HexNAc7dHex | 3172.13 |
| NeuAc2Hex7HexNAc6dHexSP | 3178.05 |
| NeuAc3Hex6HexNAc6dHex | 3227.14 |
| NeuAc2Hex6HexNAc6dHex3 | 3228.16 |
| NeuAcHex8HexNAc8 | 3229.16 |
| NeuAc3Hex7HexNAc6 | 3243.13 |
| NeuAc2Hex7HexNAc6dHex2 | 3244.16 |
| NeuAcHex7HexNAc6dHex4 | 3245.18 |
| NeuAc2Hex8HexNAc6dHex/ | 3260.15 |
| NeuGcNeuAcHex7HexNAc6dHex2 | |
| NeuAcHex8HexNAc6dHex3/ | 3261.17 |
| NeuGcHex7HexNAc6dHex4 | |
| NeuAc3Hex7HexNAc5dHexSP/ | 3266.07 |
| NeuGcNeuAc2Hex6HexNAc5dHex2SP | |
| NeuAc3Hex5HexNAc7dHex/ | 3268.17/ |
| NeuGcHex8HexNAc7dHexSP | 3268.09 |
| NeuAc2Hex5HexNAc7dHex3 | 3269.19 |
| NeuAcHex7HexNAc9 | 3270.18 |
| NeuGc2Hex7HexNAc6dHex2 | 3276.15 |
| NeuAc4Hex4HexNAc6dHex2(SP)2 | 3297.02 |
| NeuAc3Hex4HexNAc6dHex4(SP)2 | 3298.04 |
| NeuAc2Hex7HexNAc7dHex | 3301.18 |
| NeuAcHex7HexNAc7dHex3 | 3302.20 |
| NeuAc3Hex6HexNAc5dHex3 | 3316.18 |
| NeuAc2Hex8HexNAc7 | 3317.17 |
| NeuAcHex8HexNAc7dHex2 | 3318.19 |
| NeuAc3Hex7HexNAc6dHex | 3389.19 |
| NeuAc2Hex7HexNAc6dHex3 | 3390.21 |
| NeuAcHex7HexNAc6dHex5/ | 3391.23 |
| NeuAcHex9HexNAc8 | |
| NeuAc3Hex5HexNAc7dHex2 | 3414.22 |
| NeuAc2Hex5HexNAc7dHex4 | 3415.24 |
| NeuAcHex7HexNAc9dHex | 3416.24 |
| NeuAc3Hex6HexNAc7dHex | 3430.22 |
| NeuAc2Hex6HexNAc7dHex3 | 3431.24 |
| NeuAcHex8HexNAc9 | 3432.24 |
| NeuAc2Hex8HexNAc7dHex | 3463.23 |
| NeuAcHex8HexNAc7dHex3 | 3464.25 |
| NeuAc3Hex7HexNAc6dHexSP | 3469.15 |
| NeuAc2Hex7HexNAc6dHex3SP | 3470.17 |
| NeuAc3Hex5HexNAc8dHex | 3471.25 |
| NeuAc2Hex5HexNAc8dHex3 | 3472.27 |
| NeuAcHex7HexNAc10 | 3473.26 |
| NeuAc4Hex7HexNAc6 | 3534.23 |
| NeuAc3Hex7HexNAc6dHex2 | 3535.25 |

TABLE 2-continued

Preferred acidic glycan compositions. Calculated mass-to-charge ratios (calc. m/z) refer to the first isotope signal of [M − H]⁻ ion.

| Proposed composition | calc. m/z |
|---|---|
| NeuAc2Hex7HexNAc6dHex4 | 3536.27 |
| NeuAcHex9HexNAc8dHex | 3537.27 |
| NeuAc4Hex5HexNAc7dHex | 3559.26 |
| NeuAc3Hex5HexNAc7dHex3 | 3560.28 |
| NeuAc2Hex7HexNAc9 | 3561.28 |
| NeuAcHex7HexNAc9dHex2 | 3562.30 |
| NeuAc3Hex7HexNac7dHex | 3592.27 |
| NeuAc2Hex7HexNAc7dHex3 | 3593.29 |
| NeuAcHex9HexNAc9 | 3594.29 |
| NeuAc3Hex8HexNAc7 | 3608.27 |
| NeuAc2Hex8HexNac7dHex2 | 3609.29 |
| NeuAcHex8HexNac7dHex4 | 3610.31 |
| NeuAc3Hex5HexNAc8dHex2 | 3617.30 |
| NeuAc2Hex5HexNAc8dHex4 | 3618.32 |
| NeuAcHex7HexNAc10dHex | 3619.32 |
| NeuAc3Hex6HexNAc8dHex | 3633.30 |
| NeuAc4Hex7HexNAc6dHex | 3680.29 |
| NeuAc3Hex7HexNAc6dHex3 | 3681.31 |
| NeuAc2Hex9HexNAc8 | 3682.30 |
| NeuAcHex9HexNAc8dHex2 | 3683.32 |
| NeuAc4Hex6HexNAc7dHex | 3721.31 |
| NeuAc3Hex6HexNAc7dHex3 | 3722.34 |
| NeuAc2Hex8HexNAc9 | 3723.33 |
| NeuAcHex8HexNAc9dHex2 | 3724.35 |
| NeuAc3Hex7HexNac7dHex2 | 3738.33 |
| NeuAc2Hex7HexNAc7dHex4 | 3739.35 |
| NeuAcHex9HexNAc9dHex | 3740.35 |
| NeuAc3Hex8HexNAc7dHex | 3754.33 |
| NeuAc2Hex8HexNAc7dHex3 | 3755.35 |
| NeuAcHex10HexNAc9/ NeuAcHex8HexNAc7dHex5 | 3756.34 |
| NeuAc4Hex6HexNAc8 | 3778.34 |
| NeuAc3Hex6HexNAc8dHex2 | 3779.36 |
| NeuAc2Hex6HexNAc8dHex4 | 3780.38 |
| NeuAcHex8HexNAc10dHex | 3781.37 |
| NeuAc4Hex7HexNAc6dHex2 | 3826.35 |
| NeuAc3Hex7Hexnac6dHex4 | 3827.37 |
| NeuAc2Hex9HexNAc8dHex | 3828.36 |
| NeuAcHex9HexNAc8dHex3 | 3829.38 |
| NeuAc4Hex8HexNAc7 | 3899.36 |
| NeuAc3Hex8HexNAc7dHex2 | 3900.38 |
| NeuAc2Hex8HexNAc7dHex4 | 3901.40 |
| NeuAcHex10HexNAc9dHex | 3902.40 |
| NeuAc4Hex6HexNAc8dHex | 3924.39 |
| NeuAc3Hex6HexNAc8dHex3 | 3925.41 |
| NeuAc2Hex6HexNAc10 | 3926.41 |
| NeuAcHex8HexNAc10dHex2 | 3927.43 |
| NeuAc3Hex9HexNAc8 | 3973.40 |
| NeuAc2Hex9HexNAc8dHex2 | 3974.42 |
| NeuAcHex9HexNAc8dHex4 | 3975.44 |
| NeuAc4Hex8HexNAc7dHex | 4045.42 |
| NeuAc3Hex8HexNAc7dHex3 | 4046.44 |
| NeuAc2Hex10HexNAc9/ NeuAc2Hex8HexNAc7dHex5 | 4047.44 |
| NeuAcHex10HexNAc9dHex2 | 4048.46 |
| NeuAc3Hex9HexNAc8dHex | 4119.46 |
| NeuAc2Hex9HexNAc8dHex3 | 4120.48 |
| NeuAcHex11HexNAc10/ NeuAcHex9HexNAc8dHex5 | 4121.47 |
| NeuAc2Hex10HexNAc9dHex2 | 4339.55 |
| NeuAcHex10HexNAc9dHex4 | 4340.57 |
| NeuAc2Hex10HexNAc9dHex3 | 4485.61 |

TABLE 3

Neutral N-glycan profiles of cord blood mononuclear cell populations and peripheral blood mononuclear cells.

| Proposed monosaccharide composition | calc. m/z | CD34+ | CD34− | CD133+ | CD133− | LIN− | LIN+ | CB MNC | PB MNC |
|---|---|---|---|---|---|---|---|---|---|
| HexHexNAc2 | 609.21 | | | 2.14 | 0.15 | | 0.22 | 0.22 | |
| HexHexNAc2dHex | 755.27 | 0.40 | 0.83 | 0.37 | 0.95 | | 0.28 | 0.60 | |
| Hex2HexNAc2 | 771.26 | 2.37 | 4.27 | 2.29 | 3.30 | 1.72 | 2.62 | 3.34 | 4.19 |
| Hex2HexNAc2dHex | 917.32 | 9.10 | 13.32 | 5.97 | 11.61 | 6.75 | 8.24 | 7.54 | 8.41 |
| Hex3HexNAc2 | 933.31 | 8.20 | 5.84 | 4.85 | 5.02 | 3.94 | 3.71 | 4.53 | 5.67 |
| Hex2HexNAc3 | 974.34 | | | | | | 0.02 | | |
| Hex3HexNAc2dHex | 1079.38 | 7.32 | 6.70 | 4.90 | 7.02 | 4.41 | 5.51 | 5.36 | 6.45 |
| Hex4HexNAc2 | 1095.37 | 5.28 | 4.21 | 4.79 | 4.13 | 3.92 | 3.38 | 4.36 | 4.39 |
| Hex2HexNAc3dHex | 1120.40 | | 0.14 | | 0.17 | | 0.09 | 0.04 | |
| Hex3HexNAc3 | 1136.40 | 1.25 | 0.75 | 0.24 | 0.58 | 3.01 | 0.50 | 0.41 | 0.43 |
| Hex3HexNAc2dHex2 | 1225.43 | 0.10 | | | | | | | |
| Hex4HexNAc2dHex | 1241.43 | 0.43 | 0.36 | 0.27 | 0.63 | 0.40 | 0.57 | 0.51 | 0.53 |
| Hex5HexNAc2 | 1257.42 | 16.90 | 18.53 | 20.40 | 13.88 | 18.05 | 14.92 | 15.80 | 15.32 |
| Hex3HexNAc3dHex | 1282.45 | 1.15 | 1.74 | 1.14 | 1.77 | 1.55 | 1.43 | 0.96 | 0.94 |
| Hex4HexNAc3 | 1298.45 | 0.35 | 0.60 | 0.20 | 0.43 | 1.53 | 0.52 | 0.43 | 0.49 |
| HexHexNAc4dHex2 | 1307.49 | 0.40 | | | | | | | |
| Hex3HexNAc4 | 1339.48 | | | | 0.54 | 1.18 | 0.31 | 0.17 | 0.19 |
| Hex5HexNAc2dHex | 1403.48 | 0.19 | 0.45 | 0.57 | 0.57 | 0.39 | 0.55 | 0.53 | 0.53 |
| Hex6HexNAc2 | 1419.48 | 11.87 | 13.37 | 15.93 | 15.94 | 11.33 | 16.14 | 17.98 | 16.44 |
| Hex3HexNAc3dHex2 | 1428.51 | 0.48 | 0.43 | | 0.23 | | 0.09 | 0.17 | |
| Hex4HexNAc3dHex | 1444.51 | 0.65 | 0.84 | | 0.56 | 0.54 | 0.73 | 0.40 | 0.36 |
| Hex5HexNAc3 | 1460.50 | 0.28 | 0.33 | 0.33 | 0.45 | 0.83 | 0.56 | 0.56 | 0.47 |
| Hex3HexNAc4dHex | 1485.53 | 1.55 | 1.22 | 2.88 | 2.07 | 4.90 | 3.38 | 0.91 | 1.02 |
| Hex4HexNAc4 | 1501.53 | 0.18 | 0.13 | | 0.20 | 0.82 | 0.08 | 0.01 | 0.09 |
| Hex3HexNAc5 | 1542.56 | 0.28 | | | 0.06 | 0.38 | 0.03 | 0.02 | 0.01 |
| Hex6HexNAc2dHex | 1565.53 | 0.11 | | | 0.09 | 0.08 | 0.11 | 0.15 | 0.15 |
| Hex7HexNAc2 | 1581.53 | 8.68 | 8.04 | 9.78 | 10.16 | 9.58 | 11.24 | 11.50 | 11.28 |
| Hex4HexNAc3dHex2 | 1590.57 | 0.72 | 1.01 | | 0.46 | | 0.25 | 0.37 | 0.16 |
| Hex5HexNAc3dHex | 1606.56 | 0.10 | 0.08 | 0.10 | 0.22 | 0.31 | 0.31 | 0.20 | 0.14 |
| Hex6HexNAc3 | 1622.56 | 0.37 | 0.34 | 0.39 | 0.64 | 0.80 | 0.78 | 0.72 | 0.57 |
| Hex4HexNAc4dHex | 1647.59 | 0.37 | 0.35 | 0.52 | 0.22 | 0.63 | 0.82 | 0.08 | 0.13 |

TABLE 3-continued

Neutral N-glycan profiles of cord blood mononuclear cell populations and peripheral blood mononuclear cells.

| Proposed monosaccharide composition | calc. m/z | CD34+ | CD34− | CD133+ | CD133− | LIN− | LIN+ | CB MNC | PB MNC |
|---|---|---|---|---|---|---|---|---|---|
| Hex5HexNAc4 | 1663.58 | 0.39 | 0.84 | | 0.64 | 0.99 | 0.93 | 0.51 | 0.70 |
| Hex3HexNAc5dHex | 1688.61 | 0.26 | 0.43 | 0.54 | 0.59 | 0.79 | 0.65 | 0.47 | 0.49 |
| Hex4HexNAc5 | 1704.61 | | | 0.09 | | 0.14 | | 0.03 | |
| Hex7HexNAc2dHex | 1727.59 | | | | | | | 0.03 | |
| Hex8HexNAc2 | 1743.58 | 8.51 | 5.69 | 10.36 | 7.19 | 9.04 | 8.53 | 9.18 | 9.31 |
| Hex5HexNAc3dHex2 | 1752.62 | 0.05 | 0.06 | | | | 0.06 | | |
| Hex6HexNAc3dHex | 1768.61 | 0.05 | | | 0.02 | | 0.13 | 0.09 | 0.10 |
| Hex7HexNAc3 | 1784.61 | 0.06 | 0.05 | | 0.03 | | 0.05 | | |
| Hex4HexNAc4dHex2 | 1793.64 | 0.05 | 0.18 | | 0.15 | | 0.09 | 0.08 | |
| Hex5HexNAc4dHex | 1809.64 | 0.59 | 0.64 | 0.41 | 0.36 | 0.68 | 0.42 | 0.22 | 0.24 |
| Hex6HexNAc4 | 1825.63 | | | | 0.07 | 0.13 | 0.26 | 0.06 | |
| Hex5HexNAc5 | 1866.66 | | | 0.05 | 0.09 | 0.08 | 0.23 | 0.03 | |
| Hex3HexNAc6dHex | 1891.69 | | | | 0.23 | 0.16 | 0.14 | 0.06 | 0.15 |
| Hex9HexNAc2 | 1905.63 | 10.07 | 6.75 | 9.80 | 7.17 | 10.11 | 9.49 | 9.55 | 9.09 |
| Hex5HexNAc4dHex2 | 1955.70 | 0.32 | 0.33 | | 0.17 | | 0.08 | 0.15 | 0.10 |
| Hex6HexNAc4dHex | 1971.69 | | | | 0.03 | | 0.06 | 0.00 | |
| Hex7HexNAc4 | 1987.69 | | | | 0.02 | | 0.07 | 0.01 | |
| Hex5HexNAc5dHex | 2012.72 | | | | | | 0.04 | | |
| Hex6HexNAc5 | 2028.71 | | | | 0.10 | | 0.14 | 0.10 | 0.08 |
| Hex10HexNAc2 | 2067.69 | 0.27 | 0.53 | 0.69 | 0.67 | 0.63 | 0.87 | 1.14 | 1.14 |
| Hex5HexNAc4dHex3 | 2101.76 | 0.22 | 0.37 | 0.03 | 0.23 | | 0.13 | 0.13 | 0.08 |
| Hex6HexNAc4dHex2 | 2117.75 | | | | 0.06 | | | | |
| Hex8HexNAc4 | 2149.74 | | | | | 0.05 | | | |
| Hex6HexNAc5dHex | 2174.77 | 0.08 | 0.04 | | 0.05 | | 0.12 | 0.02 | |
| Hex4HexNAc6dHex2 | 2199.80 | | | | 0.01 | | | | |
| Hex5HexNAc6dHex | 2215.80 | | | | | | 0.01 | | |
| Hex11HexNAc2 | 2229.74 | | | | 0.05 | | 0.02 | 0.15 | 0.10 |
| Hex6HexNAc6 | 2231.79 | | | | | | 0.01 | | |
| Hex6HexNAc5dHex2 | 2320.83 | | | | | | 0.02 | | |
| Hex12HexNAc2 | 2391.79 | | | | 0.02 | 0.10 | 0.04 | 0.12 | 0.05 |
| Hex7HexNAc6 | 2393.85 | | | | | | 0.02 | | |
| Hex6HexNAc7 | 2434.87 | | 0.25 | | | | | | |
| Hex6HexNAc5dHex3 | 2466.89 | | | | | | 0.01 | | |
| Hex7HexNAc6dHex | 2539.90 | | | | | | 0.01 | | |

TABLE 4

Sialylated N-glycan profiles of cord blood mononuclear cell populations and peripheral blood mononuclear cells.

| Proposed monosaccharide composition | calc. m/z | CD 34+ | CD 34− | MNC |
|---|---|---|---|---|
| NeuAcHex2HexNAc | 835.28 | | 0.15 | |
| NeuAcHex2HexNAc2 | 1038.36 | | 0.12 | |
| Hex4HexNAc2SP | 1151.33 | | 0.25 | |
| NeuAcHex3HexNAc2 | 1200.42 | 0.54 | 1.06 | 0.47 |
| NeuAc2HexHexNAc2dHex | 1313.46 | | 0.22 | |
| NeuAc2Hex2HexNAc2 | 1329.46 | 0.60 | | |
| NeuAcHex4HexNAc2 | 1362.47 | | 0.54 | |
| NeuAcHex3HexNAc3 | 1403.49 | 0.62 | 0.47 | 0.38 |
| NeuAc2Hex2HexNAcdHex | 1475.52 | 0.59 | 0.67 | |
| NeuAc2Hex3HexNAc2dHex | 1491.51 | | 0.22 | |
| NeuAcHex3HexNAc3dHex | 1549.55 | 1.72 | 1.01 | 1.61 |
| NeuAc2Hex2Hexnac2dHexSP | 1555.47 | | 0.35 | |
| NeuAcHex3HexNAc3SP2 | 1563.41 | 0.63 | 3.41 | |
| NeuAcHex4HexNAc3 | 1565.55 | 1.99 | 0.42 | 2.36 |
| NeuAc2Hex3HexNAc2dHex | 1637.57 | 0.47 | 0.55 | |
| NeuAc2Hex2HexNAc3dHex | 1678.60 | 0.38 | | 0.59 |
| NeuAcHex3HexNAc3dHexSP2 | 1709.47 | | 0.08 | |
| NeuAcHex4HexNAc3dHex | 1711.61 | 6.44 | 1.45 | 7.21 |
| NeuAcHex5HexNAc3 | 1727.60 | 1.23 | 0.53 | 1.83 |
| NeuAc2Hex2HexNAc3dHexSP | 1758.55 | | 0.39 | |
| NeuAcHex4HexNAc4 | 1768.57 | 1.55 | 0.64 | 1.39 |
| NeuAcHex4HexNAc3dHexSP | 1791.56 | | 0.09 | |
| NeuAc2Hex4HexNAc2dHex | 1799.62 | | 0.12 | |
| NeuAc2Hex5HexNAc2/ | 1815.62/ | 0.47 | 0.18 | |
| NeuAc2Hex2HexNAc4SP | 1815.57 | | | |
| NeuAc2Hex4HexNAc3 | 1856.64 | | 0.28 | |
| NeuAcHex4HexNAc3dHex2 | 1857.66 | | 0.04 | |
| Hex5HexNAc4dHexSP | 1865.60 | | 0.13 | |
| NeuAcHex5HexNAc3dHex | 1873.66 | 1.50 | 0.27 | 1.80 |
| NeuAcHex6HexNAc3 | 1889.65 | 1.21 | 0.26 | 2.67 |
| NeuAcHex6HexNAc2dHexSP/ | 1912.59/ | 0.60 | 0.26 | |
| NeuAcHex3HexNAc4dHexSP2 | 1912.55 | | | |
| NeuAcHex4HexNAc4dHex | 1914.68 | 2.80 | 1.15 | 2.64 |
| NeuAc2Hex3HexNAc3dHexSP | 1920.60 | | 0.22 | |
| NeuAcHex4HexNAc4SP2 | 1928.54 | | 0.26 | |
| NeuAcHex5HexNAc4 | 1930.68 | 10.25 | 2.87 | 10.12 |
| NeuGcHex5HexNAc4 | 1946.67 | | 0.10 | |
| NeuAc2Hex4HexNAc3dHex/ | 2002.70/ | 0.65 | | |
| Hex8HexNAc3SP | 2002.62 | | | |
| NeuAc2Hex5HexNAc3 | 2018.70 | | 1.27 | |
| NeuAcHex5HexNAc3dHex2 | 2019.72 | 0.17 | 0.09 | |
| NeuAcHex6HexNAc3dHex | 2035.71 | 0.78 | | 0.71 |
| NeuAcHex7HexNAc3 | 2051.71 | | | 0.15 |
| NeuAc2Hex4HexNAc4 | 2059.72 | | 0.25 | |
| NeuAcHex4HexNAc4dHex2 | 2060.74 | | 0.20 | |
| NeuAcHex4HexNAc4dHexSP2 | 2074.60 | 0.78 | 0.13 | |
| NeuAcHex5HexNAc4dHex | 2076.74 | 10.89 | 4.35 | 14.12 |
| NeuAcHex6HexNAc4 | 2092.73 | | | 0.17 |
| NeuAc2Hex5HexNAc3SP/ | 2098.65 | | 0.24 | |
| NeuGcNeuAcHex4HexNAc3dHexSP | | | | |
| NeuAcHex5HexNAc3dHex2SP/ | 2099.67 | | 0.07 | |
| NeuGcHex4HexNAc3dHex3SP | | | | |
| NeuAcHex4HexNAc5dHex | 2117.76 | 0.57 | 0.13 | 0.52 |
| NeuAcHex5HexNAc5 | 2133.76 | 0.55 | | 1.07 |
| NeuAcHex8HexNAc2dHex/ | 2156.74/ | | 0.42 | |
| NeuAcHex5HexNAc4dHexSP | 2156.69 | | | |

TABLE 4-continued

Sialylated N-glycan profiles of cord blood mononuclear cell populations and peripheral blood mononuclear cells.

| Proposed monosaccharide composition | calc. m/z | CD 34+ | CD 34− | MNC |
|---|---|---|---|---|
| NeuAc2Hex4HexNAc4dHex | 2205.78 | | 0.26 | |
| NeuAc2Hex4HexNAc4SP2 | 2219.64 | 0.45 | 0.57 | |
| NeuAc2Hex5HexNAc4 | 2221.78 | 13.41 | 10.38 | 9.12 |
| NeuAcHex5HexNAc4dHex2 | 2222.80 | 3.80 | 2.21 | 3.28 |
| Hex6HexNAc5dHexSP | 2230.73 | | 0.09 | |
| NeuGcNeuAcHex5HexNAc4 | 2237.77 | 0.61 | 0.69 | |
| NeuAcHex6HexNAc4dHex/ NeuGcHex5HexNAc4dHex2 | 2238.79 | 0.20 | 0.13 | 0.29 |
| NeuGc2Hex5HexNAc4 | 2253.76 | | 0.44 | |
| NeuAcHex7HexNAc4/ NeuGcHex6HexNAc4dHex | 2254.79 | | 0.05 | |
| NeuAcHex5HexNAc5dHex | 2279.82 | 0.91 | 0.72 | 2.06 |
| NeuAcHex8HexNAc3SP | 2293.72 | | 0.20 | |
| NeuAcHex6HexNAc5 | 2295.81 | 0.56 | 0.30 | 1.63 |
| NeuAc2Hex5HexNAc4SP | 2301.73 | | 0.12 | |
| NeuAc2Hex4HexNAc4dHexSP2 | 2365.69 | 1.11 | 1.70 | |
| NeuAc2Hex5HexNAc4dHex | 2367.83 | 12.90 | 17.84 | 11.02 |
| NeuAcHex5HexNAc4dHex3 | 2368.85 | 3.38 | 2.05 | 2.03 |
| NeuAcHex5HexNAc4dHex2SP2 | 2382.71 | | 0.28 | |
| NeuAc2Hex6HexNAc4 | 2383.83 | | 0.21 | |
| NeuAcHex6HexNAc4dHex2 | 2384.85 | | 0.21 | |
| NeuAc2Hex5HexNAc3dHex2SP | 2390.77 | 0.68 | 0.58 | 2.18 |
| NeuAcHex5HexNAc5 | 2424.85 | 0.58 | 0.39 | 0.29 |
| NeuAcHex5HexNAc5dHex2 | 2425.87 | | 0.12 | 0.46 |
| NeuAcHex8HexNAc3dHexSP | 2439.77 | | 0.21 | |
| NeuAcHex6HexNAc5dHex | 2441.87 | 1.60 | 1.30 | 4.40 |
| NeuAc2Hex8HexNAc2dHex/ | 2447.83/ | 0.60 | 2.25 | |
| NeuAc2Hex5HexNAc4dHexSP | 2447.79 | | | |
| NeuAcHex8HexNAc2dHex3/ | 2448.85/ | | 0.18 | |
| NeuAcHex5HexNAc4dHex3SP | 2448.81 | | | |
| NeuAcHex6HexNAc3dHex4/ NeuGcHex7HexNAc5 | 2473.88 | | | 0.21 |
| NeuAcHex7HexNAc3dHex3 | 2489.88 | 0.77 | | |
| NeuAc2Hex5HexNAc4dHex2 | 2513.89 | 0.50 | 0.61 | |
| NeuAcHex6HexNAc5dHexSP/ NeuAc2Hex5HexNAc3dHex/ NeuAc3Hex2HexNAc5dHex2 | 2521.83/ 2521.87 | | 0.08 | |
| NeuGcNeuAc2Hex5HexNAc4 | 2528.87 | | 0.34 | |
| NeuAc2Hex6HexNAc4dHex/ NeuGcNeuAcHex5HexNAc4dHex2 | 2529.89/ 2529.89 | | 0.05 | |
| NeuGc2NeuAcHex5HexNAc4 | 2544.86 | | 0.13 | |
| NeuGc2Hex5HexNAc5dHex | 2570.91 | 0.81 | 1.78 | 0.99 |
| NeuAcHex5HexNAc5dHex3 | 2571.93 | 0.33 | 0.25 | 0.19 |
| NeuAc2Hex6HexNAc5 | 2586.91 | 0.97 | 0.52 | |
| NeuAcHex6HexNAc5dHex2 | 2587.93 | 1.00 | 0.28 | 0.76 |
| NeuAcHex7HexNAc5dHex/ NeuGcHex6HexNAc5dHex2 | 2603.92 | | 0.09 | |
| NeuAcHex8HexNAc5/ NeuGcHex7HexNAc5dHex | 2619.92 | 0.38 | 0.31 | |
| NeuGcHex8HexNAc5/ NeuAcHex4HexNAc5dHex4SP | 2635.91/ 2635.89 | 0.65 | 0.13 | |
| NeuAcHex6HexNAc6dHex | 2644.95 | | | 0.64 |
| NeuAc2Hex5HexNAc5dHexSP | 2650.87 | | 0.14 | |
| NeuAcHex7HexNAc6 | 2660.94 | | | 0.42 |
| NeugcNeuAc2Hex5HexNAc4dHex | 2674.92 | | 0.14 | |
| NeuAc2Hex4HexNAc5dHex2SP2 | 2714.83 | | 0.24 | |
| NeuAc2Hex5HexNAc5dHex2 | 2716.97 | | 0.21 | |
| NeuAcHex6HexNAc5dHex | 2732.97 | 1.70 | 4.43 | 2.88 |
| NeuAcHex6HexNAc5dHex3 | 2733.99 | 0.62 | 1.08 | 1.66 |
| NeuAcHex6HexNAc5dHex2SP2 | 2747.84 | | 0.21 | |
| NeuAcHex6HexNAc6dHexSP2/ NeuAc3Hex5HexNAc4dHex2 | 2804.86/ 2804.99 | | 0.18 | |
| NeuAcHex7HexNAc6dHex | 2807.00 | | 0.45 | 1.54 |
| NeuAc2Hex6HexNAc5dHexSP | 2812.92 | | 0.75 | |
| NeuAc3Hex6HexNAc5 | 2878.00 | | 0.97 | 0.17 |
| NeuAc2Hex6HexNAc5dHex2 | 2879.02 | 0.72 | 0.41 | 0.46 |
| NeuAcHex6HexNAc5dHex4 | 2880.04 | 0.15 | 0.35 | |
| NeuAc3Hex6HexNAc4dHexSP | 2900.94 | | 0.18 | |
| NeuAc2Hex6HexNAc6dHex | 2936.04 | | 0.32 | |
| NeuAcHex6HexNAc6dHex3 | 2937.06 | | 0.09 | 0.25 |
| NeuAcHex7HexNAc6dHex2 | 2953.06 | | | 0.28 |
| NeuAc2Hex6HexNAc5dHex2SP | 2958.98 | | 0.20 | |
| NeuAc3Hex6HexNAc5dHex | 3024.06 | 1.37 | 7.52 | 0.98 |
| NeuAc2Hex6HexNAc5dHex3 | 3025.09 | 0.39 | 1.16 | 0.65 |
| NeuAcHex8HexNAc7 | 3026.08 | 0.17 | | |
| NeuAc2Hex7HexNAc6dHex | 3098.10 | 0.52 | 0.85 | 0.47 |
| NeuAcHex7HexNAc6dHex3 | 3099.12 | | 0.44 | 0.24 |
| NeuAc3Hex6HexNAc5dHexSP | 3104.02 | 0.45 | 0.72 | |
| NeuAc2Hex6HexNAc5dHex3SP | 3105.04 | | 0.47 | |
| NeuAc3Hex6HexNAc5dHex2 | 3170.12 | | 0.17 | |
| NeuAc2Hex6HexNAc5dHex4 | 3171.14 | | 0.02 | |
| NeuAcHex8HexNAc7dHex | 3172.13 | | 0.12 | 0.11 |
| NeuAc2Hex7HexNAc6dHexSP | 3178.05 | | 0.10 | |
| NeuAc3Hex6HexNAc6dHex | 3227.14 | | 0.33 | |
| NeuAc2Hex7HexNAc6dHex2 | 3244.16 | | 0.20 | |
| NeuAcHex7HexNAc6dHex4 | 3245.18 | | 0.19 | |
| NeuAc3Hex7Hexnac5dHexSP | 3266.07 | | 0.10 | |
| NeuGc2Hex7HexNAc6dHex2 | 3276.15 | | 0.14 | |
| NeuAc3Hex7HexNAc6dHex | 3389.19 | 0.13 | 0.74 | |
| NeuAc2Hex7HexNAc6dHex3 | 3390.21 | | 0.37 | |
| NeuAc2Hex8HexNAc7dHex | 3463.23 | | 0.15 | |
| NeuAcHex8HexNAc7dHex3 | 3464.25 | | 0.19 | |
| NeuAc3Hex7Hexnac6dHexSP | 3469.15 | | 0.04 | |
| NeuAc2Hex7Hexnac6dHex3SP | 3470.17 | | 0.08 | |
| NeuAc3Hex7HexNAc6dHex2 | 3535.25 | | 0.15 | |
| NeuAc2Hex7HexNAc6dHex4 | 3536.27 | | 0.08 | |
| NeuAc4Hex7HexNAc6dHex | 3680.29 | | 0.40 | |
| NeuAc3Hex7HexNAc6dHex3 | 3681.31 | | 0.25 | |
| NeuAc3Hex8HexNAc7dHex | 3754.33 | | 0.22 | |
| NeuAc2Hex8HexNAc7dHex3 | 3755.35 | | 0.05 | |

TABLE 5

Neutral N-glycan grouping of cord blood cell populations, cord blood mononuclear cells (CB MNC), and peripheral blood mononuclear cells (PB MNC).

| Composition | Glycan Grouping | CD 34+ | CD 34− | CD 133+ | CD 133− | LIN− | LIN+ | CB MNC | PB MNC |
|---|---|---|---|---|---|---|---|---|---|
| General N-glycan grouping: | | | | | | | | | |
| $Hex_{5-12}HexNAc_2$ | high-mannose | 56.3 | 52.9 | 67.0 | 55.1 | 58.9 | 61.2 | 65.4 | 62.7 |
| $Hex_{1-4}HexNAc_2dHex_{0-1}$ | low-mannose | 33.1 | 35.5 | 25.6 | 32.8 | 21.1 | 24.5 | 26.5 | 29.6 |
| $n_{HexNAc} = 3$ and $n_{Hex} \geq 2$ | hybrid/monoant. | 5.5 | 6.4 | 2.4 | 5.6 | 8.6 | 5.5 | 4.3 | 3.7 |
| $n_{HexNAc} \geq 4$ and $n_{Hex} \geq 2$ | complex | 4.3 | 4.8 | 4.5 | 5.9 | 11.0 | 8.0 | 3.1 | 3.3 |
| Other types | — | 0.8 | 0.4 | 0.6 | 0.7 | 0.5 | 0.7 | 0.7 | 0.7 |
| Complex/hybrid/monoantennary N-glycan grouping: | | | | | | | | | |
| $n_{dHex} \geq 1$ | fucosylated | 67.8 | 70.6 | 81.2 | 66.4 | 49.0 | 66.8 | 58.8 | 56.4 |
| $n_{dHex} \geq 2$ | α2/3/4-linked Fuc | 18.8 | 21.3 | 0.5 | 11.5 | 0 | 5.4 | 12.2 | 4.9 |

TABLE 5-continued

Neutral N-glycan grouping of cord blood cell populations, cord blood mononuclear cells (CB MNC), and peripheral blood mononuclear cells (PB MNC).

| Neutral N-glycan Grouping: Composition | Glycan Grouping | CD 34+ | CD 34− | CD 133+ | CD 133− | LIN− | LIN+ | CB MNC | PB MNC |
|---|---|---|---|---|---|---|---|---|---|
| $n_{HexNAc} > n_{Hex} \geq 2$ | terminal HexNAc | 21.3 | 18.3 | 50.8 | 32.1 | 38.7 | 34.2 | 22.7 | 26.9 |
| $n_{HexNAc} = n_{Hex} \geq 5$ | bisecting GlcNAc | 0 | 0 | 0.8 | 0.8 | 0.4 | 2.0 | 0.4 | 0 |
| Complex N-glycan grouping: | | | | | | | | | |
| $n_{HexNAc} \geq 5$ and $n_{Hex} \geq 6$ | large N-glycans | 1.8 | 6.0 | 0 | 2.5 | 0 | 4.0 | 3.8 | 2.4 |

TABLE 6

Sialylated N-glycan grouping of cord blood cell populations, cord blood mononuclear cells (CB MNC), and peripheral blood mononuclear cells (PB MNC).

| Sialylated N-glycan Grouping: Composition | Glycan Grouping | CD 133+ | CD 133− | CB MNC |
|---|---|---|---|---|
| General N-glycan grouping: | | | | |
| $n_{HexNAc} = 3$ and $n_{Hex} \geq 5$ | hybrid | 5.7 | 3.2 | 7.7 |
| $n_{HexNAc} = 3$ and $n_{Hex} = 3$ or 4 | monoantennary | 12.1 | 7.5 | 11.6 |
| $n_{HexNAc} \geq 4$ and $n_{Hex} \geq 3$ | complex | 76.5 | 82.6 | 75.8 |
| Other types | — | 5.8 | 6.8 | 5.0 |
| Complex/hybrid/monoantennary N-glycan grouping: | | | | |
| $n_{dHex} \geq 1$ | fucosylated | 62.3 | 70.0 | 67.7 |
| $n_{dHex} \geq 2$ | α2/3/4-linked Fuc | 13.3 | 14.9 | 13.3 |
| $n_{HexNAc} > n_{Hex} \geq 3$ | terminal HexNAc | 0.6 | 0.1 | 0.6 |
| $n_{HexNAc} = n_{Hex} \geq 5$ | bisecting GlcNAc | 3.4 | 4.9 | 6.3 |
| Complex N-glycan grouping: | | | | |
| $n_{HexNAc} \geq 5$ and $n_{Hex} \geq 6$ | large N-glycans | 13.6 | 34.2 | 24.1 |
| Sialylation degree $SD_{HexNAc} = n_{NeuAc/Gc}:(n_{HexNAc} - 2)$ | | 75 | 78 | 72 |

TABLE 7

MALDI-TOF mass spectrometric analysis of endoglycoceramidase-released cord blood mononuclear cell glycolipid glycans.

| Proposed composition | calc. m/z | exp. m/z |
|---|---|---|
| A. Neutral oligosaccharides detected from glycolipids of cord blood mononuclear cells. Five major peaks are bolded. | | |
| Hex2HexNAc | 568.18 | 568.09 |
| Hex3HexNAc | 730.24 | 730.18 |
| Hex3HexNAcdHex | 876.30 | 876.27 |
| Hex4HexNAc | 892.29 | 892.27 |
| Hex3HexNAc2 | 933.31 | 933.30 |
| Hex5HexNAc | 1054.34 | 1054.33 |
| Hex4HexNAc2 | 1095.37 | 1095.36 |
| Hex4HexNAc2dHex | 1241.43 | 1241.42 |
| Hex4HexNAc2dHex2 | 1387.49 | 1387.48 |
| Hex6HexNAc2 | 1419.48 | 1419.47 |
| Hex5HexNAc3 | 1460.50 | 1460.49 |
| Hex5HexNAc4dHex | 1606.56 | 1606.55 |
| Hex5HexNac3dHex2 | 1752.62 | 752.60 |
| Hex6HexNAc4dHex2 | 2117.75 | 2117.71 |
| Hex6HexNAc4dHex3 | 2263.81 | 2263.76 |
| B. Acidic oligosaccharides detected from glycolipids of cord blood mononuclear cells. Five major peaks are bolded. | | |
| NeuAcHexHexNAc | 673.23 | 673.95 |
| NeuAcHex2HexNAc | 835.28 | 835.31 |
| NeuAcHex3HexNAc | 997.34 | 997.52 |
| NeuAcHex3HexNAc2 | 1200.42 | 1200.62 |
| NeuAcHex4HexNAc2 | 1362.47 | 1362.80 |
| NeuAcHex4HexNAc2dHex | 1508.53 | 1508.89 |
| NeuAcHex2HexNAc3dHex2 | 1533.56 | 1533.66 |
| NeuAc2Hex2HexNAc2dHexSP | 1555.47 | 1555.68 |
| NeuAcHex5HexNAc3 | 1727.60 | 1728.01 |
| NeuAcHex5HexNAc3dHex | 1873.66 | 1874.07 |
| NeuAc2Hex3HexNAc3dHexSP | 1920.60 | 1920.87 |
| NeuAcHex3HexNAc5dHex3 | 2247.83 | 2247.99 |

TABLE 8

Exoglycosidase profiling of cord blood CD34+ and CD34− cell neutral N-glycan fraction. α-Man, β1,4-Gal, β1,3-Gal, and β-GlcNAc refer to specific exoglycosidase enzymes as described in the text.

| | | α-Man | | β1,4-Gal | | β1,3-Gal | | β-GlcNAc | |
|---|---|---|---|---|---|---|---|---|---|
| Proposed composition | m/z | CD 34+ | CD 34− | CD 34+ | CD 34− | CD 34+ | CD 34− | CD 34+ | CD 34− |
| Hex2HexNAc | 568 | | −− | +++ | +++ | +++ | +++ | | |
| HexHexNAc2 | 609 | +++ | +++ | | +++ | | +++ | | |
| Hex3HexNAc | 730 | | −−− | −− | | − | | | |
| HexHexNAc2dHex | 755 | +++ | ++ | − | − | − | − | −− | |
| Hex2HexNAc2 | 771 | ++ | −− | −− | −− | −− | −− | | |
| Hex4HexNAc | 892 | −−− | −−− | − | | − | | | |
| Hex2HexNAc2dHex | 917 | −− | −− | −− | −− | −− | −− | | |
| Hex3HexNAc2 | 933 | −−− | −− | − | | − | | | |
| HexHexNAc3dHex | 958 | | +++ | | | | | | |
| Hex2HexNAc3 | 974 | | | | +++ | | +++ | | |
| Hex5HexNAc | 1054 | −−− | −− | + | | + | | − | |

TABLE 8-continued

Exoglycosidase profiling of cord blood CD34+ and CD34− cell neutral N-glycan fraction.
α-Man, β1,4-Gal, β1,3-Gal, and β-GlcNAc refer to specific exoglycosidase enzymes
as described in the text.

| | | α-Man | | β1,4-Gal | | β1,3-Gal | | β-GlcNAc | |
|---|---|---|---|---|---|---|---|---|---|
| Proposed composition | m/z | CD 34+ | CD 34− | CD 34+ | CD 34− | CD 34+ | CD 34− | CD 34+ | CD 34− |
| Hex3HexNAc2dHex | 1079 | −− | −− | | −− | − | −− | + | |
| Hex4HexNAc2 | 1095 | −−− | −−− | | | | | | |
| Hex2HexNAc3dHex | 1120 | | + | | + | | | | |
| Hex3HexNAc3 | 1136 | −−− | | | | | − | −−− | |
| Hex6HexNAc | 1216 | −−− | −− | | − | | − | − | − |
| Hex4HexNAc2dHex | 1241 | | −−− | | − | | − | − | − |
| Hex5HexNAc2 | 1257 | −−− | −− | + | + | + | + | | |
| Hex3HexNAc3dHex | 1282 | −−− | + | | | − | − | −− | |
| Hex4HexNAc3 | 1298 | −−− | | −−− | | | − | | |
| Hex2HexNAc4dHex | 1323 | | | +++ | | | | | |
| Hex3HexNAc4 | 1339 | | +++ | | +++ | | | | |
| Hex7HexNAc | 1378 | | −−− | + | | + | | +++ | |
| Hex5HexNAc2dHex | 1403 | | −−− | | | | | | |
| Hex6HexNAc2 | 1419 | −−− | −− | ++ | ++ | ++ | ++ | ++ | |
| Hex3HexNAc3dHex2 | 1428 | −−− | ++ | | +++ | | +++ | | |
| Hex4HexNAc3dHex | 1444 | −−− | | − | −− | | −− | + | |
| Hex5HexNAc3 | 1460 | −−− | − | +++ | | +++ | | −−− | |
| Hex3HexNAc4dHex | 1485 | − | | | + | | | −−− | |
| Hex4HexNAc4 | 1501 | −−− | | | −−− | | −−− | −−− | |
| Hex8HexNAc | 1540 | −−− | −−− | −−− | +++ | −−− | +++ | −−− | |
| Hex3HexNAc5 | 1542 | | +++ | | +++ | | +++ | | |
| Hex6HexNAc2dHex | 1565 | | | | | | +++ | | |
| Hex7HexNAc2 | 1581 | −−− | −− | | ++ | ++ | ++ | ++ | |
| Hex4HexNAc3dHex2 | 1590 | −−− | | −−− | − | | − | + | |
| Hex5HexNAc3dHex | 1606 | | −−− | −−− | +++ | | +++ | +++ | |
| Hex6HexNAc3 | 1622 | −−− | −−− | −−− | −−− | | | −−− | |
| Hex4HexNAc4dHex | 1647 | −−− | | | | | − | −−− | |
| Hex5HexNAc4 | 1663 | −−− | | −−− | −−− | −−− | −− | −−− | |
| Hex3HexNAc5dHex | 1688 | | | | +++ | | +++ | | |
| Hex9HexNAc | 1702 | −−− | −−− | | +++ | +++ | +++ | | |
| Hex4HexNAc5 | 1704 | | +++ | | | | | | |
| Hex8HexNAc2 | 1743 | −−− | −−− | +++ | + | +++ | ++ | ++ | |
| Hex5HexNAc3dHex2 | 1752 | | −−− | | +++ | | +++ | +++ | |
| Hex6HexNAc3dHex | 1768 | | | | +++ | | | +++ | |
| Hex7HexNAc3 | 1784 | −−− | | | | | | −−− | |
| Hex4HexNAc4dHex2 | 1793 | | | −− | +++ | −− | +++ | | |
| Hex5HexNAc4dHex | 1809 | −−− | | | −−− | +++ | − | | |
| Hex6HexNAc4 | 1825 | | +++ | | | | | | |
| Hex3HexNAc6dHex | 1891 | | +++ | | | | | | |
| Hex9HexNAc2 | 1905 | −−− | −−− | − | | + | ++ | ++ | |
| Hex5HexNAc4dHex2 | 1955 | −−− | | −−− | −− | | −− | | |
| Hex10HexNAc2 | 2067 | | −−− | − | | | | +++ | |
| Hex5HexNAc4dHex3 | 2101 | | | − | − | | − | +++ | |
| Hex5HexNAc5dHex2 | 2158 | +++ | | | +++ | | | | |
| Hex6HexNAc5dHex | 2174 | | | | | | +++ | | |
| Hex6HexNAc5dHex3 | 2466 | | | | +++ | | | | |

Code for profiling results, when compared to the profile before the reaction;
+++: new signal appears;
++: signal is significantly increased;
+: signal is increased;
−: signal is decreased;
−−: signal is significantly decreased;
−−−: signal disappears;
blank: no change.

TABLE 9

Exoglycosidase profiling of cord blood CD133+ and CD133− cell neutral N-glycan
fraction. α-Man, β1,4-Gal, β1,3-Gal, and β-GlcNAc refer to specific exoglycosidase
enzymes as described in the text.

| | | α-Man | | β1,4-Gal | | β1,3-Gal | | β-GlcNAc | |
|---|---|---|---|---|---|---|---|---|---|
| Proposed composition | m/z | CD 133+ | CD 133− | CD 133+ | CD 133− | CD 133+ | CD 133− | CD 133+ | CD 133− |
| Hex2HexNAc | 568 | | | | + | | + | | +++ |
| HexHexNAc2 | 609 | +++ | ++ | | | | | | −−− |
| Hex3HexNAc | 730 | −−− | −−− | +++ | ++ | +++ | ++ | | ++ |
| HexHexNAc2dHex | 755 | +++ | ++ | −−− | | −−− | | | |

TABLE 9-continued

Exoglycosidase profiling of cord blood CD133+ and CD133− cell neutral N-glycan fraction. α-Man, β1,4-Gal, β1,3-Gal, and β-GlcNAc refer to specific exoglycosidase enzymes as described in the text.

| Proposed composition | m/z | α-Man CD 133+ | α-Man CD 133− | β1,4-Gal CD 133+ | β1,4-Gal CD 133− | β1,3-Gal CD 133+ | β1,3-Gal CD 133− | β-GlcNAc CD 133+ | β-GlcNAc CD 133− |
|---|---|---|---|---|---|---|---|---|---|
| Hex2HexNAc2 | 771 | + | −− | ++ | ++ | + | + | | + |
| Hex4HexNAc | 892 | −−− | −−− | + | ++ | | ++ | | + |
| Hex2HexNAc2dHex | 917 | −−− | −− | ++ | ++ | ++ | + | | |
| Hex3HexNAc2 | 933 | | −− | + | + | − | | | + |
| Hex2HexNAc3 | 974 | | | | +++ | | | | |
| Hex5HexNAc | 1054 | −−− | −− | + | ++ | + | ++ | | + |
| Hex3HexNAc2dHex | 1079 | −−− | −− | ++ | + | + | | | ++ |
| Hex2HexNAc3dHex | 1120 | +++ | ++ | ++ | + | ++ | + | | −−− |
| Hex3HexNAc3 | 1136 | +++ | + | | + | | | | −−− |
| Hex6HexNAc | 1216 | −−− | − | + | | + | + | | |
| Hex4HexNAc2dHex | 1241 | −−− | −−− | + | | | | | |
| Hex5HexNAc2 | 1257 | −− | −− | − | | | | | |
| Hex3HexNAc3dHex | 1282 | | | | | | | | −− |
| Hex4HexNAc3 | 1298 | ++ | + | + | | + | | | |
| Hex3HexNAc4 | 1339 | | | | +++ | | | | −−− |
| Hex7HexNAc | 1378 | −−− | −−− | | − | +++ | | | + |
| Hex5HexNAc2dHex | 1403 | −−− | −−− | −−− | | − | | | |
| Hex6HexNAc2 | 1419 | −− | −− | −− | − | − | −− | | |
| Hex3HexNAc3dHex2 | 1428 | | +++ | | − | | − | | |
| Hex4HexNAc3dHex | 1444 | | − | − | − | | | | |
| Hex5HexNAc3 | 1460 | −−− | − | + | + | | | | |
| Hex3HexNAc4dHex | 1485 | −− | | + | + | | − | | −−− |
| Hex4HexNAc4 | 1501 | | −−− | | | | +++ | | −−− |
| Hex8HexNAc | 1540 | −−− | −−− | −−− | | | | | ++ |
| Hex3HexNAc5 | 1542 | | −−− | | + | | − | | −−− |
| Hex6HexNAc2dHex | 1565 | | | −−− | | −−− | +++ | | |
| Hex7HexNAc2 | 1581 | −−− | −− | −− | −− | − | −− | | |
| Hex4HexNAc3dHex2 | 1590 | | −−− | − | − | − | − | | + |
| Hex5HexNAc3dHex | 1606 | −−− | −−− | + | | | | | −−− |
| Hex6HexNAc3 | 1622 | −−− | −−− | −−− | −− | | | | − |
| Hex4HexNAc4dHex | 1647 | −−− | | −−− | − | | | | −−− |
| Hex5HexNAc4 | 1663 | | | −−− | − | −− | − | | − |
| Hex3HexNAc5dHex | 1688 | −−− | + | | | | −−− | | −−− |
| Hex9HexNAc | 1702 | | | | | | | | + |
| Hex4HexNAc5 | 1704 | −−− | | | −−− | | | | |
| Hex8HexNAc2 | 1743 | −−− | −−− | −− | −− | − | −− | | |
| Hex5HexNAc3dHex2 | 1752 | | | | − | | | | +++ |
| Hex6HexNAc3dHex | 1768 | | | | | | | | |
| Hex4HexNAc4dHex2 | 1793 | | | | | | | | |
| Hex5HexNAc4dHex | 1809 | −−− | | −−− | −−− | | − | | − |
| Hex6HexNAc4 | 1825 | | | | − | | | | −−− |
| Hex5HexNAc5 | 1866 | −−− | −−− | | −−− | | | | −−− |
| Hex3HexNAc6dHex | 1891 | | | | | | | | −−− |
| Hex9HexNAc2 | 1905 | −−− | −−− | −− | −− | − | −− | | |
| Hex6HexNAc3dHex2 | 1914 | | | | | −−− | −−− | | |
| Hex5HexNAc4dHex2 | 1955 | | | | −− | | − | | −−− |
| Hex6HexNAc4dHex | 1971 | | −−− | | −−− | | | | −−− |
| Hex7HexNAc4 | 1987 | | | | −−− | | | | −−− |
| Hex5HexNAc5dHex | 2012 | | | | | | +++ | | |
| Hex6HexNAc5 | 2028 | | −−− | | −−− | | | | −−− |
| Hex10HexNAc2 | 2067 | −−− | −−− | − | − | | | | |
| Hex5HexNAc4dHex3 | 2101 | | | − | − | | − | | |
| Hex6HexNAc4dHex2 | 2117 | | −−− | | −−− | −−− | | | −−− |
| Hex7HexNAc4dHex | 2133 | | | | −−− | | | | |
| Hex6HexNAc5dHex | 2174 | | −−− | | −−− | | | | −−− |
| Hex5HexNAc6dHex | 2215 | | | | −−− | | | | |
| Hex6HexNAc4dHex3 | 2263 | | | | −−− | | −−− | | |
| Hex6HexNAc5dHex2 | 2320 | | | | −−− | | | | |
| Hex6HexNAc5dHex3 | 2466 | | | | −−− | | | | |

Code for profiling results, when compared to the profile before the reaction;
+++: new signal appears;
++: signal is significantly increased;
+: signal is increased;
−: signal is decreased;
−−: signal is significantly decreased;
−−−: signal disappears;
blank: no change.

TABLE 10

Exoglycosidase profiling of cord blood Lin+ and Lin− cell neutral N-glycan fraction.

| Proposed composition | m/z | α-Man LIN+ | α-Man LIN− | β1,4-Gal LIN+ | β1,4-Gal LIN− | β1,3-Gal LIN+ | β1,3-Gal LIN− | β-GlcNAc LIN+ | β-GlcNAc LIN− |
|---|---|---|---|---|---|---|---|---|---|
| Hex2HexNAc | 568 | --- | +++ | + | | + | | − | |
| HexHexNAc2 | 609 | +++ | +++ | | | | +++ | | |
| Hex2HexNAcdHex | 714 | | | +++ | | | | | |
| Hex3HexNAc | 730 | --- | +++ | ++ | +++ | + | +++ | + | |
| HexHexNAc2dHex | 755 | +++ | +++ | + | | + | | +++ | |
| Hex2HexNAc2 | 771 | + | + | + | + | + | | + | |
| Hex4HexNAc | 892 | --- | --- | ++ | + | ++ | | + | + |
| Hex2HexNAc2dHex | 917 | -- | --- | + | ++ | − | | − | |
| Hex3HexNAc2 | 933 | − | | + | + | + | − | | + |
| Hex2HexNAc3 | 974 | +++ | | | | | | | |
| Hex5HexNAc | 1054 | -- | --- | ++ | | − | | − | |
| Hex3HexNAc2dHex | 1079 | -- | --- | | ++ | | − | ++ | ++ |
| Hex4HexNAc2 | 1095 | -- | --- | | | | − | | |
| Hex2HexNAc3dHex | 1120 | +++ | | | | | | | |
| Hex3HexNAc3 | 1136 | +++ | + | + | + | | − | +++ | --- |
| Hex6HexNAc | 1216 | − | --- | + | | + | + | | + |
| Hex4HexNAc2dHex | 1241 | --- | --- | | + | | + | | --- |
| Hex5HexNAc2 | 1257 | -- | --- | | ++ | − | − | − | + |
| Hex3HexNAc3dHex | 1282 | + | | | | | | -- | --- |
| Hex4HexNAc3 | 1298 | + | | | | | | | |
| Hex2HexNAc4dHex | 1323 | | | | +++ | | +++ | | |
| Hex3HexNAc4 | 1339 | | --- | ++ | + | | -- | | --- |
| Hex7HexNAc | 1378 | --- | --- | | | + | ++ | | |
| Hex5HexNAc2dHex | 1403 | --- | --- | | | | + | | |
| Hex6HexNAc2 | 1419 | -- | -- | | -- | − | − | − | |
| Hex3HexNAc3dHex2 | 1428 | +++ | | --- | | --- | | +++ | |
| Hex4HexNAc3dHex | 1444 | | --- | − | + | | + | | |
| Hex5HexNAc3 | 1460 | | --- | | | | | | |
| Hex3HexNAc4dHex | 1485 | | | | | | -- | --- | --- |
| Hex4HexNAc4 | 1501 | + | --- | + | − | --- | -- | --- | --- |
| Hex8HexNAc | 1540 | --- | --- | | --- | + | ++ | | |
| Hex3HexNAc5 | 1542 | +++ | | ++ | + | ++ | − | | |
| Hex6HexNAc2dHex | 1565 | | --- | --- | | | | --- | |
| Hex7HexNAc2 | 1581 | -- | --- | -- | -- | | − | | |
| Hex4HexNAc3dHex2 | 1590 | | | − | | | | +++ | |
| Hex5HexNAc3dHex | 1606 | --- | | --- | | | --- | | --- |
| Hex2HexNAc4dHex3 | 1615 | | | | | | +++ | | |
| Hex6HexNAc3 | 1622 | --- | --- | --- | --- | | | --- | --- |
| Hex4HexNAc4dHex | 1647 | | --- | -- | --- | | | --- | --- |
| Hex5HexNAc4 | 1663 | | --- | -- | --- | | − | − | -- |
| Hex3HexNAc5dHex | 1688 | | | − | | | | --- | --- |
| Hex9HexNAc | 1702 | --- | --- | | | | | | |
| Hex4HexNAc5 | 1704 | +++ | | | --- | | | | |
| Hex8HexNAc2 | 1743 | -- | --- | -- | -- | | − | | |
| Hex5HexNAc3dHex2 | 1752 | | | --- | | | | +++ | |
| Hex6HexNAc3dHex | 1768 | | | --- | | | | | |
| Hex3HexNAc4dHex3 | 1777 | | | | | | +++ | | |
| Hex7HexNAc3 | 1784 | | | --- | | | | | |
| Hex4HexNAc4dHex2 | 1793 | +++ | | | | | | | |
| Hex5HexNAc4dHex | 1809 | + | --- | -- | --- | | | | -- |
| Hex6HexNAc4 | 1825 | +++ | | − | --- | | -- | +++ | |
| Hex4HexNAc5dHex | 1850 | | | +++ | +++ | | | | |
| Hex5HexNAc5 | 1866 | +++ | | --- | | | | | |
| Hex3HexNAc6dHex | 1891 | | --- | − | | | | | |
| Hex9HexNAc2 | 1905 | --- | --- | -- | -- | | − | | |
| Hex4HexNAc4dHex3 | 1939 | | | | | | +++ | | |
| Hex5HexNAc4dHex2 | 1955 | | | --- | | | | +++ | |
| Hex6HexNAc4dHex | 1971 | | | --- | | | | | |
| Hex7HexNAc4 | 1987 | | | --- | | | | +++ | |
| Hex5HexNAc5dHex | 2012 | +++ | | --- | | | | | |
| Hex6HexNAc5 | 2028 | | | --- | | | | | |
| Hex10HexNAc2 | 2067 | --- | --- | − | | | ++ | + | |
| Hex5HexNAc4dHex3 | 2101 | | | | | | | +++ | |
| Hex8HexNAc4 | 2149 | | --- | | | | | | |
| Hex6HexNAc5dHex | 2174 | | | --- | | | | − | |
| Hex5HexNAc6dHex | 2215 | | | --- | | --- | | | |
| Hex11HexNAc2 | 2229 | | | | | | +++ | | |
| Hex6HexNAc6 | 2231 | | | --- | --- | | | | |
| Hex6HexNAc5dHex2 | 2320 | | | --- | --- | | | | |
| Hex12HexNAc2 | 2391 | | | +++ | +++ | +++ | | | |
| Hex7HexNAc6 | 2393 | | | --- | --- | | | | |

TABLE 10-continued

Exoglycosidase profiling of cord blood Lin+ and Lin− cell neutral N-glycan fraction.

| Proposed composition | m/z | α-Man LIN+ | α-Man LIN− | β1,4-Gal LIN+ | β1,4-Gal LIN− | β1,3-Gal LIN+ | β1,3-Gal LIN− | β-GlcNAc LIN+ | β-GlcNAc LIN− |
|---|---|---|---|---|---|---|---|---|---|
| Hex6HexNAc5dHex3 | 2466 | | | −−− | | −−− | | | |
| Hex7HexNAc6dHex | 2539 | +++ | | | | | | | |

TABLE 11

Differential effect of α2,3-sialidase treatment on isolated sialylated N-glycans from cord blood CD133$^+$ and CD133$^-$ cells. The neutral N-glycan columns show that neutral N-glycans corresponding to the listed sialylated N-glycans appear in analysis of CD133$^+$ cell N-glycans but not CD133$^-$ cell N-glycans. Proposed glycan compositions outside parenthesis are visible in the neutral N-glycan fraction after α2,3-sialidase digestion of CD133$^+$ cell sialylated N-glycans.

| m/z | Proposed monosaccharide composition | Sialylated N-glycan CD133$^+$ | Sialylated N-glycan CD133$^-$ | Neutral N-glycan CD133$^+$ | Neutral N-glycan CD133$^-$ |
|---|---|---|---|---|---|
| 1768 | (NeuAc$_1$)Hex$_4$HexNAc$_4$ | + | + | + | − |
| 2156 | (NeuAc$_1$)Hex$_8$HexNAc$_2$dHex$_1$/ (NeuAc$_1$Hex$_5$HexNAc$_4$dHex$_1$SO$_3$) | + | + | + | − |
| 2222 | (NeuAc$_1$)Hex$_5$HexNAc$_4$dHex$_2$ | + | + | + | − |
| 2238 | (NeuAc$_1$Hex$_6$HexNAc$_4$dHex$_1$/ (NeuGc$_1$)Hex$_5$HexNAc$_4$dHex$_2$ | + | + | + | − |
| 2254 | (NeuAc$_1$)Hex$_7$HexNAc$_4$/ (NeuGc$_1$)Hex$_6$HexNAc$_4$dHex$_1$ | + | + | + | − |
| 2368 | (NeuAc$_1$)Hex$_5$HexNAc$_4$dHex$_3$ | + | + | + | − |
| 2447 | (NeuAc$_2$)Hex$_8$HexNAc$_2$dHex$_1$/ (NeuAc$_2$Hex$_5$HexNAc$_4$dHex$_1$SO$_3$) | + | + | + | − |
| 2448 | (NeuAc$_1$)Hex$_8$HexNAc$_2$dHex$_3$/ (NeuAc$_1$Hex$_5$HexNAc$_4$dHex$_3$SO$_3$) | + | + | + | − |
| 2513 | (NeuAc$_2$)Hex$_5$HexNAc$_4$dHex$_2$ | + | + | + | − |
| 2733 | (NeuAc$_1$)Hex$_6$HexNAc$_5$dHex$_3$ | + | + | + | − |
| 2953 | (NeuAc$_1$)Hex$_7$HexNAc$_6$dHex$_2$ | + | + | + | − |

TABLE 12

Proposed neutral N-glycan grouping of the samples; hESC, human embryonal stem cell line, lines 1-4, EB, embryoid bodies derived from hESC lines 3 and 4, st.3 3, stage 3 differentiated cells from hESC line 3, HEF human fibroblasts used as feeder cells.

Neutral N-glycan Grouping:

| Composition | Glycan Grouping | hESC 1 | hESC 2 | hESC 3 | hESC 4 | EB 3 | EB 4 | st.3 3 | HEF1 | HEF2 |
|---|---|---|---|---|---|---|---|---|---|---|
| *General N-glycan grouping:* | | | | | | | | | | |
| Hex$_{5-12}$HexNAc$_2$ | high-mannose | 84.4 | 73.2 | 80.0 | 79.0 | 64.4 | 79.1 | 73.6 | 82.6 | 77.5 |
| Hex$_{1-4}$HexNAc$_2$dHex$_{0-1}$ | low-mannose | 5.6 | 10.9 | 6.8 | 7.8 | 11.5 | 9.2 | 9.4 | 7.1 | 8.0 |
| $n_{HexNAc} = 3$ and $n_{Hex} \geq 2$ | hybrid/monoantennary | 3.4 | 6.7 | 3.2 | 3.2 | 9.0 | 6.7 | 6.5 | 5.4 | 5.1 |
| $n_{HexNAc} \geq 4$ and $n_{Hex} \geq 2$ | complex | 6.2 | 8.9 | 10.1 | 10.0 | 14.5 | 5.0 | 10.3 | 4.9 | 9.1 |
| Other types | | 0.3 | 0.3 | 0.0 | 0.0 | 0.7 | 0.0 | 0.3 | 0.0 | 0.2 |
| *Complex/hybrid/monoantennary N-glycan grouping:* | | | | | | | | | | |
| $n_{dHex} \geq 1$ | fucosylated | 52.3 | 40.4 | 65.3 | 62.4 | 46.1 | 27.9 | 36.9 | 51.6 | 56.6 |
| $n_{dHex} \geq 2$ | α2/3/4-linked Fuc | 11.7 | 1.8 | 11.7 | 13.9 | 6.9 | 9.9 | 2.2 | 0.0 | 3.4 |
| $n_{HexNAc} > n_{Hex} \geq 2$ | terminal HexNAc | 9.4 | 17.4 | 6.8 | 6.0 | 17.7 | 15.5 | 18.4 | 27.2 | 16.2 |
| $n_{HexNAc} = n_{Hex} \geq 5$ | bisecting GlcNAc | 0.0 | 10.2 | 0.0 | 0.0 | 7.8 | 4.2 | 9.7 | 0.0 | 0.0 |
| *Complex N-glycan grouping:* | | | | | | | | | | |
| $n_{HexNAc} \geq 5$ and $n_{Hex} \geq 6$ | large N-glycans | 11.3 | 5.4 | 13.7 | 8.7 | 3.3 | 0.0 | 4.6 | 14.1 | 20.5 |

TABLE 13

Proposed sialylated N-glycan grouping of the samples; hESC, human embryonal stem cell line, lines 2-4, EB, embryoid bodies derived from hESC line 3, st.3 3, stage 3 differentiated cells from hESC line 3, HEF human fibroblasts used as feeder cells.

Sialylated N-glycan Grouping:

| Composition | Glycan Grouping | hESC 2 | hESC 3 | hESC 4 | EB 3 | st.3 3 | hEF |
|---|---|---|---|---|---|---|---|
| General N-glycan grouping: | | | | | | | |
| $n_{HexNAc} = 3$ and nHex ≥ 5 | hybrid | 0.0 | 3.8 | 4.5 | 9.6 | 3.6 | 3.4 |
| $n_{HexNAc} = 3$ and $n_{Hex} = 3$ or 4 | monoantennary | 2.2 | 2.3 | 5.5 | 6.4 | 2.5 | 3.6 |
| $n_{HexNAc} ≥ 4$ and $n_{Hex} ≥ 3$ | complex | 97.8 | 92.6 | 89.1 | 79.1 | 93.9 | 92.2 |
| Other types | | — | 0.0 | 1.3 | 0.9 | 4.8 | 0.0 | 0.8 |
| Complex/hybrid/monoantennary N-glycan grouping: | | | | | | | |
| $n_{dHex} ≥ 1$ | fucosylated | 93.0 | 72.6 | 74.6 | 79.3 | 85.3 | 76.2 |
| $n_{dHex} ≥ 2$ | α2/3/4-linked Fuc | 33.5 | 23.0 | 18.5 | 10.8 | 5.2 | 20.4 |
| $n_{HexNAc} > n_{Hex} ≥ 3$ | terminal HexNAc | 7.8 | 6.4 | 5.2 | 7.7 | 3.0 | 0.8 |
| $n_{HexNAc} = n_{Hex} ≥ 5$ | bisecting GlcNAc | 4.3 | 3.9 | 2.2 | 12.5 | 25.8 | 1.4 |
| $n_{NeuGc} ≥ 1$ | NeuGc-containing | 0.0 | 6.8 | 5.6 | 1.5 | 0.0 | 0.0 |
| Complex N-glycan grouping: | | | | | | | |
| $n_{HexNAc} ≥ 5$ and $n_{Hex} ≥ 6$ | large N-glycans | 22.7 | 18.7 | 14.9 | 12.4 | 26.6 | 44.5 |
| sialylation degree $SD_{HexNAc} = n_{NeuAc/Gc}:(n_{HexNAc} - 2)$ | | 51.6 | 60.4 | 63.0 | 60.7 | 56.6 | 60.3 |

TABLE 14

Mass spectrometric analysis results of sialylated N-glycans with monosaccharide compositions $NeuAc_{1-2}Hex_5HexNAc_4dHex_{0-3}$ in sequential enzymatic modification steps of human cord blood mononuclear cells. The columns show relative glycan signal intensities (% of the tabled signals) before the modification reactions (MNC), after α2,3-sialyltransferase reaction (α2,3SAT), and after sequential α2,3-sialyltransferase and α1,3-fucosyltransferase reactions (α2,3SAT + α1,3FucT). The sum of the glycan signal intensities in each column has been normalized to 100% for clarity.

| Proposed monosaccharide composition | calc m/z [M − H]⁻ | MNC | α2,3SAT | α2,3SAT + α1,3FucT |
|---|---|---|---|---|
| NeuAcHex5HexNAc4 | 1930.68 | 24.64 | 12.80 | 13.04 |
| NeuAcHex5HexNAc4dHex | 2076.74 | 39.37 | 30.11 | 29.40 |
| NeuAcHex5HexNAc4dHex2 | 2222.8 | 4.51 | 8.60 | 6.83 |
| NeuAcHex5HexNAc4dHex3 | 2368.85 | 3.77 | 6.34 | 6.45 |
| NeuAc2Hex5HexNAc4 | 2221.78 | 13.20 | 12.86 | 17.63 |
| NeuAc2Hex5HexNAc4dHex | 2367.83 | 14.04 | 29.28 | 20.71 |
| NeuAc2Hex5HexNAc4dHex2 | 2513.89 | 0.47 | n.d. | 5.94 |

TABLE 15

Mass spectrometric analysis results of selected neutral N-glycans in enzymatic modification steps of human cord blood mononuclear cells. The columns show relative glycan signal intensities (% of the total glycan signals) before the modification reactions (MNC), after broad-range sialidase reaction (SA'se), after α2,3-sialyltransferase reaction (α2,3SAT), after α1,3-fucosyltransferase reaction (α1,3FucT), and after sequential α2,3-sialyltransferase and α1,3-fucosyltransferase reactions (α2,3SAT + α1,3FucT).

| Proposed monosaccharide composition | calc m/z [M + H]⁺ | MNC | SA'ase | α2,3SAT | α1,3FucT | α2,3SAT + α1,3FucT |
|---|---|---|---|---|---|---|
| Hex5HexNAc2 | 1257.42 | 11.94 | 14.11 | 14.16 | 13.54 | 9.75 |
| Hex3HexNAc4dHex | 1485.53 | 0.76 | 0.63 | 0.78 | 0.90 | 0.78 |
| Hex6HexNAc3 | 1622.56 | 0.61 | 1.99 | 0.62 | 0.51 | 0.40 |
| Hex5HexNAc4 | 1663.58 | 0.44 | 4.81 | 0.00 | 0.06 | 0.03 |
| Hex5HexNac4dHex | 1809.64 | 0.19 | 1.43 | 0.00 | 0.25 | 0.00 |
| Hex5HexNac4dHex2 | 1955.7 | 0.13 | 0.22 | 0.00 | 0.22 | 0.00 |
| Hex6HexNAc5 | 2028.71 | 0.07 | 1.14 | 0.00 | 0.00 | 0.00 |
| Hex5HexNAc4dHex3 | 2101.76 | 0.12 | 0.09 | 0.00 | 0.22 | 0.00 |
| Hex6HexNAc5dHex | 2174.77 | 0.00 | 0.51 | 0.00 | 0.14 | 0.00 |
| Hex6HexNAc5dHex2 | 2320.83 | 0.00 | 0.00 | 0.00 | 0.08 | 0.00 |

TABLE 16

Cord blood mononuclear cell sialylated N-glycan signals.
The m/z values refer to monoisotopic masses of
[M − H]− ions.

| Proposed monosaccharide composition | m/z (calculated) | |
|---|---|---|
| NeuAcHex3HexNAc3dHex | 1549.55 | 1549 |
| NeuAcHex4HexNAc3 | 1565.55 | 1565 |
| NeuAc2Hex3HexNAc2dHex | 1637.57 | 1637 |
| NeuAc2Hex2HexNAc3dHex | 1678.60 | 1678 |
| NeuAcHex4HexNAc3dHex | 1711.61 | 1711 |
| NeuAcHex5HexNAc3 | 1727.60 | 1727 |
| NeuAcHex3HexNAc4dHex | 1752.63 | 1752 |
| NeuAcHex4HexNAc4 | 1768.57 | 1768 |
| NeuAcHex4HexNAc3dHexSO3 | 1791.56 | 1791 |
| NeuAc2Hex3HexNAc3dHex | 1840.65 | 1840 |
| NeuAcHex4HexNAc3dHex2 | 1857.66 | 1857 |
| Hex5HexNAc4dHexSO3 | 1865.60 | 1865 |
| NeuAcHex5HexNAc3dHex | 1873.66 | 1873 |
| NeuAcHex6HexNAc3 | 1889.65 | 1889 |
| NeuAcHex4HexNAc4dHex2 | 1898.69 | 1898 |
| NeuAcHex4HexNAc4dHex | 1914.68 | 1914 |
| NeuAcHex5HexNAc4 | 1930.68 | 1930 |
| NeuAc2Hex4HexNAc3dHex/ Hex8HexNAc3SO3 | 2002.70 | 2002 |
| NeuAc2Hex5HexNAc3 | 2018.70 | 2018 |
| NeuAcHex6HexNAc3dHex | 2035.71 | 2035 |
| NeuAcHex7HexNAc3 | 2051.71 | 2051 |
| Hex4HexNAc5dHex2SO3 | 2052.68 | 2052 |
| NeuAc2Hex4HexNAc4 | 2059.72 | 2059 |
| NeuAcHex4HexNAc4dHex2 | 2060.74 | 2060 |
| NeuAcHex5HexNAc4dHex | 2076.74 | 2076 |
| NeuAcHex6HexNAc4 | 2092.73 | 2092 |
| NeuAcHex4HexNAc5dHex | 2117.76 | 2117 |
| NeuAcHex5HexNAc5 | 2133.76 | 2133 |
| NeuAcHex8HexNAc2dHex/ NeuAcHex5HexNAc4dHexSO3 | 2156.74/2156.69 | 2156 |
| NeuAc2Hex5HexNAc4 | 2221.78 | 2221 |
| NeuAcHex5HexNAc4dHex2 | 2222.80 | 2222 |
| Hex6HexNAc5dHexSO3 | 2230.73 | 2230 |
| NeuAcHex6HexNAc4dHex/ NeuGcHex5HexNAc4dHex2 | 2238.79 | 2238 |
| NeuAcHex7HexNAc4/ NeuGcHex6HexNAc4dHex | 2254.79 | 2254 |
| NeuAcHex5HexNAc5dHex | 2279.82 | 2279 |
| NeuAc2Hex4HexNAc3dHex3 | 2294.82 | 2294 |
| NeuAcHex6HexNAc5 | 2295.81 | 2295 |
| NeuAc2Hex5HexNAc4dHex | 2367.83 | 2367 |
| NeuAcHex5HexNAc4dHex3 | 2368.85 | 2368 |
| NeuAc2Hex6HexNAc4 | 2383.83 | 2383 |
| NeuAcHex6HexNAc4dHex2 | 2384.85 | 2384 |
| NeuAc2Hex5HexNAc3dHexSO3 | 2390.77 | 2390 |
| NeuAc2Hex3HexNAc5dHex2 | 2392.86 | 2392 |
| NeuAcHex5HexNAc5dHex2 | 2425.87 | 2425 |
| NeuAcHex6HexNAc5dHex | 2441.87 | 2441 |
| NeuAc2Hex8HexNAc2dHex/ NeuAc2Hex5HexNAc4dHexSO3 | 2447.83/2447.79 | 2447 |
| NeuAcHex7HexNAc5 | 2457.86 | 2457 |
| NeuAc2Hex5HexNAc4dHex2 | 2513.89 | 2513 |
| NeuAcHex6HexNAc4dHex2 | 2521.83 | 2521 |
| NeuAcHex6HexNAc4dHex3 | 2530.91 | 2530 |
| NeuAc3Hex4HexNAc5 | 2553.90 | 2553 |
| NeuAc2Hex5HexNAc5dHex | 2570.91 | 2570 |
| NeuAcHex5HexNAc5dHex3 | 2571.93 | 2571 |
| NeuAc2Hex6HexNAc5 | 2586.91 | 2586 |
| NeuAcHex6HexNAc5dHex2 | 2587.93 | 2587 |
| Hex7HexNAc6dHexSO3 | 2595.86 | 2595 |
| NeuAcHex7HexNAc5dHex | 2603.92 | 2603 |
| NeuAcHex6HexNAc6dHex | 2644.95 | 2644 |
| NeuAcHex7HexNAc6 | 2660.94 | 2660 |
| NeuAc2Hex6HexNAc5dHex2(SO3)2 | 2714.83 | 2714 |
| NeuAc2Hex6HexNAc5dHex | 2732.97 | 2732 |
| NeuAcHex6HexNAc5dHex3 | 2733.99 | 2733 |
| NeuAcHex7HexNAc6dHex | 2807.00 | 2807 |
| NeuAcHex6HexNAc6dHex3SO3 | 2813.94 | 2813 |
| NeuAc3Hex6HexNAc5 | 2878.00 | 2878 |
| NeuAc2Hex6HexNAc5dHex2 | 2879.02 | 2879 |
| NeuAcHex6HexNAc5dHex4 | 2880.04 | 2880 |
| NeuAc2Hex5HexNAc6dHex2 | 2920.05 | 2920 |
| NeuAc2Hex7HexNAc6 | 2952.04 | 2952 |
| NeuAcHex7HexNAc6dHex2 | 2953.06 | 2953 |
| NeuAcHex7HexNac7dHex | 3010.08 | 3010 |
| NeuAc3Hex6HexNAc5dHex | 3024.06 | 3024 |
| NeuAc2Hex6HexNAc5dHex3 | 3025.09 | 3025 |
| NeuAcHex8HexNAc7 | 3026.08 | 3026 |
| NeuAc2Hex7HexNAc6dHex | 3098.10 | 3098 |
| NeuAcHex7HexNAc6dHex3 | 3099.12 | 3099 |
| NeuAcHex6HexNAc5dHex4 | 3171.14 | 3171 |
| NeuAcHex8HexNAc7dHex | 3172.13 | 3172 |

TABLE 17

NMR analysis of hESC neutral N-glycans (hESC sample). Reference glycans (A.-D.) are described in FIG. 26.

| Glycan residue | linkage | A proton | A ppm | B ppm | C ppm | D ppm | hESC sample ppm |
|---|---|---|---|---|---|---|---|
| D-GlcNAc | | H-1a | 5.191 | 5.187 | 5.187 | 5.188 | 5.188 |
| | | H-1b | 4.690 | 4.693 | 4.693 | 4.695 | 4.694 |
| | | NAc | 2.042 | 2.037 | 2.037 | 2.038 | 2.038 |
| β-D-GlcNAc | 4 | H-1 | 4.596 | 4.586 | 4.586 | 4.600 | 4.596 |
| | | NAc | 2.072 | 2.063 | 2.063 | 2.064 | 2.061[1)] |
| β-D-Man | 4, 4 | H-1 | 4.775 | 4.771 | 4.771 | 4.780 | |
| | | H-2 | 4.238 | 4.234 | 4.234 | 4.240 | 4.234 |
| α-D-Man | 6, 4, 4 | H-1 | 4.869 | 4.870 | 4.870 | 4.870 | 4.869 |
| | | H-2 | 4.149 | 4.149 | 4.149 | 4.150 | 4.153 |
| α-D-Man | 6, 6, 4, 4 | H-1 | 5.153 | 5.151 | 5.151 | 5.143 | 5.148 |
| | | H-2 | 4.025 | 4.021 | 4.021 | 4.020 | 4.023 |
| α-D-Man | 2, 6, 6, 4, 4 | H-1 | 5.047 | 5.042 | 5.042 | 5.041 | 5.042 |
| | | H-2 | 4.074 | 4.069 | 4.069 | 4.070 | 4.069 |
| α-D-Man | 3, 6, 4, 4 | H-1 | 5.414 | 5.085 | 5.415 | 5.092 | 5.408, 5.085 |
| | | H-2 | 4.108 | 4.069 | 4.099 | 4.070 | 4.102, 4.069 |
| α-D-Man | 2, 3, 6, 4, 4 | H-1 | 5.047 | — | 5.042 | — | 5.042 |
| | | H-2 | 4.074 | — | 4.069 | — | 4.069 |
| α-D-Man | 3, 4, 4 | H-1 | 5.343 | 5.341 | 5.341 | 5.345 | 5.346, 5.338 |
| | | H-2 | 4.108 | 4.099 | 4.099 | 4.120 | 4.102 |
| α-D-Man | 2, 3, 4, 4 | H-1 | 5.317 | 5.309 | 5.050 | 5.055 | 5.310, 5.057 |
| | | H-2 | 4.108 | 4.099 | 4.069 | 4.070 | 4.102, 4.069 |

TABLE 17-continued

NMR analysis of hESC neutral N-glycans (hESC sample). Reference glycans (A.-D.) are described in FIG. 26.

| Glycan residue | linkage | A proton | ppm | B ppm | C ppm | D ppm | hESC sample ppm |
|---|---|---|---|---|---|---|---|
| α-D-Man | 2, 2, 3, 4, 4 | H-1 | 5.047 | 5.042 | — | — | 5.042 |
|  |  | H-2 | 4.074 | 4.069 | — | — | 4.069 |

[1] Under HDO.

TABLE 18

NMR analysis of hESC acidic N-glycans (hESC sample). Reference glycans (A.-E.) are described in FIG. 27.

| Glycan residue | linkage | proton | A. ppm | B. ppm | C. ppm | D. ppm | E. ppm | hESC sample ppm |
|---|---|---|---|---|---|---|---|---|
| D-GlcNAc |  | H-1a | 5.180 | 5.188 | 5.189 | 5.181 | 5.189 | 5.182/5.188 |
|  |  | H-1b | 4.692 | n.a.[1] | 4.695 | n.a. | 4.694 | n.a. |
|  |  | NAc | 2.038 | 2.038 | 2.038 | 2.039 | 2.038 | 2.038 |
| α-L-Fuc | 6 | H-1a | 4.890 | —[2] | — | 4.892 | — | 4.893 |
|  |  | H-1b | 4.897 | — | — | 4.900 | — | 4.893 |
|  |  | H-5a | 4.098 | — | — | 4.10 | — | Overlap[3] |
|  |  | H-5b | 4.134 | — | — | n.a. | — | Overlap |
|  |  | CH3a | 1.209 | — | — | 1.211 | — | 1.210 |
|  |  | CH3b | 1.220 | — | — | 1.223 | — | 1.219 |
| β-D-GlcNAc | 4 | H-1a | 4.664 | 4.612 | 4.614 | 4.663 | 4.613 | n.a. |
|  |  | H-1b | 4.669 | 4.604 | 4.606 | n.a. | 4.604 | n.a./4.605 |
|  |  | NAc (a/b) | 2.097 | 2.081 | 2.081 | 2.096/2.093 | 2.084 | 2.081/2.095 |
| β-D-Man | 4, 4 | H-1 | 4.772 | n.a. | n.a. | n.a. | n.a. | n.a |
|  |  | H-2 | 4.257 | 4.246 | 4.253 | 4.248 | 4.258 | 4.256 |
| α-D-Man | 6, 4, 4 | H-1 | 4.929 | 4.928 | 4.930 | 4.922 | 4.948 | 4.927 |
|  |  | H-2 | 4.111 | 4.11 | 4.112 | 4.11 | 4.117 | Overlap |
| β-D-GlcpNAc | 2, 6, 4, 4 | H-1 | 4.583 | 4.581 | 4.582 | 4.573 | 4.604 | 4.579/4.605 |
|  |  | NAc | 2.048 | 2.047 | 2.047 | 2.043 | 2.066 | 2.047/2.069 |
| β-D-Gal | 4, 2, 6, 4, 4 | H-1 | 4.544 | 4.473 | 4.473 | 4.550 | 4.447 | 4.447/4.472/4.545 |
|  |  | H-3 | n.a. | n.a. | n.a. | 4.119 | n.a. | Overlap |
|  |  | H-4 | 4.185 | n.a. | n.a. | n.a. | n.a. | 4.185 |
| α-D-Galp | 3, 4, 2, 6, 4, 4 | H-1 | 5.146 | — | — | — | — | 5.146 |
| α-D-Neup5Ac | 3, 4, 2, 6, 4, 4 | H-3a | — | — | — | 1.800 | — | 1.802 |
|  |  | H-3e | — | — | — | 2.758 | — | 2.756 |
|  |  | NAc | — | — | — | 2.031 | — | 2.030 |
| α-D-Neup5Ac | 6, 4, 2, 6, 4, 4 | H-3a | — | — | — | — | 1.719 | 1.721 |
|  |  | H-3e | — | — | — | — | 2.673 | 2.669 |
|  |  | NAc | — | — | — | — | 2.029 | 2.030 |
| α-D-Man | 3, 4, 4 | H-1 | 5.135 | 5.118 | 5.135 | 5.116 | 5.133 | 5.118/5.134 |
|  |  | H-2 | 4.195 | 4.190 | 4.196 | 4.189 | 4.197 | 4.195 |
| β-D-GlcpNAc | 2, 3, 4, 4 | H-1 | 4.605 | 4.573 | 4.606 | 4.573 | 4.604 | 4.579/4.605 |
|  |  | NAc | 2.069 | 2.047 | 2.069 | 2.048 | 2.070 | 2.047/2.069 |
| β-D-Galp | 4, 2, 3, 4, 4 | H-1 | 4.445 | 4.545 | 4.445 | 4.544 | 4.443 | 4.445/4.545 |
|  |  | H-3 | n.a. | 4.113 | n.a. | 4.113 | n.a. | Overlap |
| α-D-Neup5Ac | 6, 4, 2, 3, 4, 4 | H-3a | 1.722 | — | 1.719 | — | 1.719 | 1.721 |
|  |  | H-3e | 2.666 | — | 2.668 | — | 2.667 | 2.669 |
|  |  | NAc | 2.029 | — | 2.030 | — | 2.029 | 2.030 |
| α-D-Neup5Ac | 3, 4, 2, 3, 4, 4 | H-3a | — | 1.797 | — | 1.797 | — | 1.802 |
|  |  | H-3e | — | 2.756 | — | 2.758 | — | 2.756 |
|  |  | NAc | — | 2.030 | — | 2.031 | — | 2.030 |

[1] n.a., not assigned.
[2] —, not present.
[3] Overlap, overlapping signals at 4.139-4.088 ppm.

TABLE 19

Detected neutral O-glycan fraction signals from CB MNC. Neutral O-glycan signals, [M + Na]+ ions

| Proposed structure | calc. m/z | exp. m/z |
|---|---|---|
| Hex1HexNAc2 | 611.23 | 611.19 |
| Hex2HexNAc2 | 773.28 | 773.29 |
| Hex4HexNAc2 | 1097.39 | 1097.44 |
| Hex3HexNAc3 | 1138.42 | 1138.47 |

TABLE 19-continued

Detected neutral O-glycan fraction signals from CB MNC.
Neutral O-glycan signals, [M + Na]$^+$ ions

| Proposed structure | calc. m/z | exp. m/z |
|---|---|---|
| Hex5HexNAc2 | 1259.44 | 1259.5 |
| Hex3HexNAc4 | 1341.50 | 1341.56 |
| Hex5HexNAc3 | 1462.52 | 1462.62 |
| Hex4HexNAc4 | 1503.55 | 1503.63 |
| Hex3HexNAc3dHex4 | 1722.65 | 1722.71 |
| Hex4HexNAc3dHex4 | 1884.70 | 1884.77 |
| Hex5HexNAc5dHex1 | 2014.74 | 2014.86 |
| Hex4HexNAc6dHex1 | 2055.77 | 2055.85 |
| Hex6HexNAc5dHex1 | 2176.79 | 2176.89 |

TABLE 20

Detected acidic O-glycan fraction signals from CB MNC.
Acidic O-glycan signals, [M − H]$^-$ ions

| Proposed structure | calc. m/z | exp. m/z |
|---|---|---|
| NeuAc1Hex1HexNAc1 | 675.25 | 675.27 |
| NeuAc2Hex1HexNAc1 | 966.35 | 966.37 |
| NeuAc1Hex2HexNAc2 | 1040.38 | 1040.54 |
| NeuAc1Hex2HexNAc2dHex1 | 1186.44 | 1186.47 |
| NeuGc1Hex3HexNAc2 | 1218.43 | 1218.48 |
| NeuAc2Hex2HexNAc2 | 1331.48 | 1331.61 |
| NeuAc1Hex3HexNAc3 | 1405.51 | 1405.75 |
| NeuAc2Hex2HexNAc1dHex1 | 1477.54 | 1477.65 |
| NeuAc2Hex3HexNAc3 | 1696.61 | 1696.78 |
| NeuAc1Hex3HexNAc3dHexSP2 | 1711.49 | 1711.91 |
| NeuAc1Hex4HexNAc4 | 1770.59 | 1770.97 |
| NeuAc1Hex5HexNAc4 | 1932.70 | 1932.89 |
| NeuAc1Hex4HexNAc4dHex1(SP)2 | 2076.61 | 2076.98 |
| NeuAc2Hex5HexNAc4 | 2223.80 | 2224.00 |

TABLE 21

Detected glycan signals in the neutral O-glycan fraction from hESC.
Neutral O-glycan reducing oligosaccharides, [M + Na]$^+$ ions

| Proposed structure | calc. m/z | exp. m/z |
|---|---|---|
| Hex1HexNAc2 | 609.21 | 609.26 |
| Hex3HexNAc1 | 730.24 | 730.30 |
| Hex2HexNAc2 | 771.26 | 771.33 |
| NeuAc1Hex1HexNAc1(deoxyamino)HexNAc1 | 899 | 899.39 |
| Hex2HexNAc2dHex1 | 917.32 | 917.40 |
| Hex3HexNAc2 | 933.31 | 933.39 |
| Hex2HexNAc3 | 974.34 | 974.44 |
| Hex2HexNAc2dHex2 | 1063.38 | 1063.46 |
| Hex3HexNAc2dHex1 | 1079.38 | 1079.44 |
| Hex4HexNAc2 | 1095.37 | 1095.45 |
| Hex3HexNAc3 | 1136.40 | 1136.47 |
| Hex5HexNAc2 | 1257.42 | 1257.49 |
| Hex3HexNAc3dHex1 | 1282.45 | 1282.52 |
| Hex4HexNAc3 | 1298.45 | 1298.52 |
| Hex7HexNAc1 | 1378.45 | 1378.52 |
| Hex6HexNAc2 | 1419.48 | 1419.54 |
| Hex4HexNAc3dHex1 | 1444.51 | 1444.57 |
| Hex5HexNAc3 | 1460.50 | 1460.56 |
| Hex3HexNAc4dHex1 | 1485.53 | 1485.6 |
| Hex3HexNAc5 | 1542.56 | 1542.58 |
| Hex7HexNAc2 | 1581.53 | 1581.59 |
| Hex6HexNAc3 | 1622.56 | 1622.61 |
| Hex4HexNAc4dHex1 | 1647.59 | 1647.63 |
| Hex4HexNAc5 | 1704.61 | 1704.66 |
| Hex8HexNAc2 | 1743.58 | 1743.63 |
| Hex5HexNAc4dHex1 | 1809.64 | 1809.69 |
| Hex5HexNAc5 | 1866.66 | 1866.70 |
| Hex9HexNAc2 | 1905.63 | 1905.68 |
| Hex10HexNAc2 | 2067.69 | 2067.72 |

TABLE 22

Detected acidic O-glycan signals from hESC.
Acidic O-glycan reducing oligosaccharides, [M − H]$^-$ ions

| Proposed structure | calc. m/z | exp. m/z |
|---|---|---|
| NeuAc2HexHexNAc | 964.33 | 964.35 |
| SaHex2HexNAc2 | 1038.36 | 1038.49 |
| NeuAcHex2HexNAc2dHex | 1184.42 | 1184.5 |
| Hex3HexNAc3SP | 1192.36 | 1192.73 |
| SaHex3HexNAc2 | 1200.42 | 1200.43 |
| NeuAc2Hex2HexNAc2/NeuGcNeuAcHexHexNAc2dHex | 1329.46 | 1329.56 |
| Hex3HexNAc3dHexSP | 1338.41 | 1338.6 |
| SaHex3HexNAc3 | 1403.49 | 1403.62 |
| Sa2Hex2HexNAcdHex | 1475.52 | 1475.79 |
| NeuAcHex6HexNAc/NeuAcHex3HexNAc3SP | 1483.49 | 1483.71 |
| SaHex3HexNAc3dHex | 1549.55 | 1549.9 |
| Hex4HexNAc4SP | 1557.49 | 1557.72 |
| SaHex4HexNAc3 | 1565.55 | 1565.66 |
| NeuAc2Hex3HexNAc3 | 1694.59 | 1694.8 |
| Hex4HexNAc4dHexSP | 1703.55 | 1703.9 |
| SaHex4HexNAc3dHex | 1711.61 | 1711.78 |
| SaHex5HexNAc3 | 1727.60 | 1727.96 |
| SaHex4HexNAc4 | 1768.57 | 1768.75 |
| SaHex6HexNAc3 | 1889.65 | 1889.96 |
| SaHex4HexNAc4dHex | 1914.68 | 1915.04 |
| SaHex5HexNAc4 | 1930.68 | 1930.83 |
| SaHex5HexNAc4dHex | 2076.74 | 2076.91 |
| NeuGcHex5HexNAc4dHex/SaHex6HexNAc4 | 2092.73 | 2092.86 |
| Sa2Hex5HexNAc4 | 2221.78 | 2221.82 |
| SaHex5HexNAc4dHex2 | 2222.80 | 2222.93 |
| NeuGcHex5HexNAc4dHex2/SaHex6HexNAc4dHex | 2238.79 | 2238.9 |
| SaHex7HexNAc4/NeuGcHex6HexNAc4dHex | 2254.79 | 2254.88 |
| SaHex5HexNAc4dHex3 | 2368.85 | 2368.26 |
| SaHex6HexNAc5dHex | 2441.87 | 2442.23 |

TABLE 23

Exoglycosidase analysis results of hESC line FES 29 grown on mEF.

| | | FES 29 | | | | | | |
|---|---|---|---|---|---|---|---|---|
| Proposed composition | m/z | α-Man | β-GlcNAc | β-HexNAc | β1,4Gal | β1,3-Gal | α1,3/4-Fuc | α1,2-Fuc |
| Hex2HexNAc | 568 | | +++ | +++ | | +++ | +++ | +++ |
| HexHexNAc2 | 609 | +++ | | | | +++ | +++ | |
| Hex3HexNAc | 730 | −− | + | ++ | ++ | + | | + |
| HexHexNAc2dHex | 755 | +++ | | | | | | |
| Hex2HexNAc2 | 771 | + | + | −−− | | + | + | + |
| Hex4HexNAc | 892 | −−− | + | + | −−− | + | + | + |
| Hex2HexNAc2dHex | 917 | −− | + | | | + | + | + |

TABLE 23-continued

Exoglycosidase analysis results of hESC line FES 29 grown on mEF.

| | | FES 29 | | | | | | |
|---|---|---|---|---|---|---|---|---|
| Proposed composition | m/z | α-Man | β-GlcNAc | β-HexNAc | β1,4Gal | β1,3-Gal | α1,3/4-Fuc | α1,2-Fuc |
| Hex3HexNAc2 | 933 | -- | ++ | + | | + | + | + |
| Hex2HexNAc3 | 974 | +++ | | | | +++ | +++ | +++ |
| Hex5HexNAc | 1054 | -- | + | + | + | + | + | + |
| Hex3HexNAc2dHex | 1079 | -- | ++ | | + | + | + | + |
| Hex4HexNAc2 | 1095 | -- | | + | | + | + | + |
| Hex2HexNAc3dHex | 1120 | ++ | | - | | + | -- | |
| Hex3HexNAc3 | 1136 | + | -- | -- | | + | ++ | + |
| Hex6HexNAc | 1216 | -- | + | ++ | + | + | + | + |
| Hex4HexNAc2dHex | 1241 | -- | + | | | + | | |
| Hex5HexNAc2 | 1257 | -- | | | | | | |
| Hex3HexNAc3dHex | 1282 | | - | -- | | + | + | + |
| Hex4HexNAc3 | 1298 | + | ++ | ++ | ++ | + | ++ | ++ |
| Hex3HexNAc4 | 1339 | | --- | --- | ++ | ++ | --- | --- |
| Hex7HexNAc | 1378 | -- | + | + | + | + | + | + |
| Hex5HexNAc2dHex | 1403 | --- | + | | | | | + |
| Hex6HexNAc2 | 1419 | -- | - | | | - | - | - |
| Hex3HexNAc3dHex2 | 1428 | +++ | | | | +++ | | |
| Hex4HexNAc3dHex | 1444 | | ++ | + | | + | + | |
| Hex5HexNAc3 | 1460 | - | | | | + | + | + |
| Hex3HexNAc4dHex | 1485 | | -- | --- | + | + | | + |
| Hex4HexNAc4 | 1501 | | --- | --- | --- | + | --- | --- |
| Hex8HexNAc | 1540 | --- | + | ++ | + | | + | |
| Hex3HexNAc5 | 1542 | ++ | --- | --- | ++ | ++ | | + |
| Hex6HexNAc2dHex | 1565 | --- | | --- | | | | |
| Hex7HexNAc2 | 1581 | -- | | | | - | | |
| Hex4HexNAc3dHex2 | 1590 | | ++ | + | | | | |
| Hex5HexNAc3dHex | 1606 | - | + | | | + | | |
| Hex6HexNAc3 | 1622 | -- | | | -- | + | + | + |
| Hex4HexNAc4dHex | 1647 | | -- | --- | -- | + | + | |
| Hex5HexNAc4 | 1663 | | + | | - | + | | + |
| Hex3HexNAc5dHex | 1688 | | --- | --- | | + | | + |
| Hex9HexNAc | 1702 | --- | + | ++ | + | + | | |
| Hex4HexNAc5 | 1704 | + | - | --- | --- | | | |
| Hex8HexNAc2 | 1743 | --- | - | | | - | - | - |
| Hex5HexNAc3dHex2 | 1752 | +++ | | | | | | |
| Hex6HexNAc3dHex | 1768 | -- | | -- | | | | |
| Hex7HexNAc3 | 1784 | -- | | | -- | + | | |
| Hex4HexNAc4dHex2 | 1793 | | --- | --- | --- | ++ | --- | |
| Hex5HexNAc4dHex | 1809 | | | | - | + | + | + |
| Hex6HexNAc4 | 1825 | -- | | | -- | | | |
| Hex4HexNAc5dHex | 1850 | | --- | --- | --- | | ++ | |
| Hex5HexNAc5 | 1866 | + | + | | | ++ | ++ | ++ |
| Hex3HexNAc6dHex | 1891 | +++ | | | | | +++ | +++ |
| Hex9HexNAc2 | 1905 | --- | - | - | | - | - | - |
| Hex7HexNAc3dHex | 1930 | | | | | | | +++ |
| Hex5HexNAc4dHex2 | 1955 | | | | | | - | |
| Hex6HexNAc4dHex | 1971 | | | | -- | | | |
| Hex7HexNAc4 | 1987 | | | | | + | | + |
| Hex4HexNAc5dHex2 | 1996 | | --- | --- | | | --- | |
| Hex5HexNAc5dHex | 2012 | | --- | --- | | | + | |
| Hex6HexNAc5 | 2028 | | | | - | | | |
| Hex10HexNAc2 | 2067 | --- | + | | | + | + | + |
| Hex5HexNAc6 | 2069 | +++ | | | | | | |
| Hex5HexNAc4dHex3 | 2101 | | | | | | -- | |
| Hex6HexNAc4dHex2 | 2117 | +++ | | | | +++ | | |
| Hex7HexNAc4dHex | 2311 | | | | | | | |
| Hex4HexNAc5dHex3 | 2142 | +++ | | | | +++ | | +++ |
| Hex8HexNAc4 | 2149 | | | | | +++ | | |
| Hex5HexNAc5dHex2 | 2158 | +++ | | | | +++ | | |
| Hex6HexNAc5dHex | 2174 | | | | -- | | | |
| Hex3HexNAc6dHex3 | 2183 | +++ | | | | +++ | | +++ |
| Hex7HexNAc5 | 2190 | | | | | | | |
| Hex11HexNAc2 | 2229 | --- | | | | | | |
| Hex6HexNAc6 | 2231 | +++ | | | | | | |
| Hex5HexNAc4dHex4 | 2247 | +++ | | | | | | |
| Hex7HexNAc4dHex2 | 2279 | +++ | | | | +++ | | +++ |
| Hex5HexNAc5dHex3 | 2304 | +++ | | | | +++ | | |
| Hex6HexNAc5dHex2 | 2320 | +++ | +++ | | | +++ | +++ | +++ |
| Hex7HexNAc5dHex | 2336 | | | | - | | | |
| Hex8HexNAc5 | 2352 | | | | --- | | | |
| Hex12HexNAc2 | 2391 | --- | | | | | | |
| Hex7HexNAc6 | 2393 | +++ | | | | | +++ | |
| Hex7HexNAc4dHex3 | 2425 | +++ | | | | +++ | | |
| Hex6HexNAc5dHex3 | 2466 | +++ | | | | +++ | | |

TABLE 23-continued

Exoglycosidase analysis results of hESC line FES 29 grown on mEF.

| | | FES 29 | | | | | | |
|---|---|---|---|---|---|---|---|---|
| Proposed composition | m/z | α-Man | β-GlcNAc | β-HexNAc | β1,4Gal | β1,3-Gal | α1,3/4-Fuc | α1,2-Fuc |
| Hex8HexNAc5dHex | 2498 | | | | --- | | | |
| Hex9HexNAc5 | 2514 | | | | | | | |
| Hex7HexNAc6dHex | 2539 | +++ | | | | | +++ | +++ |
| Hex13HexNAc2 | 2553 | | | | | | | +++ |
| Hex8HexNAc6 | 2555 | | | | +++ | | +++ | |
| Hex9HexNAc5dHex | 2660 | | | | | | | |
| Hex7HexNAc6dHex4 | 2978 | | | | +++ | | | |
| Hex8HexNAc6dHex4 | 3140 | | | | +++ | | | +++ |
| Hex9HexNAc6dHex4 | 3302 | | | | +++ | | +++ | +++ |
| Hex10HexNAc6dHex4 | 3464 | | | | +++ | | +++ | +++ |
| Hex11HexNAc6dHex4 | 3626 | | | | +++ | | +++ | +++ |
| Hex12HexNAc6dHex4 | 3788 | | | | +++ | | | +++ |

TABLE 24

Exoglycosidase analysis results of hESC line FES 29 (st 1) grown on hEF and embryoid bodies (EB, st 2).

| Proposed composition | m/z | FES 29 st 1 α-Man | FES 29 st 2 α-Man | FES 29 st 1 β1,4-Gal | FES 29 st 2 β1,4-Gal |
|---|---|---|---|---|---|
| HexHexNAc2 | 609 | ++ | ++ | --- | -- |
| HexHexNAc2dHex | 755 | +++ | +++ | | |
| Hex2HexNAc2 | 771 | +++ | ++ | | |
| Hex4HexNAc | 892 | | | | --- |
| Hex2HexNAc2dHex | 917 | --- | | --- | |
| Hex3HexNAc2 | 933 | ++ | ++ | + | + |
| Hex5HexNAc | 1054 | | | | |
| Hex3HexNAc2dHex | 1079 | --- | -- | | - |
| Hex4HexNAc2 | 1095 | --- | -- | + | + |
| Hex2HexNAc3dHex | 1120 | | + | | |
| Hex3HexNAc3 | 1136 | + | ++ | ++ | ++ |
| Hex6HexNAc | 1216 | | | | |
| Hex4HexNAc2dHex | 1241 | --- | --- | --- | |
| Hex5HexNAc2 | 1257 | -- | -- | | |
| Hex3HexNAc3dHex | 1282 | | | ++ | ++ |
| Hex4HexNAc3 | 1298 | + | ++ | + | + |
| Hex3HexNAc4 | 1339 | | | +++ | +++ |
| Hex7HexNAc | 1378 | --- | --- | --- | |
| Hex5HexNAc2dHex | 1403 | | --- | | |
| Hex6HexNAc2 | 1419 | -- | -- | | |
| Hex3HexNAc3dHex2 | 1428 | +++ | +++ | | |
| Hex4HexNAc3dHex | 1444 | - | + | | + |
| Hex5HexNAc3 | 1460 | | | + | + |
| Hex3HexNAc4dHex | 1485 | | | ++ | ++ |
| Hex8HexNAc | 1540 | | --- | | |
| Hex3HexNAc5 | 1542 | | + | +++ | ++ |
| Hex6HexNAc2dHex | 1565 | | --- | | --- |
| Hex7HexNAc2 | 1581 | -- | -- | | |
| Hex5HexNAc3dHex | 1606 | --- | | --- | - |
| Hex6HexNAc3 | 1622 | --- | -- | | --- |
| Hex4HexNAc4dHex | 1647 | | | | - |
| Hex5HexNAc4 | 1663 | | | --- | --- |
| Hex3HexNAc5dHex | 1688 | --- | | ++ | ++ |
| Hex9HexNAc | 1702 | | | | |
| Hex4HexNAc5 | 1704 | | | +++ | -- |
| Hex8HexNAc2 | 1743 | -- | -- | | |
| Hex6HexNAc3dHex | 1768 | | | | |
| Hex4HexNAc4dHex2 | 1793 | | | | +++ |
| Hex5HexNAc4dHex | 1809 | - | | -- | -- |
| Hex4HexNAc5dHex | 1850 | | | --- | -- |
| Hex5HexNAc5 | 1866 | | | | --- |
| Hex3HexNAc6dHex | 1891 | | | | +++ |
| Hex9HexNAc2 | 1905 | --- | --- | | |
| Hex5HexNAc4dHex2 | 1955 | - | | - | --- |
| Hex6HexNAc4dHex | 1971 | | | | --- |
| Hex4HexNAc5dHex2 | 1996 | --- | | --- | --- |
| Hex5HexNAc5dHex | 2012 | | | | -- |
| Hex6HexNAc5 | 2028 | | | --- | |
| Hex10HexNAc2 | 2067 | --- | --- | | |
| Hex5HexNAc4dHex3 | 2101 | | | | - |

TABLE 24-continued

Exoglycosidase analysis results of hESC line FES 29 (st 1) grown on hEF and embryoid bodies (EB, st 2).

| Proposed composition | m/z | FES 29 st 1 α-Man | FES 29 st 2 α-Man | FES 29 st 1 β1,4-Gal | FES 29 st 2 β1,4-Gal |
|---|---|---|---|---|---|
| Hex4HexNAc5dHex3 | 2142 | --- | | | --- |
| Hex5HexNAc5dHex2 | 2158 | --- | | | --- |
| Hex6HexNAc5dHex | 2174 | | | --- | --- |
| Hex11HexNAc2 | 2229 | | | ++ | ++ |
| Hex6HexNAc5dHex2 | 2320 | | | --- | |
| Hex12HexNAc2 | 2391 | | | +++ | ++ |
| Hex13HexNAc2 | 2553 | | | +++ | +++ |
| Hex14HexNAc2 | 2715 | | | | +++ |

TABLE 25

Exoglycosidase digestion analyses of hESC acidic N-glycans (cell line FES 29, grown on mEF).

| Proposed composition | m/z | α3SA | α3/4Fuc | α3/4Fuc →α2Fuc | SA |
|---|---|---|---|---|---|
| Hex3HexNAc2SP | 989 | + | --- | --- | --- |
| NeuAcHex3HexNAc | 997 | +++ | | | |
| Hex2HexNAc3SP | 1030 | + | --- | --- | + |
| Hex4HexNac2SP | 1151 | + | | --- | + |
| Hex3HexNAc3SP | 1192 | ++ | | ++ | ++ |
| NeuAc2Hex2HexNAcdHex | 1272 | | --- | --- | --- |
| Hex4HexNAc2dHexSP | 1297 | --- | --- | --- | + |
| NeuAc2HexHexNAc2dHex | 1313 | + | | --- | ++ |
| Hex3HexNAc3dHexSP | 1338 | + | --- | | ++ |
| Hex4HexNAc3SP | 1354 | ++ | + | ++ | ++ |
| Hex3HexNac4SP | 1395 | + | | + | ++ |
| NeuAcHex3HexNAc3 | 1403 | | | + | --- |
| NeuGcHex3HexNAc3 | 1419 | | | --- | |
| NeuAc2Hex2HexNAcdHex | 1475 | + | | + | ++ |
| Hex4HexNAc3dHexSP | 1500 | + | | | + |
| Hex5HexNAc3dHexSP/NeuAc2HexHexNAc3dHex | 1516 | + | | | + |
| Hex3HexNAc4dHexSP | 1541 | + | | ++ | ++ |
| NeuAcHex3HexNAc3dHex | 1549 | + | + | + | --- |
| Hex4HexNAc4SP | 1557 | ++ | | + | ++ |
| NeuAcHex4HexNAc3 | 1565 | − | | + | -- |
| NeuGcHex4HexNAc3 | 1581 | + | | | |
| NeuAcHex3HexNAc4 | 1606 | +++ | | | |
| NeuAc2Hex3HexNAc2dHex | 1637 | + | | | + |
| Hex4HexNAc3dHex2SP | 1646 | +++ | | | |
| Hex5HexNAc3dHexSP | 1662 | + | --- | --- | + |
| NeuAc2Hex2HexNAc3dHex | 1678 | + | − | | + |
| NeuAcHex2HexNAc3dHex3 | 1679 | | +++ | | +++ |
| Hex4HexNAc4dHexSP | 1703 | ++ | | ++ | ++ |
| NeuAcHex4HexNAc3dHex | 1711 | | | + | -- |
| Hex5HexNAc4SP | 1719 | ++ | | + | ++ |
| NeuAcHex5HexNAc3 | 1727 | − | − | | -- |
| NeuGcHex5HexNAc3 | 1743 | --- | | + | + |
| NeuAcHex3HexNAc4dHex | 1752 | | | --- | --- |
| Hex4HexNAc5SP | 1760 | + | + | | ++ |
| NeuAcHex4HexNAc4 | 1768 | | + | + | -- |
| Hex7HexNAc2dHexSP | 1783 | | | | |
| NeuGcHex4HexNAc4 | 1784 | +++ | +++ | +++ | +++ |
| Hex5HexNAc4SP2/NeuAc2Hex4HexNAc2dHex | 1799 | | | ++ | ++ |
| Hex6HexNAc3dHexSP | 1824 | +++ | | | +++ |
| NeuAc2Hex3HexNAc3dHex | 1840 | + | | | + |
| NeuAcHex3HexNAc3dHex3 | 1841 | | | | +++ |
| Hex5HexNAc4dHexSP | 1865 | ++ | | + | ++ |
| NeuAcHex5HexNAc3dHex | 1873 | − | | − | --- |
| Hex6HexNAc4SP | 1881 | ++ | + | --- | ++ |
| NeuAcHex6HexNAc3 | 1889 | − | | | -- |
| Hex4HexNAc5dHexSP | 1906 | + | | + | ++ |
| NeuAcHex4HexNAc4dHex | 1914 | − | + | + | -- |
| Hex5HexNAc5SP | 1922 | +++ | | | +++ |
| NeuAcHex5HexNAc4 | 1930 | + | + | + | -- |
| NeuGcHex5HexNAc4 | 1946 | ++ | | + | ++ |
| NeuAcHex3HexNAc5dHex | 1955 | | + | --- | --- |
| NeuAc2Hex5HexNAc2dHex/Hex6HexNAc4(SP)2 | 1961 | | | | +++ |
| NeuAcHex4HexNAc5 | 1971 | | + | + | |
| NeuAc2Hex2HexNAc3dHex/Hex8HexNAc3SP | 2002 | + | | − | |
| NeuAcHex4HexNAc3dHex3 | 2003 | --- | --- | --- | --- |

TABLE 25-continued

Exoglycosidase digestion analyses of hESC acidic N-glycans (cell line FES 29, grown on mEF).

| Proposed composition | m/z | α3SA | α3/4Fuc | α3/4Fuc →α2Fuc | SA |
|---|---|---|---|---|---|
| NeuAcHex5HexNAc4SP | 2010 | | --- | --- | --- |
| Hex5HexNAc4dHex2SP | 2011 | --- | | --- | ++ |
| NeuAc2Hex5HexNAc3 | 2018 | | | | +++ |
| NeuAcHex5HexNAc3dHex2 | 2019 | | | | +++ |
| Hex6HexNAc4dHexSP | 2027 | ++ | | + | ++ |
| NeuAcHex6HexNAc3dHex | 2035 | --- | + | --- | --- |
| NeuAc2Hex3HexNAc4dHex/Hex7HexNAc4SP | 2043 | +++ | | | +++ |
| NeuAcHex7HexNAc3 | 2051 | | − | | --- |
| Hex4HexNAc5dHex2SP | 2052 | --- | | --- | ++ |
| Hex5HexNAc5dHexSP | 2068 | +++ | +++ | | +++ |
| NeuAcHex5HexNAc4dHex | 2076 | | | + | -- |
| NeuGcHex5HexNAc4dHex/NeuAcHex6HexNAc4 | 2092 | − | − | − | |
| NeuGcHex6HexNAc4 | 2108 | − | | | + |
| NeuAcHex4HexNAc5dHex | 2117 | | + | + | − |
| NeuAcHex5HexNAc5 | 2133 | | + | ++ | |
| NeuAcHex5HexNAc4dHexSP/ NeuAcHex8HexNAc2dHex | 2156 | | + | | --- |
| Hex5HexNAc4dHex3SP | 2157 | | +++ | | +++ |
| NeuAc2Hex5HexNAc3dHex | 2164 | | | --- | |
| NeuAcHex5HexNAc3dHex3 | 2165 | | +++ | | |
| NeuAcHex9HexNAc2/NeuAcHex6HexNAc4SP/ NeuGcHex5HexNAc4dHexSP | 2172 | +++ | | | |
| NeuAcHex4HexNAc6 | 2174 | --- | --- | --- | --- |
| NeuAcHex3HexNAc4dHex2/Hex7HexNAc4dHexSP | 2189 | | | --- | |
| NeuAcHex3HexNAc4dHex4 | 2190 | --- | --- | --- | ++ |
| NeuGcNeuAcHex6HexNAc3/ NeuGc2Hex5HexNAc3dHex | 2196 | | +++ | +++ | |
| Hex4HexNAc5dHexSP | 2198 | --- | --- | --- | |
| NeuAc2Hex4HexNAc4(SP)2 | 2219 | | | | +++ |
| NeuAc2Hex5HexNAc4 | 2221 | -- | | | -- |
| NeuAcHex5HexNAc4dHex2 | 2222 | − | -- | ---?? | -- |
| Hex6HexNAc5dHexSP | 2230 | ++ | --- | --- | ++ |
| NeuGcNeuAcHex5HexNAc4 | 2237 | +++ | +++ | | |
| NeuGcHex5HexNAc4dHex2/NeuAcHex6HexNAc4dHex | 2238 | -- | − | − | -- |
| NeuGc2Hex5HexNAc4 | 2253 | + | ++ | --- | --- |
| NeuAcHex7HexNAc4/NeuGcHex6HexNAc4dHex | 2254 | ++ | − | ++ | ++ |
| NeuAcHex4HexNAc5dHex2 | 2263 | | --- | --- | --- |
| NeuAcHex5HexNAc5dHex | 2279 | | + | + | − |
| NeuAcHex6HexNAc5 | 2295 | | | + | |
| NeuAcHex5HexNAc3dHex4/NeuGcHex6HexNAc5 | 2311 | +++ | | | +++ |
| Hex6HexNAc4dHex3SP | 2319 | --- | --- | ++ | --- |
| NeuAc2Hex5HexNAc4dHex | 2367 | -- | | − | --- |
| NeuAcHex5HexNAc4dHex3 | 2368 | --- | − | --- | --- |
| NeuGcNeuAcHex5HexNAc4dHex/ NeuAc2Hex6HexNAc4 | 2383 | -- | | − | --- |
| NeuGcHex5HexNAc4dHex3/NeuAcHex6HexNAc4dHex2 | 2384 | | +++ | | |
| NeuAc3Hex5HexNAx3SP/NeuAc2Hex5HexNAc4Ac4 | 2389 | --- | + | + | --- |
| NeuAc2Hex5HexNAc3dHexSP | 2390 | | +++ | | |
| NeuAc2Hex3HexNAc5dHex2 | 2392 | | | | +++ |
| NeuAcHex3HexNAc5dHex4 | 2393 | | | | +++ |
| NeuGc2Hex5HexNAc4dHex | 2399 | --- | --- | --- | --- |
| NeuAc2Hex6HexNAc3dHexSP | 2406 | --- | ++ | --- | --- |
| NeuAc2Hex4HexNAc5dHex | 2408 | --- | --- | --- | |
| NeuAcHex5HexNAc5dHex2 | 2425 | | +++ | | |
| NeuAcHex6HexNAc5dHex | 2441 | + | + | + | |
| NeuAc2Hex5HexNAc4dHexSP/ NeuAc2Hex8HexNAc2dHex | 2447 | --- | --- | --- | --- |
| NeuAcHex5HexNAc4dHex3SP/ NeuAcHex8HexNAc2dHex3 | 2448 | --- | --- | --- | --- |
| NeuAcHex3HexNAc6dHex3 | 2450 | | | | +++ |
| NeuAcHex7HexNAc5 | 2457 | | | | ++ |
| NeuAc3Hex5HexNAc4 | 2512 | --- | | --- | --- |
| NeuAc2Hex5HexNAc4dHex2 | 2513 | --- | --- | --- | --- |
| NeuAcHex6HexNAc5dHexSP | 2521 | +++ | | | |
| NeuGcNeuAc2Hex5HexNAc4 | 2528 | --- | | --- | --- |
| NeuGcNeuAcHex5HexNAc4dHex2/ NeuAc2Hex6HexNAc4dHex | 2529 | --- | --- | --- | --- |
| NeuGc2NeuAcHex5HexNAc4 | 2544 | --- | --- | --- | --- |
| NeuAc2Hex6HexNAc5 | 2586 | --- | + | --- | --- |
| NeuAcHex6HexNAc6dHex2 | 2587 | --- | | | --- |
| Hex7HexNAc6dHexSP | 2595 | +++ | | | +++ |
| NeuAcHex7HexNAc5dHex/NeuGcHex6HexNAc5dHex2 | 2603 | | + | | |
| NeuAcHex8HexNAc5/NeuGcHex7HexNAc5dHex | 2619 | | | --- | |
| NeuAcHex6HexNAc6dHex | 2644 | +++ | | | |
| NeuAcHex7HexNAc6 | 2660 | | --- | --- | + |

TABLE 25-continued

Exoglycosidase digestion analyses of hESC acidic N-glycans (cell line FES 29, grown on mEF).

| Proposed composition | m/z | α3SA | α3/4Fuc | α3/4Fuc →α2Fuc | SA |
|---|---|---|---|---|---|
| NeuAc2Hex6HexNAc5dHex | 2732 | − | | | --- |
| NeuAcHex6HexNAc5dHex3 | 2733 | --- | | --- | --- |
| NeuAc2Hex4HexNAc6dHex2 | 2758 | +++ | | | +++ |
| NeuAcHex8HexNAc5dHex | 2765 | − | | | -- |
| NeuGcHex8HexNAc5dHex/NeuAcHex9HexNAc5 | 2781 | --- | --- | | --- |
| NeuAc2Hex5HexNAc4dHex4 | 2806 | ++ | | | +++ |
| NeuAcHex7HexNAc6dHex | 2807 | | +++ | +++ | --- |
| NeuAcHex8HexNAc6 | 2822 | +++ | +++ | | +++ |
| NeuAc3Hex6HexNAc5 | 2878 | --- | --- | --- | --- |
| NeuGcNeuAc2Hex6HexNAc5 | 2894 | --- | --- | --- | --- |
| NeuGcNeuAcHex6HexNAc5dHex2/ NeuAc2Hex7HexNAc5dHex | 2895 | | +++ | | |
| NeuAc2Hex7HexNAc6 | 2952 | --- | | --- | --- |
| NeuAcHex7HexNAc6dHex2 | 2953 | +++ | | | |
| NeuAc3Hex6HexNAc5dHex | 3024 | --- | + | --- | --- |
| NeuAc2Hex7HexNAc6dHex | 3098 | --- | --- | --- | --- |
| NeuAcHex8HexNAc7dHex | 3172 | +++ | | | |

[1]Code: +++ new signal appeared, ++ highly increased relative signal intensity, ++ increased relative signal intensity, − decreased relative signal intensity, −− greatly decreased relative signal intensity, --- signal disappeared, blank: no change.

TABLE 26

| m/z* | Preferred monosaccharide compositions | Terminal epitopes | Experimental structures included in the glycan signal according to the invention§ | Group# |
|---|---|---|---|---|
| 730 | Hex3HexNAc | Manα | (Manα→)$_2$Hex$_1$HexNAc$_1$ | S |
| 771 | Hex2HexNAc2 | Manα | Manα→Hex$_1$HexNAc$_2$ | LO |
| 892 | Hex4HexNAc | Manα | (Manα→)$_3$Hex$_1$HexNAc$_1$ | S |
| | | Galβ4 | Galβ4GlcNAc→Hex$_3$ | |
| 917 | Hex2HexNAc2dHex | Manα | Manα→Hex$_1$HexNAc$_2$dHex$_1$ | LO, F |
| 933 | Hex3HexNAc2 | Manα | (Manα→)$_2$Hex$_1$HexNAc$_2$ | LO |
| 1054 | Hex5HexNAc | Manα | (Manα→)$_4$Hex$_1$HexNAc$_1$ | S |
| 1079 | Hex2HexNAc2dHex | Manα | (Manα→)$_2$Hex$_1$HexNAc$_2$dHex$_1$ | LO, F |
| 1095 | Hex4HexNAc2 | Manα | (Manα→)$_3$Hex$_1$HexNAc$_2$ | LO |
| 1120 | Hex2HexNAc3dHex | Fucα3/4 | Fucα3/4→Hex$_2$HexNAc$_3$ | HY, F, N>H |
| 1136 | Hex3HexNAc3 | GlcNAcβ | GlcNAcβ→Hex$_3$HexNAc$_2$ | HY, N=H |
| 1216 | Hex6HexNAc | Manα | (Manα→)$_5$Hex$_1$HexNAc$_1$ | S |
| 1241 | Hex4HexNAc2dHex | Manα | (Manα)$_3$Hex$_1$HexNAc$_2$dHex$_1$ | LO, F |
| 1257 | Hex5HexNAc2 | Manα | (Manα→)$_4$Hex$_1$HexNAc$_2$ | HI |
| 1282 | Hex3HexNAc3dHex | GlcNAcβ | GlcNAcβ→Hex$_3$HexNAc$_2$dHex$_1$ | HY, F, N=H |
| 1298 | Hex4HexNAc3 | | | HY |
| 1339 | Hex3HexNAc4 | 2 × GlcNAcβ | (GlcNAcβ→)$_2$Hex$_3$HexNAc$_2$ | CO, N>H |
| 1378 | Hex7HexNAc | Manα | (Manα→)$_6$Hex$_1$HexNAc$_1$ | S |
| 1403 | Hex5HexNAc2dHex | Manα | (Manα→)$_4$Hex$_1$HexNAc$_2$dHex$_1$ | HF |
| 1419 | Hex6HexNAc2 | Manα | (Manα→)$_5$Hex$_1$HexNAc$_2$ | HI |
| 1444 | Hex4HexNAc3dHex | Manα | Manα→Hex$_3$HexNAc$_3$dHex$_1$ | HY, F |
| 1460 | Hex5HexNAc3 | Manα | Manα→Hex$_4$HexNAc$_3$ | HY |
| 1485 | Hex3HexNAc4dHex | 2 × GlcNAcβ | (GlcNAcβ→)$_2$Hex$_3$HexNAc$_2$dHex$_1$ | CO, F, N>H |
| 1501 | Hex4HexNAc4 | GlcNAcβ | GlcNAcβ→Hex$_4$HexNAc$_3$ | CO, N=H |
| | | Galβ4 | Galβ4GlcNAc→Hex$_3$HexNAc$_3$ | |
| 1540 | Hex8HexNAc | Manα | (Manα→)$_7$Hex$_1$HexNAc$_1$ | S |
| 1542 | Hex3HexNAc5 | 3 × GlcNAcβ | (GlcNAcβ→)$_3$Hex$_3$HexNAc$_2$ | CO, N>H |
| 1565 | Hex6HexNAc2dHex | Manα | (Manα→)$_5$Hex$_1$HexNAc$_2$dHex$_1$ | HF |
| 1581 | Hex7HexNAc2 | Manα | (Manα→)$_6$Hex$_1$HexNAc$_2$ | HI |
| 1590 | Hex4HexNAc3dHex2 | Fucα | Fucα→Hex$_4$HexNAc$_3$dHex$_1$ | HY, FC |
| 1606 | Hex5HexNAc3dHex | Manα | Manα→Hex$_4$HexNAc$_3$dHex$_1$ | HY, F |
| | | Galβ4 | Galβ4GlcNAc→Hex$_4$HexNAc$_2$dHex$_1$ | |
| | | | Manα→[Galβ4GlcNAc→]Hex$_3$HexNAc$_2$dHex$_1$ | |
| 1622 | Hex6HexNAc3 | Manα | Manα→Hex$_5$HexNAc$_3$ | HY |
| | | Galβ4 | Galβ4GlcNAc→Hex$_5$HexNAc$_2$ | |
| | | | Manα→[Galβ4GlcNAc→]Hex$_4$HexNAc$_2$ | |
| 1647 | Hex4HexNAc4dHex | GlcNAcβ | GlcNAcβ→Hex$_4$HexNAc$_3$dHex$_1$ | CO, F, N=H |
| | | Galβ4 | Galβ4GlcNAc→Hex$_3$HexNAc$_3$dHex$_1$ | |
| | | | GlcNAcβ→[Galβ4GlcNAc→]Hex$_3$HexNAc$_2$dHex$_1$ | |
| 1663 | Hex5HexNAc4 | 2 × Galβ4 | (Galβ4GlcNAc→)$_2$Hex$_3$HexNAc$_2$ | CO |

TABLE 26-continued

| m/z* | Preferred monosaccharide compositions | Terminal epitopes | Experimental structures included in the glycan signal according to the invention§ | Group# |
|---|---|---|---|---|
| 1688 | Hex3HexNAc5dHex | 3 × GlcNAcβ<br>Manα | (GlcNAcβ→)3Hex3HexNAc2dHex1<br>Manα→Hex2HexNAc5dHex1 | CO, F,<br>N > H |
| 1702 | Hex9HexNAc | Manα | (Manα→)8Hex1HexNAc1 | S |
| 1704 | Hex4HexNAc5 | 2 × HexNAcβ<br>(not GlcNAc)<br>Galβ4 | HexNAcβHexNAcβ→Hex4HexNAc3dHex1<br>Galβ4GlcNAc→Hex3HexNAc4dHex1<br>HexNAcβHexNAcβ→[Galβ4GlcNAc→]Hex3HexNAc2dHex1 | CO,<br>N > H |
| 1743 | Hex8HexNAc2 | Manα | (Manα→)7Hex1HexNAc2 | HI |
| 1768 | Hex6HexNAc3dHex | Manα | Manα→Hex5HexNAc3dHex1 | HY, F |
| 1784 | Hex7HexNAc3 | Manα<br>Galβ4 | Manα→Hex6HexNAc3<br>Galβ4GlcNAc→Hex6HexNAc2<br>Manα→[Galβ4GlcNAc→]Hex5HexNAc2 | HY |
| 1793 | Hex4HexNAc4dHex2 | GlcNAcβ<br>Galβ4<br>Fucα3/4 | GlcNAcβ→Hex4HexNAc3dHex2<br>Galβ4GlcNAc→Hex3HexNAc3dHex2<br>Fucα3/4→Hex4HexNAc4dHex1<br>GlcNAcβ→[Galβ4GlcNAc→]Hex3HexNAc2dHex2<br>GlcNAcβ→[Fucα3/4→]Hex4HexNAc3dHex1<br>Fucα3/4→[Galβ4GlcNAc→]Hex3HexNAc3dHex1<br>GlcNAcβ→[Fucα3/4→][Galβ4GlcNAc→]Hex4HexNAc3dHex1 | CO, FC,<br>N=H |
| 1809 | Hex5HexNAc4dHex | 2 × Galβ4 | (Galβ4GlcNAc→)2Hex3HexNAc2dHex1 | CO, F |
| 1850 | Hex4HexNAc5dHex | 2 × GlcNAcβ<br>Galβ4 | (GlcNAcβ→)2Hex4HexNAc3dHex1<br>Galβ4GlcNAc→Hex3HexNAc4dHex1<br>Galβ4GlcNAc→[GlcNAcβ→]2Hex3HexNAc2dHex1 | CO, F,<br>N > H |
| 1866 | Hex5HexNAc5 | | | CO,<br>N=H |
| 1905 | Hex9HexNAc2 | Manα | (Manα→)8Hex1HexNAc2 | HI |
| 1955 | Hex5HexNAc4dHex2 | Fucα3/4<br>Galβ4 | Fucα3/4→Hex5HexNAc4dHex1<br>Galβ4GlcNAc→Hex4HexNAc3dHex2<br>Galβ4GlcNAc→[Fucα3/4→]Hex4HexNAc3dHex1 | CO, FC |
| 1971 | Hex6HexNAc4dHex | Galβ4 | Galβ4GlcNAc→Hex5HexNAc3dHex1 | CO, F |
| 1996 | Hex4HexNAc5dHex2 | 2 × GlcNAcβ<br>Fucα3/4<br>Galβ4 | (GlcNAcβ→)2Hex4HexNAc3dHex2<br>Fucα3/4→Hex4HexNAc5dHex1<br>Galβ4GlcNAc→Hex3HexNAc4dHex2<br>(GlcNAcβ→)2[Fucα3/4→]Hex4HexNAc3dHex1<br>Galβ4GlcNAc→[Fucα3/4→]Hex3HexNAc4dHex1 | CO, FC,<br>N > H |
| 2012 | Hex5HexNAc5dHex | GlcNAcβ | GlcNAcβ→Hex5HexNAc4dHex1 | CO, F,<br>N=H |
| 2028 | Hex6HexNAc5 | Galβ4<br>3 × Galβ4 | Galβ4GlcNAc→Hex5HexNAc4<br>(Galβ4GlcNAc→)3Hex3HexNAc2 | CO |
| 2067 | Hex10HexNAc2 | Manα<br>Glc | Glc→(Manα→)8Hex1HexNAc2 | G |
| 2101 | Hex5HexNAc4dHex3 | GlcNAcβ | GlcNAcβ→Hex5HexNAc3dHex3 | CO, FC |
| 2174 | Hex6HexNAc5dHex | 3 × Galβ4 | (Galβ4GlcNAc→)3Hex3HexNAc2dHex1 | CO, F |
| 2229 | Hex11HexNAc2 | Manα<br>Glc | Glc2→(Manα→)8Hex1HexNAc2 | G |
| 2320 | Hex6HexNAc5dHex2 | Galβ4 | Galβ4GlcNAc→Hex5HexNAc4dHex2 | CO, FC |
| 2391 | Hex12HexNAc2 | Manα<br>Glc | Glc3→(Manα→)8Hex1HexNAc2 | G |

*[M + Na]+ ion, first isotope.
§"→" indicates linkage to a monosaccharide in the rest of the structure; "[ ]" indicates branch in the structure.
Preferred structure group based on monosaccharide compositions according to the present invention. HI, high-mannose; LO, low-mannose; S, soluble mannosylated; HF, fucosylated high-mannose; G, glucosylated high-mannose; HY, hybrid-type or monoantennary; CO, complex-type; F, fucosylation; FC, complex fucosylation; N=H, terminal HexNAc (HexNAc=Hex); N > H, terminal HexNAc (HexNAc > Hex).

TABLE 27

| m/z* | Preferred monosaccharide compositions | Terminal epitopes | Group# |
|---|---|---|---|
| 989 | Hex3HexNAc2SP | | SP |
| 1030 | Hex2HexNAc3SP | | HY, SP,<br>N > H |
| 1151 | Hex4HexNac2SP | | SP |
| 1192 | Hex3HexNAc3SP | | HY, SP |
| 1272 | NeuAc2Hex2HexNAcdHex | NeuAcα6/8/9<br>Fucα3/4 | F |
| 1297 | Hex4HexNAc2dHexSP | | F, SP |
| 1313 | NeuAc2HexHexNAc2dHex | Fucα2 | F |
| 1338 | Hex3HexNAc3dHexSP | Fucα3/4 | HY, F,<br>SP |
| 1354 | Hex4HexNAc3SP | | HY, SP |
| 1395 | Hex3HexNac4SP | | CO, SP,<br>N > H |
| 1403 | NeuAcHex3HexNAc3 | NeuAcα6/8/9 | HY |
| 1419 | NeuGcHex3HexNAc3 | | HY |
| 1475 | NeuAc2Hex2HexNAcdHex | | F |
| 1500 | Hex4HexNAc3dHexSP | | HY, F,<br>SP |
| 1516 | Hex5HexNAc3dHexSP/<br>NeuAc2HexHexNAc3dHex | | HY, F<br>(SP) |
| 1541 | Hex3HexNAc4dHexSP | | CO, F,<br>SP,<br>N > H |
| 1549 | NeuAcHex3HexNAc3dHex | NeuAcα6/8/9 | HY, F |
| 1557 | Hex4HexNAc4SP | | CO, SP |
| 1565 | NeuAcHex4HexNAc3 | NeuAcα6/8/9<br>NeuAcα3 | HY |

TABLE 27-continued

| m/z* | Preferred monosaccharide compositions | Terminal epitopes | Group# |
|---|---|---|---|
| 1581 | NeuGcHex4HexNAc3 | | HY |
| 1637 | NeuAc2Hex3HexNAc2dHex | | F |
| 1662 | Hex5HexNAc3dHexSP | Fucα3/4 | HY, F, SP |
| 1678 | NeuAc2Hex2HexNAc3dHex | Fucα3/4 | HY, F, N > H |
| 1703 | Hex4HexNAc4dHexSP | | CO, F, SP |
| 1711 | NeuAcHex4HexNAc3dHex | NeuAcα6/8/9 | HY, F |
| 1719 | Hex5HexNAc4SP | | CO, SP |
| 1727 | NeuAcHex5HexNAc3 | NeuAcα6/8/9 NeuAcα3 Fucα3/4 | HY |
| 1743 | NeuGcHex5HexNAc3 | NeuGcα3 | HY |
| 1752 | NeuAcHex3HexNAc4dHex | NeuAcα6/8/9 Fucα2 | CO, F, N > H |
| 1760 | Hex4HexNAc5SP | | CO, SP, N > H |
| 1768 | NeuAcHex4HexNAc4 | NeuAcα6/8/9 | CO |
| 1783 | Hex7HexNAc2dHexSP | | F, SP |
| 1799 | Hex5HexNAc4SP2/ NeuAc2Hex4HexNAc2dHex | | (CO) (F) (SP) |
| 1840 | NeuAc2Hex3HexNAc3dHex | | HY, F |
| 1865 | Hex5HexNAc4dHexSP | | CO, F, SP |
| 1873 | NeuAcHex5HexNAc3dHex | NeuAcα6/8/9 NeuAcα3 Fucα2 | HY, F |
| 1881 | Hex6HexNAc4SP | | CO, SP |
| 1889 | NeuAcHex6HexNAc3 | NeuAcα6/8/9 NeuAcα3 | HY |
| 1906 | Hex4HexNAc5dHexSP | | CO, F, SP, N > H |
| 1914 | NeuAcHex4HexNAc4dHex | NeuAcα6/8/9 NeuAcα3 | CO, F |
| 1930 | NeuAcHex5HexNAc4 | NeuAcα6/8/9 | CO |
| 1946 | NeuGcHex5HexNAc4 | | CO |
| 1955 | NeuAcHex3HexNAc5dHex | NeuAcα6/8/9 Fucα2 | CO, F, N > H |
| 1971 | NeuAcHex4HexNAc5 | | CO, N > H |
| 2002 | NeuAc2Hex4HexNAc3dHex/ Hex8HexNAc3SP | Fucα2 | HY (F) (SP) |
| 2003 | NeuAcHex4HexNAc3dHex3 | NeuAcα3 NeuAcα6/8/9 Fucα3/4 | HY, FC |
| 2010 | NeuAcHex5HexNAc4SP | NeuAcα6/8/9 Fucα3/4 | CO, SP |
| 2011 | Hex5HexNAc4dHex2SP | NeuAcα3 Fucα2 | CO, FC, SP |
| 2027 | Hex6HexNAc4dHexSP | | CO, F, SP |
| 2035 | NeuAcHex6HexNAc3dHex | NeuAcα3 NeuAcα6/8/9 Fucα2 | HY, F |
| 2051 | NeuAcHex7HexNAc3 | NeuAcα6/8/9 Fucα3/4 | HY |
| 2052 | Hex4HexNAc5dHex2SP | NeuAcα3 Fucα2 | SP |
| 2076 | NeuAcHex5HexNAc4dHex | NeuAcα6/8/9 | CO, F |
| 2092 | NeuGcHex5HexNAc4dHex/ NeuAcHex6HexNAc4 | NeuAcα3 Fucα3/4 | CO (F) |
| 2108 | NeuGcHex6HexNAc4 | NeuGcα3 | CO |
| 2117 | NeuAcHex4HexNAc5dHex | NeuAcα6/8/9 | CO, F |
| 2133 | NeuAcHex5HexNAc5 | | CO, N=H |
| 2156 | NeuAcHex5HexNAc4dHexSP/ NeuAcHex8HexNAc2dHex | NeuAcα6/8/9 | (CO) F (SP) |
| 2164 | NeuAc2Hex5HexNAc3dHex | Fucα2 | HY, F |
| 2174 | NeuAcHex4HexNAc6 | NeuAcα3 NeuAcα6/8/9 Fucα3/4 | CO, N > H |
| 2189 | NeuAc2Hex3HexNAc4dHex2/ Hex7HexNAc4dHexSP | Fucα2 | CO F(C) (SP) (N > H) |
| 2190 | NeuAcHex3HexNAc4dHex4 | NeuAcα3 Fucα3/4 | CO, FC, N > H |
| 2198 | Hex4HexNAc5dHexSP | NeuAcα3 Fucα3/4 | CO, F, SP, N > H |
| 2221 | NeuAc2Hex5HexNAc4 | NeuAcα3 NeuAcα6/8/9 | CO |
| 2222 | NeuAcHex5HexNAc4dHex2 | NeuAcα3 NeuAcα6/8/9 Fucα3/4 Fucα2 | CO, FC |
| 2230 | Hex6HexNAc5dHexSP | Fucα3/4 | CO, F, SP |
| 2238 | NeuGcHex5HexNAc4dHex2/ NeuAcHex6HexNAc4dHex | NeuAcα3 NeuAcα6/8/9 Fucα3/4 | CO, F(C) |
| 2253 | NeuGc2Hex5HexNAc4 | NeuAcα6/8/9 Fucα2 | CO |
| 2254 | NeuAcHex7HexNAc4/ NeuGcHex6HexNAc4dHex | NeuAcα6/8/9 | CO (F) |
| 2263 | NeuAcHex4HexNAc5dHex2 | NeuAcα3 Fucα3/4 | CO, FC, N > H |
| 2279 | NeuAcHex5HexNAc5dHex | | CO, F, N=H |
| 2295 | NeuAcHex6HexNAc5 | | CO |
| 2319 | Hex6HexNAc4dHex3SP | NeuAcα3 NeuAcα6/8/9 Fucα3/4 | CO, FC, SP |
| 2367 | NeuAc2Hex5HexNAc4dHex | NeuAcα6/8/9 NeuAcα3 Fucα2 | CO, F |
| 2368 | NeuAcHex5HexNAc4dHex3 | NeuAcα3 NeuAcα6/8/9 Fucα3/4 | CO, FC |
| 2383 | NeuGcNeuAcHex5HexNAc4dHex/ NeuAc2Hex6HexNAc4 | NeuAcα6/8/9 NeuAcα3 Fucα2 | CO (F) |
| 2389 | NeuAc3Hex5HexNAc3SP | NeuAcα3 NeuAcα6/8/9 | HY, SP |
| 2399 | NeuGc2Hex5HexNAc4dHex | NeuAcα3 NeuAcα6/8/9 Fucα3/4 | CO, F |
| 2406 | NeuAc2Hex6HexNAc3dHexSP | NeuAcα3 NeuAcα6/8/9 Fucα2 | HY, F, SP |
| 2408 | NeuAc2Hex4HexNAc5dHex | NeuAcα3 NeuAcα6/8/9 Fucα3/4 | CO, F, N > H |
| 2441 | NeuAcHex6HexNAc5dHex | | CO, F |
| 2447 | NeuAc2Hex5HexNAc4dHexSP | NeuAcα3 NeuAcα6/8/9 Fucα3/4 | CO, F, SP |
| 2448 | NeuAcHex5HexNAc4dHex3SP | NeuAcα3 NeuAcα6/8/9 Fucα3/4 | CO, FC, SP |
| 2457 | NeuAcHex7HexNAc5 | | CO |
| 2512 | NeuAc3Hex5HexNAc4 | NeuAcα3 NeuAcα6/8/9 Fucα2 | CO |
| 2513 | NeuAc2Hex5HexNAc4dHex2 | NeuAcα3 NeuAcα6/8/9 Fucα3/4 | CO, FC |
| 2528 | NeuGcNeuAc2Hex5HexNAc4 | NeuAcα3 NeuAcα6/8/9 Fucα2 | CO |
| 2529 | NeuGcNeuAcHex5HexNAc4dHex2/ NeuAc2Hex6HexNAc4dHex | NeuAcα3 NeuAcα6/8/9 Fucα3/4 | CO, F(C) |
| 2544 | NeuGc2NeuAcHex5HexNAc4 | NeuAcα3 Fucα3/4 | CO |
| 2586 | NeuAc2Hex6HexNAc5 | NeuAcα3 NeuAcα6/8/9 Fucα2 | CO |
| 2587 | NeuAcHex6HexNAc5dHex2 | NeuAcα3 NeuAcα6/8/9 | CO, FC |

TABLE 27-continued

| m/z* | Preferred monosaccharide compositions | Terminal epitopes | Group# |
|---|---|---|---|
| 2603 | NeuAcHex7HexNAc5dHex/ NeuGcHex6HexNAc5dHex2 | | CO, F(C) |
| 2619 | NeuAcHex8HexNAc5/ NeuGcHex7HexNAc5dHex | Fucα2 | CO (F) |
| 2660 | NeuAcHex7HexNAc6 | Fucα3/4 | CO |
| 2732 | NeuAc2Hex6HexNAc5dHex | NeuAcα6/8/9 NeuAcα3 | CO, F |
| 2733 | NeuAcHex6HexNAc5dHex3 | NeuAcα3 NeuAcα6/8/9 Fucα2 | CO, FC |
| 2765 | NeuAcHex8HexNAc5dHex | NeuAcα6/8/9 NeuAcα3 | CO, F |
| 2781 | NeuGcHex8HexNAc5dHex/ NeuAcHex9HexNAc5 | Fucα3/4 | CO (F) |
| 2878 | NeuAc3Hex6HexNAc5 | NeuAcα3 NeuAcα6/8/9 Fucα3/4 | CO |
| 2894 | NeuGcNeuAc2Hex6HexNAc5 | NeuAcα3 NeuAcα6/8/9 Fucα3/4 | CO |
| 2952 | NeuAc2Hex7HexNAc6 | NeuAcα6/8/9 | CO |
| 3024 | NeuAc3Hex6HexNAc5dHex | NeuAcα3 NeuAcα6/8/9 Fucα2 | CO, F |
| 3098 | NeuAc2Hex7HexNAc6dHex | NeuAcα3 NeuAcα6/8/9 Fucα3/4 | CO, F |

*[M − H]⁻ ion, first isotope.
Preferred structure group based on monosaccharide compositions according to the present invention. HY, hybrid-type or monoantennary; CO, complex-type; F, fucosylation; FC, complex fucosylation; N=H, terminal HexNAc (HexNAc=Hex); N > H, terminal HexNAc (HexNAc > Hex); SP, sulphate and/or phosphate ester; "( )" indicates that the glycan signal includes also other structure types.

TABLE 29

| Proposed composition | m/z | α-Man | β-GlcNAc | β4-Gal | β3-Gal |
|---|---|---|---|---|---|
| Hex2HexNAc | 568 | | --- | | |
| HexHexNAc2 | 609 | +++ | | | |
| Hex2HexNAcdHex | 714 | +++ | | | |
| Hex3HexNAc | 730 | -- | --- | | |
| HexHexNAc2dHex | 755 | +++ | | | |
| Hex2HexNAc2 | 771 | ++ | ++ | | |
| Hex4HexNAc | 892 | --- | + | | |
| Hex2HexNAc2dHex | 917 | | + | | |
| Hex3HexNAc2 | 933 | ++ | ++ | | |
| Hex2HexNAc3 | 974 | +++ | | | |
| Hex5HexNAc | 1054 | -- | | | |
| Hex3HexNAc2dHex | 1079 | -- | + | | |
| Hex4HexNAc2 | 1095 | − | + | | |
| Hex2HexNAc3dHex | 1120 | +++ | --- | | |
| Hex3HexNAc3 | 1136 | ++ | -- | + | |
| Hex2HexNAc2dHex3 | 1209 | --- | --- | | |
| Hex6HexNAc | 1216 | -- | | | |
| Hex4HexNAc2dHex | 1241 | --- | | | |
| Hex5HexNAc2 | 1257 | -- | | | |
| Hex2HexNAc3dHex2 | 1266 | | | | |
| Hex3HexNAc3dHex | 1282 | ++ | -- | + | |
| Hex4HexNAc3 | 1298 | ++ | − | | |
| Hex5HexNAc4 | 1339 | +++ | | +++ | |
| Hex7HexNAc | 1378 | -- | | | |
| Hex5HexNAc2dHex | 1403 | --- | | | |
| Hex6HexNAc2 | 1419 | -- | + | | |
| Hex3HexNAc3dHex2 | 1428 | +++ | | | |
| Hex4HexNAc3dHex | 1444 | + | − | + | |
| Hex5HexNAc3 | 1460 | + | − | ++ | |
| Hex3HexNAc4dHex | 1485 | | -- | ++ | |
| Hex4HexNAc4 | 1501 | ++ | | | |
| Hex8HexNAc | 1540 | − | | | |
| Hex3HexNAc5 | 1542 | | | +++ | |

TABLE 28

| m/z* | Preferred monosaccharide compositions | Terminal epitopes | Experimental structures included in the glycan signal according to the invention§ | Group# |
|---|---|---|---|---|
| 1825 | Hex6HexNAc4 | Galβ4 Galα | Galβ4GlcNAc→Hex₅HexNAc₃ Galα3Gal→Hex₄HexNAc₄ Galβ4GlcNAc→[Galα3Gal→]Hex₃HexNAc₃ | CO |
| 1987 | Hex7HexNAc4 | Galα | Galα3Gal→Hex₅HexNAc₄ (Galα3Gal→)₂Hex₃HexNAc₄ | CO |
| 2133 | Hex7HexNAc4dHex1 | Galα | Galα3Gal→Hex₅HexNAc₄dHex₁ (Galα3Gal→)₂Hex₃HexNAc₄dHex₁ | CO, F |
| 2190 | Hex7HexNAc5 | Galα | Galα3Gal→Hex₅HexNAc₅ | CO |
| 2336 | Hex7HexNAc5dHex | Galβ4 Galα | Galβ4GlcNAc→Hex₆HexNAc₄dHex₁ Galα3Gal→Hex₅HexNAc₅dHex₁ Galβ4GlcNAc→[Galα3Gal→]Hex₄HexNAc₄dHex₁ | CO, F |
| 2352 | Hex8HexNAc5 | Galβ4 Galα | Galβ4GlcNAc→Hex₇HexNAc₄ Galα3Gal→Hex₆HexNAc₅ Galβ4GlcNAc→[Galα3Gal→]Hex₅HexNAc₄ Galβ4GlcNAc→[Galα3Gal→]₂Hex₃HexNAc₄ | CO |
| 2498 | Hex8HexNAc5dHex | Galβ4 Galα | Galβ4GlcNAc→Hex₇HexNAc₄dHex₁ Galα3Gal→Hex₆HexNAc₅dHex₁ Galβ4GlcNAc→[Galα3Gal→]Hex₅HexNAc₄dHex₁ Galβ4GlcNAc→[Galα3Gal→]₂Hex₃HexNAc₄dHex₁ | CO, F |
| 2514 | Hex9HexNAc5 | Galα | Galα3Gal→Hex₇HexNAc₅ (Galα3Gal→)₂Hex₅HexNAc₅ (Galα3Gal→)₃Hex₃HexNAc₅ | CO |
| 2660 | Hex9HexNAc5dHex | Galα | Galα3Gal→Hex₇HexNAc₅dHex₁ (Galα3Gal→)₂Hex₅HexNAc₅dHex₁ (Galα3Gal→)₃Hex₃HexNAc₅dHex₁ | CO, F |

*[M + Na]⁺ ion, first isotope.
§"→" indicates linkage to a monosaccharide in the rest of the structure; "[ ]" indicates branch in the structure.
Preferred structure group based on monosaccharide compositions according to the present invention. HI, high-mannose; LO, low-mannose; S, soluble mannosylated; HF, fucosylated high-mannose; G, glucosylated high-mannose; HY, hybrid-type or monoantennary; CO, complex-type; F, fucosylation; FC, complex fucosylation; N=H, terminal HexNAc (HexNAc = Hex); N > H, terminal HexNAc (HexNAc > Hex).

TABLE 29-continued

| Proposed composition | m/z | α-Man | β-GlcNAc | β4-Gal | β3-Gal |
|---|---|---|---|---|---|
| Hex6HexNAc2dHex | 1565 | --- | | --- | --- |
| Hex7HexNAc2 | 1581 | -- | | | |
| Hex4HexNAc3dHex2 | 1590 | | | | |
| Hex5HexNAc3dHex | 1606 | | | -- | -- |
| Hex6HexNAc3 | 1622 | -- | - | -- | |
| Hex4HexNAc4dHex | 1647 | | --- | | |
| Hex5HexNAc4 | 1663 | | -- | --- | |
| Hex3HexNAc5dHex | 1688 | | --- | ++ | |
| Hex9HexNAc | 1702 | --- | --- | | |
| Hex8HexNAc2 | 1743 | -- | + | | |
| Hex6HexNAc3dHex | 1768 | | | --- | |
| Hex7HexNAc3 | 1784 | --- | --- | --- | |
| Hex4HexNAc4dHex2 | 1793 | | --- | ++ | |
| Hex5HexNAc4dHex | 1809 | | -- | --- | |
| Hex3HexNAc6dHex | 1891 | | | +++ | |
| Hex9HexNAc2 | 1905 | --- | - | | |
| Hex5HexNAc4dHex2 | 1955 | - | | --- | |
| Hex6HexNAc4dHex | 1971 | | | --- | |
| Hex4HexNAc5dHex2 | 1996 | | | --- | |
| Hex5HexNAc5dHex | 2012 | | --- | --- | --- |
| Hex6HexNAc5 | 2028 | | | - | --- |
| Hex10HexNAc2 | 2067 | --- | - | | |
| Hex5HexNAc4dHex3 | 2101 | | | --- | |
| Hex4HexNAc5dHex3 | 2142 | | | -- | --- |
| Hex6HexNAc5dHex | 2174 | | | -- | --- |
| Hex11HexNAc2 | 2229 | | | | |
| Hex5HexNAc5dHex3 | 2304 | | | --- | |
| Hex6HexNAc5dHex2 | 2320 | | | --- | |
| Hex7HexNAc6 | 2393 | | | --- | |
| Hex6HexNAc5dHex3 | 2466 | | | --- | |
| Hex7HexNAc6dHex | 2539 | | | --- | --- |

TABLE 30

| m/z* | Preferred monosaccharide compositions | Terminal epitopes | Experimental structures included in the glycan signal according to the invention§ | Group# |
|---|---|---|---|---|
| 568 | Hex2HexNAc | Manα | Manα→Hex$_1$HexNAc$_1$ | S |
| 730 | Hex3HexNAc | Manα<br>GlcNAc | (Manα→)$_2$Hex$_1$HexNAc$_1$<br>GlcNAc→Hex$_3$ | S |
| 771 | Hex2HexNAc2 | Manα | Manα→Hex$_1$HexNAc$_2$ | LO |
| 892 | Hex4HexNAc | Manα | (Manα→)$_3$Hex$_1$HexNAc$_1$ | S |
| 917 | Hex2HexNAc2dHex | Manα | Manα→Hex$_1$HexNAc$_2$dHex$_1$ | LO, F |
| 933 | Hex3HexNAc2 | Manα | (Manα→)$_2$Hex$_1$HexNAc$_2$ | LO |
| 1054 | Hex5HexNAc | Manα | (Manα→)$_4$Hex$_1$HexNAc$_1$ | S |
| 1079 | Hex3HexNAc2dHex | Manα | (Manα→)$_2$Hex$_1$HexNAc$_2$dHex$_1$ | LO, F |
| 1095 | Hex4HexNAc2 | Manα | (Manα→)$_3$Hex$_1$HexNAc$_2$ | LO |
| 1120 | Hex2HexNAc3dHex | GlcNAcβ | GlcNAcβ→Hex$_2$HexNAc$_2$dHex$_1$ | HY, F, N > H |
| 1136 | Hex3HexNAc3 | GlcNAcβ | GlcNAcβ→Hex$_3$HexNAc$_2$ | HY, N=H |
| 1209 | Hex2HexNAc2dHex3 | Manα<br>GlcNAc | Manα→Hex$_1$HexNAc$_2$dHex$_3$<br>GlcNAc→Hex$_2$HexNAc$_1$dHex$_3$ | FC, N=H |
| 1216 | Hex6HexNAc | Manα | (Manα→)$_5$Hex$_1$HexNAc$_1$ | S |
| 1241 | Hex4HexNAc2dHex | Manα | (Manα)$_3$Hex$_1$HexNAc$_2$dHex$_1$ | LO, F |
| 1257 | Hex5HexNAc2 | Manα | (Manα→)$_4$Hex$_1$HexNAc$_2$ | HI |
| 1266 | Hex2HexNAc3dHex2 | Fuc | Fuc→Hex$_2$HexNAc$_3$dHex$_1$ | HY, FC |
| 1282 | Hex3HexNAc3dHex | GlcNAcβ | GlcNAcβ→Hex$_3$HexNAc$_2$dHex$_1$ | HY, F, N=H |
| 1298 | Hex4HexNAc3 | | | HY |
| 1378 | Hex7HexNAc | Manα | (Manα→)$_6$Hex$_1$HexNAc$_1$ | S |
| 1403 | Hex5HexNAc2dHex | Manα | (Manα)$_4$Hex$_1$HexNAc$_2$dHex$_1$ | HF |
| 1419 | Hex6HexNAc2 | Manα | (Manα→)$_5$Hex$_1$HexNAc$_2$ | HI |
| 1444 | Hex4HexNAc3dHex | GlcNAcβ | GlcNAcβ→Hex$_4$HexNAc$_2$dHex$_1$ | HY, F |
| 1460 | Hex5HexNAc3 | GlcNAcβ | GlcNAcβ→Hex$_5$HexNAc$_2$ | HY |
| 1485 | Hex3HexNAc4dHex | 2 × GlcNAcβ | (GlcNAcβ→)$_2$Hex$_3$HexNAc$_2$dHex$_1$ | CO, F, N > H |
| 1501 | Hex4HexNAc4 | | | CO, N=H |
| 1540 | Hex8HexNAc | Manα | (Manα→)$_7$Hex$_1$HexNAc$_1$ | S |
| 1565 | Hex6HexNAc2dHex | Manα | (Manα→)$_5$Hex$_1$HexNAc$_2$dHex$_1$ | HF |
| 1581 | Hex7HexNAc2 | Manα | (Manα→)$_6$Hex$_1$HexNAc$_2$ | HI |
| 1590 | Hex4HexNAc3dHex2 | Fucα | Fucα→Hex$_4$HexNAc$_3$dHex$_1$ | HY, FC |
| 1606 | Hex5HexNAc3dHex | GlcNAcβ<br>Galβ4 | GlcNAcβ→Hex$_5$HexNAc$_2$dHex$_1$<br>Galβ4GlcNAc→Hex$_4$HexNAc$_2$dHex$_1$ | HY, F |
| 1622 | Hex6HexNAc3 | Manα<br>GlcNAcβ<br>Galβ4 | Manα→Hex$_6$HexNAc$_3$<br>GlcNAcβ→Hex$_6$HexNAc$_2$<br>Galβ4GlcNAc→Hex$_5$HexNAc$_2$<br>Manα→[GlcNAcβ→]Hex$_5$HexNAc$_2$<br>Manα→[Galβ4GlcNAc→]Hex$_4$HexNAc$_2$ | HY |
| 1647 | Hex4HexNAc4dHex | GlcNAcβ | GlcNAcβ→Hex$_4$HexNAc$_3$dHex$_1$ | CO, F, N=H |
| 1663 | Hex5HexNAc4 | 2 × Galβ4<br>GlcNAcβ | (Galβ4GlcNAc→)$_2$Hex$_3$HexNAc$_2$<br>GlcNAcβ→Hex$_5$HexNAc$_3$ | CO |
| 1688 | Hex3HexNAc5dHex | 3 × GlcNAcβ | (GlcNAcβ→)$_3$Hex$_3$HexNAc$_2$dHex$_1$ | CO, F, N > H |
| 1702 | Hex9HexNAc | Manα | (Manα→)$_8$Hex$_1$HexNAc$_1$ | S |
| 1743 | Hex8HexNAc2 | Manα | (Manα→)$_7$Hex$_1$HexNAc$_2$ | HI |
| 1768 | Hex6HexNAc3dHex | Galβ4 | Galβ4GlcNAc→Hex$_5$HexNAc$_2$dHex$_1$ | HY, F |

TABLE 30-continued

| m/z* | Preferred monosaccharide compositions | Terminal epitopes | Experimental structures included in the glycan signal according to the invention§ | Group# |
|---|---|---|---|---|
| 1784 | Hex7HexNAc3 | Manα<br>GlcNAcβ<br>Galβ4 | Manα→Hex$_6$HexNAc$_3$<br>GlcNAcβ→Hex$_7$HexNAc$_2$<br>Galβ4GlcNAc→Hex$_6$HexNAc$_2$<br>Manα→[GlcNAcβ→]Hex$_6$HexNAc$_2$<br>Manα→[Galβ4GlcNAc→]Hex$_5$HexNAc$_2$ | HY |
| 1793 | Hex4HexNAc4dHex2 | GlcNAcβ<br>Fuc | GlcNAcβ→Hex$_4$HexNAc$_3$dHex$_2$<br>Fuc→Hex$_4$HexNAc$_4$dHex$_1$<br>GlcNAcβ→[Fuc→]Hex$_4$HexNAc$_3$dHex$_1$ | CO, FC,<br>N=H |
| 1809 | Hex5HexNAc4dHex | 2 × Galβ4<br>GlcNAcβ | (Galβ4GlcNAc→)$_2$Hex$_3$HexNAc$_2$dHex$_1$<br>GlcNAcβ→Hex$_5$HexNAc$_3$dHex$_1$ | CO, F |
| 1891 | Hex3HexNAc6dHex | | | CO, F,<br>N > H |
| 1905 | Hex9HexNAc2 | Manα | (Manα→)$_8$Hex$_1$HexNAc$_2$ | HI |
| 1955 | Hex5HexNAc4dHex2 | Galβ4<br>Fuc | Galβ4GlcNAc→Hex$_4$HexNAc$_3$dHex$_2$<br>Fuc→Hex$_5$HexNAc$_4$dHex$_1$<br>Galβ4GlcNAc→[Fuc→]Hex$_4$HexNAc$_3$dHex$_1$ | CO, FC |
| 1971 | Hex6HexNAc4dHex | GlcNAcβ<br>Galβ4 | GlcNAcβ→Hex$_6$HexNAc$_3$dHex$_1$<br>Galβ4GlcNAc→Hex$_5$HexNAc$_3$dHex$_1$ | CO, F |
| 1996 | Hex4HexNAc5dHex2 | 2 × GlcNAcβ | (GlcNAcβ→)$_2$Hex$_4$HexNAc$_3$dHex$_2$ | CO, FC,<br>N > H |
| 2012 | Hex5HexNAc5dHex | GlcNAcβ<br>2 × Galβ4<br>Galβ3 | GlcNAcβ→Hex$_5$HexNAc$_4$dHex$_1$<br>(Galβ4GlcNAc→)$_2$Hex$_3$HexNAc$_3$dHex$_1$<br>Galβ3GlcNAc→Hex$_4$HexNAc$_4$dHex$_1$<br>(Galβ4GlcNAc→)$_2$[GlcNAcβ→]Hex$_3$HexNAc$_2$dHex$_1$ | CO, F,<br>N=H |
| 2028 | Hex6HexNAc5 | 3 × Galβ4 | (Galβ4GlcNAc→)$_3$Hex$_3$HexNAc$_2$ | CO |
| 2067 | Hex10HexNAc2 | Manα<br>Glc | Glc→(Manα→)$_8$Hex$_1$HexNAc$_2$ | G |
| 2101 | Hex5HexNAc4dHex3 | GlcNAcβ | GlcNAcβ→Hex$_5$HexNAc$_3$dHex$_3$ | CO, FC |
| 2142 | Hex4HexNAc5dHex3 | Galβ4 | Galβ4GlcNAc→Hex$_3$HexNAc$_4$dHex$_3$ | CO, FC,<br>N > H |
| 2174 | Hex6HexNAc5dHex | GlcNAcβ<br>3 × Galβ4 | GlcNAcβ→Hex$_6$HexNAc$_4$dHex$_1$<br>(Galβ4GlcNAc→)$_3$Hex$_3$HexNAc$_2$dHex$_1$ | CO, F |
| 2229 | Hex11HexNAc2 | Glc<br>Manα | Glc$_2$→(Manα→)$_8$Hex$_1$HexNAc$_2$ | G |
| 2304 | Hex5HexNAc5dHex3 | GlcNAcβ | GlcNAcβ→Hex$_5$HexNAc$_4$dHex$_3$ | CO, FC,<br>N=H |
| 2320 | Hex6HexNAc5dHex2 | GlcNAcβ | GlcNAcβ→Hex$_6$HexNAc$_4$dHex$_2$ | CO, FC |
| 2393 | Hex7HexNAc6 | Galβ4 | Galβ4GlcNAc→Hex$_6$HexNAc$_5$ | CO |
| 2466 | Hex6HexNAc5dHex3 | GlcNAcβ | GlcNAcβ→Hex$_6$HexNAc$_4$dHex$_3$ | CO, FC |
| 2539 | Hex7HexNAc6dHex | GlcNAcβ<br>4 × Galβ4 | GlcNAcβ→Hex$_7$HexNAc$_5$dHex$_1$<br>(Galβ4GlcNAc→)$_4$Hex$_3$HexNAc$_2$dHex$_1$ | CO, F |

*[M + Na]$^+$ ion, first isotope.
§"→" indicates linkage to a monosaccharide in the rest of the structure;
"[ ]" indicates branch in the structure.
Preferred structure group based on monosaccharide compositions according to the present invention.
HI, high-mannose;
LO, low-mannose;
S, soluble mannosylated;
HF, fucosylated high-mannose;
G, glucosylated high-mannose;
HY, hybrid-type or monoantennary;
CO, complex-type;
F, fucosylation;
FC, complex fucosylation;
N=H, terminal HexNAc (HexNAc = Hex);
N > H, terminal HexNAc (HexNAc > Hex).

TABLE 31

| Proposed composition | m/z | α-Man | β-GlcNAc | β4-Gal | β3-Gal |
|---|---|---|---|---|---|
| Hex2HexNAc | 568 | --- | --- | | |
| HexHexNAc2 | 609 | +++ | | | --- |
| Hex2HexNAcdHex | 714 | +++ | | | |
| Hex3HexNAc | 730 | − | | | |
| HexHexNAc2dHex | 755 | +++ | | | |
| Hex2HexNAc2 | 771 | ++ | ++ | − | − |
| Hex4HexNAc | 892 | --- | --- | | |
| Hex2HexNAc2dHex | 917 | − | ++ | − | − |
| Hex3HexNAc2 | 933 | ++ | ++ | − | − |
| HexHexNAc3dHex | 958 | | | | |
| Hex2HexNAc3 | 974 | +++ | | ++ | --- |
| Hex5HexNAc | 1054 | --- | | | |
| Hex3HexNAc2dHex | 1079 | -- | ++ | − | − |
| Hex4HexNAc2 | 1095 | -- | + | − | − |
| Hex2HexNAc3dHex | 1120 | +++ | | + | --- |
| Hex3HexNAc3 | 1136 | ++ | --- | ++ | -- |
| Hex2HexNAc2dHex3 | 1209 | --- | --- | | |
| Hex6HexNAc | 1216 | --- | | +++ | +++ |
| Hex4HexNAc2dHex | 1241 | --- | | | − |
| Hex5HexNAc2 | 1257 | -- | | | |
| Hex3HexNAc3dHex | 1282 | ++ | --- | + | − |
| Hex4HexNAc3 | 1298 | +++ | + | − | − |
| Hex3HexNAc4 | 1339 | | | +++ | --- |
| Hex7HexNAc | 1378 | | | +++ | +++ |

TABLE 31-continued

| Proposed composition | m/z | α-Man | β-GlcNAc | β4-Gal | β3-Gal |
|---|---|---|---|---|---|
| Hex5HexNAc2dHex | 1403 | --- |  |  | - |
| Hex6HexNAc2 | 1419 | -- | + |  |  |
| Hex3HexNAc3dHex2 | 1428 | +++ |  |  |  |
| Hex4HexNAc3dHex | 1444 | ++ |  | - | - |
| Hex5HexNAc3 | 1460 | + | -- | + | - |
| Hex3HexNAc4dHex | 1485 |  | --- | ++ | - |
| Hex4HexNAc4 | 1501 | + | --- | -- | - |
| Hex8HexNAc | 1540 |  |  | --- | - |
| Hex3HexNAc5 | 1542 |  |  | +++ |  |
| Hex6HexNAc2dHex | 1565 | --- |  |  | --- |
| Hex7HexNAc2 | 1581 | -- |  |  |  |
| Hex4HexNAc3dHex2 | 1590 |  |  |  |  |
| Hex5HexNAc3dHex | 1606 |  | -- | -- | - |
| Hex6HexNAc3 | 1622 | -- | -- | -- | - |
| Hex4HexNAc4dHex | 1647 |  | --- |  | - |
| Hex5HexNAc4 | 1663 |  | - | -- |  |
| Hex3HexNAc5dHex | 1688 |  | --- | ++ | --- |
| Hex4HexNAc5 | 1704 |  |  | +++ |  |
| Hex8HexNAc2 | 1743 | -- |  |  |  |
| Hex5HexNAc3dHex2 | 1752 |  | --- | --- |  |
| Hex6HexNAc3dHex | 1768 | -- | -- | -- |  |
| Hex7HexNAc3 | 1784 | - |  | --- |  |
| Hex4HexNAc4dHex2 | 1793 |  | --- | ++ | --- |
| Hex5HexNAc4dHex | 1809 |  | -- | --- |  |
| Hex6HexNAc4 | 1825 | +++ | +++ | -- |  |
| Hex4HexNAc5dHex | 1850 |  |  | +++ |  |
| Hex5HexNAc5 | 1866 |  |  | --- | --- |
| Hex3HexNAc6dHex | 1891 |  |  | ++ | --- |
| Hex9HexNAc2 | 1905 | --- |  |  |  |
| Hex5HexNAc4dHex2 | 1955 |  |  | -- | - |
| Hex6HexNAc4dHex | 1971 |  | --- | --- |  |
| Hex7HexNAc4 | 1987 |  | --- |  | --- |
| Hex4HexNAc5dHex2 | 1996 |  | --- | +++ |  |
| Hex5HexNAc5dHex | 2012 |  | --- | -- |  |
| Hex6HexNAc5 | 2028 |  | - | --- | - |
| Hex10HexNAc2 | 2067 | --- |  |  | - |
| Hex5HexNAc4dHex3 | 2101 |  | - |  |  |
| Hex6HexNAc4dHex2 | 2117 |  |  | --- | --- |
| Hex7HexNAc4dHex | 2133 |  | --- |  | --- |
| Hex4HexNAc5dHex3 | 2142 |  |  | --- | --- |
| Hex6HexNAc5dHex | 2174 |  | -- | --- | - |
| Hex5HexNAc7 | 2272 |  |  | +++ |  |
| Hex5HexNAc5dHex3 | 2304 |  | --- | +++ |  |
| Hex6HexNAc5dHex2 | 2320 |  | --- | --- |  |
| Hex7HexNAc6 | 2393 |  | -- | --- |  |
| Hex6HexNAc5dHex3 | 2466 |  | --- | --- |  |
| Hex7HexNAc6dHex | 2539 |  | --- | --- |  |
| Hex8HexNAc7 | 2758 |  | --- | --- | --- |

TABLE 32

| Proposed composition | m/z | β4-Gal | β-GlcNAc |
|---|---|---|---|
| Hex2HexNAc | 568 | - | --- |
| HexHexNAc2 | 609 | +++ |  |
| Hex3HexNAc | 730 |  |  |
| Hex2HexNAc2 | 771 |  | -- |
| Hex4HexNAc | 892 |  | --- |
| Hex2HexNAc2dHex | 917 |  | - |
| Hex3HexNAc2 | 933 |  | - |
| Hex2HexNAc3 | 974 | +++ |  |
| Hex5HexNAc | 1054 |  |  |
| Hex3HexNAc2dHex | 1079 |  |  |
| Hex4HexNAc2 | 1095 |  |  |
| Hex2HexNAc3dHex | 1120 | +++ |  |
| Hex3HexNAc3 | 1136 | ++ | --- |
| Hex2HexNAc2dHex3 | 1209 | --- | --- |
| Hex6HexNAc | 1216 |  |  |
| Hex4HexNAc2dHex | 1241 |  |  |
| Hex5HexNAc2 | 1257 |  |  |
| Hex3HexNAc3dHex | 1282 | + | -- |
| Hex4HexNAc3 | 1298 |  |  |
| Hex3HexNAc4 | 1339 | +++ |  |
| Hex2HexNac2dHex4 | 1355 | +++ |  |
| Hex7HexNAc | 1378 |  |  |

TABLE 32-continued

| Proposed composition | m/z | β4-Gal | β-GlcNAc |
|---|---|---|---|
| Hex5HexNAc2dHex | 1403 |  |  |
| Hex6HexNAc2 | 1419 |  |  |
| Hex4HexNAc3dHex | 1444 | + |  |
| Hex5HexNAc3 | 1460 | ++ | - |
| Hex3HexNAc4dHex | 1485 | ++ | --- |
| Hex4HexNAc4 | 1501 | -- | --- |
| Hex8HexNAc | 1540 |  |  |
| Hex3HexNAc5 | 1542 | +++ |  |
| Hex6HexNAc2dHex | 1565 |  |  |
| Hex7HexNAc2 | 1581 |  |  |
| Hex4HexNAc3dHex2 | 1590 | +++ | +++ |
| Hex5HexNAc3dHex | 1606 | - |  |
| Hex6HexNAc3 | 1622 | -- | - |
| Hex4HexNAc4dHex | 1647 |  | --- |
| Hex5HexNAc4 | 1663 | --- | ++ |
| Hex3HexNAc5dHex | 1688 | ++ | --- |
| Hex9HexNAc | 1702 | --- | --- |
| Hex4HexNAc5 | 1704 | +++ | --- |
| Hex8HexNAc2 | 1743 |  |  |
| Hex5HexNAc3dHex2 | 1752 | +++ |  |
| Hex6HexNAc3dHex | 1768 | - |  |
| Hex7HexNAc3 | 1784 | --- | --- |
| Hex4HexNAc4dHex2 | 1793 | +++ |  |
| Hex5HexNAc4dHex | 1809 | --- | + |
| Hex4HexNAc5dHex | 1850 |  | --- |
| Hex3HexNAc6dHex | 1891 | ++ | --- |
| Hex9HexNAc2 | 1905 |  |  |
| Hex5HexNAc4dHex2 | 1955 | --- |  |
| Hex4HexNAc5dHex2 | 1996 |  | --- |
| Hex5HexNAc5dHex | 2012 | --- | --- |
| Hex6HexNAc5 | 2028 | --- |  |
| Hex10HexNAc2 | 2067 |  |  |
| Hex5HexNAc4dHex3 | 2101 |  | + |
| Hex6HexNAc5dHex | 2174 | --- |  |
| Hex7HexNAc6 | 2393 | --- | --- |
| Hex7HexNAc6dHex | 2539 | --- | --- |

TABLE 33

| Proposed composition | m/z | α-Man | β4-Gal | β-GlcNAc |
|---|---|---|---|---|
| Hex2HexNAc | 568 | --- | - | --- |
| HexHexNAc2 | 609 | +++ | - | --- |
| Hex3HexNAc | 730 | -- | - |  |
| HexHexNAc2dHex | 755 | +++ |  | --- |
| Hex2HexNAc2 | 771 | ++ | - | -- |
| Hex4HexNAc | 892 | --- | - | --- |
| Hex2HexNAc2dHex | 917 | -- | - | -- |
| Hex3HexNAc2 | 933 | - |  | -- |
| Hex2HexNAc3 | 974 | ++ | + | --- |
| Hex5HexNAc | 1054 | --- |  |  |
| Hex3HexNAc2dHex | 1079 | --- | - | -- |
| Hex4HexNAc2 | 1095 | -- | - | - |
| Hex2HexNAc3dHex | 1120 | ++ | + | --- |
| Hex3HexNAc3 | 1136 | + | ++ | -- |
| Hex6HexNAc | 1216 | -- |  |  |
| Hex4HexNAc2dHex | 1241 | --- |  |  |
| Hex5HexNAc2 | 1257 | --- |  |  |
| Hex3HexNAc3dHex | 1282 |  | + | -- |
| Hex4HexNAc3 | 1298 | + |  |  |
| Hex3HexNAc4 | 1339 |  | ++ | --- |
| Hex7HexNAc | 1378 | --- |  |  |
| Hex5HexNAc2dHex | 1403 | --- |  |  |
| Hex6HexNAc2 | 1419 | -- |  |  |
| Hex3HexNAc3dHex2 | 1428 | +++ |  |  |
| Hex4HexNAc3dHex | 1444 |  |  |  |
| Hex5HexNAc3 | 1460 |  | + |  |
| Hex3HexNAc4dHex | 1485 |  | ++ | --- |
| Hex4HexNAc4 | 1501 |  | -- | --- |
| Hex8HexNAc | 1540 |  | --- | --- |
| Hex3HexNAc5 | 1542 |  | + | ++ |
| Hex6HexNAc2dHex | 1565 | --- |  | - |
| Hex7HexNAc2 | 1581 | -- |  |  |
| Hex4HexNAc3dHex2 | 1590 | --- |  | ++ |
| Hex5HexNAc3dHex | 1606 | - |  | + |

TABLE 33-continued

| Proposed composition | m/z | α-Man | β4-Gal | β-GlcNAc |
|---|---|---|---|---|
| Hex6HexNAc3 | 1622 | -- | -- | ++ |
| Hex4HexNAc4dHex | 1647 | | --- | --- |
| Hex5HexNAc4 | 1663 | | --- | + |
| Hex3HexNAc5dHex | 1688 | ++ | | --- |
| Hex4HexNAc5 | 1704 | +++ | | |
| Hex8HexNAc2 | 1743 | -- | | |
| Hex5HexNAc3dHex2 | 1752 | | | +++ |
| Hex6HexNAc3dHex | 1768 | - | -- | + |
| Hex7HexNAc3 | 1784 | --- | -- | |
| Hex4HexNAc4dHex2 | 1793 | | + | --- |
| Hex5HexNAc4dHex | 1809 | | --- | |
| Hex6HexNAc4 | 1825 | --- | - | + |
| Hex4HexNAc5dHex | 1850 | --- | | --- |
| Hex5HexNAc5 | 1866 | | --- | --- |
| Hex3HexNAc6dHex | 1891 | --- | ++ | --- |
| Hex9HexNAc2 | 1905 | --- | | |
| Hex5HexNAc4dHex2 | 1955 | | | ++ |
| Hex6HexNAc4dHex | 1971 | | --- | + |
| Hex7HexNAc4 | 1987 | | +++ | |
| Hex4HexNAc5dHex2 | 1996 | | | --- |
| Hex5HexNAc5dHex | 2012 | | --- | --- |
| Hex6HexNAc5 | 2028 | | | --- |
| Hex10HexNAc2 | 2067 | --- | | |
| Hex5HexNAc4dHex3 | 2101 | | | + |
| Hex6HexNAc5dHex | 2174 | | --- | |
| Hex6HexNAc6 | 2231 | | --- | --- |
| Hex5HexNAc5dHex3 | 2304 | | --- | --- |
| Hex6HexNAc5dHex2 | 2320 | | --- | --- |
| Hex6HexNAc6dHex | 2377 | | --- | --- |
| Hex7HexNAc6 | 2393 | | --- | -- |
| Hex6HexNAc5dHex3 | 2466 | | | |
| Hex7HexNAc6dHex | 2539 | | --- | --- |
| Hex8HexNAc6dHex4 | 3140 | | --- | --- |

TABLE 34

Sialidase resistant acidic N-glycans in cord blood CD133+ and CD133− cells.

| | m/z [M − H]⁻ |
|---|---|
| CD133+/composition | |
| Hex3HexNAc2SP | 989.28 |
| Hex4HexNAc3SP | 1354.41 |
| Hex4HexNAc3dHexSP | 1500.47 |
| Hex5HexNAc3SP | 1516.46 |
| NeuAc2Hex2HexNAc3SP | 1612.49 |
| Hex4HexNAc4dHex4SP | 1703.55 |
| Hex5HexNAc4SP | 1719.54 |
| NeuAcNeuGcHex2HexNAc4SP/NeuAcNeuGcHex5HexNAc2/Hex5HexNAc2dHex3SP2 | 1831.57 |
| Hex5HexNAc4dHexSP | 1865.60 |
| NeuAc2Hex3HexNAc4SP | 1977.63 |
| Hex5HexNAc4dHex2SP | 2011.66 |
| Hex5HexNAc5dHexSP | 2068.68 |
| Hex6HexNAc5SP | 2084.67 |
| Hex10HexNAc2SP/Hex7HexNAc4SP2/NeuAc2Hex3HexNAc4dHexSP | 2123.64 |
| NeuAc2Hex6HexNAc3/NeuGc2Hex4HexNAc3dHex2/NeuAcHex3HexNAc5SP | 2180.75 |
| Hex6HexNAc5dHexSP | 2230.73 |
| Hex7HexNAc5dSP | 2246.73 |
| NeuAc2Hex4HexNAc5SP | 2342.76 |
| Hex6HexNAc5dHex2SP | 2376.79 |
| Hex6HexNAc6dHexSP | 2433.81 |
| Hex7HexNAc6SP | 2449.81 |
| Hex7HexNAc6dHexSP | 2595.86 |
| Hex8HexNAc7dHexSP | 2960.99 |
| CD133−/composition | |
| Hex4HexNAc2SP | 1151.33 |
| Hex3HexNAc3SP | 1192.36 |
| Hex5HexNAc2SP | 1313.38 |
| Hex3HexNAc3dHexSP | 1338.41 |
| Hex4HexNAc3SP | 1354.41 |
| Hex6HexNAc2SP/NeuAc2Hex2HexNac2dHex | 1475.44 |
| Hex4HexNAc3dHexSP | 1500.47 |
| Hex5HexNAc3SP | 1516.46 |
| Hex3HexNAc4dHexSP | 1541.49 |
| Hex4HexNAc4SP | 1557.49 |
| Hex4HexNAc4SP2/Hex7HexNAc2SP/NeuAc2Hex3HexNAc2dHex | 1637.49 |
| Hex5HexNAc3dHexSP | 1662.52 |
| Hex6HexNAc3SP/NeuAc2Hex2HexNAc3dHex | 1678.51 |
| Hex4HexNAc4dHexSP | 1703.55 |
| Hex5HexNAc4SP | 1719.54 |
| NeuAcHex4HexNAc3dHexSP | 1791.56 |
| Hex5HexNAc4dHexSP | 1865.60 |
| Hex6HexNAc4SP | 1881.65 |
| NeuAcHex5HexNAc4SP | 2010.64 |
| Hex5HexNAc4dHex2SP | 2011.66 |
| Hex5HexNAc5dHexSP | 2068.68 |
| Hex6HexNAc5SP | 2084.67 |
| NeuAcHex5HexNAc4dHexSP/NeuAcHex8HexNAc2dHex | 2156.69 |
| Hex5HexNAc4dHex3SP | 2157.71 |
| Hex6HexNAc5dHexSP | 2230.73 |

TABLE 34-continued

Sialidase resistant acidic N-glycans in cord blood CD133+ and CD133− cells.

| | m/z [M − H]− |
|---|---|
| Hex6HexNAc5dHex2SP | 2376.79 |
| Hex6HexNAc6dHexSP | 2433.81 |
| NeuAcHex6HexNAc5dHexSP/NeuAcHex9HexNAc3dHex | 2521.83 |
| Hex6HexNAc5dHex3SP | 2522.85 |
| Hex7HexNAc6dHexSP | 2595.86 |
| Hex8HexNAc7dHexSP | 2960.99 |

TABLE 35

| Reagent | Target | FES 22 | FES 30 | mEF |
|---|---|---|---|---|
| FITC-PSA | α-Man | − | − | + |
| FITC-RCA | β-Gal (Galβ4GlcNAc) | + | − | +/− |
| FITC-PNA | β-Gal (Galβ3GalNAc) | + | + | − |
| FITC-MAA | α2,3-sialyl-LN | + | + | − |
| FITC-SNA | α2,6-sialyl-LN | + | n.d. | + |
| FITC-PWA | I-antigen | + | + | n.d. |
| FITC-STA | i-antigen | + | − | + |
| FITC-WFA | β-GalNAc | + | + | − |
| NeuGc-PAA-biotin | NeuGc-lectin | + | + | + |
| anti-GM3 (Gc) mAb | NeuGcα3Galβ4Glc | + | + | + |
| FITC-LTA | α-Fuc | + | − | + |
| FITC-UEA | α-Fuc | + | − | + |
| mAb Lex | Lewis$^x$ | + | n.d. | − |
| mAb sLex | sialyl-Lewis$^x$ | + | n.d. | − |

+, specific binding.
−, no specific binding.
n.d., not determined.

TABLE 36

| Lectins | Target | % of positive cells |
|---|---|---|
| FITC-GNA | α-Man | 27.8 |
| FITC-HHA | α-Man | 95.3 |
| FITC-PSA | α-Man | 95.5 |
| FITC-RCA | β-Gal (Galβ4GlcNAc) | 94.8 |
| FITC-PNA | β-Gal (Galβ3GalNAc) | 31.1 |
| FITC-MAA | α2,3-sialylation | 89.9 |
| FITC-SNA | α2,6-sialylation | 14.3 |
| FITC-PWA | I-antigen | 1.9 |
| FITC-STA | i-antigen | 11.9 |
| FITC-LTA | α-Fuc | 2.8 |
| FITC-UEA | α-Fuc | 8.0 |

TABLE 37

BM MSC

| | | lectin concentration, µg/ml | | | | | | | |
|---|---|---|---|---|---|---|---|---|---|
| Lectin | Target | 0.25 | 0.5 | 1 | 2.5 | 5 | 10 | 20 | 40 |
| FITC-GNA | α-Man | −[1] | − | ++ | ++ | ++ | ++ | ++ | ++ |
| FITC-HHA | α-Man | ++ | ++ | +++ | +++ | +++ | +++ | +++ | +++ |
| FITC-PSA | α-Man | ++ | ++ | ++ | +++ | +++ | +++ | +++ | +++ |
| FITC-RCA | β-Gal (Galβ4GlcNAc) | − | − | +/− | +/− | + | + | ++ | ++ |
| FITC-PNA | β-Gal (Galβ3GalNAc) | − | − | − | − | +/− | +/− | +/− | + |
| FITC-MAA | α2,3-sialylation | − | − | − | +/− | + | ++ | ++ | ++ |
| FITC-SNA | α2,6-sialylation | − | − | − | − | +/− | +/− | + | + |
| FITC-PWA | I-antigen | − | − | − | − | − | − | +/− | +/− |
| FITC-STA | i-antigen | − | − | − | − | − | +/− | +/− | +/− |
| FITC-LTA | α-Fuc | − | − | − | − | − | − | − | − |
| FITC-UEA | α-Fuc | − | − | +/− | +/− | + | ++ | ++ | ++ |
| FITC-MBL | α-Man/β-GlcNAc | − | − | − | − | − | − | +/− | + |

[1]Grading of staining/labelling: +++ very intense, ++ intense, + low, +/− barely detectable, − not labelled.

TABLE 38

The 15 characteristic neutral N-glycan signals of the hESC N-glycome. The signals are expressed in all the analyzed hESC samples and they are listed in order of relative abundance. The proposed structural classification is as described in the Examples.

| No | m/z [M + Na]+ | Proposed composition | Proposed classification |
|---|---|---|---|
| 1. | 1905.6 | $H_9N_2$ | high-mannose |
| 2. | 1419.5 | $H_6N_2$ | high-mannose |
| 3. | 1743.6 | $H_8N_2$ | high-mannose |
| 4. | 1257.4 | $H_5N_2$ | high-mannose |
| 5. | 1581.5 | $H_7N_2$ | high-mannose |
| 6. | 1079.4 | $H_3N_2F_1$ | low-mannose |
| 7. | 2067.7 | $H_{10}N_2$ | other types |
| 8. | 1095.4 | $H_4N_2$ | low-mannose |
| 9. | 933.3 | $H_3N_2$ | low-mannose |
| 10. | 1663.6 | $H_5N_4$ | complex-type |
| 11. | 1622.6 | $H_6N_3$ | hybrid/monoantennary |
| 12. | 1809.6 | $H_5N_4F_1$ | complex-type |
| 13. | 1460.5 | $H_5N_3$ | hybrid/monoantennary |
| 14. | 1485.5 | $H_3N_4F_1$ | complex-type; terminal N (N > H) |
| 15. | 1444.5 | $H_4N_3F_1$ | hybrid/monoantennary |

TABLE 39

The 15 characteristic acidic N-glycan signals of the hESC N-glycome. The signals are expressed in all the analyzed hESC samples and they are listed in order of relative abundance. The proposed structural classification is as described in the Examples.

| No | m/z [M − H]− | Proposed composition | Proposed classification |
|---|---|---|---|
| 1. | 2076.7 | $S_1H_5N_4F_1$ | complex-type |
| 2. | 2222.8 | $S_1H_5N_4F_2$ | complex-type; complex fucosylation |
| 3. | 2367.8 | $S_2H_5N_4F_1$ | complex-type |
| 4. | 1930.7 | $S_1H_5N_4$ | complex-type |

TABLE 39-continued

The 15 characteristic acidic N-glycan signals of the hESC N-glycome. The signals are expressed in all the analyzed hESC samples and they are listed in order of relative abundance. The proposed structural classification is as described in the Examples.

| No | m/z $[M-H]^-$ | Proposed composition | Proposed classification |
|---|---|---|---|
| 5. | 2441.9 | $S_1H_6N_5F_1$ | complex-type |
| 6. | 2092.7 | $G_1H_5N_4F_1$ | complex-type |
| 7. | 2117.8 | $S_1H_4N_5F_1$ | complex-type; terminal N (N > H) |
| 8. | 2587.9 | $S_1H_6N_5F_2$ | complex-type; complex fucosylation |
| 9. | 2368.9 | $S_1H_5N_4F_3$ | complex-type; complex fucosylation |
| 10. | 2263.8 | $S_1H_4N_5F_2$ | complex-type; complex fucosylation; terminal N (N > H) |
| 11. | 1711.6 | $S_1H_4N_3F_1$ | hybrid/monoantennary |
| 12. | 2279.8 | $S_1H_5N_5F_1$ | complex-type; terminal N (N = H) |
| 13. | 2238.8 | $G_1H_5N_4F_2$ | complex-type; complex fucosylation |
| 14. | 2733.0 | $S_2H_6N_5F_1$ | complex-type |
| 15. | 2807.0 | $S_1H_7N_6F_1$ | complex-type |

TABLE 40

Neutral and acidic N-glycan signals expressed exclusively in the four hESC samples. The signals are listed in order of increasing m/z (molecular mass) of the detected signals, first neutral N-glycans and then acidic N-glycans. The proposed structural classification is as described in the Examples.

| Neutral (5) | m/z $[M+Na]^+$ | Proposed composition | Proposed classification |
|---|---|---|---|
| | 1501.5 | $H_4N_4$ | complex-type |
| | 1590.6 | $H_4N_3F_2$ | hybrid/monoantennary; complex fucosylation |
| | 1793.6 | $H_4N_4F_2$ | complex-type; complex fucosylation |
| | 1825.6 | $H_6N_4$ | complex-type |
| | 2320.8 | $H_6N_5F_2$ | complex-type; complex fucosylation |

| Acidic (14) | m/z $[M-H]^-$ | Proposed composition | Proposed classification |
|---|---|---|---|
| | 1500.5 | $H_4N_3F_1P_1$ | hybrid/monoantennary; fucosylated |
| | 2174.8 | $S_1H_4N_6$ | complex-type; terminal N (N > H) |
| | 2263.8 | $S_1H_4N_5F_2$ | complex-type; terminal N (N > H); complex fucosylation |
| | 2457.9 | $S_1H_7N_5$ | complex-type |
| | 2660.9 | $S_1H_7N_6$ | complex-type |
| | 2953.1 | $S_1H_7N_6F_2$ | complex-type; complex fucosylation |
| | 3172.1 | $S_1H_8N_7F_1$ | complex-type |
| | 3245.2 | $S_1H_7N_6F_4$ | complex-type; complex fucosylation |
| | 3317.2 | $S_2H_8N_7$ | complex-type |
| | 3463.2 | $S_2H_8N_7F_1$ | complex-type |
| | 3608.3 | $S_3H_8N_7$ | complex-type |
| | 3610.3 | $S_1H_8N_7F_4$ | complex-type; complex fucosylation |
| | 3682.3 | $S_2H_9N_8$ | complex-type |
| | 3756.3 | $S_1H_{10}N_9$ | complex-type |

TABLE 41

N-glycan structural feature analysis based on proposed monosaccharide compositions of four hESC lines FES 21, FES 22, FES 29, and FES 30.

| | | | | | FES 21* | FES 22 | FES 29 | FES 30 | EB | st.3 |
|---|---|---|---|---|---|---|---|---|---|---|
| Neutral N-glycans | A | N = 2 and 5 ≤ H ≤ 10 | | high-mannose type | 84# | 73 | 79 | 79 | 73 | 72 |
| | B | N = 2 and 1 ≤ H ≤ 4 | | low-mannose type | 5 | 11 | 7 | 8 | 12 | 12 |
| | C | N = 3 and H ≥ 2 | | hybrid/monoantennary | 3 | 7 | 3 | 3 | 5 | 6 |
| | D | N ≥ 4 and H ≥ 3 | | complex-type | 6 | 9 | 10 | 10 | 8 | 8 |
| | E | | | other types | 2 | 0 | 1 | 0 | 2 | 2 |
| | N ≥ 3 | F | F ≥ 1 | fucosylation | 8 | 11 | 10 | 10 | 14 | 15 |
| | | G | F ≥ 2 | complex fucosylation | 1 | 0 | 2 | 2 | 2 | 2 |
| | | H§ | N > H ≥ 2 | terminal N (N > H) | 1 | 2 | 1 | 1 | 3 | 3 |
| | | I | N = H ≥ 5 | terminal N (N = H) | 0 | 2 | 0 | 0 | 1 | 1 |
| Sialylated N-glycans | J | N = 3 and H ≥ 3 | | hybrid/monoantennary | 8 | 2 | 5 | 9 | 13 | 14 |
| | K | N ≥ 4 and H ≥ 3 | | complex-type | 91 | 98 | 94 | 90 | 83 | 77 |
| | L | | | other types | 1 | 0 | 1 | 1 | 4 | 9 |
| | N ≥ 3 | M | F ≥ 1 | fucosylation | 85 | 96 | 75 | 78 | 83 | 86 |
| | | N | F ≥ 2 | complex fucosylation | 24 | 34 | 23 | 19 | 12 | 11 |
| | | O | N > H ≥ 3 | terminal N (N > H) | 10 | 8 | 6 | 5 | 10 | 10 |
| | | P | N = H ≥ 5 | terminal N (N = H) | 3 | 4 | 4 | 2 | 14 | 20 |

The numbers refer to percentage from either neutral (A-E) or acidic (J-L) N-glycan pools, or from subfractions of hybrid/monoantenary and complex-type N-glycans (N ≥ 3, F-I and M-P).
EB 29 and EB 30: embryoid bodies derived from hESC lines FES 29 and FES 30, respectively;
st.3 29: stage 3 differentiated cells derived from hESC line FES 29.
H: hexose;
N: N-acetylhexosamine;
F: deoxyhexose.

TABLE 42[1)]

| | | | FES 21 | | FES 22 | | FES 29 | | FES 30 | | EB[2)] |
|---|---|---|---|---|---|---|---|---|---|---|---|
| Affymetrix ID | Gene Bank ID | Gene | Det.[3)] | Ch.[4)] | Det. | Ch. | Det. | Ch. | Det. | Ch. | Det. |
| 206109_at | NM_000148.1 | FUT1 | P | I | P | I | P | I | P | I | A |
| 214088_s_at | AW080549 | FUT3 | M | NC | A | NC | A | NC | A | NC | A |

TABLE 42[1])-continued

| | | | FES 21 | | FES 22 | | FES 29 | | FES 30 | | EB[2]) |
|---|---|---|---|---|---|---|---|---|---|---|---|
| Affymetrix ID | Gene Bank ID | Gene | Det.[3]) | Ch.[4]) | Det. | Ch. | Det. | Ch. | Det. | Ch. | Det. |
| 209892_at | AF305083.1 | FUT4 | P | I | P | I | P | I | P | I | A |
| 211225_at | U27330 | FUT5 | A | NC | A | NC | A | NC | A | NC | A |
| 211225_at | U27329.1 | FUT5 | A | NC | A | NC | A | NC | A | NC | A |
| 210399_x_at | U27336.1 | FUT6 | A | NC | A | NC | A | NC | A | NC | A |
| 211882_x_at | U27331.1 | FUT6(1) | A | NC | A | NC | A | NC | A | NC | A |
| 211885_x_at | U27332.1 | FUT6(2) | A | NC | A | NC | A | NC | A | NC | A |
| 211465_x_at | U27335.1 | FUT6(minor) | A | NC | A | NC | A | NC | A | NC | A |
| 210506_at | U11282.1 | FUT7 | A | NC | A | NC | A | NC | A | NC | A |
| 203988_s_at | NM_004480.1 | FUT8 | P | NC | P | NC | P | NC | P | NC | P |
| 207696_at | NM_006581.1 | FUT9 | A | NC | A | NC | A | NC | A | NC | A |
| 229203_at | NM_173593 | β4GalNAc-T3 | A | NC | A | NC | A | NC | A | NC | A |
| 200016_x_at | NM_002409 | MGAT3 | P | NC | P | D | P | D | P | D | P |
| 208058_s_at | NM_002409.2 | MGAT3 | A | NC | A | NC | A | NC | A | NC | A |
| 209764_at | AL022312 | β4GlcNAcT | A | NC | A | MD | A | MD | A | NC | A |
| 206435_at | NM_001478.2 | GALGT | A | NC | A | NC | A | NC | A | NC | A |
| 206720_at | NM_002410.2 | MGAT5 | A | NC | A | NC | A | NC | A | NC | A |
| 203102_s_at | NM_002408.2 | MGAT2 | P | I | P | NC | P | I | P | I | P |
| 201126_s_at | NM_002406.2 | MGAT1 | P | NC | P | NC | P | NC | P | NC | P |
| 219797_at | NM_012214.1 | GNT4a | A | NC | P | NC | A | NC | M | NC | A |
| 220189_s_at | NM_014275.1 | GNT4b | P | D | P | NC | P | NC | P | NC | P |
| 204856_at | AB049585 | β3GlcNAc-T3 | A | NC | A | NC | A | NC | A | NC | A |
| 225612_s_at | BE672260 | β3GlcNAc-T5 | P | D | P | D | P | D | P | D | P |
| 232337_at | XM_091928 | β3GlcNAc-T7 | P | NC | P | NC | P | NC | P | NC | A |
| 221240_s_at | NM_030765.1 | β3GlcNAc-T4 | P | NC | A | NC | A | NC | P | NC | A |
| 204856_at | NM_014256.1 | β3GnT3 | A | NC | A | NC | A | NC | A | NC | A |
| 205505_at | NM_001490.1 | β6GlcNAcT | P | I | P | NC | P | NC | A | NC | A |
| 203188_at | NM_006876.1 | i β3GlcNAcT | P | D | P | D | P | MD | P | NC | P |
| 211020_at | L19659.1 | I β6GlcNAcT | A | NC | M | NC | A | NC | A | NC | A |
| 214504_at | NM_020459.1 | A α3GalNAcT | A | NC | A | NC | A | NC | A | NC | A |
| 211812_s_at | AB050856.1 | globosideT | P | NC | A | NC | P | NC | P | NC | A |
| 221131_at | NM_016161.1 | α4GlcNAcT | M | NC | P | NC | P | NC | M | NC | A |
| 221935_s_at | | AER61 | P | I | P | I | P | I | P | I | A |
| 225689_at | | AGO61 | P | NC | P | NC | P | NC | P | NC | P |
| 210571_s_at | | CMAH | A | NC | A | NC | A | NC | A | NC | A |
| 205518_s_at | | CMAH | A | D | M | NC | A | D | A | NC | P |
| 213355_at | | ST3GAL6 | A | NC | A | NC | A | NC | A | NC | A |
| 211379_x_at | | β3GALT3 | P | D | P | D | P | NC | P | D | P |
| 218918_at | | MAN1C1 | P | NC | P | NC | P | NC | P | NC | P |
| 208450_at | | LGALS2 | A | NC | A | NC | A | NC | A | NC | A |
| 208949_s_at | | LGALS3 | P | D | P | D | P | D | P | D | P |

[1])Data reference: Skottman, H., et al. (2005).
[2])EB, embryoid bodies used as reference in calculation of fold changes.
[3])Det. (detection) codes: P, present; A, absent; M, medium.
[4])Ch. (fold change) codes: I, increased; D, decreased; NC, no change.

TABLE 43

| % | m/z | proposed composition | % | m/z | proposed composition |
|---|---|---|---|---|---|
| hEF neutral N-glycans | | | mEF neutral N-glycans | | |
| 19.5[1]) | 1743 | Hex8HexNAc2 | 13.7 | 1905 | Hex9HexNAc2 |
| 17.1 | 1905 | Hex9HexNAc2 | 13.5 | 1419 | Hex6HexNAc2 |
| 16.2 | 1419 | Hex6HexNAc2 | 13.5 | 1743 | Hex8HexNAc2 |
| 12.6 | 1581 | Hex7HexNAc2 | 11.2 | 1581 | Hex7HexNAc2 |
| 4.6 | 1257 | Hex5HexNAc2 | 10.3 | 1257 | Hex5HexNAc2 |
| 3.6 | 1079 | Hex3HexNAc2dHex1 | 2.7 | 1054 | Hex5HexNAc1 |
| 2.1 | 2067 | Hex10HexNAc2 | 2.6 | 568 | Hex2HexNAc1 |
| | | | 2.4 | 2067 | Hex10HexNAc2 |
| | | | 2.1 | 1216 | Hex6HexNAc1 |
| | | | 2.0 | 892 | Hex4HexNAc1 |
| | | | 1.9 | 933 | Hex3HexNAc2 |
| hEF acidic N-glycans | | | mEF acidic N-glycans | | |
| 23.0[2]) | 2076 | NeuAc1Hex5HexNAc4dHex1 | 30.3 | 2238 | NeuAc1Hex6HexNAc4dHex1 |
| 8.5 | 2367 | NeuAc2Hex5HexNAc4dHex1 | 12.4 | 2076 | NeuAc1Hex5HexNAc4dHex1 |
| 8.1 | 2441 | NeuAc1Hex6HexNAc5dHex1 | 9.8 | 2092 | NeuAc1Hex6HexNAc4 |
| 6.0 | 2221 | NeuAc2Hex5HexNAc4 | 5.9 | 1930 | NeuAc1Hex5HexNAc4 |
| 5.9 | 1930 | NeuAc1Hex5HexNAc4 | 2.6 | 2367 | NeuAc2Hex5HexNAc4dHex1 |
| 5.3 | 2733 | NeuAc1Hex6HexNAc5dHex3 | 2.6 | 1914 | NeuAc1Hex4HexNAc4dHex1 |
| 3.5 | 2368 | NeuAc1Hex5HexNAc4dHex3 | 2.0 | 1727 | NeuAc1Hex5HexNAc3 |
| 2.9 | 2732 | NeuAc2Hex6HexNAc5dHex1 | 1.9 | 1889 | NeuAc1Hex6HexNAc3 |

TABLE 43-continued

| % | m/z | proposed composition | % | m/z | proposed composition |
|---|---|---|---|---|---|
| 2.5 | 3391 | NeuAc1Hex9HexNAc8 | 1.7 | 2221 | NeuAc2Hex5HexNAc4 |
| 2.5 | 3098 | NeuAc2Hex7HexNAc6dHex1 | 1.6 | 2441 | NeuAc1Hex6HexNAc5dHex1 |

[1] Together the tabled signals comprise over 75% of total signal intensity.
[2] Together the tabled signals comprise over 67% of total signal intensity.

TABLE 44

| Neutral N-glycan structures of feeder cells | | proportion, % | |
|---|---|---|---|
| proposed composition | proposed structure types | hEF | mEF |
| $Hex_{5-13}HexNAc_2$ | high-mannose/glucosylated | 76 | 72 |
| $Hex_{1-4}HexNAc_2dHex_{0-1}$ | low-mannose | 8 | 7 |
| $n_{HexNAc} = 3$ ja $n_{Hex} \geq 2$ | hybrid/monoantennary | 4 | 6 |
| $n_{HexNAc} \geq 4$ ja $n_{Hex} \geq 2$ | complex-type | 9 | 11 |
|  | other types | 3 | 4 |
| $n_{dHex} \geq 1$ | fucosylation | 13 | 8 |
| $n_{dHex} \geq 2$ | complex fucosylation | 0.5 | 0.2 |
| $n_{HexNAc} > n_{Hex} \geq 2$ | terminal HexNAc, N > H[1] | 2 | 2 |
| $n_{HexNAc} = n_{Hex} \geq 5$ | terminal HexNAc, N = H | — | 0.3 |

[1] N, HexNAc; H, Hex.

TABLE 45

| Acidic N-glycan structures of feeder cells | | proportion, % | |
|---|---|---|---|
| proposed composition | proposed structure types | hEF | mEF |
| $n_{HexNAc} = 3$ ja $n_{Hex} \geq 5$ | hybrid-type | 3 | 8 |
| $n_{HexNAc} = 3$ ja $n_{Hex} = 3-4$ | monoantennary | 4 | 6 |
| $n_{HexNAc} \geq 4$ ja $n_{Hex} \geq 3$ | complex-type | 92 | 86 |
| muut | — | 1 | 0 |
| $n_{dHex} \geq 1$ | fucosylation | 76 | 67 |
| $n_{dHex} \geq 2$ | complex fucosylation | 21 | 4 |
| $n_{HexNAc} > n_{Hex} \geq 2$ | terminal HexNAc, N > H[1] | 1 | 2 |
| $n_{HexNAc} = n_{Hex} \geq 5$ | terminal HexNAc, N = H | 1.5 | 1.5 |
| NeuAc + 16 Da | NeuGc | — | — |
| +80 Da | sulphate/phosphate ester | 1 | 9 |

[1] N, HexNAc; H, Hex.

TABLE 46

| Proposed composition | m/z | hESC | EB | st.3 | hEF | mEF | BM MSC | OB | CB MSC | AC | CB MNC | CD 34+ | CD 133+ | LIN− | CD 8− |
|---|---|---|---|---|---|---|---|---|---|---|---|---|---|---|---|
| $Hex_{5-9}HexNAc_2$ (including high-mannose type N-glycans) | | | | | | | | | | | | | | | |
| Hex5HexNAc2 | 1257 | + | + | + | + | + | + | + | + | + | + | + | + | + | + |
| Hex6HexNAc2 | 1419 | + | + | + | + | + | + | + | + | + | + | + | + | + | + |
| Hex7HexNAc2 | 1581 | + | + | + | + | + | + | + | + | + | + | + | + | + | + |
| Hex8HexNAc2 | 1743 | + | + | + | + | + | + | + | + | + | + | + | + | + | + |
| Hex9HexNAc2 | 1905 | + | + | + | + | + | + | + | + | + | + | + | + | + | + |
| $Hex_{1-4}HexNAc_2dHex_{0-1}$ (including low-mannose type N-glycans) | | | | | | | | | | | | | | | |
| HexHexNAc2 | 609 | + | + | | | | + | + | + | + | | + | | | + |
| HexHexNAc2dHex | 755 | | | | | | | | + | + | + | + | | | + |
| Hex2HexNAc2 | 771 | + | + | + | + | + | + | + | + | + | + | + | + | + | + |
| Hex2HexNAc2dHex | 917 | + | + | + | + | + | + | + | + | + | + | + | + | + | + |
| Hex3HexNAc2 | 933 | + | + | + | + | + | + | + | + | + | + | + | + | + | + |
| Hex3HexNAc2dHex | 1079 | + | + | + | + | + | + | + | + | + | + | + | + | + | + |
| Hex4HexNAc2 | 1095 | + | + | + | + | + | + | + | + | + | + | + | + | + | + |
| Hex4HexNAc2dHex | 1241 | + | + | + | + | + | + | + | + | + | + | + | + | + | + |
| $Hex_{10-12}HexNAc_2$ (including glucosylated high-mannose type N-glycans) | | | | | | | | | | | | | | | |
| Hex10HexNAc2 | 2067 | + | + | + | + | + | + | + | + | + | + | + | + | | + |
| Hex11HexNAc2 | 2229 | + | + | + | + | + | + | + | + | + | | | | | + |
| Hex12HexNAc2 | 2391 | + | + | | + | + | + | + | + | + | | | | | + |
| $Hex_{5-9}HexNAc_2dHex_1$ (including fucosylated high-mannose type N-glycans) | | | | | | | | | | | | | | | |
| Hex5HexNAc2dHex | 1403 | + | | + | + | + | + | + | + | + | | + | | + | + |
| Hex6HexNAc2dHex | 1565 | | + | | + | | + | + | + | + | + | | + | | + |
| Hex7HexNAc2dHex | 1727 | | | | | | | | | + | | | | | |
| $Hex_{1-9}HexNAc_1$ (including soluble glycans) | | | | | | | | | | | | | | | |
| Hex2HexNAc | 568 | | | + | + | + | + | + | + | | + | | | | |
| Hex3HexNAc | 730 | | | + | + | + | + | + | + | + | + | + | | | |
| Hex4HexNAc | 892 | + | + | + | + | + | + | + | + | + | + | + | + | + | + |
| Hex5HexNAc | 1054 | + | + | + | + | + | + | + | + | + | + | + | + | + | + |
| Hex6HexNAc | 1216 | + | + | + | + | + | + | + | + | + | + | + | + | + | + |
| Hex7HexNAc | 1378 | + | + | + | + | + | + | + | + | + | + | + | + | + | + |

TABLE 46-continued

| Proposed composition | m/z | hESC | EB | st.3 | hEF | mEF | BM MSC | OB | CB MSC | AC | CB MNC | CD 34+ | CD 133+ | LIN- | CD 8- |
|---|---|---|---|---|---|---|---|---|---|---|---|---|---|---|---|
| Hex8HexNAc | 1540 | + | + | + | + | + | + | + | + | + | + | + | + | + | |
| Hex9HexNAc | 1702 | + | + | + | + | + | + | | + | | + | + | | + | |
| HexNAc = 3 and Hex ≥ 2 (including hybrid-type and monoantennary N-glycans) | | | | | | | | | | | | | | | |
| Hex2HexNAc3 | 974 | | | | | | + | + | + | | | | | | |
| Hex2HexNAc3dHex | 1120 | | + | | | | + | + | + | + | + | + | + | | + |
| Hex3HexNAc3 | 1136 | + | + | + | + | + | + | + | + | + | + | + | + | + | + |
| Hex2HexNAc3dHex2 | 1266 | | | | | | | + | | | | | | | |
| Hex3HexNAc3dHex | 1282 | + | + | + | + | + | + | + | + | + | + | + | + | + | + |
| Hex4HexNAc3 | 1298 | + | + | + | + | + | + | + | + | + | + | + | + | + | + |
| Hex3HexNAc3dHex2 | 1428 | | | | | | | + | + | + | + | + | | | + |
| Hex4HexNAc3dHex | 1444 | + | + | + | + | + | + | + | + | + | + | + | + | + | + |
| Hex5HexNAc3 | 1460 | + | + | + | + | + | + | + | + | + | + | + | + | + | + |
| Hex4HexNAc3dHex2 | 1590 | + | | | | | | + | + | + | + | + | + | | + |
| Hex5HexNAc3dHex | 1606 | + | + | + | + | + | + | + | + | + | + | + | + | + | + |
| Hex6HexNAc3 | 1622 | + | + | + | + | + | + | + | + | + | + | + | + | + | + |
| Hex5HexNAc3dHex2 | 1752 | | | | | | | + | + | + | + | | | | |
| Hex6HexNAc3dHex | 1768 | + | + | | | + | + | + | + | + | | | + | | + |
| Hex7HexNAc3 | 1784 | | | + | + | + | + | + | + | + | | | | | |
| Hex8HexNAc3 | 1946 | | | | + | + | | | | | | | | | |
| HexNAc ≥ 4 and Hex ≥ 3 (including complex-type N-glycans) | | | | | | | | | | | | | | | |
| Hex3HexNAc4 | 1339 | | | | + | | + | + | + | + | + | | | + | |
| Hex3HexNAc4dHex | 1485 | + | | | + | + | + | + | + | + | + | + | + | + | + |
| Hex4HexNAc4 | 1501 | + | | | + | | + | + | + | + | | + | | + | + |
| Hex3HexNAc5 | 1542 | + | + | + | + | + | | | | + | + | | | + | |
| Hex4HexNAc4dHex | 1647 | + | + | + | + | + | + | + | + | + | + | + | + | + | + |
| Hex5HexNAc4 | 1663 | + | + | + | + | + | + | + | + | + | + | + | + | + | + |
| Hex3HexNAc5dHex | 1688 | + | + | + | + | + | + | | + | + | + | + | + | + | + |
| Hex4HexNAx5 | 1704 | + | + | + | + | + | | + | + | + | + | | | + | + |
| Hex4HexNAc4dHex2 | 1793 | + | | | + | | | | + | + | + | + | + | + | + |
| Hex5HexNAc4dHex | 1809 | + | + | + | + | + | + | + | + | + | + | + | + | + | + |
| Hex6HexNAc4 | 1825 | + | | + | + | + | + | + | + | + | | | | + | + |
| Hex4HexNAc5dHex | 1850 | + | + | + | | | + | | + | + | + | | | | |
| Hex5HexNAc5 | 1866 | + | + | + | + | + | + | | + | + | + | | | + | + |
| Hex3HexNAc6dHex | 1891 | | | | | | + | + | + | + | | | | + | |
| Hex5HexNAc4dHex2 | 1955 | + | + | | + | | + | + | + | + | + | + | + | | + |
| Hex6HexNAc4dHex | 1971 | | + | + | + | + | + | + | + | + | | | | | + |
| Hex7HexNAc4 | 1987 | | | | + | + | + | + | + | + | | | | | + |
| Hex4HexNAc5dHex2 | 1996 | + | + | | + | | + | + | + | + | | | | | |
| Hex5HexNAc5dHex | 2012 | + | + | + | + | | + | + | + | + | | | | | |
| Hex6HexNAc5 | 2028 | + | + | + | + | + | + | + | + | + | + | | | | + |
| Hex5HexNAc4dHex3 | 2101 | + | + | | + | | + | + | + | + | + | + | + | | + |
| Hex6HexNAc4dHex2 | 2117 | | | | | | + | + | | | | | | | |
| Hex7HexNAc4dHex | 2133 | | | | + | + | | + | | | | | | | + |
| Hex4HexNAc5dHex3 | 2142 | + | + | | + | + | + | + | | | | | | | + |
| Hex8HexNAc4 | 2149 | | | | + | + | + | + | | | | | | + | |
| Hex5HexNAc5dHex2 | 2158 | | + | | | | | + | + | + | | | | | |
| Hex6HexNAc5dHex | 2174 | + | | + | + | | + | + | + | + | | + | | | + |
| Hex7HexNAc5 | 2190 | | | | + | + | | | | | | | | | |
| Hex6HexNAc6 | 2231 | | | | | | | + | | + | | | | | |
| Hex7HexNAc4dHex2 | 2279 | | | | + | + | | | | | | | | | |
| Hex5HexNAc5dHex3 | 2304 | | | | | | + | + | | + | | | | | |
| Hex6HexNAc5dHex2 | 2320 | + | | | | | | + | + | + | | | | | + |
| Hex7HexNAc5dHex | 2336 | | | | + | + | | | | | | | | | |
| Hex8HexNAc5 | 2352 | | | | + | + | | | | | | | | | |
| Hex7HexNAc6 | 2393 | | | | + | | + | | + | + | | | | | + |
| Hex7HexNAc4dHex3 | 2425 | | | | + | + | | | | | | | | | |
| Hex6HexNAc5dHex3 | 2466 | | | | | | + | + | | + | | | | | |
| Hex8HexNAc5dHex | 2498 | | | | + | + | | | | | | | | | |
| Hex7HexNAc6dHex | 2539 | | | | | + | | | | | | | | | |
| Hex6HexNAc5dHex4 | 2612 | | | | | | + | + | | | | | | | |
| Hex8HexNAc7 | 2758 | | | | | | + | + | | | | | | | |
| HexNAc ≥ 3 and dHex ≥ 1 (including fucosylated N-glycans) | | | | | | | | | | | | | | | |
| Hex2HexNAc3dHex | 1120 | | + | | | | + | + | + | + | + | + | + | | + |
| Hex2HexNAc3dHex2 | 1266 | | | | | | | + | | | | | | | |
| Hex3HexNAc3dHex | 1282 | + | + | + | + | + | + | + | + | + | + | + | + | + | + |
| Hex3HexNAc3dHex2 | 1428 | | | | | | | + | + | + | + | + | | | + |
| Hex4HexNAc3dHex | 1444 | + | + | + | + | + | + | + | + | + | + | + | + | + | + |
| Hex4HexNAc3dHex2 | 1590 | + | | | | | | + | + | + | + | + | + | | + |
| Hex5HexNAc3dHex | 1606 | + | + | + | + | + | + | + | + | + | + | + | + | + | + |

TABLE 46-continued

| Proposed composition | m/z | hESC | EB | st.3 | hEF | mEF | BM MSC | OB | CB MSC | AC | CB MNC | CD 34+ | CD 133+ | LIN− | CD 8− |
|---|---|---|---|---|---|---|---|---|---|---|---|---|---|---|---|
| Hex5HexNAc3dHex2 | 1752 | | | | | | + | + | + | + | | | | | |
| Hex6HexNAc3dHex | 1768 | + | + | | | + | + | + | + | + | | | + | | + |
| Hex3HexNAc4dHex | 1485 | + | + | + | + | + | + | + | + | + | + | + | + | + | + |
| Hex4HexNAc4dHex | 1647 | + | + | + | + | + | + | + | + | + | + | + | + | + | + |
| Hex3HexNAc5dHex | 1688 | + | + | + | + | + | + | + | + | + | + | + | + | + | + |
| Hex4HexNAc4dHex2 | 1793 | + | | | + | | | + | + | + | + | + | + | | + |
| Hex5HexNAc4dHex | 1809 | + | + | + | + | + | + | + | + | + | + | + | + | + | + |
| Hex4HexNAc5dHex | 1850 | + | + | + | | | + | | + | + | + | | | | |
| Hex3HexNAc6dHex | 1891 | | | | | | | + | + | + | + | | | + | |
| Hex5HexNAc4dHex2 | 1955 | + | + | | + | | + | + | + | + | + | + | + | | + |
| Hex6HexNAc4dHex | 1971 | | + | | + | + | + | + | + | + | | | | | + |
| Hex4HexNAc5dHex2 | 1996 | + | + | | + | | + | + | + | + | | | | | |
| Hex5HexNAc5dHex | 2012 | + | + | + | + | | + | + | + | + | | | | | |
| Hex5HexNAc4dHex3 | 2101 | + | + | | + | | + | + | + | + | + | + | + | | + |
| Hex6HexNAc4dHex2 | 2117 | | | | | | + | + | | | | | | | |
| Hex7HexNAc4dHex | 2133 | | | | + | + | + | | | | | | | | + |
| Hex4HexNAc5dHex3 | 2142 | + | + | | + | + | + | + | | | | | | | + |
| Hex5HexNAc5dHex2 | 2158 | | + | | | | | + | + | + | | | | | |
| Hex6HexNAc5dHex | 2174 | + | + | + | + | | + | + | + | | | + | | | + |
| Hex7HexNAc4dHex2 | 2279 | | | | + | + | | | | | | | | | |
| Hex5HexNAc5dHex3 | 2304 | | | | | | + | + | | + | | | | | |
| Hex6HexNAc5dHex2 | 2320 | + | | | | | + | + | + | + | | | | | + |
| Hex7HexNAc5dHex | 2336 | | | | + | + | | | | | | | | | |
| Hex7HexNAc4dHex3 | 2425 | | | | + | + | | | | | | | | | |
| Hex6HexNAc5dHex3 | 2466 | | | | | | + | + | | + | | | | | |
| Hex8HexNAc5dHex | 2498 | | | | + | + | | | | | | | | | |
| Hex7HexNAc6dHex | 2539 | | | | + | | | + | + | + | | | | | |
| Hex6HexNAc5dHex4 | 2612 | | | | | | + | + | | | | | | | |
| HexNAc ≥ 3 and dHex ≥ 2 (including multifucosylated N-glycans) | | | | | | | | | | | | | | | |
| Hex2HexNAc3dHex2 | 1266 | | | | | | | + | | | | | | | |
| Hex3HexNAc3dHex2 | 1428 | | | | | | + | | + | + | + | + | | | + |
| Hex4HexNAc3dHex2 | 1590 | + | | | | | + | + | + | + | + | + | + | | + |
| Hex5HexNAc3dHex2 | 1752 | | | | | | + | + | + | + | | | | | |
| Hex4HexNAc4dHex2 | 1793 | + | | | + | | | + | + | + | + | + | + | | + |
| Hex5HexNAc4dHex2 | 1955 | + | + | | + | | + | + | + | + | + | + | + | | + |
| Hex4HexNAc5dHex2 | 1996 | + | + | | + | | + | + | + | + | | | | | |
| Hex5HexNAc4dHex3 | 2101 | + | + | | + | | + | + | + | + | + | + | + | | + |
| Hex6HexNAc4dHex2 | 2117 | | | | | | + | + | | | | | | | |
| Hex4HexNAc5dHex3 | 2142 | + | + | | + | + | + | + | | | | | | | + |
| Hex5HexNAc5dHex2 | 2158 | | + | | | | | + | + | + | | | | | |
| Hex7HexNAc4dHex2 | 2279 | | | | + | + | | | | | | | | | |
| Hex5HexNAc5dHex3 | 2304 | | | | | | + | + | | + | | | | | |
| Hex6HexNAc5dHex2 | 2320 | + | | | | | + | + | + | + | | | | | + |
| Hex7HexNAc4dHex3 | 2425 | | | | + | + | | | | | | | | | |
| Hex6HexNAc5dHex3 | 2466 | | | | | | + | + | | + | | | | | |
| Hex6HexNAc5dHex4 | 2612 | | | | | | + | + | | | | | | | |
| HexNAc > Hex ≥ 2 (terminal HexNAc, N > H) | | | | | | | | | | | | | | | |
| Hex2HexNAc3 | 974 | | | | | | + | + | + | | | | | | |
| Hex2HexNAc3dHex | 1120 | | + | | | | + | + | + | + | + | + | + | | + |
| Hex2HexNAc3dHex2 | 1266 | | | | | | | + | | | | | | | |
| Hex3HexNAc4 | 1339 | | | | + | + | + | + | + | + | + | | | + | |
| Hex3HexNAc4dHex | 1485 | + | + | + | + | + | + | + | + | + | + | + | + | + | + |
| Hex3HexNAc5 | 1542 | + | + | + | + | + | | | | + | + | | | + | |
| Hex3HexNAc5dHex | 1688 | + | + | + | + | + | + | + | + | + | + | + | + | + | + |
| Hex4HexNAx5 | 1704 | + | + | + | + | + | | + | + | + | | + | + | + | |
| Hex4HexNAc5dHex | 1850 | + | + | + | | | + | | + | + | + | | | | |
| Hex3HexNAc6dHex | 1891 | | | | | | | + | + | + | + | | | + | |
| Hex4HexNAc5dHex2 | 1996 | + | + | | + | | + | + | + | + | | | | | |
| Hex4HexNAc5dHex3 | 2142 | + | + | | + | + | + | + | | | | | | | + |
| HexNAc = Hex ≥ 5 (terminal HexNAc, N = H) | | | | | | | | | | | | | | | |
| Hex5HexNAc5 | 1866 | + | + | + | + | + | + | + | + | + | + | | | + | + |
| Hex5HexNAc5dHex | 2012 | + | + | + | + | | + | + | + | + | | | | | |
| Hex5HexNAc5dHex2 | 2158 | | + | | | | | + | + | + | | | | | |
| Hex6HexNAc6 | 2231 | | | | | | | + | + | + | | | | | |
| Hex5HexNAc5dHex3 | 2304 | | | | | | + | + | | + | | | | | | hESC, human embryonic stem cells;
EB, embryoid bodies derived from hESC;
st.3, stage 3 differentiated cells derived from hESC;
hEF, human fibroblast feeder cells;
mEF, murine fibroblast feeder cells;

TABLE 46-continued

BM MSC, bone-marrow derived mesenchymal stem cells;
OB, Osteoblast-differentiated cells derived from BM MSC;
CB MSC, cord blood derived mesenchymal stem cells;
OB, adipocyte-differentiated cells derived from CB MSC;
CB MNC, cord blood mononuclear cells;
CD34+, CD133+, LIN−, and CD8−: subpopulations of CB MNC.

TABLE 47

| Proposed composition | m/z | hESC | EB | st.3 | hEF | mEF | BM MSC | OB | CB MSC | AC | CB MNC | CD 34+ | CD 133+ | LIN− | CD 8− |
|---|---|---|---|---|---|---|---|---|---|---|---|---|---|---|---|
| HexNAc = 3 and Hex ≥ 2 (including hybrid-type and monoantennary N-glycans) | | | | | | | | | | | | | | | |
| Hex3HexNAc3dHexSP | 1338 | | | | | | | + | | | | | | | |
| Hex4HexNAc3SP | 1354 | | | | | | + | + | | | | | | | |
| NeuAcHex3HexNAc3 | 1403 | | + | | | + | + | + | | + | + | + | + | + | + |
| NeuGcHex3HexNAc3 | 1419 | | | | | | | | | | | | + | | |
| Hex4HexNAc3dHexSP | 1500 | + | + | | | + | + | + | + | | | + | + | + | + |
| Hex5HexNAc3SP | 1516 | | + | | | | + | + | | | | | | | + |
| NeuAcHex3HexNAc3dHex | 1549 | + | + | | + | + | + | + | | + | + | + | + | + | + |
| NeuAcHex3HexNAc3SP2 | 1563 | | | | | | | | | | | | + | + | | |
| NeuAcHex4HexNAc3 | 1565 | + | + | | + | + | + | + | + | + | + | + | + | + | + |
| NeuGcHex4HexNAc3 | 1581 | | + | | + | | + | | | | | | + | + | | |
| Hex4HexNAc3dHex2SP | 1646 | | | | | | | + | | | | + | | | | |
| Hex5HexNAc3dHexSP | 1662 | | | | | | | + | | | | | | | | |
| Hex6HexNAc3SP and/or NeuAc2Hex2HexNAc3dHex | 1678 | + | + | | + | + | + | + | + | + | + | + | + | + | + |
| NeuAc2Hex3HexNAc3 | 1694 | | | | | | + | | | | | | | | | |
| NeuAcHex3HexNAc3dHexSP2 | 1709 | | | | | | | | | | | | + | + | | |
| NeuAcHex4HexNAc3dHex | 1711 | + | + | + | + | + | + | + | + | + | + | + | + | + | + |
| NeuAcHex5HexNAc3 and/or NeuGcHex4HexNAc3dHex | 1727 | + | + | | + | + | + | + | + | + | + | + | + | + | + |
| NeuGcHex5HexNAc3 | 1743 | | | | | | + | | | | | | | | | |
| NeuAcHex4HexNAc3dHexSP | 1791 | | + | | | | + | + | + | | | | + | + | | |
| Hex5HexNAc3dHex2SP | 1808 | | | | | | | | | | | + | | | | |
| NeuAc2Hex3HexNAc3dHex | 1840 | + | + | | | | + | | + | + | | | + | | + | |
| NeuAc2Hex4HexNAc3 | 1856 | | | | | | + | | | | | + | | | | |
| NeuAcHex4HexNAc3dHex2 | 1857 | | | | | | | | | | | | + | + | | |
| NeuAcHex5HexNAc3dHex and/or NeuGcHex4HexNAc3dHex2 | 1873 | + | + | + | + | + | + | + | + | + | + | + | + | + | + |
| NeuAcHex6HexNAc3 | 1889 | + | + | | + | + | + | + | + | + | + | + | + | + | + |
| Hex8HexNAc3SP and/or NeuAc2Hex4HexNAc3dHex | 2002 | + | + | | + | + | + | + | + | | + | | | | + |
| NeuAc2Hex4HexNAc3dHex3 | 2003 | | + | | | | + | | | | | | | | | |
| NeuAc2Hex5HexNAc3 and/or NeuGcNeuAcHex4HexNAc3dHex | 2018 | | | | | | + | + | + | + | | + | + | + | | |
| NeuAcHex5HexNAc3dHex2 | 2019 | | | | | | | | | | | | + | + | | |
| NeuGcNeuAcHex5HexNAc3 and/or NeuGc2Hex4HexNAc3dHex | 2034 | | | | | | | | | | | + | | | | |
| NeuAcHex6HexNAc3dHex | 2035 | | + | | | | + | + | + | + | | + | + | + | + | |
| NeuGc2Hex5HexNAc3 | 2050 | | | | | | | | | | | | | + | | |
| NeuAcHex7HexNAc3 | 2051 | | + | | | | + | + | | | | | + | + | + | |
| NeuAc2Hex4HexNAc3dHexSP and/or Hex8HexNAc3SP2 | 2082 | | | | | | + | + | + | | | | | | | |
| NeuAcHex6HexNAc3dHexSP | 2115 | | | | | | | | | | | | + | | | |
| Hex8HexNAc3dHexSP and/or NeuAc2Hex4HexNAc3dHex2 | 2148 | | | | | | | | | | | | + | | | |
| NeuAcHex8HexNAc3SP and/or NeuAc3Hex4HexNAc3dHex | 2293 | | | | | | | | | | | | + | | | |
| NeuAc2Hex5HexNAc3dHex2 and/or NeuGcNeuAcHex4HexNAc3dHex3 | 2310 | | | | | | | | + | | | | | | | |
| NeuAc3Hex5HexNAc3SP | 2389 | | | | + | | | | | | | | | | | |
| NeuAc2Hex5HexNAc3dHex2SP | 2390 | + | + | + | + | + | + | | | | + | + | + | + | |
| NeuAc2Hex6HexNAc3dHexSP | 2406 | | | | | | + | | | | | | + | + | | |
| NeuAcHex8HexNAc3dHexSP and/or NeuAc3Hex4HexNAc3dHex2 | 2439 | | | | | | | | | | | | + | | | |
| NeuAcHex9HexNAc3dHex | 2521 | | | | | | | | | | | | + | | | |
| HexNAc ≥ 4 and Hex ≥ 3 (including complex-type N-glycans) | | | | | | | | | | | | | | | | |
| Hex4HexNAc4SP | 1557 | | + | | | + | | + | + | | | | | | | |
| NeuAcHex3HexNAc4 | 1606 | | | | | + | | | | | | | | | | |

TABLE 47-continued

| Proposed composition | m/z | hESC | EB | st.3 | hEF | mEF | BM MSC | OB | CB MSC | AC | CB MNC | CD 34+ | CD 133+ | LIN- | CD 8- |
|---|---|---|---|---|---|---|---|---|---|---|---|---|---|---|---|
| Hex4HexNAc4SP2 | 1637 | | + | | + | | + | + | | | | + | + | + | + |
| Hex4HexNAc4dHexSP | 1703 | | + | | | + | | + | | | | | | | |
| Hex4HexNAc4SP3 and/or Hex7HexNAc2SP2 | 1717 | | | | | | | | | | | | | + | |
| Hex5HexNAc4SP | 1719 | | + | | + | | + | + | + | | | | | | |
| NeuAcHex3HexNAc4dHex | 1752 | | | | | | | | | | | | | | + |
| NeuAcHex4HexNAc4 | 1768 | | + | | + | + | + | + | + | + | | + | + | + | + |
| NeuGcHex4HexNAc4 | 1784 | | | | | | | | | | | + | + | | |
| Hex5HexNAc4SP2 and/or Hex8HexNAc2SP | 1799 | | + | | | | + | | | | | | + | | |
| NeuAcHex3HexNAc5 | 1809 | | | | | | | + | | | | | | | |
| NeuGcHex3HexNAc5 | 1825 | | | | | | + | + | | | | | | | |
| Hex5HexNAc4dHexSP | 1865 | + | + | | + | + | + | + | + | | | + | + | + | + |
| Hex6HexNAc4SP | 1881 | | | | | + | | | | | | | | | |
| Hex4HexNAc5dHexSP | 1906 | + | + | | | | | | | | | | | | |
| NeuAcHex4HexNAc4dHex | 1914 | + | + | | + | + | + | + | + | + | | + | + | + | + |
| NeuAcHex4HexNAc4SP2 | 1928 | | | | | | | | | | | | + | + | | |
| NeuAcHex5HexNAc4 | 1930 | + | + | + | + | + | + | + | + | + | | + | + | + | + |
| NeuGcHex5HexNAc4 | 1946 | + | + | | + | | + | + | | | | + | + | + | |
| NeuAcHex4HexNAc5 | 1971 | + | + | | | + | + | | + | | | | + | | + |
| NeuAcHex5HexNAc4Ac | 1972 | | | | | | | | | + | | | | | |
| Hex5HexNAc5SP2 | 2002 | | + | | + | + | + | + | + | | | + | | | |
| NeuAcHex5HexNAc4SP | 2010 | | | | | | | + | | | | | | + | |
| Hex5HexNAc4dHex2SP | 2011 | | | | | | | | | | | | | + | |
| NeuGcHex5HexNAc4SP | 2026 | | | | | | | | | | | | | + | |
| Hex6HexNAc4dHexSP | 2027 | | | | | + | | | | | | | | + | |
| Hex7HexNAc4SP and/or Hex4HexNAc6SP2 and/or NeuAc2Hex3HexNAc4dHex | 2043 | | | | | | | + | | | | | | | |
| NeuAcHex4HexNAc5SP | 2051 | | + | | | | + | + | | | | | | + | + |
| Hex4HexNAc5dHex2SP | 2052 | + | + | | | | | + | + | | | | | | |
| NeuAc2Hex4HexNAc4 | 2059 | | | | | | + | | | | | | | + | |
| NeuAcHex4HexNAc4dHex2 | 2060 | | | | | | + | | + | + | | + | + | + | |
| NeuAcHex4HexNAc4dHexSP2 | 2074 | | | | | | | | | | | | + | + | | |
| NeuAcHex5HexNAc4dHex | 2076 | + | + | + | + | + | + | + | + | + | + | + | + | + | + |
| NeuAcHex6HexNAc4 and/or NeuGcHex5HexNAc4dHex | 2092 | + | + | | + | + | + | + | + | | + | + | + | + | + |
| NeuAcHex3HexNAc5dHex2 and/or NeuAc2Hex4HexNAc4Ac | 2101 | | | | | | | | + | | | | | | | |
| NeuGcHex6HexNAc4 | 2108 | | | | | | | | | | | | + | | | |
| NeuAcHex4HexNAc5dHex | 2117 | + | + | + | | + | | | | + | | + | + | + | + |
| Hex4HexNAc5dHex2SP2 | 2132 | | | + | | | | | | | | | | | |
| NeuAcHex5HexNAc5 | 2133 | + | + | | | + | + | | + | | + | + | | + | + |
| NeuAc2Hex4HexNAc4SP | 2139 | | | | | | | | | | | | | | | |
| NeuAcHex5HexNAc4dHexSP | 2156 | + | + | | | | + | + | | | | | + | + | + |
| Hex5HexNAc4dHex3SP | 2157 | | | | | | | | | | | | | + | | |
| Hex6HexNAc5SP2 | 2164 | + | + | | | + | | | | | | | | | |
| Hex6HexNAc4dHex2SP and/or Hex3HexNAc6dHex2SP2 | 2173 | | | | | | | | | | | | | + | | |
| NeuAcHex4HexNAc6 | 2174 | + | | | | | + | + | + | | | | + | + | |
| NeuAc3Hex3HexNAc4 and/or NeuGcHex6HexNAc4SP and/or NeuAc2NeuGcHex2HexNAc4dHex | 2188 | | | | | | | + | | | | | | + | | |
| NeuAc2Hex3HexNAc4dHex2 and/or Hex7HexNAc4dHexSP and/or Hex4HexNAc6dHexSP2 | 2189 | | | | + | + | | | | | | | | | | |
| NeuAc2Hex4HexNAc4dHex | 2205 | | | | | | + | | | | | | | | | |
| NeuAc2Hex4HexNAc4SP2 | 2219 | | | | | | | | | | | | + | | | |
| NeuAc2Hex5HexNAc4 | 2221 | + | + | + | + | + | + | + | + | + | + | + | + | + | + |
| NeuAcHex5HexNAc4dHex2 | 2222 | + | + | + | + | + | + | + | + | + | | + | + | + | + |
| Hex6HexNAc5dHexSP | 2230 | | + | | + | | | + | + | | | | | | |
| NeuGcNeuAcHex5HexNAc4 | 2237 | + | + | + | | | | + | | | + | + | + | | |
| NeuAcHex6HexNAc4dHex and/or NeuGcHex5HexNAc4dHex2 | 2238 | + | + | + | + | + | + | + | + | + | | + | + | + | + |
| NeuAc2Hex3HexNAc5dHex and/or Hex7HexNAc5SP | 2246 | | | | | | + | + | + | + | | | | | | |
| NeuGc2Hex5HexNAc4 | 2253 | + | + | | + | | | | | | | + | + | + | |
| NeuAcHex7HexNAc4 and/or NeuGcHex6HexNAc4dHex | 2254 | + | + | | + | | + | + | | | | + | + | + | |
| NeuAc2Hex4HexNAc5 | 2262 | | | | | | + | | | | | | | | | |
| NeuAcHex4HexNAc5dHex2 and/or NeuAcHex5HexNAc4Ac | 2263 | + | | | | | | + | | | | + | | | |
| NeuAcHex5HexNAc5dHex | 2279 | + | + | + | + | + | + | + | + | + | | + | + | + | + |
| NeuAc2Hex4HexNAc4dHexSP and/or Hex11HexNAc2SP | 2285 | | | | | | | | | | | | | + | | |
| NeuAcHex6HexNAc5 | 2295 | + | + | | + | + | + | + | + | + | | + | + | + | + |
| NeuAc2Hex5HexNAc4SP | 2301 | | | | | | | | | | | | | + | |

TABLE 47-continued

| Proposed composition | m/z | hESC | EB | st.3 | hEF | mEF | BM MSC | OB | CB MSC | AC | CB MNC | CD 34+ | CD 133+ | LIN− | CD 8− |
|---|---|---|---|---|---|---|---|---|---|---|---|---|---|---|---|
| NeuAcHex5HexNAc4dHex2SP | 2302 | | | | | | | | | | | | + | | |
| NeuAc2Hex5HexNAc4Ac2 | 2305 | | | | | | | | | + | | | | | |
| Hex6HexNAc4dHex3SP and/or NeuGcNeuAcHex3HexNAc6 | 2319 | | | | | | | + | | | | | + | + | |
| NeuAcHex4HexNAc6dHex | 2320 | | | | | | | | | | | | + | + | |
| NeuAcHex5HexNAc5dHexAc | 2321 | | | | | | | + | + | | | | | | |
| Hex7HexNAc4dHex2SP and/or Hex4HexNAc6dHex2SP2 | 2335 | | | | | | | | | | | | + | + | |
| NeuAcHex5HexNAc6 | 2336 | | | | | | | | | | | + | | + | |
| NeuAc3Hex4HexNac4 | 2350 | | | | + | | | | | | | | | | |
| NeuAc2Hex4HexNAc4dHexSP | 2365 | | | | | | | | | | | + | | + | + |
| NeuAc2Hex5HexNAc4dHex | 2367 | + | + | + | + | + | + | + | + | + | + | + | + | + | + |
| NeuAcHex5HexNAc4dHex3 | 2368 | + | + | | + | + | + | + | + | + | | + | + | + | + |
| NeuAc2Hex6HexNAc4 and/or NeuGcNeuAcHex5HexNAc4dHex | 2383 | + | + | | + | + | + | + | | | | + | + | + | |
| NeuAcHex6HexNAc4dHex2 and/or NeuGcHex5HexNAc4dHex3 | 2384 | + | + | | + | + | | + | | | | + | + | | |
| NeuAc2Hex3HexNAc5dHex2 and/or Hex7HexNAc5dHexSP | 2392 | | | | + | + | | | | | | | | | |
| NeuAcHex3HexNAc5dHex4 | 2393 | | | | + | | | | | | | | | | |
| NeuGc2Hex5HexNAc4dHex | 2399 | | + | | | | | | | | | | + | + | |
| NeuAcHex4HexNAc6dHexSP and/or NeuGcHex6HexNAc4dHex2 and/or NeuAcHex7HexNAc4dHex | 2400 | | | | | | | | | | | | + | | |
| NeuAc2Hex4HexNAc5dHex | 2408 | + | + | | | | | | | | | | | + | |
| NeuAcHex4HexNAc5dHex3 and/or NeuAc2Hex5HexNAc4dHexAc | 2409 | | | | | | | + | | | | | + | | |
| NeuAc2Hex5HexNAc5 | 2424 | | | | | + | | | + | | + | | | + | + |
| NeuAcHex5HexNAc5dHex2 | 2425 | + | + | | | | + | + | + | + | + | + | + | + | + |
| NeuAcHex6HexNAc5dHex | 2441 | + | + | + | + | + | + | + | + | + | + | + | + | + | + |
| NeuAc2Hex5HexNAc4dHexSP | 2447 | | + | | | | + | + | | | | + | + | + | + |
| NeuAcHex5HexNAc4dHex3SP | 2448 | | + | | | | | | | | | + | + | + | + |
| NeuAcHex7HexNAc5 and/or NeuAcHex6HexNAc5dHex | 2457 | + | | | + | + | + | + | | | | | | | |
| NeuGcHex7HexNAc5 | 2473 | | | | | | | | | | | + | + | | |
| NeuAcHex5HexNAc6dHex | 2482 | | | | | | | | | | | | + | | |
| NeuAcHex4HexNAc5dHex3SP | 2489 | | | | | | | | | | | + | + | | |
| Hex6HexNAc7SP | 2490 | | | | | | | | | | | | + | | |
| NeuAc3Hex5HexNAc4 | 2512 | | + | | | | | | | | | + | + | + | |
| NeuAc2Hex5HexNAc4dHex2 | 2513 | | | | | | + | + | + | | | + | | + | + |
| NeuAcHex5HexNAc4dHex4 | 2514 | | | | | | + | | | | | | | | + |
| NeuAcHex6HexNAc5dHexSP and/or NeuAc3Hex2HexNAc5dHex2 | 2521 | + | + | | | | + | | | | | | + | | |
| Hex6HexNAc5dHex3SP | 2522 | | | | | | + | | | | | | + | | |
| NeuGcNeuAc2Hex5HexNAc4 | 2528 | + | + | | | | | | | | | + | + | + | |
| NeuAc2Hex6HexNAc4dHex and/or NeuGcNeuAcHex5HexNAc4dHex2 | 2529 | | + | | | | | | | | | + | + | + | |
| NeuGc2NeuAcHex5HexNAc4 | 2544 | + | + | | | | | | | + | | + | + | + | |
| NeuGc2Hex5HexNAc4dHex2 and/or NeuGcNeuAcHex6HexNAc4dHex | 2545 | | | | | | | | | | | + | + | + | |
| NeuGc3Hex5HexNAc4 | 2560 | | + | | | | | | | | | + | + | + | |
| NeuGc2Hex6HexNAc4dHex | 2561 | | | | | | | | | | | | + | | |
| NeuAc2Hex5HexNAc5dHex | 2570 | + | + | | | | + | | | + | | + | + | + | + |
| NeuAcHex5HexNAc5dHex3 | 2571 | | + | + | | | + | | | + | | + | + | + | + |
| NeuAc2Hex6HexNAc5 | 2586 | | + | | + | | + | + | + | + | + | + | + | + | + |
| NeuAcHex6HexNAc5dHex2 | 2587 | + | + | | + | | + | + | + | + | + | + | + | + | + |
| Hex7HexNAc6dHexSP | 2595 | | | | | | + | | | | | | | | |
| NeuGcNeuAcHex6HexNAc5 | 2602 | | | | | | | | | | | + | + | + | |
| NeuAcHex7HexNAc5dHex and/or NeuGcHex6HexNAc5dHex2 | 2603 | | + | | + | + | + | + | | | | + | + | | |
| NeuAcHex8HexNAc5 and/or NeuGcHex7HexNAc5dHex | 2619 | | | | | + | | | | | | + | + | | |
| NeuAc2Hex5HexNAc6 | 2627 | | | | | | + | | | | | | | | |
| NeuGcHex8HexNAc5 and/or NeuAcHex4HexNAc5dHex4SP | 2635 | | | | | | | | | | | + | + | | |
| NeuAcHex6HexNAc6dHex | 2644 | | + | + | | | + | + | + | | + | + | + | + | + |
| NeuAc2Hex5HexNAc4dHex3 | 2659 | | | | | | + | | | | | + | | | |
| NeuAcHex7HexNAc6 | 2660 | + | | | + | | + | + | + | + | + | + | | + | |
| NeuGcNeuAc2Hex5HexNAc4dHex and/or NeuAc3Hex6HexNAc4 | 2674 | | | | | | + | + | | | | | | | |
| NeuAc2Hex4HexNAc5dHex2SP2 | 2714 | | | | | | + | | | | | + | | + | + |
| NeuAcHex4HexNAc5dHex4SP2 and/or NeuAc3Hex5HexNAc5 | 2715 | | | | | | | | | | | | + | + | + |
| NeuAc2Hex5HexNAc5dHex2 | 2716 | | | | | | | | | | | | | + | |
| NeuAc2Hex6HexNAc5dHex | 2732 | + | + | + | + | | + | + | + | + | + | + | + | + | + |
| NeuAcHex6HexNAc5dHex3 | 2733 | + | + | | + | + | + | + | + | + | + | + | + | + | + |
| NeuGcNeuAcHex6HexNAc5dHex | 2748 | | | | | | | | | | | | + | | |

TABLE 47-continued

| Proposed composition | m/z | hESC | EB | st.3 | hEF | mEF | BM MSC | OB | CB MSC | AC | CB MNC | CD 34+ | CD 133+ | LIN- | CD 8- |
|---|---|---|---|---|---|---|---|---|---|---|---|---|---|---|---|
| NeuAcHex8HexNAc5dHex | 2765 | | | | | + | | | | | | | | | |
| NeuGcHex8HexNAc5dHex and/or NeuAcHex9HexNAc5 | 2781 | | | | | | | | | | | | + | | |
| NeuAcHex6HexNAc6dHex2 | 2791 | | | | | | | | | | | + | + | + | + |
| Hex6HexNAc6dHex3SP2 | 2805 | | | | | | | | | | | | + | | |
| NeuAcHex7HexNAc6dHex | 2807 | + | + | | + | + | | + | + | + | + | + | + | + | + |
| NeuAc2Hex6HexNAc5dHexSP | 2812 | | | | | | | + | | | | + | + | + | + |
| NeuAcHex6HexNAc5dHex3SP | 2813 | | | | | | | | | | | | + | | |
| NeuGcNeuAc3Hex5HexNAc4 | 2819 | | | | | | | | | | | | + | | |
| NeuAc3Hex6HexNAc4dHex and/or NeuGcNeuAc2Hex5HexNAc4dHex2 | 2820 | | | | | | | | | | | | + | | |
| NeuAc3Hex6HexNAc5 | 2878 | + | + | | + | + | + | + | + | + | | + | + | + | |
| NeuAc2Hex6HexNAc5dHex2 | 2879 | + | + | | + | + | + | + | + | + | | + | + | + | + |
| NeuAcHex6HexNAc5dHex4 | 2880 | | | | | | + | | | | | + | + | + | + |
| NeuGcNeuAc2Hex6HexNAc5 | 2894 | | | | | | | + | | | | | + | | |
| NeuAc2Hex7HexNAc5dHex and/or NeuGcNeuAcHex6HexNAc5dHex2 | 2895 | | | | | + | | | | | | | + | | |
| NeuAc3Hex6HexNAc4dHexSP and/or NeuGcNeuAc2Hex5HexNAc4dHex2SP | 2900 | | | | | + | | | | | | | | | |
| NeuGc2Hex6HexNAc5dHex2 | 2911 | | | | | | | | | | | | | + | |
| NeuAc2Hex5HexNAc6dHex2 | 2920 | | | | | | | | + | | | | | | |
| NeuGc3Hex6HexNAc5 | 2925 | | | | | | | | | | | | + | | |
| NeuGcNeuAc2Hex5HexNAc6 | 2935 | | | | | | | | | | + | | | | |
| NeuAc2Hex6HexNAc6dHex and/or NeuGcNeuAcHex5HexNAc6dHex2 | 2936 | | + | + | | | | | + | | | + | + | + | + |
| NeuAcHex6HexNAc6dHex3 | 2937 | | | | | + | | | | | | | + | | |
| NeuGc2NeuAcHex5HexNAc6 and/or NeuAc3Hex5HexNAc4dHex3 | 2951 | | | | | | + | | | | | | | | |
| NeuAc2Hex7HexNAc6 | 2952 | | | | | + | + | + | + | | | | | + | + |
| NeuAcHex7HexNAc6dHex2 | 2953 | + | | | + | | + | + | | | + | + | | | + |
| Hex8HexNAc7dHexSP | 2961 | | | | | | | + | | | | | | | |
| NeuAc2Hex4HexNAc7dHex2 | 2961 | | | | | | | + | | | | | | | |
| NeuAcHex7HexNAc7dHex | 3010 | | + | | | | | | | | | | + | + | |
| NeuAc3Hex6HexNAc5dHex | 3024 | + | + | | + | | + | + | + | + | + | + | + | + | + |
| NeuAc2Hex6HexNAc5dHex3 | 3025 | + | + | | + | | + | + | | + | + | + | + | + | + |
| NeuAcHex8HexNAc7 | 3026 | | + | | + | + | | | | | | + | + | | |
| NeuGc3Hex6HexNAc5dHex and/or NeuGc2NeuAcHex7HexNAc5 | 3072 | | | | | | | | | | | | + | | |
| NeuAc2Hex6HexNAc6dHex2 | 3082 | | | | | | | | | | | | | + | |
| NeuAc2Hex7HexNAc6dHex | 3098 | + | + | + | + | | + | + | + | + | | + | + | + | + |
| NeuAcHex7HexNAc6dHex3 | 3099 | + | + | | + | | + | + | + | + | | + | + | + | + |
| NeuAc3Hex6HexNAc5dHexSP | 3104 | | | | | | | | | | | + | + | | |
| NeuAc2Hex6HexNAc5dHex3SP | 3105 | | | | | | | | | | | + | + | | |
| NeuAc3Hex6HexNAc5dHex2 | 3170 | | | | | | | | | | | + | + | | |
| NeuAc2Hex6HexNAc5dHex4 | 3171 | | + | | + | | + | + | | | | | + | + | |
| NeuAcHex8HexNAc7dHex | 3172 | + | | | + | | + | + | + | + | | + | + | | + |
| NeuAc3Hex6HexNAc6dHex | 3227 | | | | | | | | | | | + | + | | |
| NeuAc2Hex6HexNAc6dHex3 | 3228 | | | | | | | | | | | | + | | |
| NeuAc3Hex7HexNAc6 | 3243 | | | | | | + | + | | | | | + | | |
| NeuAc2Hex7HexNAc6dHex2 | 3244 | | | | | | + | + | | | + | + | + | | |
| NeuAcHex7HexNAc6dHex4 | 3245 | + | | | | + | | + | | | | + | + | | |
| NeuAc2Hex7HexNAc7dHex | 3301 | | | | | | | | | | | | + | | |
| NeuAcHex7HexNAc7dHex3 | 3302 | | | | | | | | | | | | + | | |
| NeuAc2Hex8HexNAc7 | 3317 | + | | | | | + | | | | | + | + | | |
| NeuAcHex8HexNAc7dHex2 | 3318 | | | | | | | + | | | | + | + | | |
| NeuAc3Hex7HexNAc6dHex | 3389 | | | | | | + | + | + | | | | + | | |
| NeuAc2Hex7HexNAc6dHex3 | 3390 | + | + | | | | + | + | + | | | + | + | + | + |
| NeuAcHex7HexNAc6dHex5 and/or NeuAcHex9HexNAc8 | 3391 | | | | + | + | | | | | | | + | | |
| NeuAc2Hex8HexNAc7dHex | 3463 | + | | | + | | + | + | + | | | + | + | | + |
| NeuAcHex8HexNAc7dHex3 | 3464 | | | | | | + | | + | + | | + | + | | |
| NeuAc2Hex7HexNAc6dHex4 | 3536 | | | | | | + | + | | | | + | | + | + |
| NeuAcHex9HexNAc8dHex | 3537 | | | | + | | + | + | + | | | | + | | |
| NeuAc3Hex8HexNAc7 | 3608 | + | | | | | | | | | | | | + | |
| NeuAc2Hex8HexNac7dHex2 | 3609 | | | | | | + | + | | | | + | | | |
| NeuAcHex8HexNac7dHex4 | 3610 | + | | | | | | + | | | | + | + | | |
| NeuAc4Hex7HexNAc6dHex | 3680 | | | | | | + | | | | | + | | + | |
| NeuAc3Hex7HexNAc6dHex3 | 3681 | | | | + | + | | + | + | | | + | + | + | |
| NeuAc2Hex9HexNAc8 | 3682 | + | | | | | | + | + | | | + | + | | |
| NeuAcHex9HexNAc8dHex2 | 3683 | | | | | | + | | | | | + | + | | + |
| NeuAc3Hex8HexNAc7dHex | 3754 | | | | | + | + | + | | | | | | + | |
| NeuAc2Hex8HexNAc7dHex3 | 3755 | | | | + | | + | + | + | | | + | + | | |
| NeuAcHex10HexNAc9 and/or NeuAcHex8HexNAc7dHex5 | 3756 | + | | | | | + | + | | | | + | | | |
| NeuAc4Hex6HexNAc8 | 3778 | | | | | | | | | | | + | | | |
| NeuAc3Hex7HexNAc6dHex4 | 3827 | | | | | + | | | | | | | | | + |
| NeuAc2Hex9HexNAc8dHex | 3828 | | | + | | + | + | | | | | + | | | |

TABLE 47-continued

| Proposed composition | m/z | hESC | EB | st.3 | hEF | mEF | BM MSC | OB | CB MSC | AC | CB MNC | CD 34+ | CD 133+ | LIN− | CD 8− |
|---|---|---|---|---|---|---|---|---|---|---|---|---|---|---|---|
| NeuAcHex9HexNAc8dHex3 | 3829 | | | | | | + | + | | | | + | + | | |
| NeuAc2Hex8HexNAc7dHex4 | 3901 | | | | | | + | | | | | + | | + | |
| NeuAc2Hex9HexNAc8dHex2 | 3974 | | | | | | | | | | | + | | + | |
| NeuAcHex9HexNAc8dHex4 | 3975 | | | | | | | | | | | + | + | | |
| NeuAc4Hex8HexNAc7dHex | 4045 | | | | | | | | | | | | | + | |
| NeuAc3Hex8HexNAc7dHex3 | 4046 | | | | | | | | | | | | + | + | |
| NeuAc2Hex10HexNAc9 and/or NeuAc2Hex8HexNAc7dHex5 | 4047 | | | | + | | | | + | | | | | | |
| NeuAc3Hex9HexNAc8dHex | 4119 | | | | | | | | | | | | | + | |
| NeuAc2Hex9HexNAc8dHex3 | 4120 | | | | | | | | | | | | + | | |
| HexNAc ≥ 3 and dHex ≥ 1 (including fucosylated N-glycans) | | | | | | | | | | | | | | | |
| Hex3HexNAc3dHexSP | 1338 | | | | | | + | | | | | | | | |
| Hex4HexNAc3dHexSP | 1500 | + | + | | + | + | + | + | | | | + | + | + | + |
| NeuAcHex3HexNAc3dHex | 1549 | + | + | | + | + | + | + | | + | + | + | + | + | + |
| Hex4HexNAc3dHex2SP | 1646 | | | | | | + | | | | | + | | | |
| Hex5HexNAc3dHexSP | 1662 | | | | | | + | | | | | | | | |
| Hex6HexNAc3SP and/or NeuAc2Hex2HexNAc3dHex | 1678 | + | + | | + | + | + | + | + | + | + | + | + | + | + |
| NeuAcHex3HexNAc3dHexSP2 | 1709 | | | | | | | | | | | + | + | | |
| NeuAcHex4HexNAc3dHex | 1711 | + | + | + | + | + | + | + | + | + | + | + | + | + | + |
| NeuAcHex5HexNAc3 and/or NeuGcHex4HexNAc3dHex | 1727 | + | + | | + | + | + | + | + | + | + | + | + | + | + |
| NeuAcHex4HexNAc3dHexSP | 1791 | | + | | | + | + | + | | | | + | + | | |
| Hex5HexNAc3dHex2SP | 1808 | | | | | | | | | | | + | | | |
| NeuAc2Hex3HexNAc3dHex | 1840 | + | + | | | | + | | + | + | | + | | | + |
| NeuAcHex4HexNAc3dHex2 | 1857 | | | | | | | | | | | + | + | | |
| NeuAcHex5HexNAc3dHex and/or NeuGcHex4HexNAc3dHex2 | 1873 | + | + | + | + | + | + | + | + | + | + | + | + | + | + |
| Hex8HexNAc3SP and/or NeuAc2Hex4HexNAc3dHex | 2002 | + | + | | + | + | + | + | + | | | + | | | + |
| NeuAcHex4HexNAc3dHex3 | 2003 | | + | | | + | | | | | | | | | |
| NeuAc2Hex5HexNAc3 and/or NeuGcNeuAcHex4HexNAc3dHex | 2018 | | | | | | + | | + | + | | + | + | + | |
| NeuGcHex5HexNAc3dHex2 | 2019 | | | | | | | | | | | + | + | + | |
| NeuGcNeuAcHex5HexNAc3 and/or NeuGc2Hex4HexNAc3dHex | 2034 | | | | | | | | | | | + | | | |
| NeuAcHex6HexNAc3dHex | 2035 | | + | | | + | + | + | + | + | + | + | + | + | + |
| NeuAc2Hex4HexNAc3dHexSP and/or Hex8HexNAc3SP2 | 2082 | | | | | | + | + | + | | | | | | |
| NeuAcHex6HexNAc3dHexSP | 2115 | | | | | | | | | | | | + | | |
| Hex8HexNAc3dHexSP and/or NeuAc2Hex4HexNAc3dHex2 | 2148 | | | | | | | | | | | | + | | |
| NeuAcHex8HexNAc3SP and/or NeuAc3HexNAc4HexNAc3dHex | 2293 | | | | | | | | | | | | + | | |
| NeuAc2Hex5HexNAc3dHex2 and/or NeuGcNeuAcHex4HexNAc3dHex3 | 2310 | | | | | | | | + | | | | | | |
| NeuAc2Hex5HexNAc3dHex2SP | 2390 | + | + | + | + | + | + | | | | + | + | + | | |
| NeuAc2Hex6HexNAc3dHexSP | 2406 | | | | | + | | | | | | + | + | | |
| NeuAcHex8HexNAc3dHexSP and/or NeuAc3Hex4HexNAc3dHex2 | 2439 | | | | | | | | | | | + | | | |
| NeuAcHex9HexNAc3dHex | 2521 | | | | | | | | | | | | + | | |
| Hex4HexNAc4dHexSP | 1703 | | + | | + | | + | | | | | | | | |
| NeuAcHex3HexNAc4dHex | 1752 | | | | | | | | | | | | | | + |
| Hex5HexNAc4dHexSP | 1865 | + | + | | + | + | + | + | | | | + | + | + | + |
| Hex4HexNAc5dHexSP | 1906 | + | + | | | | | | | | | | | | |
| NeuAcHex4HexNAc4dHex | 1914 | + | + | | + | + | + | + | + | + | + | + | + | + | + |
| Hex5HexNAc4dHex2SP | 2011 | | | | | | | | | | | + | | | |
| Hex6HexNAc4dHexSP | 2027 | | | | + | | | | | | | + | | | |
| Hex7HexNAc4SP and/or Hex4HexNAc6SP2 and/or NeuAc2Hex3HexNAc4dHex | 2043 | | | | | | + | | | | | | | | |
| Hex4HexNAc5dHex2SP | 2052 | + | + | | | | + | + | | | | | | | |
| NeuAcHex4HexNAc4dHex2 | 2060 | | | | | + | | + | + | | | + | + | + | |
| NeuAcHex4HexNAc4dHexSP2 | 2074 | | | | | | | | | | | + | + | | |
| NeuAcHex5HexNAc4dHex | 2076 | + | + | + | + | + | + | + | + | + | + | + | + | + | + |
| NeuAcHex6HexNAc4 and/or NeuGcHex5HexNAc4dHex | 2092 | + | + | | + | + | + | + | + | | + | + | + | | + |
| NeuAcHex3HexNAc5dHex2 and/or NeuAc2Hex4HexNAc4Ac | 2101 | | | | | | | | + | | | | | | |
| NeuAcHex4HexNAc5dHex | 2117 | + | + | + | + | | | | | | + | + | + | + | + |
| Hex4HexNAc5dHex2SP2 | 2132 | | | + | | | | | | | | | | | |
| NeuAcHex5HexNAc4dHexSP | 2156 | + | + | | | | + | + | | | | + | + | | |
| Hex5HexNAc4dHex3SP | 2157 | | | | | | | | | | | | + | | |

TABLE 47-continued

| Proposed composition | m/z | hESC | EB | st.3 | hEF | mEF | BM MSC | OB | CB MSC | AC | CB MNC | CD 34+ | CD 133+ | LIN- | CD 8- |
|---|---|---|---|---|---|---|---|---|---|---|---|---|---|---|---|
| Hex6HexNAc4dHex2SP and/or Hex3HexNAc6dHex2SP2 | 2173 | | | | | | | | | | | | | + | |
| NeuAc3Hex3HexNAc4 and/or NeuGcHex6HexNAc4SP and/or NeuAc2NeuGcHex2HexNAc4dHex | 2188 | | | | | | | + | | | | | + | | |
| NeuAc2Hex3HexNAc4dHex2 and/or Hex7HexNAc4dHexSP and/or Hex4HexNAc6dHexSP2 | 2189 | | | | + | + | | | | | | | | | |
| NeuAc2Hex4HexNAc4dHex | 2205 | | | | | | | + | | | | | | | |
| NeuAcHex5HexNAc4dHex2 | 2222 | + | + | + | + | + | + | + | + | + | + | + | + | + | + |
| Hex6HexNAc5dHexSP | 2230 | | + | | + | | | + | + | | | | | | |
| NeuAcHex6HexNAc4dHex and/or NeuGcHex5HexNAc4dHex2 | 2238 | + | + | | + | + | + | + | + | + | + | + | + | + | + |
| NeuAc2Hex3HexNAc5dHex and/or Hex7HexNAc5SP | 2246 | | | | | | + | + | + | + | | | | | |
| NeuAcHex7HexNAc4 and/or NeuGcHex6HexNAc4dHex | 2254 | + | + | | + | + | + | + | + | | | + | + | + | |
| NeuAcHex4HexNAc5dHex2 and/or NeuAc2Hex5HexNAc4Ac | 2263 | + | | | | | | | | + | | | + | | |
| NeuAcHex5HexNAc5dHex | 2279 | + | + | + | + | + | + | + | + | + | + | + | + | + | + |
| NeuAc2Hex4HexNAc4dHexSP and/or Hex11HexNAc2SP | 2285 | | | | | | | | | | | | | + | |
| NeuAcHex5HexNAc4dHex2SP | 2302 | | | | | | | | | | | | + | | |
| Hex6HexNAc4dHex3SP and/or NeuGcNeuAcHex3HexNAc6 | 2319 | | | | | | | + | | | | | + | + | |
| NeuAcHex4HexNAc6dHex | 2320 | | | | | | | | | | | | + | + | |
| NeuAcHex5HexNAc5dHexAc | 2321 | | | | | | | + | + | | | | | | |
| Hex7HexNAc4dHex2SP and/or Hex4HexNAc6dHex2SP2 | 2335 | | | | | | | | | | | | + | + | |
| NeuAc2Hex4HexNAc4dHexSP | 2365 | | | | | | | | | | | + | + | + | |
| NeuAc2Hex5HexNAc4dHex | 2367 | + | + | + | + | + | + | + | + | + | + | + | + | + | + |
| NeuAcHex5HexNAc4dHex3 | 2368 | + | + | | + | + | + | + | + | + | + | + | + | + | + |
| NeuAc2Hex6HexNAc4 and/or NeuGcNeuAcHex5HexNAc4dHex | 2383 | + | + | | + | + | + | + | | | | + | + | + | |
| NeuAcHex6HexNAc4dHex2 and/or NeuGcHex5HexNAc4dHex3 | 2384 | + | | | + | + | | | + | | | + | + | | |
| NeuAc2Hex3HexNAc5dHex2 and/or Hex7HexNAc5dHexSP | 2392 | | | | + | + | | | | | | | | | |
| NeuAcHex3HexNAc5dHex4 | 2393 | | | | + | | | | | | | | | | |
| NeuGc2Hex5HexNAc4dHex | 2399 | | + | | | | | | | | | | | + | + |
| NeuAcHex4HexNAc6dHexSP and/or NeuGcHex6HexNAc4dHex2 and/or NeuAcHex7HexNAc4dHex | 2400 | | | | | | | | | | | | + | | |
| NeuAc2Hex4HexNAc5dHex | 2408 | + | + | | | | | | | | | | | + | |
| NeuAcHex4HexNAc5dHex3 and/or NeuAc2Hex5HexNAc4dHexAc | 2409 | | | | | | | + | | | | | + | | |
| NeuAcHex5HexNAc5dHex2 | 2425 | + | + | | | | | + | + | + | + | + | + | + | + |
| NeuAcHex6HexNAc5dHex | 2441 | + | + | + | + | + | + | + | + | + | + | + | + | + | + |
| NeuAc2Hex5HexNAc4dHexSP | 2447 | | + | | | | | + | + | | | + | + | + | + |
| NeuAcHex5HexNAc4dHex3SP | 2448 | | + | | | | | | | | | + | + | + | + |
| NeuAcHex7HexNAc5 and/or NeuGcHex6HexNAc5dHex | 2457 | + | | | + | + | + | + | | | | | | | |
| NeuAcHex5HexNAc6dHex | 2482 | | | | | | | | | | | | | + | |
| NeuAcHex4HexNAc5dHex3SP | 2489 | | | | | | | | | | | + | + | | |
| NeuAc2Hex5HexNAc4dHex2 | 2513 | | | | | | + | + | + | | | + | + | + | |
| NeuAcHex5HexNAc4dHex4 | 2514 | | | | | | | + | | | | | | | + |
| NeuAcHex6HexNAc5dHexSP and/or NeuAc3Hex2HexNAc5dHex2 | 2521 | + | + | | | | | + | | | | | + | | |
| Hex6HexNAc5dHex3SP | 2522 | | | | | | | + | | | | | + | | |
| NeuAc2Hex6HexNAc4dHex and/or NeuGcNeuAcHex5HexNAc4dHex2 | 2529 | | + | | | | | | | | | | + | + | |
| NeuGc2Hex5HexNAc4dHex2 and/or NeuGcNeuAcHex6HexNAc4dHex | 2545 | | | | | | | | | | | | + | + | |
| NeuGc2Hex6HexNAc4dHex | 2561 | | | | | | | | | | | | + | | |
| NeuAc2Hex5HexNAc5dHex | 2570 | + | + | | | | + | | | + | | + | + | + | + |
| NeuAcHex5HexNAc5dHex3 | 2571 | | + | + | | | + | | | + | | + | + | + | + |
| NeuAcHex6HexNAc5dHex2 | 2587 | + | + | | + | | + | + | + | + | | + | + | + | + |
| Hex7HexNAc6dHexSP | 2595 | | | | | | | + | | | | | | | |
| NeuAcHex7HexNAc5dHex and/or NeuGcHex6HexNAc5dHex2 | 2603 | | + | | + | | + | + | + | | | + | + | | |
| NeuAcHex8HexNAc5 and/or NeuGcHex7HexNAc5dHex | 2619 | | | | | + | | | | | | | + | + | |
| NeuGcHex8HexNAc5 and/or NeuAcHex4HexNAc5dHex4SP | 2635 | | | | | | | | | | | | + | + | |
| NeuAcHex6HexNAc6dHex | 2644 | | + | + | | | + | + | | + | | + | + | + | + |
| NeuAc2Hex5HexNAc4dHex3 | 2659 | | | | | | + | | | | | | + | | |

TABLE 47-continued

| Proposed composition | m/z | hESC | EB | st.3 | hEF | mEF | BM MSC | OB | CB MSC | AC | CB MNC | CD 34+ | CD 133+ | LIN- | CD 8- |
|---|---|---|---|---|---|---|---|---|---|---|---|---|---|---|---|
| NeuGcNeuAc2Hex5HexNAc4dHex and/or NeuAc3Hex6HexNAc4 | 2674 | | | | | | + | + | | | | | | | |
| NeuAc2Hex4HexNAc5dHex2SP2 | 2714 | | | | | | | + | | | | + | + | + | |
| NeuAcHex4HexNAc5dHex4SP2 and/or NeuAc3Hex5HexNAc5 | 2715 | | | | | | | | | | | | + | + | |
| NeuAc2Hex5HexNAc5dHex2 | 2716 | | | | | | | | | | | | | + | |
| NeuAc2Hex6HexNAc5dHex | 2732 | + | + | + | + | | + | + | + | + | + | + | + | + | + |
| NeuAcHex6HexNAc5dHex3 | 2733 | + | + | | + | + | + | + | + | + | + | + | + | + | + |
| NeuGcNeuAcHex6HexNAc5dHex | 2748 | | | | | | | | | | | + | | | |
| NeuAcHex8HexNAc5dHex | 2765 | | | | | + | | | | | | | | | |
| NeuAcHex6HexNAc6dHex2 | 2791 | | | | | | | | | | | + | + | + | + |
| Hex6HexNAc6dHex3SP2 | 2805 | | | | | | | | | | | | + | | |
| NeuAcHex7HexNAc6dHex | 2807 | + | + | + | + | | + | + | + | + | | + | + | + | + |
| NeuAc2Hex6HexNAc5dHexSP | 2812 | | | | | | | + | | | + | | + | + | + |
| NeuAcHex6HexNAc5dHex3SP | 2813 | | | | | | | | | | | | + | | |
| NeuAc3Hex6HexNAc4dHex and/or NeuGcNeuAc2Hex5HexNAc4dHex2 | 2820 | | | | | | | | | | | | + | | |
| NeuAc2Hex6HexNAc5dHex2 | 2879 | + | + | | + | + | + | + | + | + | | + | + | + | + |
| NeuAcHex6HexNAc5dHex4 | 2880 | | | | | | | + | | | | + | + | + | + |
| NeuAc2Hex7HexNAc5dHex and/or NeuGcNeuAcHex6HexNAc5dHex2 | 2895 | | | | | + | | | | | | | + | | |
| NeuAc3Hex6HexNAc4dHexSP and/or NeuGcNeuAc2Hex5HexNAc4dHex2SP | 2900 | | | | | | | + | | | | | | | |
| NeuGc2Hex6HexNAc5dHex2 | 2911 | | | | | | | | | | | | | + | |
| NeuAc2Hex5HexNAc6dHex2 | 2920 | | | | | | | | | + | | | | | |
| NeuGcNeuAc2Hex5HexNAc6 | 2935 | | | | | | | | | | | + | | | |
| NeuAc2Hex6HexNAc6dHex and/or NeuGcNeuAcHex5HexNAc6dHex2 | 2936 | | + | + | | | | | | + | | + | + | + | + |
| NeuAcHex6HexNAc6dHex3 | 2937 | | | | | | | + | | | | | + | | |
| NeuGc2NeuAcHex5HexNAc6 and/or NeuAc3Hex5HexNAc4dHex3 | 2951 | | | | | | | + | | | | | | | |
| NeuAcHex7HexNAc6dHex2 | 2953 | + | | | + | | + | + | + | | | + | + | | + |
| Hex8HexNAc7dHexSP | 2961 | | | | | | | + | | | | | | | |
| NeuAc2Hex4HexNAc7dHex2 | 2961 | | | | | | | + | | | | | | | |
| NeuAcHex7HexNAc7dHex | 3010 | | + | | | | | | | | | + | + | | |
| NeuAc3Hex6HexNAc5dHex | 3024 | + | + | | + | | + | + | + | + | + | + | + | + | + |
| NeuAc2Hex6HexNAc5dHex3 | 3025 | + | + | | + | | + | + | | + | + | + | + | + | + |
| NeuGc3Hex6HexNAc5dHex and/or NeuGc2NeuAcHex7HexNAc5 | 3072 | | | | | | | | | | | + | | | |
| NeuAc2Hex6HexNAc6dHex2 | 3082 | | | | | | | | | | | | + | | |
| NeuAc2Hex7HexNAc6dHex | 3098 | + | + | + | + | | + | + | + | + | + | + | + | + | + |
| NeuAcHex7HexNAc6dHex3 | 3099 | + | + | | + | | + | + | + | + | | + | + | + | + |
| NeuAc3Hex6HexNAc5dHexSP | 3104 | | | | | | | | | | | + | + | | |
| NeuAc2Hex6HexNAc5dHex3SP | 3105 | | | | | | | | | | | + | + | | |
| NeuAc3Hex6HexNAc5dHex2 | 3170 | | | | | | | | | | | + | + | | |
| NeuAc2Hex6HexNAc5dHex4 | 3171 | | + | | + | | + | + | | | | | + | + | |
| NeuAcHex8HexNAc7dHex | 3172 | + | | | + | | + | + | + | + | | + | + | | + |
| NeuAc3Hex6HexNAc6dHex | 3227 | | | | | | | | | | | + | + | | |
| NeuAc2Hex6HexNAc6dHex3 | 3228 | | | | | | | | | | | | + | | |
| NeuAc2Hex7HexNAc6dHex2 | 3244 | | | | | | | + | + | | | + | + | + | |
| NeuAcHex7HexNAc6dHex4 | 3245 | + | | | | | | + | + | | | + | + | | |
| NeuAc2Hex7HexNAc7dHex | 3301 | | | | | | | | | | | | + | | |
| NeuAcHex7HexNAc7dHex3 | 3302 | | | | | | | | | | | | + | | |
| NeuAcHex8HexNAc7dHex2 | 3318 | | | | | | | + | | | | + | + | | |
| NeuAc3Hex7HexNAc6dHex | 3389 | | | | | | + | + | + | + | | + | + | + | |
| NeuAc2Hex7HexNAc6dHex3 | 3390 | + | + | | | | + | + | + | + | | + | + | | + |
| NeuAcHex7HexNAc6dHex5 and/or NeuAcHex9HexNAc8 | 3391 | | | | + | | + | | | | | | + | | |
| NeuAc2Hex8HexNAc7dHex | 3463 | + | | | + | | + | + | + | + | | + | + | | + |
| NeuAcHex8HexNAc7dHex3 | 3464 | | | | | | + | + | + | | | + | + | | |
| NeuAc2Hex7HexNAc6dHex4 | 3536 | | | | | | + | + | | | | + | | + | + |
| NeuAcHex9HexNAc8dHex | 3537 | | | | + | | + | + | + | | | + | | | |
| NeuAc2Hex8HexNAc7dHex2 | 3609 | | | | | | | + | + | | | + | + | | |
| NeuAcHex8HexNAc7dHex4 | 3610 | + | | | | | | + | | | | + | + | | |
| NeuAc4Hex7HexNAc6dHex | 3680 | | | | | | | + | | | | | + | + | |
| NeuAc3Hex7HexNAc6dHex3 | 3681 | | | | + | | + | + | + | + | | + | + | + | |
| NeuAcHex9HexNAc8dHex2 | 3683 | | | | | | | | + | | | + | + | | |
| NeuAc3Hex8HexNAc7dHex | 3754 | | | | | | + | + | + | | | | | | + |
| NeuAc2Hex8HexNAc7dHex3 | 3755 | | | | + | | | + | + | | | + | + | + | |
| NeuAcHex10HexNAc9 and/or NeuAcHex8HexNAc7dHex5 | 3756 | + | | | | | | + | + | | | + | | | |
| NeuAc3Hex7HexNAc6dHex4 | 3827 | | | | | | | + | | | | | | | + |
| NeuAc2Hex9HexNAc8dHex | 3828 | | | + | | | | + | + | | | + | | | |
| NeuAcHex9HexNAc8dHex3 | 3829 | | | | | | | + | + | | | + | + | | |
| NeuAc2Hex8HexNAc7dHex4 | 3901 | | | | | | | + | | | | + | | + | |
| NeuAc2Hex9HexNAc8dHex2 | 3974 | | | | | | | | | | | + | + | | |
| NeuAcHex9HexNAc8dHex4 | 3975 | | | | | | | | | | | + | + | | |

TABLE 47-continued

| Proposed composition | m/z | hESC | EB | st.3 | hEF | mEF | BM MSC | OB | CB MSC | AC | CB MNC | CD 34+ | CD 133+ | LIN− | CD 8− |
|---|---|---|---|---|---|---|---|---|---|---|---|---|---|---|---|
| NeuAc4Hex8HexNAc7dHex | 4045 | | | | | | | | | | | | | + | |
| NeuAc3Hex8HexNAc7dHex3 | 4046 | | | | | | | | | | | | + | + | |
| NeuAc2Hex10HexNAc9 and/or NeuAc2Hex8HexNAc7dHex5 | 4047 | | | + | | | | | + | | | | | | |
| NeuAc3Hex9HexNAc8dHex | 4119 | | | | | | | | | | | | | + | |
| NeuAc2Hex9HexNAc8dHex3 | 4120 | | | | | | | | | | | | + | | |
| HexNAc ≥ 3 and dHex ≥ 1 (including multifucosylated N-glycans) | | | | | | | | | | | | | | | |
| Hex5HexNAc3dHex2SP | 1808 | | | | | | | | | | | + | | | |
| NeuAcHex4HexNAc3dHex2 | 1857 | | | | | | | | | | | + | + | | |
| NeuAcHex5HexNAc3dHex and/or NeuGcHex4HexNAc3dHex2 | 1873 | + | + | + | + | + | + | + | + | + | + | + | + | + | + |
| NeuAcHex4HexNAc3dHex3 | 2003 | | + | | | + | | | | | | | | | |
| NeuAcHex5HexNAc3dHex2 | 2019 | | | | | | | | | | | + | + | + | |
| Hex8HexNAc3dHexSP and/or NeuAc2Hex4HexNAc3dHex2 | 2148 | | | | | | | | | | | + | | | |
| NeuAc2Hex5HexNAc3dHex2 and/or NeuGcNeuAcHex4HexNAc3dHex3 | 2310 | | | | | | | | | + | | | | | |
| NeuAc2Hex5HexNAc3dHex2SP | 2390 | + | + | + | + | + | + | | | + | | + | + | + | |
| NeuAcHex8HexNAc3dHexSP and/or NeuAc3Hex4HexNAc3dHex2 | 2439 | | | | | | | | | | + | | | | |
| Hex5HexNAc4dHex2SP | 2011 | | | | | | | | | | | | + | | |
| Hex4HexNAc5dHex2SP | 2052 | + | + | | | | | + | + | | | | | | |
| NeuAcHex4HexNAc4dHex2 | 2060 | | | | | | + | | + | + | | + | | + | |
| NeuAcHex3HexNAc5dHex2 and/or NeuAc2Hex4HexNAc4Ac | 2101 | | | | | | | | | + | | | | | |
| Hex4HexNAc5dHex2SP2 | 2132 | | | + | | | | | | | | | | | |
| Hex5HexNAc4dHex3SP | 2157 | | | | | | | | | | | | + | | |
| Hex6HexNAc4dHex2SP and/or Hex3HexNAc6dHex2SP2 | 2173 | | | | | | | | | | | | | + | |
| NeuAcHex5HexNAc4dHex2 | 2222 | + | + | + | + | + | + | + | + | + | + | + | + | + | + |
| NeuAcHex6HexNAc4dHex and/or NeuGcHex5HexNAc4dHex2 | 2238 | + | + | | + | + | + | + | + | + | + | + | + | + | + |
| NeuAcHex4HexNAc5dHex2 and/or NeuAc2Hex5HexNAc4Ac | 2263 | + | | | | | | | | + | | | + | | |
| NeuAcHex5HexNAc4dHex2SP | 2302 | | | | | | | | | | | | + | | |
| Hex6HexNAc4dHex3SP and/or NeuGcNeuAcHex3HexNAc6 | 2319 | | | | | | | | + | | | | + | + | |
| Hex7HexNAc4dHex2SP and/or Hex4HexNAc6dHex2SP2 | 2335 | | | | | | | | | | | | + | + | |
| NeuAcHex5HexNAc4dHex3 | 2368 | + | + | | + | + | + | + | + | | + | + | + | + | + |
| NeuAcHex6HexNAc4dHex2 and/or NeuGcHex5HexNAc4dHex3 | 2384 | + | + | | + | + | | | + | | | + | + | | |
| NeuAc2Hex3HexNAc5dHex2 and/or Hex7HexNAc5dHexSP | 2392 | | | | + | + | | | | | | | | | |
| NeuAcHex3HexNAc5dHex4 | 2393 | | | | + | | | | | | | | | | |
| NeuAcHex4HexNAc6dHexSP and/or NeuGcHex6HexNAc4dHex2 and/or NeuAcHex7HexNAc4dHex | 2400 | | | | | | | | | | | | + | | |
| NeuAcHex4HexNAc5dHex3 and/or NeuAc2Hex5HexNAc4dHexAc | 2409 | | | | | | | + | | | | | + | | |
| NeuAcHex5HexNAc5dHex2 | 2425 | + | + | | | | | + | + | + | | + | + | + | + |
| NeuAcHex5HexNAc4dHex3SP | 2448 | | + | | | | | | | | | + | + | + | + |
| NeuAcHex4HexNAc5dHex3SP | 2489 | | | | | | | | | | | + | + | + | |
| NeuAc2Hex5HexNAc4dHex2 | 2513 | | | | + | + | + | | | | | + | | + | + |
| NeuAcHex5HexNAc4dHex4 | 2514 | | | | | + | | | | | | | | | + |
| NeuAcHex6HexNAc5dHexSP and/or NeuAc3Hex2HexNAc5dHex2 | 2521 | + | + | | | | | + | | | | | + | | |
| NeuAc2Hex6HexNAc4dHex and/or NeuGcNeuAcHex5HexNAc4dHex2 | 2529 | | + | | | | | | | | | + | + | | |
| NeuGcHex5HexNAc4dHex2 and/or NeuGcNeuAcHex6HexNAc4dHex | 2545 | | | | | | | | | | | + | + | | |
| NeuAcHex5HexNAc5dHex3 | 2571 | | + | + | | | + | | | + | | + | + | + | + |
| NeuAcHex6HexNAc5dHex2 | 2587 | + | + | | + | | + | + | + | + | | + | + | + | + |
| NeuAcHex7HexNAc5dHex and/or NeuGcHex6HexNAc5dHex2 | 2603 | | + | | + | | + | + | + | | | + | + | | |
| NeuGcHex8HexNAc5 and/or NeuGcHex4HexNAc5dHex4SP | 2635 | | | | | | | | | | | + | + | | |
| NeuAc2Hex5HexNAc4dHex3 | 2659 | | | | | | + | | | | | + | | | |
| NeuGcNeuAc2Hex5HexNAc4dHex and/or NeuAc3Hex6HexNAc4 | 2674 | | | | + | + | | | | | | | | | |
| NeuAc2Hex4HexNAc5dHex2SP2 | 2714 | | | | | | + | | | | | + | + | + | |
| NeuAcHex4HexNAc5dHex4SP2 and/or NeuAc3Hex5HexNAc5 | 2715 | | | | | | | | | | | | + | + | |
| NeuAc2Hex5HexNAc5dHex2 | 2716 | | | | | | | | | | | | | + | |

TABLE 47-continued

| Proposed composition | m/z | hESC | EB | st.3 | hEF | mEF | BM MSC | OB | CB MSC | AC | CB MNC | CD 34+ | CD 133+ | LIN− | CD 8− |
|---|---|---|---|---|---|---|---|---|---|---|---|---|---|---|---|
| NeuAcHex6HexNAc5dHex3 | 2733 | + | + | | + | + | + | + | + | + | + | + | + | + | + |
| NeuAcHex6HexNAc6dHex2 | 2791 | | | | | | | | | + | | + | + | + | + | + |
| Hex6HexNAc6dHex3SP2 | 2805 | | | | | | | | | | | | | | + | |
| NeuAcHex6HexNAc5dHex3SP | 2813 | | | | | | | | | | | | + | | | |
| NeuAc3Hex6HexNAc4dHex and/or NeuGcNeuAc2Hex5HexNAc4dHex2 | 2820 | | | | | | | | | | | | + | | | |
| NeuAc2Hex6HexNAc5dHex2 | 2879 | + | + | | + | + | + | + | + | + | + | + | + | + | + |
| NeuAcHex6HexNAc5dHex4 | 2880 | | | | | | + | | | | | + | + | + | + | |
| NeuAc2Hex7HexNAc5dHex and/or NeuGcNeuAcHex6HexNAc5dHex2 | 2895 | | | | | + | | | | | | | + | | | |
| NeuAc3Hex6HexNAc4dHexSP and/or NeuGcNeuAc2Hex5HexNAc4dHex2SP | 2900 | | | | | | + | | | | | | | | | |
| NeuGc2Hex6HexNAc5dHex2 | 2911 | | | | | | | | | | | | | | + | |
| NeuAc2Hex5HexNAc6dHex2 | 2920 | | | | | | | | | + | | | | | | |
| NeuAc2Hex6HexNAc6dHex and/or NeuGcNeuAcHex5HexNAc6dHex2 | 2936 | | + | + | | | | | | + | | + | + | + | + | + |
| NeuAcHex6HexNAc6dHex3 | 2937 | | | | | | | + | | | | | | | + | |
| NeuGc2NeuAcHex5HexNAc6 and/or NeuAc3Hex5HexNAc4dHex3 | 2951 | | | | | | | + | | | | | | | | |
| NeuAcHex7HexNAc6dHex2 | 2953 | + | | | + | | + | + | + | | | + | + | | + | |
| NeuAc2Hex4HexNAc7dHex2 | 2961 | | | | | | | | + | | | | | | | |
| NeuAc2Hex6HexNAc5dHex3 | 3025 | + | + | | + | | + | + | | + | + | + | + | + | + | + |
| NeuAc2Hex6HexNAc6dHex2 | 3082 | | | | | | | | | | | | | + | | |
| NeuAcHex7HexNAc6dHex3 | 3099 | + | + | | + | | + | + | + | + | + | + | + | + | + | + |
| NeuAc2Hex6HexNAc5dHex3SP | 3105 | | | | | | | | | | | | + | + | | |
| NeuAc3Hex6HexNAc5dHex2 | 3170 | | | | | | | | | | | | + | + | | |
| NeuAc2Hex6HexNAc5dHex4 | 3171 | | + | | + | | + | + | | | | | + | + | | |
| NeuAc2Hex6HexNAc6dHex3 | 3228 | | | | | | | | | | | | | + | | |
| NeuAc2Hex7HexNAc6dHex2 | 3244 | | | | | | | + | + | | | + | + | + | | |
| NeuAcHex7HexNAc6dHex4 | 3245 | + | | | | | + | | + | | | + | + | + | | |
| NeuAcHex7HexNAc7dHex3 | 3302 | | | | | | | | | | | | + | | | |
| NeuAcHex8HexNAc7dHex2 | 3318 | | | | | | | + | | | | + | + | + | | |
| NeuAc2Hex7HexNAc6dHex3 | 3390 | + | + | | | | + | + | + | + | | + | + | + | + | + |
| NeuAcHex7HexNAc6dHex5 and/or NeuAcHex9HexNAc8 | 3391 | | + | | + | + | | | | | | | + | | | |
| NeuAcHex8HexNAc7dHex3 | 3464 | | | | | | + | | + | + | | + | + | | + | |
| NeuAc2Hex7HexNAc6dHex4 | 3536 | | | | | | + | + | | | | + | + | + | + | |
| NeuAc2Hex8HexNac7dHex2 | 3609 | | | | | | + | + | | | | + | + | | | |
| NeuAcHex8HexNAc7dHex4 | 3610 | + | | | | | | + | | | | + | + | | | |
| NeuAc3Hex7HexNAc6dHex3 | 3681 | | | | + | | + | | + | + | | + | + | + | | |
| NeuAcHex9HexNAc8dHex2 | 3683 | | | | | | | + | | | | + | + | + | | |
| NeuAc2Hex8HexNAc7dHex3 | 3755 | | | | + | | | | + | + | | + | + | + | | |
| NeuAcHex10HexNAc9 and/or NeuAcHex8HexNAc7dHex5 | 3756 | + | | | | | | + | + | | | + | | | | |
| NeuAc3Hex7HexNAc6dHex4 | 3827 | | | | | | + | | | | | | | | | + |
| NeuAcHex9HexNAc8dHex3 | 3829 | | | | | | | + | + | | | + | + | | | |
| NeuAc2Hex8HexNAc7dHex4 | 3901 | | | | | | | + | | | | | + | | + | |
| NeuAc2Hex9HexNAc8dHex2 | 3974 | | | | | | | | | | | | + | + | | |
| NeuAcHex9HexNAc8dHex4 | 3975 | | | | | | | | | | | | + | + | | |
| NeuAc3Hex8HexNAc7dHex3 | 4046 | | | | | | | | | | | | + | + | | |
| NeuAc2Hex10HexNAc9 and/or NeuAc2Hex8HexNAc7dHex5 | 4047 | | | | + | | | + | | | | | | | | |
| NeuAc2Hex9HexNAc8dHex3 | 4120 | | | | | | | | | | | | + | | | |

HexNAc > Hex ≥ 2
(terminal HexNAc, N > H)

| Proposed composition | m/z | hESC | EB | st.3 | hEF | mEF | BM MSC | OB | CB MSC | AC | CB MNC | CD 34+ | CD 133+ | LIN− | CD 8− |
|---|---|---|---|---|---|---|---|---|---|---|---|---|---|---|---|
| NeuAcHex3HexNAc4 | 1606 | | | | | + | | | | | | | | | | |
| NeuAcHex3HexNAc4dHex | 1752 | | | | | | | | | | | | | | + | |
| NeuAcHex3HexNac5 | 1809 | | | | | | + | | | | | | | | | |
| NeuGcHex3HexNac5 | 1825 | | | | | | + | + | | | | | | | | |
| Hex4HexNAc5dHexSP | 1906 | + | + | | | | | | | | | | | | | |
| NeuAcHex4HexNAc5 | 1971 | + | + | | + | + | + | | | | | | + | | | + |
| Hex7HexNAc4SP and/or Hex4HexNAc6SP2 and/or NeuAc2Hex3HexNAc4dHex | 2043 | | | | | | + | | | | | | | | | |
| NeuAcHex4HexNAc5SP | 2051 | | + | | + | + | | | | | | | + | + | | |
| Hex4HexNAc5dHex2SP | 2052 | + | + | | | + | + | | | | | | | | | |
| NeuAcHex3HexNAc5dHex2 and/or NeuAc2Hex4HexNAc4Ac | 2101 | | | | | | | | + | | | | | | | |
| NeuAcHex4HexNAc5dHex | 2117 | + | + | + | | + | | | | | + | | + | + | + | + |
| Hex4HexNAc5dHex2SP2 | 2132 | | + | | | | | | | | | | | | | |
| Hex6HexNAc4dHex2SP and/or Hex3HexNAc6dHex2SP2 | 2173 | | | | | | | | | | | | | + | | |
| NeuAcHex4HexNAc6 | 2174 | + | | | | | + | + | | | | | + | + | | |
| NeuAc3Hex3HexNAc4 and/or NeuGcHex6HexNAc4SP and/or NeuAc2NeuGcHex2HexNAc4dHex | 2188 | | | | | | + | | | | | | + | | | |

TABLE 47-continued

| Proposed composition | m/z | hESC | EB | st.3 | hEF | mEF | BM MSC | OB | CB MSC | AC | CB MNC | CD 34+ | CD 133+ | LIN- | CD 8- |
|---|---|---|---|---|---|---|---|---|---|---|---|---|---|---|---|
| NeuAc2Hex3HexNAc4dNex2 and/or Hex7HexNAc4dHexSP and/or Hex4HexNAc6dHexSP2 | 2189 | | | | | + | + | | | | | | | | |
| NeuAc2Hex3HexNAc5dHex and/or Hex7HexNAc5SP | 2246 | | | | | + | + | + | + | | | | | | |
| NeuAc2Hex4HexNAc5 | 2262 | | | | | | + | | | | | | | | |
| NeuAcHex4HexNAc5dHex2 and/or NeuAc2Hex5HexNAc4Ac | 2263 | + | | | | | | | + | | | + | | | |
| Hex6HexNAc4dHex3SP and/or NeuGcNeuAcHex3HexNAc6 | 2319 | | | | | | | + | | | | | + | + | |
| NeuAcHex4HexNAc6dHex | 2320 | | | | | | | | | | | | + | + | |
| Hex7HexNAc4dHex2SP and/or Hex4HexNAc6dHex2SP2 | 2335 | | | | | | | | | | | | + | + | |
| NeuAcHex5HexNAc6 | 2336 | | | | | | | | | | | + | | + | |
| NeuAc2Hex3HexNAc5dHex2 and/or Hex7HexNAc5dHexSP | 2392 | | | | | + | + | | | | | | | | |
| NeuAcHex3HexNAc5dHex4 | 2393 | | | | | + | | | | | | | | | |
| NeuAcHex4HexNAc6dHexSP and/or NeuGcHex6HexNAc4dHex2 and/or NeuAcHex7HexNAc4dHex | 2400 | | | | | | | | | | | | + | | |
| NeuAc2Hex4HexNAc5dHex | 2408 | + | + | | | | | | | | | | | + | |
| NeuAcHex4HexNAc5dHex3 and/or NeuAc2Hex5HexNAc4dHexAc | 2409 | | | | | | | + | | | | | + | | |
| NeuAcHex5HexNAc6dHex | 2482 | | | | | | | | | | | | | + | |
| NeuAcHex4HexNAc5dHex3SP | 2489 | | | | | | | | | | | + | + | | |
| Hex6HexNAc7SP | 2490 | | | | | | | | | | | | + | | |
| NeuAcHex6HexNAc5dHexSP and/or NeuAc3Hex2HexNAc5dHex2 | 2521 | + | + | | | | | + | | | | | + | | |
| NeuAc2Hex5HexNAc6 | 2627 | | | | | | | + | | | | | | | |
| NeuGcHex8HexNAc5 and/or NeuAcHex4HexNAc5dHex4SP | 2635 | | | | | | | | | | | + | + | | |
| NeuAc2Hex4HexNAc5dHex2SP2 | 2714 | | | | | | | + | | | | + | + | + | |
| NeuAcHex4HexNAc5dHex4SP2 and/or NeuAc3Hex5HexNAc5 | 2715 | | | | | | | | | | | | + | + | |
| NeuGcNeuAc2Hex5HexNAc6 | 2935 | | | | | | | | | | | + | | | |
| NeuGc2NeuAcHex5HexNAc6 and/or NeuAc3Hex5HexNAc4dHex3 | 2951 | | | | | | | + | | | | | | | |
| NeuAc2Hex4HexNAc7dHex2 | 2961 | | | | | | | | | + | | | | | |
| HexNAc = Hex ≥ 5 (terminal HexNAc, N = H) | | | | | | | | | | | | | | | |
| Hex5HexNAc5SP2 | 2002 | | | + | + | + | + | + | + | + | + | | | | |
| NeuAcHex5HexNAc5 | 2133 | + | + | | | + | + | | + | + | | + | + | + | + |
| NeuAcHex5HexNAc5dHex | 2279 | + | + | + | + | + | + | + | + | + | + | + | + | + | + |
| NeuAc2Hex5HexNAc5 | 2424 | | | | | + | | | + | + | | + | + | + | + |
| NeuAcHex5HexNAc5dHex2 | 2425 | + | + | | | | + | + | + | + | | + | + | + | + |
| NeuAc2Hex5HexNAc5dHex | 2570 | + | + | | | | + | | | + | | + | + | + | + |
| NeuAcHex5HexNAc5dHex3 | 2571 | | + | + | | | + | | | + | | + | + | + | + |
| NeuAcHex6HexNAc6dHex | 2644 | | + | + | | | + | + | + | | + | + | + | + | + |
| NeuAcHex4HexNAc5dHex4SP2 and/or NeuAc3Hex5HexNAc5 | 2715 | | | | | | | | | | | | + | + | | |
| NeuAc2Hex5HexNAc5dHex2 | 2716 | | | | | | | | | | | | | + | |
| NeuAcHex6HexNAc6dHex2 | 2791 | | | | | | | | | | | + | + | + | + |
| Hex6HexNAc6dHex3SP2 | 2805 | | | | | | | | | | | | + | | |
| NeuAc2Hex6HexNAc6dHex and/or NeuGcNeuAcHex5HexNAc6dHex2 | 2936 | | + | + | | | | | + | | | + | + | + | + |
| NeuAcHex6HexNAc6dHex3 | 2937 | | | | | | + | | | | | | + | | |
| NeuAcHex7HexNAc7dHex | 3010 | | + | | | | | | | | | | + | + | |
| NeuAc3Hex6HexNAc6dHex | 3227 | | | | | | | | | | | + | | + | |
| NeuAc2Hex6HexNAc6dHex3 | 3228 | | | | | | | | | | | | | + | |
| NeuAc2Hex7HexNAc7dHex | 3301 | | | | | | | | | | | | | + | |
| NeuAcHex7HexNAc7dHex3 | 3302 | | | | | | | | | | | + | | | |
| SP ≥ 1 (including sulphated and/or phosphorylated glycans) | | | | | | | | | | | | | | | |
| Hex3HexNAc2SP | 989 | | | | + | + | + | | | | | | | | |
| Hex3HexNAc2dHexSP | 1135 | | | | | | | | | | | + | + | | |
| Hex4HexNAc2SP | 1151 | | | | + | + | + | + | | | | + | | | |
| Hex3HexNAc3SP | 1192 | | | | | | + | | | | | | | | |
| Hex5HexNAc2SP | 1313 | | | | | | | | | | | + | | | |
| Hex3HexNAc3dHexSP | 1338 | | | | | | + | | | | | | | | |
| Hex4HexNAc3SP | 1354 | | | | | + | + | | | | | | | | |
| Hex6HexNAc2SP | 1475 | | + | | + | | + | + | | + | | + | + | + | |
| Hex4HexNAc3dHexSP | 1500 | + | + | | | + | + | + | + | | | + | + | + | + |
| Hex5HexNAc3SP | 1516 | | | | | | + | + | | | | | | | + |
| Hex6HexNAc2SP2 | 1555 | | | | | | | | | | | | + | | |

TABLE 47-continued

| Proposed composition | m/z | hESC | EB | st.3 | hEF | mEF | BM MSC | OB | CB MSC | AC | CB MNC | CD 34+ | CD 133+ | LIN− | CD 8− |
|---|---|---|---|---|---|---|---|---|---|---|---|---|---|---|---|
| Hex4HexNAc4SP | 1557 | | + | | + | | + | + | | | | | | | |
| NeuAcHex3HexNAc3SP2 | 1563 | | | | | | | | | | | + | + | | |
| Hex4HexNAc4SP2 and/or Hex7HexNAc2SP | 1637 | | | | + | | + | + | | | | + | + | + | + |
| Hex4HexNAc3dHex2SP | 1646 | | | | | | | + | | | | + | | | |
| Hex5HexNAc3dHexSP | 1662 | | | | | | | + | | | | | | | |
| Hex6HexNAc3SP | 1678 | + | + | | + | + | + | + | + | + | | + | + | + | |
| Hex4HexNAc4dHexSP | 1703 | | + | | + | | + | | | | | | | | |
| NeuAcHex3HexNAc3dHexSP2 | 1709 | | | | | | | | | | | + | + | | |
| Hex4HexNAc4SP3 and/or Hex7HexNAc2SP2 | 1717 | | | | | | | | | | | | | + | |
| Hex5HexNAc4SP | 1719 | | + | | + | + | + | + | | | | | | | |
| Hex7HexNAc2dHexSP | 1783 | | | | | | | | | | | | | + | |
| NeuAcHex4HexNAc3dHexSP | 1791 | | + | | | | + | + | | | | | + | + | |
| Hex5HexNAc4SP2 and/or Hex8HexNAc2SP | 1799 | | | | | | + | | | | | | + | | |
| Hex5HexNAc3dHex2SP | 1808 | | | | | | | | | | | + | | | |
| NeuAc2Hex5HexNAc2 and/or NeuAc2Hex2HexNAc4SP | 1815 | | | | | | | | | | | + | | | |
| Hex5HexNAc4dHexSP | 1865 | + | + | | + | + | + | + | + | | | + | + | + | + |
| Hex6HexNAc4SP | 1881 | | | | | + | | | | | | | | | |
| Hex4HexNAc5dHexSP | 1906 | + | + | | | | | | | | | | | | |
| NeuAcHex6HexNAc2dHexSP and/or NeuAcHex3HexNAc4dHexSP2 | 1912 | | | | | | | | | | | | + | | |
| NeuACHex4HexNAc4SP2 | 1928 | | | | | | | | | | | + | + | | |
| Hex8HexNAc3SP and/or Hex5HexNAc5SP2 and/or NeuAc2Hex4HexNAc3dHex | 2002 | | | | + | + | + | + | + | + | | + | | | + |
| NeuAcHex5HexNAc4SP | 2010 | | | | | | | + | | | | | + | | |
| Hex5HexNAc4dHex2SP | 2011 | | | | | | | | | | | | + | | |
| NeuGcHex5HexNAc4SP | 2026 | | | | | | | | | | | | + | | |
| Hex6HexNAc4dHexSP | 2027 | | | | + | | | | | | | | + | | |
| Hex7HexNAc4SP and/or Hex4HexNAc6SP2 and/or NeuAc2Hex3HexNAc4dHex | 2043 | | | | | | | + | | | | | | | |
| NeuAcHex7HexNAc3 and/or NeuAcHex4HexNAc5SP | 2051 | | + | | + | + | | | | + | | + | + | + | + |
| Hex4HexNAc5dHex2SP | 2052 | + | + | | | | + | + | | | | | | | |
| NeuAcHex4HexNAc4SP2 | 2074 | | | | | | | | | | | + | + | | |
| NeuAc2Hex4HexNAc3dHexSP and/or Hex8HexNAc3SP2 and/or Hex5HexNAc5SP3 | 2082 | | | | | | + | + | + | | | | | | |
| NeuAcHex6HexNAc3dHexSP | 2115 | | | | | | | | | | | | + | | |
| Hex7HexNAc3dHex2SP and/or NeuAc2Hex3HexNAc3dHex3 and/or Hex4HexNAc5dHex2SP2 | 2132 | | | | + | | | | | | | | | | |
| Hex8HexNAc3dHexSP and/or NeuAc2Hex4HexNAc3dHex2 | 2148 | | | | | | | | | | | | + | | |
| NeuAcHex5HexNAc4dHexSP and/or NeuAcHex8HexNAc2dHex | 2156 | + | + | | | | + | + | | | | + | + | + | + |
| Hex5HexNAc4dHex3SP | 2157 | | | | | | | | | | | | + | | |
| NeuAc2Hex5HexNAc3dHex and/or Hex6HexNAc5SP2 | 2164 | + | + | | | + | | | | | | | | | |
| NeuAc2Hex4HexNAc4SP2 | 2219 | | | | | | | | | | | + | | | |
| Hex6HexNAc5dHexSP | 2230 | | + | | + | | + | + | | | | | | | |
| NeuAc2Hex3HexNAc5dHex and/or Hex7HexNAc5SP | 2246 | | | | | | + | + | + | + | | | | | |
| NeuAc2Hex4HexNAc4dHexSP and/or Hex11HexNAc2SP | 2285 | | | | | | | | | | | | | + | |
| NeuAcHex8HexNAc3SP and/or NeuAc3Hex4HexNAc3dHex | 2293 | | | | | | | | | | | | + | | |
| NeuAc2Hex5HexNAc4SP | 2301 | | | | | | | | | | | | + | | |
| NeuAcHex5HexNAc4dHex2SP | 2302 | | | | | | | | | | | | + | | |
| Hex6HexNAc4dHex3SP | 2319 | | | | | | | + | | | | | | | |
| Hex7HexNAc4dHex2SP and/or Hex4HexNAc6dHex2SP2 | 2335 | | | | | | | | | | | | + | + | |
| NeuAc2Hex4HexNAc4dHexSP | 2365 | | | | | | | | | | | + | + | + | |
| NeuAc3Hex5HexNAc3SP and/or NeuAc2Hex5HexNAc4Ac4 | 2389 | | | | + | | | | | | | | | | |
| NeuAc2Hex5HexNAc3dHex2SP | 2390 | + | + | + | + | + | + | | | + | + | | + | | |
| NeuAc2Hex3HexNAc5dHex2 and/or Hex7HexNAc5dHexSP | 2392 | | | | + | + | | | | | | | | | |
| NeuAcHex4HexNAc6dHexSP and/or NeuGcHex6HexNAc4dHex2 and/or NeuAcHex7HexNAc4dHex | 2400 | | | | | | | | | | | | + | | |
| NeuAc2Hex6HexNAc3dHexSP | 2406 | | | | + | | | | | | | + | + | | |

TABLE 47-continued

| Proposed composition | m/z | hESC | EB | st.3 | hEF | mEF | BM MSC | OB | CB MSC | AC | CB MNC | CD 34+ | CD 133+ | LIN− | CD 8− |
|---|---|---|---|---|---|---|---|---|---|---|---|---|---|---|---|
| NeuAcHex8HexNAc3dHexSP and/or NeuAc3Hex4HexNAc3dHex2 | 2439 | | | | | | | | | | | + | | | |
| NeuAc2Hex5HexNAc4dHexSP and/or NeuAc2Hex8HexNAc2dHex and/or Hex12HexNAc2SP | 2447 | | + | | | | + | + | | | | + | + | + | + |
| NeuAcHex5HexNAc4dHex3SP and/or NeuAcHex8HexNAc2dHex3 | 2448 | | + | | | | | | | | | + | + | + | + |
| NeuAcHex7HexNAc3dHex3 and/or NeuAcHex4HexNAc5dHex3SP | 2489 | | | | | | | | | | | + | + | | |
| Hex6HexNAc7SP | 2490 | | | | | | | | | | | | + | | |
| NeuAcHex6HexNAc5dHexSP and/or NeuAcHex9HexNAc3dHex and/or NeuAc3Hex2HexNAc5dHex2 | 2521 | + | + | | | | + | | | | | | + | | |
| Hex6HexNAc5dHex3SP | 2522 | | | | | | + | | | | | | + | | |
| Hex7HexNAc6dHexSP | 2595 | | | | | | + | | | | | | | | |
| NeuGcHex8HexNAc5 and/or NeuAcHex4HexNAc5dHex4SP | 2635 | | | | | | | | | | | + | + | | |
| NeuAc2Hex4HexNAc5dHex2SP2 | 2714 | | | | | | + | | | | | + | + | + | |
| NeuAcHex4HexNAc5dHex4SP2 and/or NeuAc3Hex5HexNAc5 | 2715 | | | | | | | | | | | | + | + | |
| NeuAc3Hex5HexNAc4dHex2 and/or NeuAcHex6HexNAc6dHexSP2 | 2804 | | | | | | | | | | | | + | + | |
| Hex6HexNAc6dHex3SP2 | 2805 | | | | | | | | | | | | + | | |
| NeuAc2Hex6HexNAc5dHexSP | 2812 | | | | | | | + | | | | + | + | + | + |
| NeuAcHex6HexNAc5dHex3SP | 2813 | | | | | | | | | | | | + | | |
| NeuAc3Hex6HexNAc4dHexSP and/or NeuGcNeuAc2Hex5HexNAc4dHex2SP | 2900 | | | | | + | | | | | | | | | |
| NeuAc3Hex6HexNAc5dHexSP | 3104 | | | | | | | | | | | + | + | | |
| NeuAc2Hex6HexNAc5dHex3SP | 3105 | | | | | | | | | | | + | + | | | hESC, human embryonic stem cells; EB, embryoid bodies derived from hESC;
st.3, stage 3 differentiated cells derived from hESC;
hEF, human fibroblast feeder cells;
mEF, murine fibroblast feeder cells;
BM MSC, bone-marrow derived mesenchymal stem cells;
OB, Osteoblast-differentiated cells derived from BM MSC;
CB MSC, cord blood derived mesenchymal stem cells;
OB, adipocyte-differentiated cells derived from CB MSC;
CB MNC, cord blood mononuclear cells;
CD34+, CD133+, LIN−, and CD8−: subpopulations of CB MNC.

TABLE 48

| Neutral N-glycan fraction (FIG. 1.A) | | | | Sialylated N-glycan fraction (FIG. 1.B) | | | | Neutral N-glycan fraction (FIG. 1.A) | | | | Sialylated N-glycan fraction (FIG. 1.B) | | | |
|---|---|---|---|---|---|---|---|---|---|---|---|---|---|---|---|
| FIG. | m/z | Composition | ST | FIG. | m/z | Composition | ST | FIG. | m/z | Composition | ST | FIG. | m/z | Composition | ST |
| 609 | 609.21 | H1N2 | M | 1565 | 1565.55 | S1H4N3 | O | 1663 | 1663.58 | H5N4 | C | 2295 | 2295.81 | S1H6N5 | C |
| 771 | 771.26 | H2N2 | M | 1678 | 1678.60 | S2H2N3F1 | O | 1688 | 1688.61 | H3N5F1 | C | 2367 | 2367.83 | S2H5N4F1 | C |
| 917 | 917.32 | H2N2F1 | M | 1711 | 1711.61 | S1H4N3F1 | H | 1704 | 1704.61 | H4N5 | C | 2368 | 2368.85 | S1H5N4F3 | C |
| 933 | 933.31 | H3N2 | M | 1727 | 1727.60 | S1H5N3 | H | 1743 | 1743.58 | H8N2 | M | 2383 | 2383.83 | S2H6N4 | C |
| 1079 | 1079.38 | H3N2F1 | M | 1768 | 1768.57 | S1H4N4 | C | 1768 | 1768.61 | H6N3F1 | H | 2384 | 2384.85 | S1H6N4F2 | C |
| 1095 | 1095.37 | H4N2 | M | 1799 | 1799.62 | S2H4N2F1 | O | 1793 | 1793.64 | H4N4F2 | C | 2408 | 2408.86 | S2H4N5F1 | C |
| 1120 | 1120.40 | H2N3F1 | H | 1840 | 1840.65 | S2H3N3F1 | H | 1809 | 1809.64 | H5N4F1 | C | 2425 | 2425.83 | S1H5N5F2 | C |
| 1136 | 1136.40 | H3N3 | H | 1873 | 1873.66 | S1H5N3F1 | H | 1825 | 1825.63 | H6N4 | C | 2441 | 2441.87 | S1H6N5F1 | C |
| 1241 | 1241.43 | H4N2F1 | M | 1889 | 1889.65 | S1H6N3 | H | 1850 | 1850.67 | H4N5F3 | C | 2482 | 2482.90 | S1H5N6F2 | C |
| 1257 | 1257.42 | H5N2 | M | 1914 | 1914.68 | S1H4N4F1 | C | 1866 | 1866.66 | H5N5 | C | 2570 | 2570.91 | S2H5N5F1 | C |
| 1282 | 1282.45 | H3N3F1 | H | 1930 | 1930.68 | S1H5N4 | C | 1905 | 1905.63 | H9N2 | M | 2571 | 2571.93 | S1H5N5F3 | C |
| 1298 | 1298.45 | H4N3 | H | 1946 | 1946.67 | G1H5N4 | C | 1955 | 1955.70 | H5N4F2 | C | 2587 | 2587.93 | S1H6N5F2 | C |
| 1323 | 1323.48 | H2N4F1 | C | 1971 | 1971.71 | S1H4N5 | C | 1987 | 1987.69 | H7N4 | C | 2603 | 2603.92 | S1H7N5F1 | C |
| 1339 | 1339.48 | H3N4 | C | 2002 | 2002.70 | S2H4N3F1 | H | 1996 | 1996.72 | H4N5F2 | C | 2644 | 2644.95 | S1H6N6F1 | C |
| 1403 | 1403.48 | H5N2F1 | M | 2035 | 2035.71 | S1H6N3F1 | H | 2012 | 2012.72 | H5N5F1 | C | 2732 | 2732.97 | S2H6N5F1 | C |
| 1419 | 1419.48 | H6N2 | M | 2076 | 2076.74 | S1H5N4F1 | C | 2028 | 2028.71 | H6N5 | C | 2733 | 2733.99 | S1H6N5F3 | C |
| 1444 | 1444.51 | H4N3F1 | H | 2092 | 2092.73 | G1H5N4F1 | C | 2067 | 2067.69 | H10N2 | M | 2807 | 2807.00 | S1H7N6F1 | C |
| 1460 | 1460.50 | H5N3 | H | 2117 | 2117.76 | S1H4N5F1 | C | 2101 | 2101.76 | H5N4F3 | C | 2878 | 2878.00 | S3H6N5 | C |
| 1485 | 1485.53 | H3N4F1 | C | 2133 | 2133.76 | S1H5N5 | C | 2142 | 2142.78 | H4N5F3 | C | 2879 | 2879.02 | S2H6N5F2 | C |
| 1501 | 1501.53 | H4N4 | C | 2164 | 2164.75 | S2H5N3F1 | H | 2174 | 2174.77 | H6N5F1 | C | 2953 | 2953.06 | S1H7N6F2 | C |
| 1542 | 1542.56 | H3N5 | C | 2221 | 2221.78 | S1H5N4 | C | 2229 | 2229.74 | H11N2 | M | 3098 | 3098.10 | S2H7N6F1 | C |
| 1565 | 1565.53 | H6N2F1 | M | 2222 | 2222.80 | S1H5N4F2 | C | 2304 | 2304.83 | H5N5F3 | C | 3099 | 3099.12 | S1H7N6F3 | C |
| 1581 | 1581.53 | H7N2 | M | 2237 | 2237.77 | G1S1H5N4 | C | 2361 | 2361.87 | H5N6F2 | C | 3172 | 3172.13 | S1H8N7F1 | C |
| 1590 | 1590.57 | H4N3F2 | H | 2238 | 2238.79 | S1H6N4F1 | C | | | | | | | | |
| 1606 | 1606.56 | H5N3F1 | H | 2253 | 2253.76 | G2H5N4 | C | | | | | | | | |
| 1622 | 1622.56 | H6N3 | H | 2263 | 2263.82 | S1H4N5F2 | C | | | | | | | | |
| 1647 | 1647.59 | H4N4F1 | C | 2279 | 2279.82 | S1H5N5F1 | C | | | | | | | | | m/z: neutral = [M + Na]$^+$, sialylated = [M − H]$^−$;
Composition: S = NeuAc, G = NeuGc, H = Hex, N = HexNAc, F = dHex;
ST (structure class): M = mannose-type, H = hybrid-type, C = complex-type, O = other.

TABLE 49

Comparison of lectin ligand profile in hESCs and MEFs

| Lectin | hESC | MEF |
|---|---|---|
| PSA | − | + |
| MAA | + | − |
| PNA | + | − |
| RCA | + | + |

+ present in cell surface
− not present in cell surface

TABLE 50

Summary of the results of BM MSC grown on different immobilized lectin surfaces.

| Coating | Proliferation factor | Effect vs. plastic |
|---|---|---|
| plastic | 3.8 | |
| RCA | 1.0 | n.g. |
| PSA | 3.9 | (+) |
| LTA | 4.0 | + |
| SNA | 3.7 | (−) |
| GS II | 4.9 | + |
| UEA | 2.1 | − |
| ECA | 4.4 | + |
| MAA | 3.7 | (−) |
| STA | 3.1 | − |
| PWA | 4.2 | + |
| WFA | 2.9 | − |
| NPA | 3.6 | (−) |

Proliferation factor = the number of cells on day 3/the number of cells on day 1.
Triplicates were used in calculations.
Effect vs. plastic: 'n.g.' = no growth; '−' = slower growth rate; '+' = faster growth rate than on plastic; '( )' nearly equal to plastic.

TABLE 52

Neutral glycan signals of human stem cell glycosphingolipid glycans.

| Proposed composition | m/z | |
|---|---|---|
| Hex2dHex | 511.24 | 511 |
| Hex3 | 527.15 | 527 |
| Hex2HexNAc | 568.19 | 568 |
| Hex2HexNAcdHex | 714.24 | 714 |
| Hex3HexNAc | 730.24 | 730 |
| Hex2HexNAc2 | 771.26 | 771 |
| HexHexNAc3 | 812.29 | 812 |
| Hex3HexNAcdHex | 876.30 | 876 |
| Hex4HexNAc | 892.29 | 892 |
| HexHexNAc2dHex2 | 901.33 | 901 |
| Hex2HexNAc2dHex | 917.32 | 917 |
| Hex3HexNAc2 | 933.31 | 933 |
| Hex2HexNAc3 | 974.34 | 974 |
| Hex2HexNAcdHex3 | 1006.36 | 1006 |
| Hex3HexNAcdHex2 | 1022.35 | 1022 |
| Hex5HexNAc | 1054.34 | 1054 |
| Hex2HexNAc2dHex2 | 1063.38 | 1063 |
| Hex2HexNAc2dHex | 1079.38 | 1079 |
| Hex4HexNAc2 | 1095.37 | 1095 |
| Hex3HexNAc3 | 1136.40 | 1136 |
| Hex6HexNAc | 1216.40 | 1216 |
| Hex3HexNAc2dHex2 | 1225.43 | 1225 |
| Hex4HexNAc2dHex | 1241.43 | 1241 |
| Hex5HexNAc2 | 1257.42 | 1257 |
| Hex3HexNAc3dHex | 1282.45 | 1282 |
| Hex4HexNAc3 | 1298.45 | 1298 |
| Hex2HexNAc4dHex | 1323.48 | 1323 |
| Hex3HexNAc2dHex3 | 1371.49 | 1371 |
| Hex7HexNAc | 1378.45 | 1378 |
| Hex4HexNAc2dHex2 | 1387.49 | 1387 |
| Hex5HexNAc2dHex | 1403.48 | 1403 |
| Hex6HexNAc2 | 1419.48 | 1419 |
| Hex3HexNAc3dHex2 | 1428.51 | 1428 |

TABLE 51

Detected N-linked and soluble glycome structural type distribution in stem cells.
The column 'All' includes all CB stem cell populations.

| Glycan feature | Proposed structure | hESC Proportion, % | MSC Proportion, % | All Proportion, % |
|---|---|---|---|---|
| Neutral N-glycan structural features: | | | | |
| $Hex_{5-10}HexNAc_2$ | High-mannose type/$Glc_1$ | 50-90 | 30-80 | 30-90 |
| $Hex_{1-4}HexNAc_2dHex_{0-1}$ | Low-mannose type | 5-20 | 5-20 | 5-50 |
| $n_{HexNAc} = 3$ ja $n_{Hex} \geq 2$ | Hybrid-type/Monoantennary | 1-20 | 5-20 | 1-20 |
| $n_{HexNAc} \geq 4$ ja $n_{Hex} \geq 2$ | Complex-type | 1-10 | 5-40 | 1-40 |
| $Hex_{1-9}HexNAc_1$ | Soluble | 1-20 | 1-30 | 1-30 |
| $n_{dHex} \geq 1$ | Fucosylation | 5-20 | 10-40 | 5-40 |
| $n_{dHex} \geq 2$ | α2/3/4-linked Fuc | 0-5 | 1-5 | 0-5 |
| $n_{HexNAc} > n_{Hex} \geq 2$ | Terminal HexNAc (N > H) | 0-20 | 0-5 | 0-20 |
| $n_{HexNAc} = n_{Hex} \geq 5$ | Terminal HexNAc (N = H) | 0-10 | 0-2 | 0-10 |
| Acidic N-glycan structural features: | | | | |
| $n_{HexNAc} = 3$ ja $n_{Hex} \geq 3$ | Hybrid-type/Monoantennary | 1-25 | 2-20 | 1-25 |
| $n_{HexNAc} \geq 4$ ja $n_{Hex} \geq 3$ | Complex-type | 70-99 | 70-95 | 70-99 |
| $n_{dHex} \geq 1$ | Fucosylation | 60-99 | 50-80 | 50-99 |
| $n_{dHex} \geq 2$ | α2/3/4-linked Fuc | 1-40 | 1-20 | 1-40 |
| $n_{HexNAc} > n_{Hex} \geq 2$ | Terminal HexNAc (N > H) | 1-25 | 0-5 | 0-25 |
| $n_{HexNAc} = n_{Hex} \geq 5$ | Terminal HexNAc (N = H) | 1-30 | 0-5 | 0-30 |
| +80 Da | Sulphate or phosphate ester | 0-50 | 0-40 | 0-50 |

TABLE 52-continued

Neutral glycan signals of human stem cell glycosphingolipid glycans.

| Proposed composition | m/z | |
|---|---|---|
| Hex4HexNAc3dHex | 1444.51 | 1444 |
| Hex5HexNAc3 | 1460.50 | 1460 |
| Hex4HexNAc2dHex3 | 1533.54 | 1533 |
| Hex8HexNAc | 1540.5 | 1540 |
| Hex6HexNAc2dHex | 1565.53 | 1565 |
| Hex4HexNAc3dHex2 | 1590.57 | 1590 |
| Hex5HexNAc3dHex | 1606.56 | 1606 |
| Hex6HexNAc3 | 1622.56 | 1622 |
| Hex9HexNAc | 1702.56 | 1702 |
| Hex4HexNAc3dHex3 | 1736.62 | 1736 |
| Hex5HexNAc3dHex2 | 1752.62 | 1752 |
| Hex4HexNAc3dHex | 1850.67 | 1850 |
| Hex10HexNAc | 1864.61 | 1864 |
| Hex7HexNAc2dHex2 | 1873.64 | 1873 |
| Hex4HexNAc3dHex4 | 1882.68 | 1882 |
| Hex5HexNAc3dHex3 | 1898.68 | 1898 |
| Hex5HexNAc4dHex2 | 1955.70 | 1955 |
| Hex11HexNAc | 2026.66 | 2026 |
| Hex5HexNAc4dHex3 | 2101.76 | 2101 |
| Hex6HexNAc4dHex2 | 2117.75 | 2117 |
| Hex4HexNAc5dHex3 | 2142.78 | 2142 |
| Hex12HexNAc | 2188.71 | 2188 |

TABLE 53

Acidic glycan signals of human stem cell glycosphingolipid glycans.

| Proposed composition | m/z | |
|---|---|---|
| NeuAcHexHexNAcdHex | 819.29 | 819 |
| NeuAcHex2HexNAc | 835.28 | 835 |
| NeuAc2Hex2 | 905.30 | 905 |
| NeuAcHexHexNAcdHex2 | 965.35 | 965 |
| NeuAcHex3HexNAc | 997.34 | 997 |
| NeuAc2Hex2HexNAc | 1126.38 | 1126 |
| NeuAcHex3HexNAcdHex | 1143.39 | 1143 |
| Hex4HexNAc2SP | 1151.33 | 1151 |
| NeuAcHex4HexNAc | 1159.39 | 1159 |
| NeuAcHexHexNAc2dHex2 | 1168.43 | 1168 |
| NeuAcHex3HexNAc2 | 1200.42 | 1200 |
| NeuGcHex3HexNAc2 | 1216.41 | 1216 |
| Hex2HexNAc4SP | 1233.38 | 1233 |
| NeuAc2Hex3HexNAc | 1288.43 | 1288 |
| NeuAc2Hex2HexNAc2dHex | 1313.46 | 1313 |
| NeuAc2Hex2HexNAc2dHex2 | 1330.48 | 1330 |
| NeuAcHex4HexNAc2 | 1362.47 | 1362 |
| NeuAc2Hex4HexNAc/ NeuAc2HexHexNAc3SP | 1450.48 | 1450 |
| NeuAcHex4HexNAc2dHex | 1508.53 | 1508 |
| NeuAcHex2HexNAc3dHex2 | 1533.56 | 1533 |
| Hex6HexNAc2SP2/ NeuAc2Hex2HexNac2dHexSP | 1555.47/1555.39 | 1555 |
| NeuAcHex4HexNAc3 | 1565.55 | 1565 |
| NeuAcHex5HexNAc3 | 1727.60 | 1727 |
| NeuGcHex5HexNAc3 | 1743.60 | 1743 |
| NeuAcHex5HexNAc3dHex | 1873.66 | 1873 |
| NeuAcHex6HexNAc3 | 1889.65 | 1889 |
| NeuAcHex3HexNAc4dHex2 | 1898.69 | 1898 |
| NeuAc2Hex3HexNac3dHexSP | 1920.60 | 1920 |
| NeuAc2Hex5HexNAc3 | 2018.70 | 2018 |
| NeuAcHex6HexNAc3dHex | 2035.71 | 2035 |
| NeuAcHex6HexNAc4 | 2092.73 | 2092 |
| NeuGcHex6HexNAc4 | 2108.73 | 2108 |
| NeuAc2Hex4HexNAc4dHex3SP | 2286.76 | 2286 |
| NeuAc2Hex5HexNAc4SP | 2301.73 | 2301 |
| NeuGc3Hex4HexNAc4 | 2398.80 | 2398 |
| NeuAcHex5HexNAc4dHex3SP/ NeuAcHex8HexNAc2dHex3 | 2448.81 | 2448 |
| Hex7HexNAc6SP | 2449.81 | 2449 |
| NeuGc2Hex7HexNAc5 | 2780.95 | 2780 |
| NeuGcHex8HexNAc5dHex/ NeuAcHex9HexNAc5 | 2781.97 | 2781 |

REFERENCES

Altmann, F., et al (1999) *Glycoconj. J.* 16:109-23
Harvey, D. J., et al. (1993) *Rapid Commun. Mass Spectrom.* 7(7):614-9
Hirabayashi, J., et al. (2002) *Biochim. Biophys. Acta.* 1572: 232-54.
Jaatinen, T., et al. (2006) *Stem cells.* 24:631-41.
Karlsson, H., et al. (2000) *Glycobiology* 10(12):1291-309
Kretzchmar, E., et al. (1994) *Biol. Chem. Hoppe Seyler* 375 (5):23-7
Kubelka, V., et al. (1994) *Arch. Biochem. Biophys.* 308(1): 148-57
Leskelä, H., et al. (2003) *Biochem. Biophys. Res. Commun.* 311:1008-13
Miller-Podraza, H., et al. (2000) *Glycobiologvy.* 10:975-982
Moore (1999) *Trends Cell Biol.* 9:441-6
Naven, T. J. & Harvey, D. J. (1996) *Rapid Commun. Mass Spectrom.* 10(11):1361-6
Nyman, T. A., et al. (1998) *Eur. J. Biochem.* 253(2):485-93
Papac, D., et al. (1996) *Anal. Chem.* 68(18):3215-23
Saarinen, J., et al. (1999) *Eur. J. Biochem.* 259(3):82940
Skottman, H. et al. (2005) Stem cells
Staudacher, E., et al. (1992) *Eur. J. Biochem.* 207(3):987-93
Thomson, J. A., et al. (1998) *Science* 282:1145-7
Venable et al. (2005) BMC Developmental biology.

The invention claimed is:

1. A method of detecting a glycan structure from a sample of human mesenchymal, hematopoietic or embryonal type stem cells, comprising the step of (a) contacting the stem cells with a binding agent specifically binding to said glycan structure or (b) preparing a glycan containing fraction from the stem cells and identifying the glycan structures by mass spectrometric profiling, wherein said glycan structure is selected from the group consisting of at least one terminal or core glycan sequence structure according to the Formula $$R_1 Hex\beta z\{R_3\}_{n1} Hex(NAc)_{n2} XyR_2,$$

wherein X is glycosidically linked disaccharide epitope $\beta 4 (Fuc\alpha 6)_n GN$, wherein n is 0 or 1, or X is nothing, or when n2 is 0, X can be $\beta Cer$, a ceramide or part or derivative thereof and $yR_2$ is nothing or reducing end glycan core part comprising a glycolipid, or O-glycan or glycosaminoglycan or N-glycan core structures;

Hex is Gal or Man or GlcA;
HexNAc is GlcNAc or GalNAc;
y is anomeric linkage structure α and/or β or linkage from derivatized anomeric carbon;
z is linkage position 3 or 4, with the provision that when z is 4 then HexNAc is GlcNAc and then Hex is Man or Gal or GlcA, and when z is 3 then Hex is GlcA or Gal and HexNAc is GlcNAc or GalNAc and with the provision that Hex can be Man only when n1 is 0 and n2 is 1, n1 is 0 or 1 indicating presence or absence of R3;

n2 is 0 or 1, indicating the presence or absence of NAc, with the provision that n2 can be 0 only when Hexβz is Galβ4, and n2 is 0 or 1;

$R_1$ indicates 1-4 naturally occurring carbohydrate substituents linked to the core structures or nothing;
$R_2$ is a natural O-glycan, N-glycan or glycolipid reducing end structure or a chemical reducing end derivatization structure;
$R_3$ is nothing or a branching structure representing a GlcNAcβ6 or an oligosaccharide with GlcNAβ6 at its reducing end linked to GalNAc or when Hex is Gal and HexNAc is GlcNAc then when z is 3 R3 is Fucα4 or nothing and when z is 4 R3 is Fucα3 or nothing, with the provisions that i) the stem cells are not cells of a cancer cell line, and
ii) when the cells are embryonal stem cells, the glycan structure is not a SSEA3 or -4 structure, and
iii) when cells are hematopoietic CD34+ cells, the structure is not a single structure comprising SAα3Galβ4GlcNAc.

2. A method of detecting a glycan structure from a sample of human mesenchymal, hematopoietic or embryonal type stem cells, comprising the step of (a) contacting the stem cells with a binding agent specifically binding to said glycan structure or (b) preparing a glycan containing fraction from the stem cells and identifying the glycan structures by mass spectrometric profiling, wherein said glycan structure is selected from the group consisting of: a terminal lactosamine structure $(R1)_{n1}Gal(NAc)_{n3}β3/4(Fucα4/3)_{n2}GlcNAcβR$ wherein R1 is Fucα2, or SAα3/6 linked to Galβ4GlcNAc, and R is the reducing end core structure of N-glycan, O-glycan and/or glycolipid;

or structure $(SAα3)n_1Galβ3(SAα6)n_2GalNAc$;

wherein n1, n2 and n3 are 0 or 1 indicating the presence or absence of a structure wherein SA is a sialic acid;

or branched epitope Galβ3(GlcNAcβ6)GalNAc or $R_1Galβ4(R_3)GlcNAcβ6(R_2Galβ3)GalNAc$, wherein $R_1$ and $R_2$ are independently either nothing or SAα3; and $R_3$ is independently either nothing or Fucα3;

or

Manβ4GlcNAc structure in the core structure of N-linked glycan;

or epitope Galβ4Glc, or terminal mannose, or terminal SAα3/6Gal, wherein SA is a sialic acid, with the provisions that i) the stem cells are not cells of a cancer cell line and
ii) when the cells are embryonal stem cells, the glycan structure is not a SSEA3 or -4 structure, and
iii) when cells are hematopoietic CD34+ cells, the structure is not a single structure comprising SAα3Galβ4GlcNAc.

3. The method according to claim 2, wherein a following glycan structure with a terminal structure is detected from a sample of stem cells:

iv) $(SAα3/Fucα2)_{n1}Galβ3 (Fucα4)_{n2}GlcNAc$,
v) $(SAα3/6 or Fucα2)_{n1}Galβ4(Fucα3)_{n2}GlcNAc$ with the provisions that when n2 is 0, the cells are mesenchymal or embryonal stem cells or hematopoietic CD133+ cells; or
vi) $(SAα3)_{n1}Galβ3(SAα6)_{n2}GalNAc$ with the provisions that the structure is O-glycan, wherein SA is sialic acid and n1 or n2 is 0 or 1.

4. The method according to claim 2, wherein the disaccharide epitope is terminal structure of a complex N-glycan or a neolacto or lacto glycolipid or an O-glycan and or O-glycan core structure $R_1Galβ3\{R_3\}n_1HexNAc$, wherein HexNAc is GalNAc or GlcNAc.

5. The method according to claim 2, wherein the terminal structure is Galβ3GlcNAc or Galβ3(Fucα4)GlcNAc (Lewis a), Fucα2Galβ3GlcNAc (H-type 1), Fucα2Galβ3 (Fucα4) GlcNAc (Lewis b), SAα3 Galβ3 GlcNAc or SAα3 Galβ3 (Fucα4)GlcNAc (sialyl-Lewis a), or terminal structure is type 2 lactosamine; Galβ4GlcNAc, Galβ4(Fucα3)GlcNAc (Lewis x), Fucα2Galβ4GlcNAc (H-type 2), Fucα2Gal34 (Fucα3)GlcNAc (Lewis y), SAα3 Galβ4GlcNAc (Lewis x), SAα6Galβ4GlcNAc or SAα3Galβ4(Fucα4)GlcNAc (sialyl-Lewis x).

6. The method according to claim 5, wherein the terminal structure is Galβ3 GlcNAc or Galβ3(Fucα4)GlcNAc (Lewis a), Fucα2Galβ3GlcNAc (H-type 1) Fucα2Galβ3(Fucα4) GlcNAc (Lewis b), SAα3 Galβ3 GlcNAc or SAα3 Galβ3 (Fucα4)G1 cNAc (sialyl-Lewis a).

7. The method according to claim 2, wherein the structures recognized by specific binder reagent being a protein selected from the group consisting of: lectin or antibody or enzyme, monoclonal antibody, glycosidase, glycosyl transferring enzyme, plant lectin, animal lectin and a peptide mimetic thereof, the recombinant protein being a high specificity binder recognizing at least partially two monosaccharide structures and bond structure between the monosaccharide residues, or a binder protein being labelled by a detectable marker structure.

8. The method according to claim 1, wherein the detection is performed by methods selected from the group:

by mass spectrometry from a stem cell glycome produced by the method comprising steps of 1) releasing non-derivatized glycome composition from stem cells and 2) purifying the glycome composition by microchromatography methods involving use of hydrophobic and hydrophilic chromatography and optionally anion exchange chromatography or preparation of substrate cell materials for analysis by the use of a chemical buffer solution, or by the use of detergents, chemical reagents and/or enzymes;

release of glycome(s) from the cells, wherein the glycome is optionally non-derivatized or singly derivatized, or reducing end derivatized oligosaccharide composition, including various subglycome types based on glycan core, charge and other structural features, by the use of reagents, the carbohydrate content of which is controlled;

purification of glycomes and various subglycomes from complex mixtures;

glycome analysis, including profiling methods such as mass spectrometry and/or NMR spectroscopy; the data processing and analysis, comparative methods between different sample types and quantitative analysis of glycome data obtained.

9. The method according to claim 1, wherein the disaccharide epitope is Manβ4GlcNAc structure in the core structure of N-linked glycan according to the Formula:

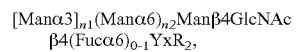

wherein n1 and n2 are integers 0 or 1, independently indicating the presence or absence of the terminal Man-residue, and wherein the non-reducing end terminal Manα3/Manα6-residues can be elongated to the complex type for the analysis of the status of stem cells and/or manipulation of the stem cells.

10. The method according to claim 9, wherein the Manβ4GlcNAc-epitope is essentially devoid of additional GlcNAc-substitutions, the amount of the GlcNAc substitution of N-glycan core is between 1-8%.

11. The method according to claim 2, wherein the terminal mannose structure is low mannose type glycan marker, wherein the structure of the marker glycan is according to Formula

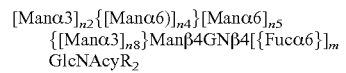

wherein p, n2, n4, n5, n8, and m are either independently 0 or 1; with the provision that when n2 is 0, also n1 is 0; when n4 is 0, also n3 is 0; when n5 is 0, also n1, n2, n3, and n4 are 0; when n7 is 0, also n6 is 0; when n8 is 0, also n6 and n7 are 0; the sum of n1, n2, n3, n4, n5, n6, n7, and n8 is less than or equal to (m+3); [ ] indicates determinant either being present or absent depending on the value of n2, n4, n5, n8, and m; and indicates a branch in the structure, y is an anomeric linkage structure a and/or or linkage from derivatized anomeric carbon and $R_2$ is a natural O-glycan, N-glycan or glycolipid reducing end structure or a chemical reducing end derivatization structure.

12. The method according to claim 9, wherein the terminal mannose structure is according to Formula:

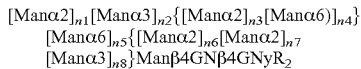
$[Man\alpha 6]_{n5}\{[Man\alpha 2]_{n6}[Man\alpha 2]_{n7}$
$[Man\alpha 3]_{n8}\}Man\beta 4GN\beta 4GNyR_2$ wherein n1, n2, n3, n4, n5, n6, n7, and n8 are either independently 0 or 1; with the provision that when n2 is 0, also n1 is 0; when n4 is 0, also n3 is 0; when n5 is 0, also n1, n2, n3, and n4 are 0;

when n7 is 0, also n6 is 0; when n8 is 0, also n6 and n7 are 0; and the sum of n1, n2, n3, n4, n5, n6, n7, and n8 is an integer from 4 to 8;

y is anomeric linkage structure α and/or β or linkage from derivatized anomeric carbon, and $R_2$ is reducing end hydroxyl, chemical reducing end derivative or natural asparagine N-glycoside derivative such as asparagine N-glycosides including asparagines N-glycoside amino acid and/or peptides derived from protein; [ ] indicates determinant either being present or absent depending on the value of n1, n2, n3, n4, n5, n6, n7, and n8; and { } indicates a branch in the structure.

13. The method according to claim 9 comprising a step of cleaving the structure by α-mannosidase.

14. The method according to claim 2, wherein the amount of cells analysed is between 1000 and 10 million or wherein the amount of cells to be analysed is between $10^3$ and $10^6$ cells.

15. The method according to claim 8, wherein the glycans are selected from the group: glycome comprises oligosaccharides with molecular weight from about 400 to about 4000, from about 600 to about 3500 or a N-glycan subglycome comprising N-glycans with N-glycan core structure and said N-glycans being releasable from cells by N-glycosidase, or N-glycans, wherein N-glycan core structure is Manβ4GlcNAcβ4(Fucα6)$_n$GlcNAc, wherein n is 0 or 1, or group of glycan structures comprises oligosaccharides in specific amounts shown in Tables 2, 4, 5, and FIGS. 1-6, 10-12, and 15 of the specification, or glycans released from the surface of the cells.

16. The method according to claim 8, wherein the stem cell preparation comprises cells selected from the group: human early blood cells or mesenchymal cells derived thereof, a cord blood cell population, or embryonal-type cell population.

17. The method according to claim 8 for evaluating the status or differentiation status of an isolated early human cell population, comprising a step of quantification of the amount of the glycan structure and/or comparing the amount of the glycan structure with glycan amount in another cell sample or corresponding information in a database.

18. A method of detecting a glycan structure from a sample of human mesenchymal, hematopoietic or embryonal type stem cells, comprising the step of (a) contacting the stem cells with a binding agent specifically binding to said glycan structure or (b) preparing a glycan containing fraction from the stem cells and identifying the glycan structures by mass spectrometric profiling, wherein said glycan structure is selected from the group consisting of: a terminal lactosamine structure

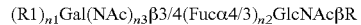

wherein R1 is Fucα2, or SAα3/6 linked to Galβ4GlcNAc, and

R is the reducing end core structure of N-glycan, O-glycan and/or glycolipid;

or structure (SAα3)$_{n1}$Galβ3(SAα6)$_{n2}$GalNAc;

wherein n1, n2 and n3 are 0 or 1 indicating the presence or absence of a structure wherein SA is a sialic acid;

or branched epitope Galβ3(GlcNAcβ6)GalNAc or $R_1$Galβ4($R_3$)GlcNAcβ6($R_2$Galβ3)GalNAc, wherein $R_1$ and $R_2$ are independently either nothing or SAα3; and $R_3$ is independently either nothing or Fucα3;

or

Manβ4GlcNAc structure in the core structure of N-linked glycan;

or epitope Galβ4Glc, or terminal mannose, or terminal SAα3/6Gal, wherein SA is a sialic acid, with the provisions that i) the stem cells are not cells of a cancer cell line and ii) when the cells are embryonal stem cells, the glycan structure is not a SSEA structure, and iii) cells are not hematopoietic CD34$^+$ cells.

19. The method according to claim 2, wherein the method is directed to a lacto- or neolacto type glycolipid marker structure, wherein the terminal disaccharide structure is either Galβ3GlcNAc or Galβ4GlcNAc, and the terminal structure is β-linked to glycolipid structure (HexHexNAc)$_n$Galβ4GlcβCer, wherein n is either 0, 1, or 2 or a fucosylated lacto- or neolacto type glycolipid marker glycan marker structure described above, wherein the structure further contains 1 or 2 Fucα residues, or an additional SSEA-3 or SSEA-4 glycolipid structure is analyzed.

20. The method according to claim 2, wherein the presence or absence of detected glycan structure is evaluated with regard to a contaminating structure in a cell population of said cell preparation or with regard to a change in the status of the cell population or with regard to the control of cell status and/or potential contaminations by physical and/chemical means or with regard to the control of a variation in raw material cell population or wherein at least one specific variation is detected, and wherein the method, comprises a step of quantification of the amount of the glycan structure and/or comparing the amount of the glycan structure with glycan amount in another cell sample or corresponding information in a database.

21. The method according to claim 2, wherein the cell status is controlled during cell culture or during cell purification, in context with cell storage or handling at lower temperatures, or in context with cryopreservation of cells or time dependent changes of cell status are detected or time dependent changes of cell status depend on the nutritional status of the cells, confluency of the cell culture, density of the cells, changes in genetic stability of the cells, integrity of the cell structures or cell age, or chemical, physical, or biochemical factors affecting the cells or for evaluating the malignancy of an isolated early human cell population, and wherein the method, comprises a step of quantification of the amount of the glycan structure and/or comparing the amount of the glycan structure with glycan amount in another cell sample or corresponding information in a database.

22. The method according to claim 7, wherein the binder is used for sorting or selecting human stem cells from biological materials or samples including cell materials comprising other cell types or for sorting or selecting between different human stem cell types.

23. The method according to claim 1 or 2, comprising the further steps of quantifying the amount of said glycan structure, and comparing cell samples of different differentiation status and correlating the amount of said glycan structure with differentiation status of the stem cells.

24. The method according to claim 9 or 14, wherein the cells are mesenchymal, hematopoietic or embryonal type stem cells.

25. The method of sorting according to claim 22, wherein the sorting is performed by beads or fluorescence activated cell sorting or by binder immobilized on a matrix or cell culture container.

26. A method of detecting a glycan structure from a sample of human stem cells, comprising the step (a) contacting the stem cells with a binding agent specifically binding to said glycan structure or (b) preparing a glycan containing fraction from the stem cells and identifying the glycan structures by mass spectrometric profiling,
wherein said glycan structure is selected from the group consisting of at least one terminal or core glycan sequence structure according to the Formula

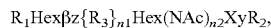

$R_1 Hex\beta z\{R_3\}_{n1} Hex(NAc)_{n2} XyR_2$, wherein X is glycosidically linked disaccharide epitope $\beta 4(Fuc\alpha 6)_n GN$,
wherein n is 0 or 1, or X is nothing, or when n2 is 0, X can be $\beta Cer$, a ceramide or part or derivative thereof and $yR_2$ is nothing or reducing end glycan core part comprising a glycolipid, or O-glycan or glycosaminoglycan or N-glycan core structures;
Hex is Gal or Man or GlcA;
HexNAc is GlcNAc or
GalNAc;
y is anomeric linkage structure a and/or p or linkage from derivatized anomeric carbon; z is linkage position 3 or 4, with the provision that when z is 4 then HexNAc is GlcNAc
and then Hex is Man or Gal or GlcA, and when z is 3 then Hex is GlcA or Gal and HexNAc is GlcNAc or GalNAc and with the provision that Hex can be Man only when n1 is 0 and n2 is 1, n1 is 0 or 1 indicating presence or absence of R3;
n2 is 0 or 1, indicating the presence or absence of NAc, with the provision that n2 can be 0 only when $Hex\beta z$ is $Gal\beta 4$, and n2 is or 1;
$R_1$ indicates 1-4 naturally occurring carbohydrate substituents linked to the core structures or nothing;
$R_2$ is a natural O-glycan, N-glycan or glycolipid reducing end structure or a chemical reducing end derivatization structure;
$R_3$ is nothing or a branching structure representing a $GlcNAc\beta 6$ or an oligosaccharide with $GlcNAc\beta 6$ at its reducing end linked to GalNAc or when Hex is Gal and HexNAc is
GlcNAc then when z is 3 R3 is $Fuc\alpha 4$ or nothing and when z is 4 R3 is $Fuc\alpha 3$ or nothing, with the provisions that
i) the stem cells are not cells of a cancer cell line and
ii) when the cells are embryonal stem cells, the glycan structure is not a SSEA3 or -4 structure, and
iii) when cells are hematopoietic CD34+ cells, the structure is not single structure comprising $SA\alpha 3Gal\beta 4GlcNAc$, wherein the detection is performed by methods selected from the group:
by mass spectrometry from a stem cell glycome produced by the method comprising steps of 1) releasing non-derivatized glycome composition from stem cells and 2) purifying the glycome composition by micro chromatography methods involving use of hydrophobic and hydrophilic chromatography and optionally anion exchange chromatography or preparation of substrate cell materials for analysis by the use of a chemical buffer solution, or by the use of detergents, chemical reagents and/or enzymes;
release of glycome(s) from the cells, wherein the glycome is optionally non-derivatized or singly derivatized, or reducing end derivatized oligosaccharide composition, including various subglycome types based on glycan core, charge and other structural features, by the use of reagents, the carbohydrate content of which is controlled;
purification of glycomes and various subglycomes from complex mixtures;
glycome analysis, including profiling methods such as mass spectrometry and/or NMR spectroscopy; the data processing and analysis, comparative methods between different sample types and quantitative analysis of glycome data obtained.

27. The method according to claim 26, wherein the glycans are selected from the group: glycome comprises oligosaccharides with molecular weight from about 400 to about 4000, from about 600 to about 3500 or a N-glycan subglycome comprising N-glycans with N-glycan core structure and said N-glycans being releasable from cells by N-glycosidase, or N-glycans, wherein N-glycan core structure is $Man\beta 4GlcNAc\beta 4(Fuc\alpha 6)_n GlcNAc$, wherein n is 0 or 1, or group of glycan structures comprises oligosaccharides in specific amounts shown in Tables 2, 4, 5, and FIGS. 1-6, 10-12, and 15 of the specification, or glycans released from the surface of the cells.

28. The method according to claim 26, wherein the stem cell preparation comprises cells selected from the group: human early blood cells or mesenchymal cells derived thereof, a cord blood cell population, or embryonal-type cell population.

29. The method according to claim 26 for evaluating the status or differentiation status of an isolated early human cell population, comprising step of quantification of the amount of the glycan structure and/or comparing the amount of the glycan structure with glycan amount in another cell sample or corresponding information in a database.

30. A method of detecting a glycan structure from a sample of human stem cells, comprising the step (a) contacting the stem cells with a binding agent specifically binding to said glycan structure or (b) preparing a glycan containing fraction from the stem cells and identifying the glycan structures by mass spectrometric profiling,
wherein said glycan structure is selected from the group consisting of at least one terminal or core glycan sequence structure according to the Formula $Man\beta 4GlcNAcXyR_2$,
wherein X is glycosidically linked disaccharide epitope $\beta 4(Fuc\alpha 6)_n GN$,
wherein n is 0 or 1, or X is nothing and $yR_2$ is nothing or reducing end glycan core part comprising N-glycan core structures;
with the provision that the stem cells are not cells of a cancer cell line and,
wherein the disaccharide epitope is $Man\beta 4GlcNAc$ structure in the core structure of N-linked glycan according to the Formula:

[Manα3]$_{n1}$(Manα6)$_{n2}$Manβ4GlcNAc
β4(Fucα6)$_{0-1}$YxR$_2$, wherein n1 and n2 are integers 0 or 1, independently indicating the presence or absence of the terminal Man-residue, and wherein the non-reducing end terminal Manα3/Manα6-residues can be elongated to the complex type for the analysis of the status of stem cells and/or manipulation of the stem cells.

31. The method according to claim 30, wherein the Manβ4GlcNAc-epitope is essentially devoid of additional GlcNAc-substitutions, the amount of the GlcNAc substitution of N-glycan core is between 1-8%.

32. The method according to claim 30, wherein the terminal mannose structure is low mannose type glycan marker, wherein the structure of the marker glycan is according to Formula

[Manα3]$_{n2}${[Manα6]$_{n4}$}[Manα6]$_{n5}$
{[Manα3]$_{n8}$}Manβ4GNβ4[{Fucα6}]$_m$GlcNAcyR$_2$ wherein p, n2, n4, n5, n8, and m are either independently 0 or 1; with the provision that when n2 is 0, also n1 is 0; when n4 is 0, also n3 is 0; when n5 is 0, also n1, n2, n3, and n4 are 0; when n7 is 0, also n6 is 0; when n8 is 0, also n6 and n7 are 0; the sum of n1, n2, n3, n4, n5, n6, n7, and n8 is less than or equal to (m+3); [ ] indicates determinant either being present or absent depending on the value of n2, n4, n5, n8, and m; and { } indicates a branch in the structure, y is an anomeric linkage structure a and/or b or linkage from derivatized anomeric carbon and R$_2$ is a natural 0glycan, N-glycan or glycolipid reducing end structure or a chemical reducing end derivatization structure.

33. The method according to claim 30, wherein the terminal mannose structure is according to Formula:

[Manα2]$_{n1}$[Manα3]$_{n2}${[Manα2]$_{n3}$[Manα6]}$_{n4}$}
[Manα6]$_{n5}${[Manα2]$_{n6}$[Manα2]$_{n7}$
[Manα3]$_{n8}$}Manβ4GNβ4GNyR$_2$ wherein n1, n2, n3, n4, n5, n6, n7, and n8 are either independently 0 or 1; with the provision that when n2 is 0, also n1 is 0; when n4 is 0, also n3 is 0; when n5 is 0, also n1, n2, n3, and n4 are 0;

when n7 is 0, also n6 is 0; when n8 is 0, also n6 and n7 are 0; and the sum of n1, n2, n3, n4, n5, n6, n7, and n8 is an integer from 4 to 8;

y is anomeric linkage structure α and/or β or linkage from derivatized anomeric carbon, and R$_2$ is reducing end hydroxyl, chemical reducing end derivative or natural asparagine N-glycoside derivative such as asparagine N-glycosides including asparagines N-glycoside amino acid and/or peptides derived from protein; [ ] indicates determinant either being present or absent depending on the value of n1, n2, n3, n4, n5, n6, n7, and n8; and { } indicates a branch in the structure.

34. The method according to claim 30 comprising a step of cleaving the structure by α-mannosidase.

35. A method of detecting a glycan structure from a sample of human stem cells, comprising the step (a) contacting the stem cells with a binding agent specifically binding to said glycan structure or (b) preparing a glycan containing fraction from the stem cells and identifying the glycan structures by mass spectrometric profiling, wherein said glycan structure is selected from the group consisting of: a terminal lactosamine structure (R1)$_{n1}$Gal(NAc)$_{n3}$β3/4(Fucα4/3)$_{n2}$GlcNAcβR wherein R1 is Fucα2, or SAα3/6 linked to Galβ4GlcNAc, and R is the reducing end core structure of N-glycan, O-glycan and/or glycolipid; or structure (SAα3)$_{n1}$Galβ3(SAα6)$_{n2}$GalNAc;

wherein n1, n2 and n3 are 0 or 1 indicating the presence or absence of a structure wherein SA is a sialic acid;

or branched epitope Galβ3(GlcNAcβ6)GalNAc or R$_1$Galβ4(R$_3$)GlcNAcβ6(R$_2$Galβ3)GalNAc, wherein R1 and R2 are independently either nothing or SAα3; and R$_3$ is independently either nothing or Fucα3; or Manβ4GlcNAc structure in the core structure of N-linked glycan; or epitope Galβ4Glc, or terminal mannose, or terminal SAα3/6Gal, wherein SA is a sialic acid, with the provisions that i) the stem cells are not cells of a cancer cell line and ii) when the cells are embryonal stem cells, the glycan structure is not a SSEA3 or -4 structure, and iii) when cells are hematopoietic CD34⁺ cells, the structure is not single structure comprising SAα3Galβ4GlcNAc, wherein the amount of cells analysed is between 1000 and 10 million or wherein the amount of cells to be analysed is between $10^3$ and $10^6$ cells.

36. The method according to claim 26, 30 or 35, wherein the cells are mesenchymal, hematopoietic or embryonal type stem cells.

* * * * *